(12) United States Patent
Hadari et al.

(10) Patent No.: US 12,168,668 B2
(45) Date of Patent: *Dec. 17, 2024

(54) COMPOUNDS FOR THE TREATMENT OF CANCER AND INFLAMMATORY DISEASE

(71) Applicant: SHY Therapeutics LLC, Harrison, NY (US)

(72) Inventors: Yaron R. Hadari, Harrison, NY (US); Luca Carta, Scarsdale, NY (US); Michael Schmertzler, St. Petersburg, FL (US); Theresa M. Williams, Harleysville, PA (US); Charles H. Reynolds, Austin, TX (US)

(73) Assignee: SHY Therapeutics LLC, Harrison, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/976,267

(22) Filed: Oct. 28, 2022

(65) Prior Publication Data

US 2023/0286997 A1 Sep. 14, 2023

Related U.S. Application Data

(60) Continuation of application No. 17/023,266, filed on Sep. 16, 2020, now Pat. No. 11,560,390, which is a division of application No. 16/246,027, filed on Jan. 11, 2019, now Pat. No. 10,870,657, which is a continuation of application No. 15/387,349, filed on Dec. 21, 2016, now Pat. No. 10,221,191.

(60) Provisional application No. 62/271,185, filed on Dec. 22, 2015.

(51) Int. Cl.
| | |
|---|---|
| C07D 495/04 | (2006.01) |
| A61K 31/52 | (2006.01) |
| A61P 29/00 | (2006.01) |
| A61P 35/00 | (2006.01) |
| C07D 221/04 | (2006.01) |
| C07D 239/94 | (2006.01) |
| C07D 265/30 | (2006.01) |
| C07D 271/06 | (2006.01) |
| C07D 401/04 | (2006.01) |
| C07D 401/12 | (2006.01) |
| C07D 401/14 | (2006.01) |
| C07D 407/14 | (2006.01) |
| C07D 409/14 | (2006.01) |
| C07D 413/14 | (2006.01) |
| C07D 417/14 | (2006.01) |
| C07D 471/04 | (2006.01) |
| C07D 473/30 | (2006.01) |
| C07D 487/04 | (2006.01) |
| C07D 495/14 | (2006.01) |
| C07D 513/04 | (2006.01) |

(52) U.S. Cl.
CPC ......... *C07D 495/04* (2013.01); *C07D 221/04* (2013.01); *C07D 239/94* (2013.01); *C07D 265/30* (2013.01); *C07D 271/06* (2013.01); *C07D 401/04* (2013.01); *C07D 401/12* (2013.01); *C07D 401/14* (2013.01); *C07D 407/14* (2013.01); *C07D 409/14* (2013.01); *C07D 413/14* (2013.01); *C07D 417/14* (2013.01); *C07D 471/04* (2013.01); *C07D 473/30* (2013.01); *C07D 487/04* (2013.01); *C07D 495/14* (2013.01)

(58) Field of Classification Search
CPC .... C07D 495/04; C07D 513/04; A61K 31/52; A61P 29/00; A61P 35/00
See application file for complete search history.

(56) References Cited

U.S. PATENT DOCUMENTS

| | | |
|---|---|---|
| 5,102,877 A | 4/1992 | Murata et al. |
| 5,187,168 A | 2/1993 | Primeau et al. |
| 5,654,307 A | 8/1997 | Bridges et al. |
| 6,133,271 A | 10/2000 | Pamukcu et al. |
| 6,492,383 B1 | 12/2002 | Munchhof et al. |
| 7,173,040 B2 | 2/2007 | Angibaud et al. |
| 8,022,076 B2 | 9/2011 | Ford et al. |
| 8,153,639 B2 | 4/2012 | Chuckowree et al. |
| 8,211,897 B2 | 7/2012 | Holsinger |
| 8,314,112 B2 | 11/2012 | Leblanc et al. |
| 8,691,829 B2 | 4/2014 | Ulrich |
| 9,163,003 B2 | 10/2015 | Chen et al. |
| 9,238,034 B2 | 1/2016 | Tran et al. |
| 9,249,155 B2 | 2/2016 | Ford et al. |
| 9,260,400 B2 | 2/2016 | Leopoldo et al. |
| 9,260,462 B2 | 2/2016 | Leopoldo et al. |
| 9,290,511 B2 | 3/2016 | Madge et al. |
| 9,604,994 B2 | 3/2017 | Dorsey et al. |
| 9,797,882 B2 | 10/2017 | Tran et al. |
| 10,463,649 B2 | 11/2019 | Srivastava et al. |

(Continued)

FOREIGN PATENT DOCUMENTS

| | | |
|---|---|---|
| CN | 101583616 A | 11/2009 |
| CN | 104230952 A | 12/2014 |

(Continued)

OTHER PUBLICATIONS

Al-Zaydi, K. M. et al., 2003, "Microwave assisted reaction of condensed thiophenes with electron poor olefins," J. Korean Chem. Soc., 47(6):591-596.

(Continued)

*Primary Examiner* — Bruck Kifle
(74) *Attorney, Agent, or Firm* — Jones Day

(57) ABSTRACT

Provided herein are compounds that inhibit the phosphorylation of MAPK and thus are useful in compositions and methods for treating cancer and inflammatory disease.

16 Claims, No Drawings

(56) References Cited

U.S. PATENT DOCUMENTS

| | | |
|---|---|---|
| 2005/0176701 A1 | 8/2005 | Borchardt et al. |
| 2006/0167029 A1 | 7/2006 | Matasi et al. |
| 2007/0099877 A1 | 5/2007 | Cai et al. |
| 2007/0287717 A1 | 12/2007 | Fanning et al. |
| 2008/0161254 A1 | 7/2008 | Green et al. |
| 2008/0161559 A1 | 7/2008 | Penning et al. |
| 2008/0161578 A1 | 7/2008 | Penning et al. |
| 2008/0269228 A1 | 10/2008 | Moore et al. |
| 2009/0030196 A1 | 1/2009 | Wang et al. |
| 2009/0163545 A1 | 6/2009 | Goldfarb et al. |
| 2010/0069383 A1 | 3/2010 | Anderson et al. |
| 2010/0093702 A1 | 4/2010 | Barbay et al. |
| 2011/0144140 A1 | 6/2011 | Eriksen et al. |
| 2012/0046290 A1 | 2/2012 | Dumas et al. |
| 2013/0116267 A1 | 5/2013 | Katsikis et al. |
| 2013/0317045 A1 | 11/2013 | Hadd et al. |
| 2014/0072536 A1 | 3/2014 | Burkin et al. |
| 2014/0228565 A1 | 8/2014 | Choo et al. |
| 2014/0256717 A1 | 9/2014 | Fernandez et al. |
| 2014/0256719 A1 | 9/2014 | Finlay et al. |
| 2015/0175558 A1 | 6/2015 | Stockwell et al. |
| 2015/0239900 A1 | 8/2015 | Li et al. |
| 2015/0291590 A1 | 10/2015 | Kandula |
| 2015/0315207 A1 | 11/2015 | Morales et al. |
| 2017/0131278 A1 | 5/2017 | Patricelli et al. |
| 2017/0158706 A1 | 6/2017 | Dorsey |
| 2017/0174699 A1 | 6/2017 | Hadari et al. |
| 2018/0118761 A1 | 5/2018 | Sebti et al. |
| 2019/0022074 A1 | 1/2019 | Hadari et al. |
| 2019/0218229 A1 | 7/2019 | Hadari et al. |
| 2020/0054614 A1 | 2/2020 | Hadari et al. |

FOREIGN PATENT DOCUMENTS

| | | |
|---|---|---|
| CN | 107721982 A | 8/2018 |
| DE | 1959402 A1 | 6/1971 |
| DE | 1959403 A1 | 6/1971 |
| DE | 2039662 A1 | 2/1972 |
| DE | 2050814 A1 | 4/1972 |
| DE | 2050815 A1 | 4/1972 |
| DE | 2050816 A1 | 4/1972 |
| DE | DD 295381 A5 | 10/1991 |
| EP | 0 404 356 A1 | 12/1990 |
| EP | 0 407 899 A2 | 1/1991 |
| EP | 2 014 663 A1 | 5/1991 |
| EP | 0 502 725 A2 | 9/1992 |
| EP | 0 519 307 A2 | 12/1992 |
| EP | 0 579 424 A1 | 1/1994 |
| EP | 0 807 633 A2 | 11/1997 |
| EP | 0 276 057 A2 | 7/1998 |
| EP | 0 884 310 A1 | 12/1998 |
| EP | 0 900 568 A2 | 3/1999 |
| EP | 0 900 799 A1 | 3/1999 |
| EP | 1 254 903 A1 | 11/2002 |
| EP | 0 934 321 B1 | 8/2003 |
| EP | 1 997 812 A1 | 12/2008 |
| EP | 2 508 184 A1 | 10/2012 |
| EP | 3 290 412 A1 | 3/2018 |
| GB | 1057612 A | 2/1967 |
| JP | 56059778 A | 5/1981 |
| JP | H04305630 A | 10/1992 |
| JP | 2010-512337 A | 4/2010 |
| KR | 20180066985 A | 6/2018 |
| WO | WO 1992/020687 | 11/1992 |
| WO | WO 1993/003040 | 2/1993 |
| WO | WO 1994/008975 | 4/1994 |
| WO | WO 1997/029110 | 8/1997 |
| WO | WO 1997/046560 | 12/1997 |
| WO | WO 1998/006722 | 2/1998 |
| WO | WO 1998/023620 | 6/1998 |
| WO | WO 1998/049899 | 11/1998 |
| WO | WO 1999/014202 | 3/1999 |
| WO | WO 1999/024440 | 5/1999 |
| WO | WO 1999/040091 | 8/1999 |
| WO | WO 2000/059912 | 10/2000 |
| WO | WO 2001/002409 | 1/2001 |
| WO | WO 2001/083456 | 11/2001 |
| WO | WO 2002/002549 | 1/2002 |
| WO | WO 2002/026745 | 4/2002 |
| WO | WO 2002/055524 | 7/2002 |
| WO | WO 2003/033476 | 4/2003 |
| WO | WO 2003/035076 | 5/2003 |
| WO | WO 2003/035653 | 5/2003 |
| WO | WO 2003/050064 | 6/2003 |
| WO | WO 2003/059913 | 7/2003 |
| WO | WO 2003/106435 | 12/2003 |
| WO | WO 2004/037176 | 5/2004 |
| WO | WO 2004/065392 | 8/2004 |
| WO | WO 2004/071460 | 8/2004 |
| WO | WO 2004/074270 | 9/2004 |
| WO | WO 2004/111058 | 12/2004 |
| WO | WO 2005/023782 | 3/2005 |
| WO | WO 2005/026126 | 3/2005 |
| WO | WO 2005/047292 | 5/2005 |
| WO | WO 2005/047293 | 5/2005 |
| WO | WO 2005/082887 | 9/2005 |
| WO | WO 2005/105760 | 11/2005 |
| WO | WO 2005/105780 | 11/2005 |
| WO | WO 2005/121147 | 12/2005 |
| WO | WO 2006/022955 | 3/2006 |
| WO | WO 2006/040966 | 4/2006 |
| WO | WO 2006/043145 | 4/2006 |
| WO | WO 2006/046040 | 5/2006 |
| WO | WO 2006/072831 | 7/2006 |
| WO | WO 2006/122200 | 11/2006 |
| WO | WO 2007/002701 | 1/2007 |
| WO | WO 2007/035010 | 3/2007 |
| WO | WO 2007/056214 | 5/2007 |
| WO | WO 2007/064883 | 6/2007 |
| WO | WO 2007/076085 | 7/2007 |
| WO | WO 2007/093365 | 8/2007 |
| WO | WO 2007/102679 | 9/2007 |
| WO | WO 2007/127183 | 11/2007 |
| WO | WO 2007/132171 | 11/2007 |
| WO | WO 2007/139951 | 12/2007 |
| WO | WO 2008/012413 | 1/2008 |
| WO | WO 2008/016123 | 2/2008 |
| WO | WO 2008/020622 | 2/2008 |
| WO | WO 2008/024433 | 2/2008 |
| WO | WO 2008/024724 | 2/2008 |
| WO | WO 2008/028935 | 3/2008 |
| WO | WO 2008/063668 | 5/2008 |
| WO | WO 2008/064018 | 5/2008 |
| WO | WO 2008/066664 | 6/2008 |
| WO | WO 2008/092860 | 8/2008 |
| WO | WO 2008/092861 | 8/2008 |
| WO | WO 2008/092862 | 8/2008 |
| WO | WO 2008/094909 | 8/2008 |
| WO | WO 2008/131050 | 10/2008 |
| WO | WO 2008/134397 | 11/2008 |
| WO | WO 2009/026241 | 2/2009 |
| WO | WO 2009/027346 | 3/2009 |
| WO | WO 2009/064388 | 5/2009 |
| WO | WO 2009/065472 | 5/2009 |
| WO | WO 2009/087225 | 7/2009 |
| WO | WO 2009/119880 | 10/2009 |
| WO | WO 2009/121036 | 10/2009 |
| WO | WO 2010/027236 | 3/2010 |
| WO | WO 2010/037765 | 4/2010 |
| WO | WO 2010/045006 | 4/2010 |
| WO | WO 2010/126960 | 11/2010 |
| WO | WO 2010/138828 | 12/2010 |
| WO | WO 2011/011550 | 1/2011 |
| WO | WO 2011/101429 | 2/2011 |
| WO | WO 2011/025774 | 3/2011 |
| WO | WO 2011/102399 | 8/2011 |
| WO | WO 2011/104183 | 9/2011 |
| WO | WO 2012/004900 | 1/2012 |
| WO | WO 2012/009452 | 1/2012 |
| WO | WO 2012/030894 | 3/2012 |
| WO | WO 2012/037204 | 3/2012 |
| WO | WO 2012/151567 | 11/2012 |
| WO | WO 2012/153796 | 11/2012 |
| WO | WO 2012/156756 | 11/2012 |

(56) References Cited

FOREIGN PATENT DOCUMENTS

| WO | WO 2013/008217 | 1/2013 |
|---|---|---|
| WO | WO 2013/032591 | 3/2013 |
| WO | WO 2013/078126 | 5/2013 |
| WO | WO 2013/087578 | 6/2013 |
| WO | WO 2013/154878 | 10/2013 |
| WO | WO 2014/040077 | 3/2014 |
| WO | WO 2014/045039 | 3/2014 |
| WO | WO 2014/124757 | 8/2014 |
| WO | WO 2014/138562 | 9/2014 |
| WO | WO 2014/143610 | 9/2014 |
| WO | WO 2014/169167 | 10/2014 |
| WO | WO 2015/025026 | 2/2015 |
| WO | WO 2015/042497 | 3/2015 |
| WO | WO 2015/043398 | 4/2015 |
| WO | WO 2015/050798 | 4/2015 |
| WO | WO 2015/054572 | 4/2015 |
| WO | WO 2015/148714 | 10/2015 |
| WO | WO 2015/160192 | 10/2015 |
| WO | WO 2015/169421 | 11/2015 |
| WO | WO 2015/183989 | 12/2015 |
| WO | WO 2016/044772 | 3/2016 |
| WO | WO 2016/049568 | 3/2016 |
| WO | WO 2016/068580 | 5/2016 |
| WO | WO 2016/142312 | 9/2016 |
| WO | WO 2016/161361 | 10/2016 |
| WO | WO 2016/164675 | 10/2016 |
| WO | WO 2016/172692 | 10/2016 |
| WO | WO 2016/183398 | 11/2016 |
| WO | WO 2016/201257 | 12/2016 |
| WO | WO 2017/015425 | 1/2017 |
| WO | WO 2017/015562 | 1/2017 |
| WO | WO 2017/031176 | 2/2017 |
| WO | WO 2017/034377 | 3/2017 |
| WO | WO 2017/040448 | 3/2017 |
| WO | WO 2017/058728 | 4/2017 |
| WO | WO 2017/058768 | 4/2017 |
| WO | WO 2017/058805 | 4/2017 |
| WO | WO 2017/058807 | 4/2017 |
| WO | WO 2017/058902 | 4/2017 |
| WO | WO 2017/059191 | 4/2017 |
| WO | WO 2017/070256 | 4/2017 |
| WO | WO 2017/087528 | 5/2017 |
| WO | WO 2017/112777 | 6/2017 |
| WO | WO 2017/172565 | 10/2017 |
| WO | WO 2018/237084 | 12/2018 |
| WO | WO 2019/018359 | 1/2019 |
| WO | WO 2019/105734 | 6/2019 |
| WO | WO 2019/129059 | 7/2019 |
| WO | WO 2019/180141 | 9/2019 |

OTHER PUBLICATIONS

Anastassiadis et al., 2013, "A Highly Selective Dual Insulin Receptor (IR)/insulin-like Growth Factor 1 Receptor (IGF-1R) Inhibitor Derived From an Extracellular Signal-Regulated Kinase (ERK) Inhibitor," J. Biol. Chem., 28(29):26068-28077.
Andrews, M. et al., 2015, "Cellular Mechanisms Underlying Complete Hematological Response of Chronic Myeloid Leukemia to BRAF and MEK1/2 Inhibition in a Patient with Concomitant Metastatic Melanoma," Clin Cancer Res., 21(23):5222-5234.
Arlt, A. et al., 2011, "Role of the immediate early response 3 (IER3) gene in cellular stress response, inflammation and tumorigenesis," Eur J Cell Biol., 90(6-7):545-52.
Arnst et al., 2017, "Discovery and characterization of small molecule Rac1 inhibitors," Oncotarget, 8(21):34586-34600.
Arthur, J. et al., 2013, "Mitogen-activated protein kinases in innate immunity," Nat. Rev. Immunol., 13:679-692.
Bakir-Gungor, B. et al., 2015, "Identification of possible pathogenic pathways in Behçet's disease using genome-wide association study data from two different populations," Eur. J. Hum. Genet., 23:678-687.

Barili et al., 1985, "A facile one pot synthesis of 2,9-disubstiuted 8-azapurin-6-ones (3,5-disubstiued 7-hydroxy-3H-1,2,3-triazolo[4,5-d]pyrimidines)," J. Heterocyclic Chem., 22(6):1607-1609.
Bartold, P. M. et al., 2006, "Molecular and cell biology of healthy and diseased periodontal tissues," Periodontol. 2000, 40:29-49.
Bhatia, M. et al., 2004, "Role of inflammatory mediators in the pathophysiology of acute respiratory distress syndrome," J. Pathol., 202:145-156.
Bivona et al., 2005, "Analysis of Ras and Rap activation in living cells using fluorescent Ras binding domains," Methods, 37:138-145.
Bogolubsky et al., 2018, "An old story in the parallel synthesis world: an approach to hydantoin libraries," ACS Comb. Sci., 20(1):35-43.
Bogolubsky et al., 2008, "Dry HCl in parallel synthesis of fused pyrimidin-4-ones," J. Comb. Chem., 10(6):858-862.
Böhm et al., 1986, "Über thieno-verbindungen 5. Mitteilung: basisch substituierte thieno[2,3-]pyrimidine," Pharmazie, Govi Verlag Pharmazeutischer Verlag GmbH, DE, 41(1):23-25.
Bonventre, J. V. et al., 2004, "Ischemic acute renal failure: An inflammatory disease?," Kidney Int., 66:480-485.
Bouskine A. et al., 2008, "Estrogens promote human testicular germ cell cancer through a membrane-mediated activation of extracellular regulated kinase and protein kinase A," Endocrinology, 149(2):565-73.
Briel et al., 1992, "Synthesis of thieno[3,3-d]- and -[3,4-d]pyrimidines by alternative ring closure reactions," Pharmazie, 47(8):577-579. English Abstract Only.
Briel et al., 2005, "Selective nucleophilic replacement of the benzylsulfanyl group in 2,4-disulfanyl-substituted thieno[2,3-d]pyrimidin-6-carboxylic acid derivatives by secondary amines," J. Heterocyclic Chem., 42(5):841-846.
Briel, 1998, "Synthesis of thieno-heterocycles from substituted 5-(methylthio)thiophene-4-carbonitriles," Pharmazie, 53(4):227-231. English Abstract Only.
Buhler et al., 2014, "p38 MAPK inhibitors: a patent review (2012-2013)," Expert Opinion on Therapeutic Patents, 24(5):535-554.
Burgess, J. K.. et al., 2008, "Dual ERK and phosphatidylinositol 3-kinase pathways control airway smooth muscle proliferation: Differences in asthma," J. Cell. Physiol., 216:673-679.
Burotto et al., 2014, "The MAPK Pathway Across Different Malignancies: A New Perspective," Cancer, 120(22):3446-3456.
Caunt, C. et al., 2015, "MEK1 and MEK2 inhibitors and cancer therapy: the long and winding road," Nat Rev Cancer, 15(10):577-592.
Chang, L. et al., 2001, "Mammalian MAP kinase signalling cascades," Nature, 410:37-40.
Chapman, M. S. et al., 2011, "Novel mitogen-activated protein kinase kinase inhibitors," Expert Opin Investig Drugs, 20(2):209-220.
Choi et al., 2018, "In silico discovery of quinoxaline derivatives as novel LRP5/6-sclerostin interaction inhibitors," Bioorg. Med. Chem. Lett., 28(6):1116-1121.
Choi et al., 2005, "Pathogenesis of Gout," Ann. Intern. Med., 143(7):499-516.
Chu, A. J., 2014, "Antagonism by bioactive polyphenols against inflammation: a systematic view," Inflamm. Allergy Drug Targets, 13(1):34-64.
Chung, 2001, "Pentafluorophenylhydrazine," Encyclopedia Reagents Organic Synthesis (e-EROS), 5 pages.
Cichero et al., 2016, "Exhaustive 3D-QSAR analyses as a computational tool to explore the potency and selectivity profiles of thieno[3,2-d]pyrimidin-4(3H)-one derivatives as PDE7 inhibitors," RSC Advances, 6(66):61088-61108.
Collin et al., 2018, "Discovery of Rogaratinib (BAY 1163877): A pan-FGFR Inhibitor," Chem. Med. Chem., 13(5):437-445.
Colvin, R. B. et al., 2005, Antibody-mediated organ-allograft rejection. Nat. Rev. Immunol., 5:807-817.
Crespo et al., 1998, "Design, synthesis, and biological activities of new thieno[3,2-d] pyrimidines as selective type 4 phosphodiesterase inhibitors," J. Med. Chem., 41(21):4021-4035.
Croft, M. et al., 2013, "Clinical targeting of the TNF and TNER superfamilies," Nat. Rev. Drug Discov. 12:147-168.

(56) References Cited

OTHER PUBLICATIONS

Cuevas, B. et al., 2007, Role of mitogen-activated protein kinase kinase kinases in signal integration. Oncogene, 26:3159-3171.
Cummins, A. et al., 2003, "Persistent Localization of Activated Extracellular Signal-Regulated Kinases (ERK1/2) Is Epithelial Cell-Specific in an Inhalation Model of Asbestosis," Am. J. Pathol., 162:713-720.
De Schutter et al., 2017, "Targeting Bacillosamine Biosynthesis in Bacterial Pathogens: Development of Inhibitors to a Bacterial Amino-Sugar Acetyltransferase from *Campylobacter jejuni*," J. Med. Chem., 60(5):2099-2118.
Desai et al., 1997, "Thieno(3,2-d)pyrimidines. Part-I. Preparation and Antimicrobial Activity of 3-N-Substituted-thioureido-2-methyl-6-phenylthieno(3, 2-d)pyrimidin-4(3H)-ones," J. Indian Chem. Soc., 74(2):160.
Desai et al., 1995, "Thieno[3,2-d]pyrimidines. Part II: Preparation and antimicrobial activity of 2-methyl-3-N-arylsulfonamido-6-phenylthieno[3,2-d]pyrimidin-4(3H)-ones," J. Institution of Chemists (India), 67(5):136-137.
Desroches et al., 2017, "Discovery of new hit-molecules targeting Plasmodium falciparum through a global SAR study of the 4-substituted-2-trichloromethylquinazoline antiplasmodial scaffold," Eur. J. Med. Chem., 125:68-86.
Dhillon et al., 2007, "MAP kinase signaling pathways in cancer," Oncogene, 26:3279-3290.
Doddareddy, M. R. et al., 2012, "Targeting mitogen-activated protein kinase phosphatase-1 (MKP-1): structure-based design of MKP-1 inhibitors and upregulators," Curr Med Chem., 19(2):163-73.
Dolly et al., 2016, "Phase I study of apitolisib (GDC-0980), dual phosphatidylinositol-3-kinase and mammalian target of rapamycin kinase inhibitor, in patients with advanced solid tumors," Clin. Cancer Res., 22(12):2874-2884.
Dumaitre et al., 1996, "Synthesis and cyclic GMP phosphodiesterase inhibitory activity of a series of 6-phenylpyrazolo[3,4-d]pyrimidones," J. Med. Chem., 39(8):1635-1644.
Dumitru, C. D. et al., 2000, "TNF-alpha induction by LPS is regulated posttranscriptionally via a Tpl2/ERK-dependent pathway," Cell, 103:1071-1083.
Dupati et al., 2014, "Vemurafenib: Background, Patterns of Resistance, and Strategies to Combat Resistance in Melanoma," Med. Student Res. Journal, 3:36-43.
Elneairy et al., 2012, "Bis-(cyanoacetamide)alkanes in heterocyclic synthesis: synthesis of bis-heteryl(carboxymido)alkanes and bis-(heteryl)alkanes of thiophene, pyrrole, thiazole and pyrimidinone series," J. Sulfur Chem., 33(3):373-383.
Endo et al., 2015, "2-(Isopropylamino)thieno[3,2-d]pyrimidin-4(3H)-one derivatives as selective phosphodiesterase 7 inhibitors with potent in vivo efficacy," Bioorg. Med. Chem. Lett., 25(9):1910-1914.
Englert et al., 2010, "Fragment-based lead discovery: screening and optimizing fragments for thermolysin inhibition," ChemMedChem,5(6):930-940.
Fan, W. et al., 2015, "Marsdenia tenacissima extract induces G0/G1 cell cycle arrest in human esophageal carcinoma cells by inhibiting mitogen-activated protein kinase (MAPK) signaling pathway," Chin J Nat Med., 13(6):428-437.
Feuerstein et al., 1987, "Characterisation of the metal-ion-GDP complex at the active sites of transforming and nontransforming p21 proteins by observation of the $^{17}$O-Mn superhyperfine coupling and by kinetic methods," Eur. J. Biochem., 162:49-55.
Fortea, 1973, "4-Oxo-1,2,3,4-tetrahydrothienopyrimidine," Afinidad, 30(305):225-229 (English Abstract Only).
Gaestel, M. et al., 2009, "Targeting innate immunity protein kinase signalling in inflammation," Nat. Rev. Drug Discov., 8:480-499.
Gantke, T. et al., 2012, "IKB kinase regulation of the TPL-2/ERK Mapk pathway," Immunol Rev., 246(1):168-182.

Garg et al., 2017, "Identification of new insulin growth factor receptor-1 (IGF-1R) inhibitors via exploring ATPas kinase domain of IGF-1R through virtual screening," Med. Chem. Res., 26:205-219.
Gascoigne et al., 2008, "Cancer cells display profound intra- and interline variation following prolonged exposure to antimitotic drugs," Cancer Cell, 14(2):111-122.
Gellibert et al., 2009, "Design of novel quinazoline derivatives and related analogues as potent and selective ALK5 inhibitors," Bioorganic & Medicinal Chemistry Letters, 19(8):2277-2281.
Gillespie et al., 2008, "Antagonists of the human adenosine A2A receptor. Part 1: Discovery and synthesis of thieno[3,2-d]pyrimidine-4-methanone derivatives," Bioorg. Med. Chem. Lett., 18(9):2916-2919.
Gillespie et al., 2008, "Antagonists of the human adenosine A2A receptor. Part 2: Design and synthesis of 4-arylthieno[3,2-d]pyrimidine derivatives," Bioorg. Med. Chem. Lett., 18(9):2920-2923.
Girolomoni, G. et al., 2001, "The role of keratinocytes in the pathogenesis of atopic dermatitis," J. Am. Acad. Dermatol., 45:S25-S28.
Gronowitz et al., 1968, "On thiophene analogues of metaqualone-like compounds," Acta Pharm. Suec., 5(6):563-578.
Guilding, C. et al., 2007, "Restored plasticity in a mouse model of neurofibromatosis type 1 via inhibition of hyperactive ERK and CREB," Eur J Neurosci., 25(1):99-105.
Gupta et al., 2012, "Identification of novel HIV-1 integrase inhibitors using shape-based screening, QSAR, and docking approach," Chem. Biol. Drug Des., 79(5):835-849.
Haase et al., 2002, "Activation of Epidermal Growth Factor Receptor/ERK Signaling Correlates with Suppressed Differentiation in Malignant Acanthosis Nigricans," J. Invest. Dermatol., 118:891-893.
Hajjem et al., 1992, "Action Des Amines Et Des Hydrazines Sur Les Imidates Issus Du Methyl 3-Amino-2-Thiophene Carboxylate. Nouvelle Voie D'Acces Aux [3,2-d]4(3H) Thienopyrimidinones," Bulletin des Societes Chimiques Belges, 101(6):445-448. (English Abstract Only).
Harikrishnan et al., 2018, "Heterobicyclic Inhibitors of Transforming Growth Factor Beta Receptor I (TGFβRI)," Bioorg. Med. Chem., 26(5):1026-1034.
Haswani et al., 2011, "Synthesis and antimicrobial activity of novel 2-(pyridine-2-yl)thieno[2,3- d]pyrimidin-4(3H)-ones," Turk. J. Chem., 35:915-924.
Hayakawa et al., 2006, "Synthesis and biological evaluation of 4-morpholino-2-phenylquinazolines and related derivatives as novel PI3 kinase p110alpha inhibitors," Bioorg. Med. Chem., 14(20):6847-6858.
Hilger et al., 2002, "The Ras-Raf-MEK-ERK Pathway in the Treatment of Cancer," Onkologie, 25:511-518.
Holland et al., 1975, "Antiallergic activity of 8-azapurin-6-ones with heterocyclic 2-substituents," European Journal of Medicinal Chemistry, 10(5):447-449.
Howlett, M. et al., 2009, "Cytokine signalling via gp130 in gastric cancer," Biochim Biophys Acta., 1793(11):1623-1633.
Hrast et al., 2017, "Synthesis and structure-activity relationship study of novel quinazolinone-based inhibitors of MurA," Bioorg. Med. Chem. Lett., 27(15):3529-3533.
Huang et al., 2010, "MAPK signaling in inflammation-associated cancer development," Protein Cell, 1(3):218-226.
Huang et al., 2013, "B-RAf and the inhibitors: from bench to bedside," J. of Hematol. & Oncology, 6(1):30.
Hyman et al., 2015, "Vemurafenib in Multiple Nonmelanoma Cancers with BRAF V600 Mutations," N Engl J Med., 373(8):726-736.
Iyer et al., 2016, "Synthesis of 1,3,4-oxadizoles as promising anticoagulant agents," RSC Adv., 6:24797-24807.
Jeffrey, K. et al., 2007, "Targeting dual-specificity phosphatases: manipulating MAP kinase signalling and immune responses," Nat. Rev. Drug Discov., 6:391-403.
Ji, R. et al., 2009, "MAP kinase and pain," Brain Res. Rev., 60:135-148.
Ji, R. et al., 2007, "p38 MAPK, microglial signaling, and neuropathic pain," Mol. Pain, 3:33-43.

(56) References Cited

OTHER PUBLICATIONS

Johansen, C. et al., 2005, "The mitogen-activated protein kinases p38 and ERK1/2 are increased in lesional psoriatic skin," Br. J. Dermatol., 152:37-42.

John et al., 1993, "Kinetic and structural analysis of the Mg2+-binding site of the guanine nucleotide-binding protein p21$^{H\text{-}ras}$," J. Bio. Chem., 268(2):923-929.

John et al., 1990, "Kinetics of interaction of nucleotides with nucleotide-free H-ras p21," Biochem., 29:6058-6065.

Jokinen et al., 2015, "MEK and PI3K inhibition in solid tumors: rationale and evidence to date," Ther Adv Med Oncol., 7(3): 170-180.

Juszczak, M. et al., 2012, "2-Amino-1,3,4-thiadiazole derivative (FABT) inhibits the extracellular signal-regulated kinase pathway and induces cell cycle arrest in human non-small lung carcinoma cells," Bioorg. & Med. Chem. Lett., 22(17):5466-5469.

Kabir, S., 2011, "The role of interleukin-17 in the *Helicobacter pylori* induced infection and immunity," Helicobacter, 16(1):1-8.

Kadmiel et al., 2013, "Glucocorticoid receptor signaling in health and disease," Trends Pharmacol. Sci., 34:518-530.

Kammoun et al., 2000, "Action des hydrazines perfluoroalkylees sur les iminoesters synthese des perfluoroalkyl-3-aminothienopyrimidinones et des perfluoroalkyl-1,2,4-triazin-6-ones," J. Fluorine Chem., 105(1):83-86.

Karnoub et al., 2008, "Ras oncogenes: split personalities," Nat. Rev. Mol. Cell Biol., 9(7):517-531.

Kaul, M. et al., 2001, "Pathways to neuronal injury and apoptosis in HIV-associated dementia," Nature, 410:988-994.

Kfoury, A. et al., 2014, "Dual function of MyD88 in inflammation and oncogenesis: implications for therapeutic intervention," Curr Opin Oncol., 26(1):86-91.

Khan et al., 2013, "2,5-Disubstituted-1,3,4-oxadiazoles: thymidine phosphorylase inhibitors," Medicinal Chemistry Research, 22(12):6022-6028.

Kim et al., 2015, "Compromised MAPK signaling in human diseases: an update," Arch Toxicol., 89(6):867-882.

Kim et al., 2014, "Serendipitous discovery of 2-((phenylsulfonyl)methyl)-thieno[3,2-d]pyrimidine derivatives as novel HIV-1 replication inhibitors," Bioorg. Med. Chem. Lett., 24(23):5473-5477.

Kim et al., 2016, "Structural modifications at the 6-position of thieno[2,3-d]pyrimidines and their effects on potency at FLT3 for treatment of acute myeloid leukemia," Eur. J. Med. Chem., 120:74-85.

Kim et al., 2010, "Pathological roles of MAPK signaling pathways in human diseases," Biochim. Biophys. Acta, 1802(4):396-405.

King et al., 2013, "Dabrafenib; preclinical characterization, increased efficacy when combined with trametinib, while BRAF/MEK tool combination reduced skin legions," PLoS One, 8(7):e67583.

Ko et al., 2013, "Target-oriented mechanisms of novel herbal therapeutics in the chemotherapy of gastrointestinal cancer and inflammation," Curr Pharm Des., 19(1):48-66.

Kolata, G., 2015, "A Faster Way to Try Many Drugs on Many Cancers," The New York Times (5 pages).

Kontoyiannis, D. et al., 2002, "Genetic dissection of the cellular pathways and signaling mechanisms in modeled tumor necrosis factor-induced Crohn's-like inflammatory bowel disease," J. Exp. Med., 196:1563-1574.

Kopra et al., 2014, "A homogeneous quenching resonance energy transfer assay for the kinetic analysis of the GTPase nucleotide exchange reaction," Anal. Bioanal. Chem., 406:4147-4156.

Kucherenko et al., 2008, "Positional isomers of thienopyrimidinones," Chem. Heterocycl. Comp., 44(6):750-758.

Kumar et al., 2016, "Merging C—H Bond Functionalization with Amide Alcoholysis: En Route to 2-Aminopyridines," ACS Catalysis, 6(6):3531-3536.

Kumar et al., 2009, "An efficient synthesis and biological study of novel indolyl-1,3,4-oxadiazoles as potent anticancer agents," Bioorganic & Medicinal Chemistry Letters, 19(15):4492-4494.

Kumar, S. et al., 2001, "Intracellular signaling pathways as a target for the treatment of rheumatoid arthritis," Curr. Opin. Pharmacol., 1:307-313.

Kurasawa et al., 2017, "2-Aminomethylthieno[3,2-d]pyrimidin-4(3H)-ones bearing 3-methylpyrazole hinge binding moiety: Highly potent, selective, and time-dependent inhibitors of Cdc7 kinase," Bioorg. Med. Chem., 25(14):3658-3670.

Kyriakis et al., 2001, "Mammalian Mitogen-Activated Protein Kinase Signal Transduction Pathways Activated by Stress and Inflammation," Physiol. Rev., 81:807-869.

Kyrmizi, I. et al., 2013, "Tpl2 kinase regulates FcγR signaling and immune thrombocytopenia in mice," J. Leukoc. Biol., 94:751-757.

Labib et al., 2016, "Design, synthesis and biological evaluation of novel thiophene and theinopyrimidine derivatives as anticancer agents," Med. Chem. Res., 25(11):2607-2618.

Lack et al., 2012, "Correction to Targeting the Binding Function 3 (BF3) Site of the Human Androgen Receptor through Virtual Screening," J. Med. Chem., 55(1):565.

Lack et al., 2011, "Targeting the binding function 3 (BF3) site of the human androgen receptor through virtual screening," J. Med. Chem., 54(24):8563-8573.

Lawrenz, M. et al., 2012, "Genetic and pharmacological targeting of TPL-2 kinase ameliorates|experimental colitis: a potential target for the treatment of Crohn's disease?," Mucosal Immunol., 5:129-139.

Lee et al., 1998, "A facile synthesis of 3-substituted 2-cyanoquinazolin-4(3H)-ones and 3-alkyl-2-cyanothieno[3,2-d]pyrimidin-4(3H)-ones via 1,2,3-dithiazoles," J. Heterocyc. Chem., 35(3):659-668.

Lenzen et al., 1998, "Kinetic analysis by fluorescence of the interaction between Ras and the catalytic domain of the guanine nucleotide exchange factor Cdc25," Biochem., 37:7420-7430.

Leung, P. S. et al., 2009, "Role of oxidative stress in pancreatic inflammation," Antioxid. Redox Signal. 11:135-165.

Li et al., 2011, "Induction of Cancer Cell Death by Isoflavone: The Role of Multiple Signaling Pathways," Nutrients, 3:877-896.

Lindh et al., 2015, "Toward a benchmarking data set able to evaluate ligand- and structure-based virtual screening using public HTS data," J. Chem. Inf. Model., 55(2):343-353.

Lingayya et al., 2017, "Palladium(ii)-catalyzed direct O-alkenylation of 2-arylquinazolinones with N-tosylhydrazones: an efficient route to O-alkenylquinazolines," Chem. Commun. (Camb)., 53(10):1672-1675.

Liu et al., 2014, "Design, synthesis and biological evaluation of novel thieno[3,2-d]pyrimidine derivatives containing diaryl urea moiety as potent antitumor agents," Eur. J. Med. Chem., 85:215-227.

Liu et al., 2014, "Design, synthesis and biological evaluation of novel thieno[3,2-d]pyrimidinederivatives possessing diaryl semicarbazone scaffolds as potent antitumor agents," Eur. J. Med. Chem., 87:782-793.

Liu et al., 2007, "MAPK phosphatases—regulating the immune response," Nat. Rev. Immunol., 7:202-212.

Lorusso et al., 2020, "One step at a time—clinical evidence that KRAS is indeed druggable," N. Engl. J. Med., 383:1277-1278.

Manzoor et al., 2012, "Mitogen-activated protein kinases in inflammation," J. Bacter. Virology, 42(3):189-195.

Mao, H. et al., 2012, "Deregulated Signaling Pathways in Glioblastoma Multiforme: Molecular Mechanisms and Therapeutic Targets," Cancer Invest., 30(1):48-56.

McCoull et al., 2013, "Identification of pyrazolo-pyrimidinones as GHS-R1a antagonists and inverse agonists for the treatment of obesity," Med. Chem. Commun., 4(2):456-462.

McLendon, R. et al., 2008, "Comprehensive genomic characterization defines human glioblastoma genes and core pathways," Nature, 455(7216):1061-1068.

"Memorial Sloan Kettering Cancer Center Researchers Publish Landmark Basket Study," Press Release from Memorial Sloan Kettering, Aug. 19, 2015, (3 pages), retrieved on Apr. 4, 2018. Retrieved from the Internet: < https://www.mskcc.org/news-releases/memorial-sloan-kettering-center-researchers-publish-landmark-basket-study>.

"FDA Announces First Approval of Targeted Therapy Based on Basket Study," Press Release from Memorial Sloan Kettering, Nov. 6, 2017, (3 pages), retrieved on Apr. 4, 2018. Retrieved from the

(56) References Cited

OTHER PUBLICATIONS internet: <https://www.mskcc.org/trending-topics/fda-announces-first-approval-targeted-therapy-based-basket-study>.
Metz et al., 2013, "From determinants of RUNX1/ETO tetramerization to small-molecule protein- protein interaction inhibitors targeting acute myeloid leukemia," J. Chem. Inf. Model., 53(9):2197-2202.
Milligan, E. D. et al., 2009, "Pathological and protective roles of glia in chronic pain," Nat. Rev. Neurosci., 10:23-36.
Mitra et al., 2009, "Molecular pathogenesis and diagnostics of bladder cancer," Annu Rev Pathol., 4:251-285.
Miyamoto, 1985, "Antitumor activity of 5-substituted 2-acylamino-1,3,4-thiadiazoles against transplantable rodent tumors," Chem. Pharm. Bull., 33(11):5126-5129.
Mohan et al., 2004, "A facile synthesis and thio-Claisen rearrangement of 3-aryl-2-phenyl-5-prop-2-ynylsulfanyl-3H-pyrimidin-4-ones: regioselective transformation to thieno[3,2-d]pyrimidin-4-ones," Tetrahedron, 45(31):6075-6077.
Mohan et al., 2005, "Facile synthesis and regioselective thio-Claisen rearrangements of 5-prop-2-ynyl/enyl-sulfanyl pyrimidinones: transformation to thienopyrimidinones," Tetrahedron, 61(45):10774-10780.
Mohanta et al., 2002, "A short synthesis of quinazolinocarboline alkaloids rutaecarpine, hortiacine, euxylophoricine A and euxylophoricine D from methyl N-(4-chloro-5H-1,2,3-dithiazol-5-ylidene) anthranilates," Tetrahedron Letters, 43(22):3993-3996.
Mohanta et al., 2002, "New Synthetic Route to Tetracyclic Quinazolin-4(3H)-one Ring System," Heterocycles, 57(8):1471-1485.
Morel, J. et al., 2004, "Signal transduction pathways: new targets for treating rheumatoid arthritis," Joint Bone Spine, 71:503-510.
Mossman, B. et al., 2006, "Oxidants and Signaling by Mitogen-Activated Protein Kinases in Lung Epithelium," Am. J. Respir., Cell Mol. Biol., 34:666-669.
Muranen et al., 2016, "ERK and p38 MAPK activities determine sensitivity to PI3K/mTOR inhibition via regulation of MYC and YAP," Cancer Res., 76(24):7168-7180.
Murdoch et al., 1986, "Synthesis of [1,2,4]triazoloquinazolinones and imidazoquinazolinones," J. of Heterocyclic Chem., 23(3):833-841.
Nara et al., 2014, "Thieno[2,3-d]pyrimidine-2-carboxamides bearing a carboxybenzene group at 5-position: highly potent, selective, and orally available MMP-13 inhibitors interacting with the S1" binding site," Bioorg. Med. Chem., 22(19):5487-5505.
"MEK: A Single Drug Target Shows Promise in Multiple Cancers," 2013, MEK Inhibitor Research Update—National Cancer Institute (8 pages), retrieved on Nov. 27, 2017. Retrieved from the internet: <https://www.cancer.gov/about-cancer/treatment/research/mek>.
Neidlein et al., 1991, "Synthesis of 1,2,3,4-Tetrahydro-4-oxothieno[3,2-d]pyrimidine and Perhydropyrimidine Derivates from Alkyl Dicyanoacetates," Helvetica Chimica Acta, 74(3):579-584.
Nolan et al., 2011, "Identification of a novel selective serotonin reuptake inhibitor by coupling monoamine transporter-based virtual screening and rational molecular hybridization," ACS Chem. Neurosci., 2(9):544-552.
Obata, K. et al., 2004, "MAPK activation in nociceptive neurons and pain hypersensitivity," Life Sci., 74(21):2643-2653.
O'Dowd et al., 2018, "Identification and Structure-Guided Development of Pyrimidinone Based USP7 Inhibitors," ACS Med. Chem. Lett., 9(3):238-243.
Oh et al., 2017, "Synthetic strategy for increasing solubility of potential FLT3 inhibitor thieno[2,3-d]pyrimidine derivatives through structural modifications at the C2 and C6 positions," Bioorg. Med. Chem. Lett., 27:496-500.
Ostrem et al., 2016, "Direct small-molecule inhibitors of KRAS: from structural insights to mechanism-based design," Nature Reviews Drug Discovery, 139:1-25.
Pace et al., 2007, "Dihydroxypyrimidine-4-carboxamides as Novel Potent and Selective HIV Integrase Inhibitors," J. Med. Chem., 50:2225-2239.
Pagare et al., 2016, "1,2,4-triazole—a versatile azole, proves and popular as an antifungal agent," Int. J. Chem. Concepts, 2(2):132-144.
Papke et al., 2017, "Drugging RAS: know the enemy," Science, 355:1158-1163.
Park et al., 2014, "Discovery of thienopyrimidine-based FLT3 inhibitors from the structural modification of known IKKB inhibitors," Bioorg. Med. Chem. Letts., 24(12):2655-2660.
Pearson et al., 2017, "Targeting cellular pathways in glioblastoma multiforme," Signal Transduction and Targeted Therapy, 2(1):e17040.
Pereda, J. et al., 2004, "Effect of Simultaneous Inhibition of TNF-α Production and Xanthine Oxidase in Experimental Acute Pancreatitis," Ann. Surg., 240:108-116.
Pereira et al., 2005, "Synthesis of novel 2,3-condensed thieno[2,3-d ]pyrimidin-4-ones via Appel's salt chemistry," J. Sulfur Chem., 27(1):49-55.
Perspicace et al., 2013, "Design, synthesis and biological evaluation of new classes of thieno[3,2- d]pyrimidinone and thieno[1,2,3]triazine as inhibitor of vascular endothelial growth factor receptor-2 (VEGFR-2)," Eur. J. Med. Chem., 63:765-781.
Perspicace et al., 2013, "Synthesis and biological evaluation of thieno[3,2-d]- pyrimidinones, thieno[3,2-d]pyrimidines and quinazolinones: conformationally restricted 17b-hydroxysteroid dehydrogenase type 2 (17b-HSD2) inhibitors," Molecules, 18(4):4487-4509.
Peti, W. et al., 2013, "Molecular basis of MAP kinase regulation," Protein Sci., 22(12):1698-1710.
Plaskon et al., 2008, "A synthesis of 5-hetaryl-3-(2-hydroxybenzoyl)pyrroles," Tetrahedron, 64(25):5933-5943.
Principi, M. et al., 2013, Fibrogenesis and fibrosis in inflammatory bowel diseases: Good and bad side of same coin?, World J Gastrointest Pathophysiol., 4(4):100-107.
Puneet, P. et al., 2005, "Chemokines in acute respiratory distress syndrome," Am J Physiol Lung Cell Mol Physiol., 288(1):L3-L15.
Qiu et al., 2015, "Potassium hydroxide-promoted transition-metal-free synthesis of 4(3H)-quinazolinones," Monatsh. Chem., 146(8):1343-1347.
Rhee et al., 1999, "Synthesis and biological studies of catechol ether type derivatives as potential phosphodiesterase (PDE) IV inhibitors," Arch. Pharm. Res., 22(2):202-207.
Ried et al., 1968, "New 4-hydroxythienopyrimidines," Angewandte Chemie, 7(2):136.
Ried et al., 1968, "Reactions with imidic acid esters," Justus Liebigs Annalen der Chemie, 713:143-148. (English Abstract Only).
Ried et al., 1968, "Thienopyrimidones," Justus Liebigs Annalen der Chemie, 716:219-221. (English Abstract Only).
Ryabukhin et al., 2007, "Chlorotrimethylsilane-mediated synthesis of 2-ayl-1-chloro-1-heteroarylalkenes," Synthesis, 20:3163-3170.
Sampognaro et al., 2010, "Proline Isosteres in a Series of 2,4-disubstituted pyrrolo[1,2- f][1,2,4]triazine Inhibitors of IGF-1R Kinase and IR Kinase," Bioorg. Med. Chem. Lett., 20(17):5027-5030.
Sanchez et al., 2014, "Microwave-assisted synthesis of potent PDE7 inhibitors containing a thienopyrimidin-4-amine scaffold," Org. Biomol. Chem., 12(24):4233-4242.
Santarpia et al., 2012, "Targeting the MAPK-RAS-RAF signaling pathway in cancer therapy," Expert Opin. Ther. Targets, vol. 16(1):103-119.
Sanz-Garcia, C. et al., 2013, Sterile inflammation in acetaminophen-induced liver injury is mediated by Cot/tpl2, J. Biol. Chem., 288:15342-15351.
Sarker et al., 2015, "First-in-human phase I study of pictilisib (GDC-0941), a potent pan-class I phosphatidylinositol-3-kinase (PI3K) inhibitor, in patients with advanced solid tumors," Clin Cancer Res. 21(1):77-86.
Sasaki, K. et al., 2011, "The role of MAPK pathway in bone and soft tissue tumors," Anticancer Res., 31(2):549-554.
Sasikumar et al., 2010, "A-ring Modifications on the Triazafluorenone Core Structure and Their mGluR1 Antagonist Properties," Bioorg. Med. Chem. Lett., 20(8):2474-2477.
Savino, B. et al., 2014, "ERK-dependent downregulation of the atypical chemokine receptor D6 drives tumor aggressiveness in Kaposi sarcoma," Cancer Immunol Res., 2(7):679-89.

(56) References Cited

OTHER PUBLICATIONS

Schuh, K. et al., 2009, "Inhibition of the MAP kinase ERK protects from lipopolysaccharide-induced lung injury," Biochem. Pharmacol., 77:1827-1834.
Schultze, S. et al., 2012, "PI3K/AKT, Mapk and AMPK signalling: protein kinases in glucose homeostasis," Expert Rev. Mol. Med., 14:e1.
Shishoo et al., 1994, "Synthesis of some tituted-6-phenyl-thieno(3,2-D)pyrimidin-4(3H)-ones and 7-phenyl-thieno[3,2-D]pyrimidin-4(3H)-ones," Indian J. Chem. Sect. B: Organic Chemistry, including Medicinal Chemistry, 33B(5):436-440.
Shutes et al., 2007, "Specificity and mechanism of action of EHT 1864, a novel small molecule inhibitor of Rac family small GTPases," J. Biol. Chem., 282(49):35666-35678.
Smith et al., 2010, "Activating K-Ras mutations outwith 'hotspot' codons in sporadic colorectal tumours—implications for personalised cancer medicine," Br. J. Cancer, 102:693-703.
Smith, R. et al., 2006, "Recent advances in the research and development of RAF kinase inhibitors," Curr Top Med Chem., 6(11):1071-1089.
Snegaroff et al., 2009, "Direct metallation of thienopyrimidines using a mixed lithium-cadmium base and antitumor activity of functionalized derivatives," Org. Biomol. Chem., 7(22):4782-4788.
Souza, R. F. et al., 2002, "Acid exposure activates the mitogen-activated protein kinase pathways in Barrett's esophagus," Gastroenterology, 122:299-307.
Spangler et al., 2009, "Kinetic determination of the GTPase activity of Ras proteins by means of a luminescent terbium complex," Anal. Bioanal. Chem., 394(4):989-996.
Sriskantharajah, S. et al., 2014, "Regulation of experimental autoimmune encephalomyelitis by TPL-2 kinase," J. Immunol., 192:3518-3529.
Stephen et al., 2014, "Dragging Ras back in the ring," Cancer Cell, 25:272-281.
Supuran et al., 2000, "Carbonic anhydrase inhibitors- Part 94. 1,3,4-Thiadiazole-2-sulfonamide derivatives as antitumor agents?," European J. of Medicinal Chemistry, Editions Scientifique, 35(9):867-874.
Supuran et al., 2001, "Carbonic Anhydrase Inhibitors: Sulfonamides as Antitumor Agents?," Bioorganic & Medicinal Chemistry, 9(3):703-714.
Sutherlin et al., 2011, "Discovery of a potent, selective, and orally available class I phosphatidylinositol 3-kinase (PI3K)/mammalian target of rapamycin (mTOR) kinase inhibitor (GDC-0980) for the treatment of cancer," J Med Chem. 54(21):7579-7587.
Svejda B. et al., 2011, "Limitations in small intestinal neuroendocrine tumor therapy by mTor kinase inhibition reflect growth factor-mediated PI3K feedback loop activation via ERK1/2 and AKT," Cancer, 117(18):4141-4154.
Theoclitou et al., 2011, "Discovery of (+)-N-(3-aminopropyl)-N-[1-(5-benzyl-3-methyl-4-oxo-[1,2]thiazolo[5,4-d]pyrimidin-6-yl)-2-methylpropyl]-4-methylbenzamide (AZD4877), a kinesin spindle protein inhibitor and potential anticancer agent," J. Med. Chem., 54(19):6734-6750.
Tominaga et al., 1979, "Synthesis and Reaction of 3, 4-Diaminothiophenes," Yakugaku Zasshi, 99(11):1081-1090. (English Abstract).
Toney et al., 1998, "Antibiotic sensitization using biphenyl tetrazoles as potent inhibitors of Bacteroides fragilis metallo-beta-lactamase," Chem. Biol., 5(4):185-196.
Trujillo, 2011, "MEK inhibitors: a patent review 2008-2010," Expert Opinion on Therapeutic Patents, 21(7):1045-1069.
Tsuboi et al., 2011, "Potent and selective inhibitors of glutathione S-transferase omega 1 that impair cancer drug resistance," J. Am. Chem. Soc., 133(41):16605-16616.
Turkmen et al., 2005, "Carbonic anhydrase inhibitors. Novel sulfanilimide/acetazolamide derivatives obtained by the tail approach and their interaction with the cytosolic isozymes I and II, and the tumor-associated isozyme IX," Bioorganic & Medicinal Chemistry Letters, 15(2):367-372.
Vairaktaris, E. et al., 2007, "Diabetes and oral oncogenesis," Anticancer Res., 27(6B):4185-4193.
Vasan et al., 2010, "Inhibitors of the salicylate synthase (Mbt1) from *Mycobacterium tuberculosis* discovered by high-throughput screening," ChemMedChem, 5(12):2079-2087.
Vigil et al., 2010, "Ras superfamily GEFs and GAPs: validated and tractable targets for cancer therapy?," Nat. Rev. Cancer, 10(12):842-857.
Vlaeminck-Guillem, V. et al., 2014, "SRC: marker or actor in prostate cancer aggressiveness," Front Oncol., 4:222.
Vougioukalaki, M. et al., 2011, "Tpl2 kinase signal transduction in inflammation and cancer," Cancer Lett., 304:80-89.
Vyas et al., 2016, "Pharmacophore and docking-based hierarchical virtual screening for the designing of aldose reductase inhibitors: synthesis and biological evaluation," Med. Chem. Res., 25(4):609-626.
Wang et al., 2005, "Inhibition of tumor cell proliferation by thieno[2,3-d]pyrimidin-4(1H)-one-based analogs," Bioorg. Med. Chem. Lett., 15(16):3763-3766.
Wang et al., 2013, "MicroRNA-302b suppresses cell proliferation by targeting EGFR in human hepatocellular carcinoma SMMC-7721 cells," BMC Cancer, 13:448.
Wei et al., 2015, "An environment-friendly synthesis of 4(3H)-quinazolinones," Toxicol. Environ. Chem., 97(1):2-10.
Welsch, M. E. et al., 2017, "Multivalent Small-Molecule Pan-RAS Inhibitors," Cell, 168:878-889.
Westerlund, 1980, "The synthetic utility of heteroaromatic azido compounds. Part VII. Preparation of some 2-and 4-substituted thieno[3,2-d]pyrimidines," J. Heterocyclic Chem., 17(8):1771-1775.
Wick, G. et al., 2004, "Autoimmune and Inflammatory Mechanisms in Atherosclerosis," Annu. Rev. Immunol. 22, 361-403.
Williams, C., 2006, "Reverse fingerprinting, similarity searching by group fusion and fingerprint bit importance," Mol. Divers., 10(3):311-332.
Williams, B. et al., 2007, "Age-dependent loss of NGF signaling in the rat basal forebrain is due to disrupted MAPK activation," Neurosci. Lett. 413:110-114.
Wong, W. F., 2005, "Inhibitors of the tyrosine kinase signaling cascade for asthma," Curr. Opin. Pharmacol., 5:264-271.
Wu et al., 2015, "MEK1/2 Inhibitors: Molecular Activity and Resistance Mechanisms," Semin Oncol., 42(6):849-862.
Wu et al., 2010, "Cyclooxygenase-2 in tumorigenesis of gastrointestinal cancers: an update on the molecular mechanisms," Cancer Lett., 295(1):7-16.
Xia et al., 2010, "Synthesis and biological activity test of some new five membered heterocycles," Chinese J. of Chemistry, 28(12):2433-2440.
Yamamoto, R. et al., 2009, "B7-H1 expression is regulated by MEK/ERK signaling pathway in anaplastic large cell lymphoma and Hodgkin lymphoma," Cancer Sci., 100(11):2093-2100.
Yang et al., 2014, "Synthesis and biological evaluation of novel thieno[2,3-d]pyrimidine-based FLT3 inhibitors as anti-leukemic agents," Eur. J. Med. Chem., 85:399-407.
Yin, D. et al., 2013, "mi-R-34a functions as a tumor suppressor modulating EGFR in glioblastoma multiforme," Oncogene, 32:1155-1163.
Yurchenko et al., 2010, "Hodgkin's lymphoma: the role of cell surface receptors in regulation of tumor cell fate," Exp Oncol., 32(4):214-223.
Zadorozhny et al., 2008, "Condensed isoquinolines 32. Synthesis of 4H-thieno-[3',2':5,6]-and- [2',3': 5,6]pyrimido-[1,2-b]isoquinolines and 6, 12-dihydro-5H-isoquino-[2,3-a]quinazoline-5,12-dione derivatives," Chem. Heterocycl. Comp., 44(7):845-851.
Zadorozhny et al., 2010, "Synthesis of substituted 4-oxo-3,4-dihydro-thieno[3,4-d]pyrimidines and comparison of their properties with those of positionally isomeric thienopyrimidinones and benzo isosteres," Chem. Heterocycl. Comp., 46(8):991-997.
Zaganjor et al., 2011, "Functions and modulation of MAP kinase pathways," Tocris Bioscience Scientific Review Series, 35, 12 pages.
Zebisch, A. et al., 2007, "Signaling through RAS-RAF-MEK-ERK: from basics to bedside," Curr Med Chem., 14(5):601-623.

(56) References Cited

OTHER PUBLICATIONS

Zenali, M. et al., 2009, "Morphoproteomic confirmation of constitutively activated mTOR, ERK, and NF-kappaB pathways in Ewing family of tumors," Ann Clin Lab Sci., 39(2):160-166.

Zhang, H. Y. et al., 2008, "Differences in activity and phosphorylation of MAPK enzymes in esophageal squamous cells of GERD patients with and without Barrett's esophagus," Am. J. Physiol. Gastrointest. Liver Physiol. 295(3):G470-G478.

Zhao et al., 2014, "Mechanisms and therapeutic advances in the management of endocrine-resistant breast cancer," World J Clin Oncol., 5(3):248-262.

Zhou et al., 2015, "Larynx carcinoma regulates tumor-associated macrophages through PLGF signaling," Sci Rep., 5:10071.

Zhu et al., 2016, "In-Water Synthesis of Quinazolinones from 1,1-Dichloro-2-nitroethene and Anthranilamides," Synlett, 27(14):2167-2170.

COMPOUNDS FOR THE TREATMENT OF CANCER AND INFLAMMATORY DISEASE

This application is a continuation application of U.S. application Ser. No. 17/023,266, filed Sep. 16, 2020, now U.S. Pat. No. 11,560,390, which is further a divisional application of U.S. application Ser. No. 16/246,027, filed Jan. 11, 2019, now U.S. Pat. No. 10,870,657, which is further a continuation of U.S. application Ser. No. 15/387,349, filed Dec. 21, 2016, now U.S. Pat. No. 10,221,191, and which further claims the benefit of U.S. Provisional Application No. 62/271,185, filed Dec. 22, 2015. The foregoing related applications, in their entirety, are incorporated by reference.

1. FIELD

Provided herein are methods and compositions for treating cancer and inflammatory disease using the compounds described herein.

2. BACKGROUND

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., Immunology, 17.1-17.12 (3rd ed., Mosby, St. Louis, Mo., 1993).

There is an enormous variety of cancers which are described in detail in the medical literature. Examples include cancer of the lung, colon, rectum, pancreatic, prostate, breast, brain, and intestine. The incidence of cancer continues to climb as the general population ages, as new cancers develop, and as susceptible populations grow. A tremendous demand therefore exists for new methods and compositions that can be used to treat patients with cancer.

Solid Tumors

Over 85% of human cancers are solid tumors, including carcinomas, sarcomas and lymphomas. Jain, et al. *Int J Pharm Pharm Sci*, 2011, Vol 3, Suppl 5, 45-51. Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non small-cell lung carcinoma (NSCLC) and carcinoma of unknown primary.

The effectiveness of cancer therapy in solid tumors depends on adequate delivery of the therapeutic agent to tumor cells. Inadequate delivery would result in residual tumor cells, which in turn would lead to regrowth of tumors and possibly development of resistant cells. In addition, the long-standing problem of chemotherapy is the lack of tumor-specific treatments. Cancer chemotherapeutic agents are often administered systemically. Following a systemic administration, drug delivery to cells in solid tumors involves three processes, i.e., transport within a vessel (e.g., blood circulation), transport across vasculature walls into surrounding tissues, and transport through interstitial space within a tumor. These processes are determined by the physicochemical properties of a drug or particle (e.g., molecular or particle size, diffusivity, drug binding to cellular macromolecules) and the biologic properties of a tumor (e.g., tumor vasculature, extracellular matrix components, interstitial fluid pressure (IFP), tumor cell density, tissue structure and composition). Cancer drug delivery is no longer simply wrapping the drug in new formulations for different routes of delivery. Nanotechnology, polymer chemistry and electronic engineering technologies are being brought for developing novel methods of drug delivery. Various stages of tumor development can be explained as follows:

a) Tumor evolution commences when a cell within a normal population sustains a genetic mutation that expands its tendency to proliferate when it would normally rest.

b) Genetically altered cells and their offspring continue to appear normal, but they reproduce excessively and lead to a condition termed to as hyperplasia. After some time (months or years) one in a million of these cells sustain additional mutation with subsequent loss of control of cell growth.

c) The offspring of these cells not only proliferate excessively but also appear abnormal in shape and in orientation. The tissue is now said to exhibit a condition termed to as dysplasia. After some time, a further mutation that alters cell behavior results.

d) The influenced and genetically altered cells turn still more abnormal in growth and appearance. If the tumor mass does not invade through any boundaries between tissues, it is termed as an in situ tumor. This tumor may stay contained indefinitely, however, some cells may acquire additional mutations.

e) A malignant or invasive tumor results if the genetic changes allow the tumor mass to initiate invading underlying tissue and to cast off cells into the blood or lymph. The defector cells may install new tumors loci (metastases) throughout the body.

Metastases represent the end products of a multistep cell-biological process termed the invasion-metastasis cascade, which involves dissemination of cancer cells to anatomically distant organ sites and their subsequent adaptation to foreign tissue microenvironments. Each of these events is driven by the acquisition of genetic and/or epigenetic alterations within tumor cells and the co-option of nonneoplastic stromal cells, which together endow incipient metastatic cells with traits needed to generate macroscopic metastases. Volastyan, S., et al., *Cell*, 2011, vol. 147, 275-292.

Whereas surgical resection and adjuvant therapy can cure well-confined primary tumors, metastatic disease is largely incurable because of its systemic nature and the resistance of disseminated tumor cells to existing therapeutic agents. This explains why >90% of mortality from cancer is attributable to metastases, not the primary tumors from which these malignant lesions arise.

Carcinomas are a type of cancer that develops from epithelial cells. Specifically, a carcinoma is a cancer that begins in a tissue that lines the inner or outer surfaces of the body, and that generally arises from cells originating in the endodermal or ectodermal germ layer during embryogenesis. The term carcinoma has also come to encompass malignant tumors composed of transformed cells whose origin or developmental lineage is unknown (see cancer of unknown primary origin (CUP)), but that possess certain specific molecular, cellular, and histological characteristics typical of epithelial cells. This may include the production of one or more forms of cytokeratin or other intermediate filaments, intercellular bridge structures, keratin pearls, and/or tissue architectural motifs such as stratification or pseudo-stratification. Common malignancies, such as breast, colon, and lung cancer, are almost always carcinoma. Other types of carcinomas include squamous-cell carcinomas (oral cancers), lung cancers, breast (ductal) carcinoma, prostate (adenocarcinoma), colon and rectum (adenocarcinoma or squamous cell carcinoma), pancreatic (adenocarcinoma), ovarian, hepatocellular and renal cell carcinoma.

A sarcoma is a cancer that arises from transformed cells of mesenchymal origin. Thus, malignant tumors made of cancellous bone, cartilage, fat, muscle, vascular, or hematopoietic tissues are, by definition, considered sarcomas. Sarcomas occur much less frequently in humans than carcinomas. Types of sarcomas include, for example, osteosarcoma, chondrosarcoma, liposarcoma, and leiomyosarcoma.

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., CA Cancer J Clin 2007; 57(1):43-66. The probability of developing NHL increases with age and the incidence of NHL in the elderly has been steadily increasing in the past decade, causing concern with the aging trend of the US population. Id. Clarke C A, et al., Cancer 2002; 94(7):2015-2023.

Diffuse large B-cell lymphoma (DLBCL) accounts for approximately one third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., Blood 2001, 98:3066-3073. Absolute lymphocyte count (ALC) has been shown to be a prognostic factor in follicular non Hodgkin's lymphoma and recent results have suggested that ALC at diagnosis is an important prognostic factor in diffuse large B-cell lymphoma. See D. Kim et al., Journal of Clinical Oncology, 2007 ASCO Annual Meeting Proceedings Part I. Vol 25, No. 18S (June 20 Supplement), 2007: 8082.

Hematological Cancers

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. The Merck Manual, 944-952 (17th ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. The Merck Manual, 946-949 (17th ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). The Merck Manual, 949-952 (17th ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

In addition to the acute and chronic categorization, neoplasms are also categorized based upon the cells giving rise to such disorder into precursor or peripheral. Precursor neoplasms include ALLs and lymphoblastic lymphomas and occur in lymphocytes before they have differentiated into either a T- or B cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843 1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

The incidence of cancer continues to climb as the general population ages, as new cancers develop, and as susceptible populations grow. A tremendous demand therefore exists for new methods, treatments and compositions that can be used to treat patients with cancer.

The role of mitogen-activated protein kinase (MAPK), such as MAPK1/2 (ERK1/2), signaling in the development of cancer has been studied extensively. The "MAPK pathway," or the RAS-RAF-MEK-MAPK/ERK pathway, involves signaling and phosphorylation that plays a key role in regulation of cell growth differentiation, proliferation, apoptosis and migration functions. MAPKs play an important role in the transmission of extracellular signals into intracellular responses. Activation of MAPK results from a three-kinase cascade consisting of a MAPK kinase kinase (MAPK3)(e.g., Raf, MLK, TAK) which phosphorylates and activates a MAPK kinase (e.g., MEK), which then phosphorylates and increases the activity of one or more MAPKs (e.g., ERK1/2). MAPK3s are regulated by growth factor dependent Ras proteins. Activated MAPKs phosphorylate various intracellular targets. Dhillon, et al., 2007, *Oncogene*, vol. 26, 3279-3290.

Dysregulation or abnormal activation of the MAPK pathway has been implicated in human cancers. Therefore, inhibitors targeting the MAPK pathway have been the subject of intense study in recent years. Santarpia, et al., 2012, *Expert Opin. Ther. Targets*, vol. 16(1), 103-119); Zaganjor, et al., 2011, *Tocris Reviews*, no. 35 (available at http://www.komabiotech.co.kr/pdf/mapk_signaling_review.pdf).

It has also been shown that mutations in genes encoding receptors (e.g., EGFR) and signal transducers (e.g., RAS) upstream of MAPK, as well as downstream kinases (e.g., BRAF) are implicated in human cancers. Burotto, et al., 2014, Cancer, 3446-3456. Thus, the MAPK pathway presents a logical target for anticancer drug development.

Methods of Treating Cancer

Current cancer therapy may involve surgery, chemotherapy, hormonal therapy and/or radiation treatment to eradicate neoplastic cells in a patient (see, for example, Stockdale, 1998, Medicine, vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: The Pharmacological Basis of Therapeutics, Tenth Ed. (McGraw Hill, New York).

Despite availability of a variety of chemotherapeutic agents, chemotherapy has many drawbacks. Stockdale, Medicine, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. While targeted therapy with chemotherapeutic agents, in particular small molecules, may address some of these issues, they are not a panacea and do not resolve all such issues. See, e.g., http://www.cancer.org/treatmentsandsideeffects/treatmenttypes/targetedtherapy/targeted-therapy-toc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

Thus, there exists a significant need for compounds, compositions and methods for treating, preventing and managing cancer.

Inflammatory Disease

In addition to ERK1/2, the MAPKs ERK5, c-Jun N-terminal kinases (JNKs) and p38 isoforms (p38α, p38β, p38γ and p38δ) have been shown to be implicated in inflammatory response. Huang, et al. 2010, *Protein Cell*, 1(3), 218-226. MAPKs have been shown to play important roles in embryonic development and adult tissue homeostasis, and in particular chronic inflammation and inflammation-associated cancer development.

JNKs (also referred to as stress-activated kinases (SAPKs)) are activated by a MAPK3 cascade via MEK4 and MEK7. Manzoor, et al., 2012, *J. Bacter. Virology*, vol. 42(3), 189-195. JNKs regulate cell proliferation and apoptosis by activating various targets, including the AP-1 transcript factors. AP-1s are activated by, e.g., cytokines, stress, growth factors and infections, and are involved in managing proliferation, differentiation and apoptosis.

Therefore, compounds that inhibit MAPKs are expected to be effective in treatment of inflammatory conditions.

3. SUMMARY

Provided herein are compounds which inhibit phosphorylation of mitogen-activated protein kinases (MAPKs), cellular proliferation, secretion of IL-6 and TNF-α cytokines, and methods and compositions for treating cancer and inflammatory diseases using such compounds. In one embodiment, the compounds are inhibitors of MAPK1/2 phosphorylation. As discussed above, phosphorylation of MAPKs, in particular MAPK1/2, is known to be key in the development of many cancers and in the inflammatory response.

In one embodiment, the compounds provided herein are active in a MAPK cellular assay that measures phosphorylation inhibition and in cellular proliferation assays described herein.

4. DETAILED DESCRIPTION

4.1. Definitions

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include, but are not limited to, salts, esters, enol ethers, enol esters, acetals, ketals, orthoesters, hemiacetals, hemiketals, acids, bases, clathrates, solvates or hydrates thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating inflammation.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the $IC_{50}$ refers to an amount, concentration or dosage of a particular test compound that achieves a 50% inhibition of a maximal response in an assay that measures such response.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter enzymatic and biological activities of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as chiral reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenyl and hexynyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight or branched aliphatic hydrocarbon group having, inserted in the hydrocarbon chain one or more oxygen, sulfur, including $S(=O)$ and $S(=O)_2$ groups, or substituted or unsubstituted nitrogen atoms, including —NR— and —N⁺RR— groups, where the nitrogen substituent(s) is(are) alkyl, aryl, aralkyl, heteroaryl, heteroaralkyl, $S(=O)_2R'$ or COR', where R' is alkyl, aryl, aralkyl, heteroaryl, heteroaralkyl, OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond. In some embodiments, the cycloalkyl ring is unsaturated or partially saturated.

As used herein, "carbocyclic" refers to a mono- or multicyclic ring system, in which all of the atoms composing the ring are carbon atoms, such as benzene or cyclopropane. In some embodiments, the carbocyclic ring is unsaturated or partially saturated.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, in one embodiment selected from Q.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "heterocyclyl" or "heterocyclic" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, amidino, sulfonyl or the nitrogen may be quaternized to form an ammonium group where the substituents are selected as above. In some embodiments, the heterocyclyl ring is saturated. In some embodiments, the heterocyclyl ring is unsaturated or partially saturated.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, in one embodiment selected from Q.

As used herein, "aralkyl" or "arylalkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO in which R is a haloalkyl group.

As used herein, "carboxy" refers to a divalent radical, —C(O)O—.

As used herein, "aminocarbonyl" refers to —C(O)NH₂.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR-'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

Where substitution is not specified (e.g., "aryl"), there may be one or more substituents present. For example, "aryl" may include a "substituted aryl" group. In some embodiments, each alkyl, alkenyl, alkynyl, cycloalkyl, cycloalkenyl, cycloalkynyl, aryl, aralkyl, heteroaryl, and heterocyclyl is optionally substituted with one or more substituents, in one embodiment one, two, three or four substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl. In some embodiments, two Q substituents together with the atoms to which they are attached, may form a fused ring system.

As used herein, the abbreviations for any protective groups, amino acids and other compounds, are, unless indicated otherwise, in accord with their common usage, recognized abbreviations, the IUPAC-IUB Commission on Biochemical Nomenclature (see, (1972) Biochem. 11:942-944), or the IUPAC Nomenclature of Organic Chemistry (see, Favre H A and Powell W H, Nomenclature of Organic Chemistry: IUPAC Recommendations and Preferred Names 2013, Cambridge, UK: The Royal Society of Chemistry, 2013: Print ISBN 978-0-85404-182-4, PDF eISBN 978-1-84973-306-9, DOI 10.1039/9781849733069; Nomenclature of Organic Chemistry, Sections A, B, C, D, E, F, and H, Pergamon Press, Oxford, 1979. Copyright 1979 IUPAC; and A Guide to IUPAC Nomenclature of Organic Compounds (Recommendations 1993), 1993, Blackwell Scientific publications, Copyright 1993 IUPAC).

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. A therapeutically effective amount of a compound provided herein can be administered in one dose (i.e., a single dose administration) or divided and administered over time (i.e., continuous administration or multiple sub-dose administration). Single dose administration, continuous administration, or multiple sub-dose administration can be repeated, for example, to maintain the level of the compound in a biological molecule (e.g., a protein, enzyme, RNA, or DNA), cell, tissue, system, animal, or human.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; Loyd et al., Eds.; The Pharmaceutical Press, 2012; *Handbook of Pharmaceutical Excipients,* 7th ed.; Rowe et al., Eds.; The Pharmaceutical Press, 2012; *Handbook of Pharmaceutical Additives,* 3rd ed.; Ash and Ash Eds.; Synapse Information Resources, Inc., 2007; *Pharmaceutical Preformulation and Formulation,* 2nd ed.; Gibson Ed.; CRC Press LLC, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%1, 5%1, 0%, 9%, 8%, 7%, 6%, 5%, 4%, 3%, 2%, 1%, 0.5%, or 0.05% of a given value or range.

The term "percent by weight" or "% by weight" refers to the weight of a specified component (e.g., an active compound or excipient) in a composition (e.g., a pharmaceutical composition) as a percentage of the total weight of the composition. Thus, the sum of the weight percentages of all the components in a composition is 100%.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen (H), deuterium ($^2$H), tritium (H), carbon-11 ($^{11}$C), carbon-12 ($^{12}$C), carbon-13 ($^{13}$C), carbon-14 ($^{14}$C), nitrogen-13 ($^{13}$N), nitrogen-14 (14N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I) iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium (3H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$p), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium. In some embodiments, a pharmaceutically acceptable derivative of a compound is an isotopic variant.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable salt thereof; or a pharmaceutically acceptable solvate thereof" has the same meaning as the phrase "an isotopic variant of the compound referenced therein; or a pharmaceutically acceptable salt of the compound referenced therein; or a pharmaceutically acceptable salt of an isotopic variant of the compound referenced therein; or a pharmaceutically acceptable solvate of the compound referenced therein; or a pharmaceutically acceptable solvate of an isotopic variant of the compound referenced therein; or a pharmaceutically acceptable solvate of a pharmaceutically acceptable salt of the compound referenced therein; or a pharmaceutically acceptable solvate of a pharmaceutically acceptable salt of an isotopic variant of the compound referenced therein or its variant or its variant."

4.2. Compounds for Use in Compositions and Methods

Provided herein are compounds which inhibit phosphorylation of MAPK, in particular MAPK1/2, cellular proliferation, secretion of IL-6 and TNF-α cytokines, which are therefore useful in compositions and methods of treating cancer and inflammatory diseases.

In certain embodiments, the compounds for use in the compositions and methods provided herein are of Formula I:

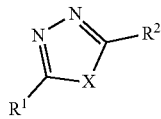

Formula I or pharmaceutically acceptable derivatives thereof,
wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

X is O, S or $NR^5$.

In another embodiment, the compound of Formula I is a compound of Formula Ia:

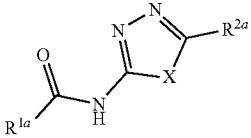

Formula Ia or pharmaceutically acceptable derivatives thereof,
wherein $R^{1a}$ is selected from the group consisting of H, alkyl, alkenyl, alkynyl, aryl, cycloalkyl, heterocyclyl, heteroaryl, $OR^3$, and $NR^6R^7$;
wherein $R^{2a}$ is selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

X is O, S or $NR^5$.

In another embodiment, the compound of Formula I is a compound of Formula Ia or pharmaceutically acceptable derivatives thereof, wherein:

$R^{1a}$ is selected from the group consisting of H, phenyl, pyridinyl, or from one of the following:

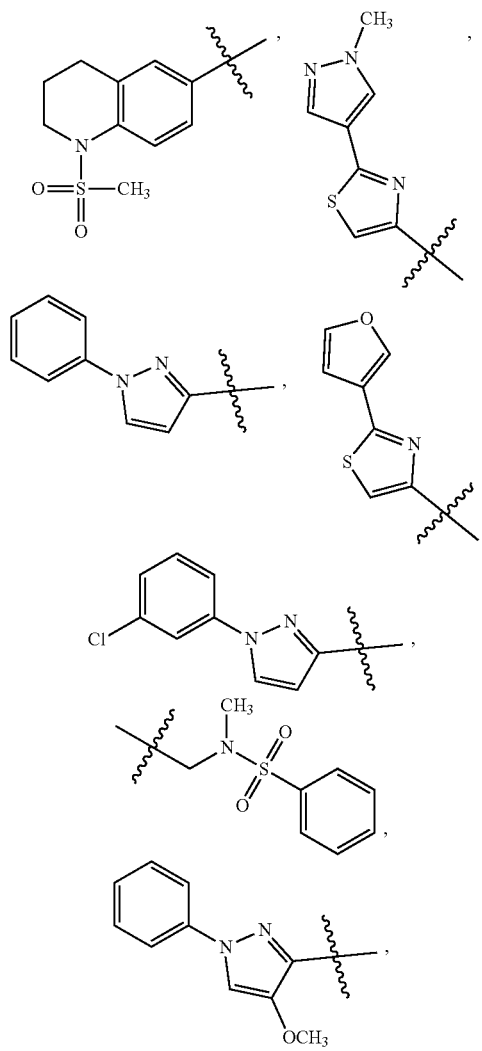

-continued
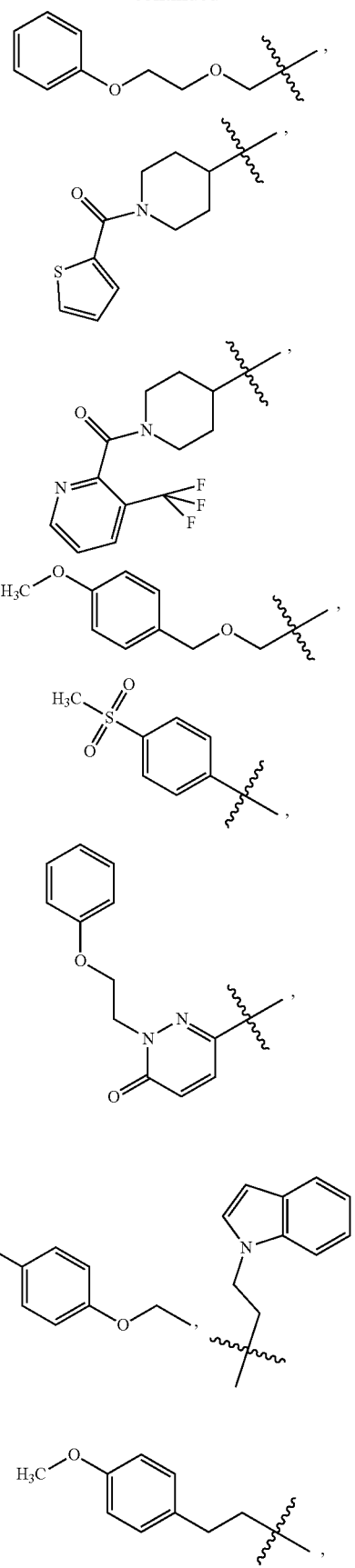
-continued
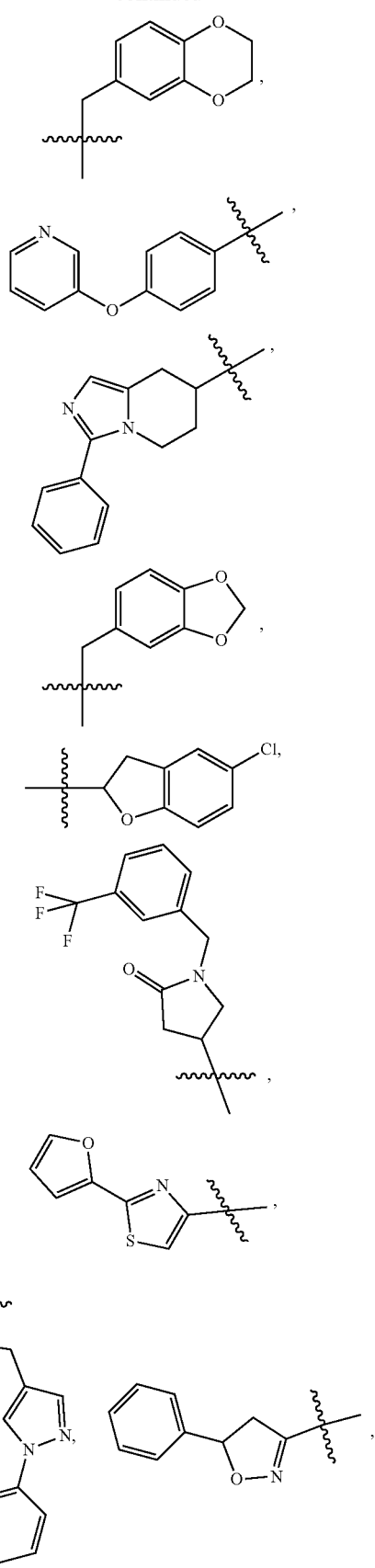

-continued
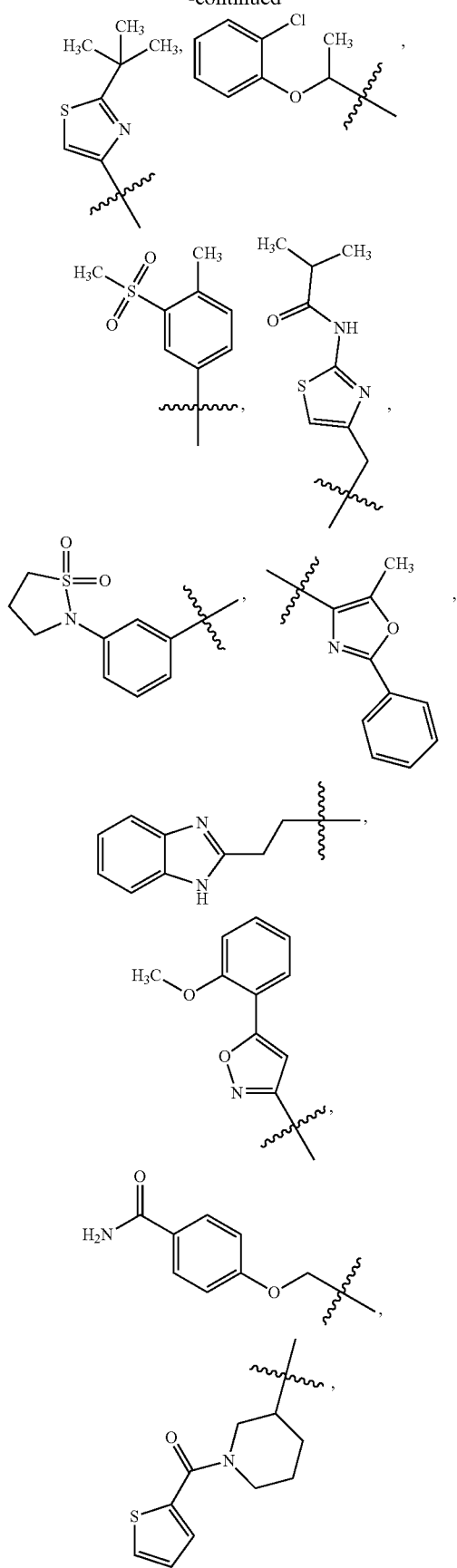
-continued
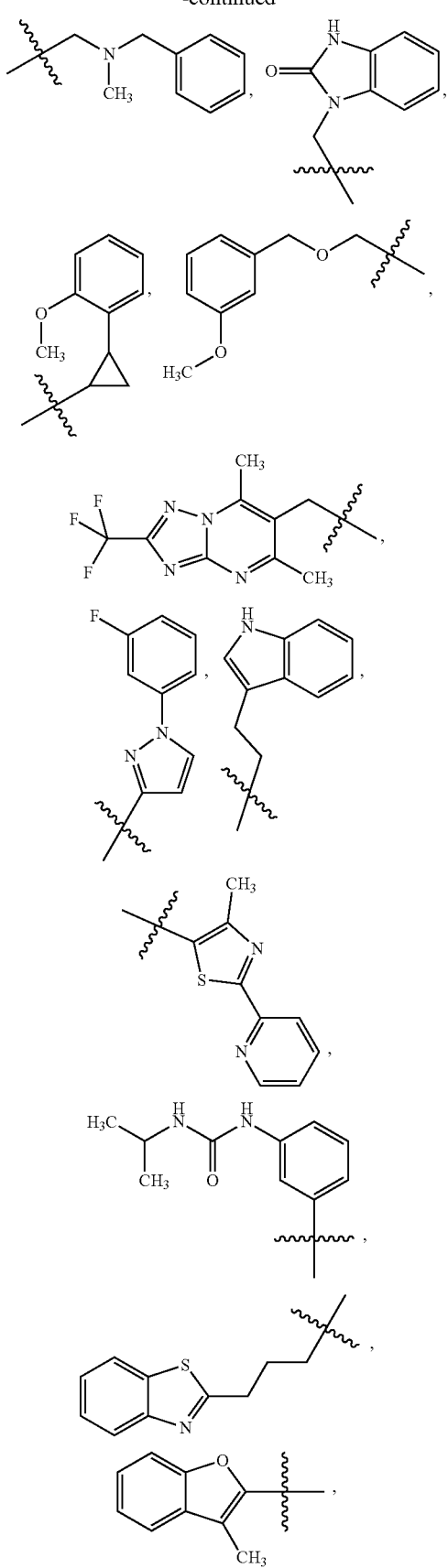

21
-continued
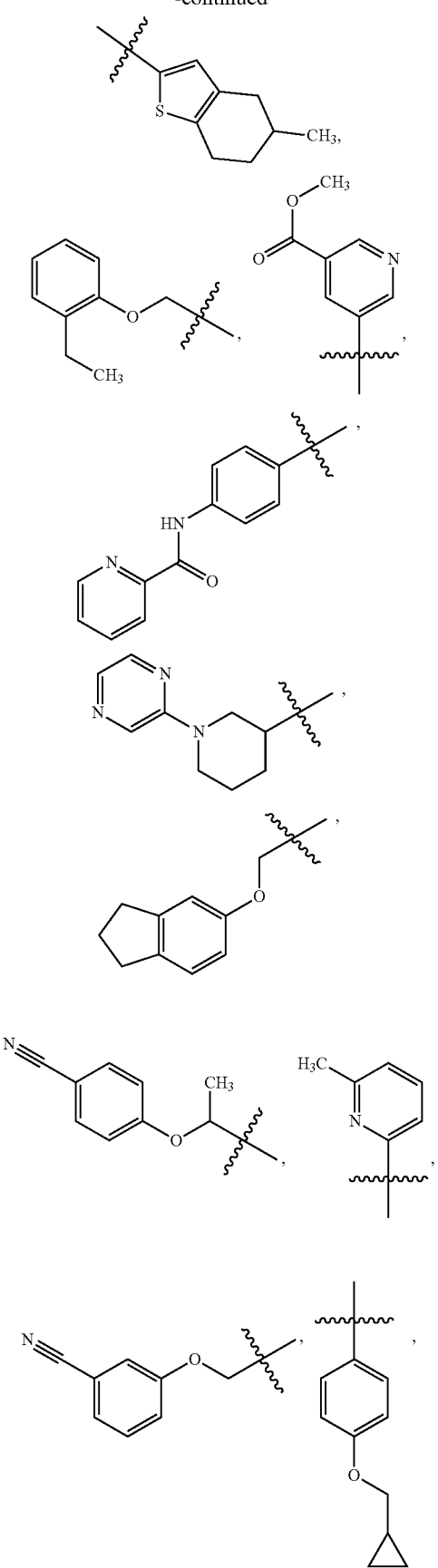
22
-continued
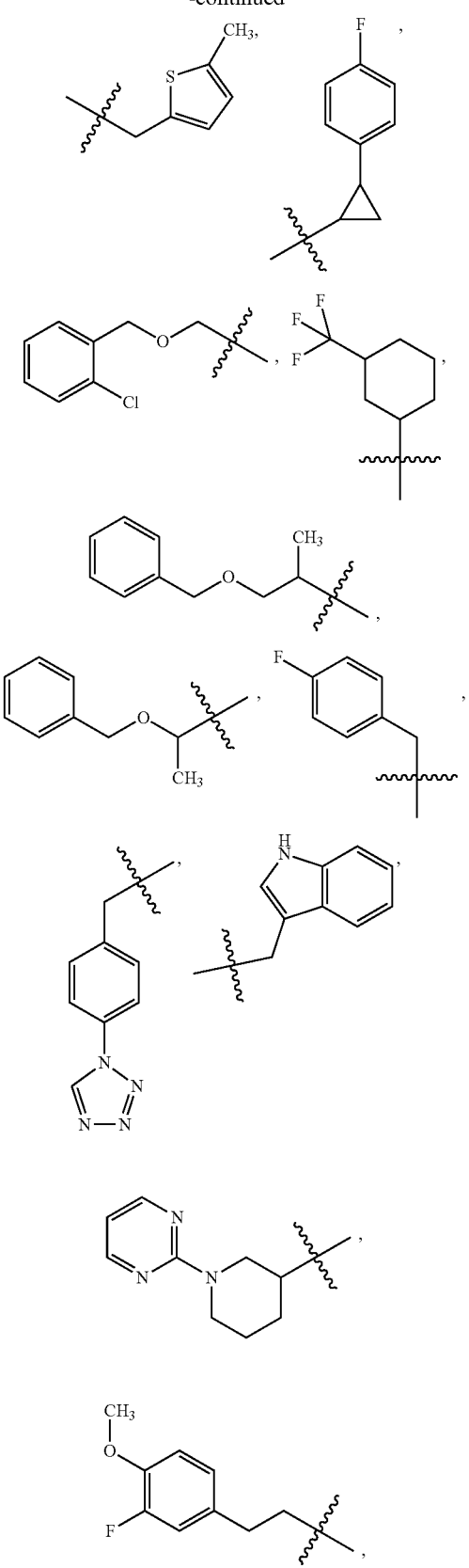

-continued
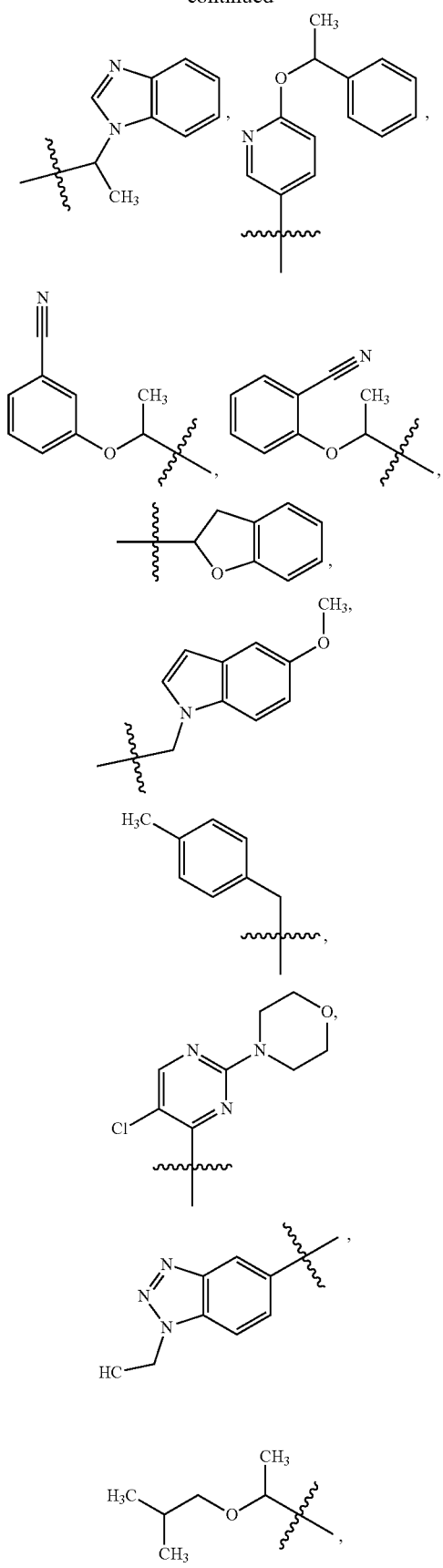
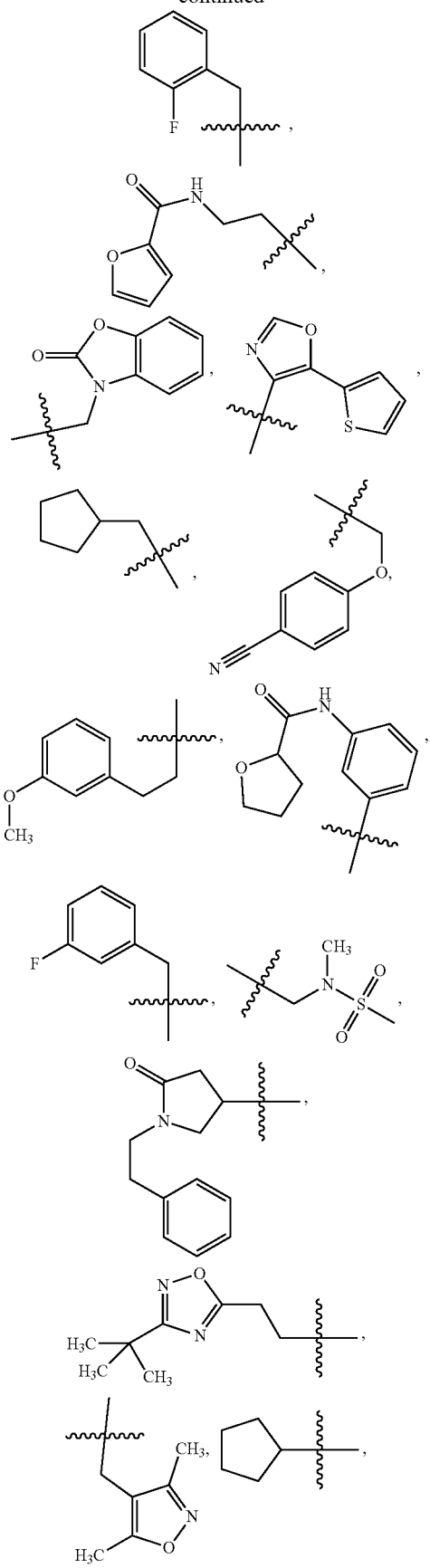

-continued
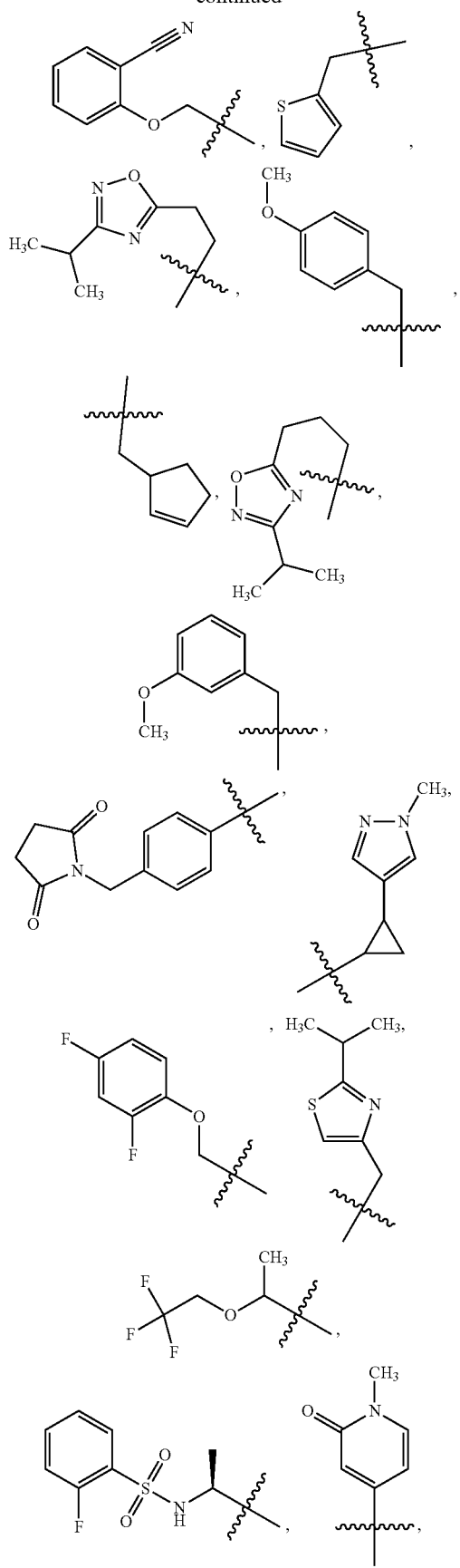
-continued
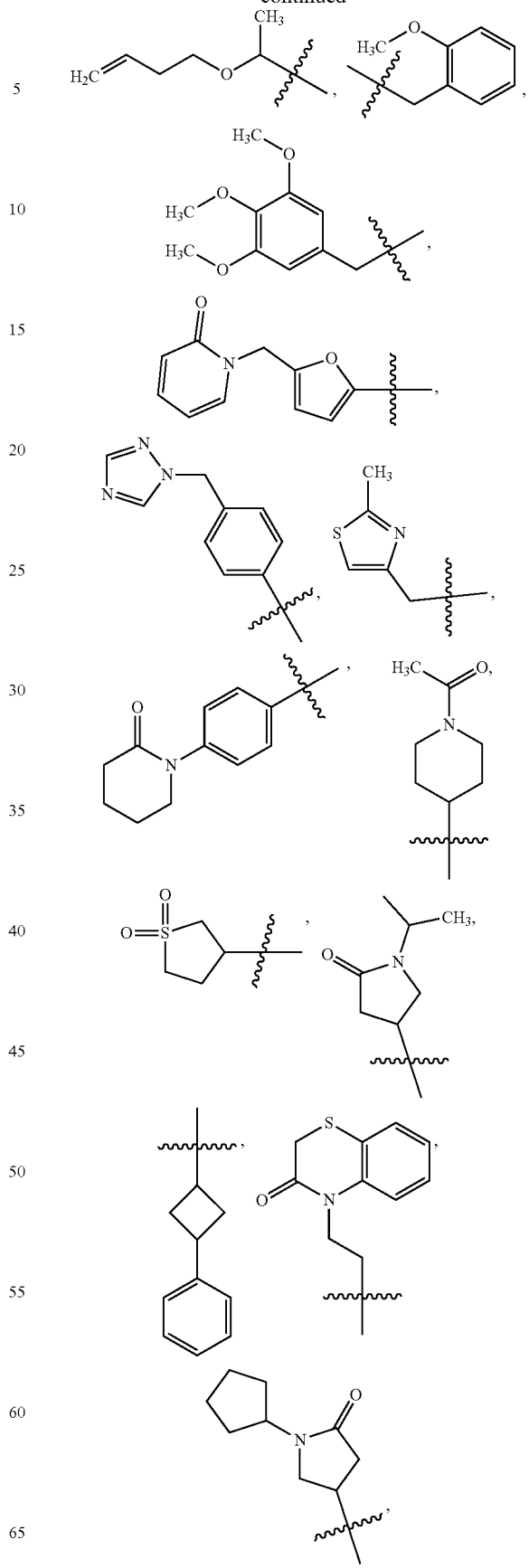

-continued
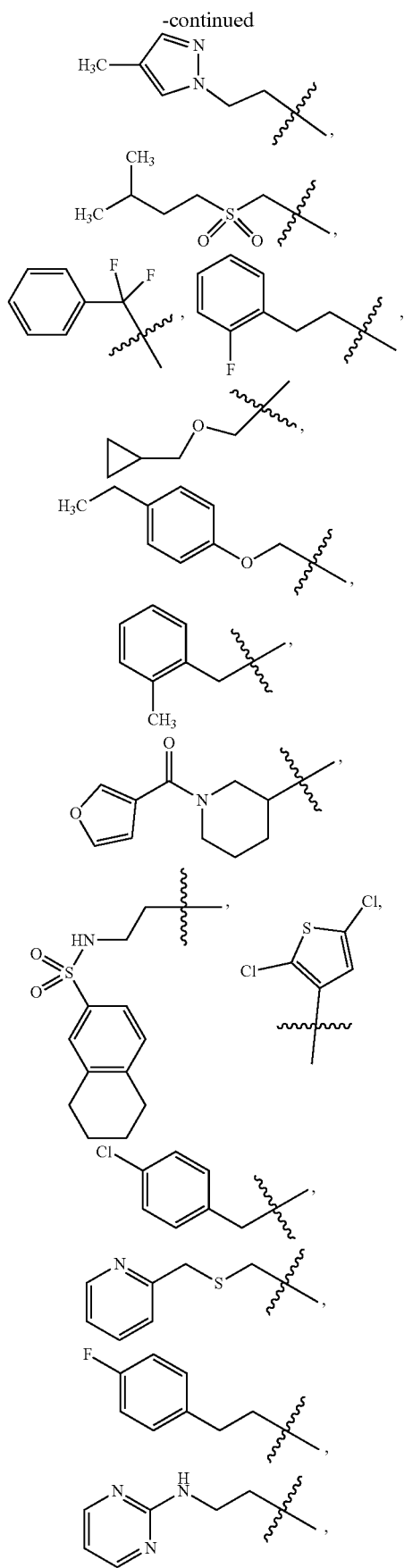
-continued
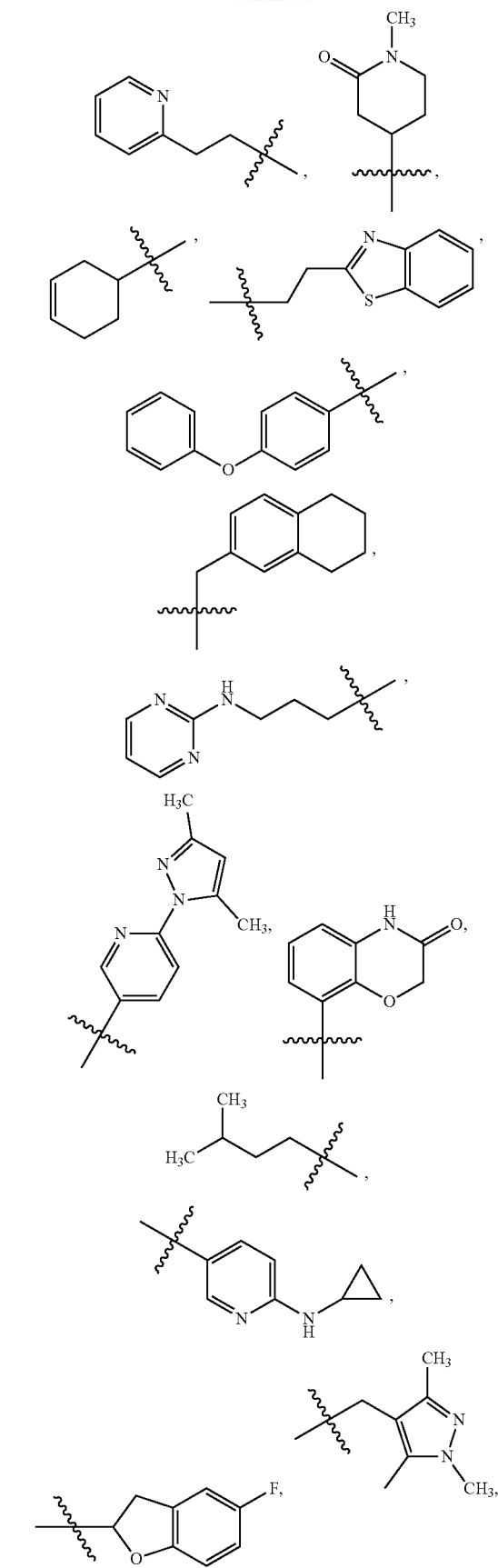

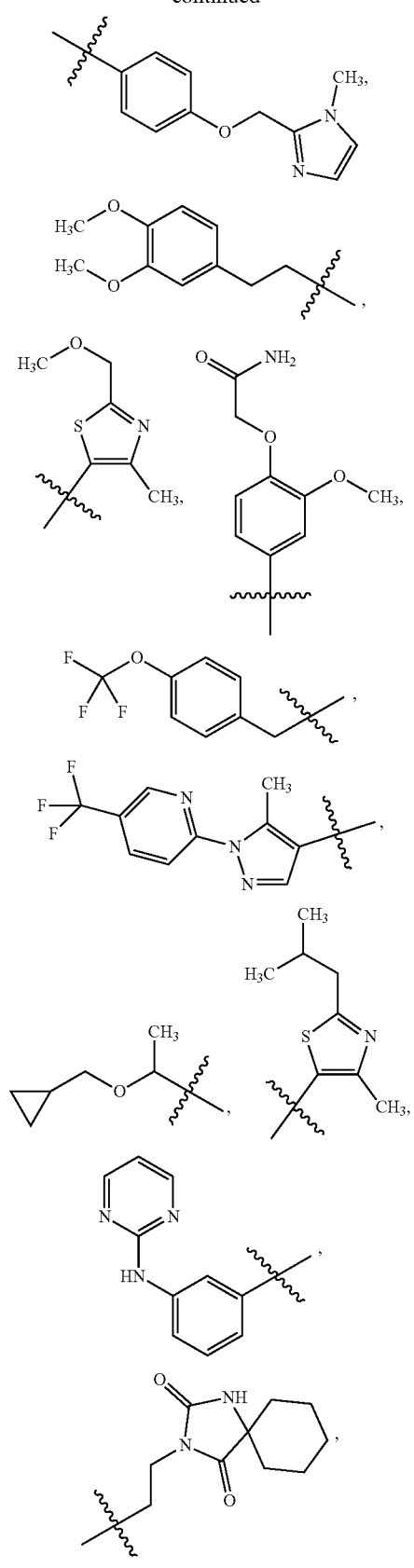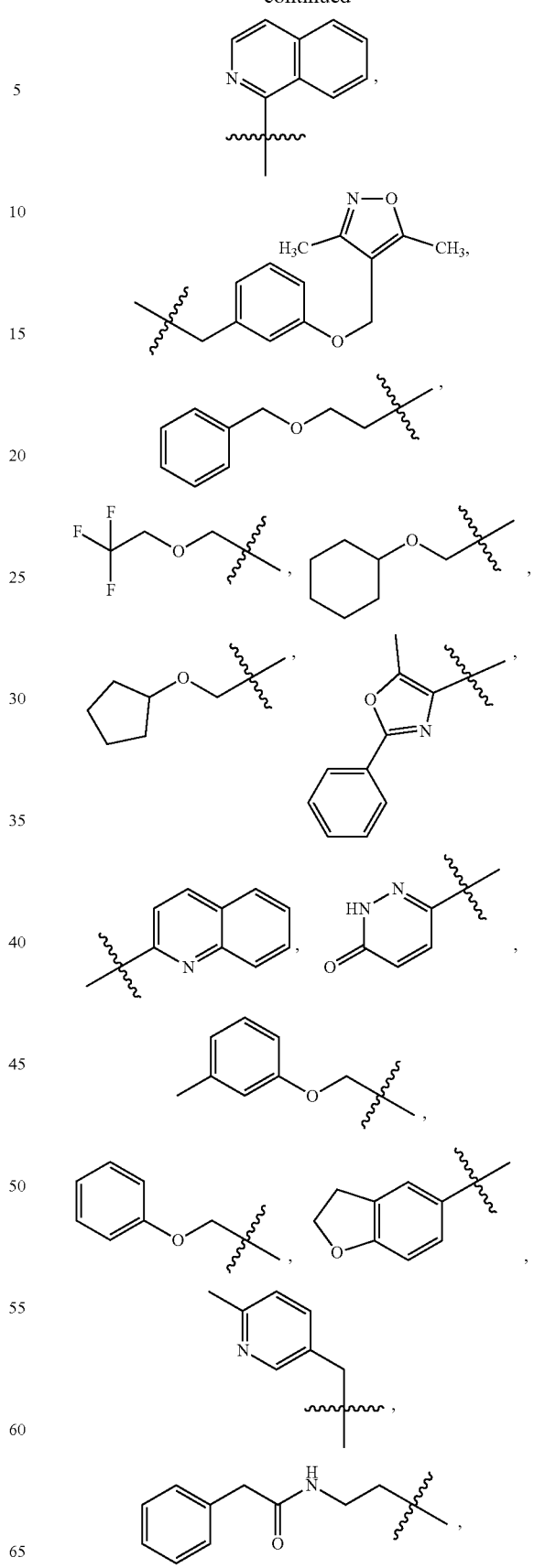

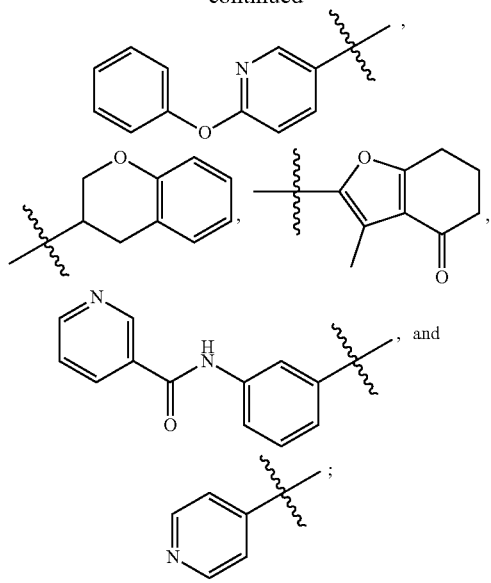
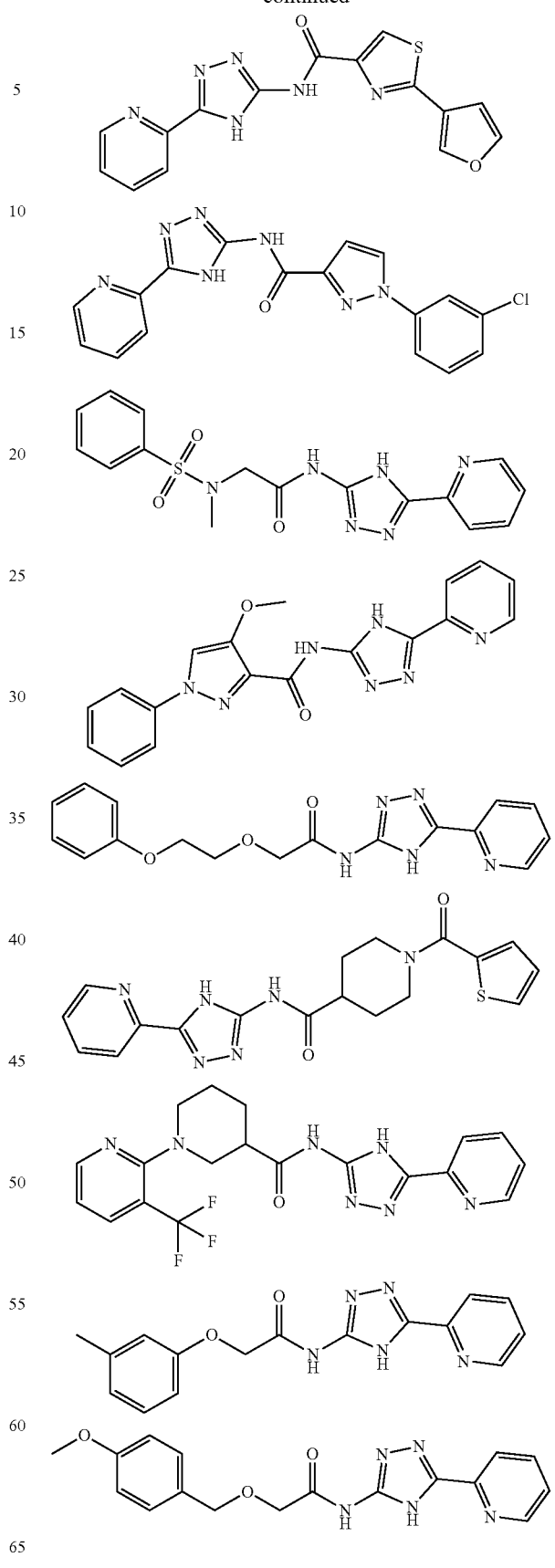
$R^{2a}$ is aryl or heteroaryl; and X is NH or S.
In one embodiment, the compound of Formula Ia is:
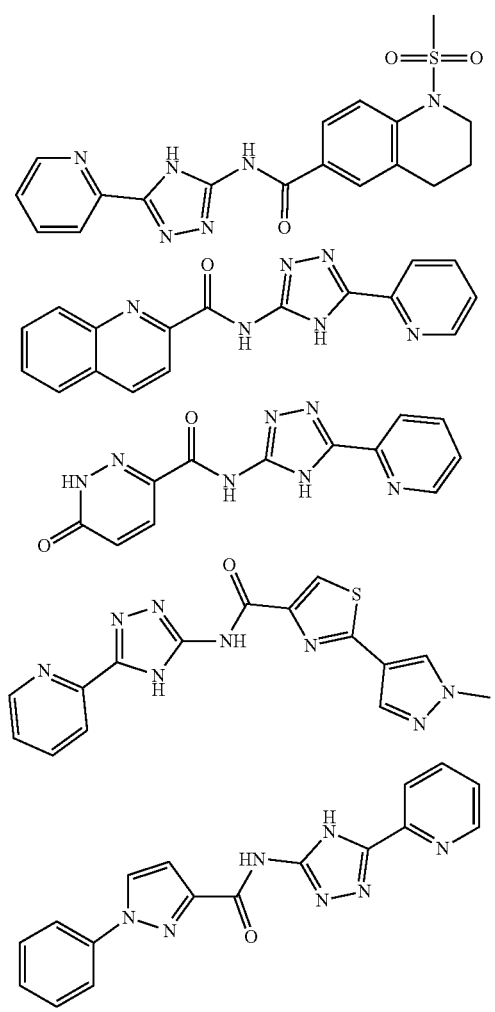

33
-continued
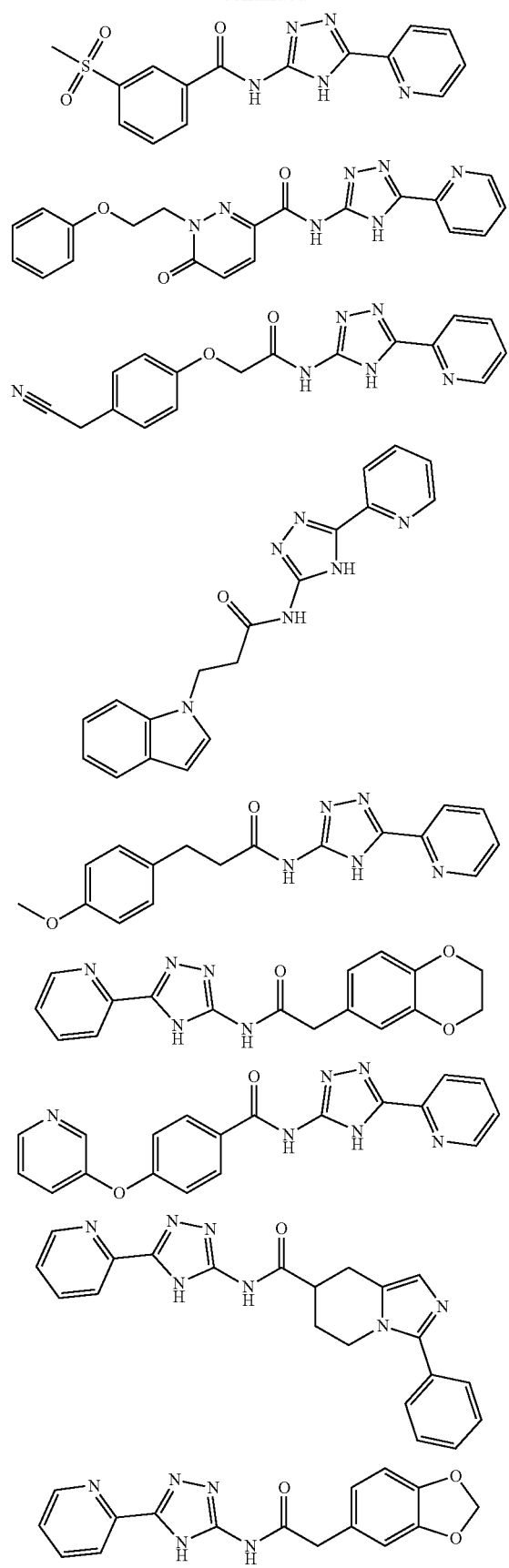
34
-continued
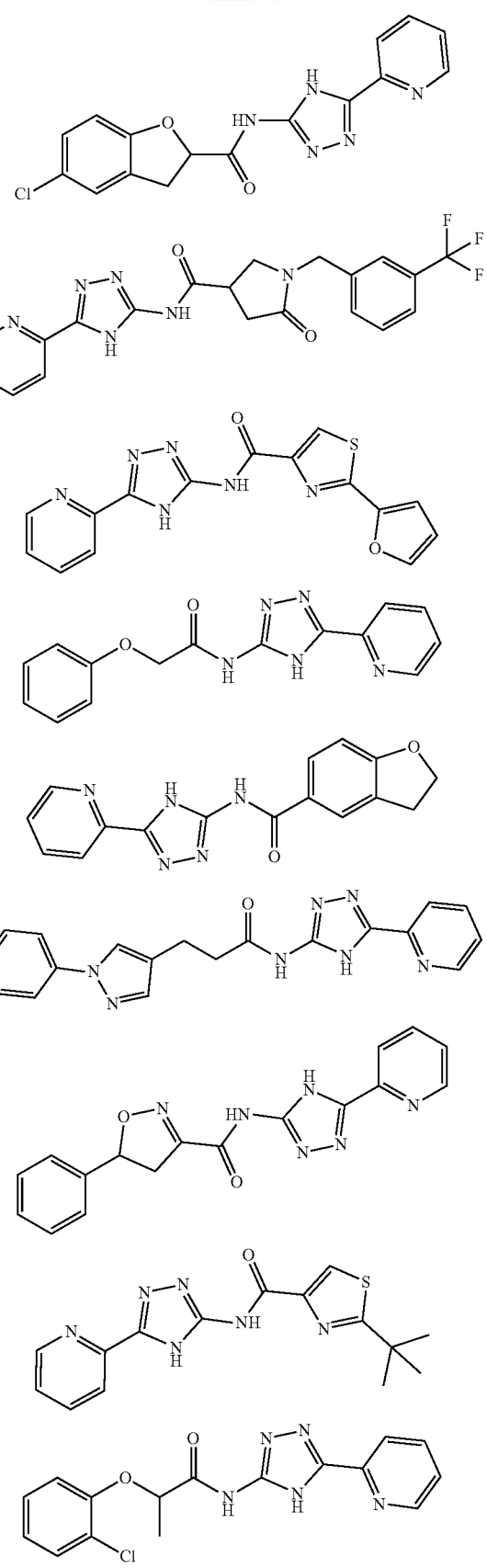

35
-continued
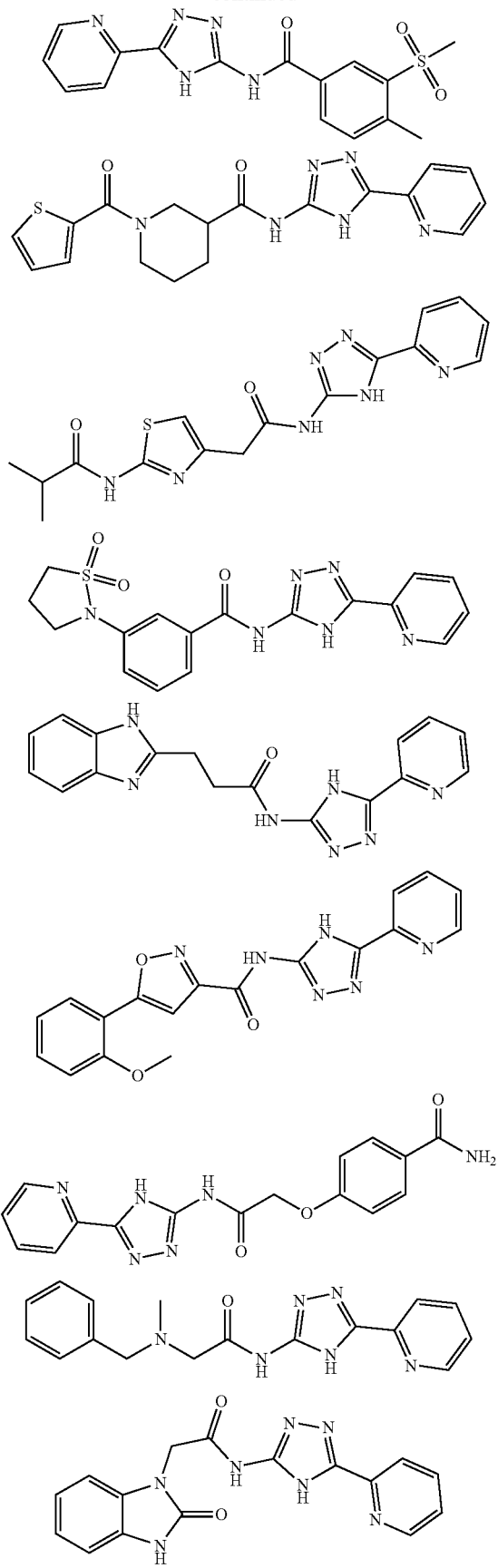
36
-continued
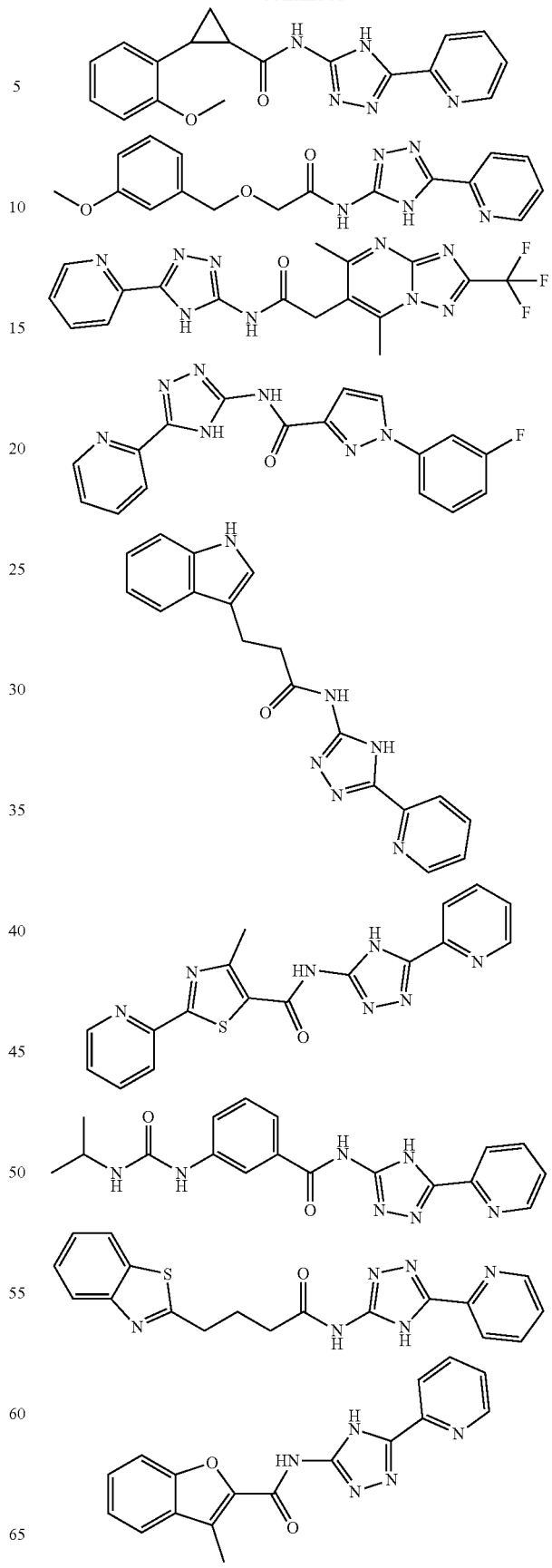

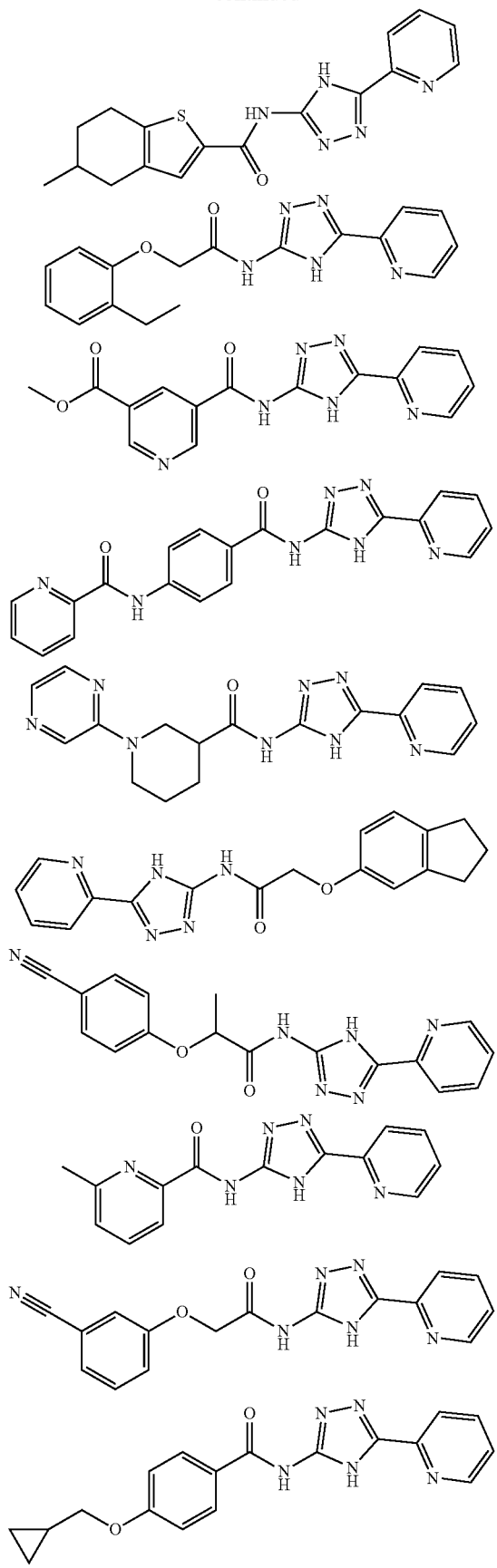
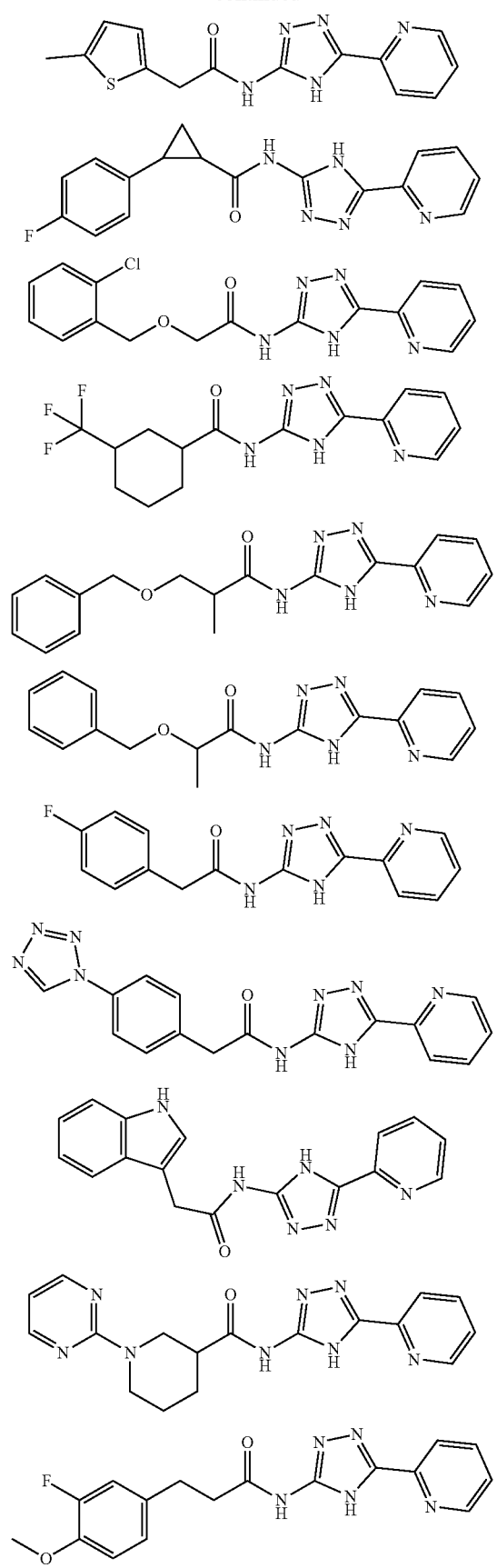

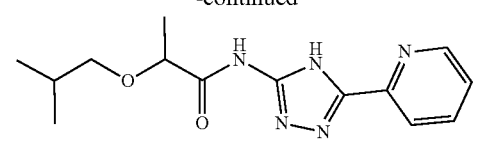

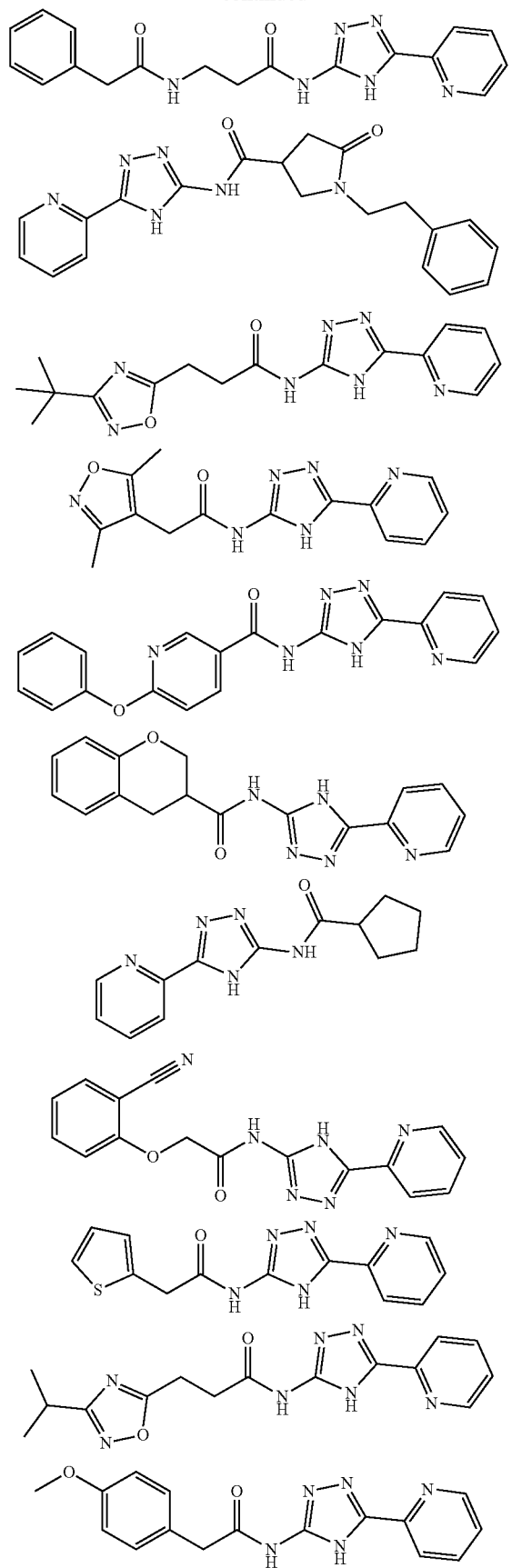
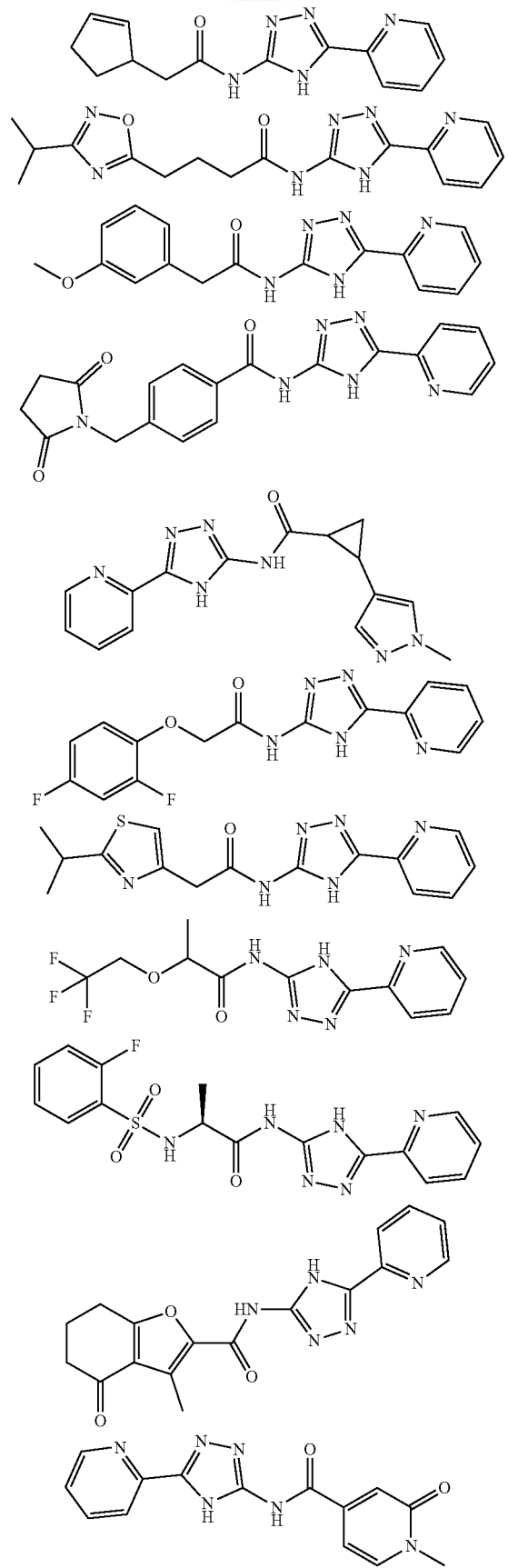

-continued
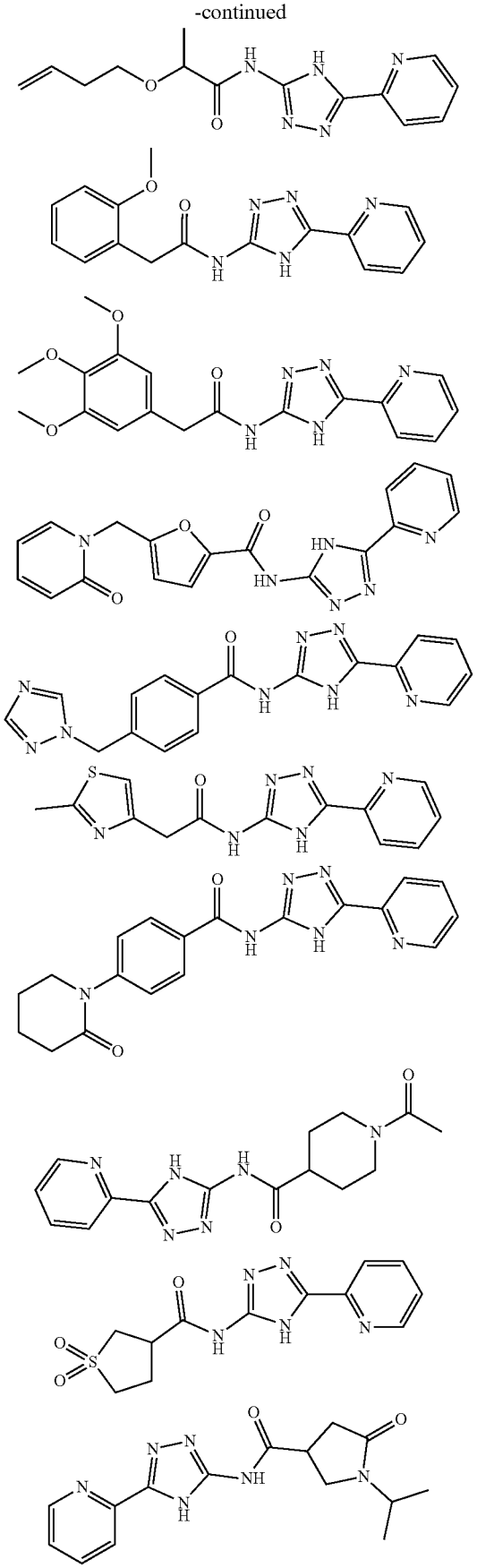
-continued
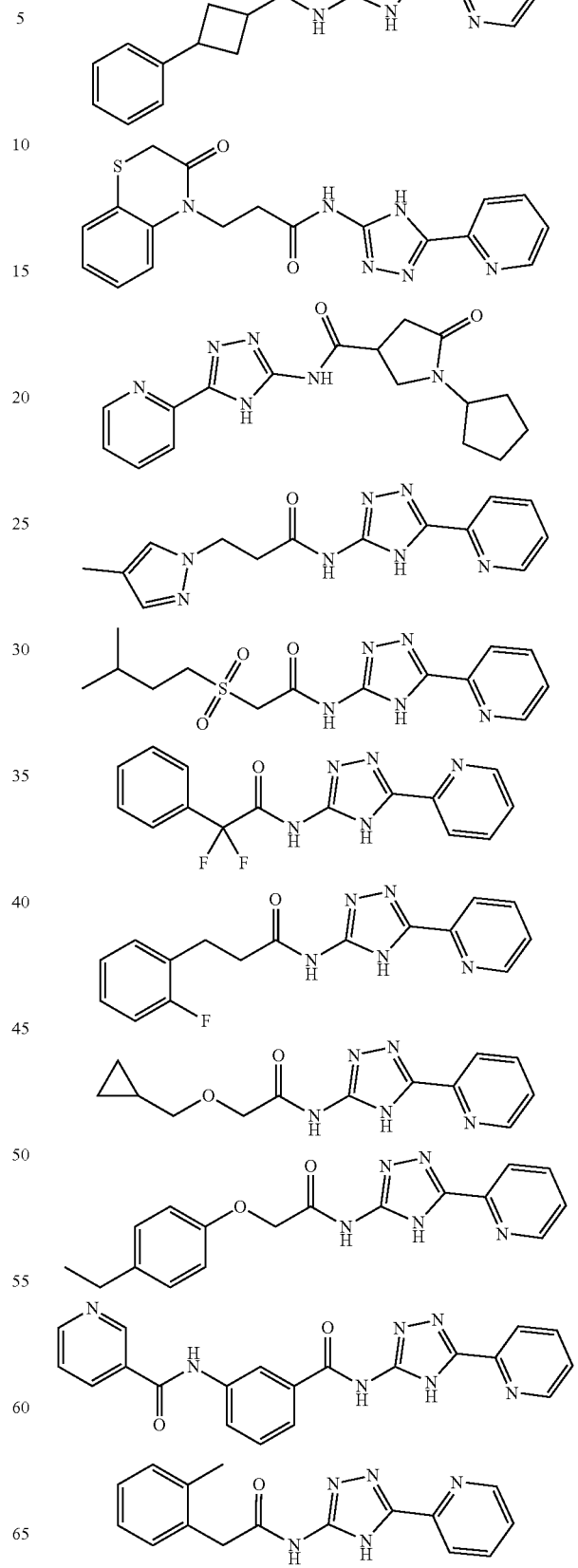

-continued

-continued
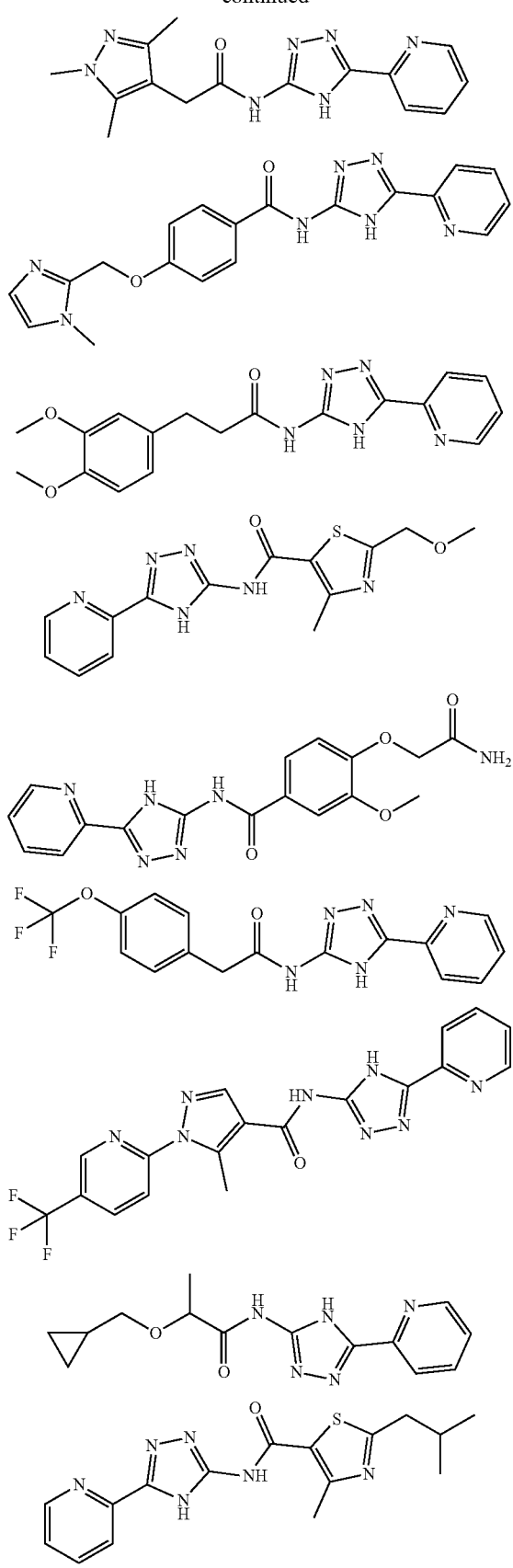
-continued
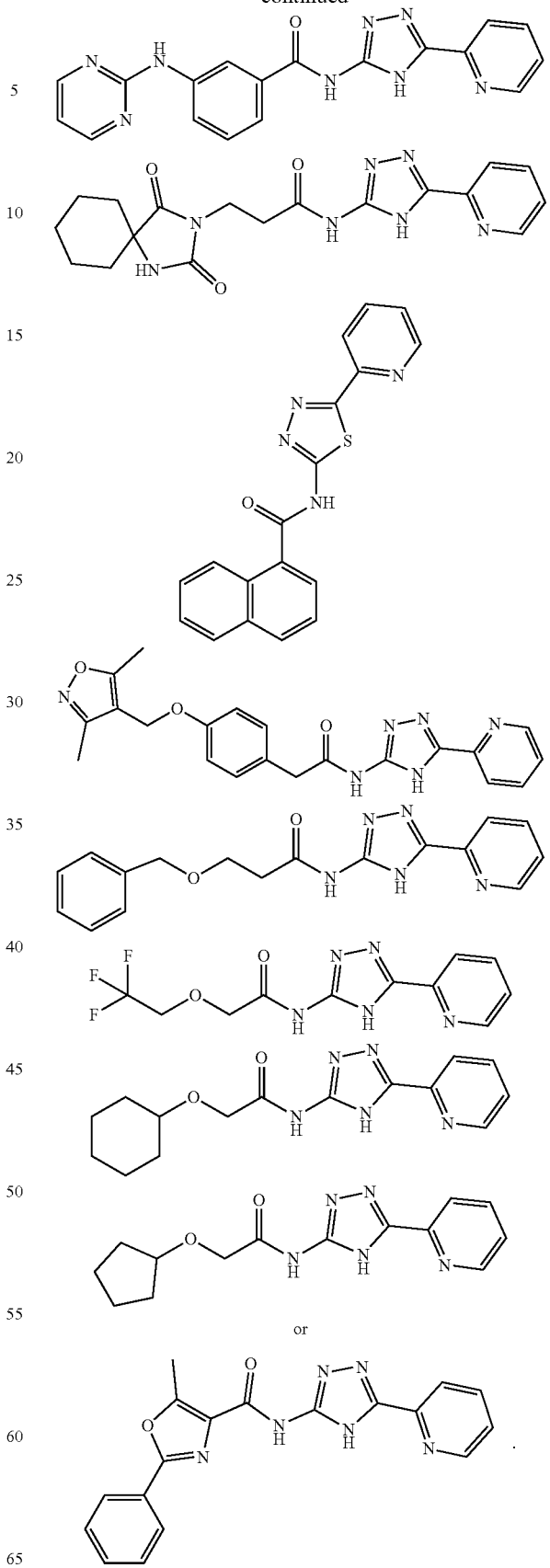

In another embodiment, the compound of Formula I is a compound of Formula Ib:

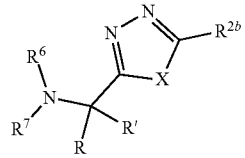

Formula Ib or pharmaceutically acceptable derivatives thereof,
wherein $R^{2b}$ is selected from the group consisting of alkyl, aryl, cycloalkyl, heterocyclyl and heteroaryl;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
R and R' are independently selected from hydrogen and alkyl, and R and R' are combined to form a cyclic structure including the carbon atom to which they are both attached;
p is 0-2; and
X is O or $NR^5$.

In another embodiment, the compound of Formula I is a compound of Formula Ib or pharmaceutically acceptable derivatives thereof, wherein:
$R^6$ and $R^7$ are independently selected from hydrogen, methyl, isopropyl, phenyl, cyclopropyl, adamantyl, or selected from one of the following:

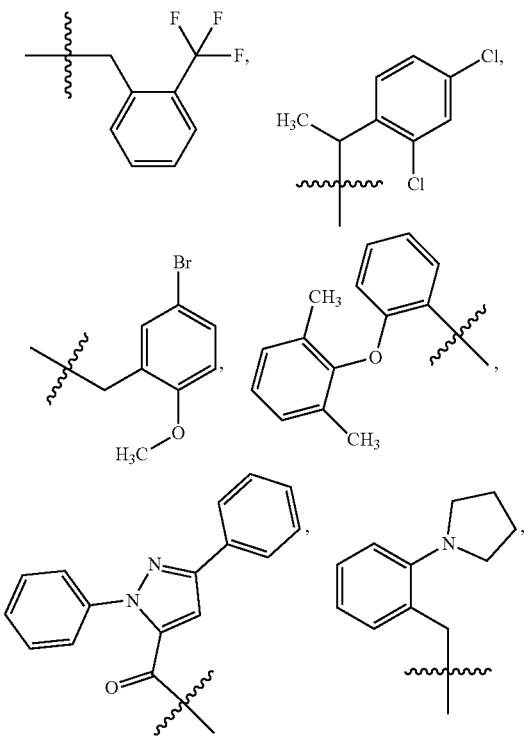

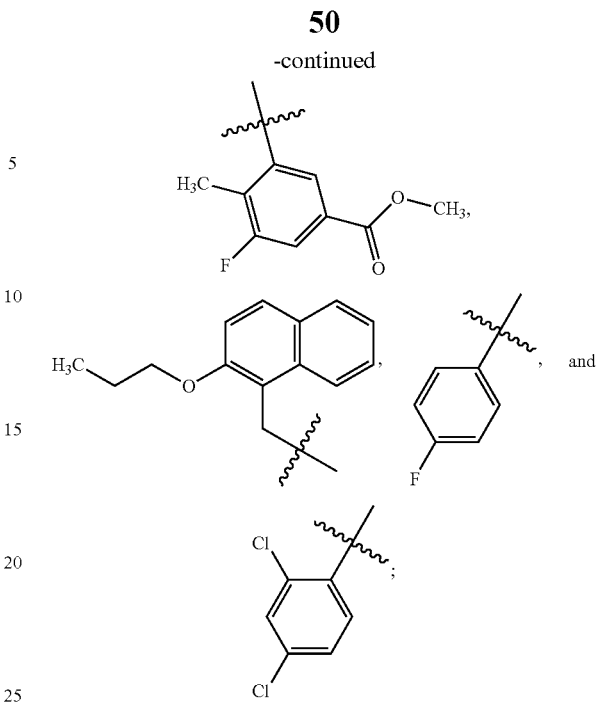

wherein phenyl is optionally substituted with one, two, or three substituents each selected from halogen, and $R^6$ and $R^7$ are combined to form a cyclic structure including the nitrogen atom to which they are both attached, wherein the cyclic structure is selected from one of the following:

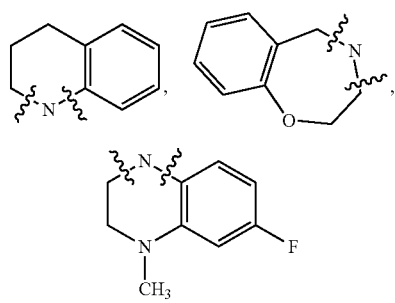

R and R' are independently selected from hydrogen and methyl; and

X is O or NH.

In one embodiment, the compound of Formula Ib is:

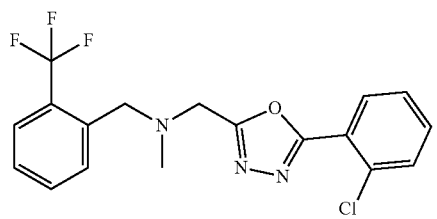

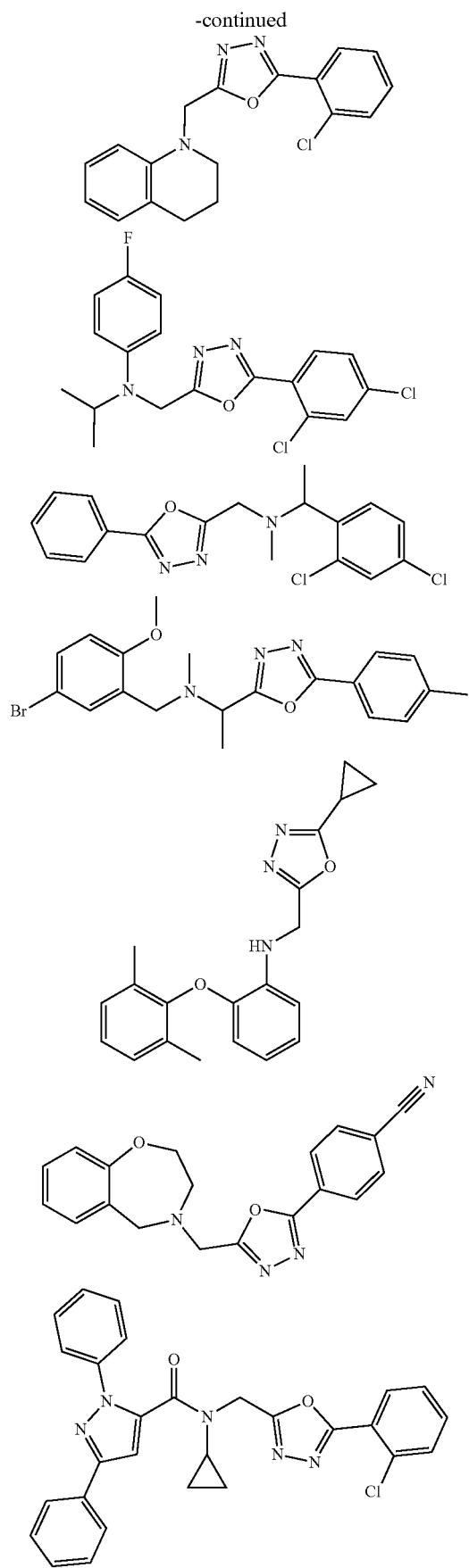
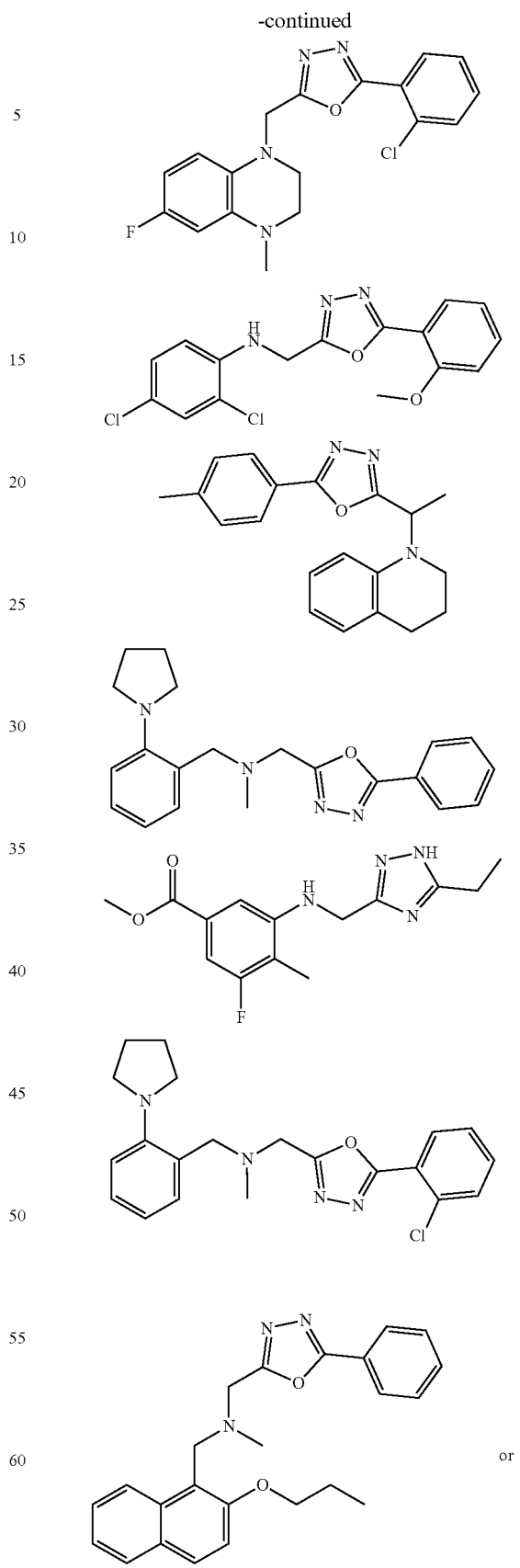

-continued

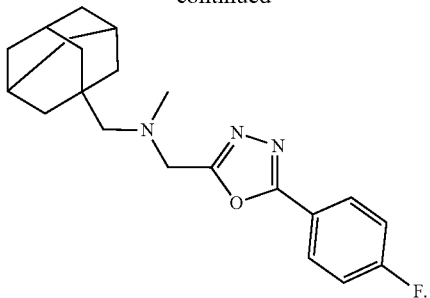

In another embodiment, the compound of Formula I is a compound of Formula Ic:

Formula Ic

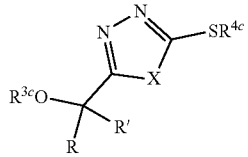

or pharmaceutically acceptable derivatives thereof, $R^{3c}$ is hydrogen, alkyl, alkenyl, alkynyl, aryl, heteroaryl, heterocyclyl, cycloalkyl, alkylcarbonyl, cycloalkylcarbonyl or arylcarbonyl;

$R^{4c}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached;

p is 0-2; and

X is O or NR$^5$.

In another embodiment, the compound of Formula I is a compound wherein:

$R^{3c}$ is phenyl or $R^{3C}$, R and R' are combined to form a cyclic structure, as shown below

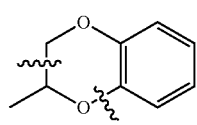

wherein phenyl is optionally substituted with one, two, or three substituents each selected from halogen, cyano, and methyl;

$R^{4c}$ is selected from one of the following;

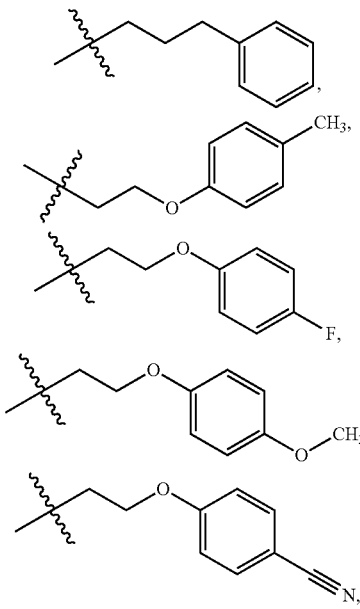

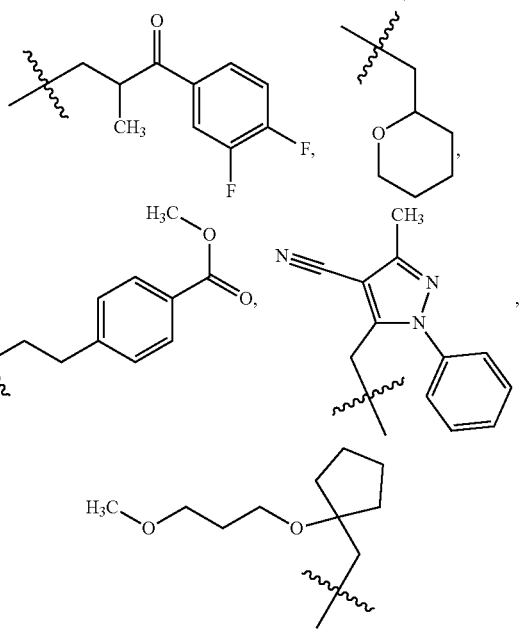

R and R' are independently selected from hydrogen and methyl, or R and R' are combined to form a cyclic structure including the carbon atom to which they are both attached; and X is O or N-phenyl.

In one embodiment, the compound of Formula Ic is:

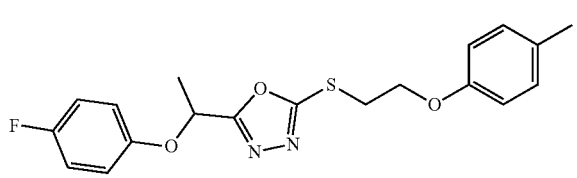

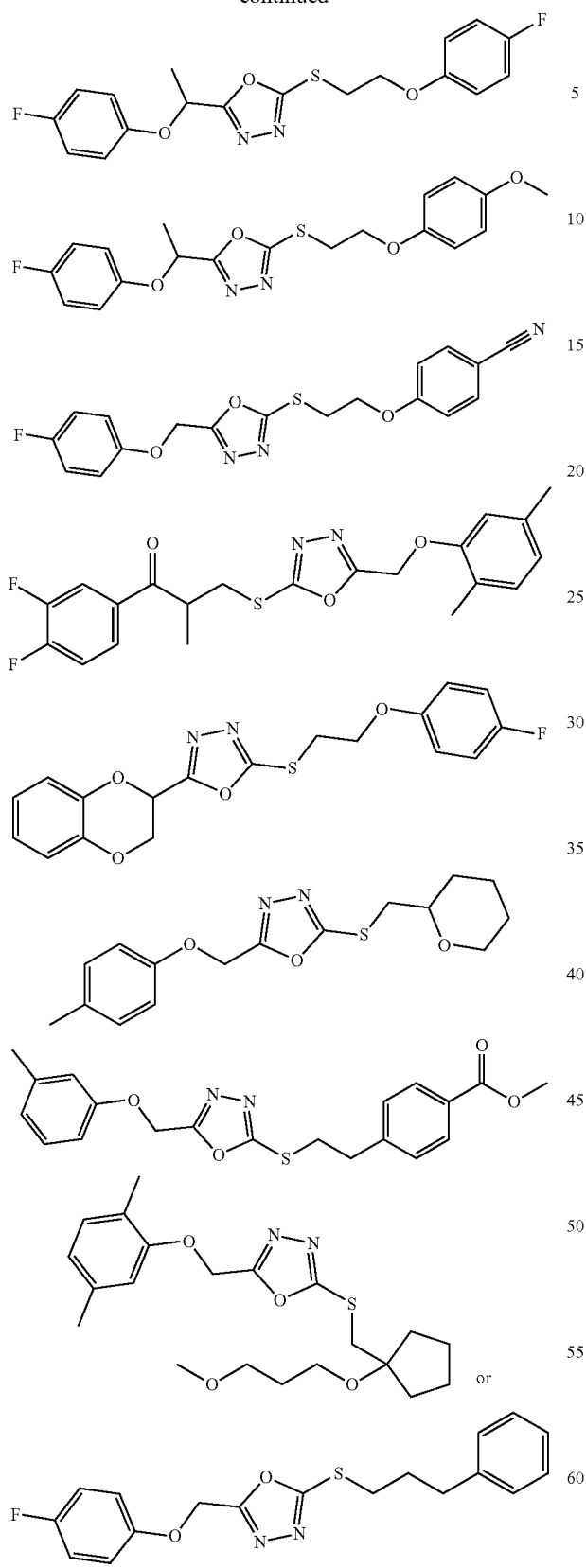

In another embodiment, the compound of Formula I is a compound of a Formula Id:

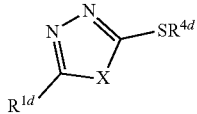

Formula Id or pharmaceutically acceptable derivatives thereof,
wherein $R^{1d}$ is selected from the group consisting of alkyl, aryl, cycloalkyl, heterocyclyl, heteroaryl and $SR^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^{4d}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and X is O, S or $NR^5$.

In another embodiment, the compound of Formula I is a compound of Formula Id wherein:

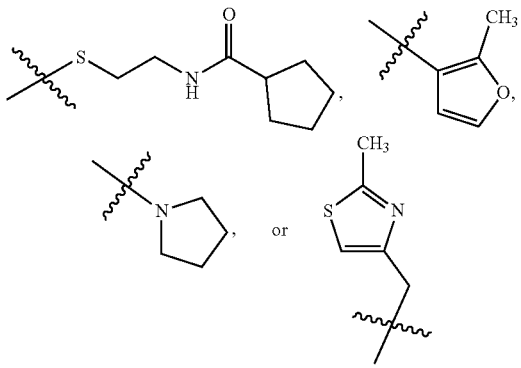

$R^{4d}$ is selected from one of the following:

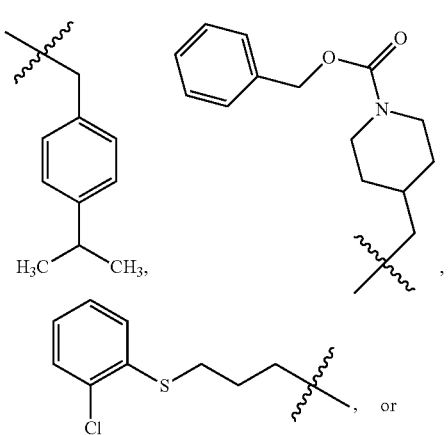

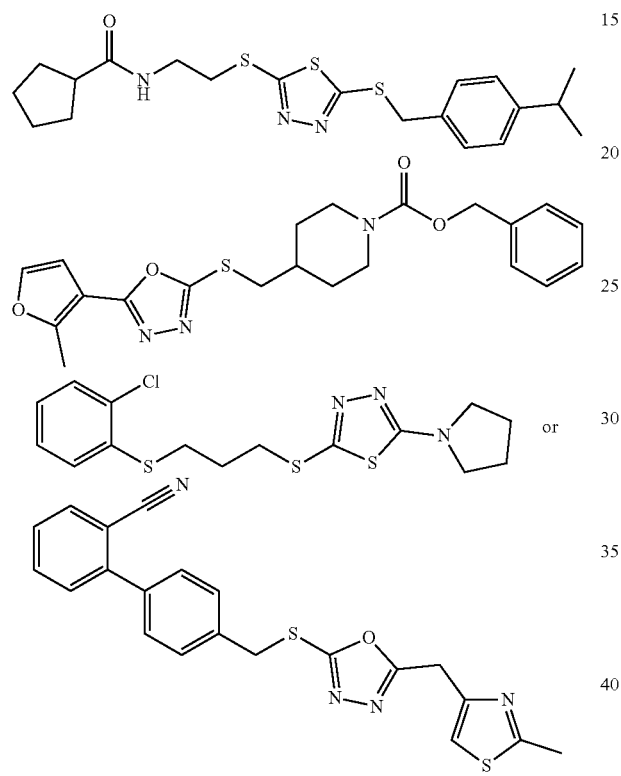

X is O or S.

In one embodiment, the compound of Formula Id is:

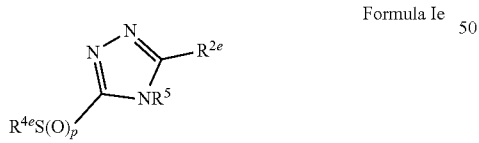

In another embodiment, the compound of Formula I is a compound of Formula Ie:

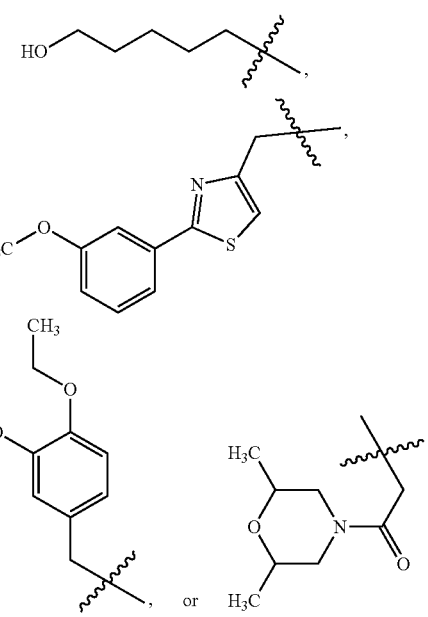
Formula Ie wherein R$^{2e}$ is selected from the group consisting of aryl, heteroaryl, arylalkyl or heteroarylalkyl;

R$^3$ is hydrogen, alkyl, alkenyl, alkynyl, aryl, heteroaryl, heterocyclyl, cycloalkyl, alkylcarbonyl, cycloalkylcarbonyl or arylcarbonyl;

R$^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;

R$^{4e}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;

R$^5$ is hydrogen, alkyl, alkenyl, alkynyl, aryl, heteroaryl, heterocyclyl, cycloalkyl, alkylcarbonyl, cycloalkylcarbonyl, or arylcarbonyl;

R$^6$ and R$^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R$^6$ and R$^7$ are combined to form a cyclic structure including the nitrogen atom to which they are both attached; and p is 0-2.

In another embodiment of Formula Ie, the compound of Formula Ie is a compound wherein:

R$^{2e}$ is selected from the group consisting of furyl, pyridinyl, phenyl, and naphthylmethyl,
wherein phenyl is substituted with methyl;

R$^{4e}$ is selected from one of the following:

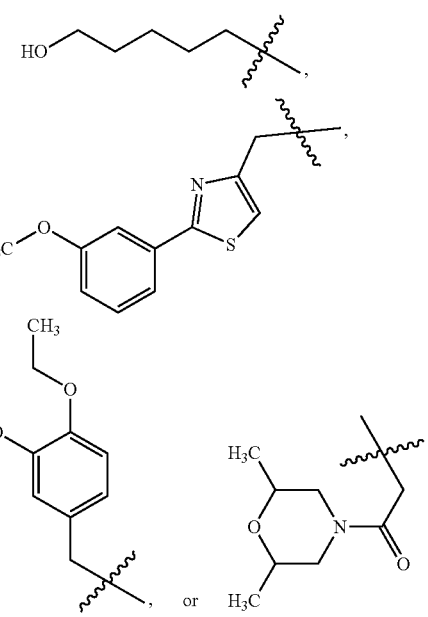

R$^5$ is hydrogen, propyl, cyclohexyl or phenyl; and
p is 0-2.

In one embodiment, the compound of Formula Ie is:

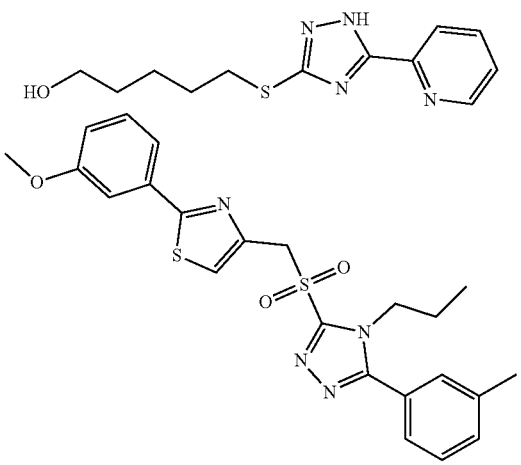

-continued

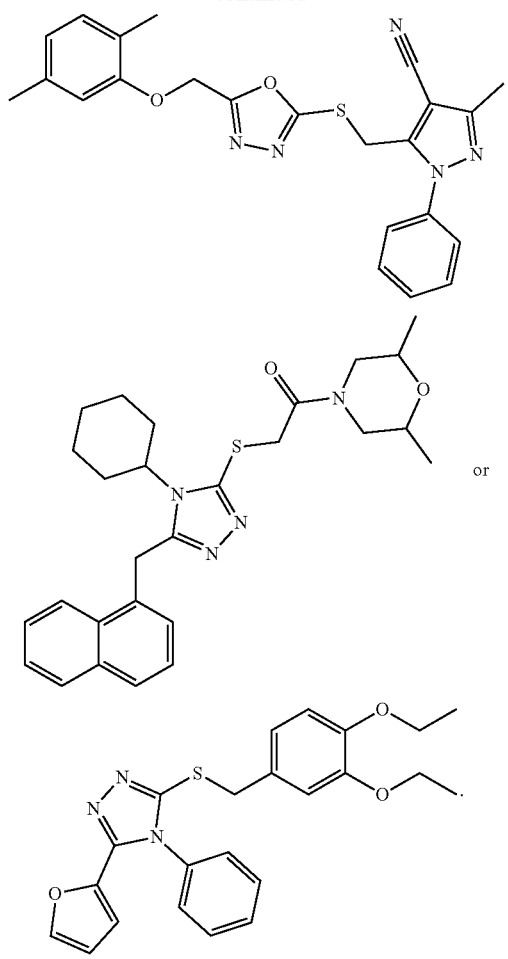

In one embodiment, the compound of Formula I is selected with the proviso that the compound is not

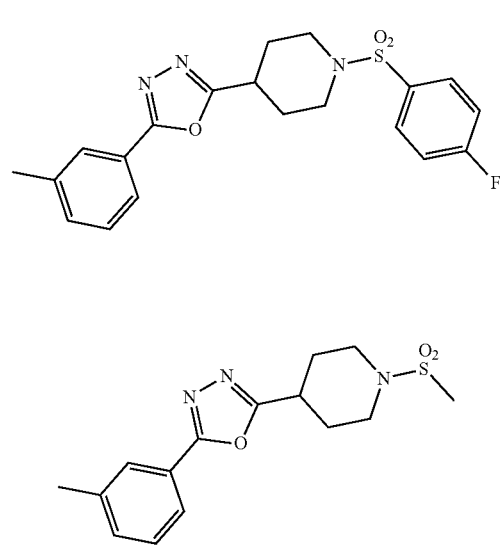

-continued

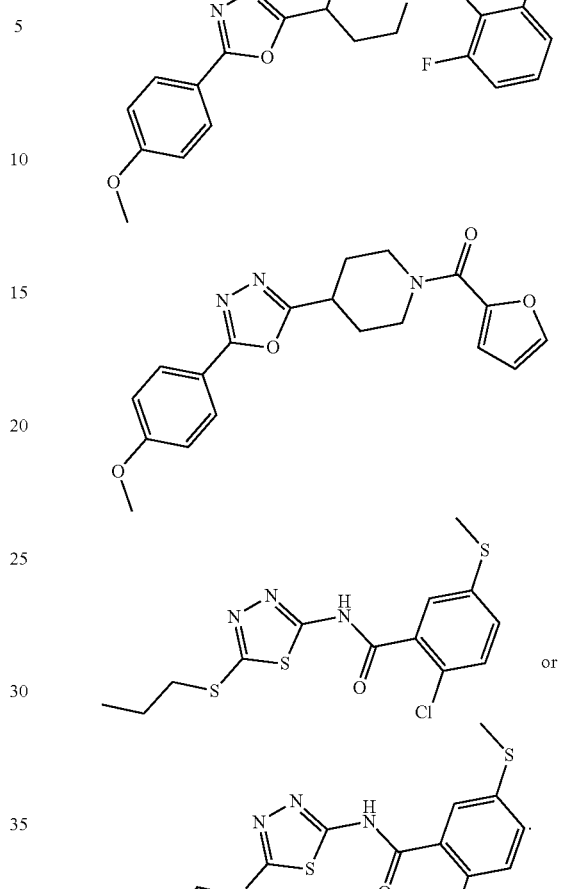

In one embodiment, the compound of Formula Ia is selected with the proviso that the compound is not

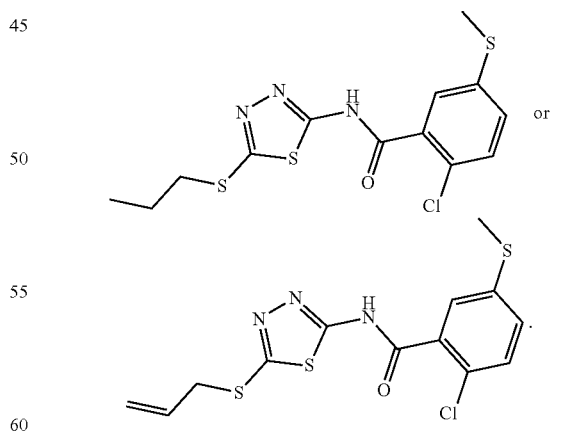

In one embodiment, the compound of Formula I is selected with the proviso that if X is NH and $R^1$ is phenyl, then $R^2$ is not pyridyl.

In certain embodiments, the compounds for use in the compositions and methods provided herein are of Formula II:

Formula II

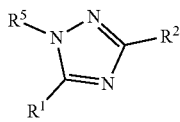

or pharmaceutically acceptable derivatives thereof,
wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and p is 0-2.

In another embodiment, the compound of Formula II is a compound of Formula IIa:

Formula IIa

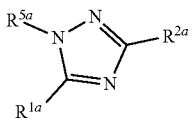

or pharmaceutically acceptable derivatives thereof,
wherein $R^{1a}$ is heterocyclyl or $NR^6R^7$;
wherein $R^{2a}$ is H, aryl, or heteroaryl;
$R^{5a}$ is alkyl, alkylcarbonyl, cycloalkylcarbonyl or arylcarbonyl; and
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula IIa, the compound of Formula II is a compound wherein:

$R^a$ is amino, or as depicted below:

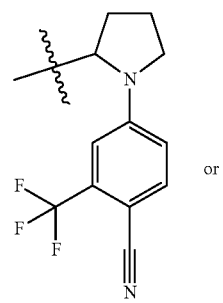

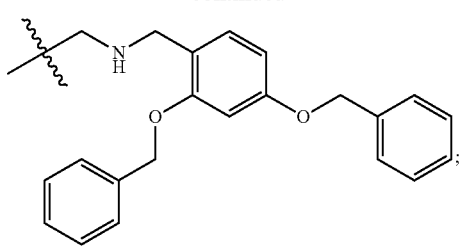

wherein $R^{2a}$ is H or pyridinyl;

$R^{5a}$ is isopropyl, or as depicted below:

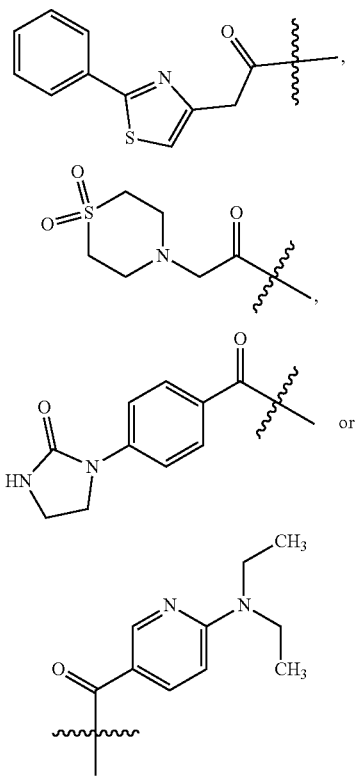

In one embodiment, the compound of Formula IIa is:

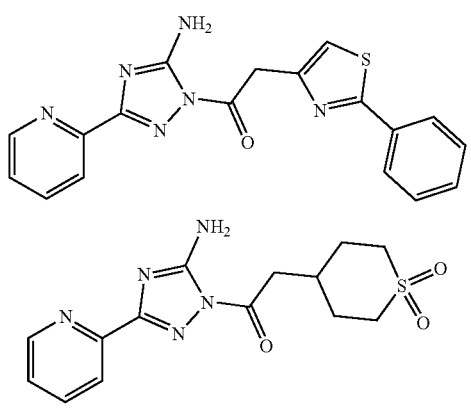

-continued

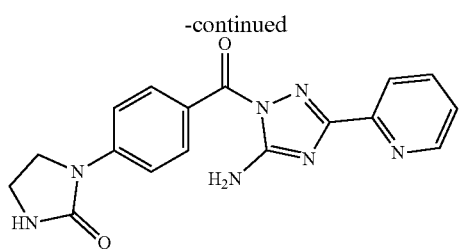

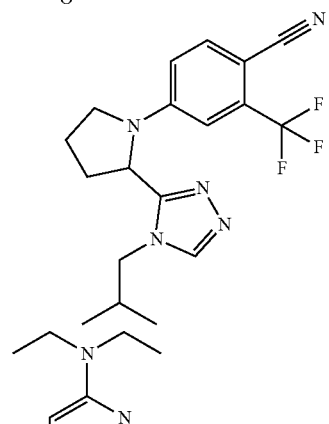
or

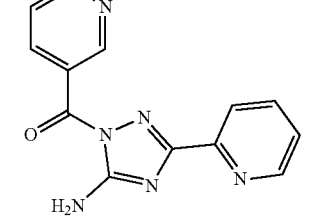

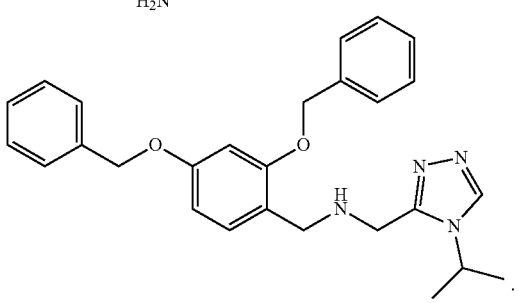

In certain embodiments, the compounds for use in the compositions and methods provided herein are of Formula III:

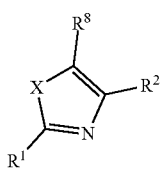

Formula III or pharmaceutically acceptable derivatives thereof,
wherein $R^1$ $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

X is O or S; or X is NR, wherein R forms a non-aromatic ring with one of the carbon atoms adjacent to the nitrogen on the five-membered ring to which it is attached.

In another embodiment of Formula III, the compound of Formula III is a compound wherein $R^1$ is phenyl or as depicted below:

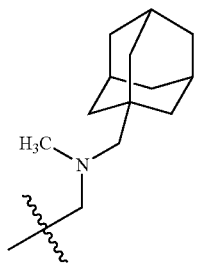 [SMILES: *CN(C)CC12CC3CC(CC(C3)C1)C2]

$R^2$ is methyl or as depicted below:

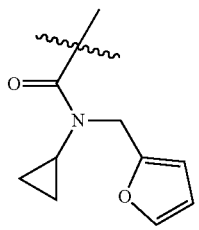 [SMILES: *C(=O)N(Cc1ccco1)C1CC1]

p is 0-2; and

X is O; or X is NR, wherein R forms a seven-membered ring with one of the carbon atoms adjacent to the nitrogen on the five-membered ring to which it is attached.

In one embodiment, the compound of Formula III is:

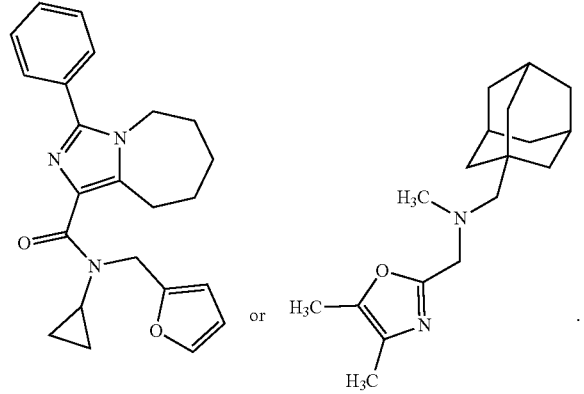 [SMILES: O=C(c1nc(-c2ccccc2)n2c1CCCCC2)N(Cc1ccco1)C1CC1 ; Cc1nc(CN(C)CC23CC4CC(CC(C4)C2)C3)oc1C]

In another embodiment, the compound of Formula III is a compound of Formula IIIa:

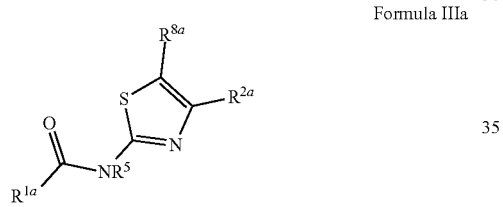

Formula IIIa or pharmaceutically acceptable derivatives thereof, wherein $R^{1a}$ is selected from the group consisting of H, alkyl, alkenyl, alkynyl, aryl, cycloalkyl, heterocyclyl, heteroaryl, $OR^3$, and $NR^6R^7$;

wherein $R^{2a}$ is aryl or heteroaryl;

wherein $R^{8a}$ are is H or alkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula IIIa, a compound of Formula IIIa is a compound wherein:

$R^{1a}$ is selected from the group consisting of pyridinyl, isoxazolyl, phenyl, benzodioxalyl, quinoxalinyl, pyrolidinonyl, aminoalkyl, benzimidazolyl, benzyl, benzofuranyl, and one of the following:

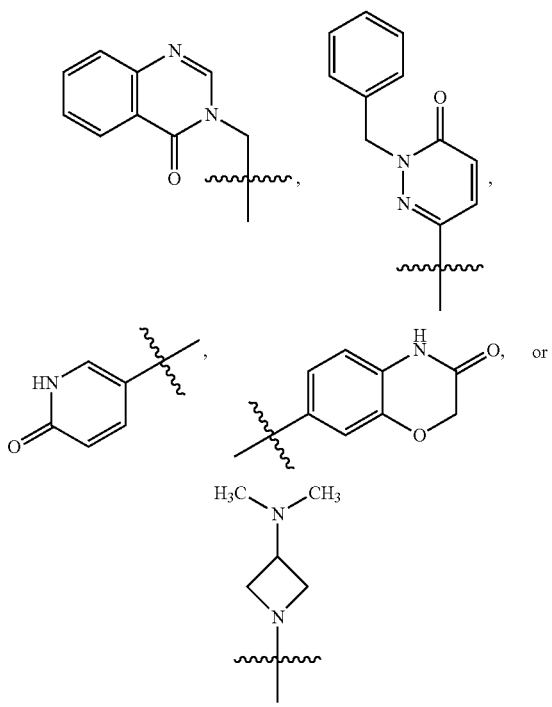

wherein pyridinyl, isoxazolyl, phenyl, furanyl and benzyl is optionally substituted with one or two substituents each selected from methyl, halogen, methoxy, benzodioxalyl, pyridinyl, tetrazolyl;

$R^{2a}$ is pyridinyl;

$R^{8a}$ is hydrogen; and $R^5$ is hydrogen.

In one embodiment, the compound of Formula IIIa is:

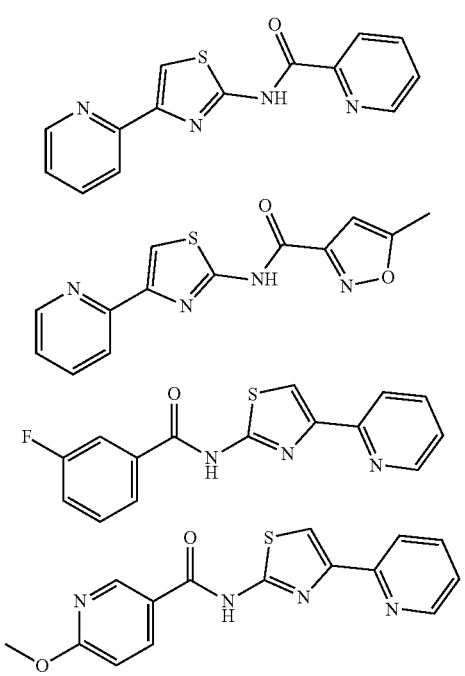

-continued
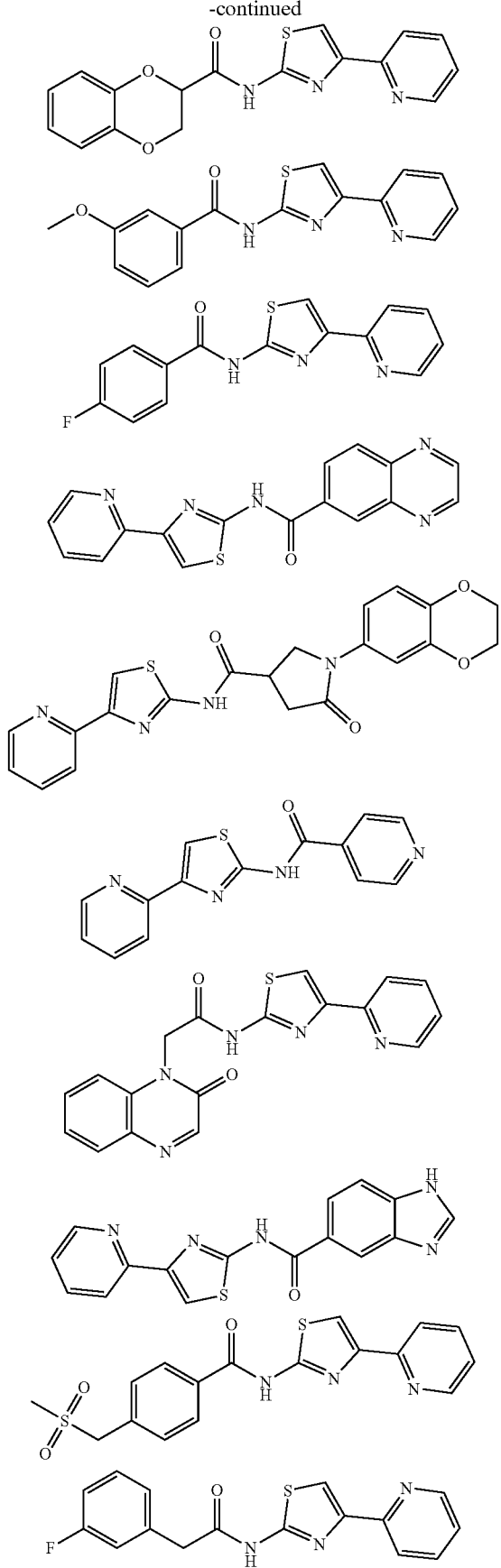
-continued
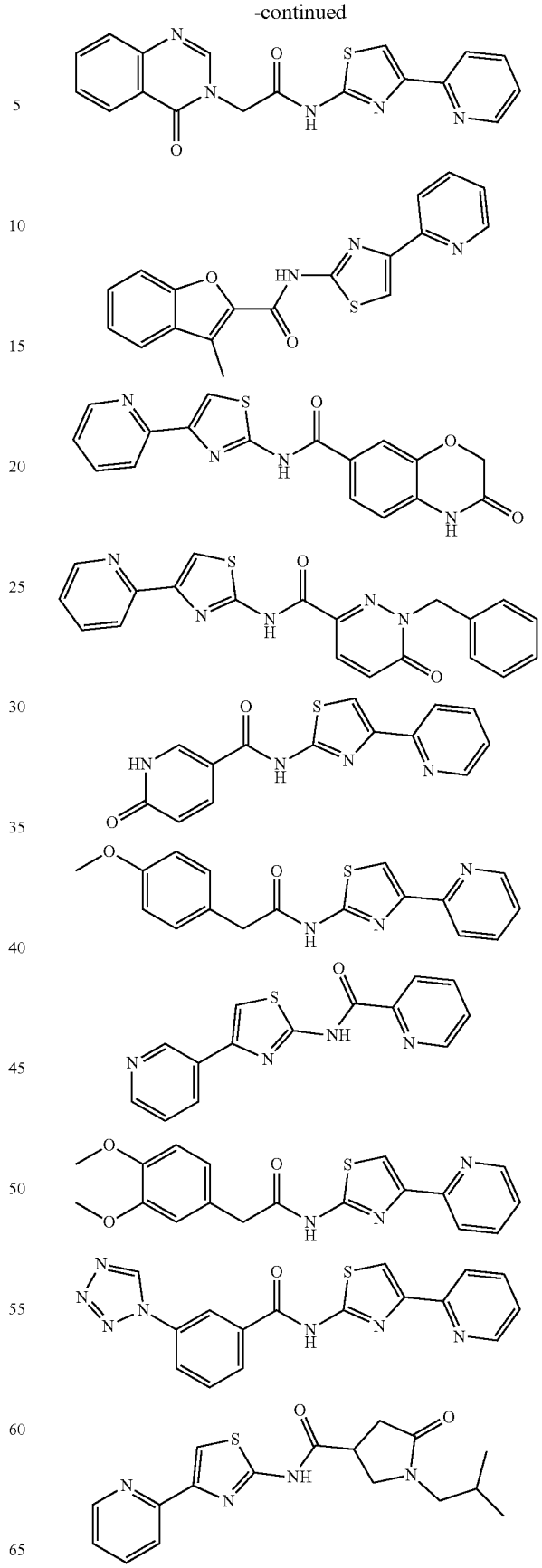

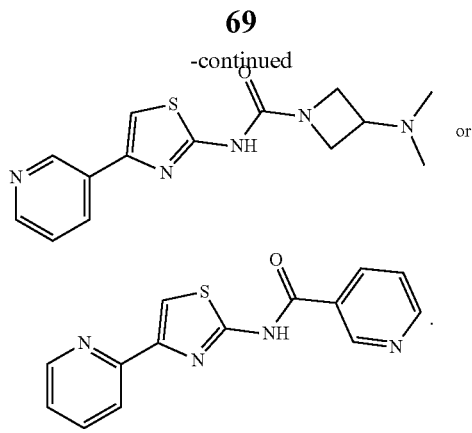

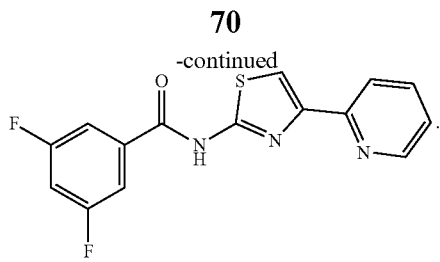

In another embodiment, the compound of Formula III is a compound of Formula IIIb:

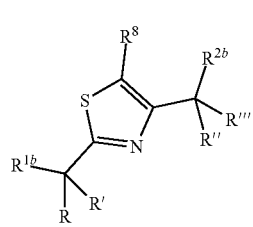

Formula IIIb

In another embodiment of Formula IIIa, a compound of Formula IIIa is a compound wherein:

$R^{1a}$ is selected from the group consisting of:

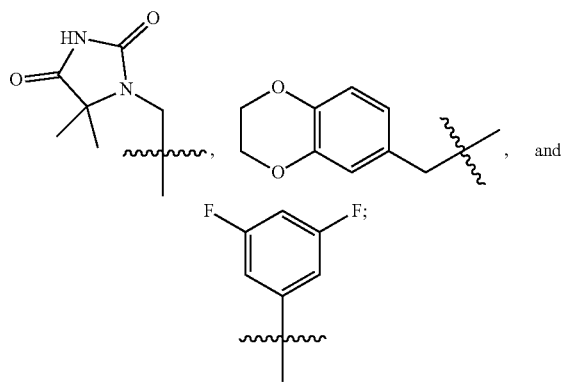

$R^{2a}$ is pyridinyl;
$R^{8a}$ is hydrogen; and
$R^5$ is hydrogen.

In one embodiment, the compound of Formula IIIa is:

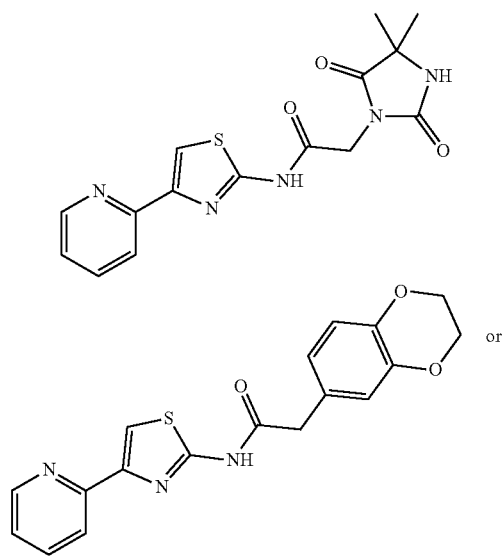

or pharmaceutically acceptable derivatives thereof, wherein $R^{1b}$ is $OR^3$, $NR^5C(O)R^4$ or $NR^6R^7$;

$R^{2b}$ is $OR^3$, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and R" and R'" are independently selected from hydrogen and alkyl, and R" and R'" are combined to form a cyclic structure including the carbon atom to which they are both attached.

In another embodiment of Formula IIIb, a compound of Formula IIIb is a compound wherein:

$R^{1b}$ is $OR^3$, or phenyl;
$R^{2b}$ is $OR^3$, or as follows:

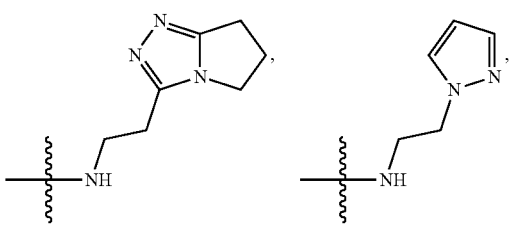

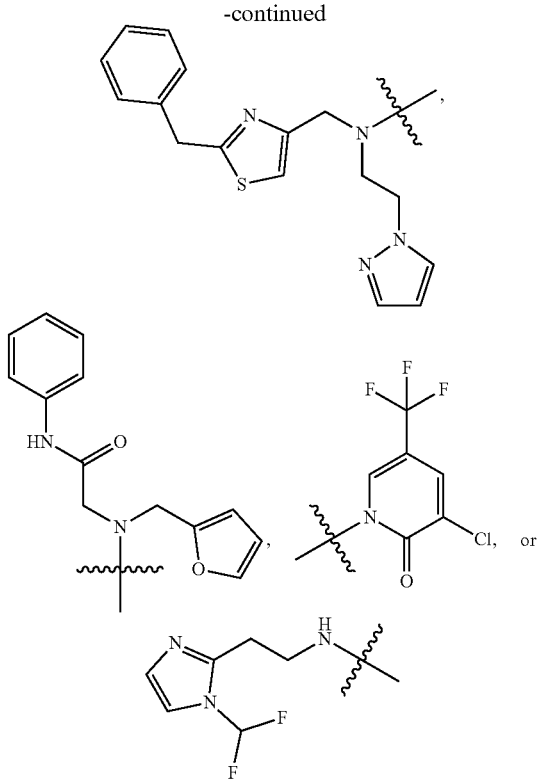

R³ is phenyl,
wherein phenyl is optionally substituted with one or two substituents each selected from methoxy, 1,1,1-trifluoroporpan-2-ol, and halogen
R⁵ is hydrogen, alkyl, alkenyl, alkynyl, aryl, heteroaryl, heterocyclyl, cycloalkyl, alkylcarbonyl, cycloalkylcarbonyl, or arylcarbonyl;
R⁸ is hydrogen; and
R and R' are hydrogen.
In one embodiment, the compound of Formula IIIb is:

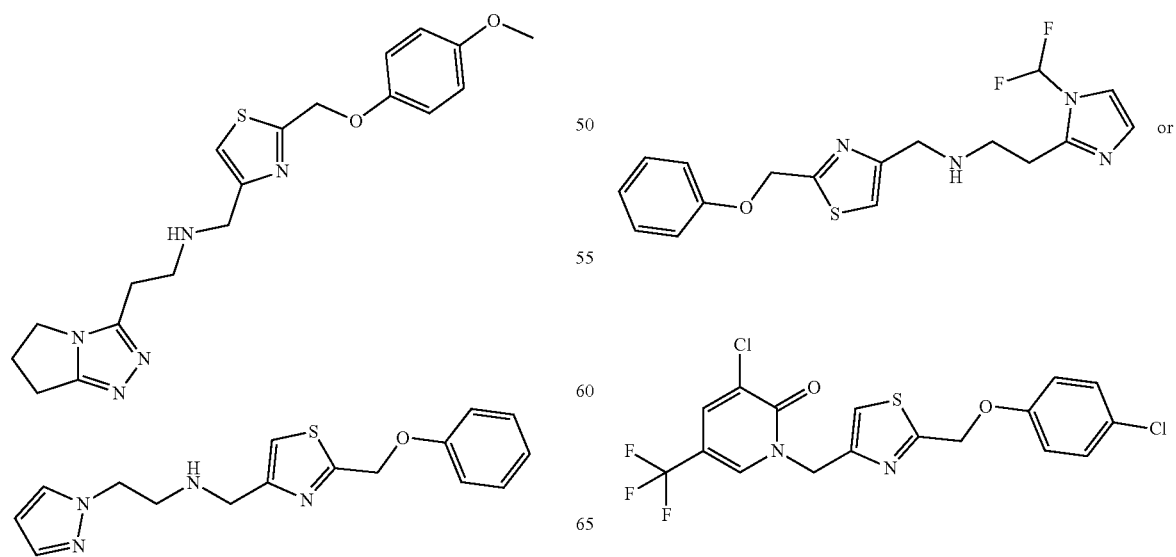

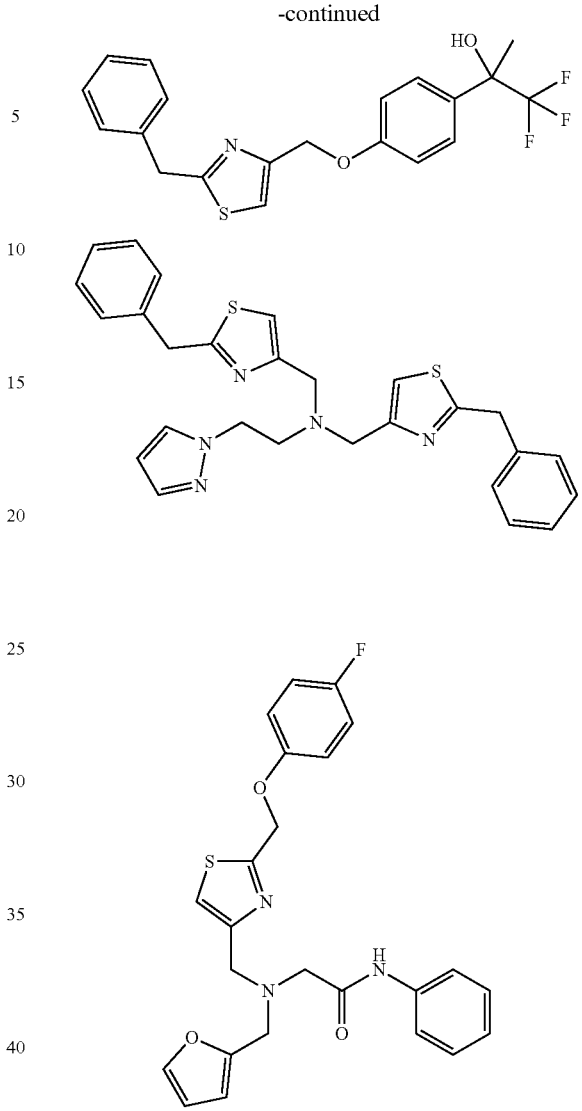

In another embodiment, the compound of Formula III is a compound of Formula IIIc:

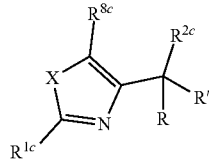

Formula IIIc or pharmaceutically acceptable derivatives thereof, wherein $R^{1c}$ is aryl, or heteroaryl;

$R^{2c}$ is $SR^4$, $NR^5C(O)R^4$ or $NR^6R^7$;

$R^{8c}$ is H or alkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and X is O or S.

In another embodiment of Formula III, a compound of Formula IIIc is a compound wherein $R^{1c}$ is $SR^4$, phenyl, or pyridinyl, or thienyl;

wherein phenyl is optionally substituted with one or two substituents selected from methyl, methoxy, ethoxy, halogen;

$R^{2c}$ is $SR^4$, $CH_2SR^4$, or selected from the following:

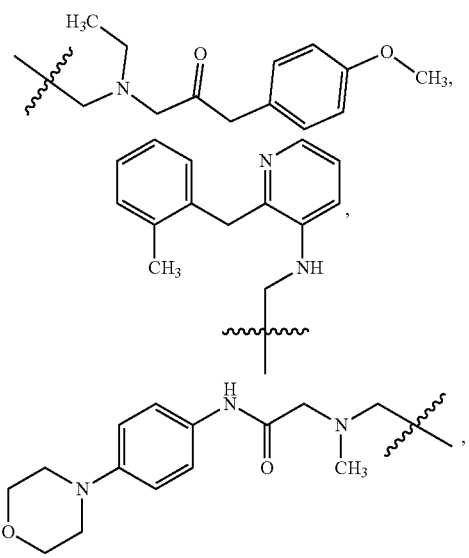

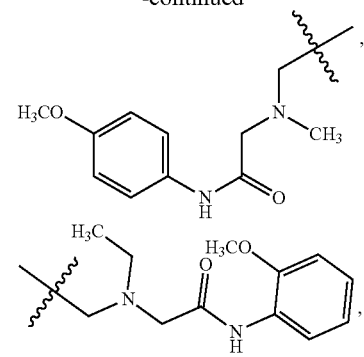

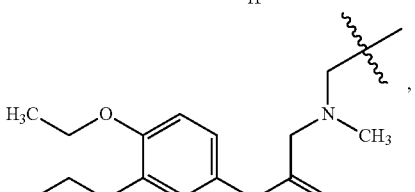

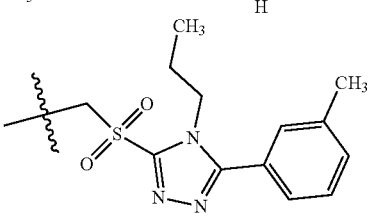

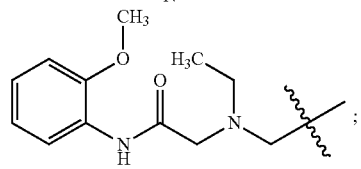

$R^{8c}$ is H or methyl;

$R^4$ is selected from the following:

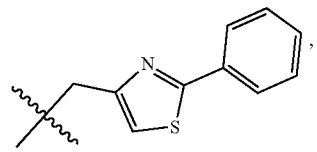

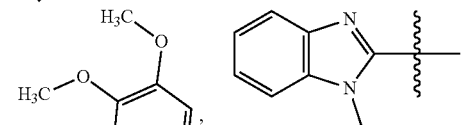

and

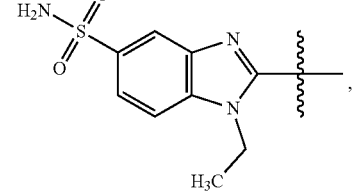

-continued

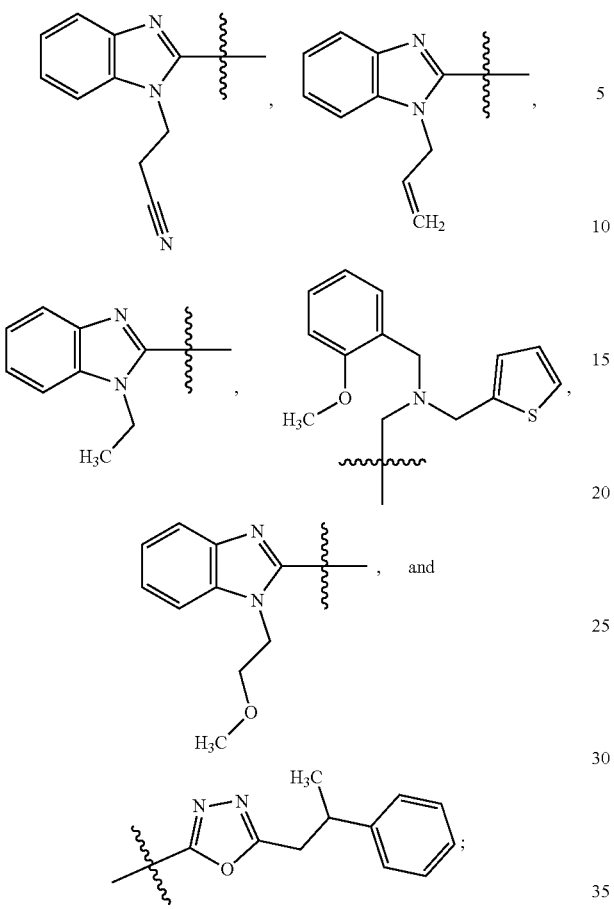

R and R' are hydrogen; and
X is O or S.

In another embodiment of Formula III, a compound of Formula IIIc is a compound wherein $R^{1c}$ is $SR^4$, phenyl, or pyridinyl, or thienyl;

wherein phenyl is optionally substituted with one or two substituents selected from methyl, methoxy, ethoxy, halogen;

$R^{2c}$ is $SR^4$, $CH_2SR^4$, or selected from the following:

-continued

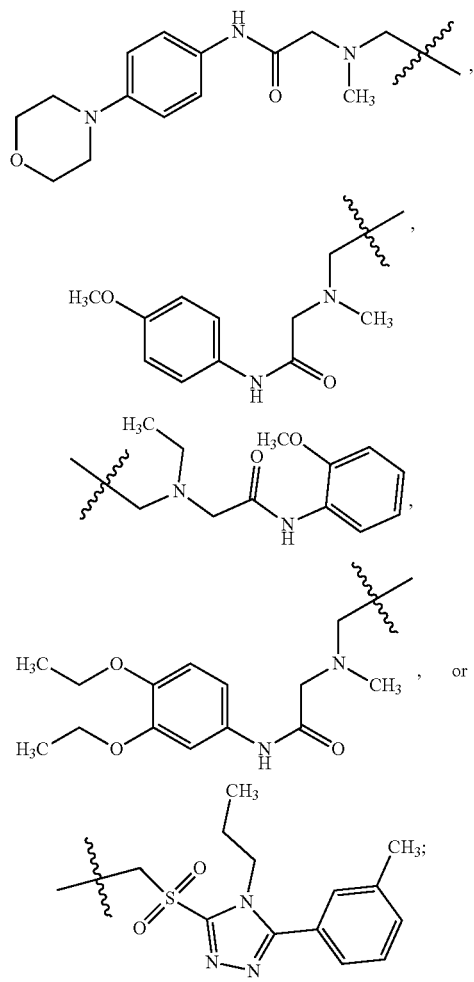

$R^{8c}$ is H or methyl;
$R^4$ is selected from the following:

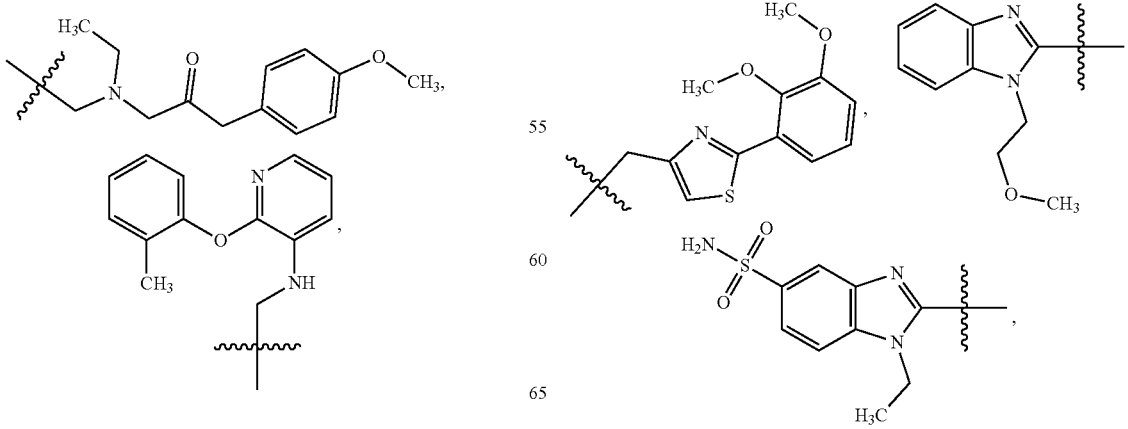

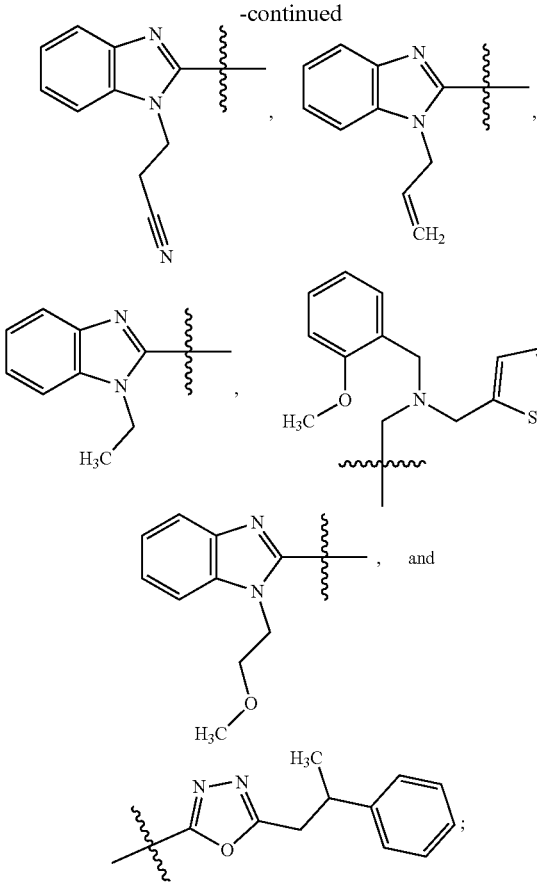
R and R' are hydrogen; and
X is O or S.
In one embodiment, the compound of Formula IIIc is:
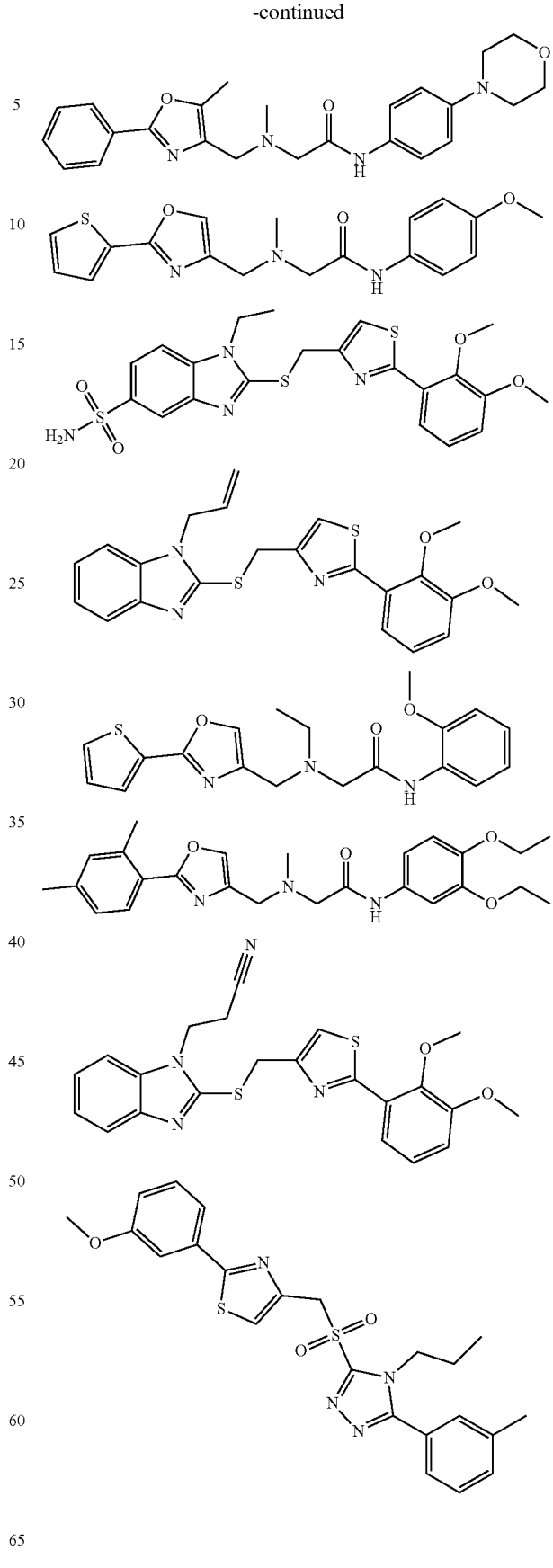

-continued

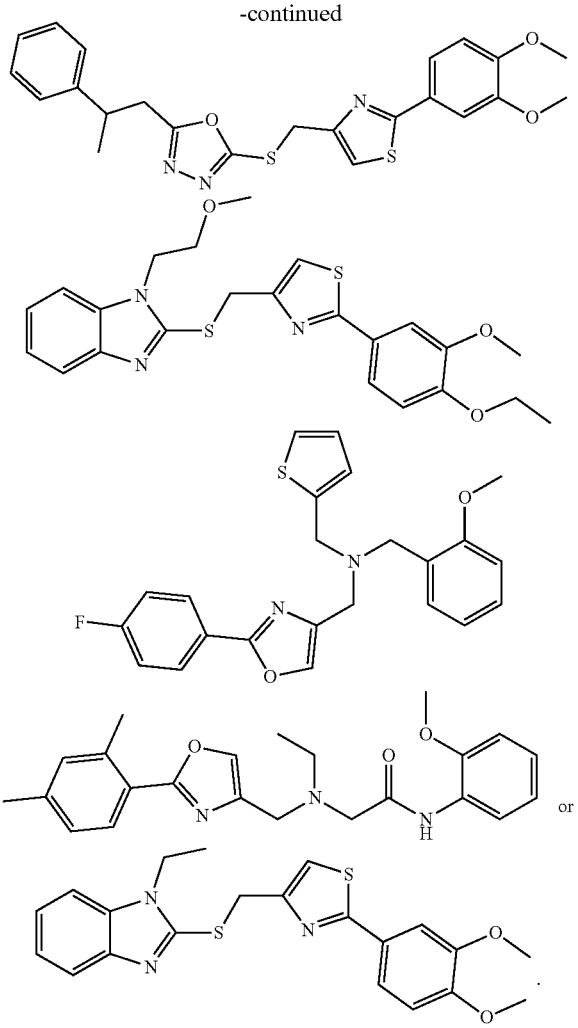

In another embodiment, the compound of Formula III is a compound of Formula IIId:

Formula IIId

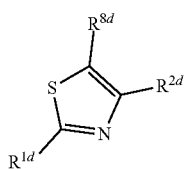

or pharmaceutically acceptable derivatives thereof,
wherein $R^{1d}$ is alkyl, cycloalkyl, $S(O)_pR^4$, $NR^5C(O)R^4$, or $NR^6R^7$;
$R^{2d}$ is aryl or heteroaryl;
$R^{8d}$ is H or alkyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl; and
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula IIId, a compound of Formula IIId is a compound wherein:
wherein $R^{1d}$ is cyclopropyl, phenyl, $S(O)_2R^4$, $NR^5C(O)R^4$, or $NR^6R^7$,
wherein phenyl is optionally substituted with one or two substituents each selected from hydroxyl and $CONH_2$;
$R^{2d}$ is phenyl or as depicted below:

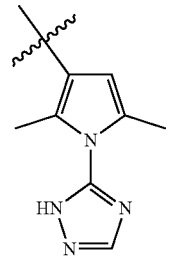

wherein phenyl is optionally substituted with 1-3 substituents each selected from methoxy, halogen, methyl, and hydroxyl;
$R^{8d}$ is hydrogen, methyl, or $CH_2CH_2CO_2CH_3$;
$R^4$ is phenyl or selected from one of the following:

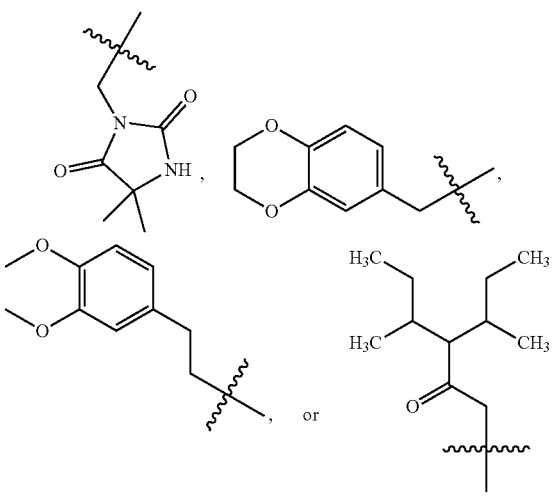

wherein phenyl is optionally substituted with two halogens;
$R^5$ is hydrogen; and
$R^6$ and $R^7$ are independently selected from hydrogen, cyclohexyl, and $R^6$ and $R^7$ are combined to form a six-membered cyclic structure including the nitrogen atom to which they are both attached.

In another embodiment of Formula IIId, a compound of Formula IIId is a compound wherein:
wherein $R^{1d}$ is cyclopropyl, phenyl, $S(O)_2R^4$, $NR^5C(O)R^4$, or $NR^6R^7$,
wherein phenyl is optionally substituted with one or two substituents each selected from hydroxyl and $CONH_2$;

$R^{2d}$ is phenyl or as depicted below:

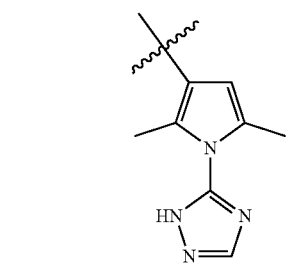

wherein phenyl is optionally substituted with 1-3 substituents each selected from methoxy, halogen, methyl, and hydroxyl;
$R^{8d}$ is hydrogen, methyl, or $CH_2CH_2CO_2CH_3$;
$R^4$ is phenyl or selected from one of the following:

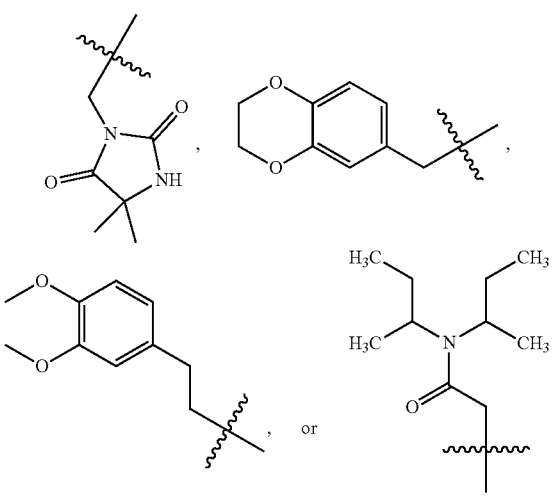

wherein phenyl is optionally substituted with two halogens;
$R^5$ is hydrogen; and
$R^6$ and $R^7$ are independently selected from hydrogen, cyclohexyl, and $R^6$ and $R^7$ are combined to form a six-membered cyclic structure including the nitrogen atom to which they are both attached.

In one embodiment, the compound of Formula IIId is:

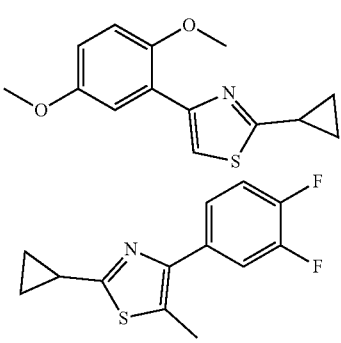

-continued

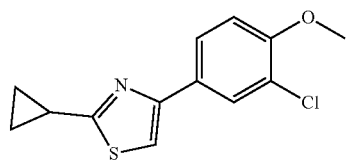

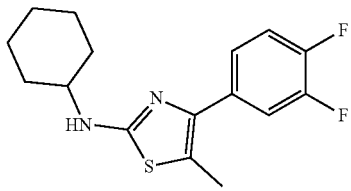

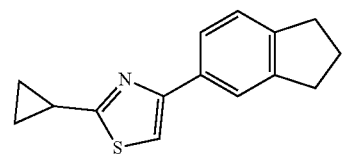

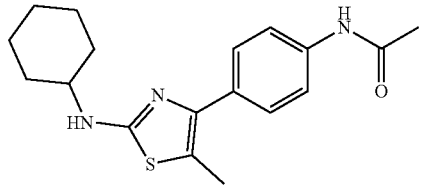

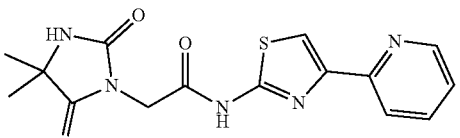

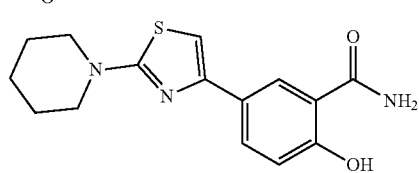

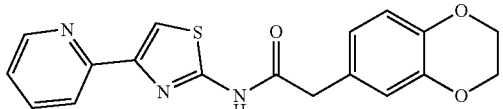

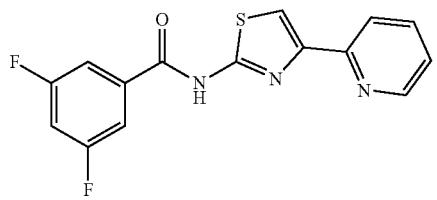

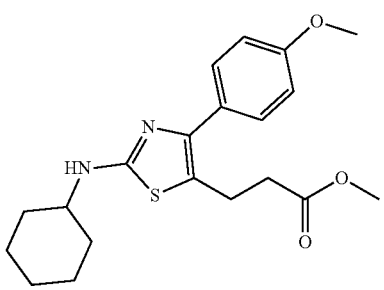

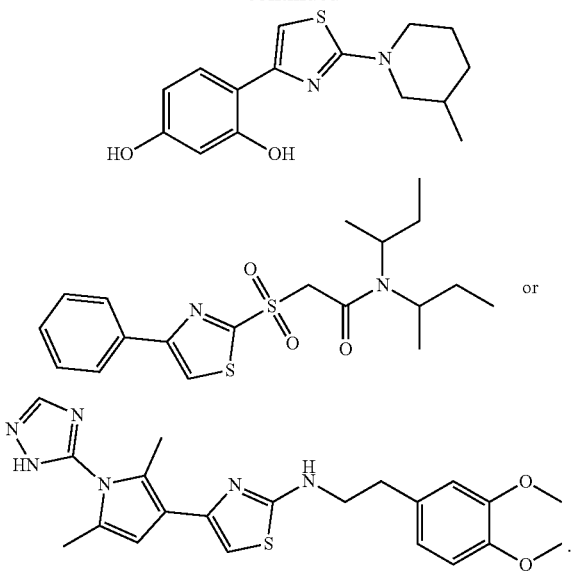
In one embodiment, the compound of Formula IIId is:
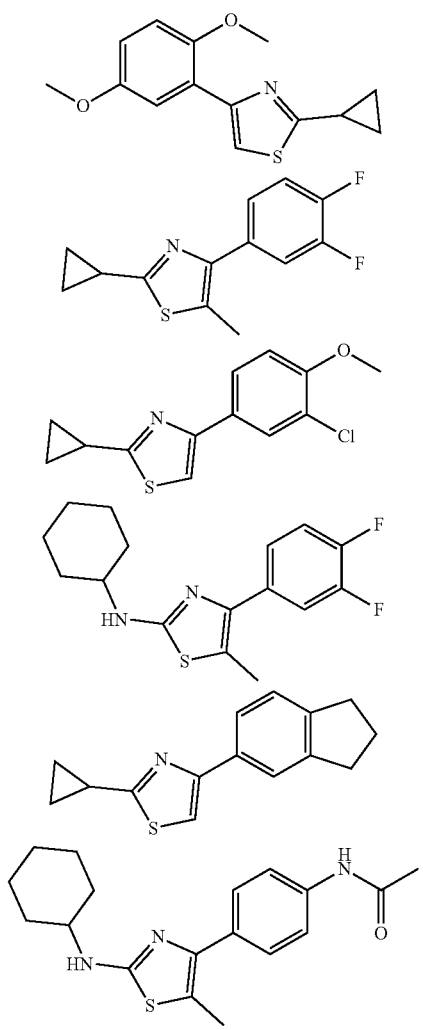
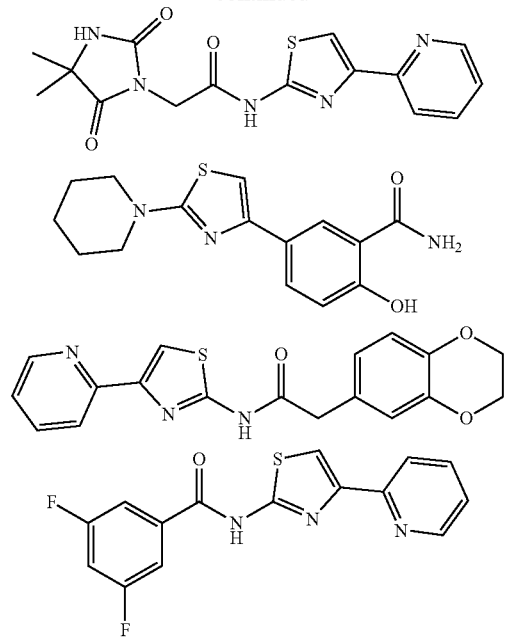
In another embodiment, the compound of Formula III is:
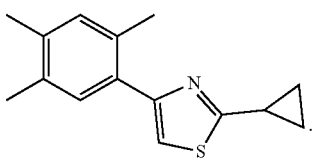 [SMILES: Cc1cc(C)c(-c2csc(C3CC3)n2)cc1C]
In another embodiment, the compound of Formula III is a compound of Formula IIIe:

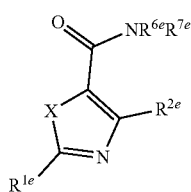

Formula IIIe or pharmaceutically acceptable derivatives thereof, wherein $R^{1e}$ is aryl or heteroaryl;

$R^{2e}$ is H or alkyl;

$R^{6e}$ and $R^{7e}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and X is O or S.

In another embodiment of Formula IIIe, a compound of Formula IIIe is a compound wherein:

$R^{1e}$ is pyridinyl, phenyl;

wherein phenyl is optionally substituted with one substituent selected from halogen, and ethyl;

$R^{2e}$ is methyl or hydrogen;

$R^{6e}$ and $R^{7e}$ are independently selected from hydrogen or one of the following

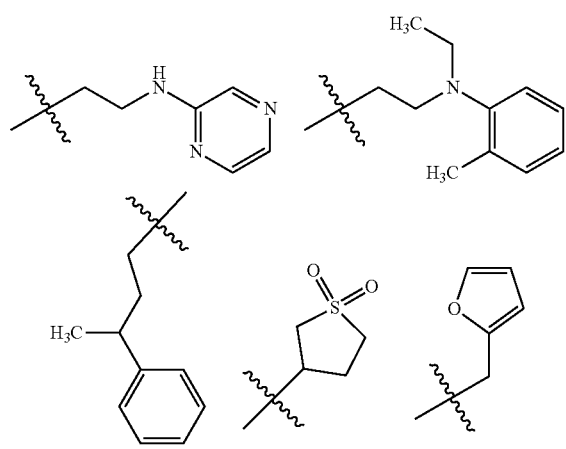

and $R^{6e}$ and $R^{7e}$ are combined to form a piperidine including the nitrogen atom to which they are both attached, and this piperidinyl ring is substituted with phenyl; and X is O or S.

In another embodiment of Formula IIIe, a compound of Formula IIIe is a compound wherein:

$R^{1e}$ is pyridinyl, phenyl;

wherein phenyl is optionally substituted with one substituent selected from halogen, and ethyl;

$R^{2e}$ is methyl or hydrogen;

$R^{6e}$ and $R^{7e}$ are independently selected from hydrogen or one of the following

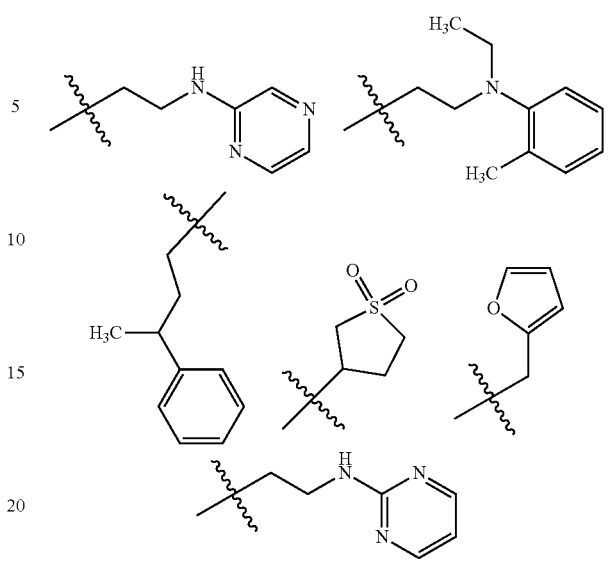

and $R^{6e}$ and $R^{7e}$ are combined to form a piperidine including the nitrogen atom to which they are both attached, and this piperidinyl ring is substituted with phenyl; and X is O or S.

In one embodiment, the compound of Formula IIIe is:

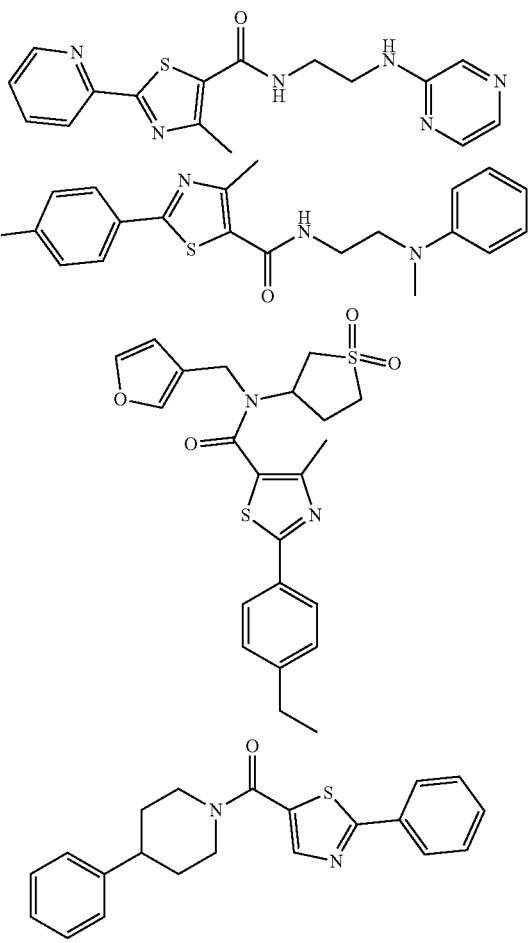

-continued

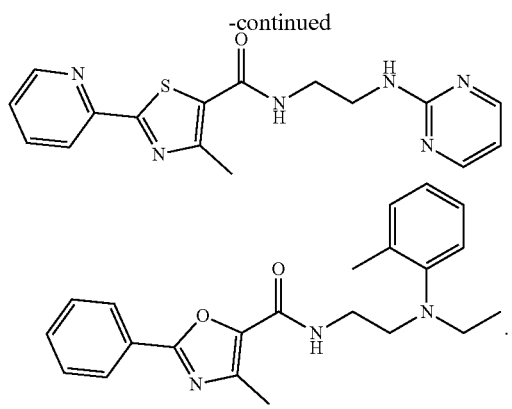

In another embodiment, the compound of Formula III is a compound of Formula IIIf:

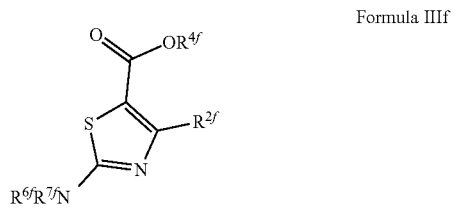

Formula IIIf or pharmaceutically acceptable derivatives thereof,
wherein $R^2$ is H or alkyl;
$R^{4f}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
$R^{6f}$ and $R^{7f}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula IIIf, a compound of Formula IIIf is a compound wherein
$R^{2f}$ is H or methyl;
$R^{4f}$ is methyl or ethyl; and
$R^{6f}$ and $R^{7f}$ are independently selected from cyclopropyl, ethyl, or one of the following

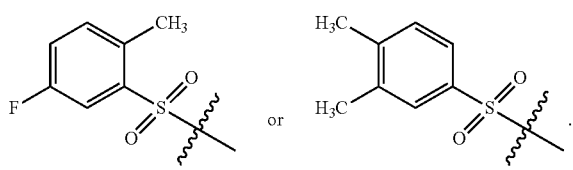 [SMILES: *S(=O)(=O)c1cc(F)ccc1C ; *S(=O)(=O)c1ccc(C)c(C)c1]

In one embodiment, the compound of Formula IIIf is:

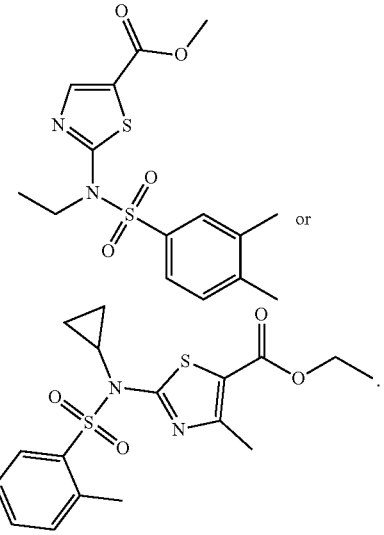

In another embodiment, the compound of Formula III is a compound of Formula IIIg:

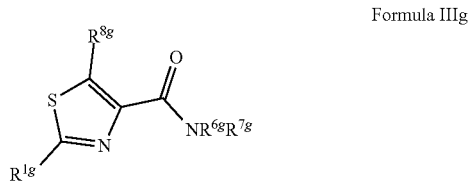

Formula IIIg or pharmaceutically acceptable derivatives thereof,
wherein $R^{1g}$ is aryl or heteroaryl;
$R^{6g}$ and $R^{7g}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
$R^{8g}$ is H or alkyl.

In another embodiment of Formula IIIg, a compound of Formula IIIg is a compound wherein:
$R^{1g}$ is phenyl, or pyrimidinyl;
wherein phenyl is optionally substituted with one or two substituents each selected from methoxy, halogen, or propyl;
$R^{1g}$ and $R^{7g}$ are independently selected from hydrogen or one of the following:

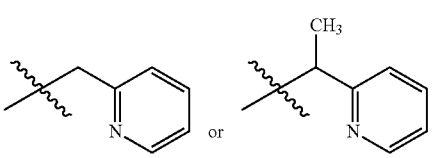

$R^6$ and $R^7$ are combined to form a cyclic structure including the nitrogen atom to which they are both attached, as depicted below:

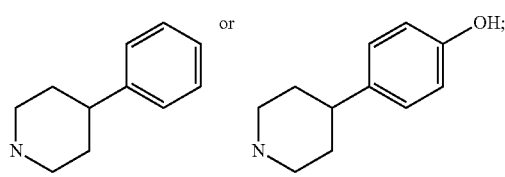 [SMILES: c1ccc(C2CCNCC2)cc1 ; Oc1ccc(C2CCNCC2)cc1]
and
R$^{8g}$ is H.
In one embodiment, the compound of Formula IIIg is:
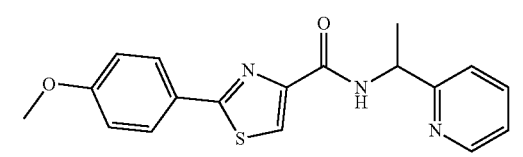
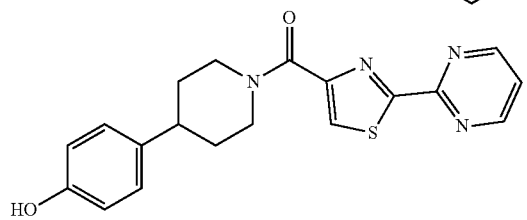
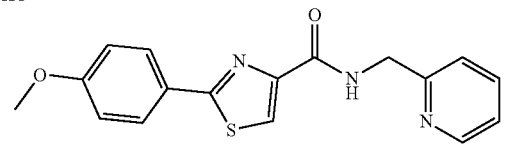
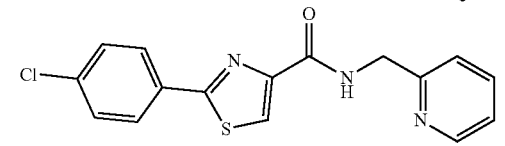
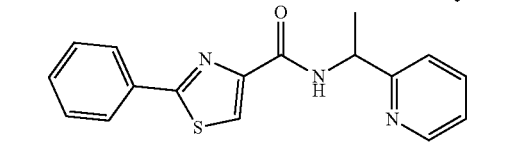
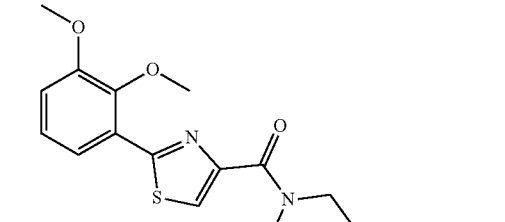
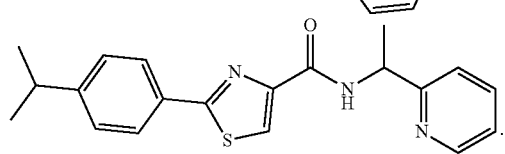
In one embodiment, the compound of Formula III is selected with the proviso that the compound is not
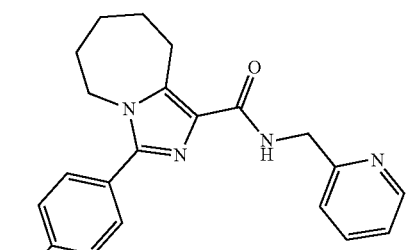
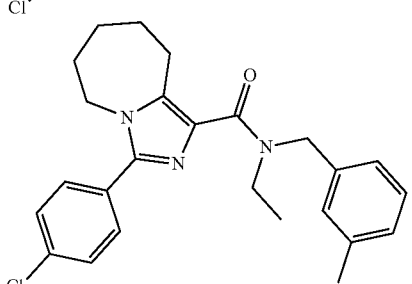
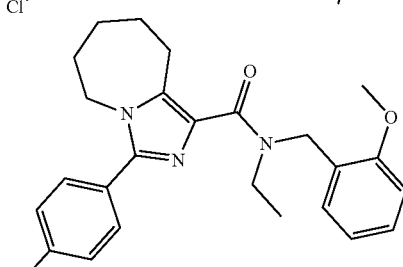
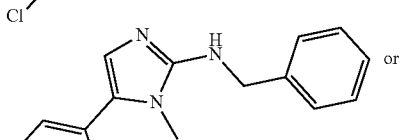
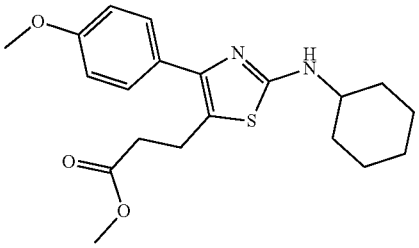
In one embodiment, the compound of Formula IIId is selected with the proviso that the compound is not
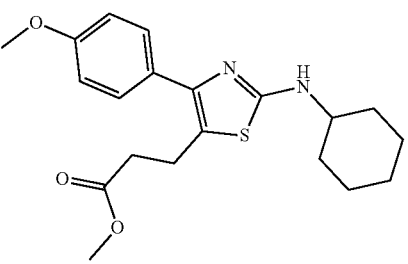

In one embodiment, the compound of Formula III is selected with the proviso that if X is S, then $R^1$ is not optionally substituted morpholino, thiomorpholino, piperinyl, indolyl, pyridyl, thienyl, aminophenyl, phenyl, methoxyphenyl, chloromethyl, amido, imadazothiazolyl, piperizinyl, pyrrolidino, thiazolyl, imidazolyl, or pyrazolyl.

In one embodiment, the compound of Formula IIId is selected with the proviso that Rid is not optionally substituted morpholino, thiomorpholino, piperinyl, indolyl, aminophenyl, chloromethyl, amido, imadazothiazolyl, piperizinyl, pyrrolidino, imidazolyl or pyrazolyl.

In one embodiment, the compound of Formula III is selected with the proviso that if X is S, then $R^2$ is not naphthyl or tetrahydronaphthyl.

In one embodiment, the compound of Formula III is selected with the proviso that if X is O and $R^1$ is phenyl or thienyl, then $R^8$ is not morpholino.

In one embodiment, the compound of Formula III is selected with the proviso that if X is NH and $R^1$ is heteroaryl, then $R^8$ is not morpholino.

In one embodiment, the compound of Formula IIId is selected with the proviso that $R^{2d}$ is not naphthyl or tetrahydronaphthyl.

In certain embodiments, the compounds for use in the compositions and methods provided herein are of Formula IV:

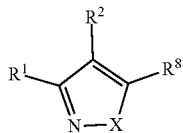

Formula IV or pharmaceutically acceptable derivatives thereof,
wherein $R^{1'}$ $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_p R^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

X is O or $NR^5$.

In another embodiment, the compound of Formula IV is a compound of Formula IVa:

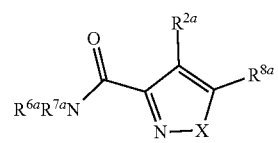

Formula IVa or pharmaceutically acceptable derivatives thereof,
wherein $R^{2a}$ is H or alkyl;

$R^{8a}$ is aryl or heteroaryl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and X is O or $NR^5$.

In another embodiment, the compound of Formula IVa is a compound wherein $R^{2a}$ is H;

$R^{8a}$ is phenyl, pyridinyl, or as shown below

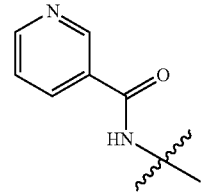 [SMILES: *NC(=O)c1cccnc1]

wherein phenyl is optionally substituted with a halogen;

$R^{6a}$ and $R^{7a}$ are independently selected from H, pyridinyl, cyclopropyl, cyclopentyl, or one of the following:

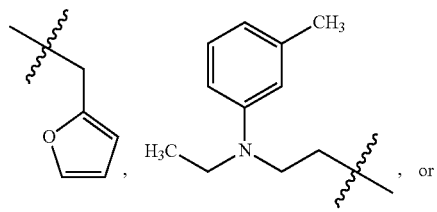

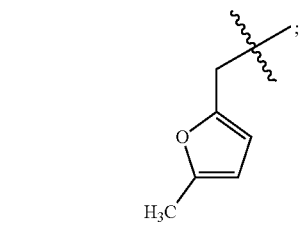

X is O or NH, or $NCH_3$.

In one embodiment, the compound of Formula IVa is:

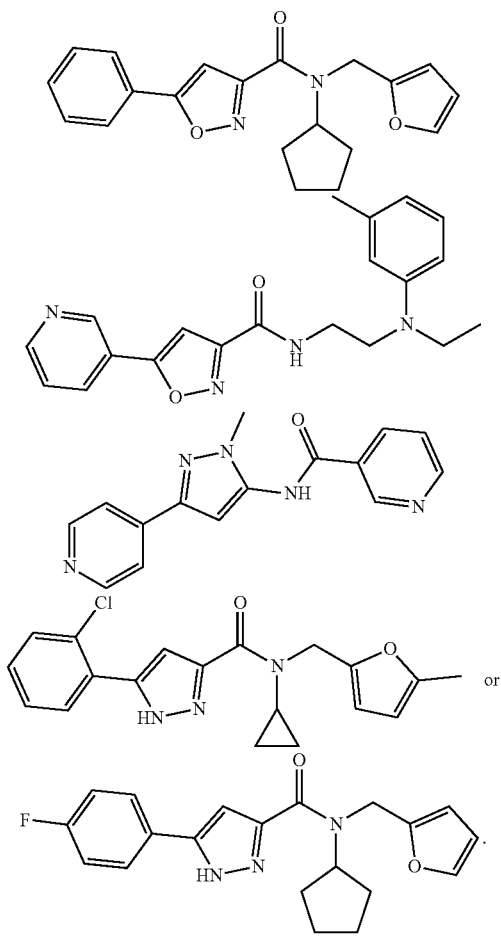

or

In another embodiment, the compound of Formula IV is a compound of Formula IVb:

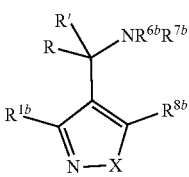

Formula IVb or pharmaceutically acceptable derivatives thereof,
wherein $R^{1a}$ is H or alkyl;
$R^{8a}$ is H or alkyl;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b}$ and $R^{7b}$ are combined to form a cyclic structure including the nitrogen atom to which they are both attached; and
R and R' are independently selected from hydrogen and alkyl, and R and R' are combined to form a cyclic structure including the carbon atom to which they are both attached; and
X is O or $NR^5$.

In another embodiment, Formula IVb is:

Formula IVb

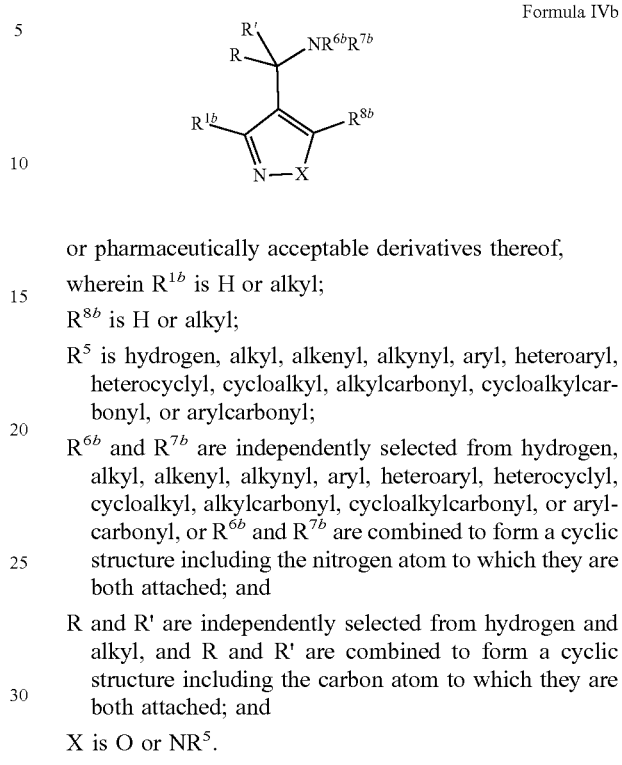

or pharmaceutically acceptable derivatives thereof,
wherein $R^{1b}$ is H or alkyl;
$R^{8b}$ is H or alkyl;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b}$ and $R^{7b}$ are combined to form a cyclic structure including the nitrogen atom to which they are both attached; and
R and R' are independently selected from hydrogen and alkyl, and R and R' are combined to form a cyclic structure including the carbon atom to which they are both attached; and
X is O or $NR^5$.

In another embodiment of Formula IVb, a compound of Formula IVb is a compound wherein
$R^{1b}$ is methyl;
$R^{8b}$ is methyl;
$R^{6b}$ and $R^{7b}$ are independently selected from hydrogen, methyl, or one of the following:

R and R' are hydrogen,
X is O or $NR^5$; and
$R^5$ is benzyl
wherein benzyl is substituted with a halogen.

In one embodiment, the compound of Formula IVb is:

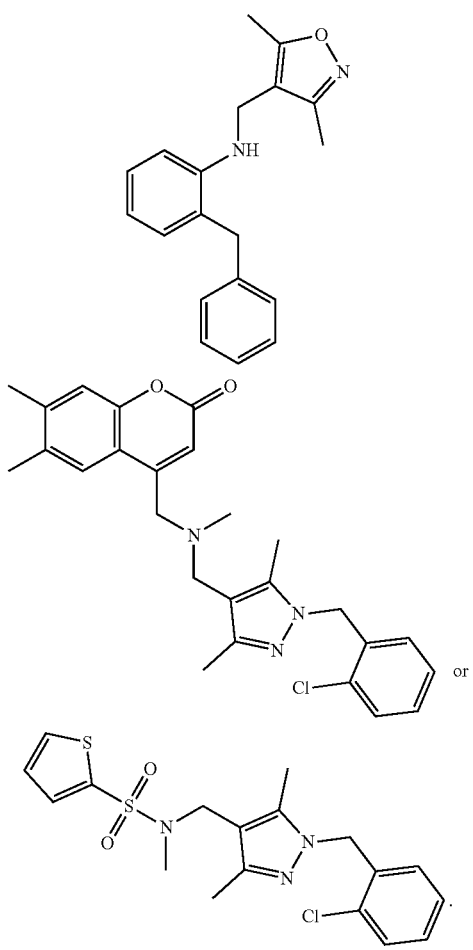

In another embodiment, the compound of Formula IV is a compound of Formula IVc:

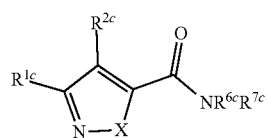

Formula IVc or pharmaceutically acceptable derivatives thereof,
wherein $R^{1c}$ is aryl or heteroaryl;
$R^{2c}$ is H, halo or alkyl;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^{6c}$ and $R^{7c}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6c}$ and $R^{7c}$ are combined to form a cyclic structure including the nitrogen atom to which they are both attached; and
X is O or $NR^5$.

In another embodiment of Formula IVc, a compound of Formula IVc is a compound wherein
$R^{1c}$ is phenyl
wherein phenyl is optionally substituted with methyl;
$R^{2e}$ is H or a halogen;
$R^{6c}$ and $R^{7c}$ are independently selected from cyclopropyl or one of the following:

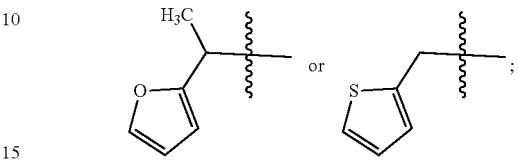

and
X is O or NH.

In one embodiment, the compound of Formula IVc is:

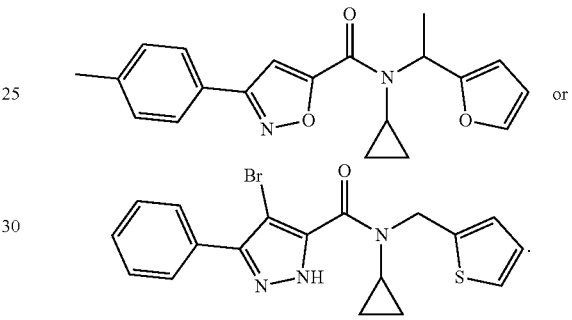

In another embodiment, the compound of Formula IV is a compound of Formula IVd:

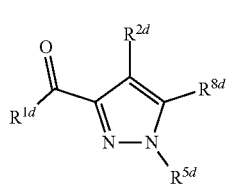

Formula IVd or pharmaceutically acceptable derivatives thereof,
wherein $R^{1d}$ is $OR^{3a}$ or $NR^{6d}R^{7d}$;
$R^{2d}$ is H, alkyl or halo;
$R^{3d}$ is hydrogen, alkyl, alkenyl, alkynyl, aryl, heteroaryl, heterocyclyl or cycloalkyl;
$R^{5d}$ is aryl, heteroaryl, arylalkyl or heteroarylalkyl;
$R^{6d}$ and $R^{7d}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6d}$ and $R^{7d}$ are combined to form a cyclic structure including the nitrogen atom to which they are both attached;
$R^{8d}$ is H or alkyl.

In another embodiment of Formula IVd, a compound of Formula IVd is a compound wherein
$R^{1d}$ is $OR^{3d}$ or $NR^{6d}R^{7d}$;
$R^{2d}$ is H, alkyl or halo;
$R^{3d}$ is hydrogen, alkyl, alkenyl, alkynyl, aryl, heteroaryl, heterocyclyl or cycloalkyl;
$R^{5d}$ is aryl, heteroaryl, arylalkyl or heteroarylalkyl;

$R^{6d}$ and $R^{7d}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6d}$ and $R^{7d}$ are combined to form a cyclic structure including the nitrogen atom to which they are both attached;

$R^{8d}$ is H or alkyl.

In another embodiment of Formula IVd, a compound of Formula IVd is a compound wherein $R^{1d}$ is $OR^{3d}$ or $NR^{6d}R^{7d}$;

$R^{2d}$ is H or Br;

$R^{3d}$ is methyl;

$R^{5d}$ is phenyl or as depicted below

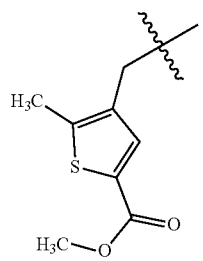

wherein phenyl is optionally substituted with one or two substituents each selected from halogen, methyl, or methoxy;

$R^{6d}$ and $R^{7d}$ are independently selected from hydrogen, pyridinylmethyl, bromophenyl, or as depicted below:

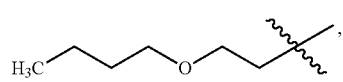 [SMILES: *CCOCCCC]

or $R^{6d}$ and $R^{7d}$ are combined to form a cyclic structure including the nitrogen atom to which they are both attached, as shown below

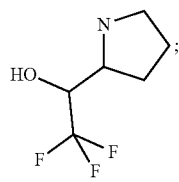 [SMILES: OC(C1CCCN1)C(F)(F)F]

and $R^{8d}$ is H or cyclopropyl.

In one embodiment, the compound of Formula IVd is:

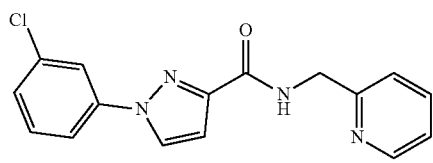

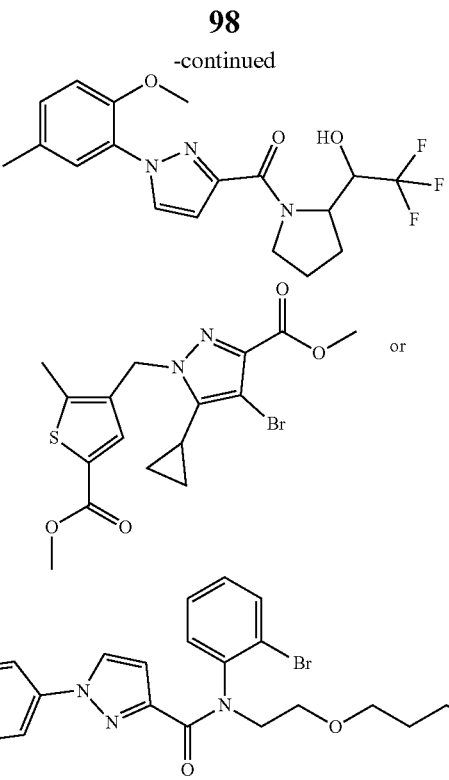

In another embodiment, the compound of Formula IV is a compound of Formula IVe:

Formula IVe or pharmaceutically acceptable derivatives thereof, wherein $R^{1e}$ is aryl or heteroaryl;

$R^2$ is H or alkyl;

$R^{5e}$ is H or alkyl; and $R^{6e}$ and $R^{7e}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6e}$ and $R^{7e}$ are combined to form a cyclic structure including the nitrogen atom to which they are both attached.

In another embodiment of Formula IV, a compound of Formula IVe is a compound wherein $R^{1e}$ is pyridinyl;

$R^{2e}$ is H;

$R^{5e}$ is H or methyl; and $R^{6e}$ and $R^{7e}$ are independently selected from hydrogen or the substituent as depicted below:

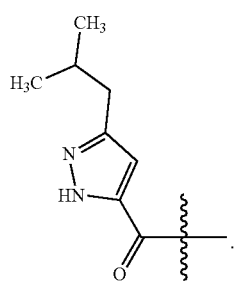 [SMILES: *C(=O)c1cc(CC(C)C)n[nH]1]

In one embodiment, the compound of Formula IVe is:

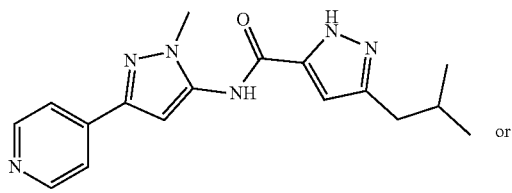

or

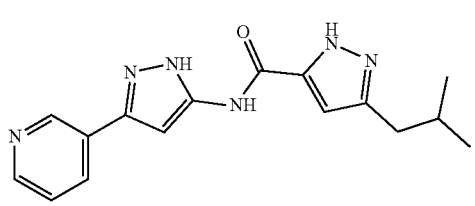

In another embodiment, the compound of Formula IV is a compound of Formula IVf:

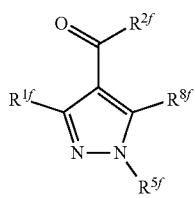

Formula IVf or pharmaceutically acceptable derivatives thereof, wherein $R^{1f}$ is H or alkyl;

$R^{2f}$ is aryl, heteroaryl or $NR^{6f}R^{7f}$;

$R^{5f}$ is aryl or heteroaryl;

$R^{8f}$ is H or alkyl;

$R^{6f}$ and $R^{7f}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6f}$ and $R^{7f}$ are combined to form a cyclic structure including the nitrogen atom to which they are both attached.

In another embodiment of Formula IVf, a compound of Formula IVf is a compound wherein:

$R^{1f}$ is H;

$R^{2f}$ is selected from one of the following:

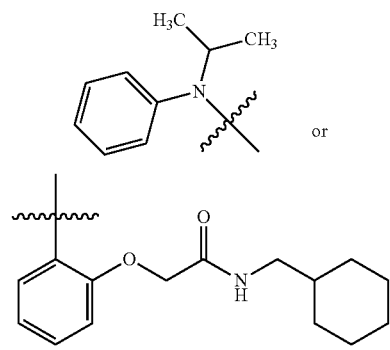

$R^{5f}$ is phenyl or pyridinyl; and $R^{8f}$ is H or methyl.

In one embodiment, the compound of Formula IVf is:

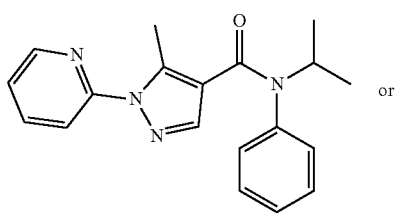

or

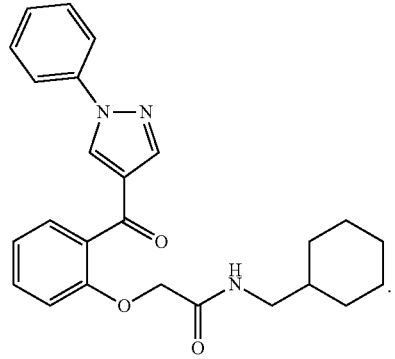

In one embodiment, the compound of Formula IV is selected with the proviso that the compound is not

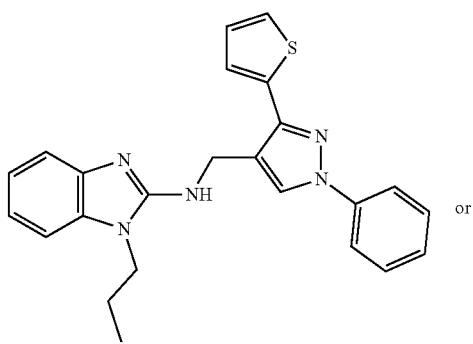

or

-continued

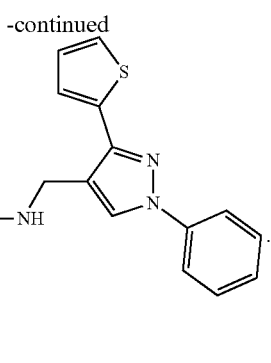

In one embodiment, the compound of Formula IVa is selected with the proviso that the compound is not

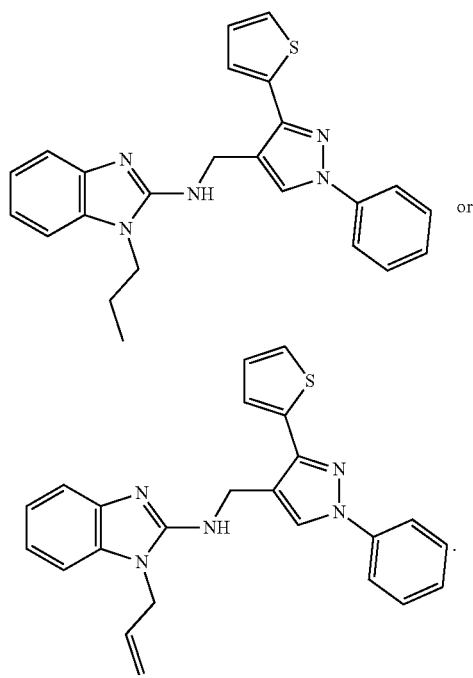

In one embodiment, the compound of Formula IV is selected with the proviso that if X is O, then $R^8$ is not optionally substituted morpholino.

In one embodiment, the compound of Formula IV is selected with the proviso that if X is N-aryl, then $R^2$ is not heteroaryl.

In certain embodiments, the compounds for use in the compositions and methods provided herein are of Formula V:

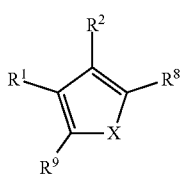

Formula V or pharmaceutically acceptable derivatives thereof, wherein $R^{1'}$ $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$; wherein $R^2$ and $R^8$ are combined to form a cyclic structure including the carbon atoms to which they are attached in the five-membered ring;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

X is O, S or $NR^5$.

In another embodiment, the compound of Formula V is a compound of Formula Va:

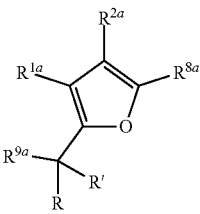

Formula Va or pharmaceutically acceptable derivatives thereof, wherein $R^{1a}$ is H or alkyl;

$R^{2a}$ is H or alkyl;

$R^{8a}$ is aryl, heteroaryl, $C(O)R^4$ or $S(O)_pR^4$;

$R^{9a}$ is $OR^3$, $NR^5C(O)R^4$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and p is 0-2.

In another embodiment of Formula V, a compound of Formula Va is a compound wherein $R^{1a}$ is H;
$R^{2a}$ is H;
$R^{8a}$ is phenyl, C(O)R$^4$ or S(O)$_p$R$^4$;
  wherein phenyl is substituted with halogen;
$R^{9a}$ is OR$^3$, NR$^6$R$^7$, or selected from one of the following

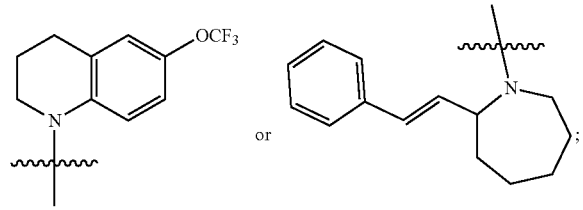 [SMILES: *N1CCCc2cc(OC(F)(F)F)ccc21 ; *N1CCCCCC1/C=C/c1ccccc1]

$R^3$ is phenyl,
  wherein phenyl is optionally substituted with one or two substituents each selected from halogen, methoxy and methyl;
$R^4$ is selected from the following:

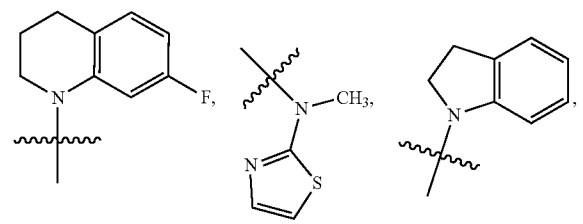

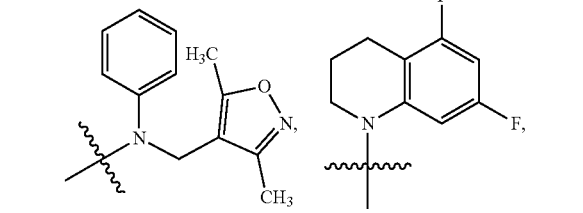

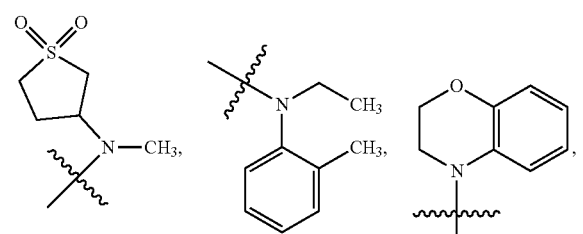

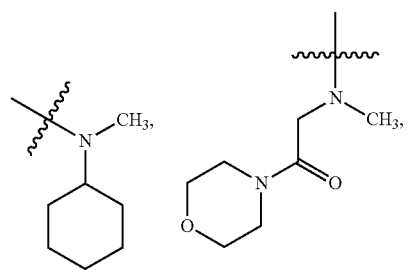

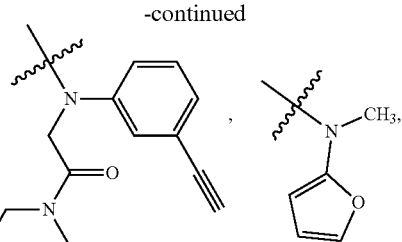

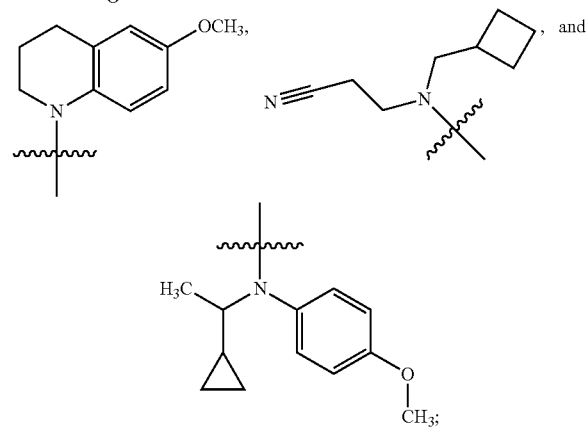

$R^6$ and $R^7$ are independently selected from ethyl, phenyl, or biphenyl;
R and R' are H; and
p is 2.

In another embodiment of Formula V, a compound of Formula Va is a compound wherein
$R^{1a}$ is H;
$R^{2a}$ is H;
$R^{8a}$ is phenyl, C(O)R$^4$ or S(O)$_p$R$^4$;
  wherein phenyl is substituted with halogen;
$R^{9a}$ is OR$^3$, NR$^6$R$^7$, or selected from one of the following

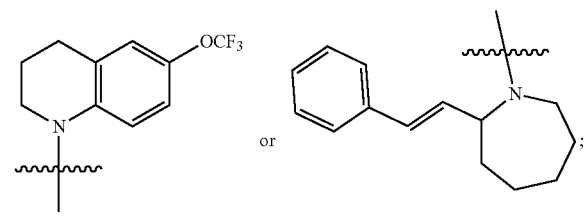 [SMILES: *N1CCCc2cc(OC(F)(F)F)ccc21 ; *N1CCCCCC1/C=C/c1ccccc1]

$R^3$ is phenyl,
  wherein phenyl is optionally substituted with one or two substituents each selected from halogen, methoxy and methyl;
$R^4$ is selected from the following:

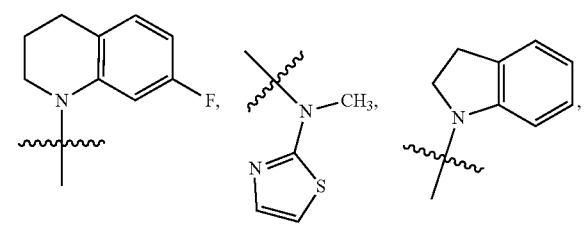

105
-continued
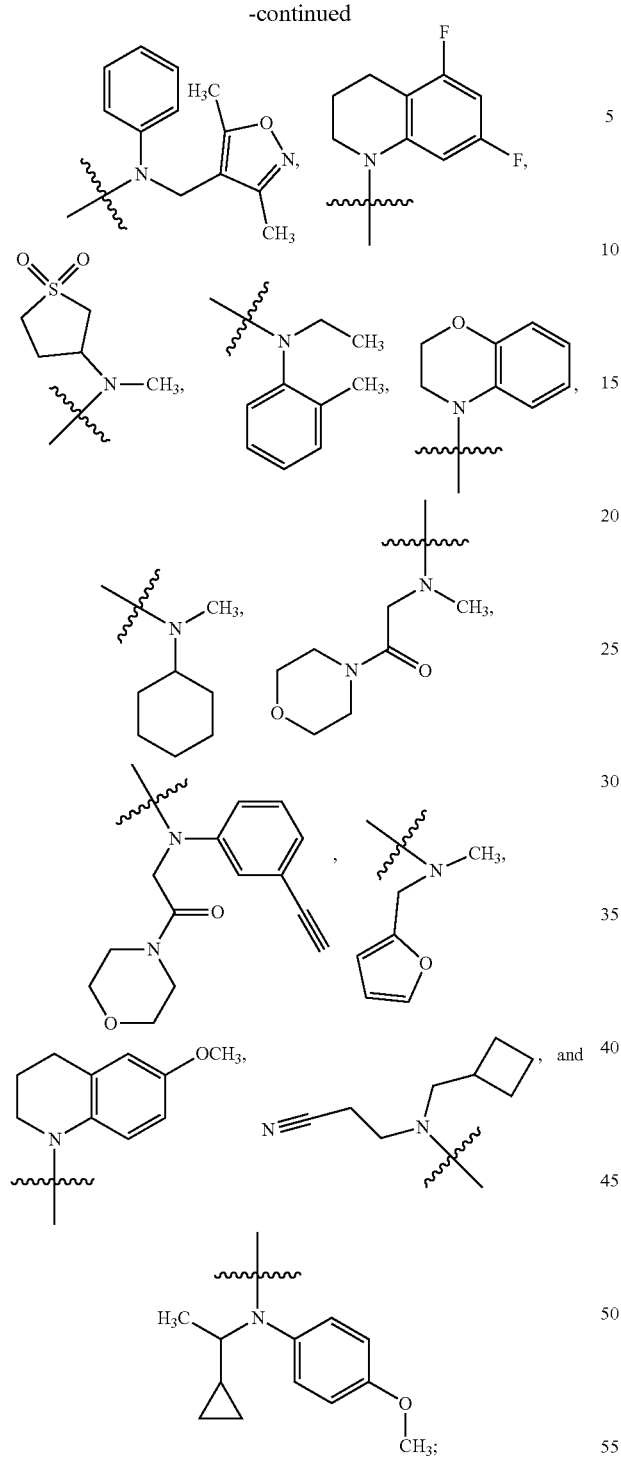
106
In one embodiment, the compound of Formula Va is:
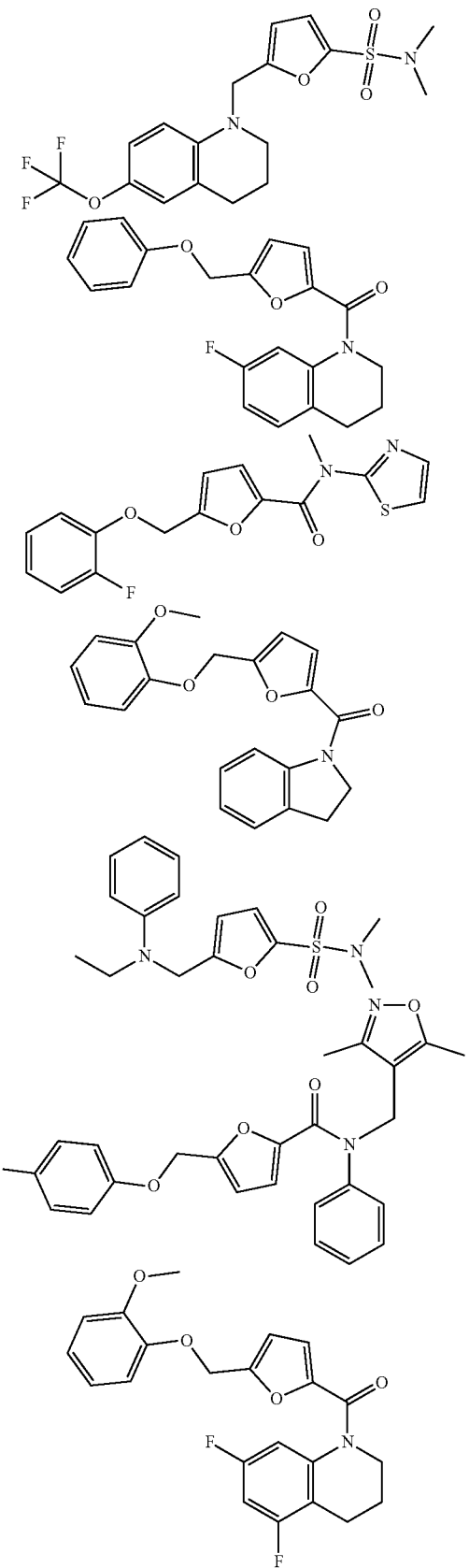
$R^6$ and $R^7$ are independently selected from ethyl, phenyl, or biphenyl;
R and R' are H; and
p is 2.

107
-continued
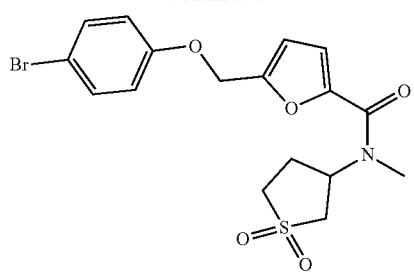
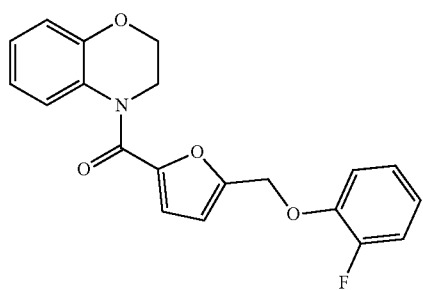
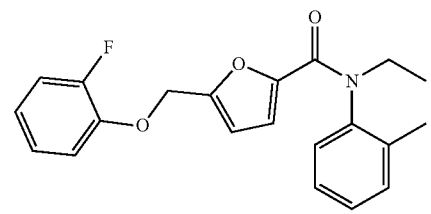
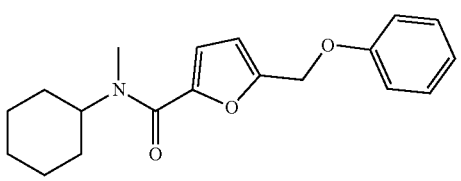
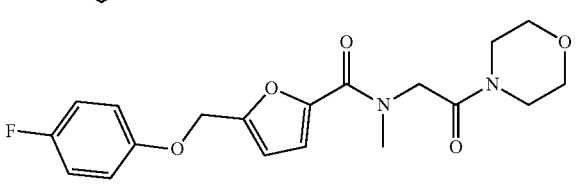
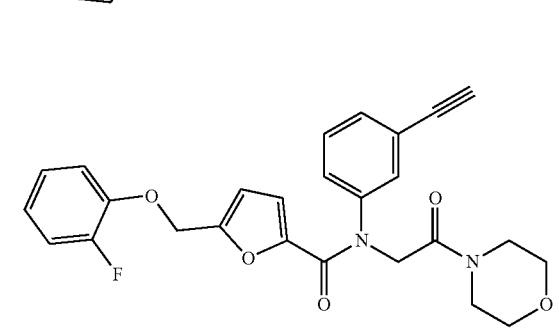
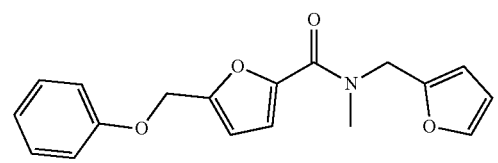
108
-continued
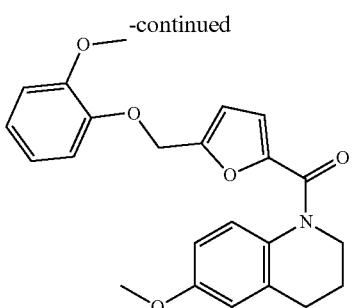
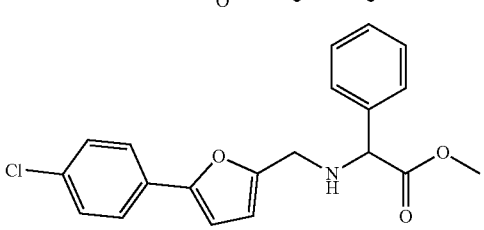
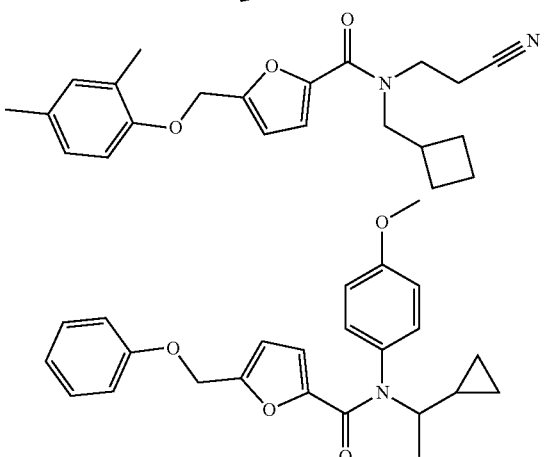
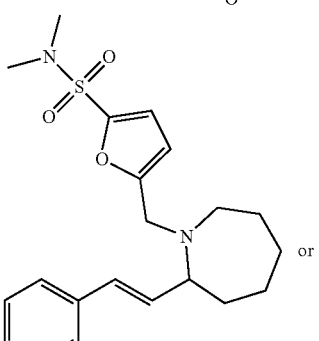
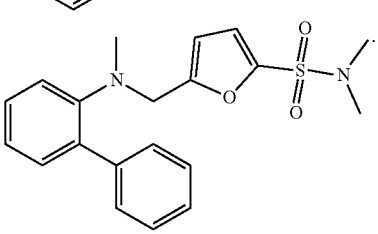
In another embodiment, the compound of Formula V is a compound of Formula Vb:

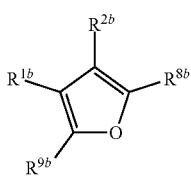

Formula Vb or pharmaceutically acceptable derivatives thereof, wherein $R^{1b}$ is H or alkyl;
$R^{2b}$ is H or alkyl;
$R^{8b}$ is $C(O)R^4$ or $S(O)_pR^4$;
$R^{9b}$ is aryl, heteroaryl, halo or $C(O)R^4$;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
X is O or $NR^5$; and
p is 0-2.

In another embodiment, Formula Vb is:

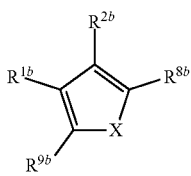

Formula Vb or pharmaceutically acceptable derivatives thereof, wherein $R^{1b}$ is H or alkyl;
$R^{2b}$ is H or alkyl;
$R^{8b}$ is $C(O)R^4$ or $S(O)_pR^4$;
$R^{9b}$ is aryl, heteroaryl, halo or $C(O)R^4$;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
X is O, S or $NR^5$; and
p is 0-2.

In another embodiment of Formula Vb, a compound of Formula Vb is a compound wherein
$R^{1b}$ is H, halogen, or $COCH_3$;
$R^{2b}$ is H, halogen, or $COCH_3$;

$R^{8b}$ is $C(O)R^4$;
$R^{9b}$ is H, halogen, phenyl, or $C(O)R^4$;
wherein phenyl is optionally substituted with halogen;
$R^4$ is $NR^6R^7$;
$R^6$ and $R^7$ are independently selected from H, cyclopropyl, thienylmethyl, furanylmethyl, cyclopentyl, methyl, and benzyl;
wherein benzyl is substituted with two methoxy substituents;
X is O, S or $NCH_3$; and
p is 2.

In one embodiment, the compound of Formula Vb is:

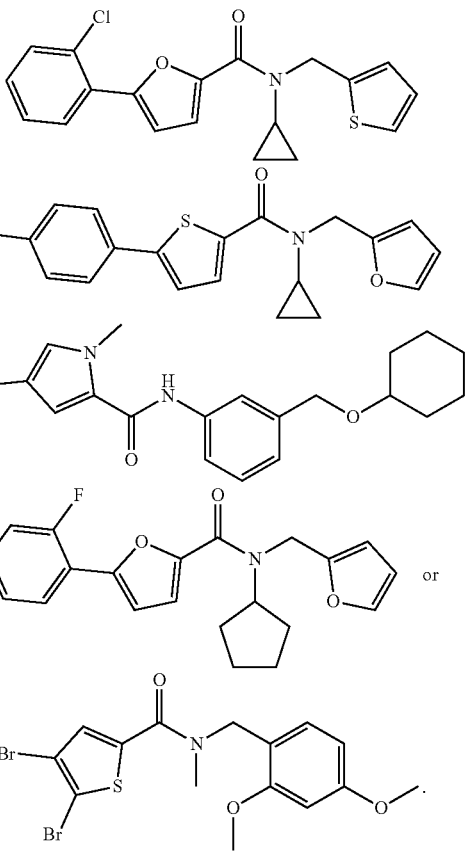

In another embodiment, the compound of Formula V is a compound of Formula Vc:

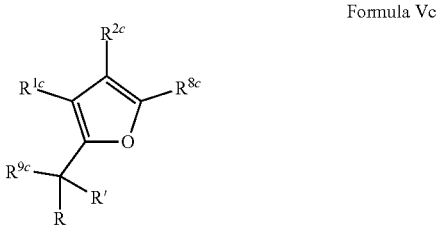

Formula Vc or pharmaceutically acceptable derivatives thereof, wherein $R^{1c}$ is H, alkyl or $C(O)R^4$;
$R^{2c}$ is H, alkyl or $C(O)R^4$;
$R^{8c}$ is H or alkyl;
$R^{9c}$ is $OR^3$, $NR^5C(O)R^4$ or $NR^6R^7$;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and R and R' are independently selected from hydrogen and alkyl, and R and R' are combined to form a cyclic structure including the carbon atom to which they are both attached.

In another embodiment of Formula Vc, a compound of Formula Vc is a compound wherein R$^{1c}$ is H or C(O)R⁴;
R$^{2c}$ is H or C(O)R⁴;
R$^{8c}$ is H or methyl;
R$^{9c}$ is OR³;
R³ is selected from one of the following:

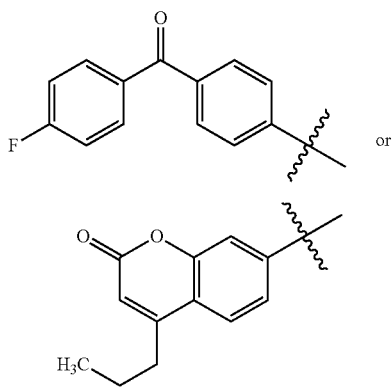

R⁴ is methyl; and
R and R' are H.

In one embodiment, the compound of Formula Vc is:

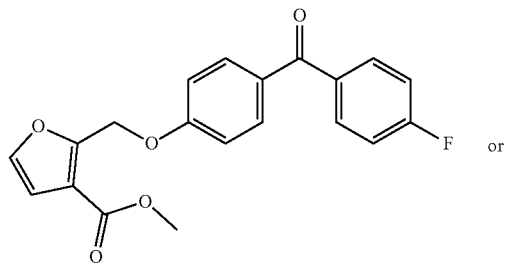

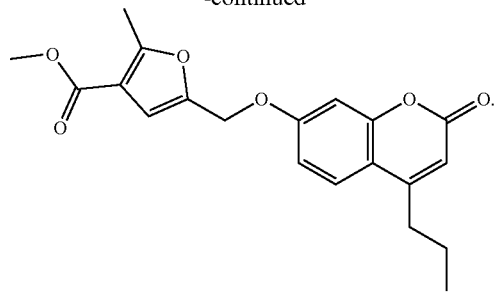

In another embodiment, the compound of Formula V is a compound of Formula Vd:

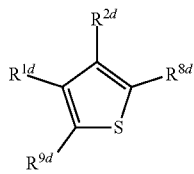

Formula Vd or pharmaceutically acceptable derivatives thereof,
wherein R$^{1d}$ is H, alkyl, aryl or heteroaryl;
R$^{2d}$ is C(O)R⁴;
R$^{1d}$ is NR⁵C(O)R⁴ or N=C(R)NR⁶R⁷;
R$^{9d}$ is H, alkyl, arylalkyl or heteroarylalkyl; wherein R$^{1d}$ and R$^{9d}$ are combined to form a cyclic structure including the carbon atoms to which they are attached in the five-membered ring;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and R and R' are independently selected from hydrogen and alkyl, or R and R' are combined to form a cyclic structure including the carbon atom to which they are both attached.

In another embodiment of Formula Vd, a compound of Formula Vd is a compound wherein
wherein R$^{1d}$ is H, methyl, or phenyl,
wherein phenyl is optionally substituted with methyl or halogen;
R$^{2d}$ is C(O)R⁴, or as depicted below

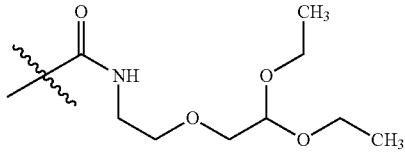 [SMILES: *C(=O)NCCOCC(OCC)OCC]

$R^{8d}$ is phenyl or $NR^5C(O)R^4$, wherein phenyl is substituted with propyl;

$R^{9d}$ is H, methyl, benzodioxylphenylmethyl, and wherein $R^{1d}$ and $R^{9d}$ are combined to form a seven-membered cyclic structure including the carbon atoms to which they are attached in the five-membered ring;

$R^4$ is ethyl, methyl, t-butyl, benzyl or as depicted below

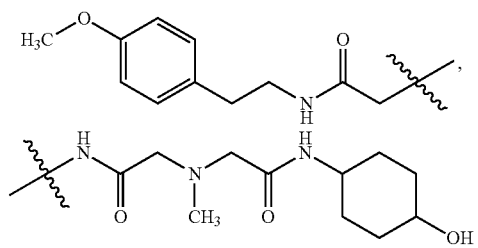

wherein benzyl is optionally substituted with 1-3 substituents each selected from methoxy $R^5$ is H; and R and R' are H.

In another embodiment of Formula Vd, a compound of Formula Vd is a compound wherein wherein $R^{1d}$ is H, methyl, or phenyl, wherein phenyl is optionally substituted with methyl or halogen;

$R^{2d}$ is $C(O)R^4$, or as depicted below

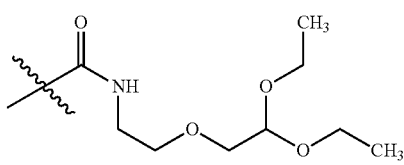 [SMILES: *C(=O)NCCOCC(OCC)OCC]

$R^{8d}$ is phenyl or $NR^5C(O)R^4$, wherein phenyl is substituted with propyl;

$R^{9d}$ is H, methyl, benzodioxylphenylmethyl, and wherein $R^{1d}$ and $R^{9d}$ are combined to form a seven-membered cyclic structure including the carbon atoms to which they are attached in the five-membered ring;

$R^4$ is ethyl, methyl, t-butyl, benzyl, p-isopropylphenyl or as depicted below

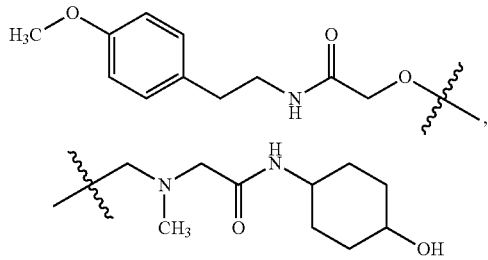

wherein benzyl is optionally substituted with 1-3 substituents each selected from methoxy $R^5$ is H; and R and R' are H.

In one embodiment, the compound of Formula Vd is:

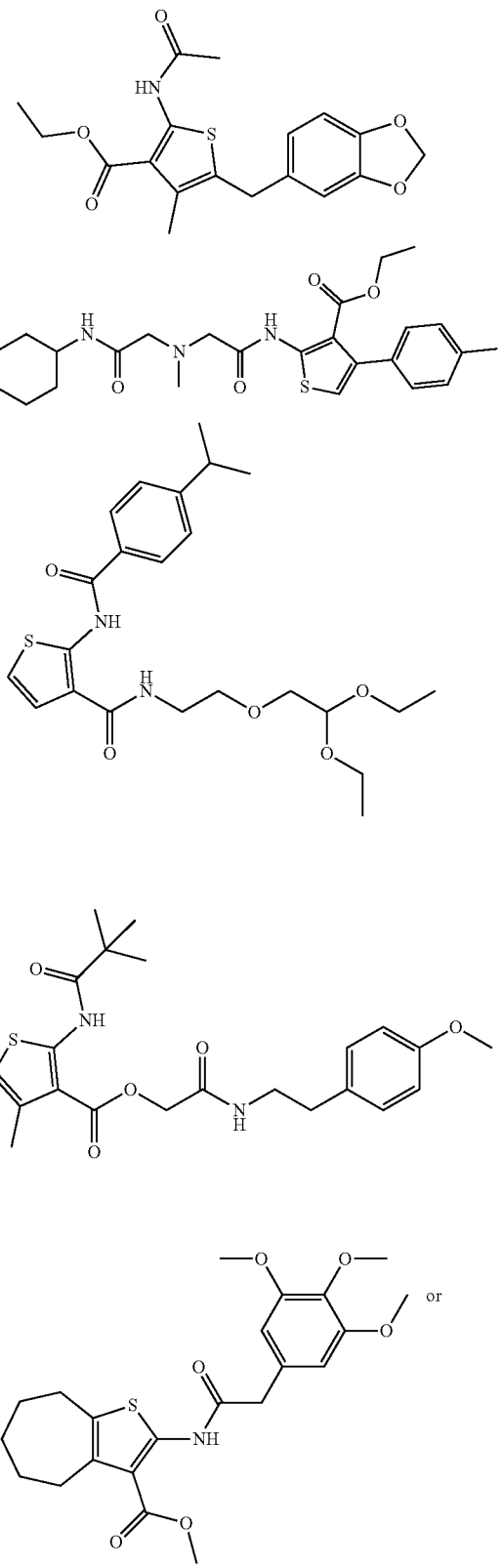

-continued

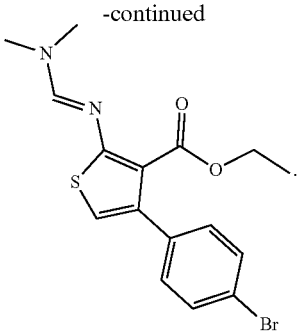

In another embodiment, the compound of Formula V is a compound of Formula Ve:

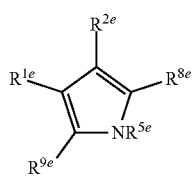

Formula Ve or pharmaceutically acceptable derivatives thereof,
wherein $R^{1e}$ is H or alkyl;
$R^{2e}$ is $C(O)R^4$;
$R^{8e}$ is H or alkyl;
$R^{9e}$ is H or alkyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^{5e}$ is hydrogen, alkyl, alkenyl, alkynyl, aryl, heteroaryl, heterocyclyl, cycloalkyl, alkylcarbonyl, cycloalkylcarbonyl, or arylcarbonyl; and
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula Ve, a compound of Formula Ve is a compound wherein
$R^{1e}$ is H;
$R^{2e}$ is $C(O)R^4$;
$R^{8e}$ is H or alkyl;
$R^{9e}$ is H or alkyl;
$R^4$ is selected from the following:

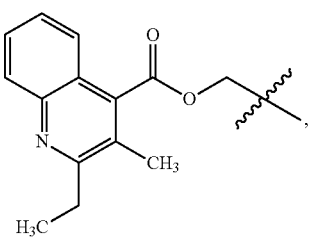

-continued

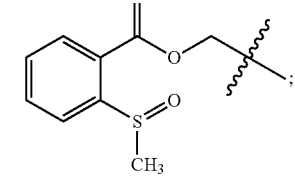

, or

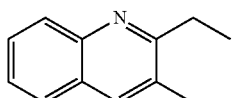

;

$R^{5e}$ is methoxyethyl, propenyl, or cyclohexenylpropyl.
In one embodiment, the compound of Formula Ve is:

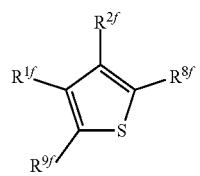

In another embodiment, the compound of Formula V is a compound of Formula Vf:

Formula Vf

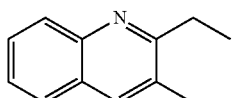

or pharmaceutically acceptable derivatives thereof, wherein $R^{1f}$ is H or alkyl;
$R^{2f}$ is $S(O)_pR^4$;
$R^{8f}$ is $C(O)R^4$;
$R^{9f}$ is aryl, H or alkyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In another embodiment of Formula Vf, a compound of Formula Vf is a compound wherein
$R^{1f}$ is H;
$R^{2f}$ is $S(O)_pR^4$;
$R^{8f}$ is $C(O)R^4$;
$R^{9f}$ is aryl H or alkyl;
$R^4$ is thiomorpholinyl or as depicted below

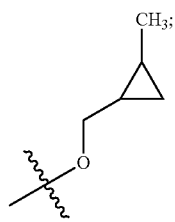 [SMILES: *OCC1CC1C]

and
p is 2.

In one embodiment, the compound of Formula Vf is:

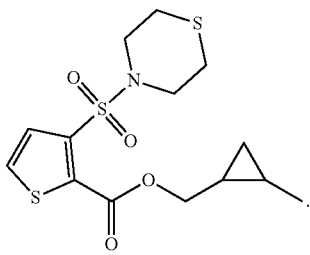 [SMILES: CC1CC1COC(=O)c1sccc1S(=O)(=O)N1CCSCC1]

In one embodiment, the compound of Formula V is selected with the proviso that the compound is not

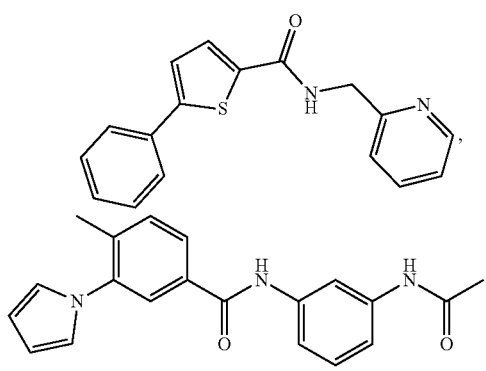

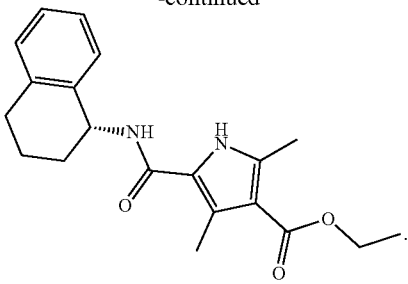

In one embodiment, the compound of Formula V is selected with the proviso that if X is S and $R^9$ is aryl, then neither $R^8$ nor $R^2$ is morpholino.

In one embodiment, the compound of Formula V is selected with the proviso that if X is S and $R^9$ is aryl, heteroaryl, oxazolidinonyl, arylcarbonyl, then $R^8$ is not morpholino, acyl or an ester.

In certain embodiments, the compounds for use in the compositions and methods provided herein are of Formula VI:

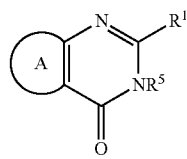

Formula VI or pharmaceutically acceptable derivatives thereof, wherein $R^{1i}$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

A is a substituted or unsubstituted 5 or 6 membered aryl, heteroaryl, carbocyclic or heterocyclic ring.

In another embodiment, the compound of Formula VI is a compound of Formula VIa:

Formula VIa

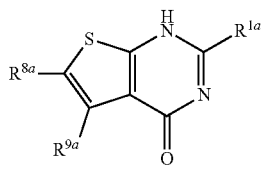

or pharmaceutically acceptable derivatives thereof,
wherein $R^{1a}$ is aryl or heteroaryl;
$R^a$, is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^{9a}$, is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In one embodiment of Formula VIa, a compound of Formula VIa is a compound wherein
wherein $R^{8a}$ is aryl or heteroaryl;
$R^{8a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^{9a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In another embodiment of Formula VIa, a compound of Formula VIa is a compound wherein
$R^a$ is pyridinyl,
wherein pyridinyl is optionally substituted with one or two substituents each selected from $OR^3$;
$R^3$ is difluoroethyl;

$R^{8a}$ is H, methyl, phenyl, $C(O)R^4$;
$R^{9a}$ is H, phenyl, methyl, thienyl, ethyl, furanyl, or butyl, wherein phenyl is optionally substituted with a substituent selected from halogen or methoxy;
$R^4$ is —$NR^6R^7$; and
$R^6$ and $R^7$ are independently selected from H, methyl, and ethyl.

In one embodiment, the compound of Formula VIa is:

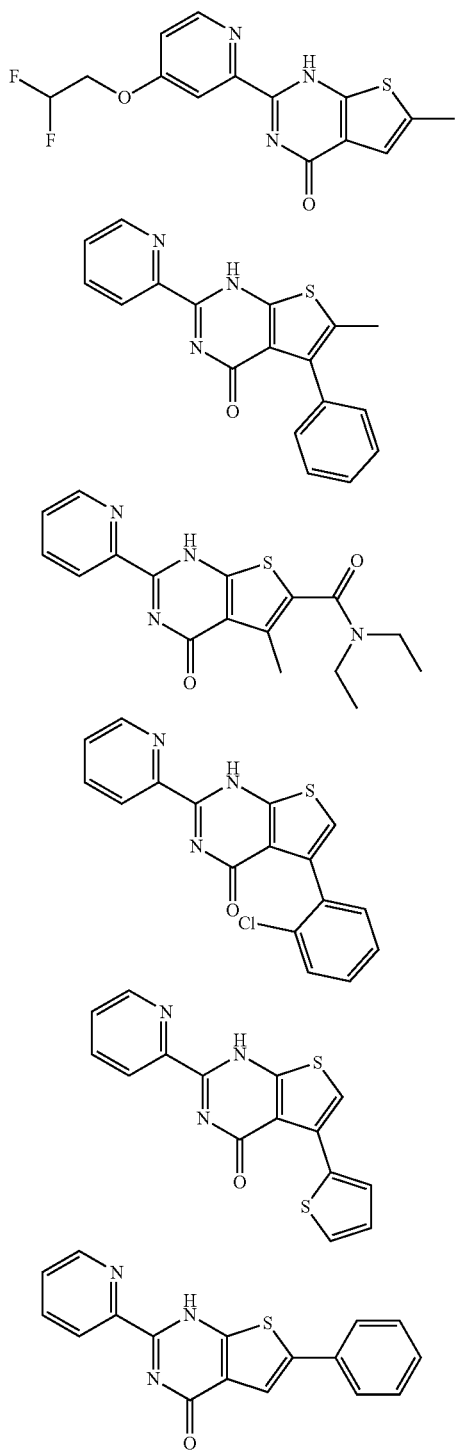

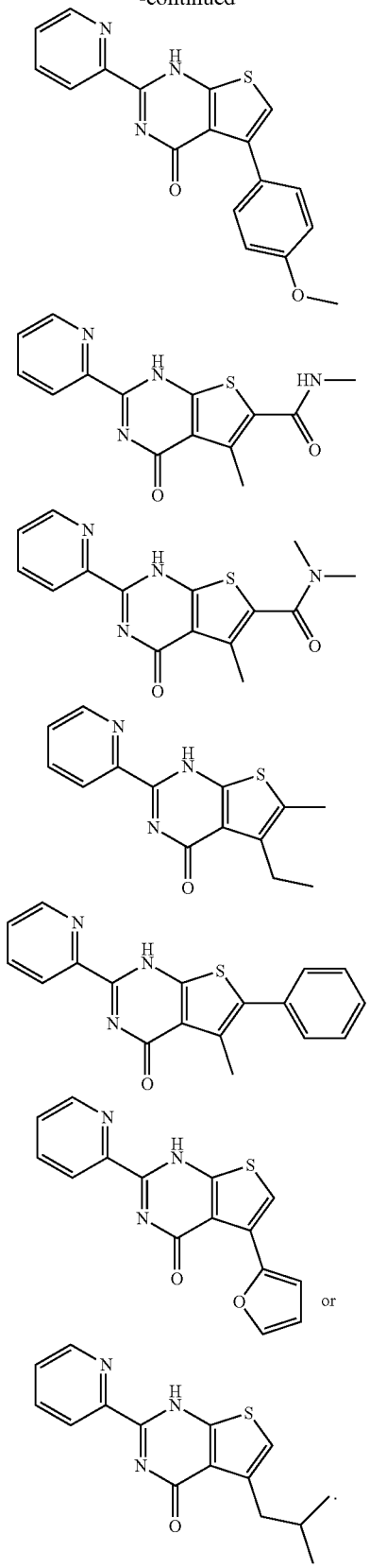

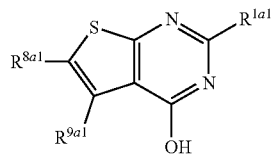

Formula VIa1 or pharmaceutically acceptable derivatives thereof, wherein $R^{1a1}$ is aryl, heteroaryl or $NR^6R^7$;
$R^{8a1}$ is H or alkyl;
$R^{9a1}$ is H, alkyl, alkenyl, carbocyclic, halo, pseudohalo, trifluoromethyl, cyano, or $C(O)NR^6R^7$; and
$R^6$ and $R^7$ are independently selected from H, methyl, and ethyl.

In another embodiment of Formula VIa1, a compound of Formula VIa1 is a compound wherein
$R^{1a1}$ is aryl, heteroaryl $NR^6R^7$;
$R^{8a1}$ is H, aryl, or alkyl;
$R^{9a1}$ is H, alkyl, alkenyl, halo or pseudohalo; and
$R^6$ and $R^7$ are independently selected from H, methyl, and ethyl.

In another embodiment of Formula VIa1, a compound of Formula VIa1 is a compound wherein
$R^{1a1}$ is aryl, heteroaryl or $NR^6R^7$;
$R^{8a1}$ is H or alkyl;
$R^{9a1}$ is alkyl, alkenyl, halo or pseudohalo, wherein the alkyl group is not $CH_3$; and
$R^6$ and $R^7$ are independently selected from H, methyl, and ethyl.

In another embodiment of Formula VIa1, a compound of Formula VIa1 is a compound wherein
$R^{1a1}$ is pyridinyl or $NH_2$,
$R^{8a1}$ is H or methyl;
$R^{9a1}$ is H or methyl.

In one embodiment, the compound of Formula VIa1 is:

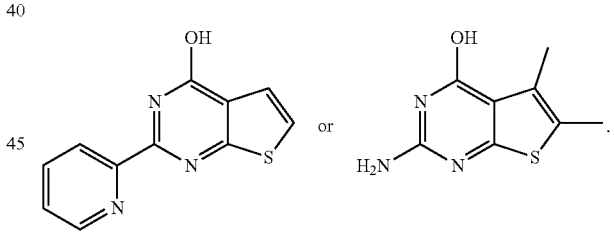

In another embodiment of Formula VIa1, a compound of Formula VIa1 is a compound wherein
$R^{1a1}$ is pyridinyl,
$R^{8a1}$ is H or methyl;
$R^{9a1}$ is fluoro, bromo, chloro or iodo.

In one embodiment, the compound of Formula VIa1 is:

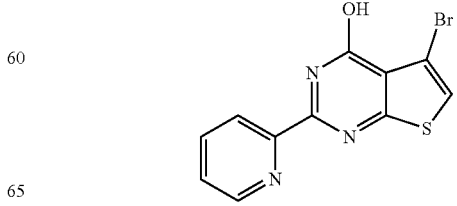

In another embodiment, the compound of Formula VI is a compound of Formula VIa1:

In another embodiment of Formula VIa1, a compound of Formula VIa1 is a compound wherein
$R^{1a1}$ is 2-pyridinyl.

In another embodiment of Formula VIa1, a compound of Formula VIa1 is a compound wherein $R^{1a1}$ is methoxypyridinyl.

In another embodiment of Formula VIa1, a compound of Formula VIa1 is a compound wherein
$R^{1a1}$ is 2-pyridyl;
$R^{8a1}$ is H or Ph;
$R^{9a1}$ is carbocyclic, halo, trifluoromethyl, cyano, or C(O)NR$^6$R$^7$;
$R^6$ is H or alkyl;
and $R^7$ is alkyl.

In another embodiment of Formula VIa1, a compound of Formula VIa1 is a compound wherein
$R^{1a1}$ is 2-pyridyl;
$R^{8a1}$ is H or methyl;
$R^{9a1}$ is carbocyclic, halo, trifluoromethyl, cyano, or C(O)NR$^6$R$^7$;
$R^6$ is H or alkyl;
and $R^7$ is alkyl.

In another embodiment, the compound of Formula VI is a compound of Formula VIb:

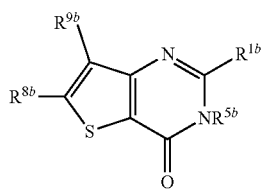

Formula VIb or pharmaceutically acceptable derivatives thereof,
wherein $R^{1b}$ is aryl, heteroaryl, S(O)$_p$R$^4$, NR$^5$C(O)R$^4$, or NR$^6$R$^7$;
$R^{8b}$ is H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, or NR$^6$R$^7$;
$R^{9b}$ is H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, or NR$^6$R$^7$; or $R^{8b}$ and $R^{9b}$ are combined to form a cyclic structure including the carbon atoms to which they are attached in the five-membered ring;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^{5b}$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In another embodiment of Formula VIb, a compound of Formula VIb is a compound wherein
$R^{1b}$ is pyridinyl, S(O)$_p$R$^4$,

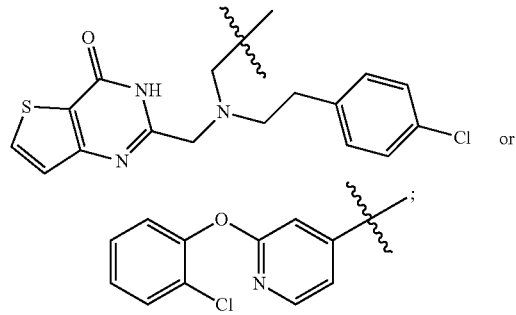

$R^{8b}$ is H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, or NR$^6$R$^7$;
$R^{9b}$ is H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, or NR$^6$R$^7$; wherein $R^{8b}$ and $R^{9b}$ are combined to form a cyclic structure including the carbon atoms to which they are attached in the five-membered ring;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is depicted below

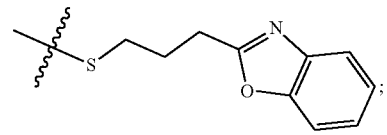 [SMILES: *SCCCc1nc2ccccc2o1]

$R^{5b}$ is hydrogen or ethyl;
p is 0.

In one embodiment, the compound of Formula VIb is:

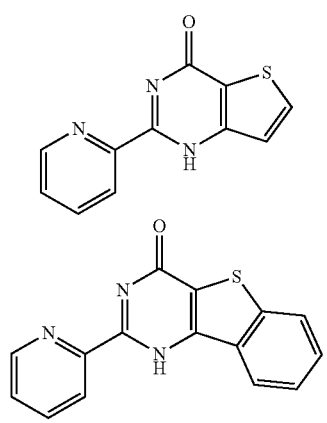

-continued

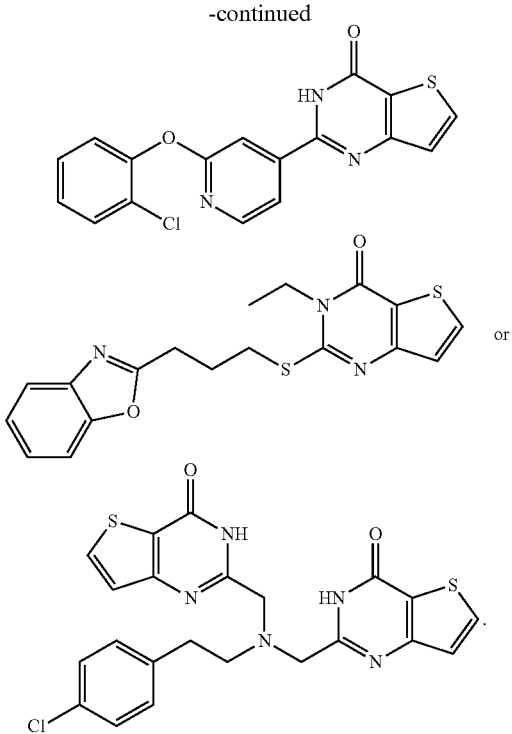

In another embodiment, the compound of Formula VIb is a compound of Formula VIb1:

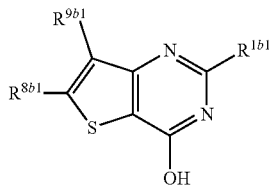

Formula VIb1 or pharmaceutically acceptable derivatives thereof, wherein $R^{1b1}$ is aryl, heteroaryl, or $NR^6R^7$;
$R^{8b1}$ is H or alkyl;
$R^{9b1}$ is aryl, heteroaryl, heterocyclyl, halo, pseudohalo, $C(O)R^4$, or $S(O)_pR^4$;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In another embodiment of Formula VIb1, a compound of Formula VIb1 is a compound wherein
$R^{1b1}$ is pyridyl;
$R^{8b1}$ is H or alkyl;
$R^{9b1}$ is substituted phenyl, heteroaryl, heterocyclyl, fluoro, chloro, iodo, $C(O)R^4$, or $S(O)_pR^4$, wherein the heteroaryl group is not a substituted pyrazole;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.

In another embodiment of Formula VIb1, a compound of Formula VIb1 is a compound wherein
$R^{1b1}$ is pyridinyl or $NH_2$;
$R^{8b1}$ is H;
$R^{9b1}$ is aryl, heteroaryl, halo, heterocyclyl or $C(O)R^4$;
$R^4$ is —$NR^6R^7$; and
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In another embodiment of Formula VIb1, a compound of Formula VIb1 is a compound wherein
$R^{1b1}$ is 2-pyridyl;
$R^{8b1}$ is H or methyl;
$R^{9b1}$ is substituted phenyl, heteroaryl, heterocyclyl, $C(O)NR^6R^7$, wherein the heteroaryl group is not a substituted pyrazole; and
$R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, a compound of Formula VIb1 is a compound wherein
$R^{1b1}$ is 2-pyridyl;
$R^{8b1}$ is H;
$R^{9b1}$ is substituted phenyl, heteroaryl, heterocyclyl, $C(O)NR^6R^7$, wherein the heteroaryl group is not a substituted pyrazole; and
$R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, a compound of Formula VIb1 is a compound wherein
$R^{1b1}$ is $NH_2$;
$R^{8b1}$ is H;
$R^{9b1}$ is Br,

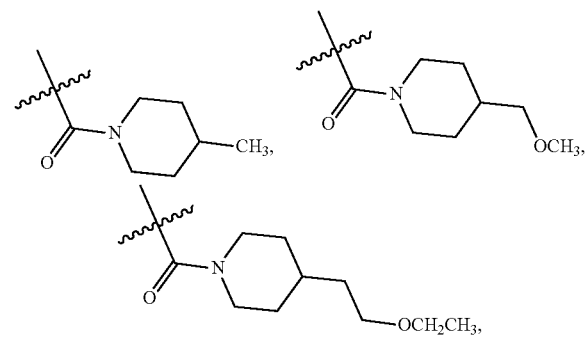

-continued
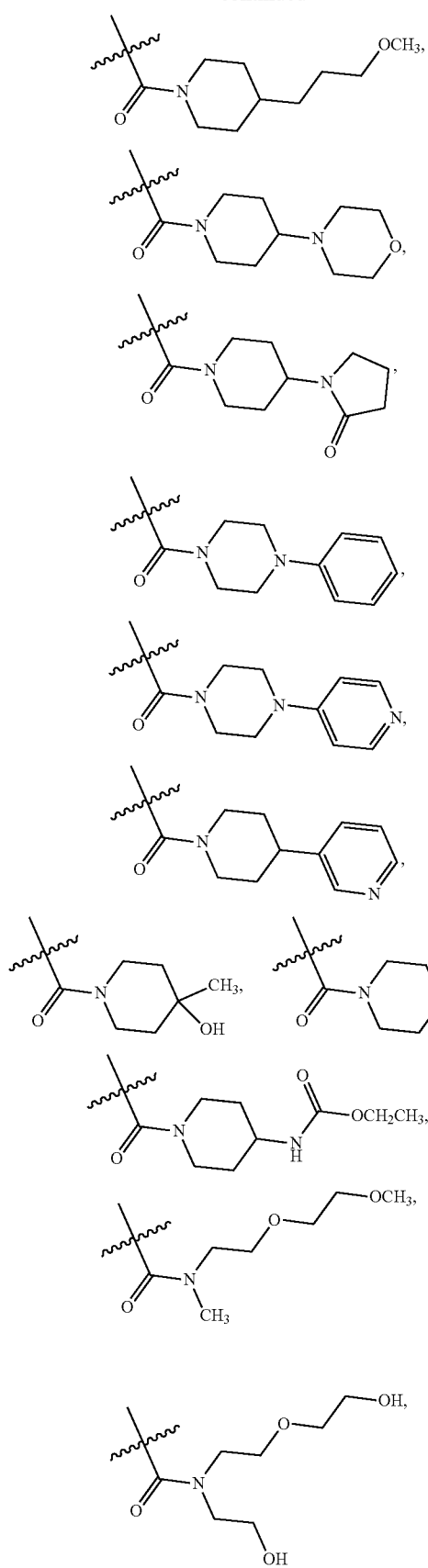
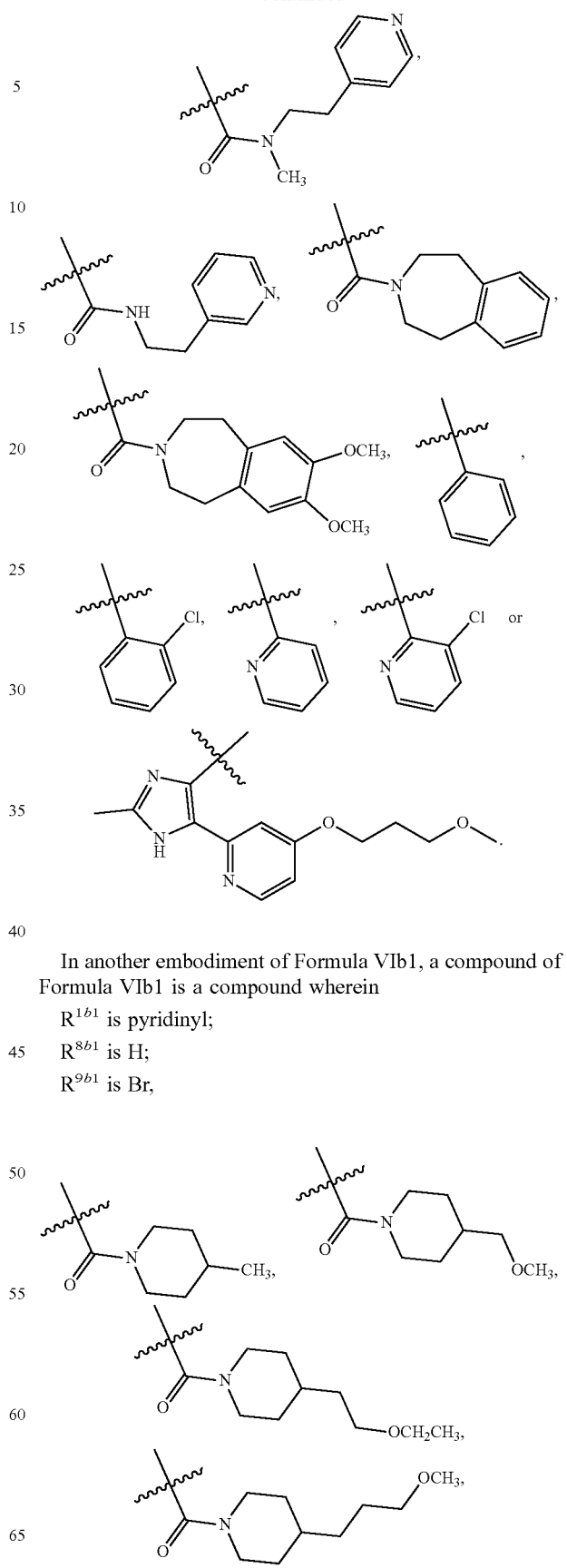
In another embodiment of Formula VIb1, a compound of Formula VIb1 is a compound wherein
$R^{1b1}$ is pyridinyl;
$R^{8b1}$ is H;
$R^{9b1}$ is Br, 129
-continued
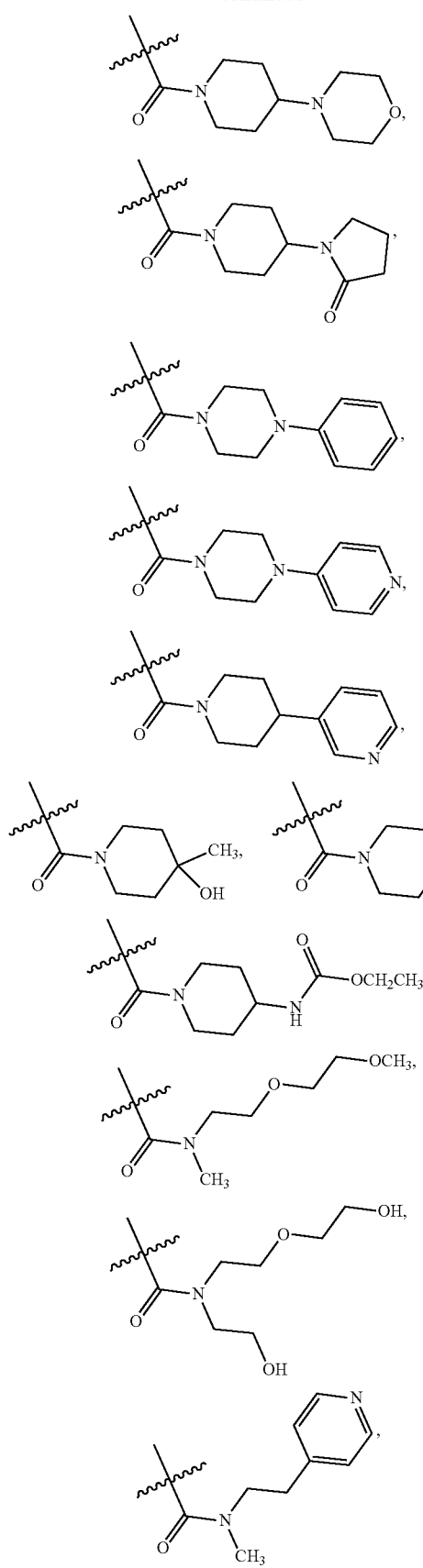
130
-continued
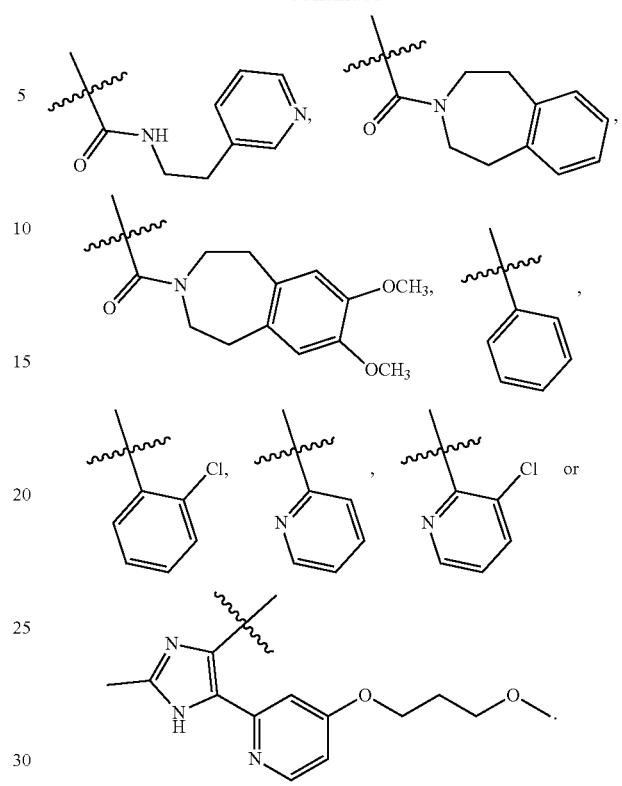
In another embodiment of Formula VIb1, a compound of Formula VIb1 is a compound wherein $R^{161}$ is 2-pyridyl.
In one embodiment, the compound of Formula VIb1 is:
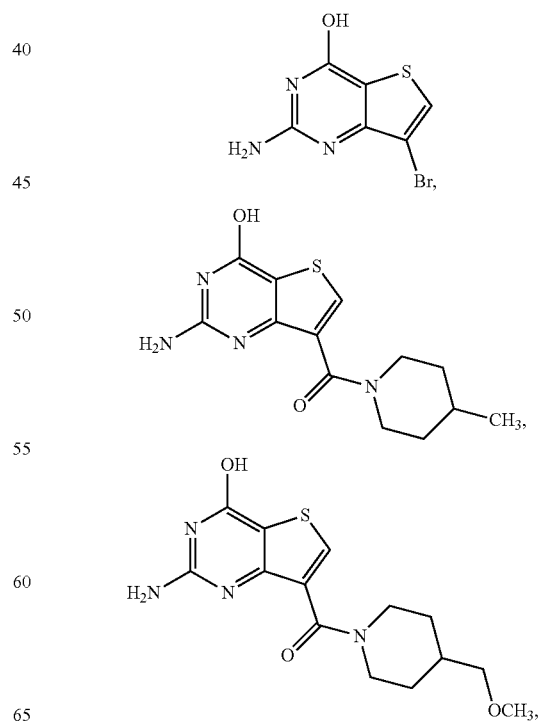

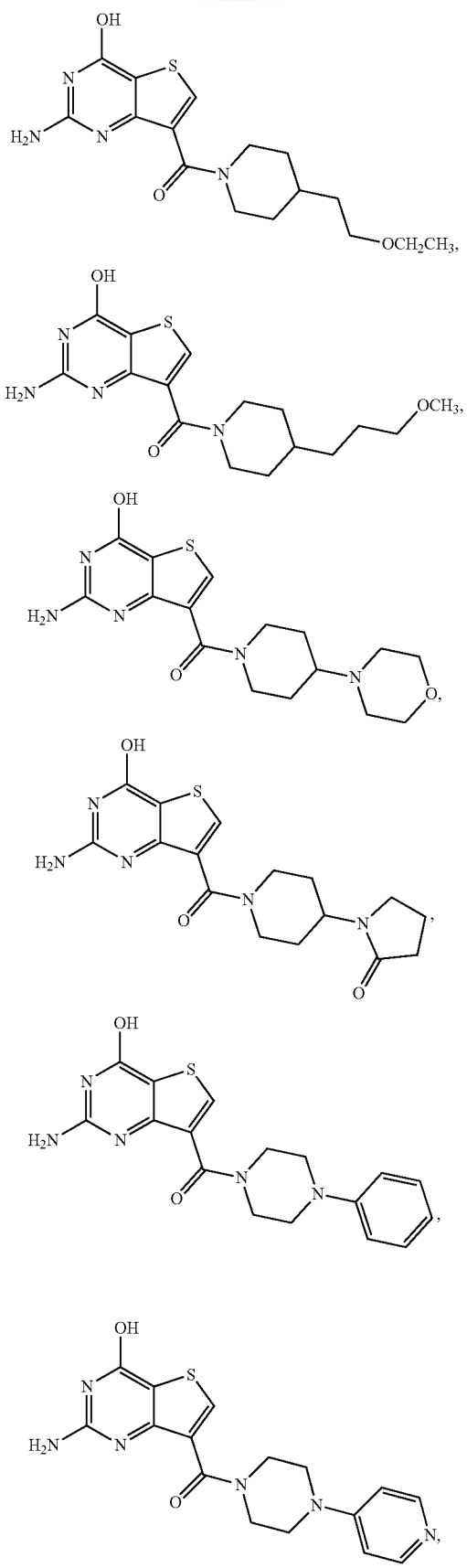
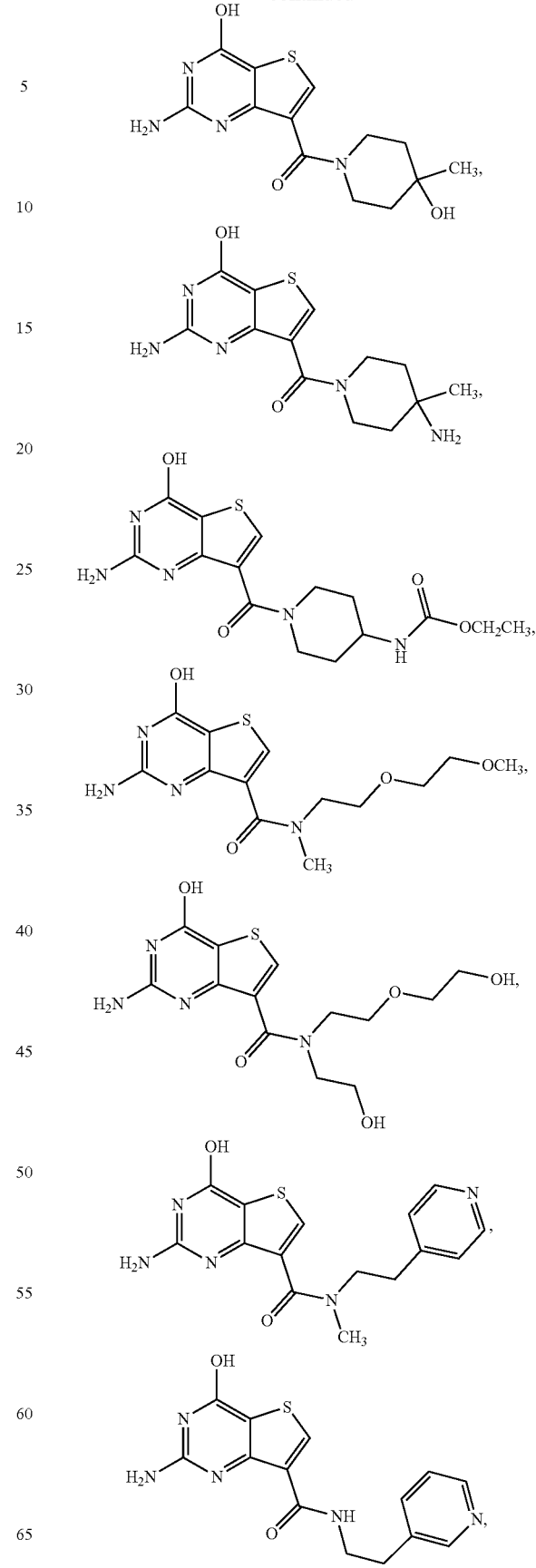

133
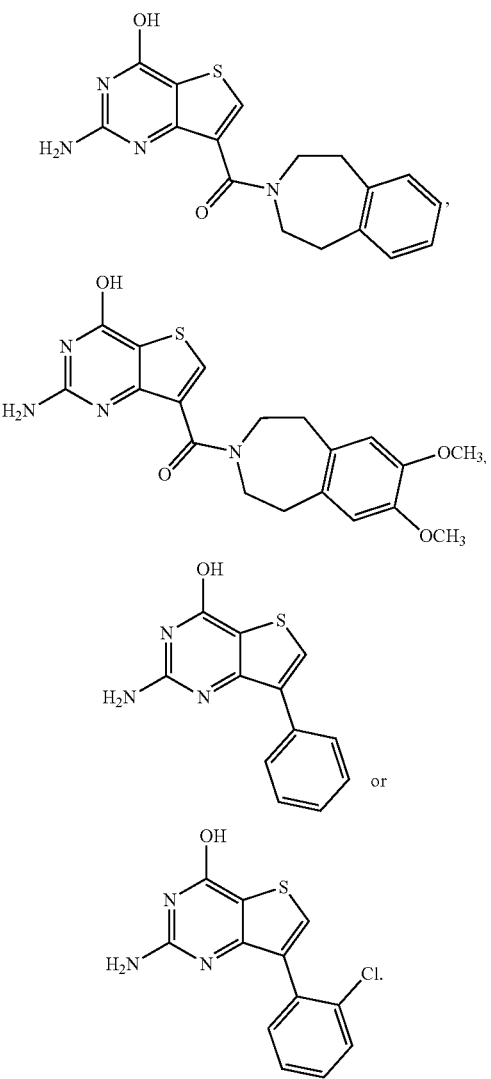
In one embodiment, the compound of Formula VIb1 is:
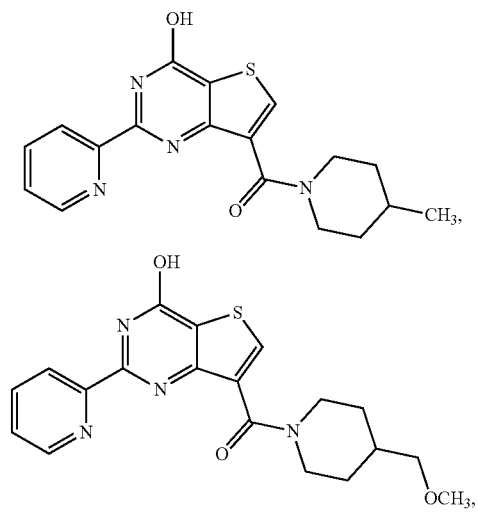
134
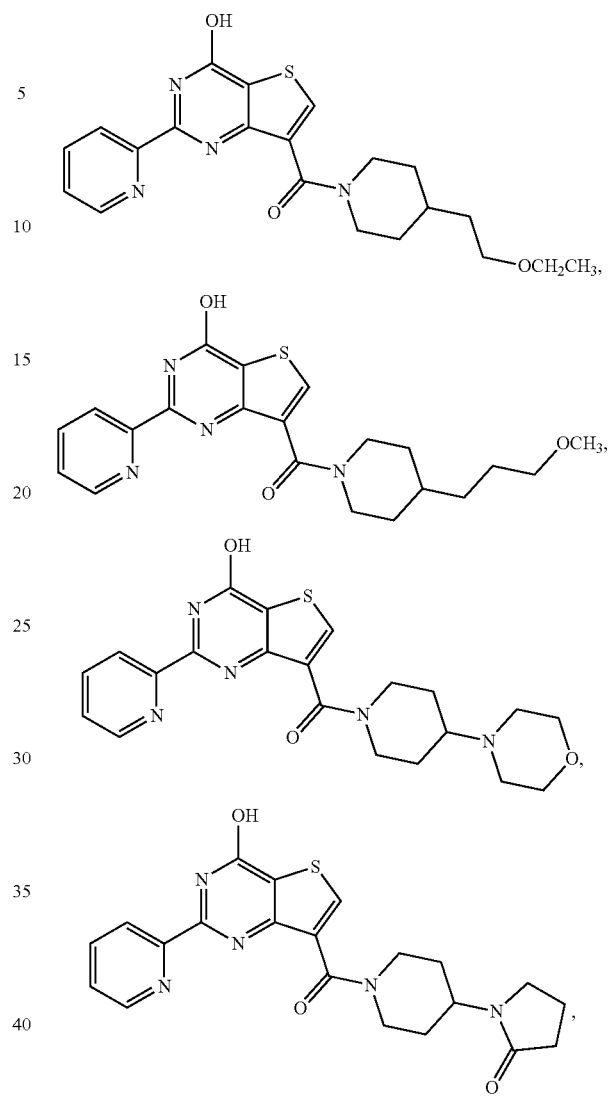
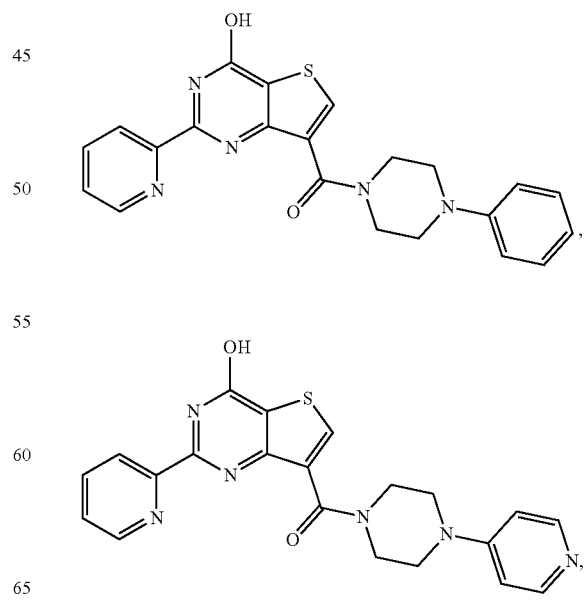

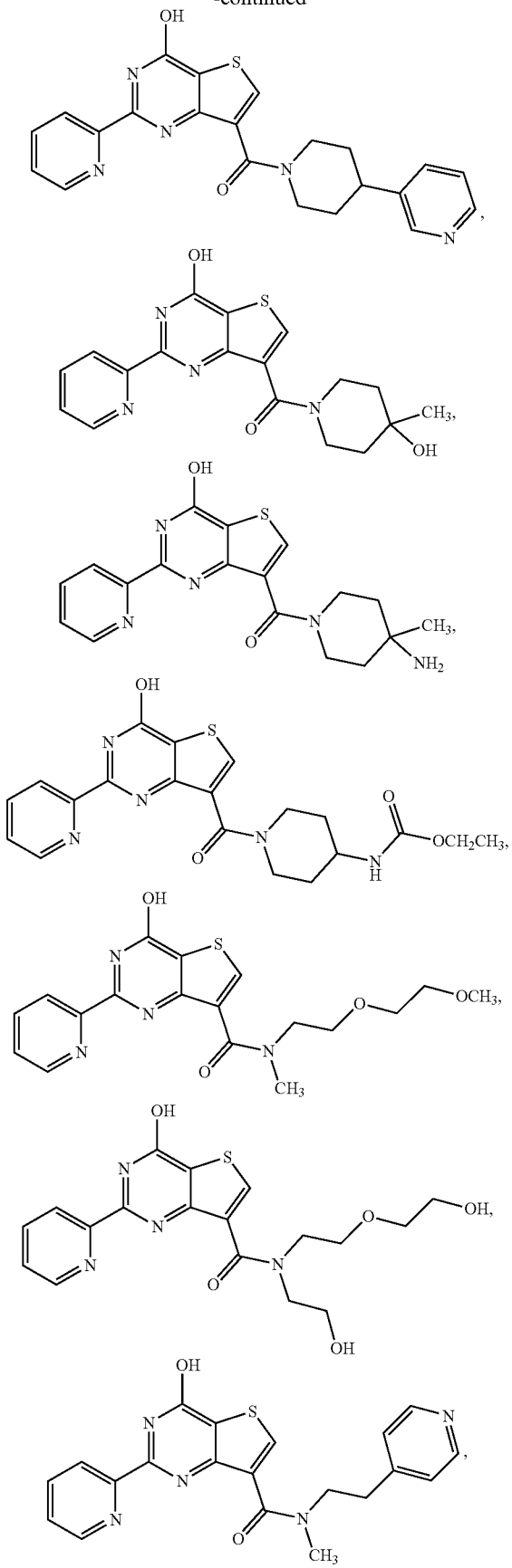
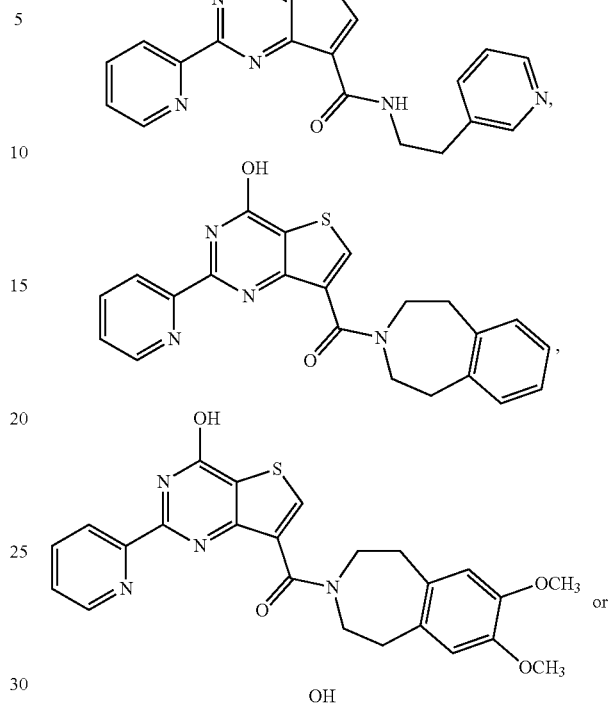
In one embodiment, the compound of Formula VIb1 is:
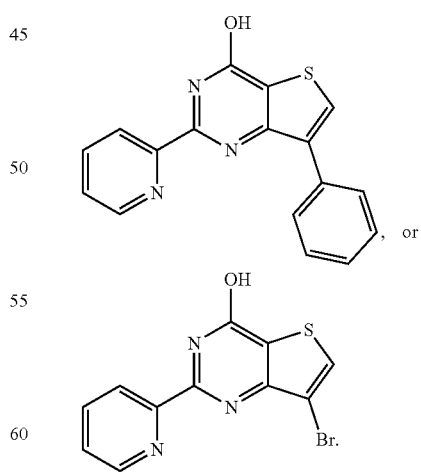
In another embodiment of Formula VIb1, a compound of Formula VIb1 is a compound wherein
$R^{1b1}$ is pyridinyl;
$R^{8b1}$ is H;

$R^{9b1}$ is
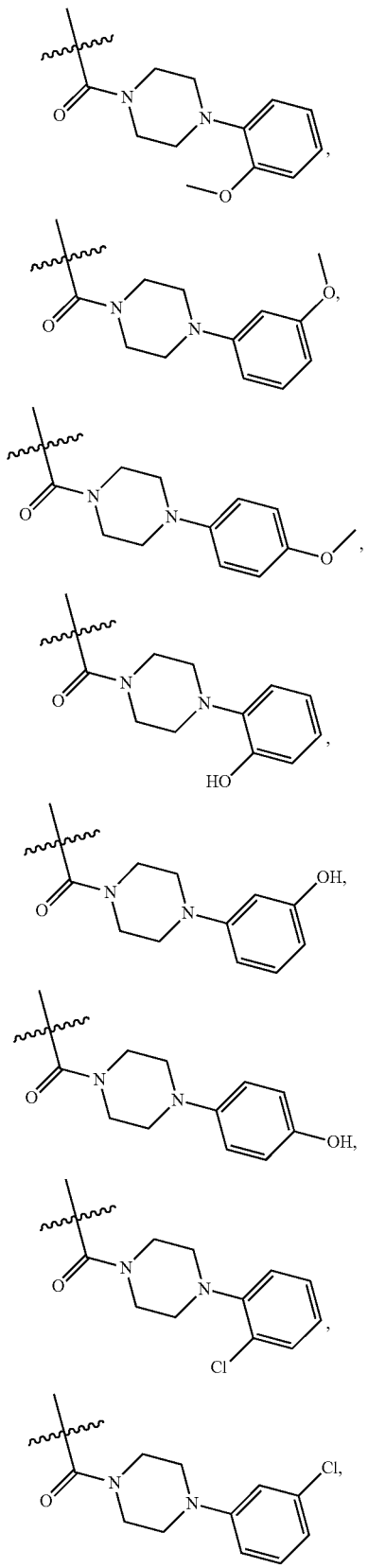
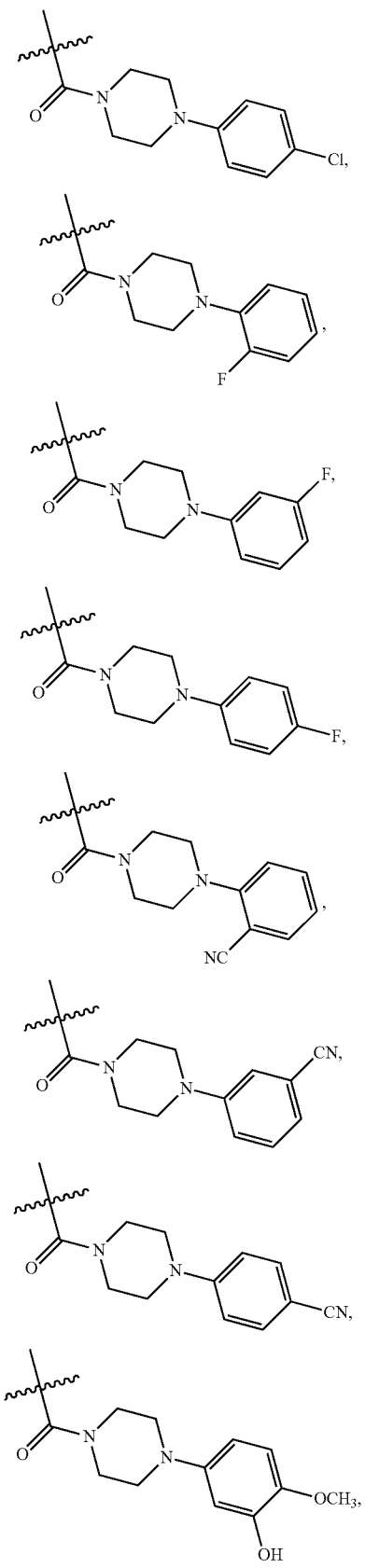

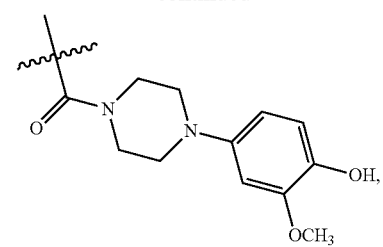
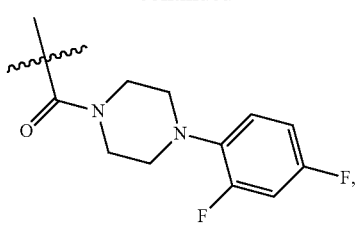
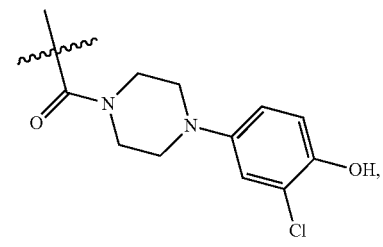
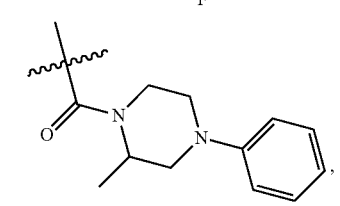
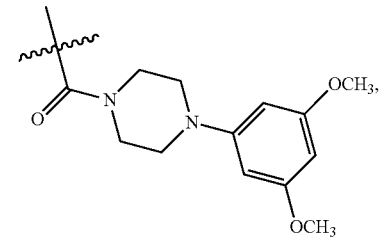
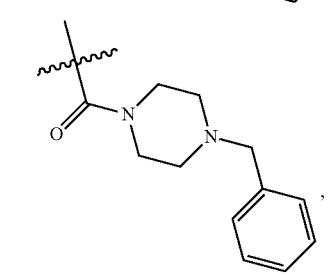
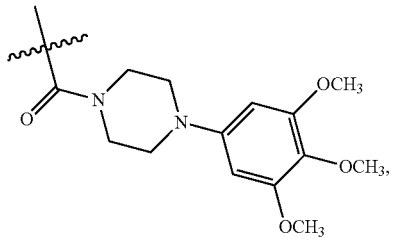
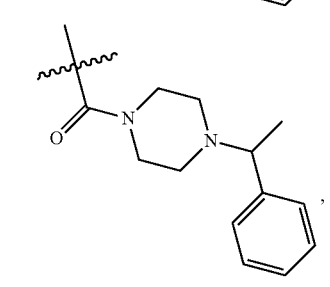
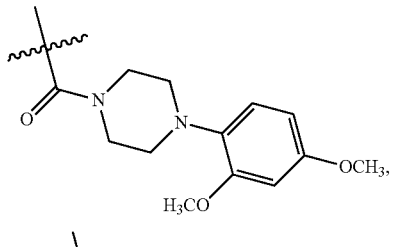
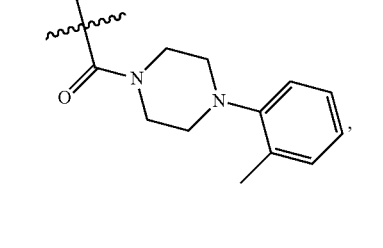
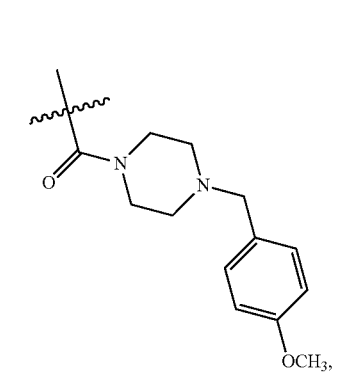
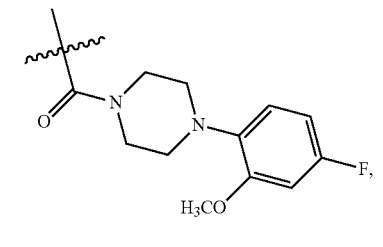
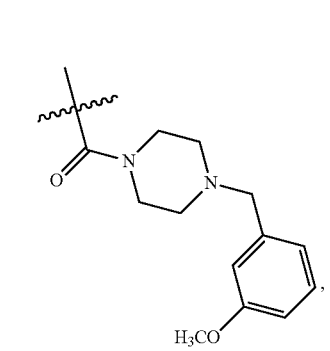

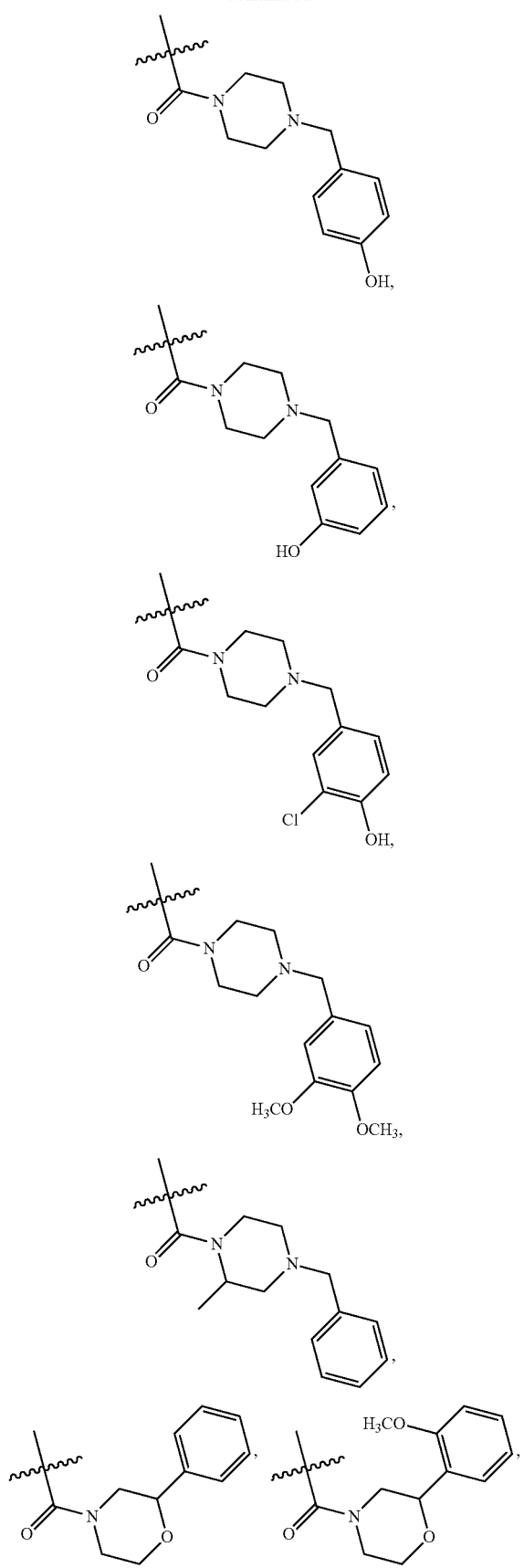
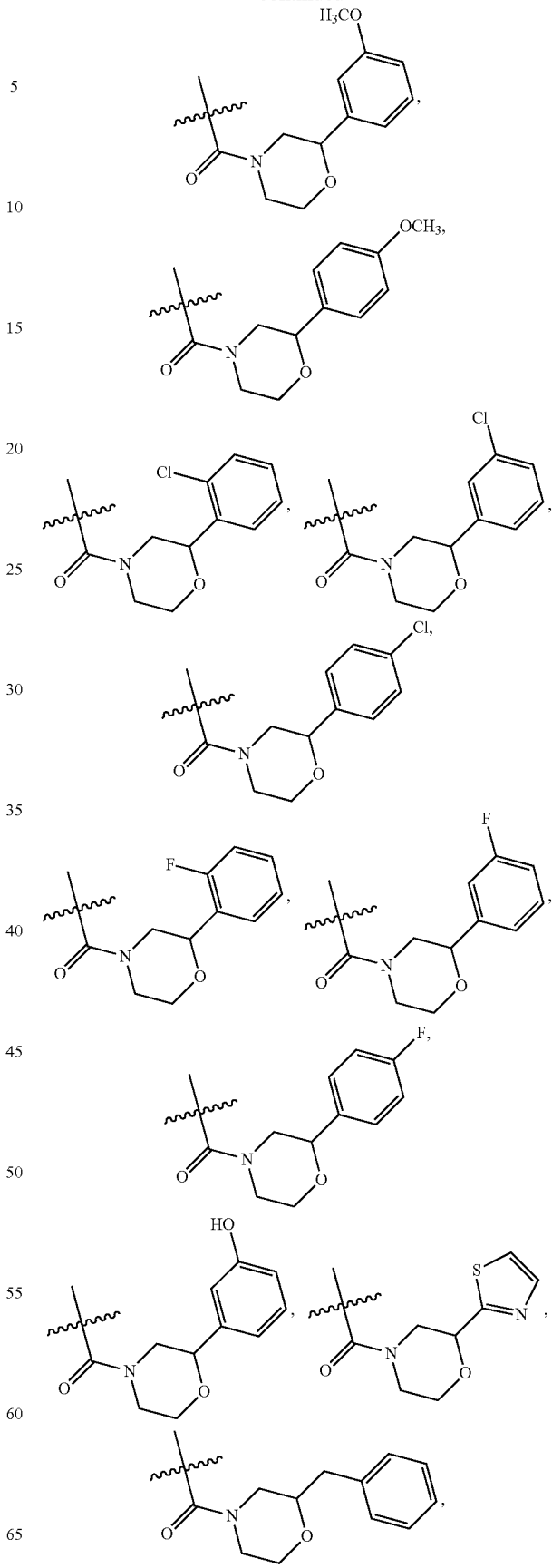

143
-continued
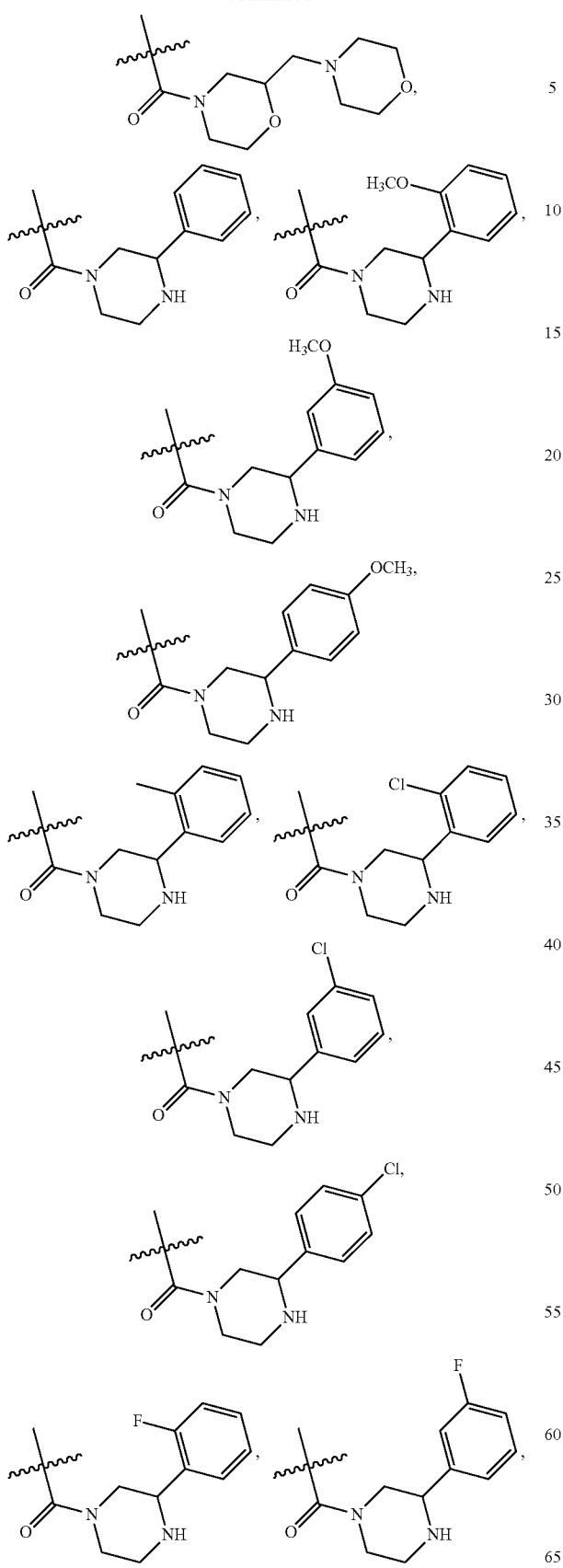
144
-continued
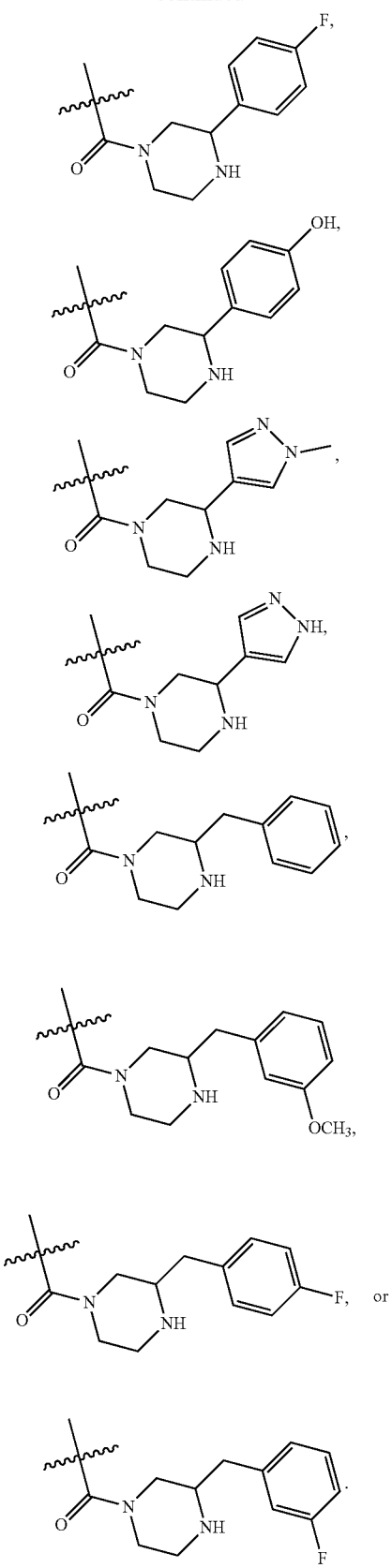

In another embodiment of Formula VIb1, a compound of Formula VIb1 is a compound wherein
$R^{1b1}$ is pyridinyl;
$R^{8b1}$ is H;
$R^{9b}$ is
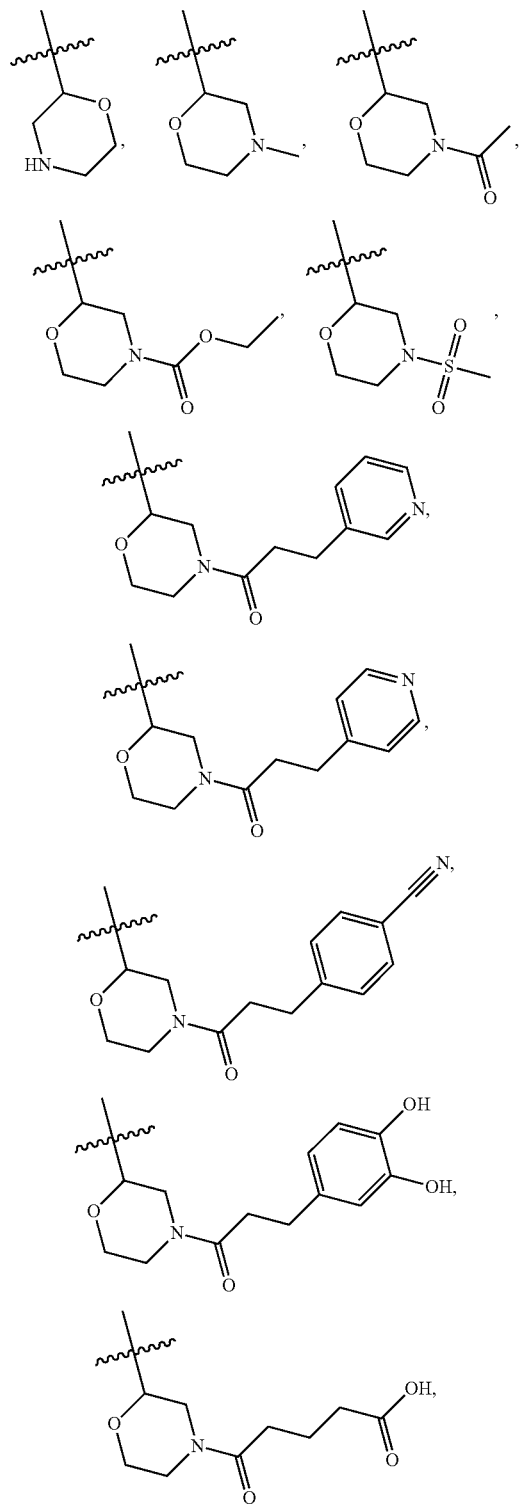
-continued
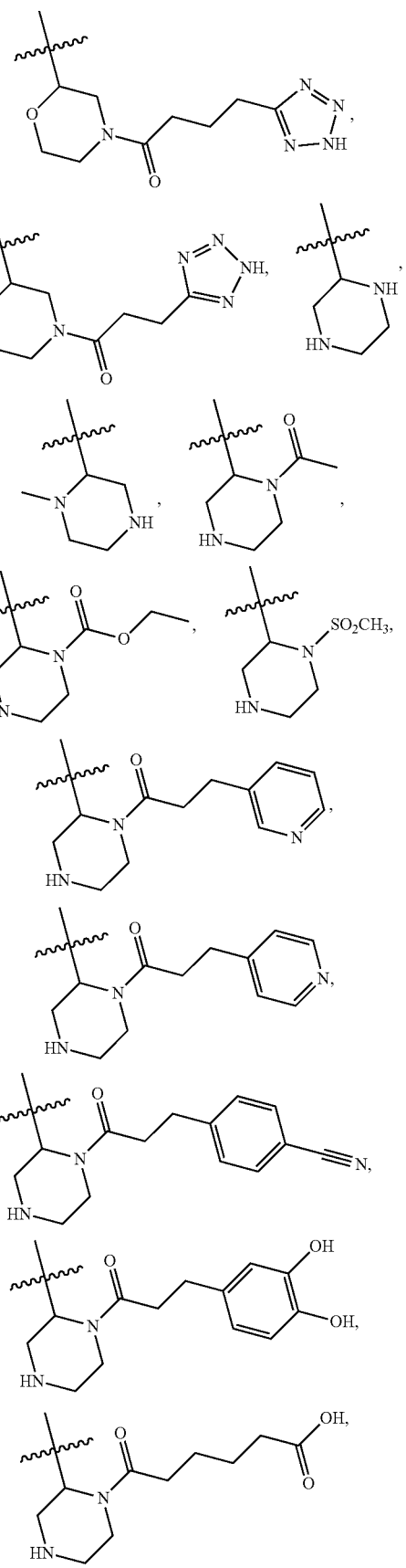

-continued

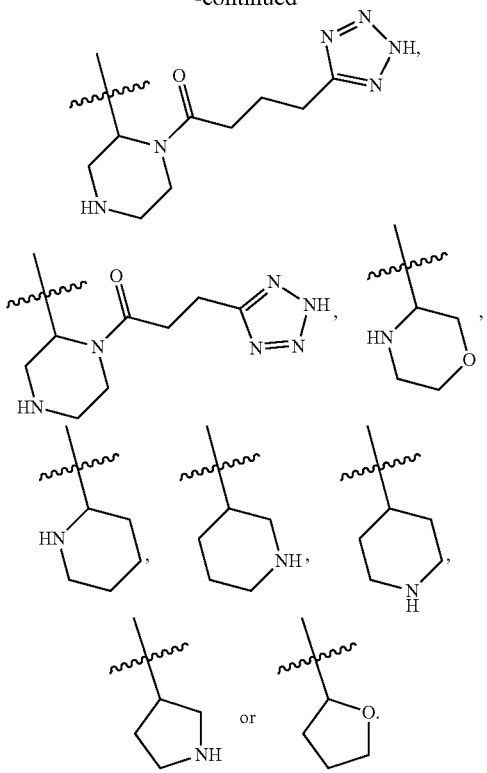

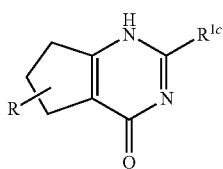 or 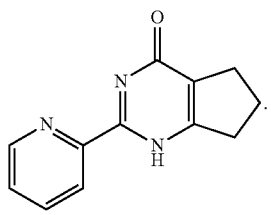 [SMILES: O=c1nc(-c2ccccn2)[nH]c2c1CCC2]

In another embodiment, the compound of Formula VI is a compound of Formula VIc:

Formula VIc

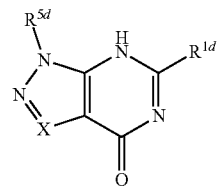

or pharmaceutically acceptable derivatives thereof,
wherein $R^{1c}$ is aryl, or heteroaryl; and
R may consist of 0-6 subsituents independently selected from H or alkyl.

In another embodiment of Formula VIc, a compound of Formula VIc is a compound wherein
$R^{1c}$ is pyridinyl; and
R is H.

In one embodiment, the compound of Formula VIc is:

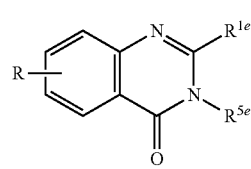

In another embodiment, the compound of Formula VI is a compound of Formula VId:

Formula VId

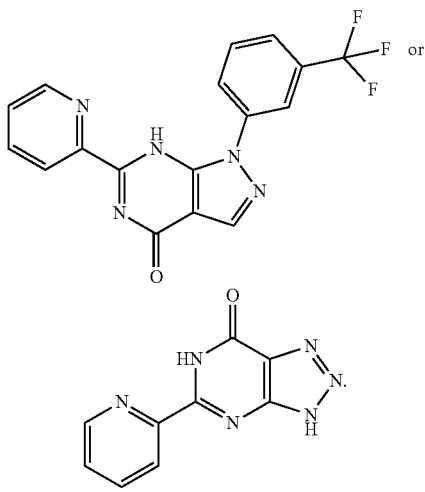

or pharmaceutically acceptable derivatives thereof,
wherein $R^{1d}$ is aryl or heteroaryl;
$R^{5d}$ is hydrogen, alkyl, alkenyl, alkynyl, aryl, heteroaryl, heterocyclyl, cycloalkyl, alkylcarbonyl, cycloalkylcarbonyl, or arylcarbonyl; and
X is CH or N.

In another embodiment of Formula VId, a compound of Formula VId is a compound wherein
$R^{1d}$ is pyridinyl;
$R^{5d}$ is hydrogen or phenyl,
wherein phenyl is substituted with $CF_3$;
X is CH or N.

In one embodiment, the compound of Formula VId is:

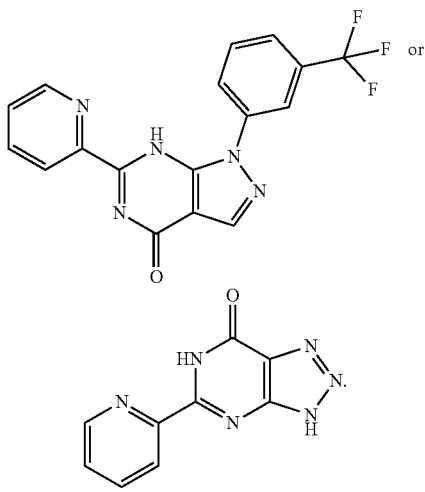

In another embodiment, the compound of Formula VI is a compound of Formula VIe:

Formula VIe

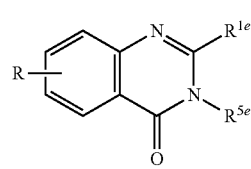

or pharmaceutically acceptable derivatives thereof,
wherein $R^{1e}$ is $S(O)_p R^4$, $NR^5C(O)R^4$ or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^{5e}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

R may consist of 0-4 subsituents independently selected from H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$.

In another embodiment, the compound of Formula VI is a compound of Formula VIe:

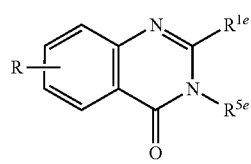

Formula VIe or pharmaceutically acceptable derivatives thereof, wherein $R^{1e}$ is $S(O)_pR^4$ or $NR^6R^7$;

$R^4$ is

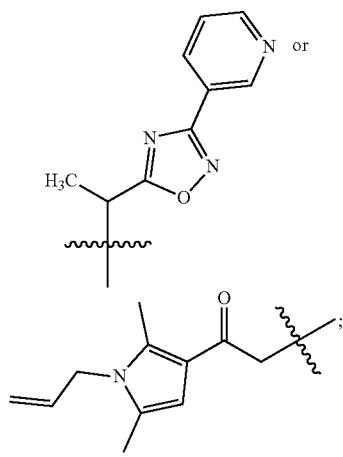

$R^{5e}$ is H, methoxyethyl or $CH_3OCH_2(CH_3)CH—$;

$R^6$ and $R^7$ are independently selected from hydrogen or as depicted below

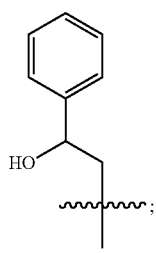 [SMILES: *CC(O)c1ccccc1]

p is 0; and

R is H or halogen.

In one embodiment, the compound of Formula VIe is:

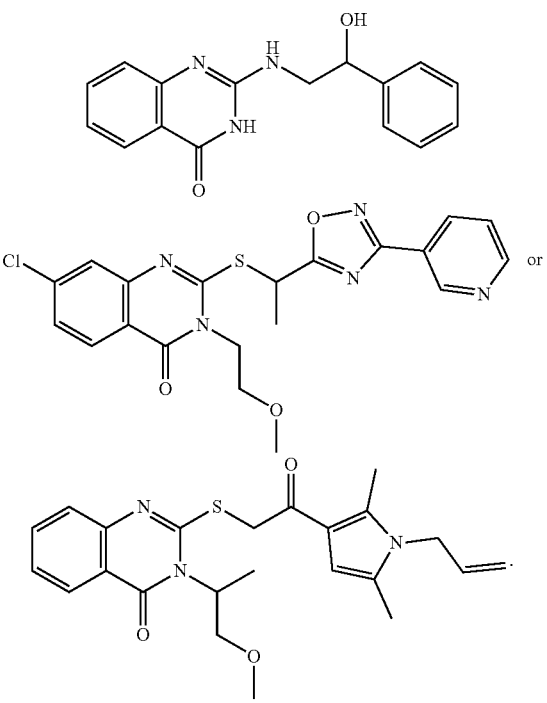

or

In another embodiment, the compound of Formula VI is a compound of Formula VIf:

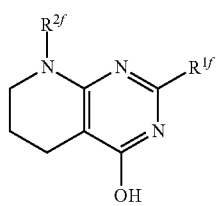

Formula VIf or pharmaceutically acceptable derivatives thereof, wherein $R^{1f}$ is aryl, or heteroaryl; and $R^{2f}$ is H, —C(O)R, —C(O)OR, —S(O)$_2$R, —S(O)R or alkyl, wherein R is aryl, heteroaryl or alkyl.

In another embodiment of Formula VIf, a compound of Formula VIf is a compound wherein $R^{1f}$ is 2-pyridyl; and $R^{2f}$ is —C(O)R, —C(O)OR or SO$_2$R, wherein R is aryl, heteroaryl or alkyl.

In another embodiment of Formula VIf, a compound of Formula VIf is a compound wherein $R^{1f}$ is 2-pyridyl; and $R^{2f}$ is —C(O)R, wherein R is aryl, heteroaryl or alkyl.

In another embodiment of Formula VIf, a compound of Formula VIf is a compound wherein $R^{1f}$ is pyridinyl; and $R^{2f}$ is H,

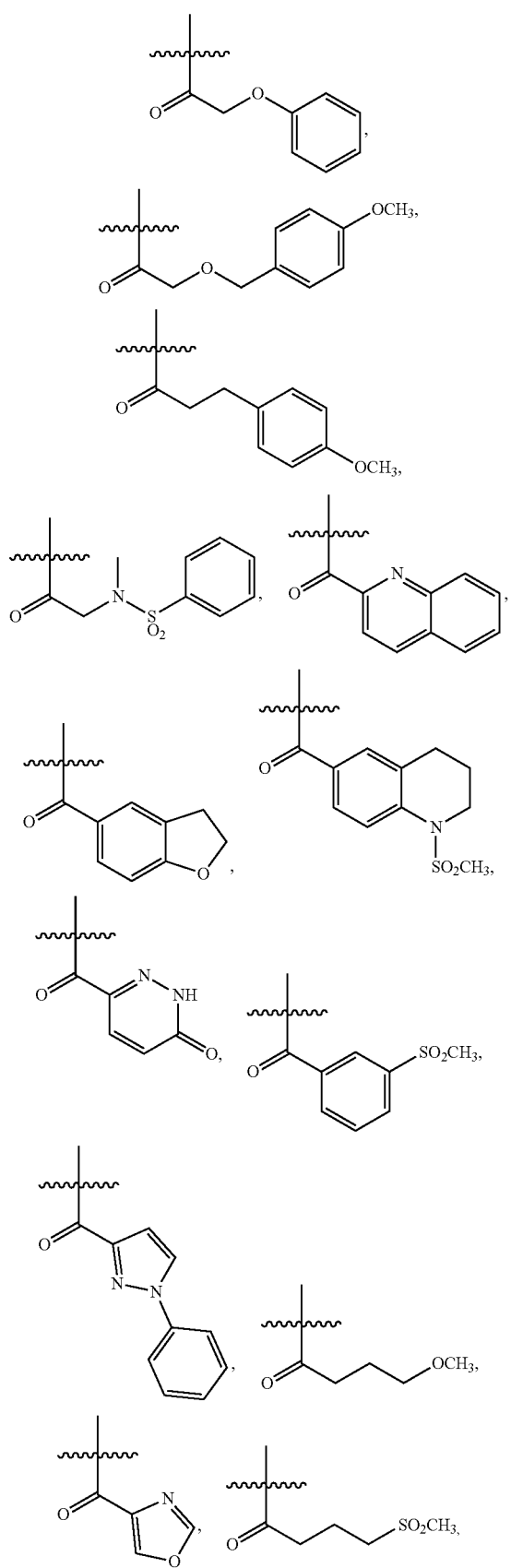
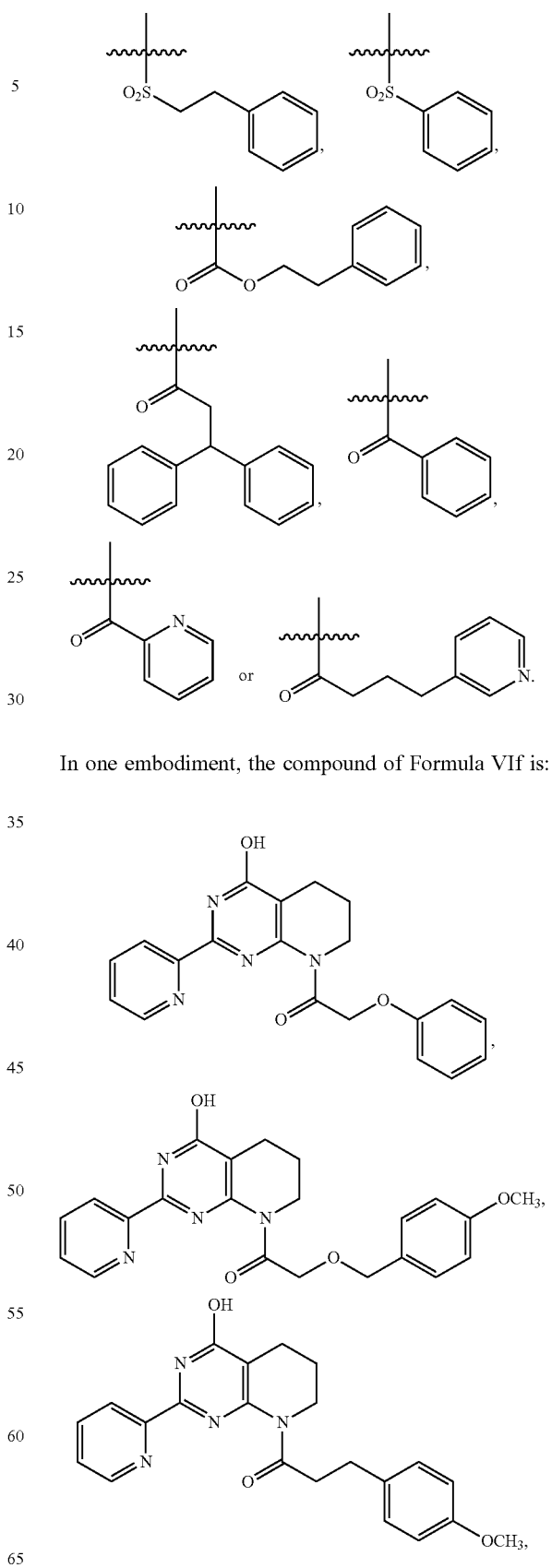
In one embodiment, the compound of Formula VIf is:
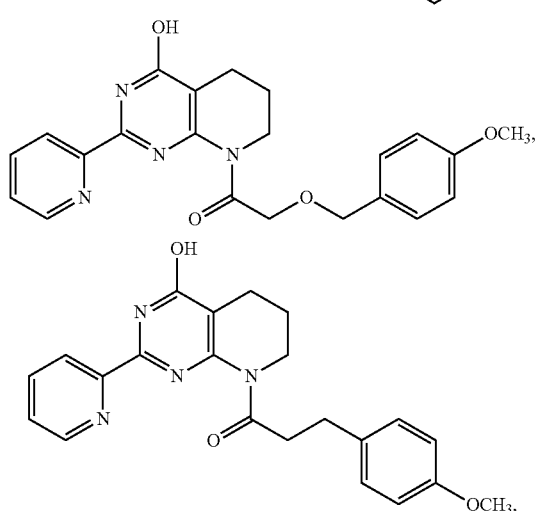

153
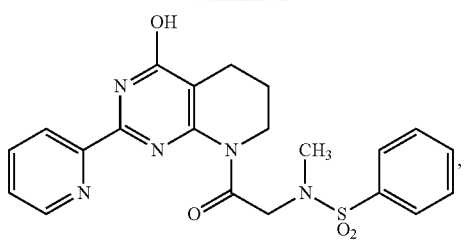
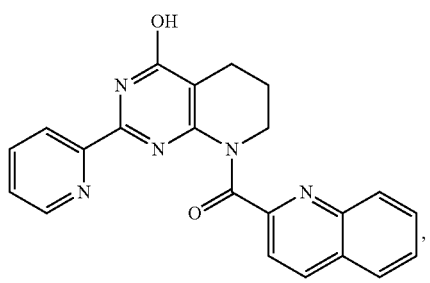
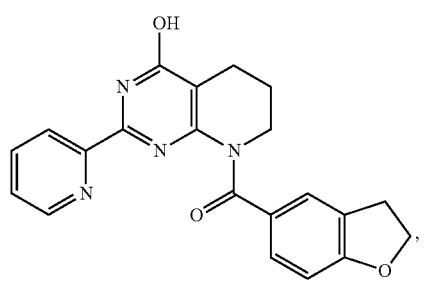
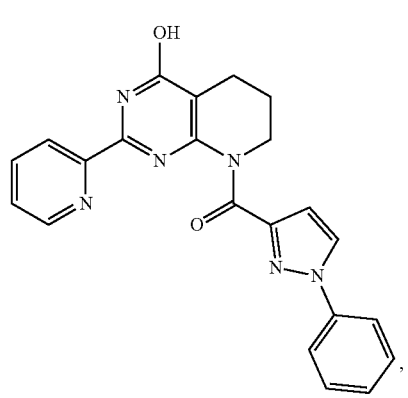
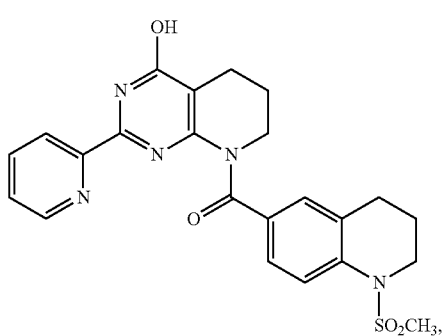
154
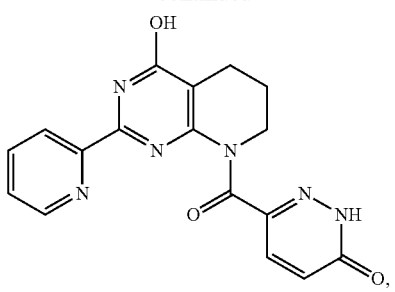
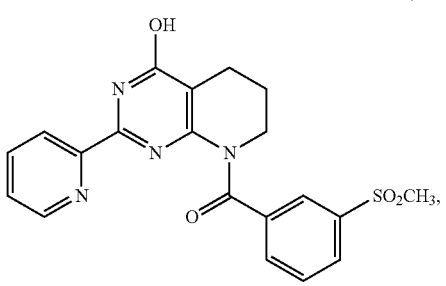
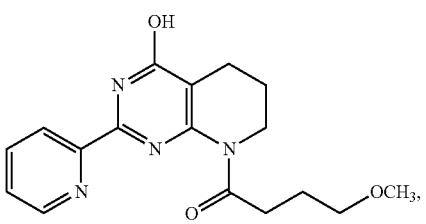
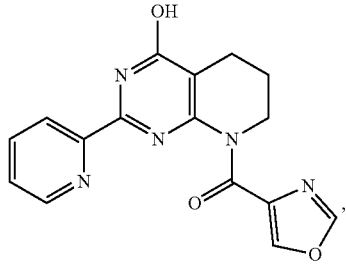
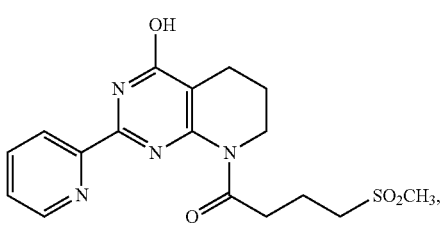
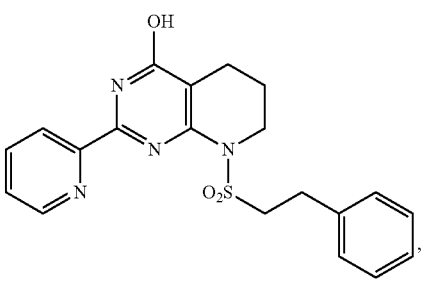

-continued

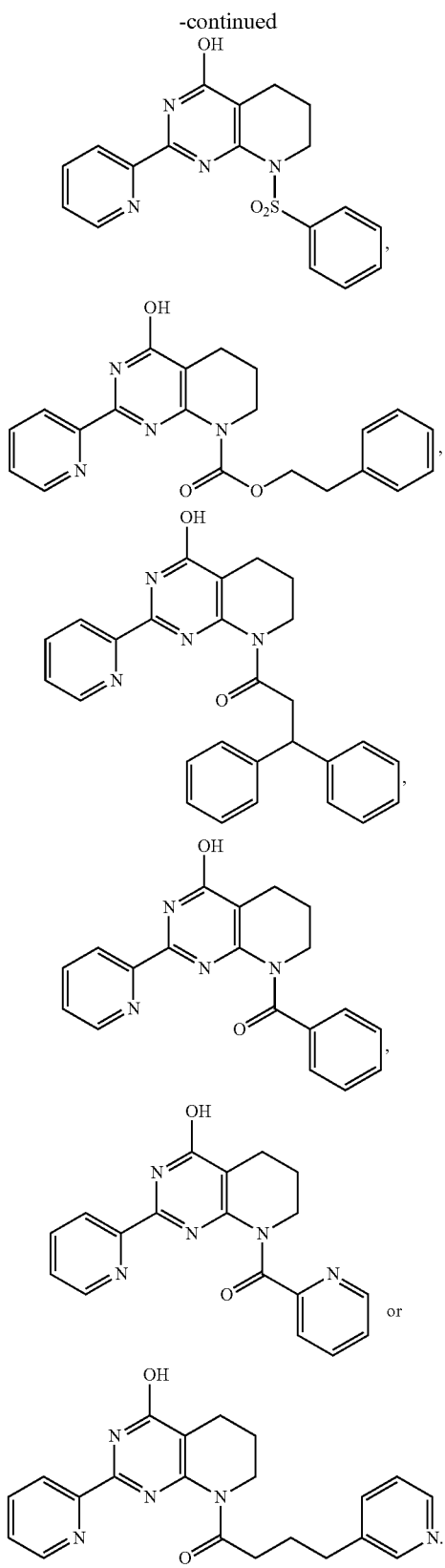

In another embodiment, the compound of Formula VI is a compound of Formula VIg:

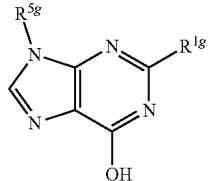

Formula VIg or pharmaceutically acceptable derivatives thereof, wherein $R^{1g}$ is aryl or heteroaryl; and $R^{1g}$ is hydrogen, alkyl, alkenyl, alkynyl, aryl, heteroaryl, heterocyclyl, cycloalkyl, alkylcarbonyl, cycloalkylcarbonyl, or arylcarbonyl.

In another embodiment of Formula VIg, a compound of Formula VIg is a compound wherein $R^{1g}$ is 2-pyridyl; and $R^{5g}$ is aryl, heteroaryl, heterocyclyl, cycloalkyl, $CH_2C(O)$ R, wherein R is $NH_2$, NHalkyl, $N(alkyl)_2$, piperidine, OH or Oalkyl.

In another embodiment of Formula VIg, a compound of Formula VIg is a compound wherein $R^{1g}$ is pyridinyl; and $R^{5g}$ is hydrogen, phenyl, pyridyl or

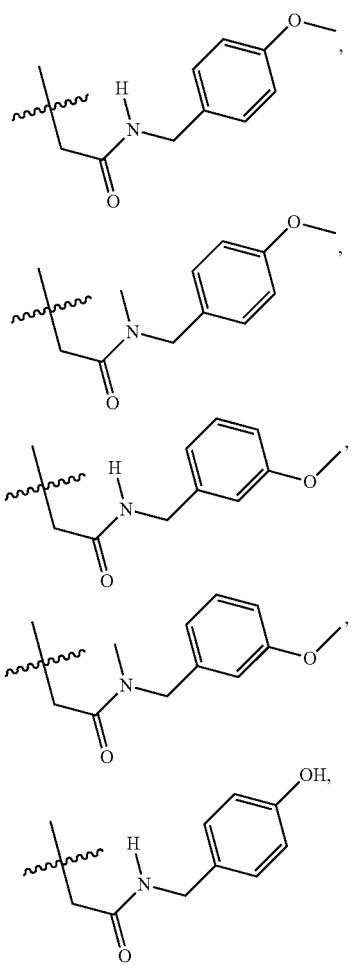

157
-continued
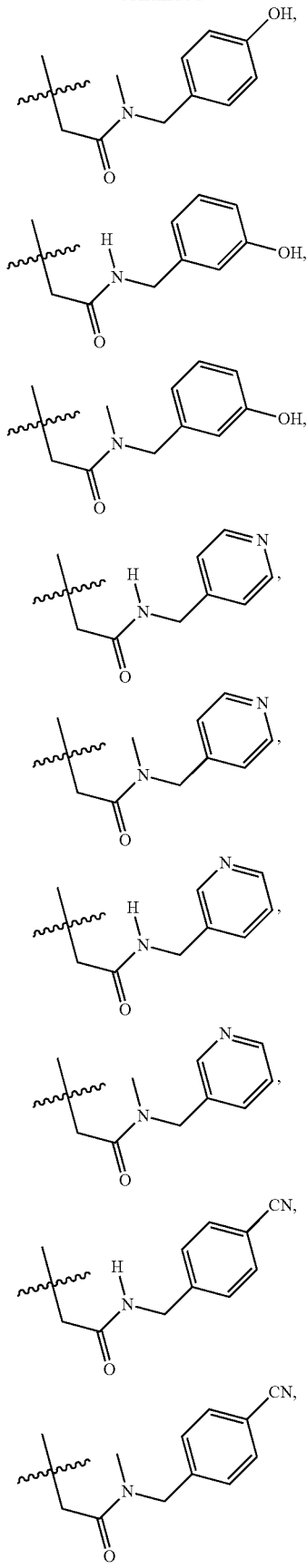
158
-continued
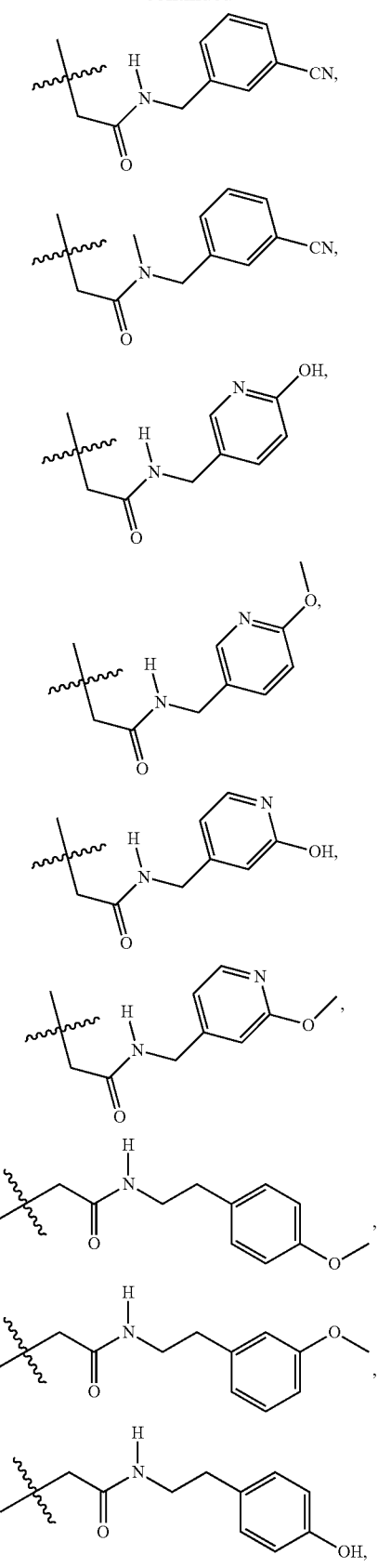

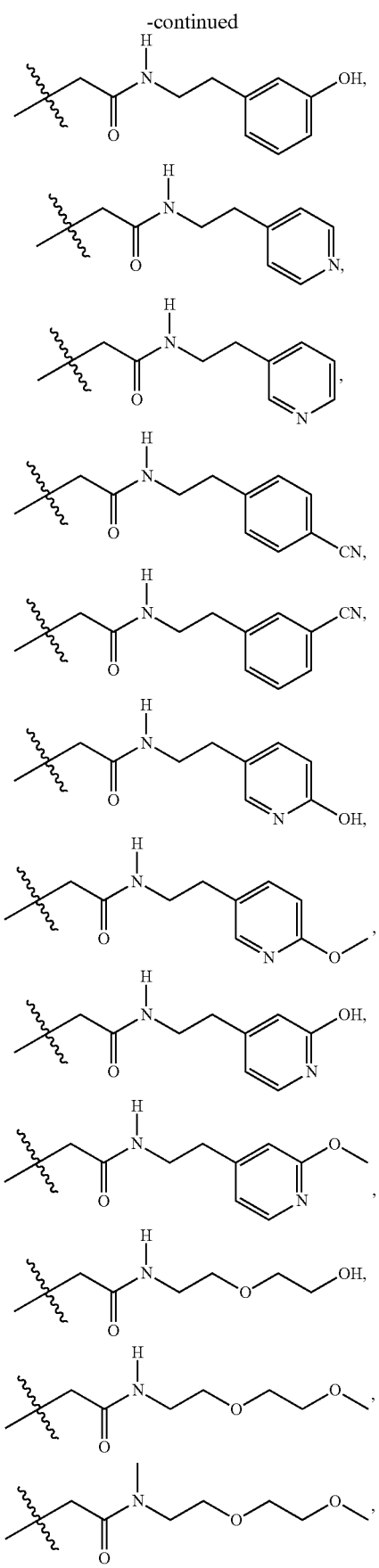

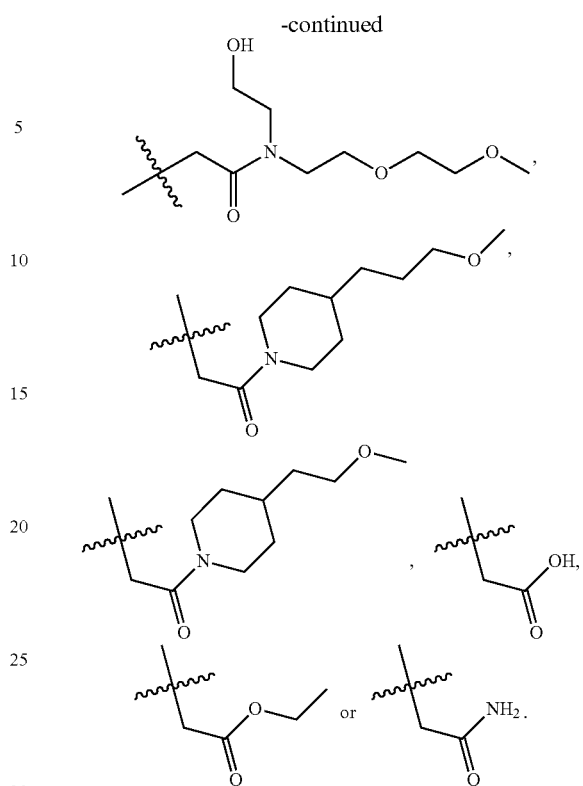

In certain embodiments, the compounds for use in the compositions and methods provided herein are of Formula VII:

Formula VII or pharmaceutically acceptable derivatives thereof,
wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2.

In another embodiment, the compound of Formula VII is a compound of Formula VIIa:

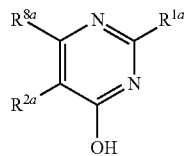

Formula VIIa or pharmaceutically acceptable derivatives thereof,
wherein $R^{1a}$ is aryl or heteroaryl;
$R^{2a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;
$R^{8a}$ is H or alkyl;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
p is 0-2.

In another embodiment of Formula VIIa, a compound of Formula VIIa is a compound wherein
$R^{1a}$ is pyridinyl;
$R^{2a}$ is selected from one of the following:

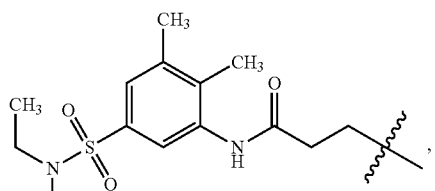

,

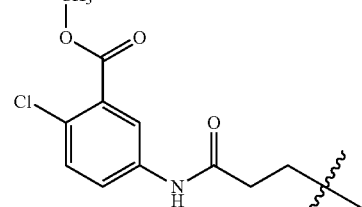

,

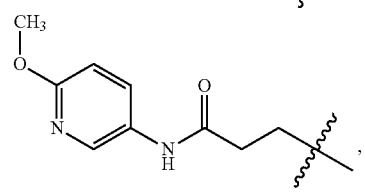

,

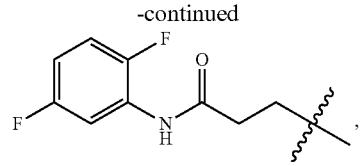

,

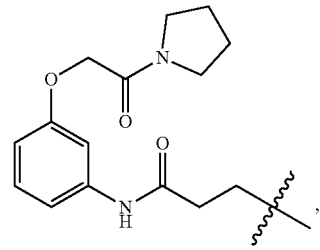

,

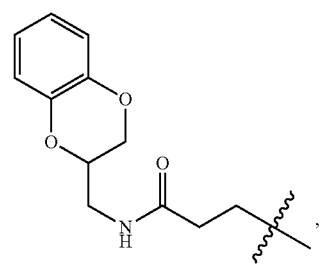

,

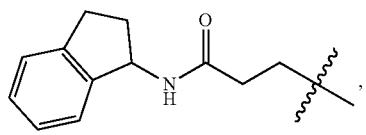

,

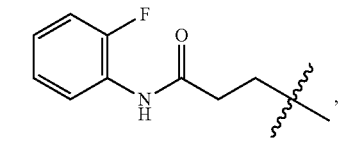

,

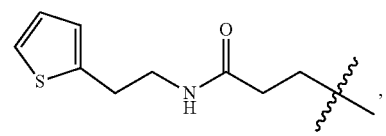

,

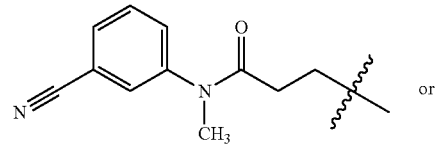

or

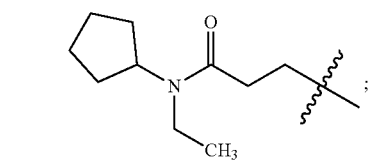

;

$R^{8a}$ is methyl.

In another embodiment of Formula VIIa, a compound of Formula VIIa is a compound wherein
$R^{1a}$ is pyridinyl;
$R^{2a}$ is selected from one of the following:
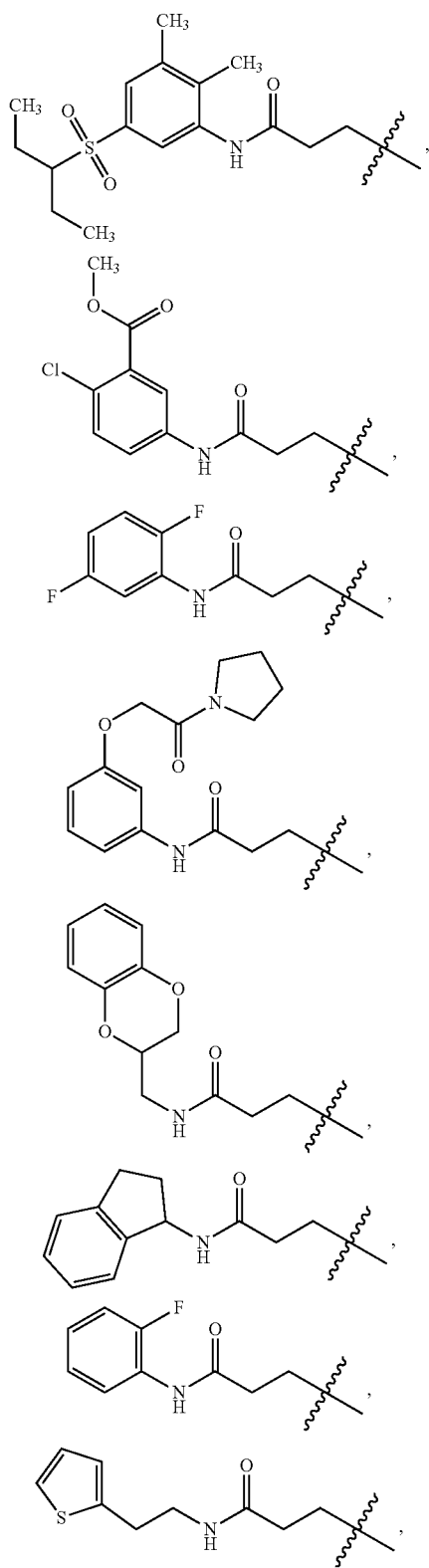
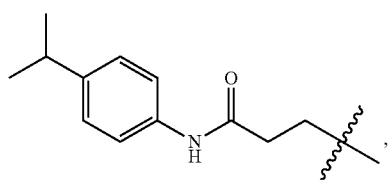
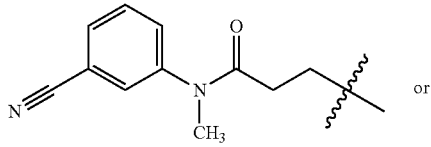 or
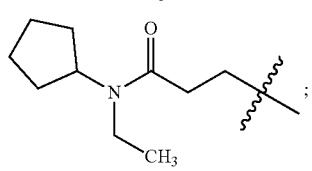 ;
$R^{8a}$ is methyl.
In one embodiment, the compound of Formula VIIa is:
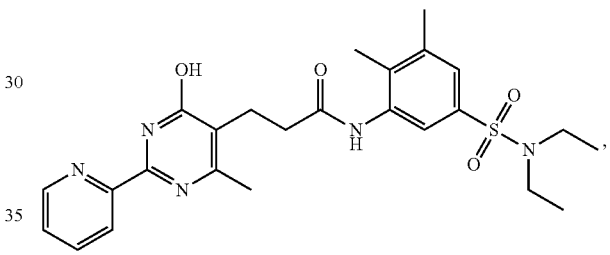
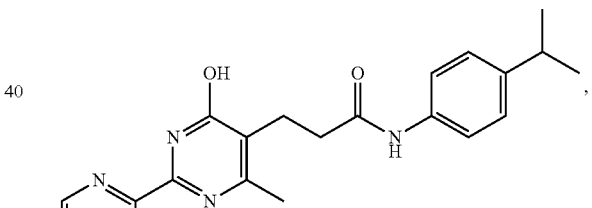
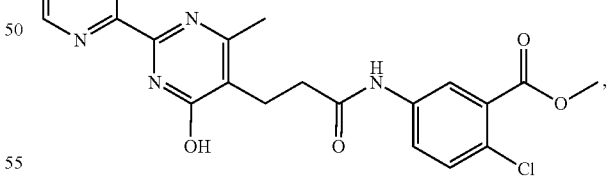
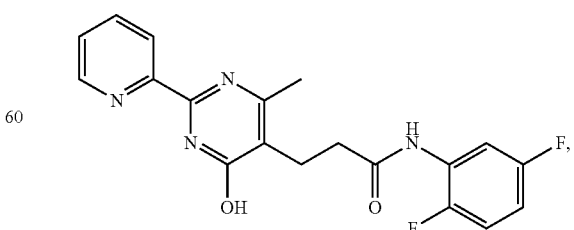

-continued

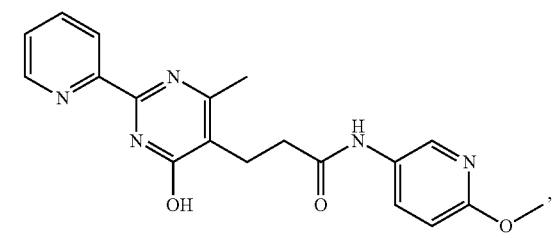

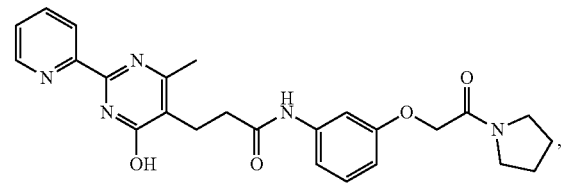

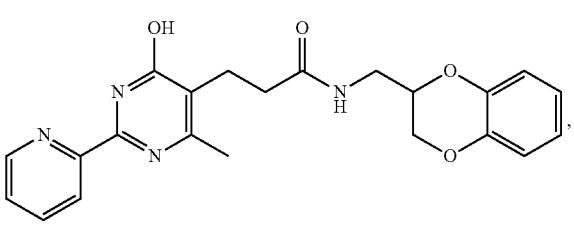

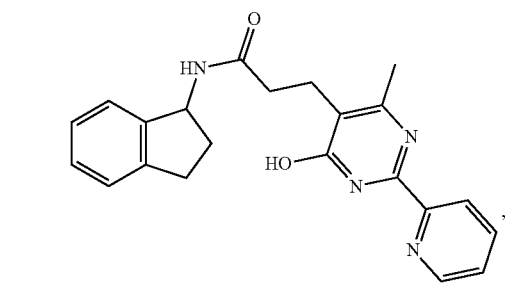

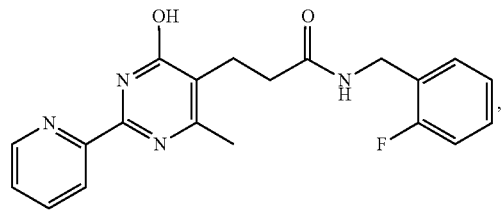

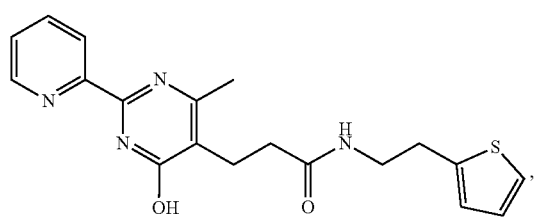

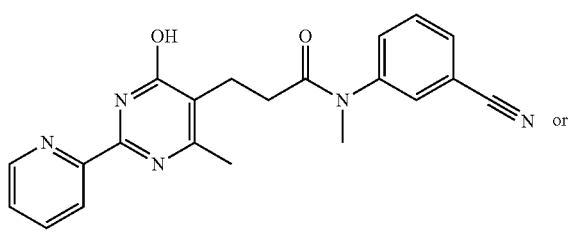 or

-continued

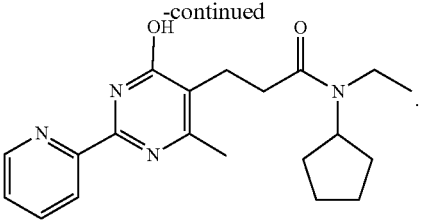

In certain embodiments, the compounds for use in the compositions and methods provided herein are of Formula VIIIa or Formula VIIIb:

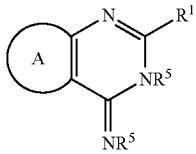

Formula VIIIa

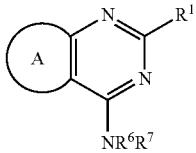

Formula VIIIb or pharmaceutically acceptable derivatives thereof,
wherein $R^{1'}$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

A is a substituted or unsubstituted 5 or 6 membered aryl, heteroaryl, carbocyclic or heterocyclic ring.

In another embodiment, the compound of Formula VIIIa is a compound of Formula VIIIa1:

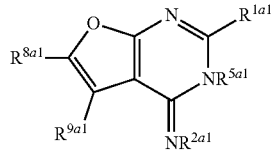

Formula VIIIa1 or pharmaceutically acceptable derivatives thereof, wherein $R^{1a1}$ is H, aryl or heteroaryl;
$R^{2a1}$ is H, alkyl, alkoxy or aryloxy;
$R^{8a1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^{9a1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^{5a1}$ is selected from hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and
p is 0-2.
In another embodiment of Formula VIIIa1, a compound of Formula VIIIa1 is a compound wherein
$R^{1a1}$ is H;
$R^{2a1}$ is H;
$R^{8a1}$ is phenyl,
wherein phenyl is substituted with methoxy;
$R^{9a1}$ is phenyl,
wherein phenyl is substituted with methoxy;
$R^{5a1}$ is depicted below:

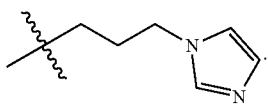 [SMILES: *CCCn1ccnc1]

In one embodiment, the compound of Formula VIIIa1 is:

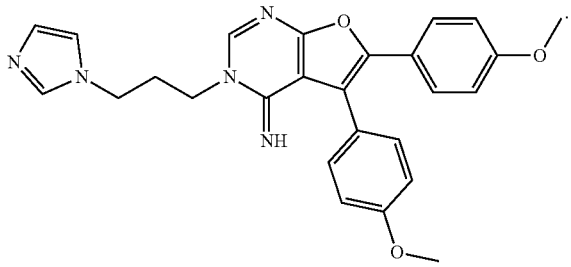 [SMILES: COc1ccc(-c2oc3ncn(CCCn4ccnc4)c(=N)c3c2-c2ccc(OC)cc2)cc1]

In another embodiment, the compound of Formula VIIIb is a compound of Formula VIIIb1:

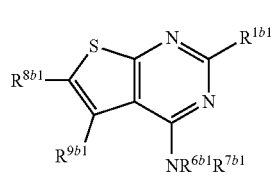

Formula VIIIb1 or pharmaceutically acceptable derivatives thereof, wherein $R^{1b1}$ is H, alkyl, aryl or heteroaryl;
$R^{8b1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^{9b1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
$R^{6b1}$ and $R^{7b1}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b1}$ and $R^{7b1}$ are combined to form a cyclic structure including the nitrogen atom to which they are both attached; and
p is 0-2.
In another embodiment of Formula VIIIb1, a compound of Formula VIIIb1 is a compound wherein
$R^{1b1}$ is 2-pyridyl;
$R^{8b1}$ is H, methyl or phenyl;
$R^{9b1}$ is H, alkyl, alkenyl, alkynyl, substituted aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
$R^{6b1}$ and $R^{7b1}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b1}$ and $R^{7b1}$ are combined to form a cyclic structure including the nitrogen atom to which they are both attached; and
wherein $NR^{6b1}R^{7b1}$ is not NHMe, NHEt, NHn-Pr, NHbenzyl or NH-2-phenethyl; and
wherein $NR^{6b1}R^{7b1}$ is not morpholine when $R^{8b1}$ and $R^{9b1}$ are both hydrogen; and
p is 0-2.
In another embodiment of Formula VIIIb1, a compound of Formula VIIIb1 is a compound wherein $R^{1b1}$ is 2-pyridyl;
$R^{8b1}$ is H;
$R^{9b1}$ is substituted aryl, cycloalkyl, heterocyclyl, heteroaryl, halo, $C(O)NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
$R^{6b1}$ and $R^{7b1}$ are independently selected from hydrogen, alkyl, alkenyl, alkynyl, aryl, heterocyclyl, cycloalkyl, alkylcarbonyl, cycloalkylcarbonyl, or arylcarbonyl, or $R^{6b1}$ and $R^{7b1}$ are combined to form a cyclic structure including the nitrogen atom to which they are both attached; and
wherein $NR^{6b1}R^{7b1}$ is not NHMe, NHEt, NHn-Pr, $NHCH_2CH_2OH$, NHbenzyl optionally substituted on the phenyl ring, or NH-2-phenethyl optionally substituted on the phenyl ring; and
wherein $NR^{6b1}R^{7b1}$ is not morpholine when $R^{8b1}$ and $R^{9b1}$ are both hydrogen.

In another embodiment of Formula VIIIb1, a compound of Formula VIIIb1 is a compound wherein
$R^{1b1}$ is H, methyl, or pyridinyl;
$R^{8b1}$ is H or methyl;
$R^{9b1}$ is H or phenyl,
wherein phenyl is optionally substituted with one or two substituents selected from methoxy;
each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;
$R^{6b1}$ and $R^{7b1}$ are independently selected from H, methyl, hydroxypropyl, methoxypropyl, hydroxyethyl, morpholinylethyl, furanylmethyl, or one of the following:

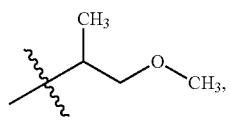
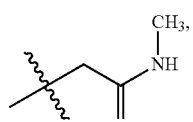
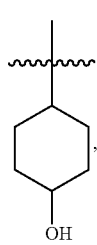
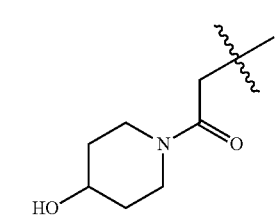

or $R^{6b1}$ and $R^{7b}$ are combined to form a cyclic structure including the nitrogen atom to which they are both attached, as depicted below

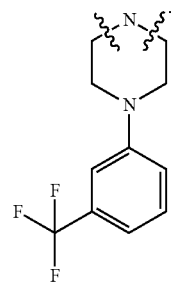

In one embodiment, the compound of Formula VIIIb1 is:

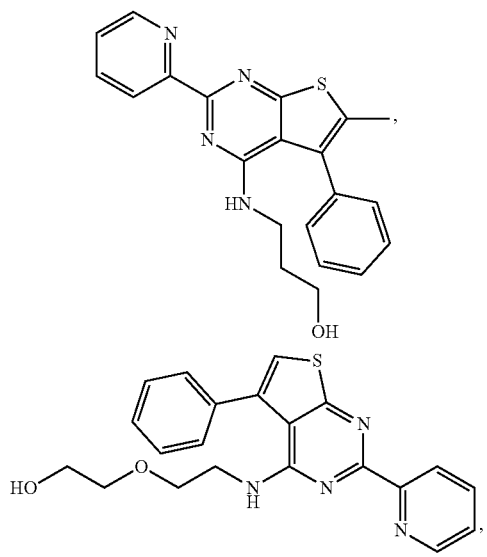

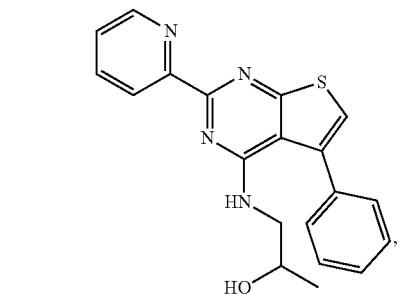

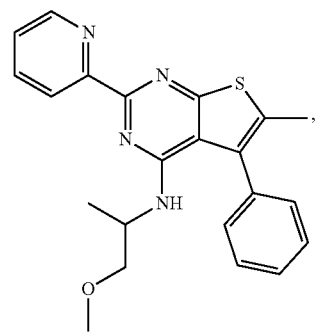

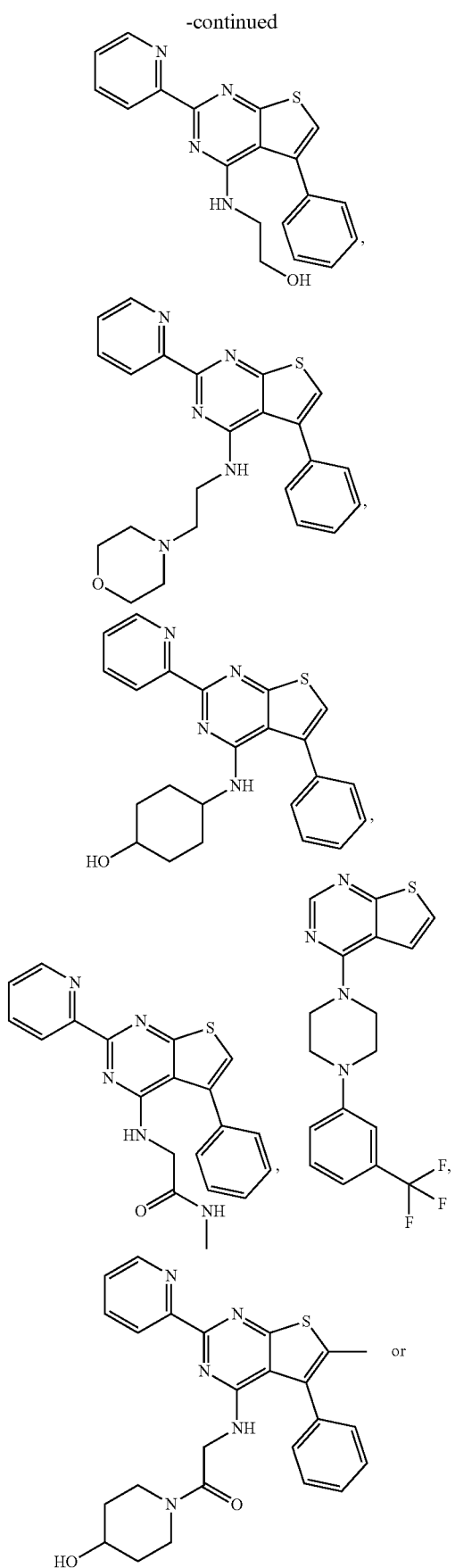
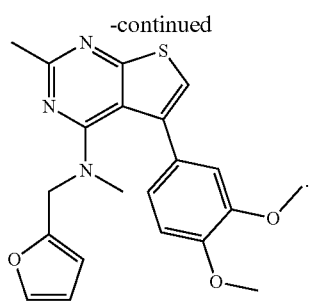
In another embodiment of Formula VIIIb1, a compound of Formula VIIIb1 is a compound wherein
$R^{1b1}$ is pyridinyl;
$R^{8b1}$ is H, methyl or phenyl;
$R^{9b1}$ is H, bromo or phenyl; and
$NR^{6b1}R^{7b1}$ is selected from
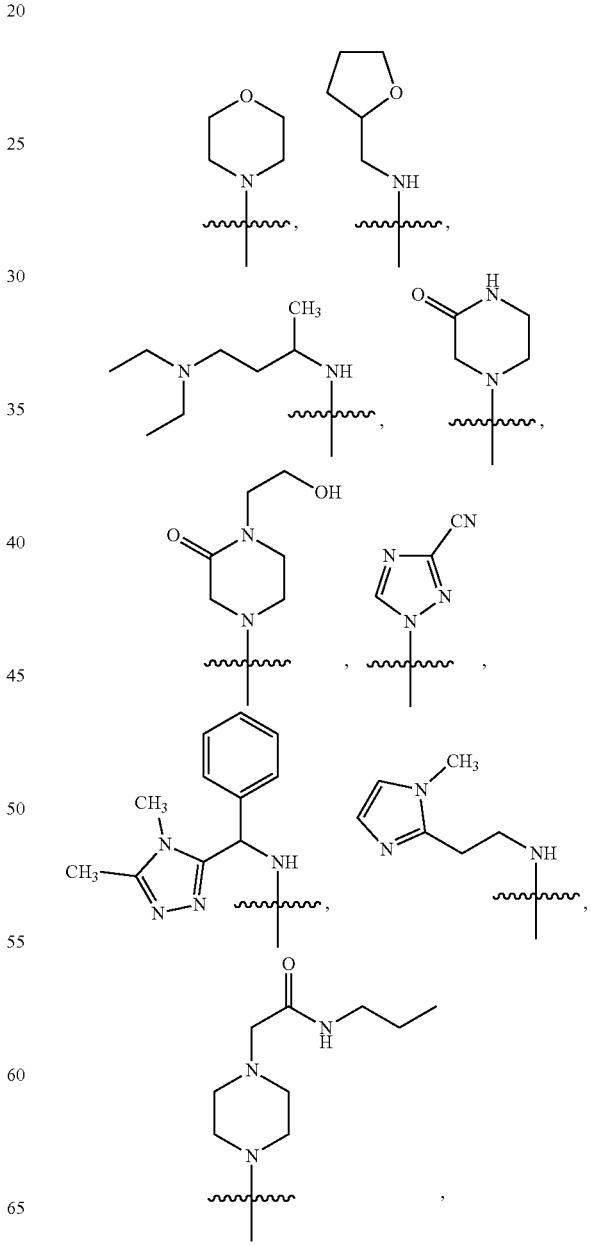

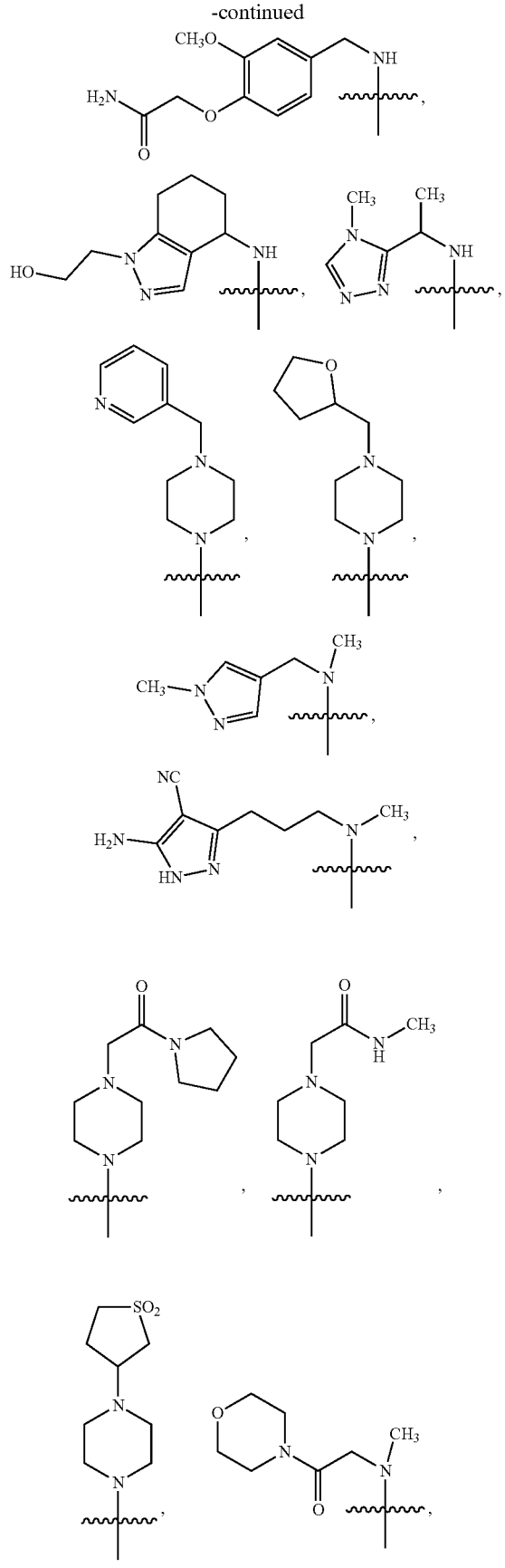
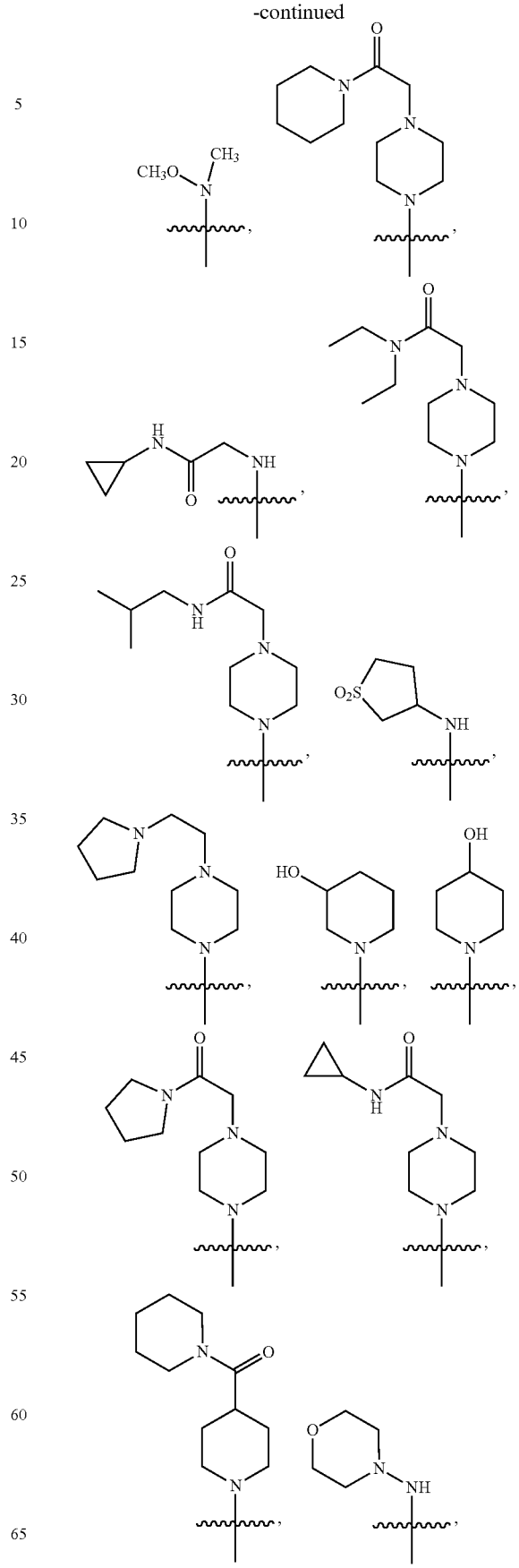

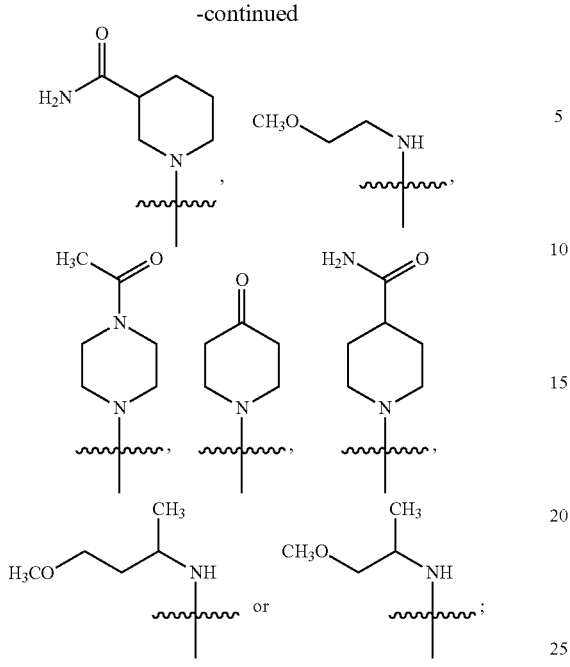
wherein NR$^{6b1}$R$^{7b1}$ is not morpholine when R$^{8b1}$ and R$^{9b1}$ are both hydrogen.
In one embodiment, the compound of Formula VIIIb1 is:
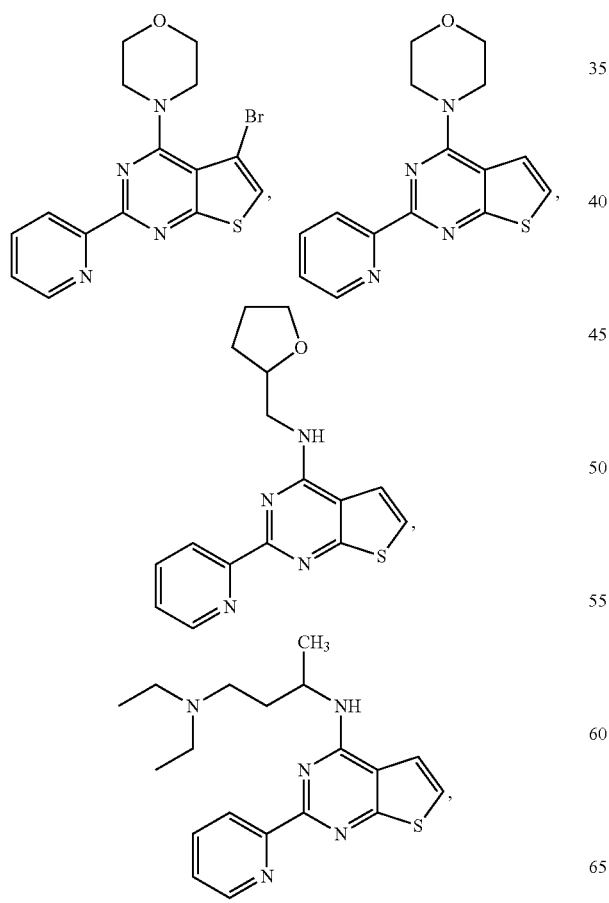
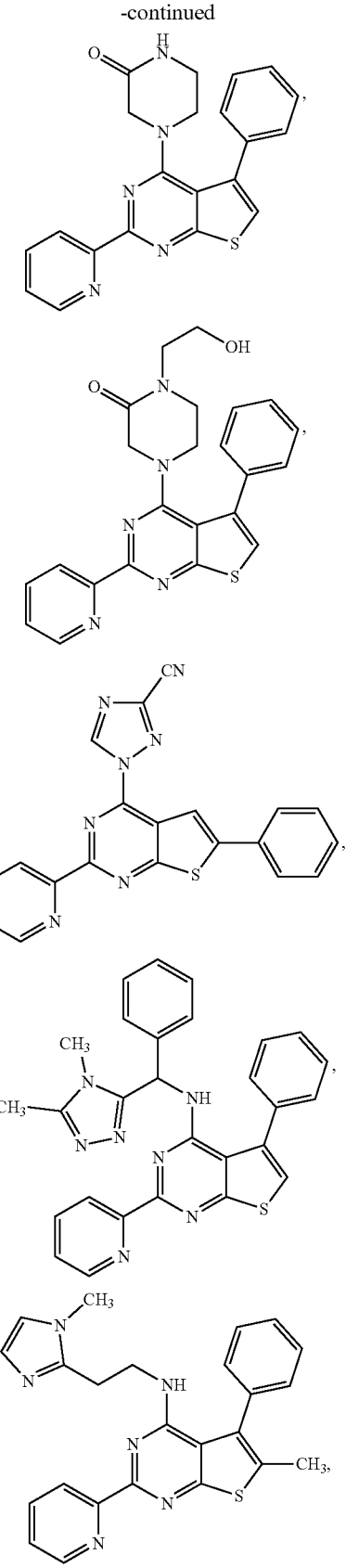

177
-continued
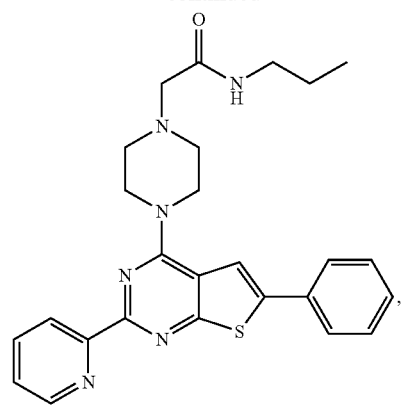
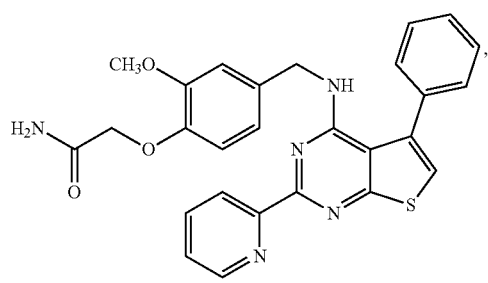
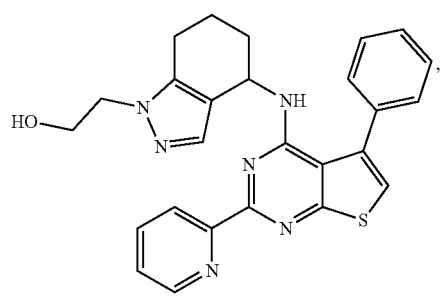
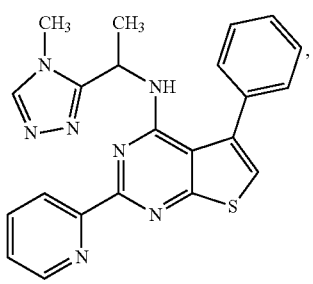
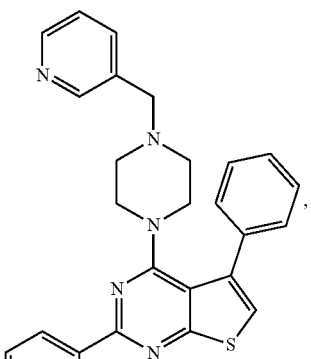
178
-continued
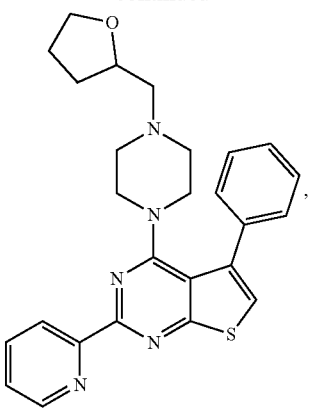
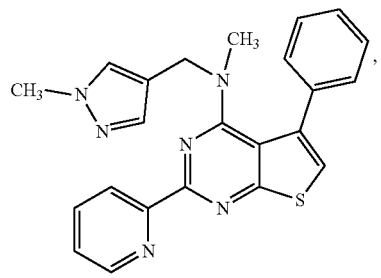
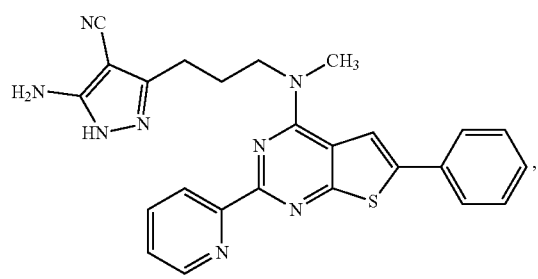
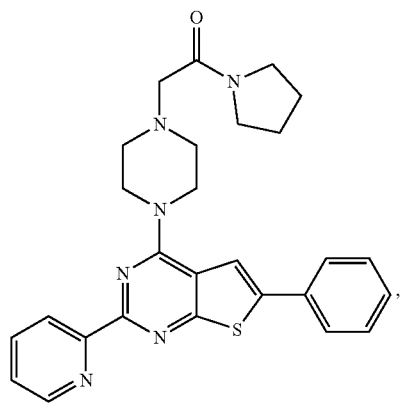

179
-continued
180
-continued
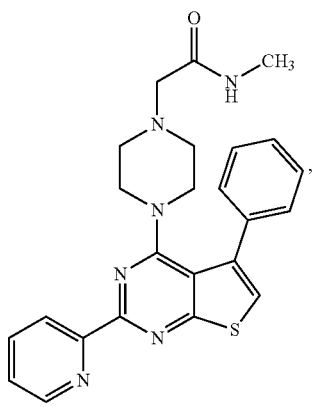
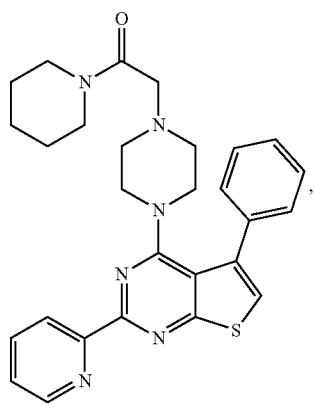

181
-continued
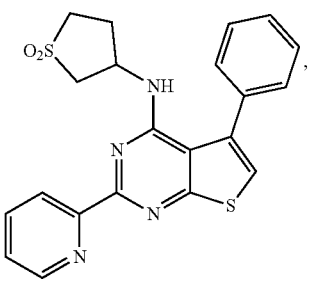
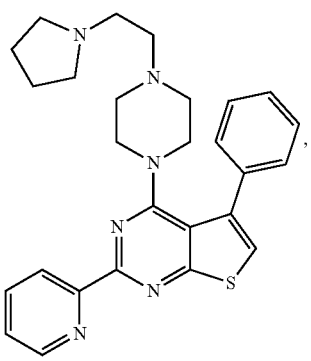
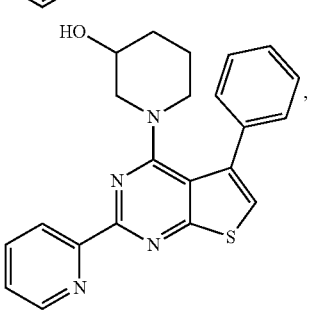
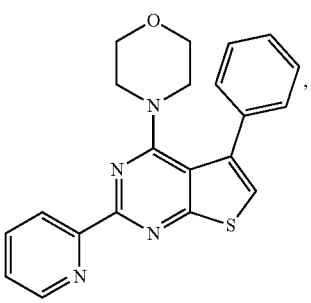
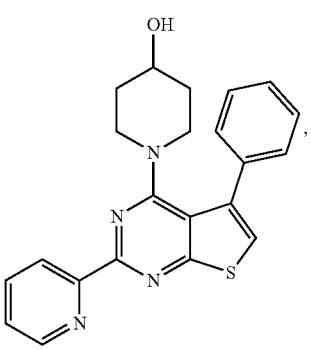
182
-continued
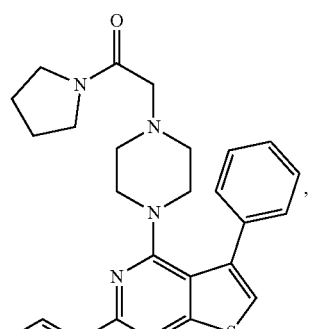
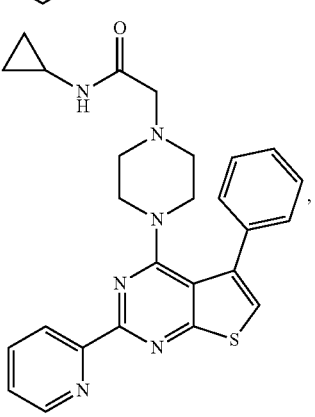
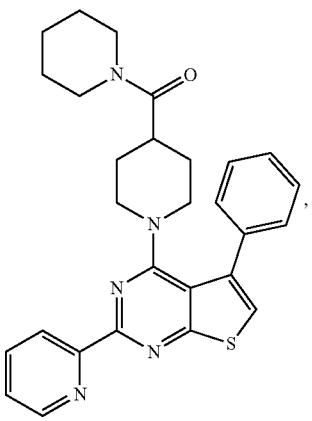
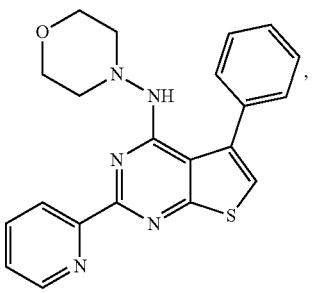

-continued
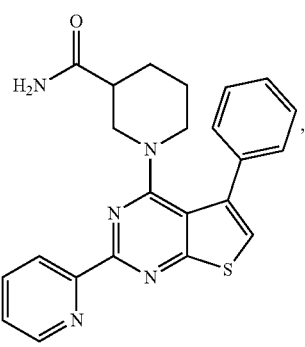
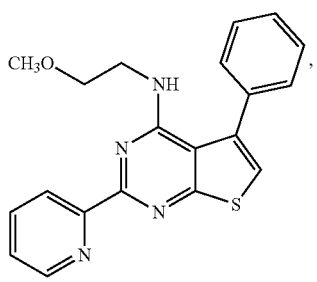
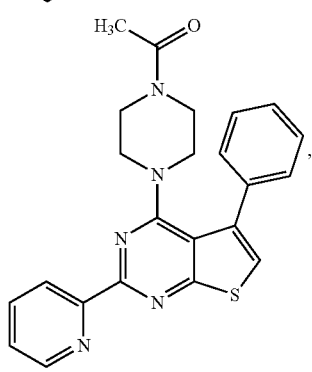
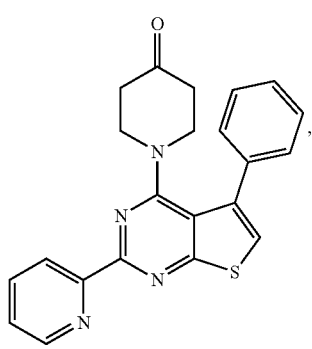
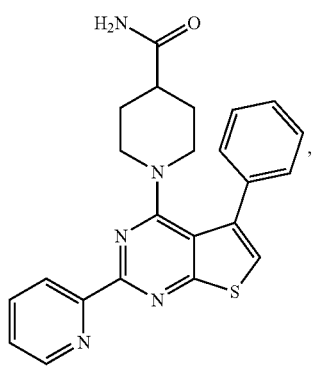
-continued
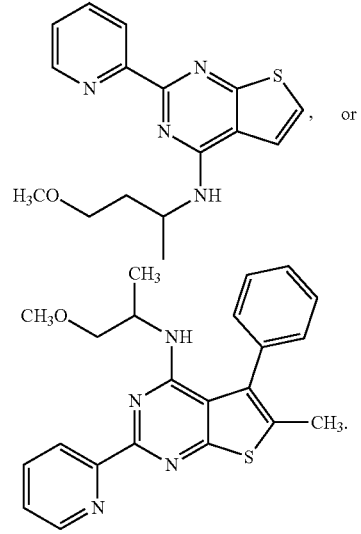, or
In another embodiment of Formula VIIIb1, a compound of Formula VIIIb1 is a compound wherein
R$^{1b1}$ is pyridinyl;
R$^{8b1}$ is H, methyl or phenyl;
R$^{9b1}$ is —C(O)NR$^6$R$^7$; and is selected from
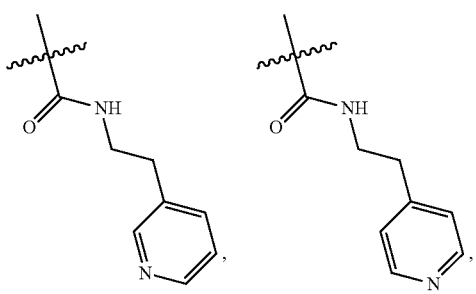
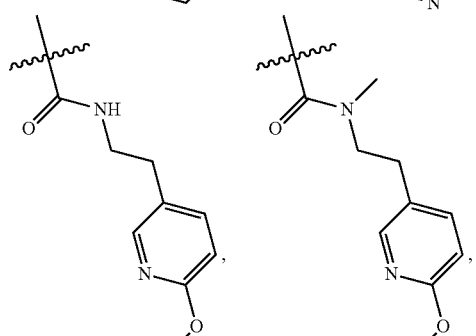
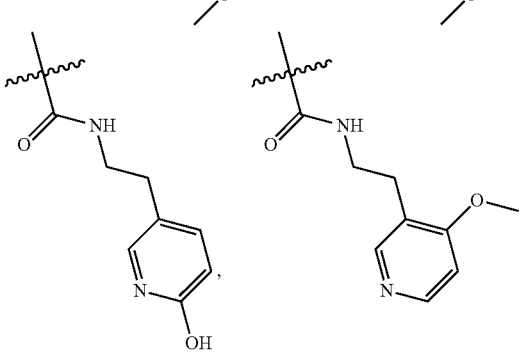

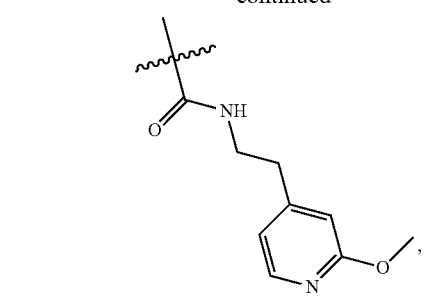
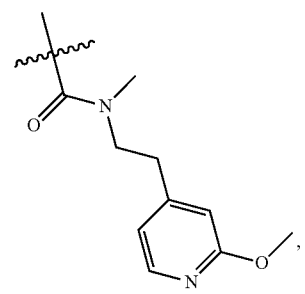
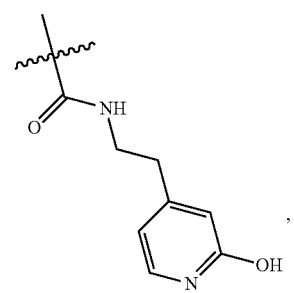
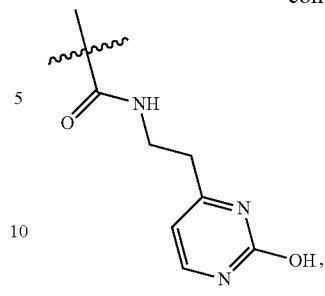
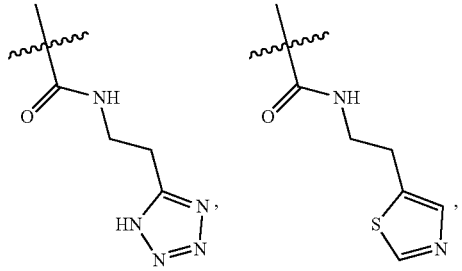
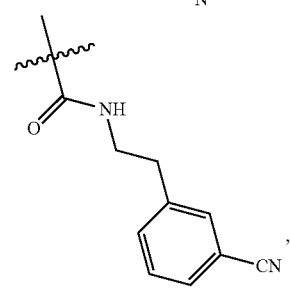
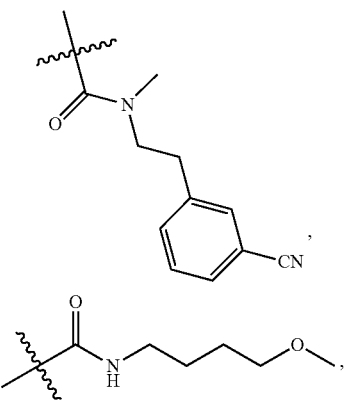

$NR^{6b1}R^{7b1}$ is selected from
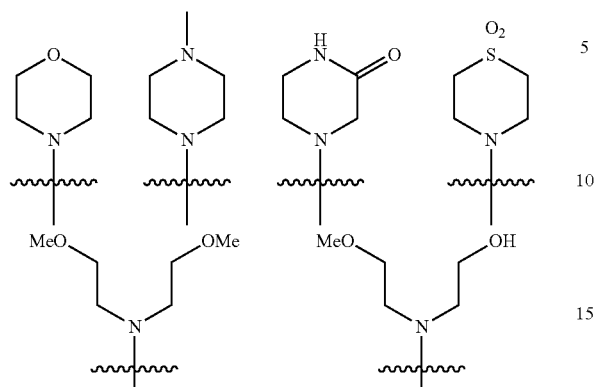
In another embodiment of Formula VIIIb1, a compound of Formula VIIIb1 is a compound wherein
$R^{1b1}$ is pyridinyl;
$R^{8b1}$ is H;
$R^{9b1}$ is H;
$R^{6b1}$ and $R^{7b1}$ are independently selected from H,
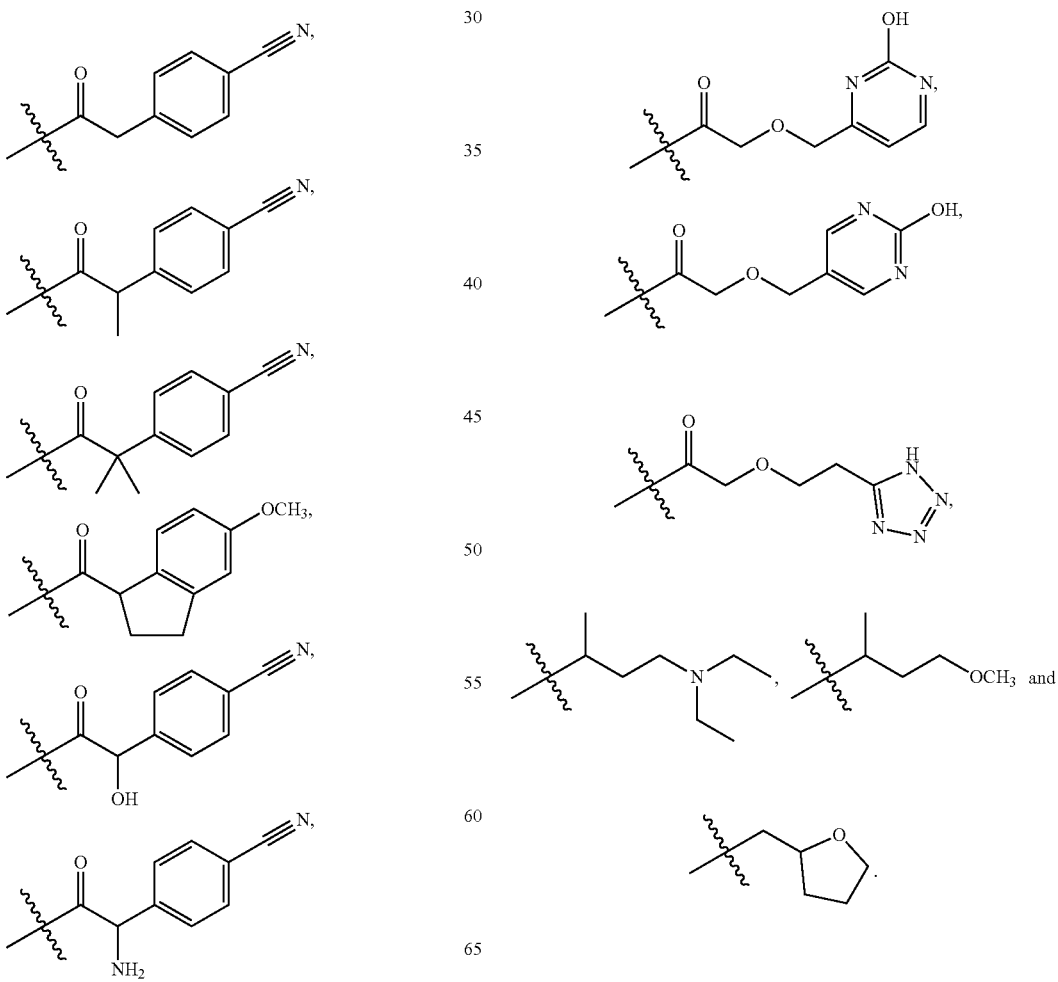
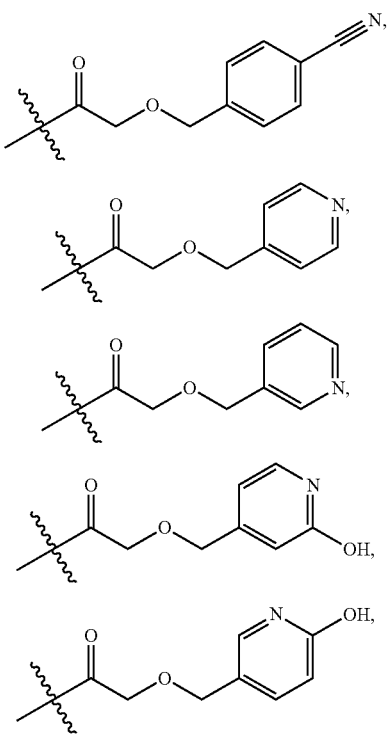

In one embodiment, the compound of Formula VIIIb11 is:

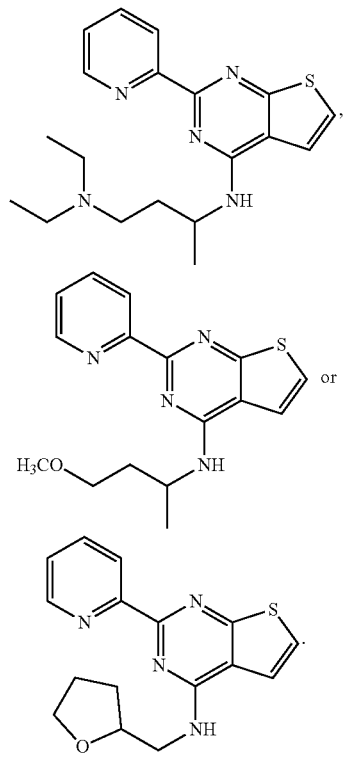

In another embodiment of Formula VIIIb, a compound of Formula VIIIb1 is a compound wherein $R^{1b1}$ is pyridinyl or methoxypyridinyl;

$R^{8b1}$ is H;

$R^{9b1}$ is H, bromo, chloro, cyano, trifluoromethyl or phenyl; and $NR^{6b1}R^{7b1}$ is

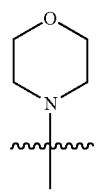 [SMILES: *N1CCOCC1]

In one embodiment, the compound of Formula VIIIb1 is:

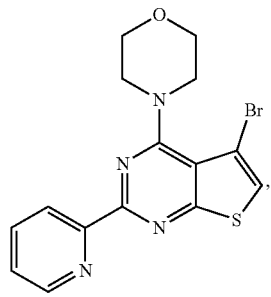

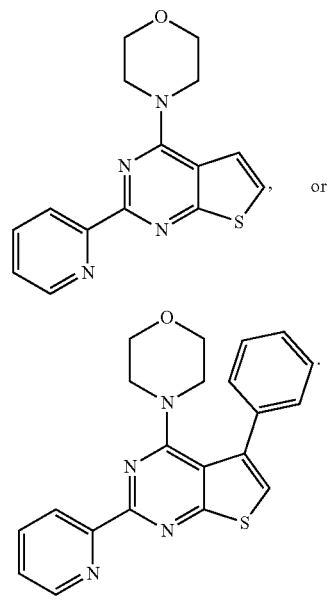

In another embodiment, the compound of Formula VIIIb is a compound of Formula VIIIb2:

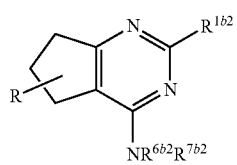

Formula VIIIb2 or pharmaceutically acceptable derivatives thereof, wherein $R^{1b2}$ is H, aryl or heteroaryl;

$R^{6b2}$ and $R^{7b2}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b2}$ and $R^{7b2}$ are combined to form a cyclic structure including the nitrogen atom to which they are both attached;

p is 0-2; and

R may consist of 0-6 subsituents independently selected from H or alkyl.

In another embodiment, the compound of Formula VIIIb is a compound wherein $R^{1b2}$ is pyridinyl;

$R^{6b2}$ and $R^{7b2}$ are independently selected from one of the following:

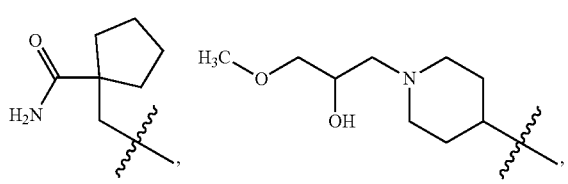

-continued
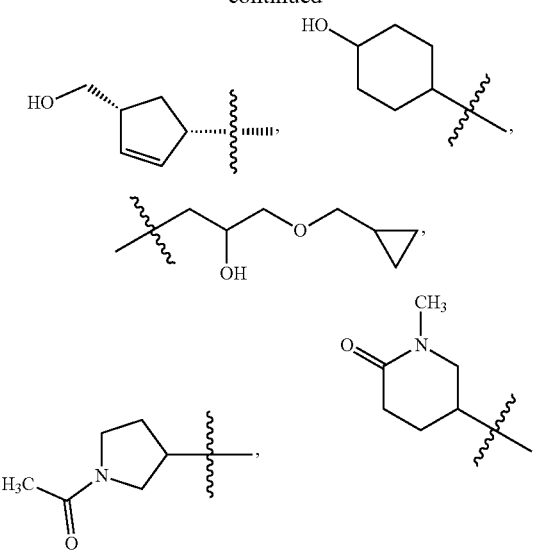
or
R$^{6b2}$ and R$^{7b2}$ are combined to form a cyclic structure including the nitrogen atom to which they are both attached, as depicted below:
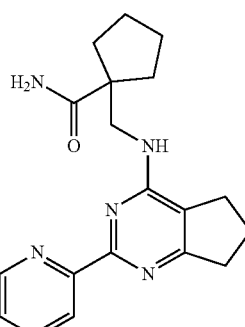
R is H.
In one embodiment, the compound of Formula VIIIb2 is:
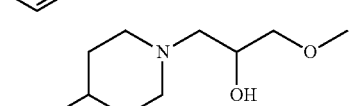
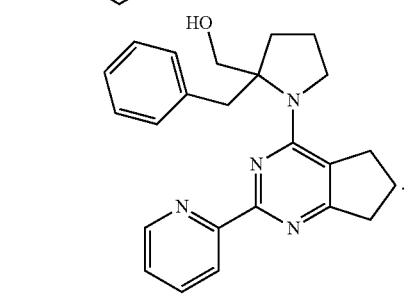
-continued
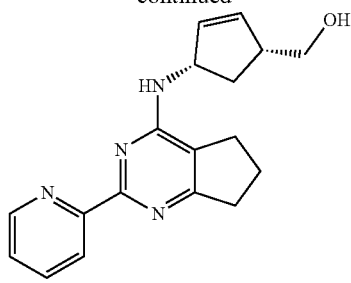
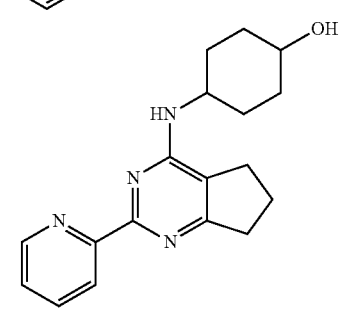
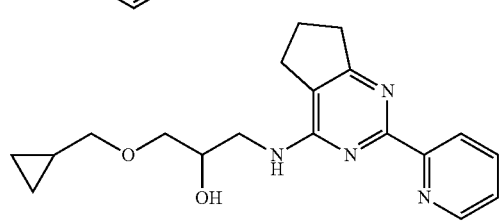
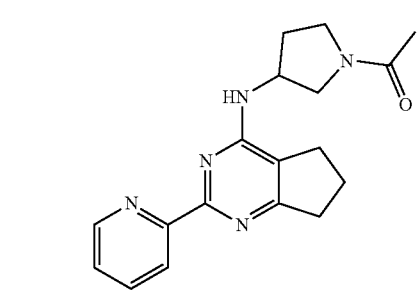
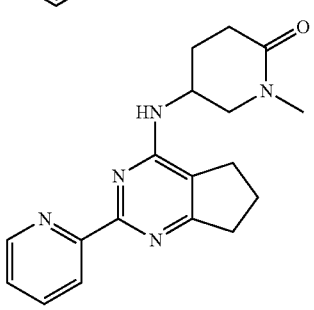
or
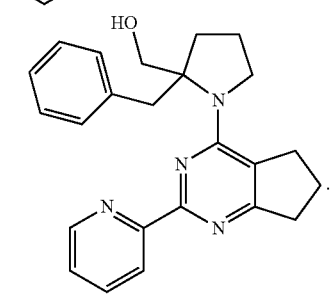
In another embodiment, the compound of Formula VIIIb is a compound of Formula VIIIb3:

Formula VIIIb3

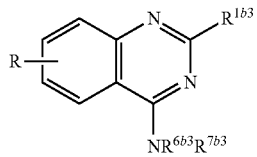

or pharmaceutically acceptable derivatives thereof, wherein $R^{1b3}$ is H, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

$R^{6b3}$ and $R^{7b3}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b3}$ and $R^{7b3}$ are combined to form a cyclic structure including the nitrogen atom to which they are both attached;

p is 0-2; and

R may consist of 0-4 subsituents independently selected from H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$.

In another embodiment, the compound of Formula VIIIb3 is a compound wherein:

$R^{1b3}$ is thienyl;

$R^{6b3}$ and $R^{7b3}$ are combined to form a cyclic structure including the nitrogen atom to which they are both attached, as depicted below

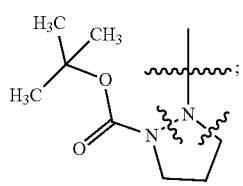

and

R is H.

In one embodiment, the compound of Formula VIIIb3 is:

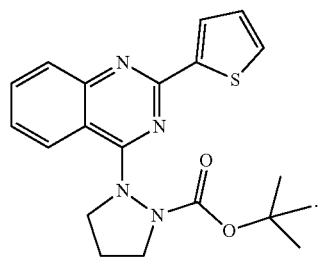 [SMILES: CC(C)(C)OC(=O)N1CCCN1c1nc(-c2cccs2)nc2ccccc12]

In another embodiment, the compound of Formula VIIIb is a compound of Formula VIIIb4:

Formula VIIIb4

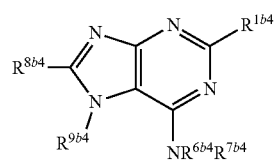

or pharmaceutically acceptable derivatives thereof, wherein $R^{1b4}$ is H, alkyl, aryl or heteroaryl;

$R^{8b4}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b4}$ is alkyl, alkenyl, alkynyl, aryl, cycloalkyl, heterocyclyl, heteroaryl, $C(O)R^4$, or $S(O)_pR^4$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

$R^{6b4}$ and $R^{7b4}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6b4}$ and $R^{7b4}$ are combined to form a cyclic structure including the nitrogen atom to which they are both attached; and p is 0-2.

In one embodiment of Formula VIIIb4, a compound of Formula VIIIb4 is a compound wherein wherein $R^{1b4}$ is 2-pyridyl;

$R^{8b4}$ is H;

$R^{9b4}$ is $CH_2CONHR$, wherein R is H, alkyl, aryl, arylakyl, heteroaryl;

$NR^{6b4}R^{7b4}$ is a morpholine ring; and p is 0-2.

In one embodiment of Formula VIIIb4, a compound of Formula VIIIb4 is a compound wherein $R^{1b4}$ is pyridinyl;

$R^{8b4}$ is H;

$R^{9b4}$ is $CH_2CONHR$, wherein R is H,

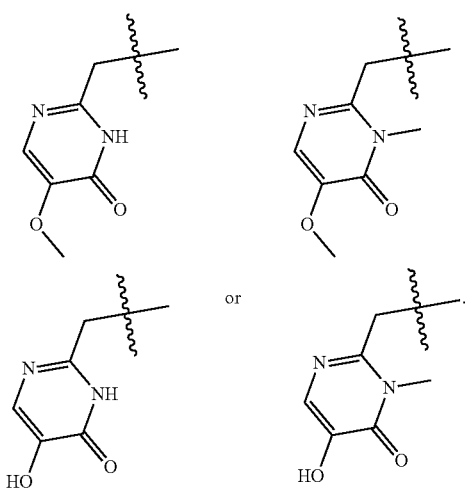

NR$^{6b4}$R$^{7b4}$ is

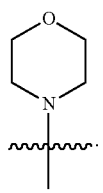

In one embodiment, the compound of formula VIIIb is selected with the proviso that if A is a substituted or unsubstituted phenyl or thienyl ring, and R$^6$ is H; then R$^7$ is not 4-pyridyl, pyrimidinyl, chloropyridinyl or indazole.

In one embodiment, the compound of formula VIIIb1 is selected with the proviso that if R$^6$ is H; then R$^7$ is not 4-pyridyl, pyrimidinyl, chloropyridinyl or indazole.

In one embodiment, the compound of formula VIIIb3 is selected with the proviso that if R$^6$ is H; then R$^7$ is not 4-pyridyl, pyrimidinyl, chloropyridinyl or indazole.

In certain embodiments, the compounds for use in the compositions and methods provided herein are of Formula IXa or Formula IXb:

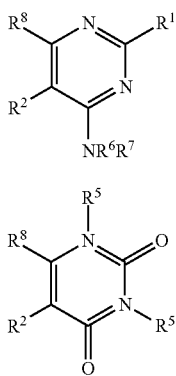

Formula IXa

Formula IXb or pharmaceutically acceptable derivatives thereof,
wherein R$^1$, R$^2$ and R$^8$ are independently selected from the group consisting of H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, and NR$^6$R$^7$;

R$^3$ is hydrogen, alkyl, alkenyl, alkynyl, aryl, heteroaryl, heterocyclyl, cycloalkyl, alkylcarbonyl, cycloalkylcarbonyl or arylcarbonyl;

R$^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;

R$^5$ is hydrogen, alkyl, alkenyl, alkynyl, aryl, heteroaryl, heterocyclyl, cycloalkyl, alkylcarbonyl, cycloalkylcarbonyl, or arylcarbonyl;

R$^6$ and R$^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R$^6$ and R$^7$ are combined to form a cyclic structure including the nitrogen atom to which they are both attached; and p is 0-2.

In another embodiment, the compound of Formula IXa is a compound of Formula IXa1:

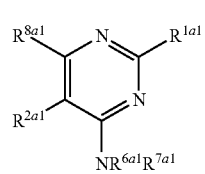

Formula IXa1 or pharmaceutically acceptable derivatives thereof,
wherein R$^{1a1}$ is aryl or heteroaryl;
R$^{2a1}$ is H or alkyl;
R$^{8a1}$ is alkyl;
R$^{6a1}$ and R$^{7a1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, arylamino, alkylamino, arylcarbonylamino, heteroarylcarbonylamino and alkylcarbonylamino; or R$^{6a1}$ and R$^{7a1}$ are combined to form a cyclic structure including the nitrogen atom to which they are both attached.

In one embodiment of Formula IXa1, R$^{1a1}$ is aryl or heteroaryl;
R$^{2a1}$ is H or alkyl;
R$^{8a1}$ is alkyl;
R$^{6a1}$ and R$^{7a1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, arylamino, alkylamino, arylcarbonylamino, heteroarylcarbonylamino and alkylcarbonylamino; or R$^{6a1}$ and R$^{7a1}$ are combined to form a cyclic structure including the nitrogen atom to which they are both attached.

In one embodiment of Formula IXa1, R$^{1a1}$ is 2-pyridyl;
R$^{2a1}$ is H or alkyl;
R$^{8a1}$ is alkyl;
R$^{6a1}$ and R$^{7a1}$ are independently selected from hydrogen, C(O)R, wherein R is alkyl, cycloalkyl, or heterocycloalkyl.

In one embodiment, R$^{1a1}$ is

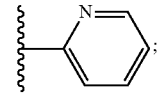

$R^{2a1}$ is H or methyl;
$R^{8a1}$ is methyl, ethyl, or trifluoromethyl;
$R^{6a1}$ and $R^{7a1}$ are independently selected from H,
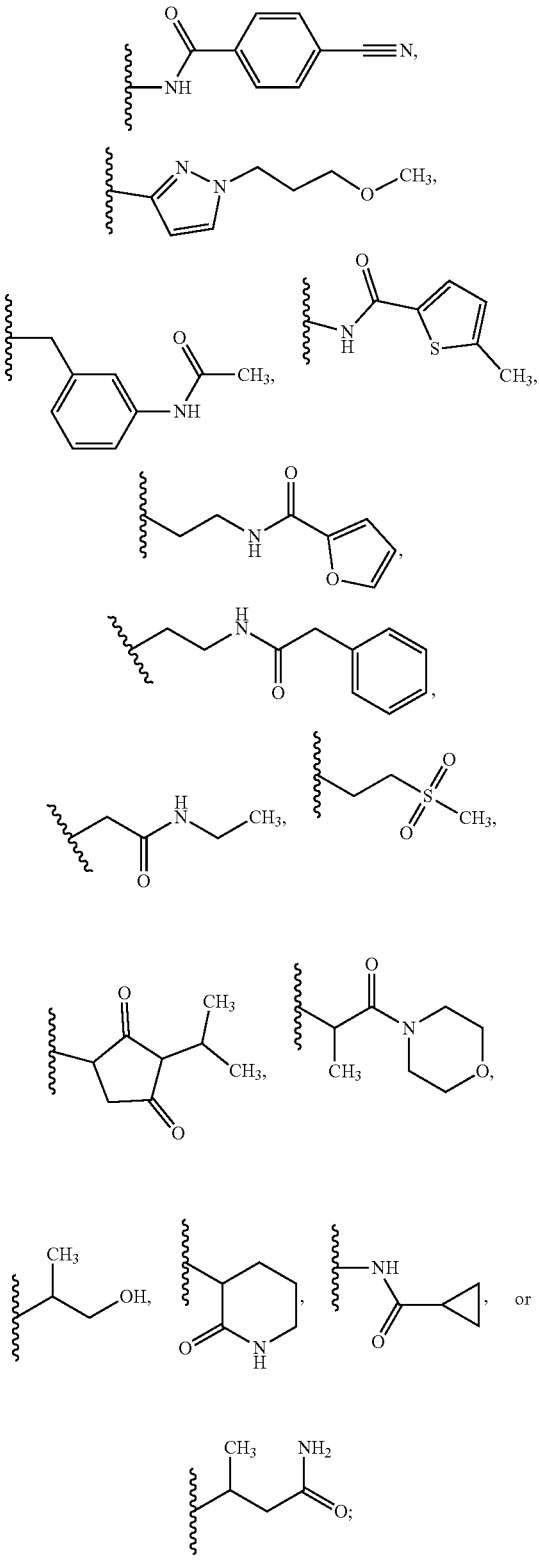
or $R^{6a1}$ and $R^{7a1}$ are combined to form
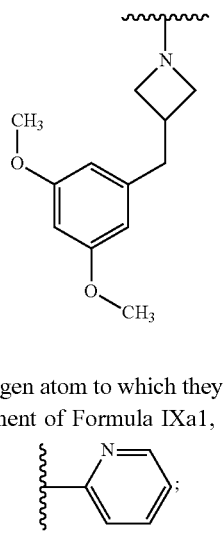
including the nitrogen atom to which they are both attached.
In one embodiment of Formula IXa1, $R^{1a1}$ is
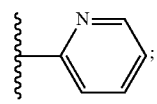 [SMILES: *c1ccccn1]
$R^{2a1}$ is H or methyl;
$R^{8a1}$ is H;
$R^{6a1}$ and $R^{7a1}$ are independently selected from H,
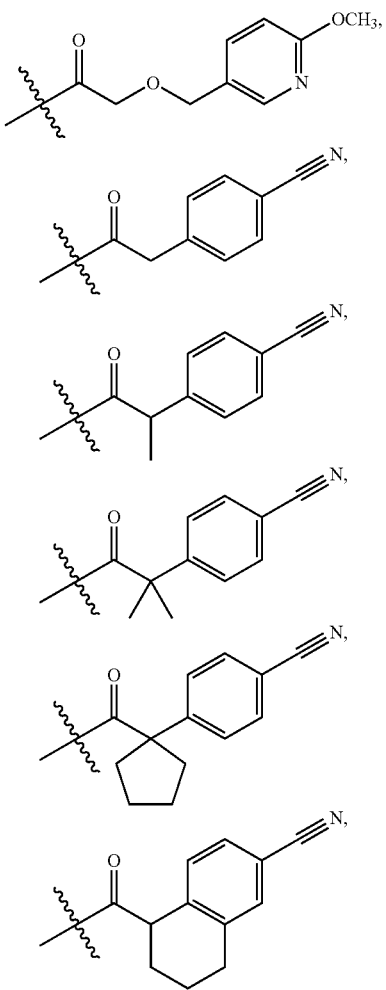

-continued
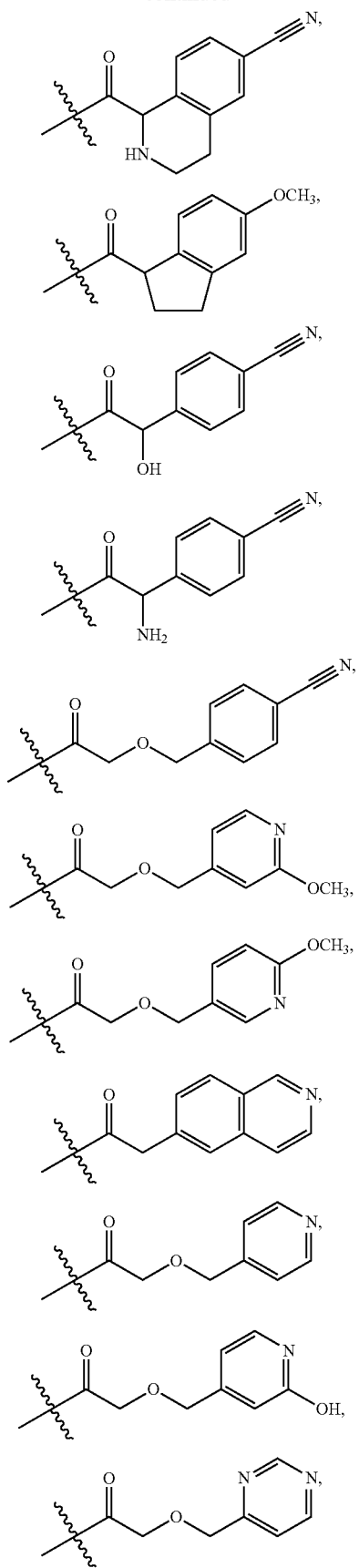
-continued
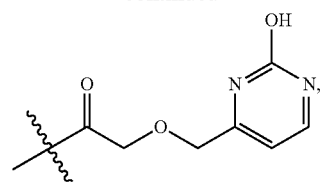
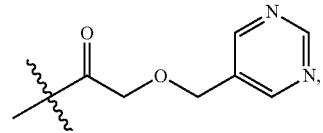
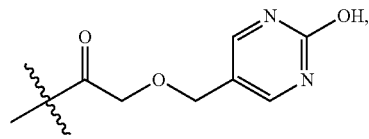
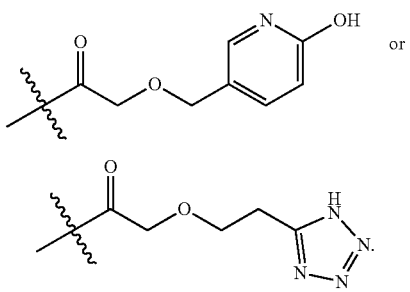
In one embodiment, the compound of Formula IXa1 is:
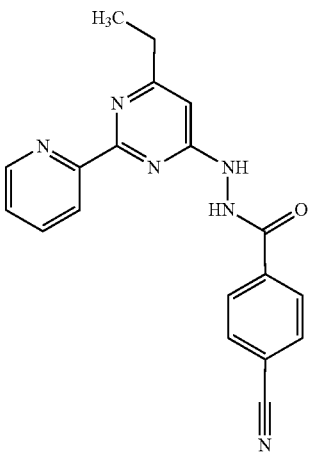
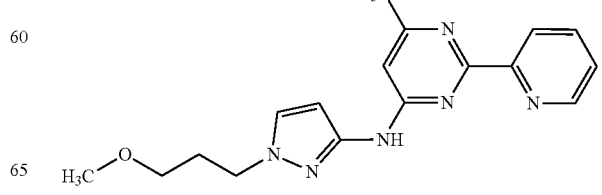

-continued
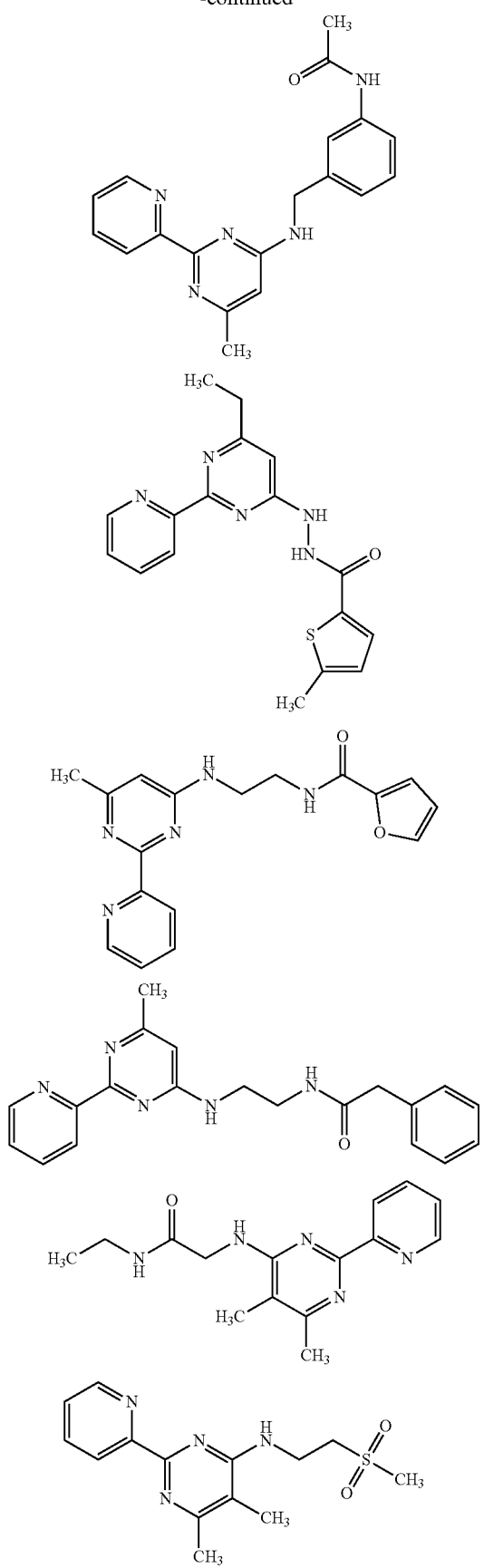
-continued
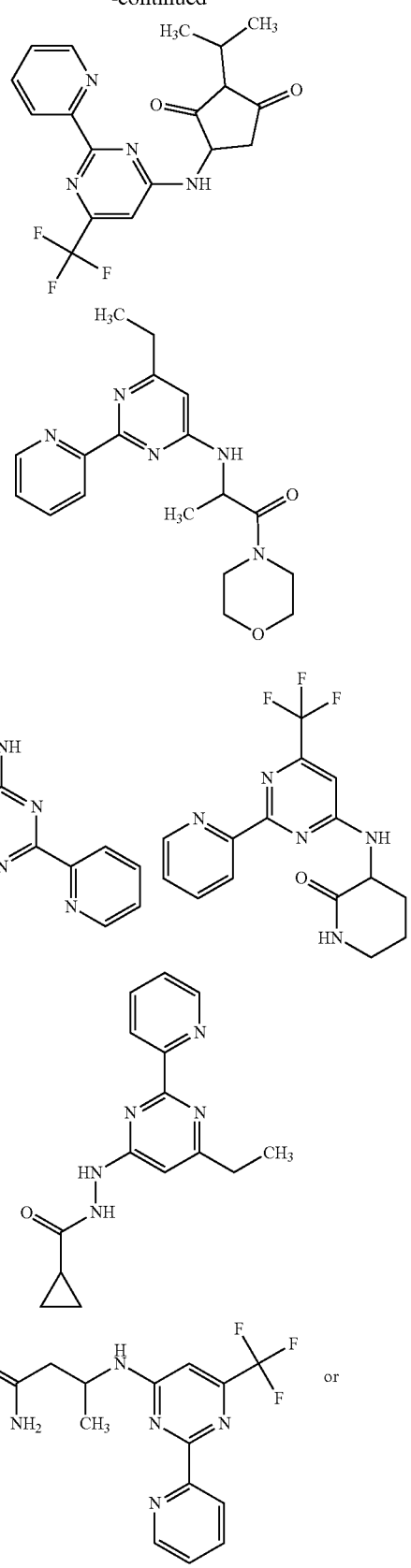

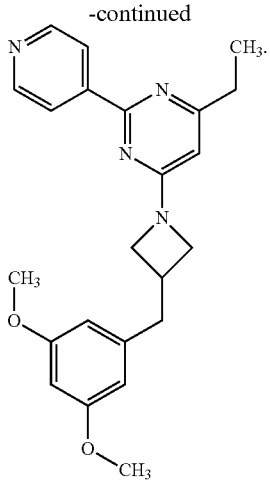

In one embodiment, the compound of Formula IXa1 is:

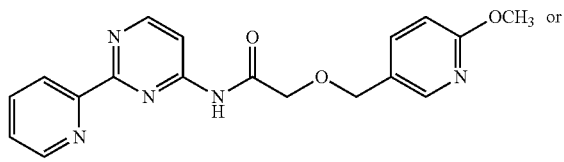

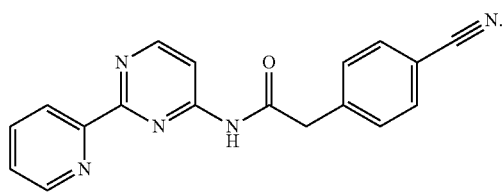

In another embodiment, the compound of Formula IXb is a compound of Formula IXb1:

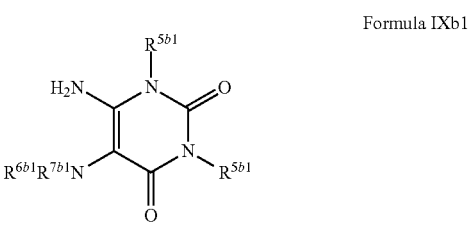

Formula IXb1 or pharmaceutically acceptable derivatives thereof, wherein each $R^{5b1}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6b1}$ and $R^{7b1}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In one embodiment, each $R^{5b1}$ is methyl or

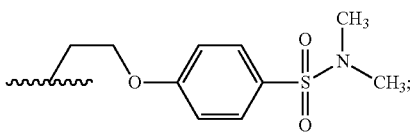 [SMILES: *CCOc1ccc(S(=O)(=O)N(C)C)cc1]

$R^{6b1}$ and $R^{7b1}$ are combined to form a piperidine structure including the nitrogen atom to which they are both attached.

In one embodiment, the compound of Formula IXb1 is:

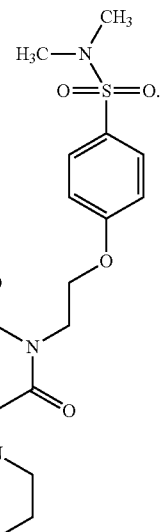

In one embodiment, the compound of Formula IXa is selected with the proviso that if $R^1$ is heteroaryl, then $NR^6R^7$ is not morpholino.

In one embodiment, the compound of Formula IXa1 is selected with the proviso that if $R^{1a}$ is heteroaryl, then $NR^{6a}R^{7a}$ is not morpholino.

In one embodiment, the compound of Formula IXa is selected with the proviso that if $R^1$ is morpholino, then $NR^6R^7$ is not $NH_2$.

In certain embodiments, the compounds for use in the compositions and methods provided herein are of Formula X:

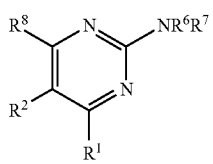

Formula X or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and p is 0-2.

In another embodiment, the compound of Formula X is a compound of Formula Xa:

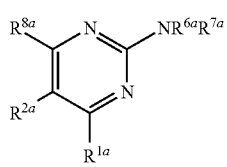

Formula Xa or pharmaceutically acceptable derivatives thereof, wherein R¹ᵃ is H or alkyl;
R²ᵃ is H or halo;
R⁸ᵃ is H or alkyl;
R⁶ᵃ and R⁷ᵃ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ᵃ and R⁷ᵃ are combined to form a cyclic structure including the nitrogen atom to which they are both attached.

In one embodiment, R¹ᵃ is H, methyl, or trifluoromethyl;
R²ᵃ is H or Br;
R⁸ᵃ is H, methyl, or trifluoromethyl;
R⁶ᵃ and R⁷ᵃ are independently selected from hydrogen, or R⁶ᵃ and R⁷ᵃ are combined to form

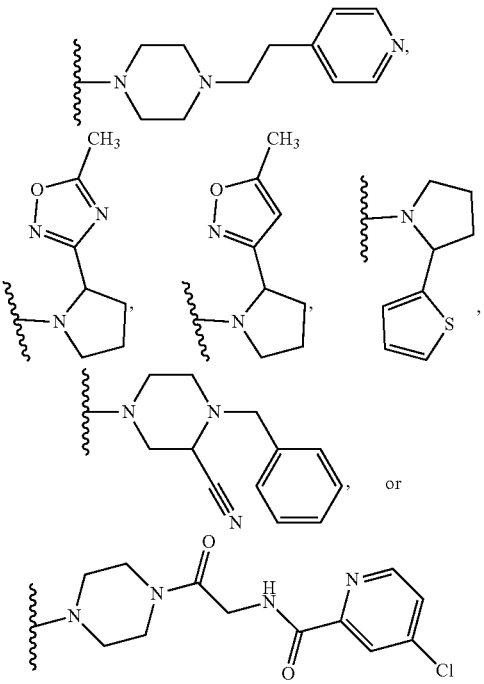

including the nitrogen atom to which they are both attached.

In one embodiment, the compound of Formula Xa is:

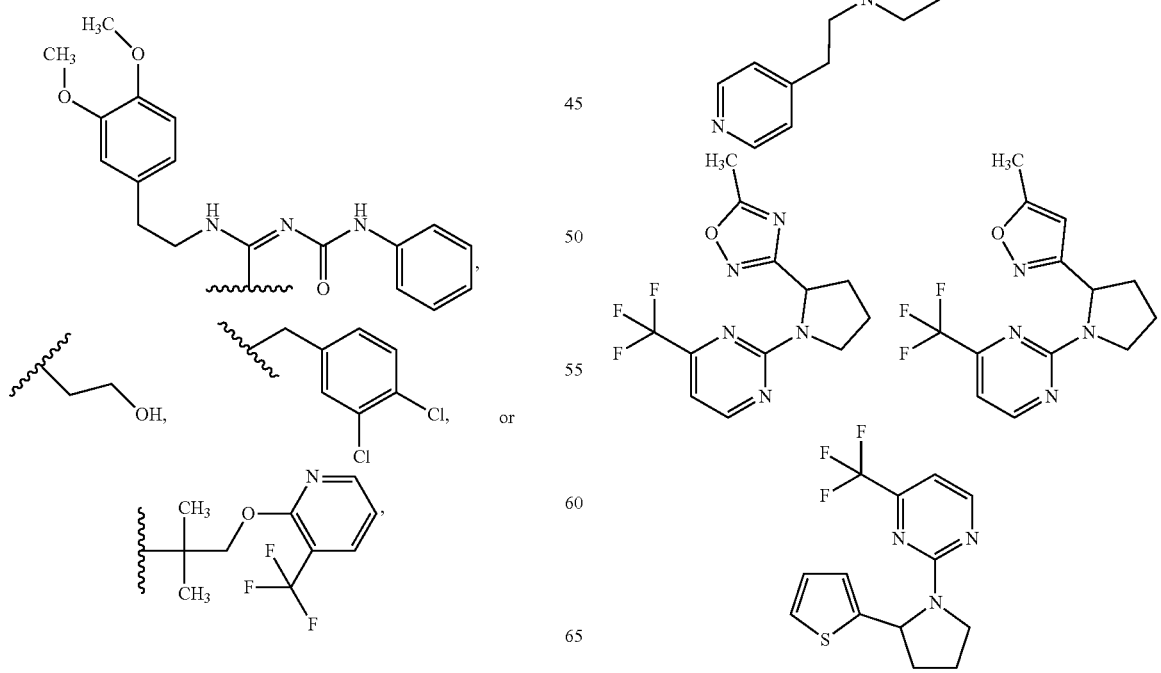

-continued

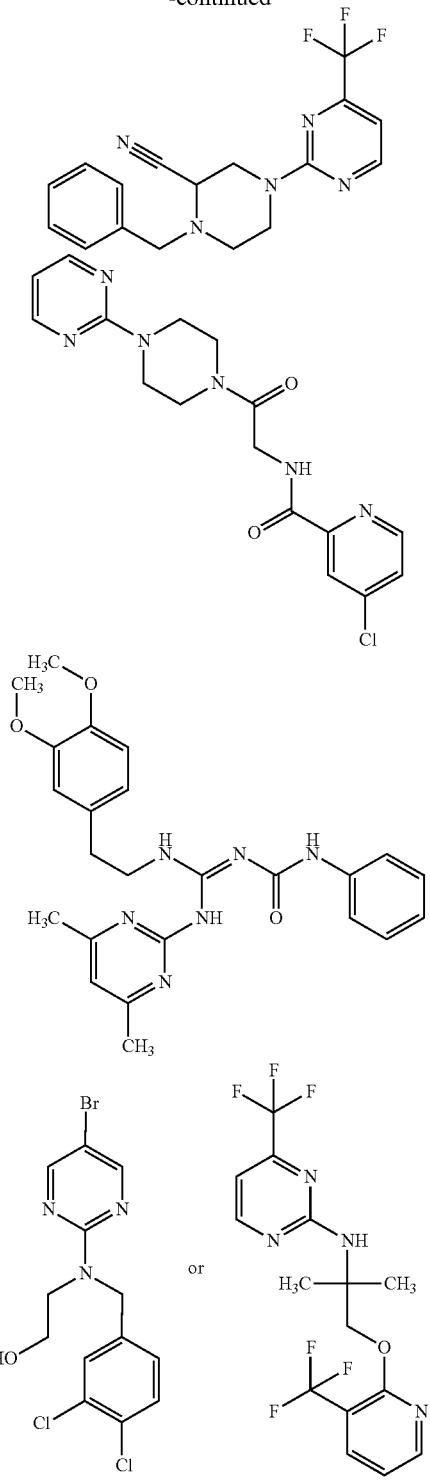

In one embodiment, the compound of Formula X is selected with the proviso that if $R^1$ is methyl and $NR^6R^7$ is $NH_2$, then $R^8$ is not aryl.

In certain embodiments, the compounds for use in the compositions and methods provided herein are of Formula XI:

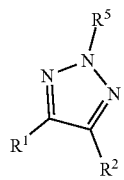

Formula XI or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and p is 0-2.

In another embodiment, the compound of Formula XI is a compound of Formula XIa:

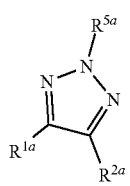

Formula XIa or pharmaceutically acceptable derivatives thereof, wherein $R^{1a}$ is H or alkyl;

$R^{2a}$ is $C(O)R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5a}$ is H, aryl or heteroaryl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached.

In one embodiment, $R^{1a}$ is H or methyl;

$R^{2a}$ is

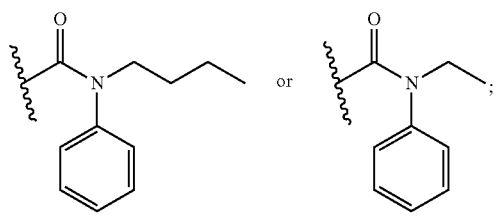 [SMILES: *C(=O)N(CCCC)c1ccccc1 ; *C(=O)N(CC)c1ccccc1]

and $R^{5a}$ is Ph.

In one embodiment, the compound of Formula XIa is:

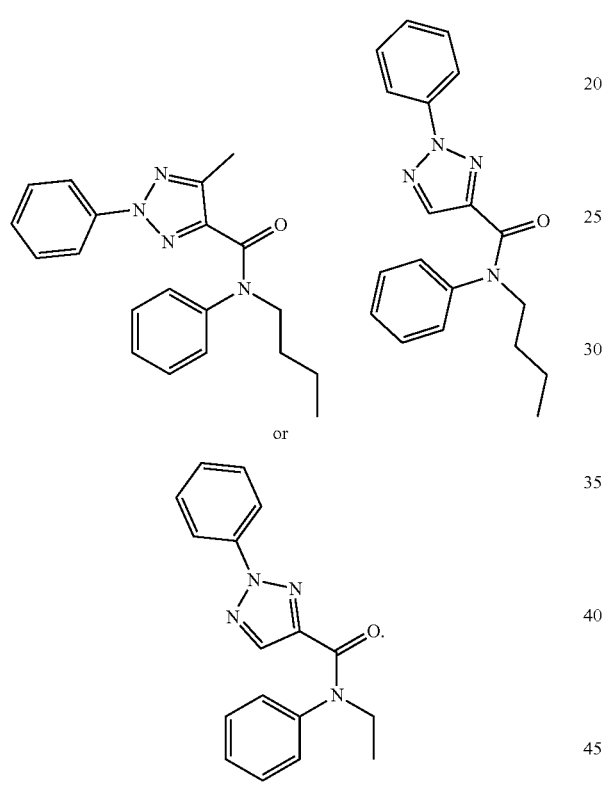

In certain embodiments, the compounds for use in the compositions and methods provided herein are of Formula XII:

Formula XII

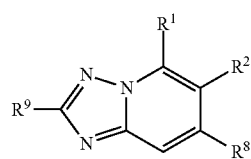

or pharmaceutically acceptable derivatives thereof, wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and p is 0-2.

In another embodiment, the compound of Formula XII is a compound of Formula XIIa:

Formula XIIa

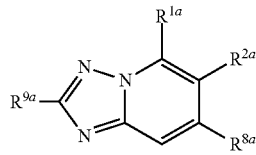

or pharmaceutically acceptable derivatives thereof,
wherein $R^{1a}$ is alkyl or $NR^6R^7$;
$R^{2a}$ is H or alkyl;
$R^{8a}$ is H or alkyl;
$R^{9a}$ is H or $R^{6'}R^{7'}NC(O)$alkyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and $R^{6'}$ and $R^{7'}$ are independently selected from hydrogen, alkyl, alkenyl, alkynyl, aryl, heteroaryl, heterocyclyl and cycloalkyl; or $R^{6'}$ and $R^{7'}$ are combined to form a cyclic structure including the nitrogen atom to which they are both attached.

In one embodiment, $R^{1a}$ is methyl,

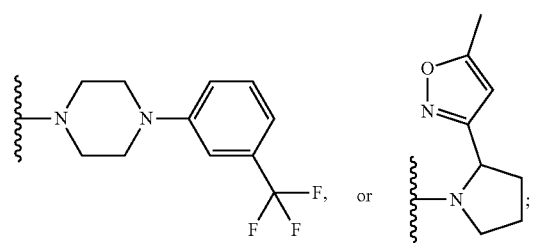 [SMILES: *N1CCN(c2cccc(C(F)(F)F)c2)CC1 ; *N1CCCC1c1cc(C)on1]

$R^{2a}$ is H;
$R^{8a}$ is methyl or trifluoromethyl; and
$R^{9a}$ is H,

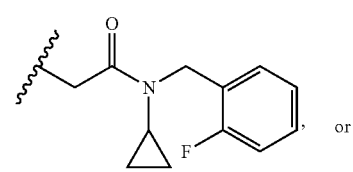

211

-continued

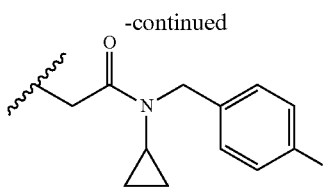

In one embodiment, the compound of Formula XIIa is:

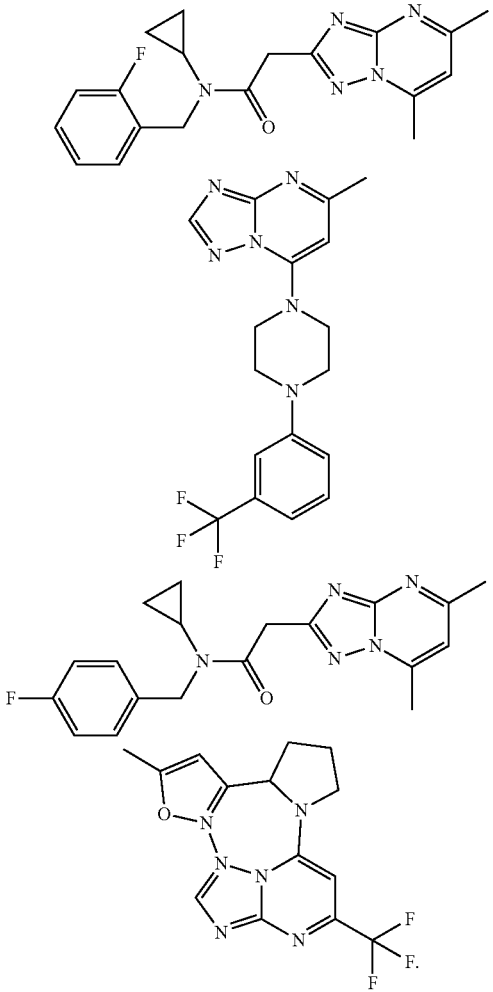

In one embodiment, the compound of Formula XII is selected with the proviso that the compound is not

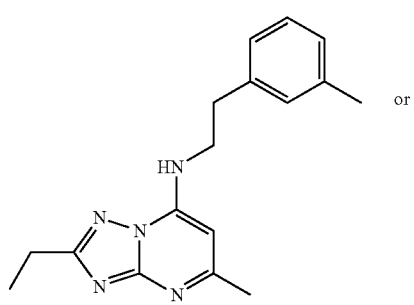

or

212

-continued

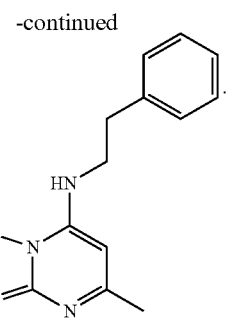

In certain embodiments, the compounds for use in the compositions and methods provided herein are of Formula XIII:

Formula XIII

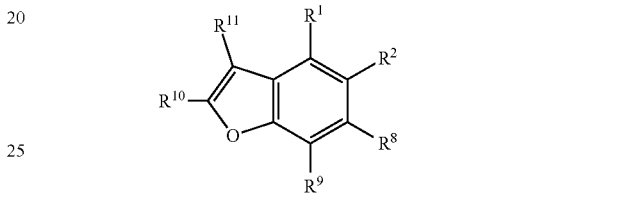

or pharmaceutically acceptable derivatives thereof,
wherein $R^1$, $R^2$, $R^1$, $R^9$, $R^{10}$ and $R^{11}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and p is 0-2.

In another embodiment, the compound of Formula XIII is a compound of Formula XIIIa:

Formula XIIIa

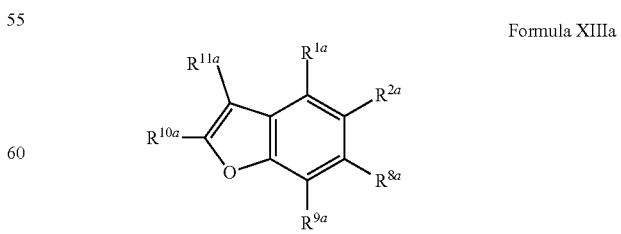

or pharmaceutically acceptable derivatives thereof,
wherein $R^{1a}$ is H or alkyl;
$R^{2a}$ is H or alkyl;

R[8] is H or alkyl;
R[9a] is H or alkyl;
R[10a] is aryl, heteroaryl or C(O)R[4];
R[11a] is H, -alkylOR[3] or C(O)R[4];
R[3] is hydrogen, alkyl, alkenyl, alkynyl, aryl, heteroaryl, heterocyclyl, cycloalkyl, alkylcarbonyl, cycloalkylcarbonyl or arylcarbonyl;
R[4] is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR[6]R[7];
R[6] and R[7] are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R[6] and R[7] are combined to form a cyclic structure including the nitrogen atom to which they are both attached.

In another embodiment, R[1a] is H or alkyl;
R[2a] is H, OR[3a] or alkyl;
R[8a] is H or alkyl;
R[9a] is H or alkyl;
R[10a] is aryl, heteroaryl or C(O)R[4];
R[11a] is H, -alkylOR[3] or C(O)R[4];
R[3] is hydrogen, alkyl, alkenyl, alkynyl, aryl, heteroaryl, heterocyclyl, cycloalkyl, alkylcarbonyl, cycloalkylcarbonyl or arylcarbonyl;
R[4] is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR[6]R[7];
R[6] and R[7] are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R[6] and R[7] are combined to form a cyclic structure including the nitrogen atom to which they are both attached.

In one embodiment, R[1a] is H;
R[2a] is H or

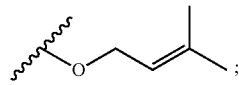

R[8a] is H;
R[9a] is H;
R[10a] is

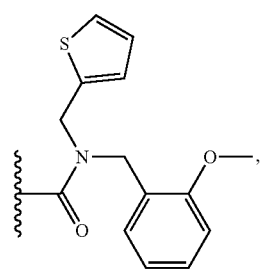

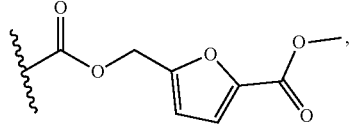

-continued

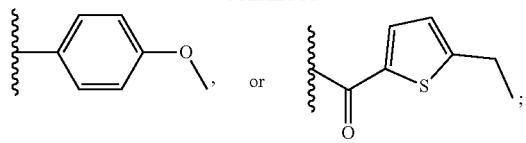

and
R[11a] is H,

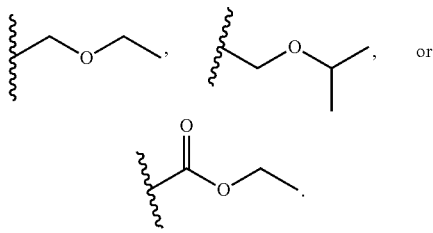

In one embodiment, the compound of Formula XIIIa is:

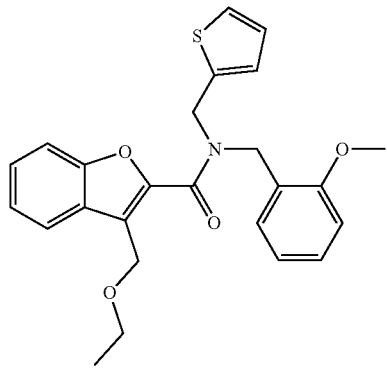

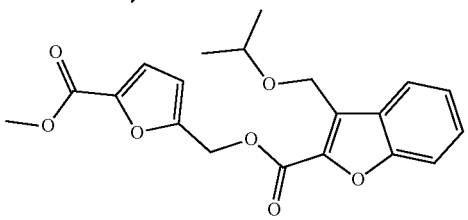

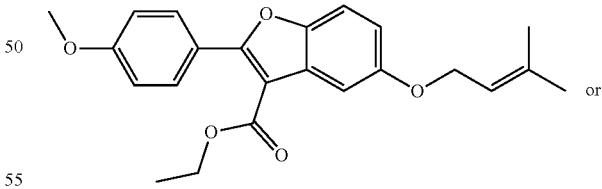

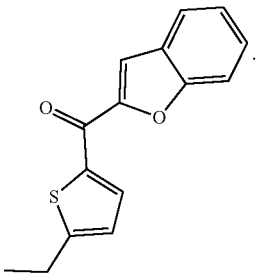

In certain embodiments, the compounds for use in the compositions and methods provided herein are of Formula XIV:

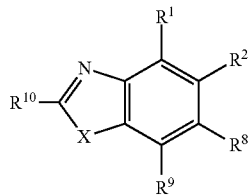

Formula XIV or pharmaceutically acceptable derivatives thereof,
wherein $R^1$, $R^2$, $R^1$, $R^9$ and $R^{10}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
p is 0-2; and
X is S or $NR^5$.
In another embodiment, the compound of Formula XIV is a compound of Formula XIVa:

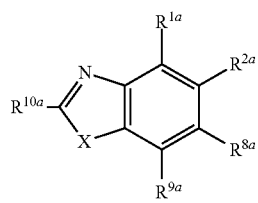

Formula XIVa or pharmaceutically acceptable derivatives thereof,
wherein $R^{1a}$, $R^{8a}$ and $R^{9a}$ are independently selected from the group consisting of H, alkyl or halo;
$R^{2a}$ is H, alkyl, halo, $C(O)R^4$ and $S(O)_pR^4$;
$R^{10a}$ is heterocyclyl, -alkylNR^6R^7 or $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
p is 0-2; and
X is S or $NR^5$.
In one embodiment, $R^{1a}$, $R^{8a}$ and $R^{9a}$ are H;
$R^{2a}$ is H or

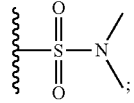

$R^{10a}$ is

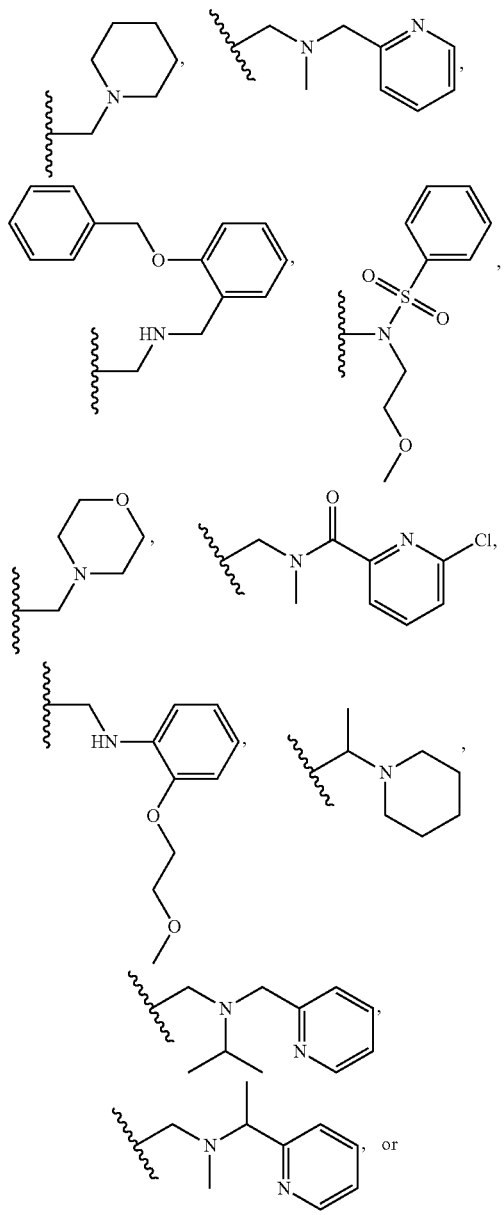

217
-continued
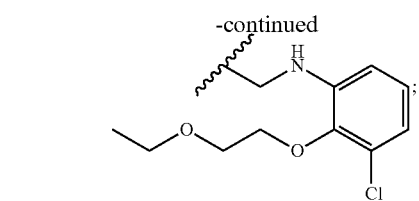
$R^5$ is H, methyl, n-propyl
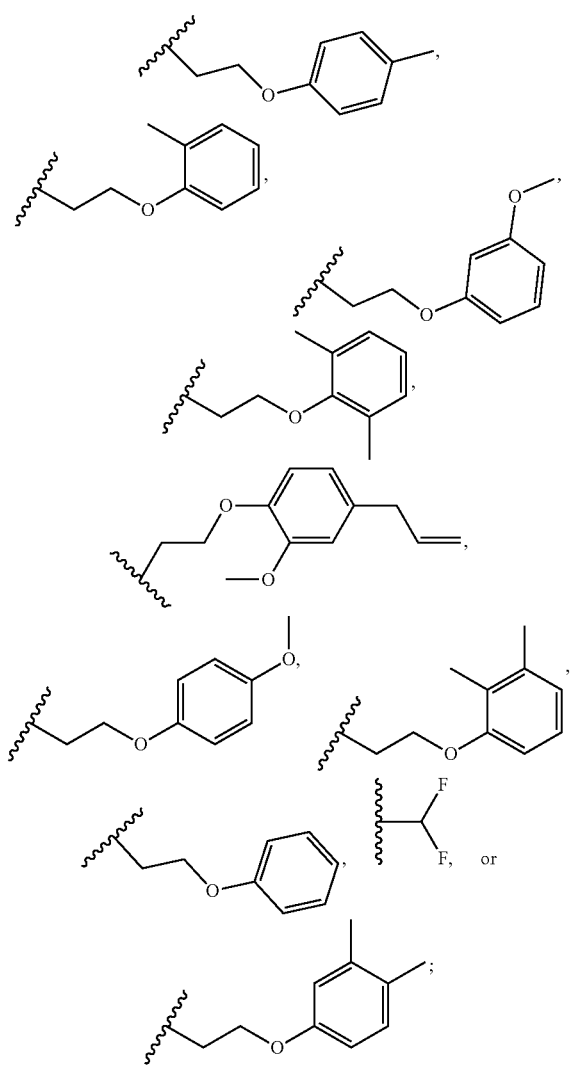
and
X is S or NR$^5$.
In one embodiment, R$^{1a}$, R$^{8a}$ and R$^{9a}$ are H;
R$^{2a}$ is H, —CO(O)Et, or
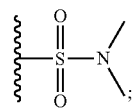
218
R$^{10a}$ is
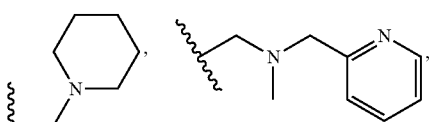
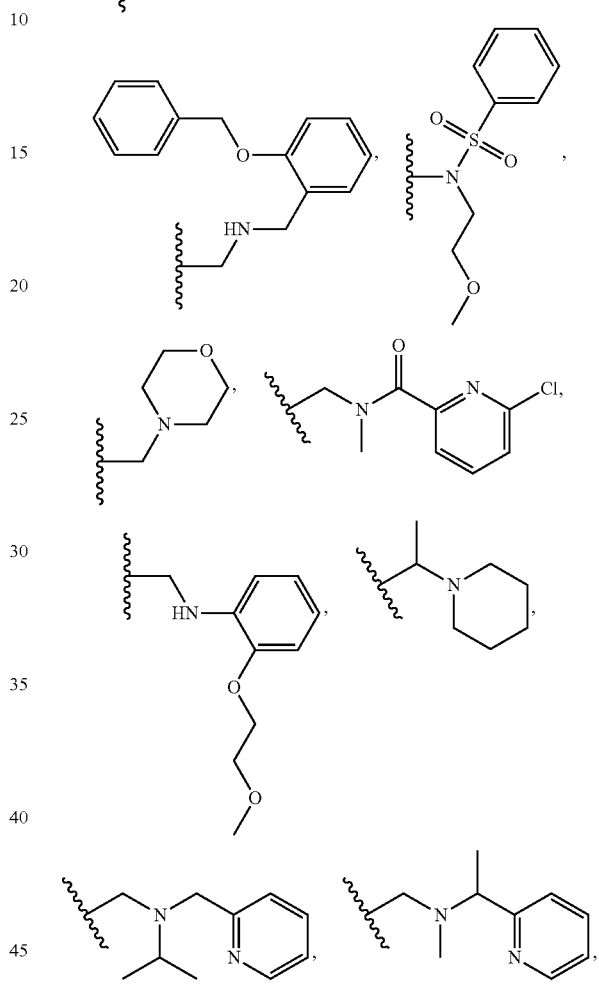
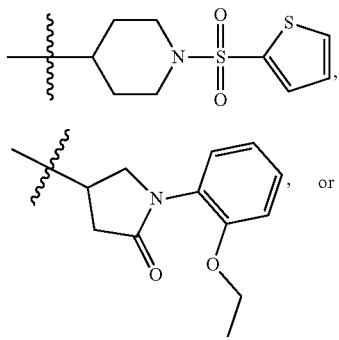

-continued
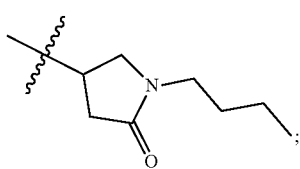
R⁵ is H, methyl, n-propyl,
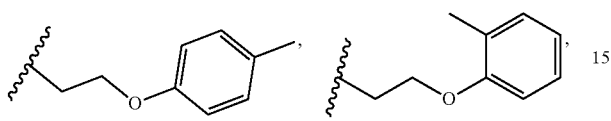
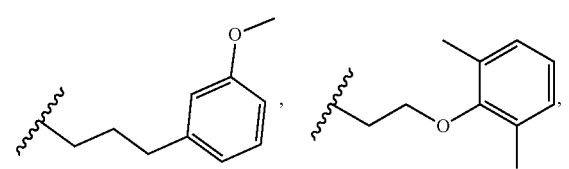
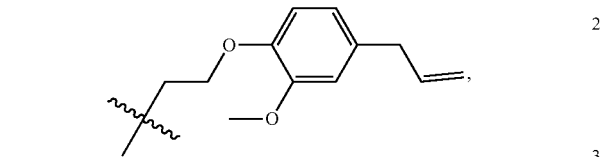
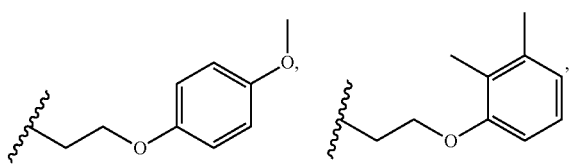
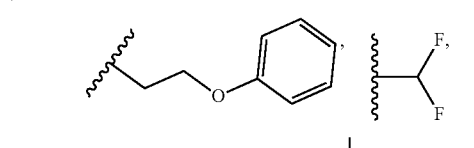
and
X is S or NR⁵.
In one embodiment, the compound of Formula XIVa is:
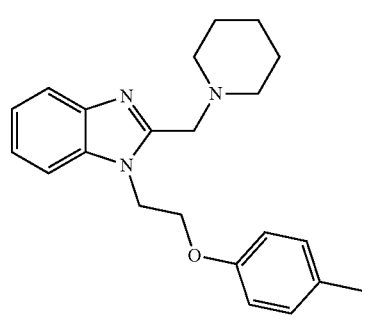
-continued
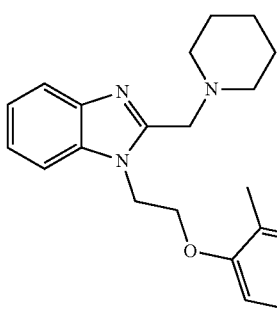
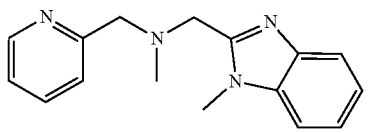
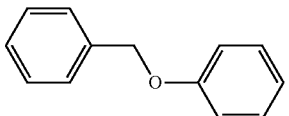
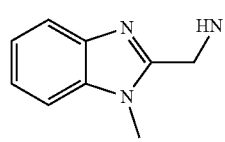
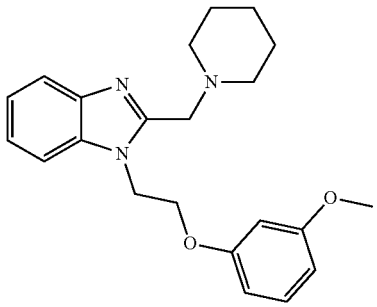
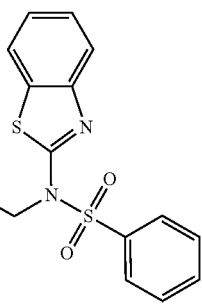
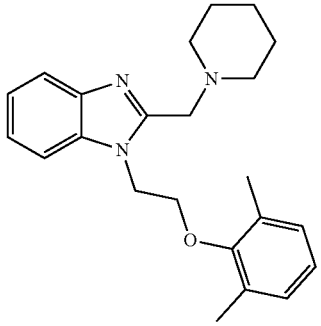

221
-continued
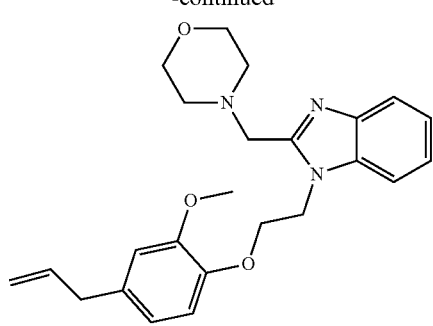
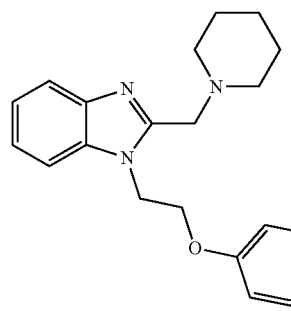
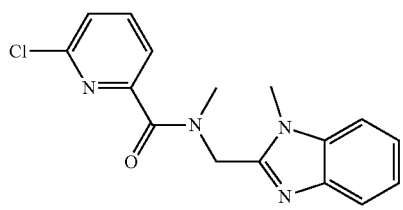
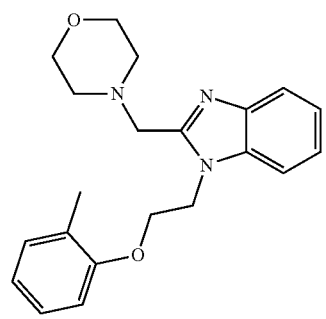
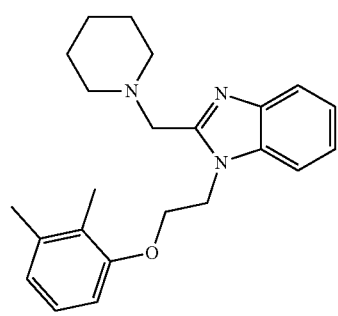
222
-continued
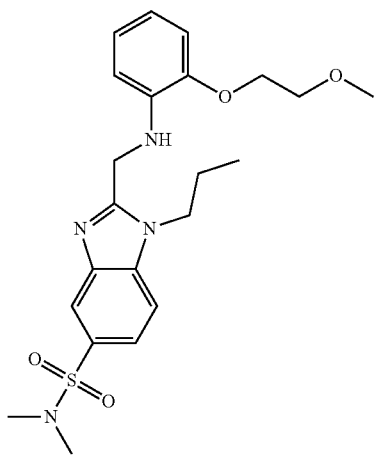
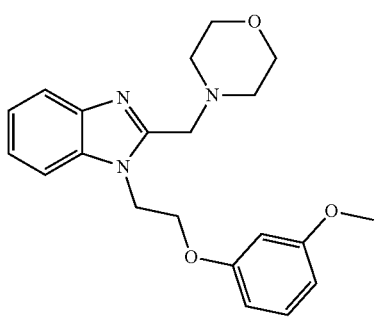
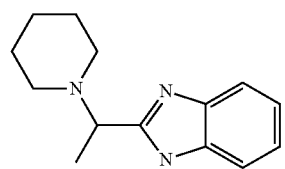
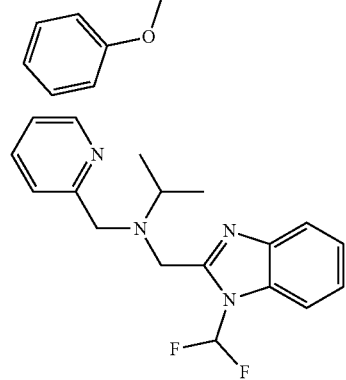
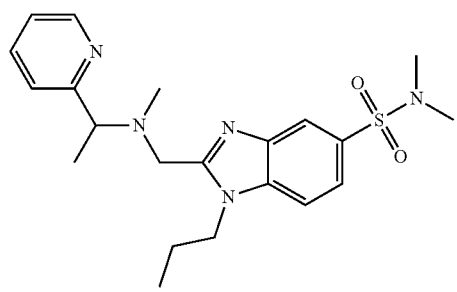

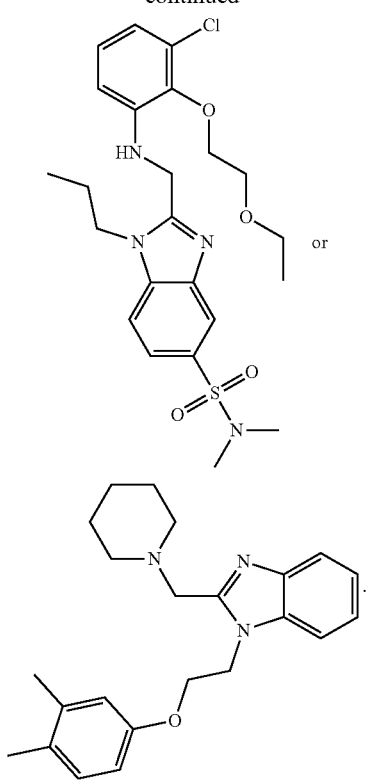

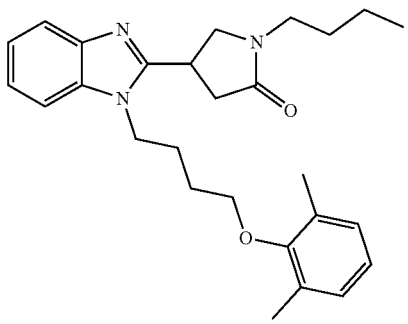

In one embodiment, the compound of formula XIV is selected with the proviso that $R^{10}$ is not morpholinomethyl, piperidinylmethyl, methylpiperizinylmethyl, morpholino-$CH(CH_3)$—, piperidinyl-$CH(CH_3)$—, methylpiperizinyl-$CH(CH_3)$—; and X is not $NR^5$ if $R^5$ is aryloxyalkyl or arylalkyl.

In another embodiment, the disease to be treated with the compounds of formula XIV is not a retinal tumor.

In one embodiment, the compound of formula XIVa is selected with the proviso that $R^{10a}$ is not morpholinomethyl, piperidinylmethyl, methylpiperizinylmethyl, morpholino-$CH(CH_3)$—, piperidinyl-$CH(CH_3)$—, methylpiperizinyl-$CH(CH_3)$—; and X is not $NR^5$ if $R^5$ is aryloxyalkyl or arylalkyl.

In another embodiment, the disease to be treated with the compounds of formula XIVa is not a retinal tumor.

In one embodiment, the compound of Formula XIV is selected with the proviso that the compound is not

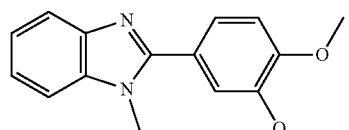

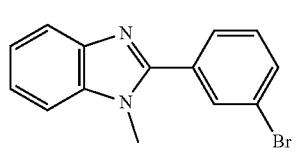
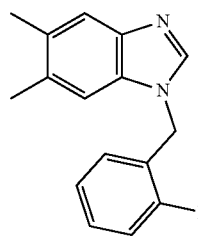

In another embodiment, the compound of Formula XIVa is:

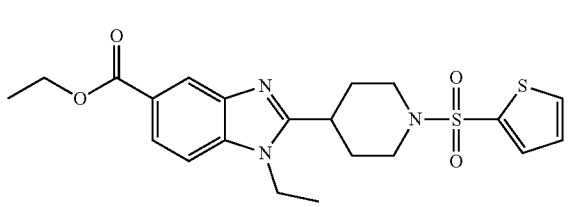

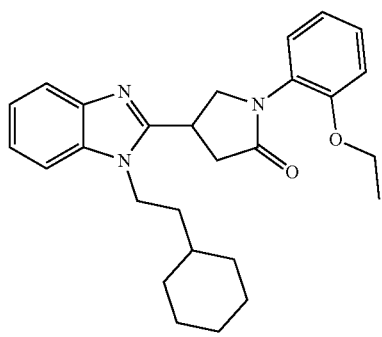 or

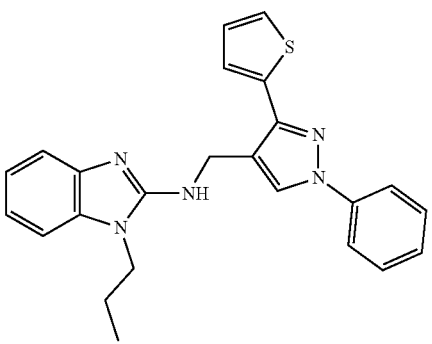 or

-continued

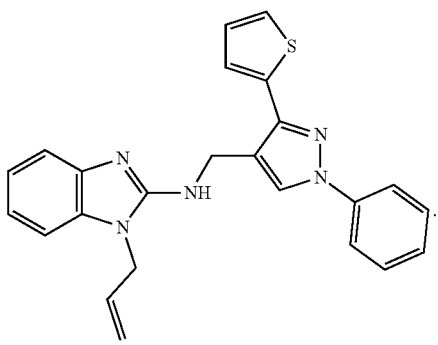

In one embodiment, the compound of Formula XIVa is selected with the proviso that the compound is not

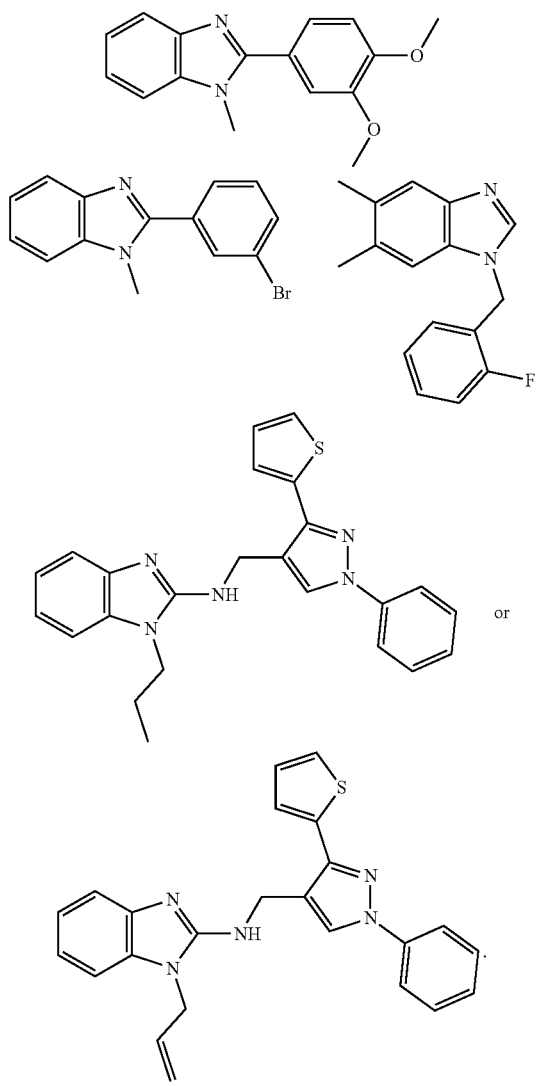

In certain embodiments, the compounds for use in the compositions and methods provided herein are of Formula XVa or Formula XVb:

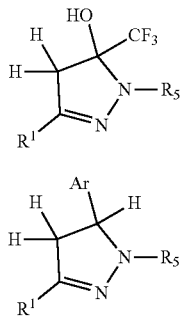

Formula XVa

Formula XVb or pharmaceutically acceptable derivatives thereof,
wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, arylcarbonyl or heteroarylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2; and

Ar is aryl or heteroaryl.

In another embodiment, the compound of Formula XVa is a compound of Formula XVa1:

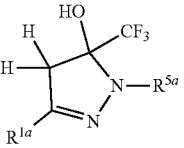

Formula XVa1 or pharmaceutically acceptable derivatives thereof,
wherein $R^{1a}$ is H, aryl or heteroaryl; and
$R^{5a}$ is alkylcarbonyl, cycloalkylcarbonyl, arylcarbonyl or heteroarylcarbonyl.

In one embodiment, $R^{1a}$ is H, phenyl; and
$R^{5a}$ is

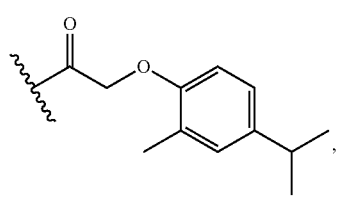

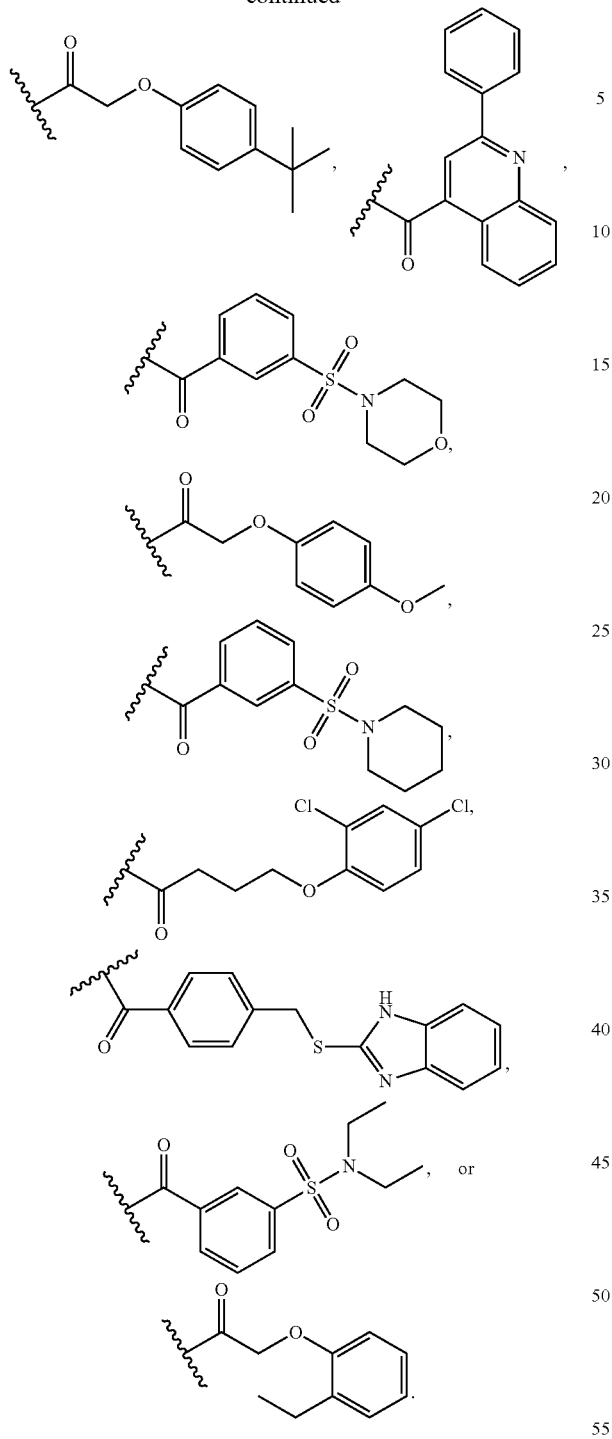
In one embodiment, the compound of Formula XVa1 is:
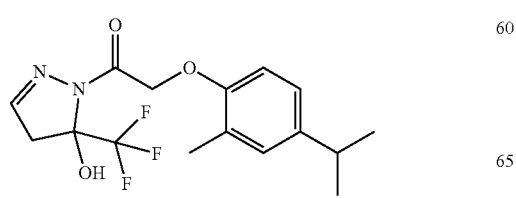
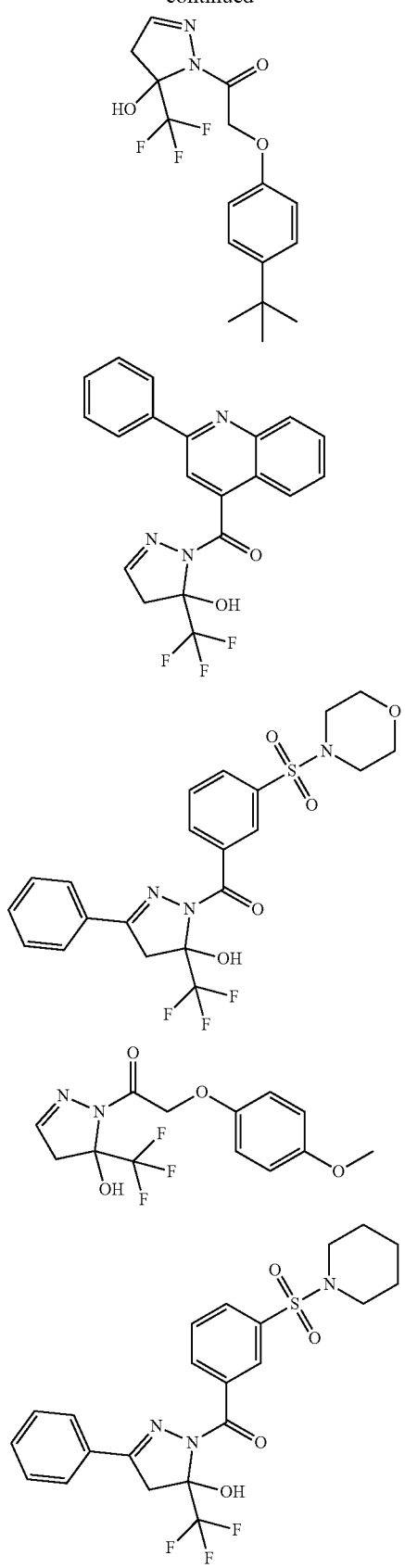

-continued

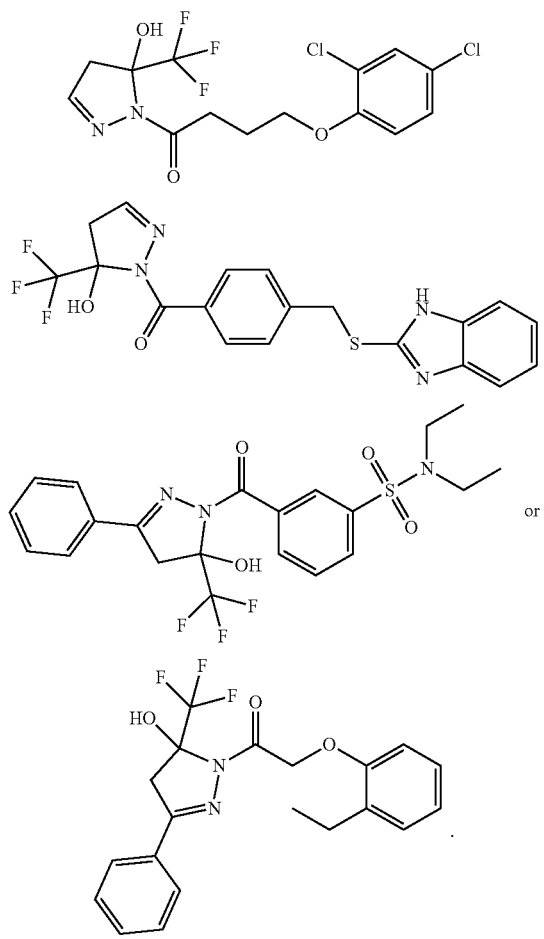

In another embodiment, the compound of Formula XVb is a compound of Formula XVb1:

Formula XVb1

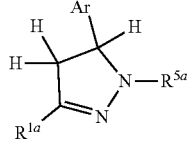

or pharmaceutically acceptable derivatives thereof,
wherein $R^{1a}$ is H, aryl or heteroaryl;
$R^{5a}$ is alkylcarbonyl, cycloalkylcarbonyl, arylcarbonyl or heteroarylcarbonyl; and
Ar is aryl or heteroaryl.
In one embodiment, $R^{1a}$ is

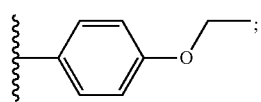

$R^{5a}$ is

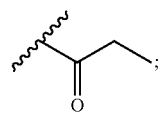 [SMILES: *C(=O)CC]

and
Ar is

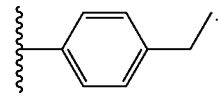

In one embodiment, the compound of Formula XVb1 is:

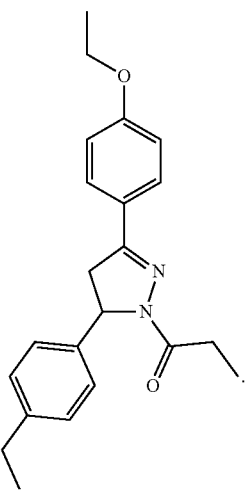 [SMILES: CCOc1ccc(C2=NN(C(=O)CC)C(c3ccc(CC)cc3)C2)cc1]

In certain embodiments, the compounds for use in the compositions and methods provided herein are of Formula XVI:

Formula XVI

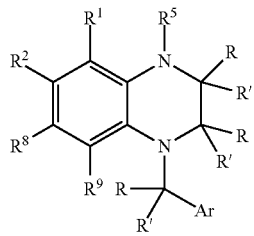

or pharmaceutically acceptable derivatives thereof,
wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached;

p is 0-2;

each R and R' are independently selected from H, alkyl, or cycloalkyl; and

Ar is aryl or heteroaryl.

In another embodiment, the compound of Formula XVI is a compound of Formula XVIa:

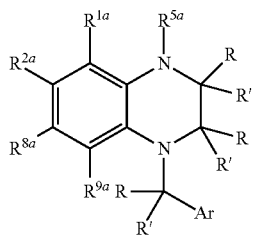

Formula XVIa or pharmaceutically acceptable derivatives thereof, wherein R¹ᵃ, R²ᵃ, R⁸ᵃ and R⁹ᵃ are independently selected from the group consisting of H, alkyl and halo;

R⁵ᵃ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ᵃ and R⁷ᵃ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ᵃ and R⁷ᵃ are combined to form a cyclic structure including the nitrogen atom to which they are both attached;

p is 0-2;

each R and R' are independently selected from H, alkyl, or cycloalkyl; and

Ar is aryl or heteroaryl.

In one embodiment, R¹ᵃ, R²ᵃ, R⁸ᵃ and R⁹ᵃ are independently selected from the group consisting of H, and F;

R⁵ᵃ is cyclopropyl or

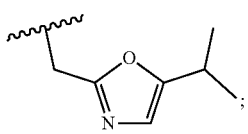 [SMILES: *Cc1ncc(C(C)C)o1]

each R and R' are H or methyl; and

Ar is

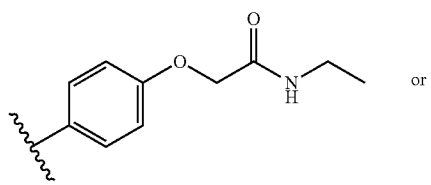

or

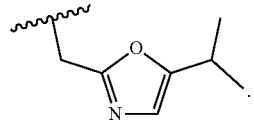

In one embodiment, the compound of Formula XVIa is:

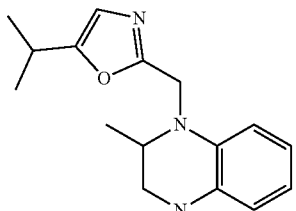

or

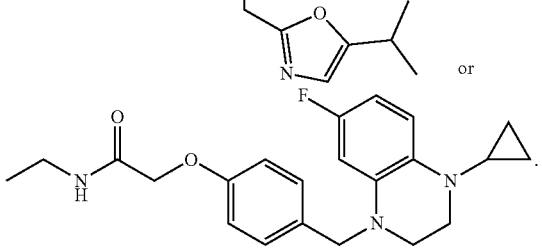

In certain embodiments, the compounds for use in the compositions and methods provided herein are of Formula XVII:

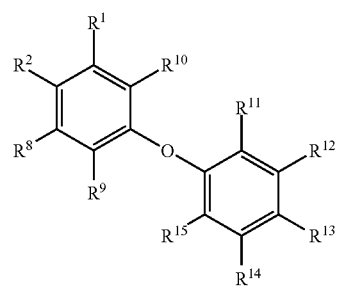

Formula XVII or pharmaceutically acceptable derivatives thereof, wherein R¹, R², R¹, R⁹, R¹⁰, R¹¹, R¹², R¹³, R¹⁴ and R¹⁵ are independently selected from the group consisting of H, alkyl, alkenyl, alkynyl, aryl, cycloalkyl, heterocyclyl, heteroaryl, halo, pseudohalo, OR³, C(O)R⁴, S(O)ₚR⁴, NR⁵C(O)R⁴, and NR⁶R⁷;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and p is 0-2.

In another embodiment, the compound of Formula XVII is a compound of Formula XVIIa:

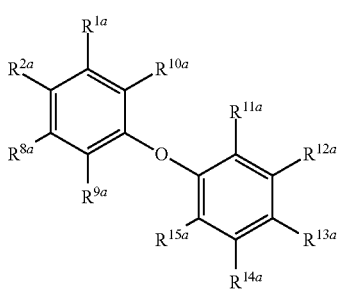

Formula XVIIa or pharmaceutically acceptable derivatives thereof, wherein $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{11a}$ is $NR^{6a}R^{7a}$;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and R⁶' is arylalkyl or heteroarylalkyl;

R⁷' is H or alkyl, and R⁶ and R⁷ are combined to form a cyclic structure including the nitrogen atom to which they are both attached; and p is 0-2.

In one embodiment, $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{11a}$ is $NR^{6a}R^{7a}$;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and R⁶ is arylalkyl or heteroarylalkyl;

R⁷ is H or alkyl, and R⁶ and R⁷ are combined to form a cyclic structure including the nitrogen atom to which they are both attached; and p is 0-2.

In one embodiment, wherein $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, methyl, F, trifluoromethyl, or OEt; and $R^{11a}$ is

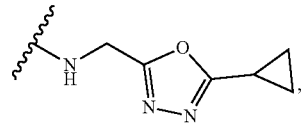

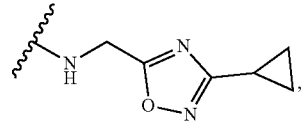

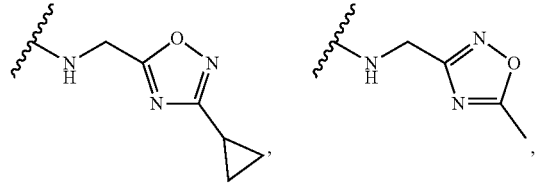

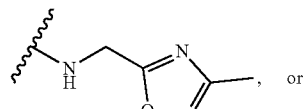, or

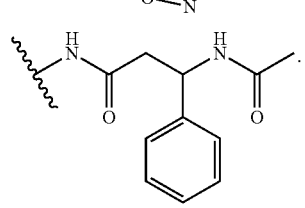

In one embodiment, the compound of Formula XVIIa is:

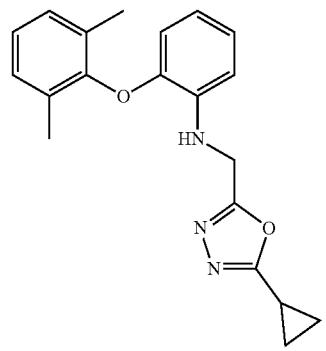

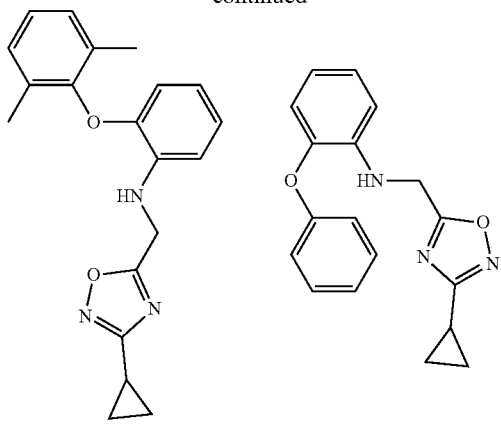

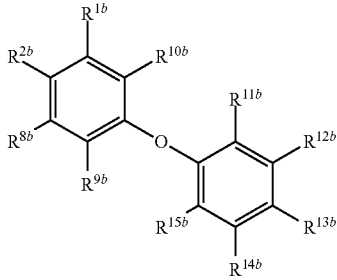

Formula XVIIb

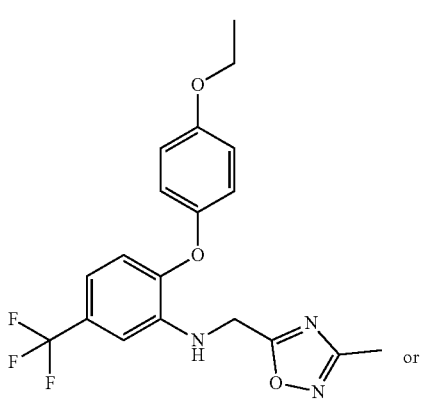

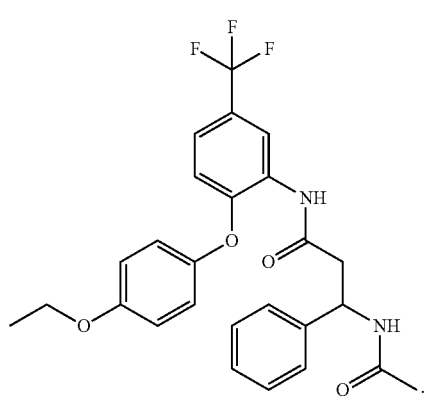 [SMILES: CCOc1ccc(Oc2ccc(C(F)(F)F)cc2NC(=O)CC(NC(C)=O)c2ccccc2)cc1]

In another embodiment, the compound of Formula XVII is a compound of Formula XVIIb:

or pharmaceutically acceptable derivatives thereof, wherein $R^{1a}$, $R^{2a}$, $R^{8a}$, $R^{9a}$, $R^{10a}$ are independently selected from the group consisting of H, alkyl, halo, and $OR^3$;

$R^{11a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and $R^{6'}$ is arylalkyl or heteroarylalkyl;

$R^{7'}$ is H or alkyl, and $R^6$ and $R^7$ are combined to form a cyclic structure including the nitrogen atom to which they are both attached; and p is 0-2.

In one embodiment, $R^{1b}$, $R^{2b}$, $R^{8b}$, $R^{9b}$, $R^{10b}$ are independently selected from the group consisting of H, alkyl, halo, and $OR^3$;

$R^{11b}$, $R^{12b}$, $R^{13b}$, $R^{14b}$ and $R^{15b}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and $R^6$ is arylalkyl or heteroarylalkyl;

R⁷ is H or alkyl, and R⁶ and R⁷ are combined to form a cyclic structure including the nitrogen atom to which they are both attached; and p is 0-2.

In one embodiment, wherein R¹ᵃ, R²ᵃ, R⁸ᵃ, R⁹ᵃ, R¹⁰ᵃ are independently selected from the group consisting of H, F, OMe, OPh, CF₃, and

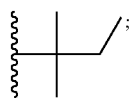

and

R¹¹ᵃ, R¹²ᵃ, R¹³ᵃ, R¹⁴ᵃ and R¹⁵ᵃ are independently selected from the group consisting of H, CF₃,

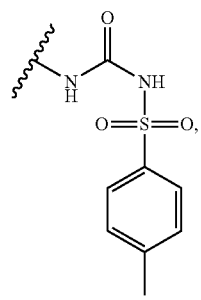

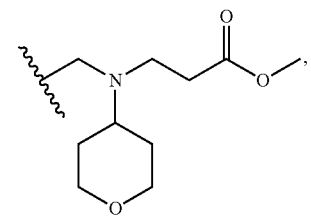

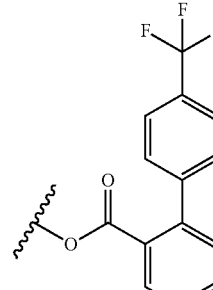

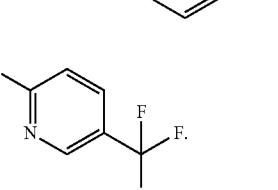

In one embodiment, wherein R¹ᵇ, R²ᵇ, R⁸ᵇ, R⁹ᵇ, R¹⁰ᵇ are independently selected from the group consisting of H, F, OMe, OPh, CF₃, and

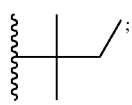

and

R¹¹ᵇ, R¹²ᵇ, R¹³ᵇ, R¹⁴ᵇ and R¹⁵ᵇ are independently selected from the group consisting of H, CF₃,

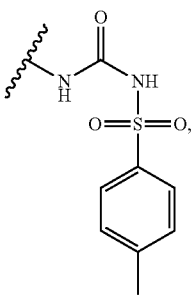

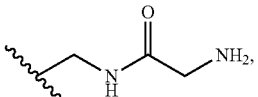

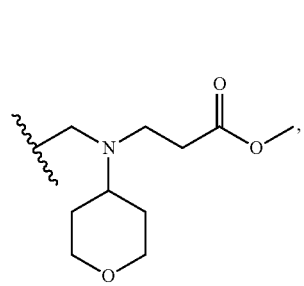

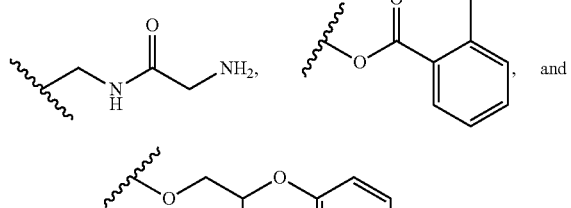

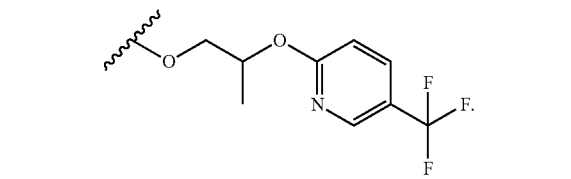

In one embodiment, the compound of Formula XVIIb is:

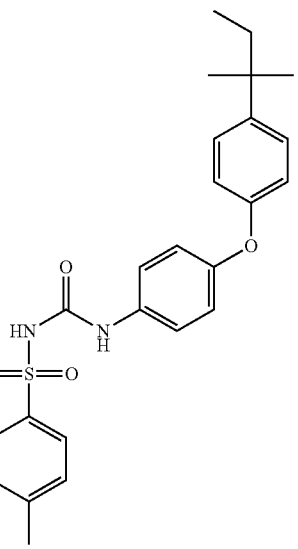

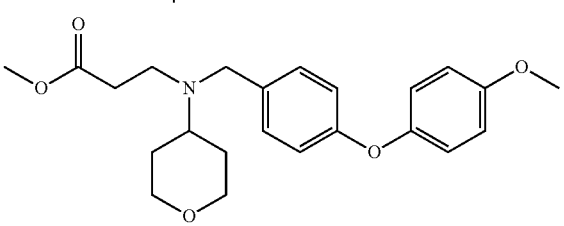

-continued

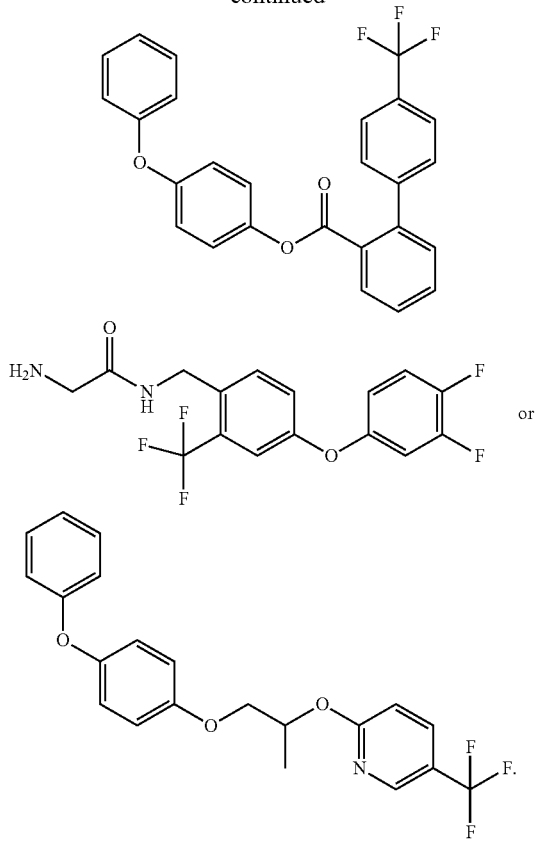

In certain embodiments, the compounds for use in the compositions and methods provided herein are of Formula XVIII.

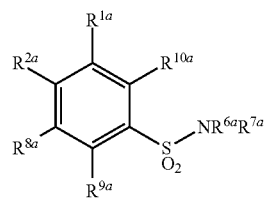

or pharmaceutically acceptable derivatives thereof,
wherein $R^1$, $R^2$, $R^1$, $R^9$ and $R^{10}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
p is 0-2; and
X is $S(O)_p$ or $CR_2$, wherein each R is independently selected from hydrogen and lower alkyl.

In another embodiment, the compound of Formula XVIII is a compound of Formula XVIIIa:

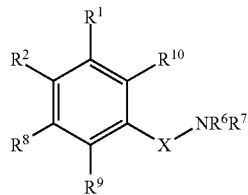

Formula XVIIIa or pharmaceutically acceptable derivatives thereof,
wherein $R^{1a}$, $R^{2a}$, $R^{8a}$, $R^{9a}$ and $R^{10a}$ are independently selected from the group consisting of H, alkyl, alkenyl, alkynyl, aryl, cycloalkyl, heterocyclyl, heteroaryl, nitro, halo, pseudohalo, $OR^3$, $C(O)R^4$, $S(O)_pR^4$, $NR^5C(O)R^4$, and $NR^6R^7$;
$R^3$ is hydrogen, alkyl, alkenyl, alkynyl, aryl, heteroaryl, heterocyclyl, cycloalkyl, alkylcarbonyl, cycloalkylcarbonyl or arylcarbonyl;
$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;
$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;
$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^{6a}$ and $R^{7a}$ are combined to form a cyclic structure including the nitrogen atom to which they are both attached; and
p is 0-2.

In one embodiment, $R^{1a}$, $R^{2a}$, $R^{8a}$, $R^{9a}$ and $R^{10a}$ are independently selected from the group consisting of H, $CH_3$, $C_1$, $CF_3$, $NO_2$, $OCH_3$,

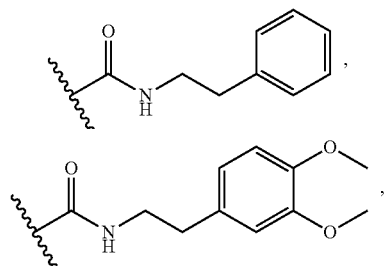

and R⁶ and R⁷ are combined to form including the nitrogen atom to which they both attached.

In one embodiment, R¹ᵃ, group consisting of H, CH₃, Cl, CF₃, NO₂, OCH₃,

R⁶ and R⁷ are independently selected from hydrogen, CH₃, CH₂CH₃ cyclopropyl,

-continued
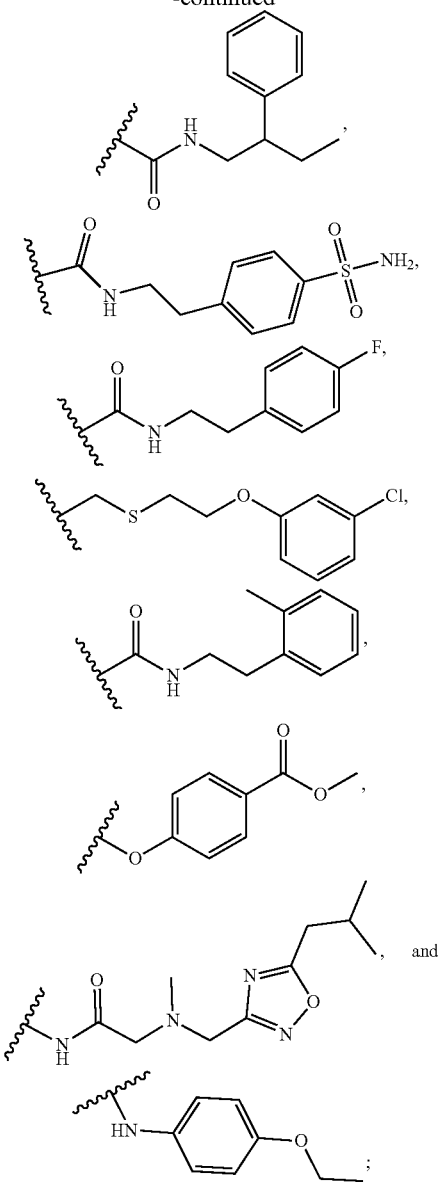
$R^{6a}$ and $R^{7a}$ are independently selected from hydrogen, $CH_3$, $CH_2CH_3$ cyclopropyl,
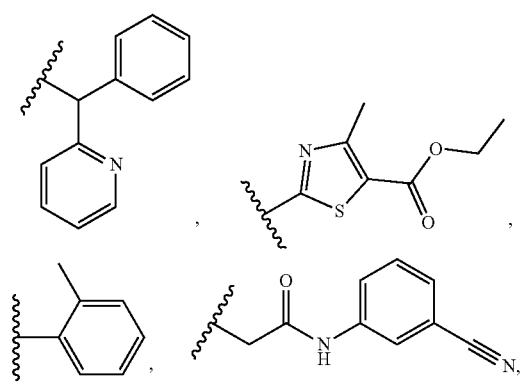
and $R^{6a}$ and $R^{7a}$ are combined to form
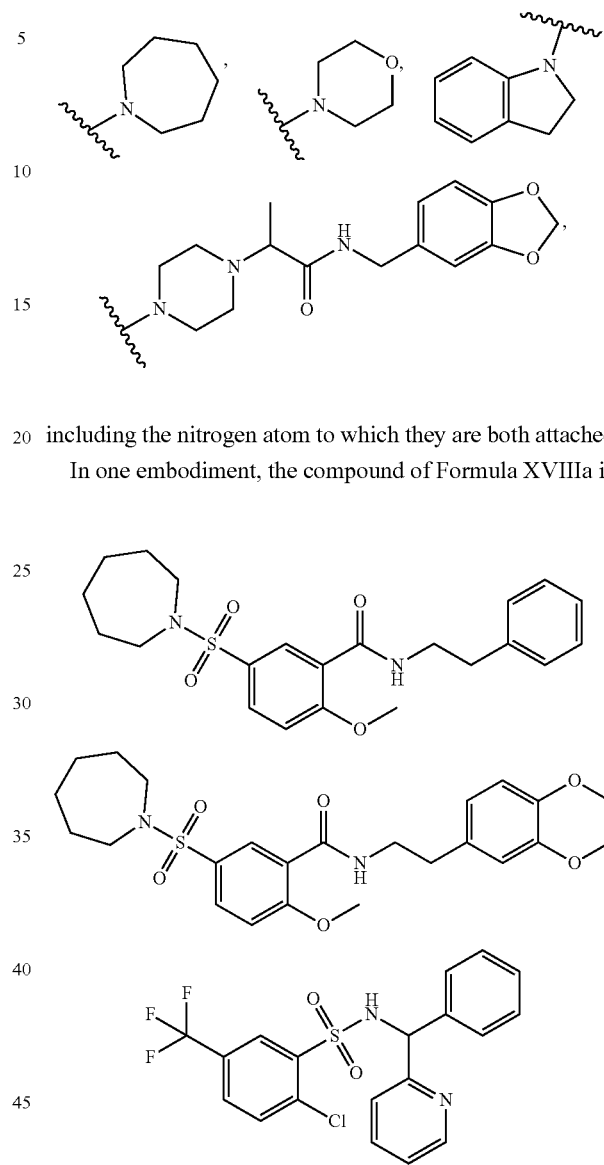
including the nitrogen atom to which they are both attached.
In one embodiment, the compound of Formula XVIIIa is:
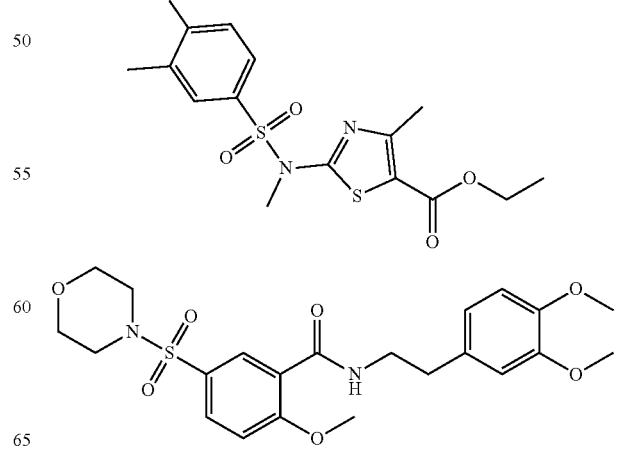

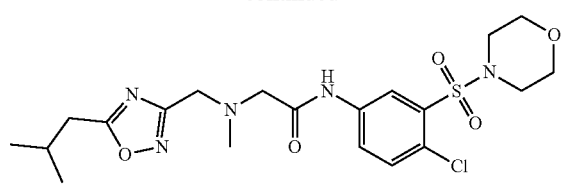
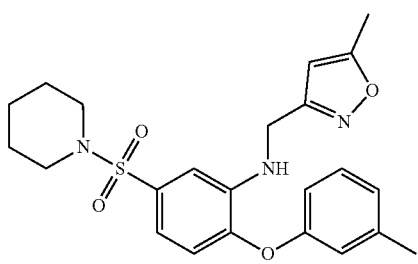
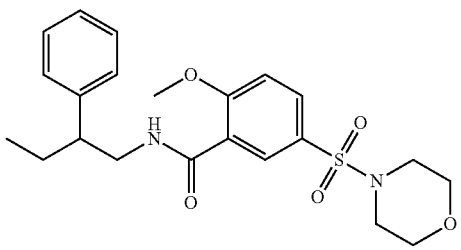
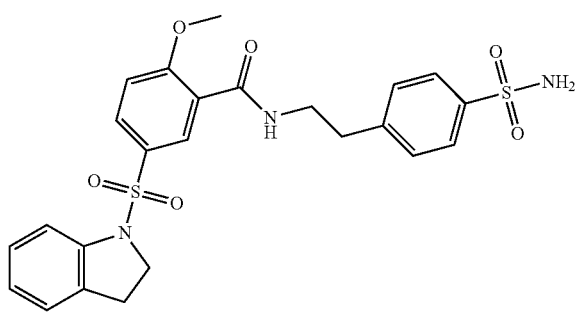
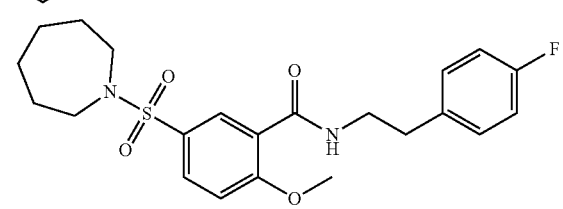
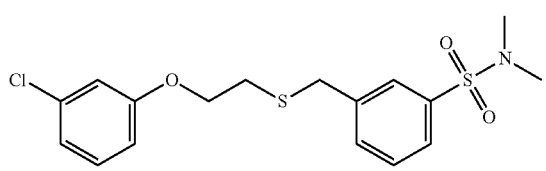
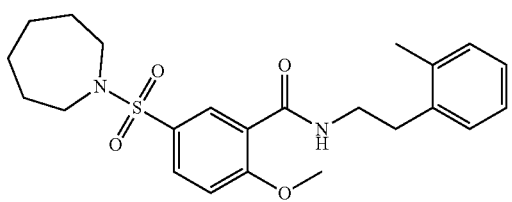

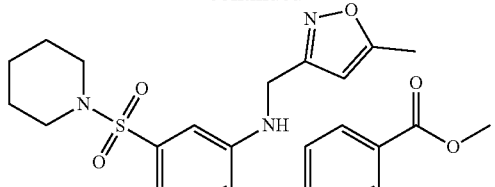
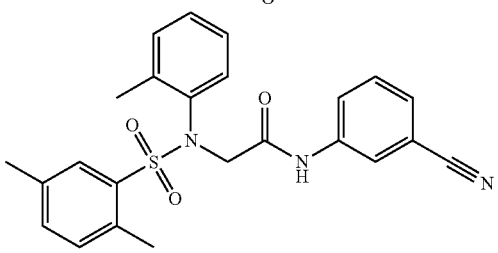
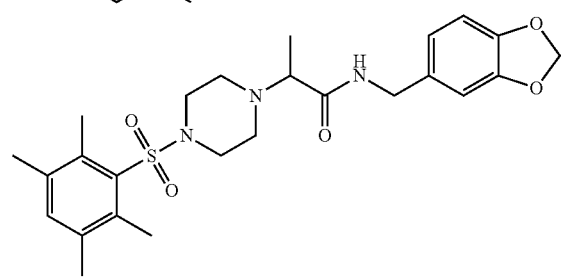

or

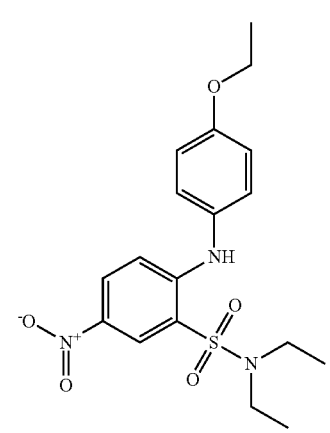

In another embodiment, the compound of Formula XVIII is a compound of Formula XVIIIb:

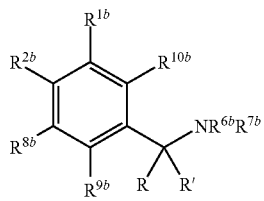

Formula XVIIIb or pharmaceutically acceptable derivatives thereof, wherein $R^{1b}$, $R^{2b}$, $R^{8a}$, $R^{9b}$ and $R^{10b}$ are independently selected from the group consisting of H, alkyl, alkenyl, alkynyl, aryl, cycloalkyl, heterocyclyl, heteroaryl, nitro, halo, pseudohalo, $OR^3$, $C(O)R^4$, $S(O)_p R^4$, $NR^5C(O)R^4$, and $NR^6R^7$;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached;

R⁶ᵇ and R⁷ᵇ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ᵃ and R⁷ᵃ are combined to form a cyclic structure including the nitrogen atom to which they are both attached;

R and R' are independently selected from hydrogen and lower alkyl; and p is 0-2.

In another embodiment, R¹ᵇ, R²ᵇ, R¹ᵇ, R⁹ᵇ and R¹⁰ᵇ are independently selected from the group consisting of H, alkyl, alkenyl, alkynyl, aryl, cycloalkyl, heterocyclyl, heteroaryl, nitro, halo, pseudohalo, OR³, C(O)R⁴, S(O)ₚR⁴, NR⁵C(O)R⁴, and NR⁶R⁷;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, aryl, heteroaryl, heterocyclyl, cycloalkyl, alkylcarbonyl, cycloalkylcarbonyl, or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached;

R⁶ᵇ and R⁷ᵇ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ᵃ and R⁷ᵃ are combined to form a cyclic structure including the nitrogen atom to which they are both attached;

R and R' are independently selected from hydrogen and lower alkyl; and p is 0-2.

In one embodiment, R¹ᵇ, R²ᵇ, R⁸ᵃ, R⁹ᵇ and R¹⁰ᵇ are independently selected from the group consisting of H, OCH₃, SCF₃;

R⁶ᵇ and R⁷ᵇ are independently selected from CH₃ and

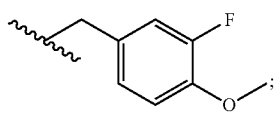 [SMILES: *Cc1ccc(OC)c(F)c1]

and

R and R' are H.

In another embodiment, R¹ᵇ, R²ᵇ, R¹ᵇ, R⁹ᵇ and R¹⁰ᵇ are independently selected from the group consisting of H, OCH₃, SCF₃;

R⁶ᵇ and R⁷ᵇ are independently selected from CH₃ and

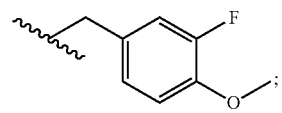 [SMILES: *Cc1ccc(OC)c(F)c1]

and

R and R' are H.

In one embodiment, the compound of Formula XVIIIb is:

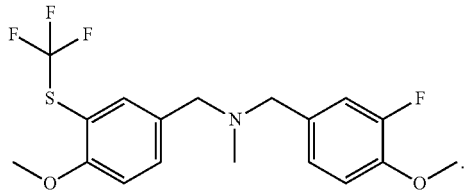

In one embodiment, the compound of Formula XVIII is selected with the proviso that if X is CH₂, then NR⁶R⁷ is not indolinone or benzoimidazolone.

In one embodiment, the compound of Formula XVIIIb is selected with the proviso that if R and R' are both H, then NR⁶R⁷ is not indolinone or benzoimidazolone.

In certain embodiments, the compounds for use in the compositions and methods provided herein are of Formula XIX:

Formula XIX

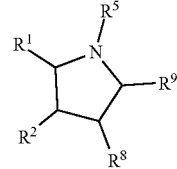

or pharmaceutically acceptable derivatives thereof, wherein R¹, R², R⁸ and R⁹ are independently selected from the group consisting of H, alkyl, alkenyl, alkynyl, aryl, cycloalkyl, heterocyclyl, heteroaryl, halo, pseudohalo, oxo, OR³, C(O)R⁴, S(O)ₚR⁴, NR⁵C(O)R⁴, and NR⁶R⁷;

R³ is hydrogen, alkyl, alkenyl, alkynyl, aryl, heteroaryl, heterocyclyl, cycloalkyl, alkylcarbonyl, cycloalkylcarbonyl or arylcarbonyl;

R⁴ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

R⁵ is hydrogen, alkyl, alkenyl, alkynyl, arylalkyl, heteroarylalkyl, aryl, heteroaryl, heterocyclyl, cycloalkyl, alkylcarbonyl, cycloalkylcarbonyl, heterocyclylcarbonyl, heteroarylcarbonyl or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R⁶ and R⁷ are combined to form a cyclic structure including the nitrogen atom to which they are both attached; and p is 0-2.

In another embodiment, the compound of Formula XIX is a compound of Formula XIXa:

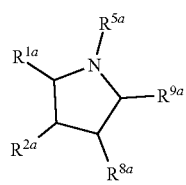

Formula XIXa or pharmaceutically acceptable derivatives thereof,
wherein $R^{1a}$, $R^{2a}$, $R^{8a}$ and $R^{9a}$ are independently selected from the group consisting of H, alkyl, aryl, cycloalkyl, heterocyclyl, heteroaryl, oxo and $C(O)R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR⁶R⁷;

$R^{5a}$ is alkyl, arylalkyl, heteroarylalkyl, aryl, heteroaryl, heterocyclyl, cycloalkyl, alkylcarbonyl, cycloalkylcarbonyl, heterocyclylcarbonyl, heteroarylcarbonyl or arylcarbonyl;

R⁶ and R⁷ are independently selected from hydrogen, alkyl, alkenyl, alkynyl, aryl, heteroaryl, heterocyclyl, cycloalkyl, alkylcarbonyl, cycloalkylcarbonyl, arylcarbonyl or heteroarylcarbonyl, or R⁶ and R⁷ are combined to form a cyclic structure including the nitrogen atom to which they are both attached; and p is 0-2.

In one embodiment, $R^{1a}$, $R^{2a}$, $R^{8a}$ and $R^{9a}$ are independently selected from the group consisting of H, cyclopentyl, cyclohexyl, NO₂,

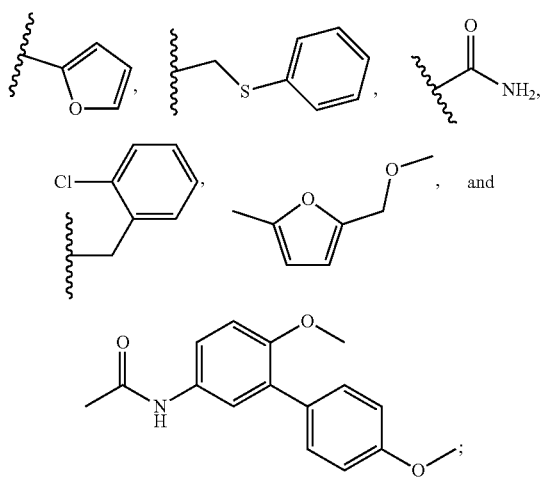

and
$R^{5a}$ is

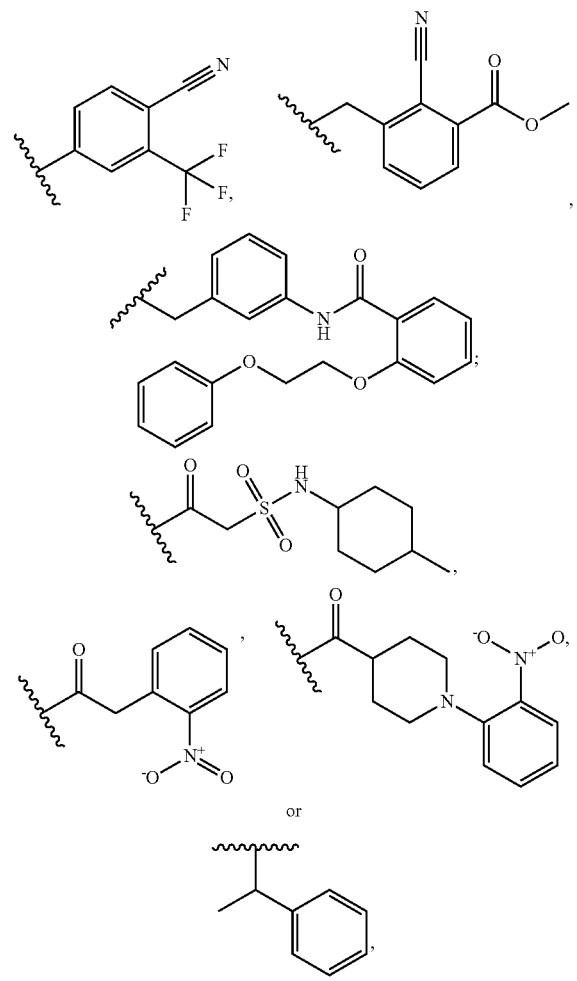

In another embodiment, $R^{1a}$, $R^{2a}$, $R^{8a}$ and $R^{9a}$ are independently selected from the group consisting of H, cyclopentyl, cyclohexyl, oxo,

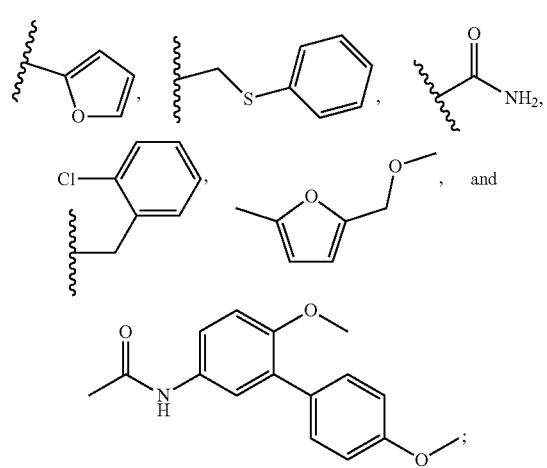

and $R^{5a}$ is

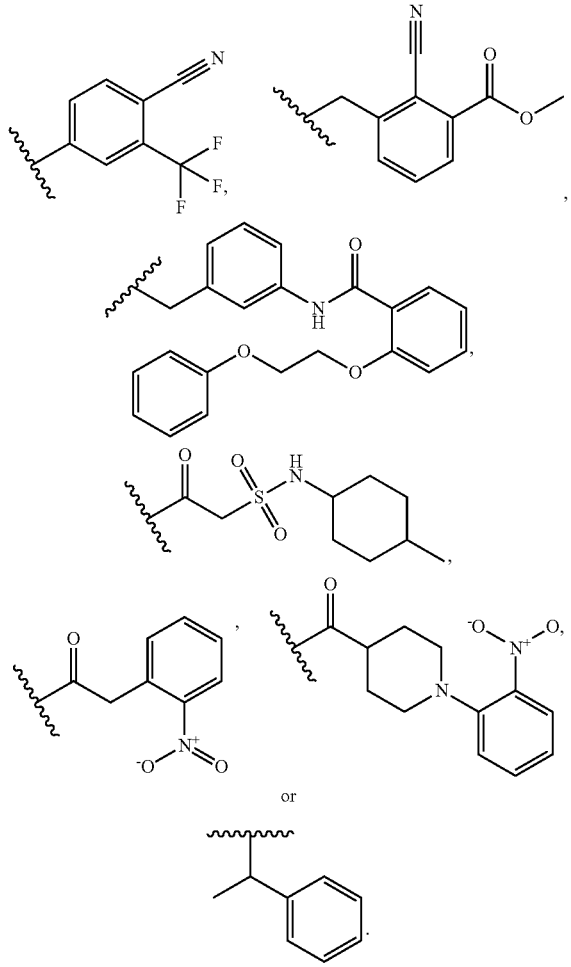

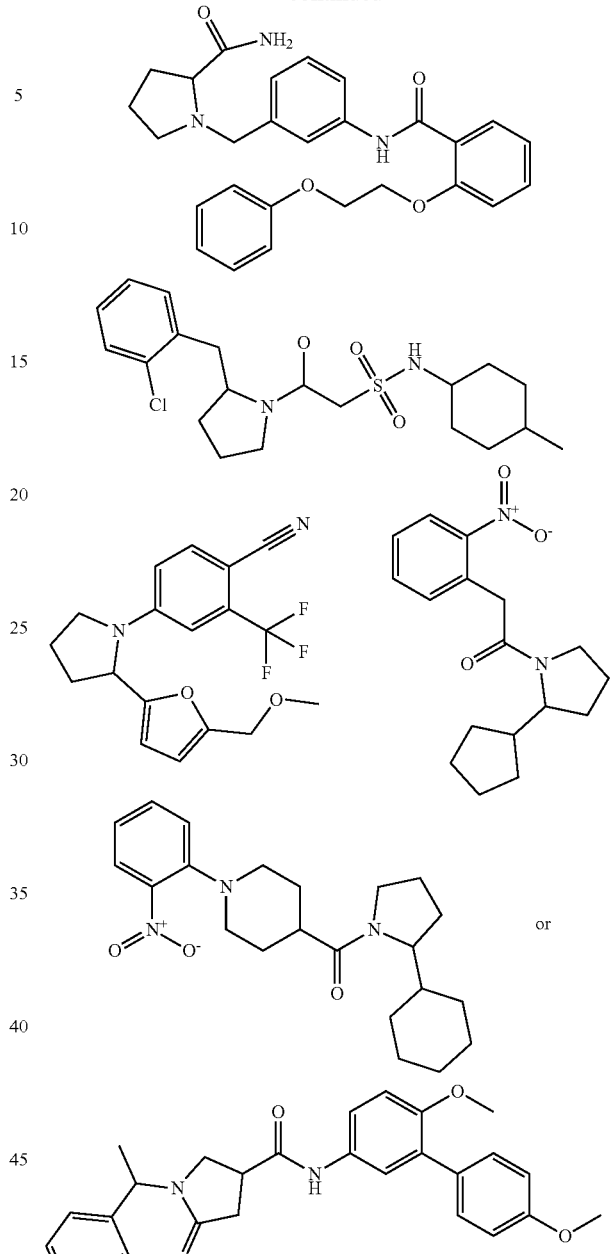

In one embodiment, the compound of Formula XIXa is:

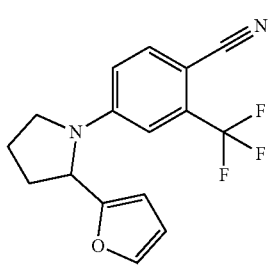

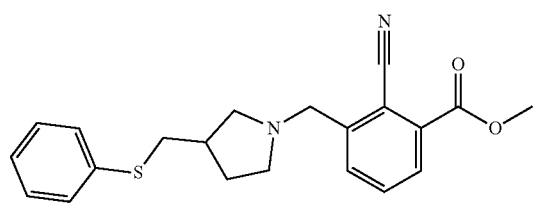

In one embodiment, the compound of formula XIX is selected with the proviso that the compound does not contain a hydrazide, a macrocycle, a thienopyridine or a thienopyrimidine.

In another embodiment, the disease to be treated with the compounds of formula XIX is not hepatocellular cancer.

In one embodiment, the compound of formula XIXa is selected with the proviso that the compound does not contain a hydrazide, a macrocycle, a thienopyridine or a thienopyrimidine.

In another embodiment, the disease to be treated with the compounds of formula XIXa is not hepatocellular cancer.

In certain embodiments, the compounds for use in the compositions and methods provided herein are of Formula XX:

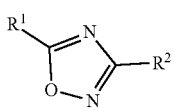

Formula XX or pharmaceutically acceptable derivatives thereof,
wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and p is 0-2.

In another embodiment, the compound of Formula XX is a compound of Formula XXa:

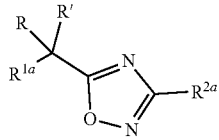

Formula XXa or pharmaceutically acceptable derivatives thereof,
wherein $R^{1a}$ is $OR^3$, $S(O)_pR^4$, $NR^5C(O)R^4$ or $NR^6R^7$;

$R^{2a}$ is alkyl, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and lower alkyl; and p is 0-2.

In one embodiment, $R^{1a}$ is $CH_3$, Bn,

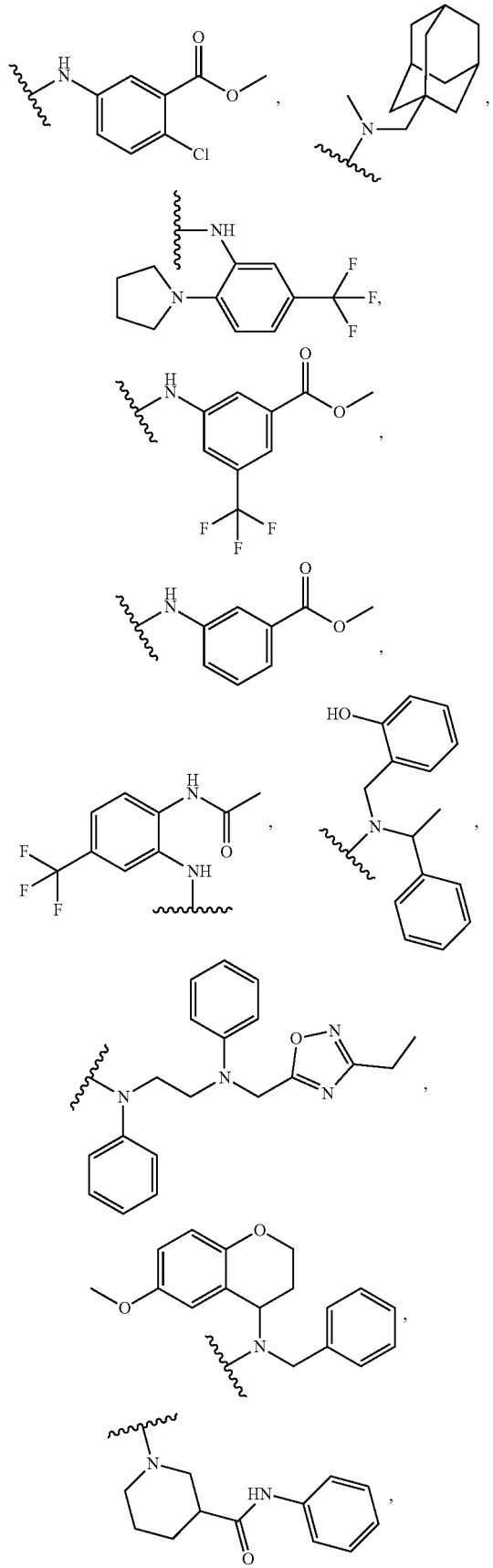

255
-continued
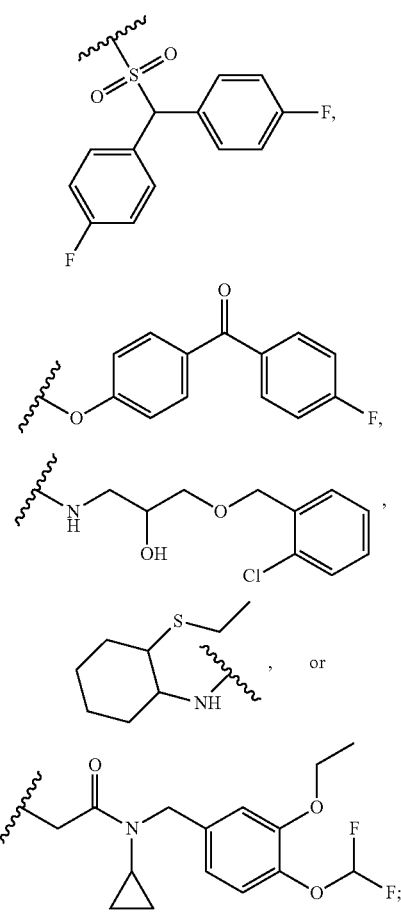
$R^{2a}$ is $CH_3$, $CH_2CH_3$, t-Bu, Ph,
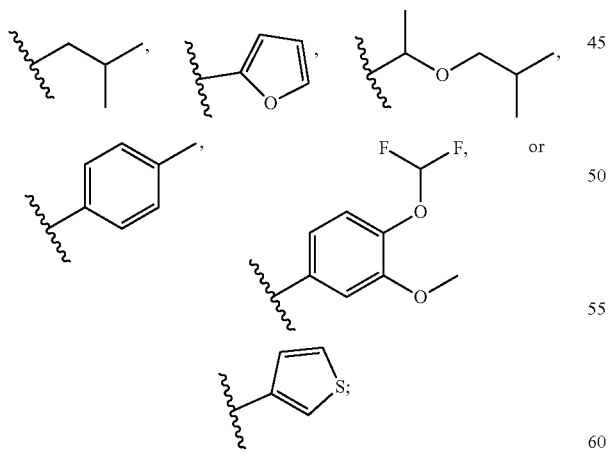
and
R and R' are independently selected from hydrogen and $CH_3$.
256
In one embodiment, the compound of Formula XXa is:
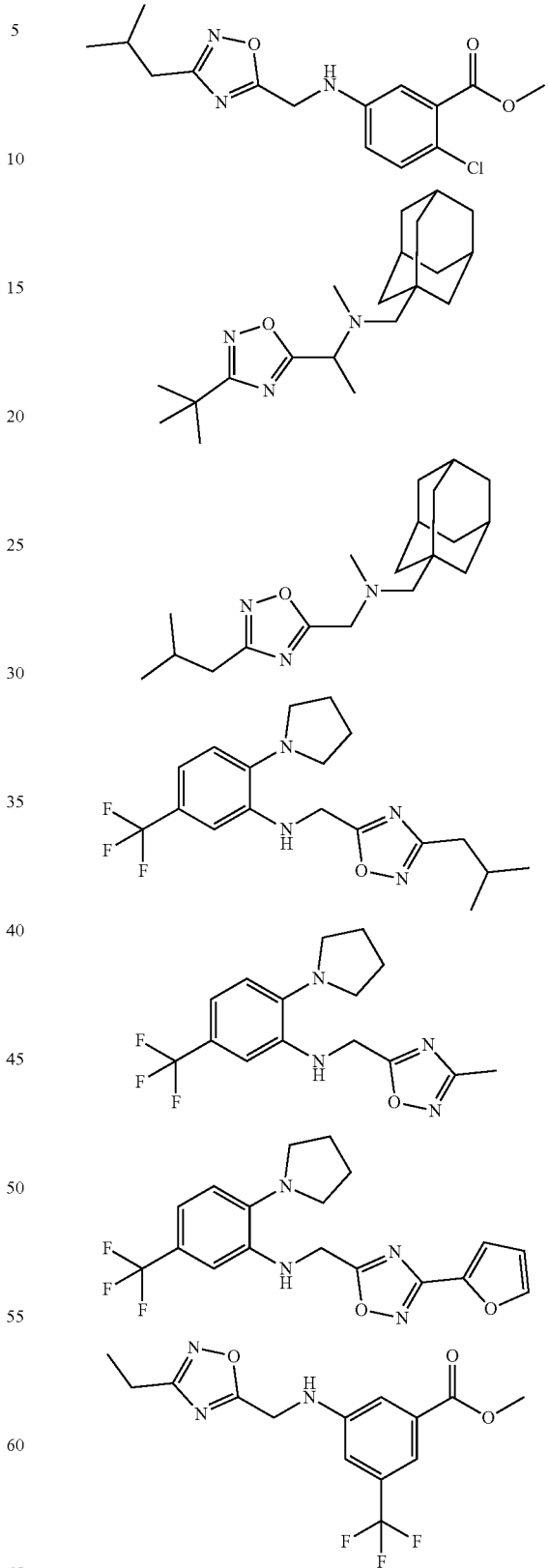

257
-continued

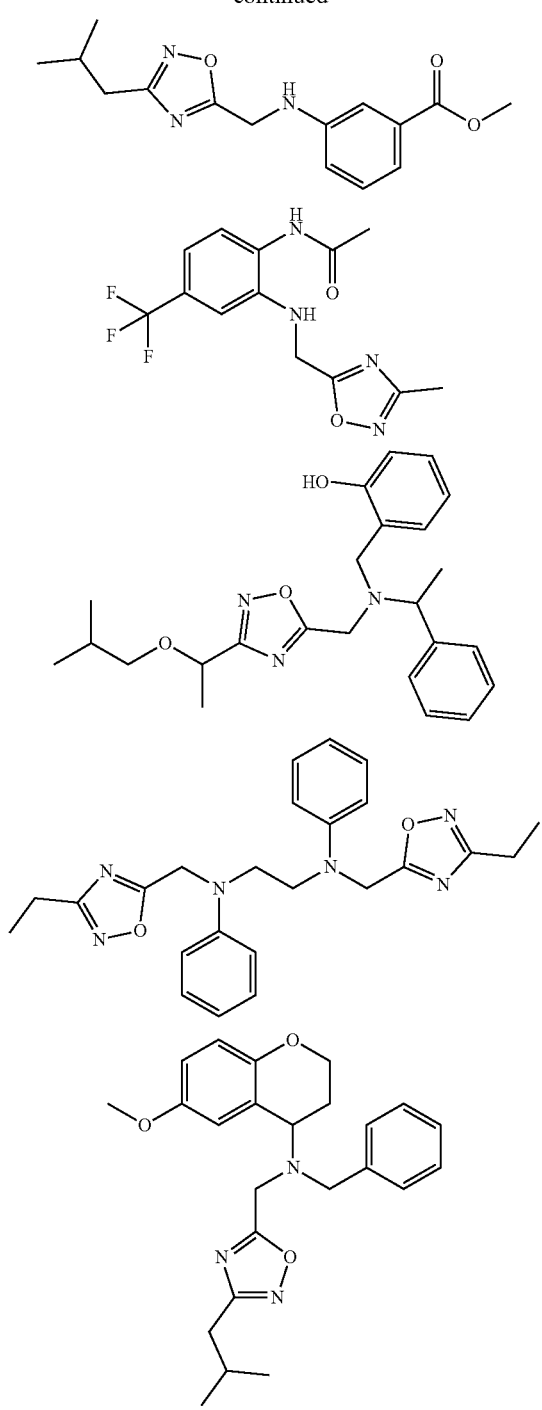

258
-continued

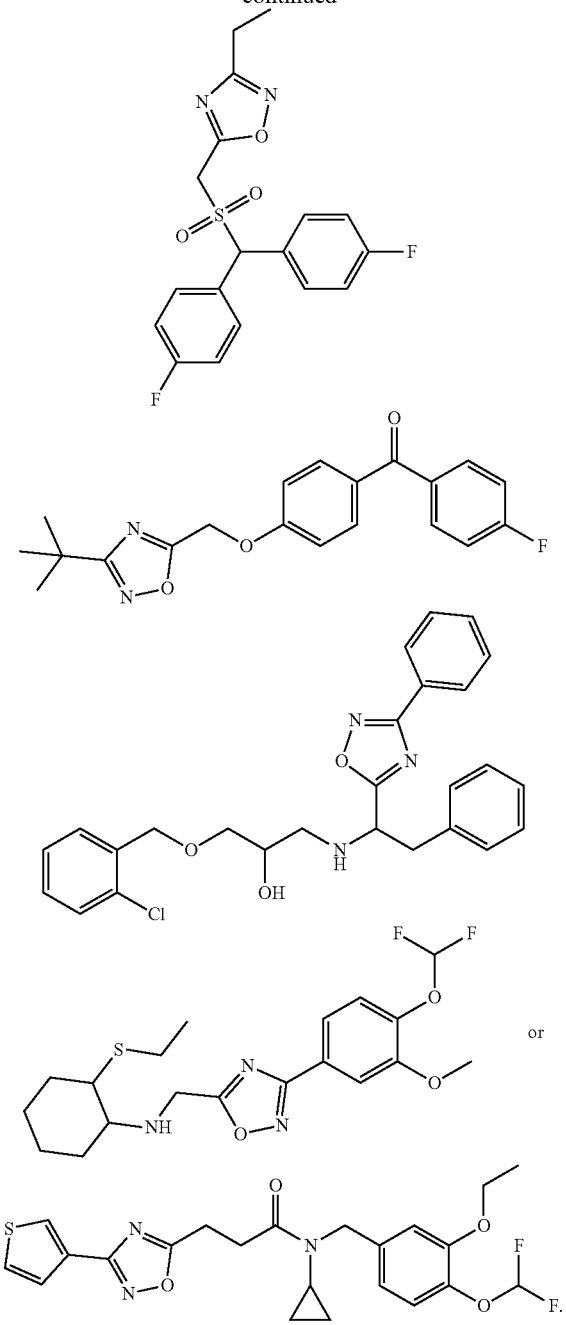

In another embodiment, the compound of Formula XX is a compound of Formula XXb:

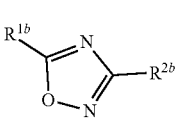

Formula XXb or pharmaceutically acceptable derivatives thereof, wherein $R^{1b}$ is alkyl, arylalkyl or heteroarylalkyl;
$R^{2b}$ is aryl, heteroaryl, or $C(R)(R')NR^6R^7$;
$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached; and R and R' are independently selected from hydrogen and lower alkyl.

In one embodiment, $R^{1b}$ is $CH_3$,

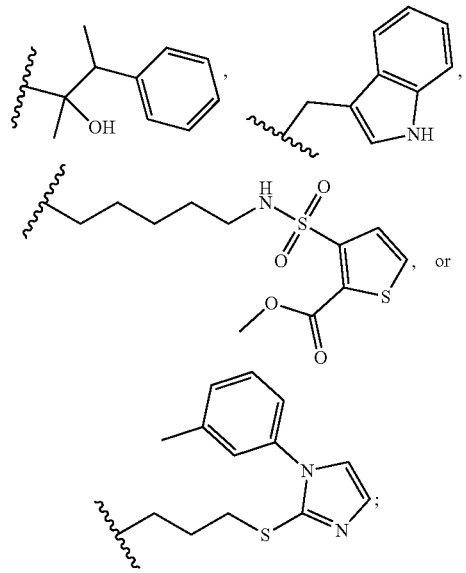

and
$R^{2b}$ is

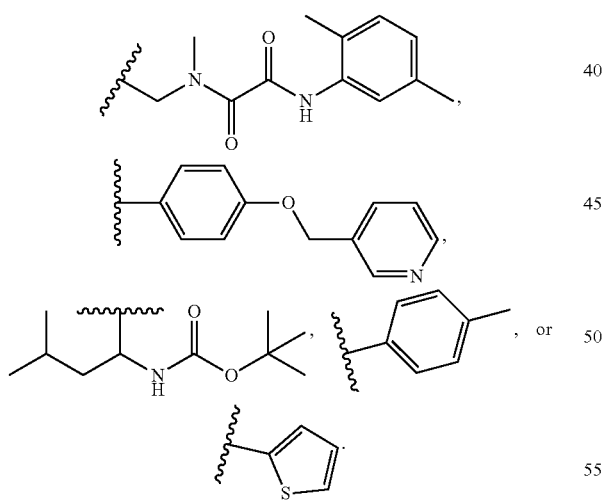

In one embodiment, the compound of Formula XXb is:

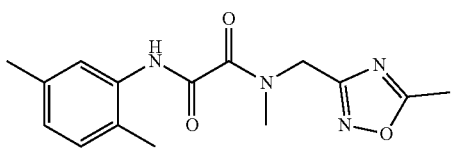

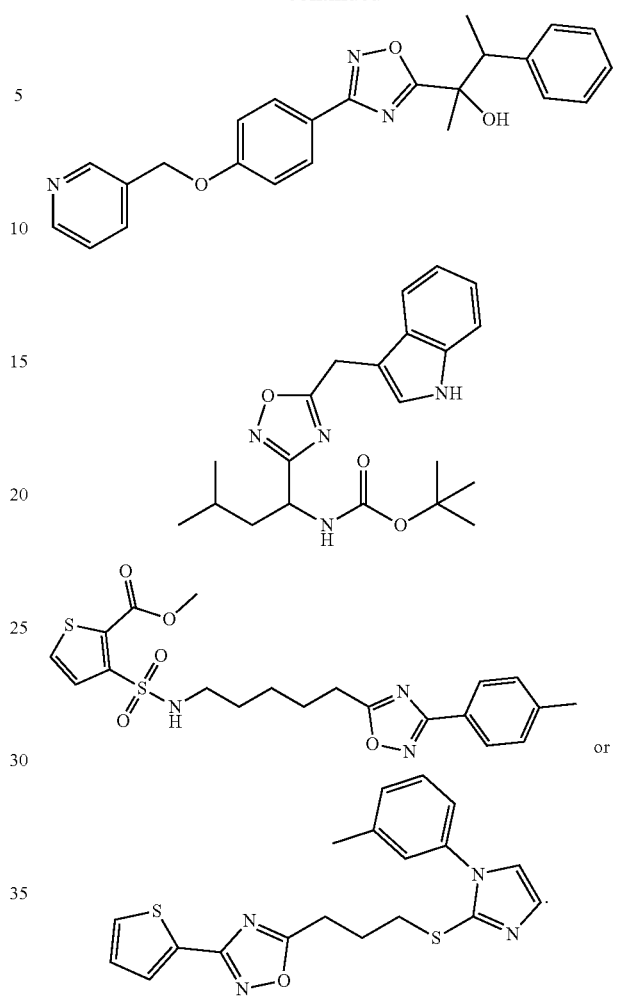

In another embodiment, the compound of Formula XX is a compound of Formula XXc:

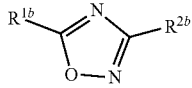

Formula XXc or pharmaceutically acceptable derivatives thereof, wherein $R^{1b}$ is aryl or heteroaryl; and
$R^{2b}$ is heterocyclyl.

In one embodiment, $R^{1b}$ is

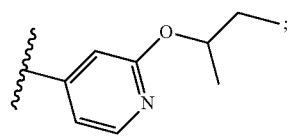 [SMILES: *c1ccnc(OC(C)CC)c1]

and
R$^{2b}$ is

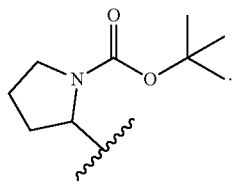 [SMILES: *C1CCCN1C(=O)OC(C)(C)C]

In one embodiment, the compound of Formula XXc is:

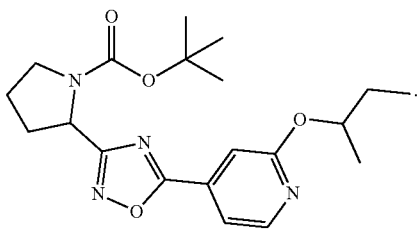 [SMILES: CCC(C)Oc1cc(-c2nc(C3CCCN3C(=O)OC(C)(C)C)no2)ccn1]

In one embodiment, the compound of Formula XX is selected with the proviso that if R$^1$ is pyridyl, then R$^2$ is not phenyl.

In one embodiment, the compound of Formula XX is selected with the proviso that if R$^2$ is pyridyl, then R$^1$ is not phenyl or cyclohexyl.

In certain embodiments, the compounds for use in the compositions and methods provided herein are of Formula XXI:

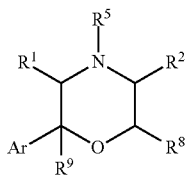

Formula XXI or pharmaceutically acceptable derivatives thereof,
wherein R$^1$, R$^2$ and R$^8$ are independently selected from the group consisting of H, alkyl, alkenyl, alkynyl, aryl, cycloalkyl, heterocyclyl, heteroaryl, halo, pseudohalo, OR$^3$, C(O)R$^4$, S(O)$_p$R$^4$, NR$^5$C(O)R$^4$, and NR$^6$R$^7$;
R$^9$ is H or alkyl;
R$^3$ is hydrogen, alkyl, alkenyl, alkynyl, aryl, heteroaryl, heterocyclyl, cycloalkyl, alkylcarbonyl, cycloalkylcarbonyl or arylcarbonyl;
R$^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —NR$^6$R$^7$;
R$^5$ is hydrogen, alkyl, alkenyl, alkynyl, aryl, heteroaryl, heterocyclyl, cycloalkyl, alkylcarbonyl, cycloalkylcarbonyl, or arylcarbonyl;
R$^6$ and R$^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or R$^6$ and R$^7$ are combined to form a cyclic structure including the nitrogen atom to which they are both attached;
p is 0-2; and
Ar is aryl or heteroaryl.

In another embodiment, the compound of Formula XXI is a compound of Formula XXIa:

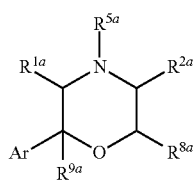

Formula XXIa or pharmaceutically acceptable derivatives thereof,
wherein R$^{1a}$, R$^{2a}$ and R$^{8a}$ are H or alkyl;
R$^{9a}$ is H or alkyl;
R$^{5a}$ is hydrogen, alkyl, alkenyl, alkynyl, aryl, heteroaryl, heterocyclyl, cycloalkyl, alkylcarbonyl, cycloalkylcarbonyl, or arylcarbonyl; and
Ar is aryl or heteroaryl.

In one embodiment, R$^{1a}$, R$^{2a}$ and R$^{8a}$ are H;
R$^9$ is H or CH$_3$;
R$^{5a}$ is Bn,

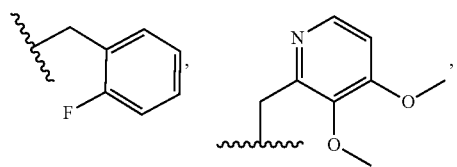

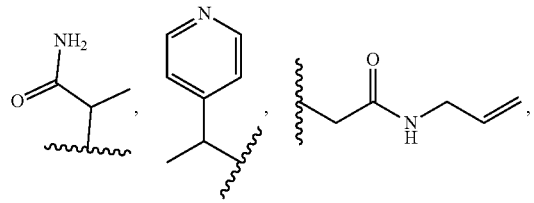

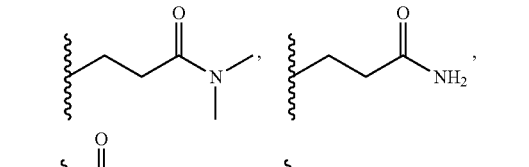

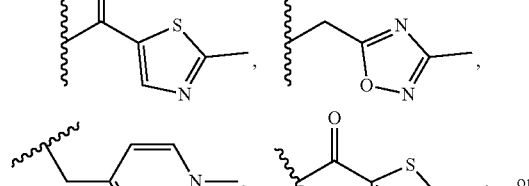

 or

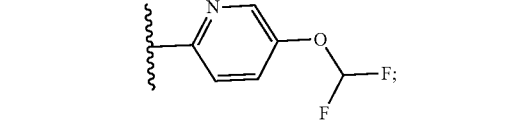

and
Ar is Ph,
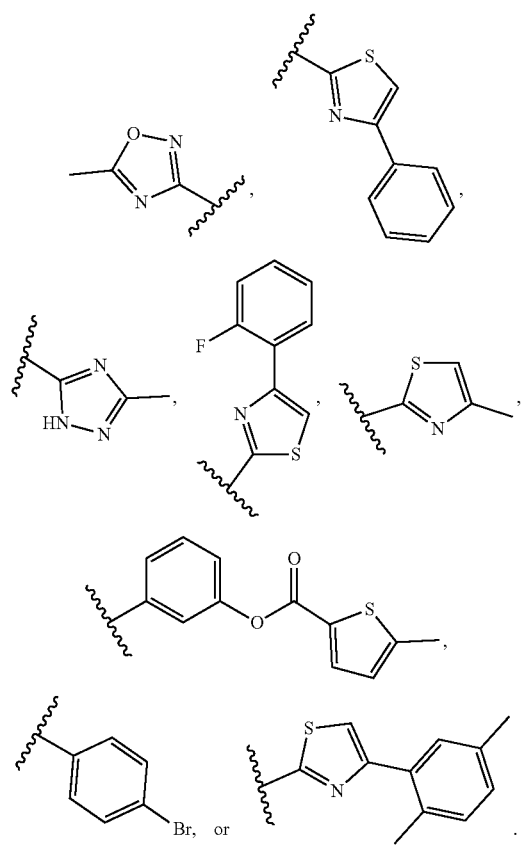
In one embodiment, the compound of Formula XXIa is:
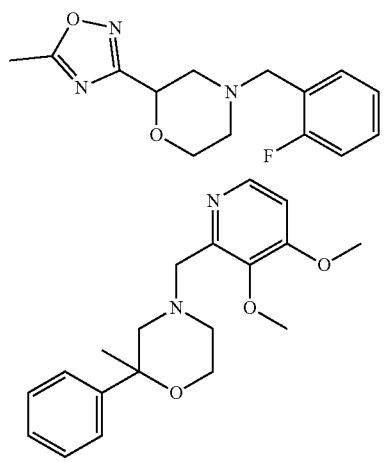
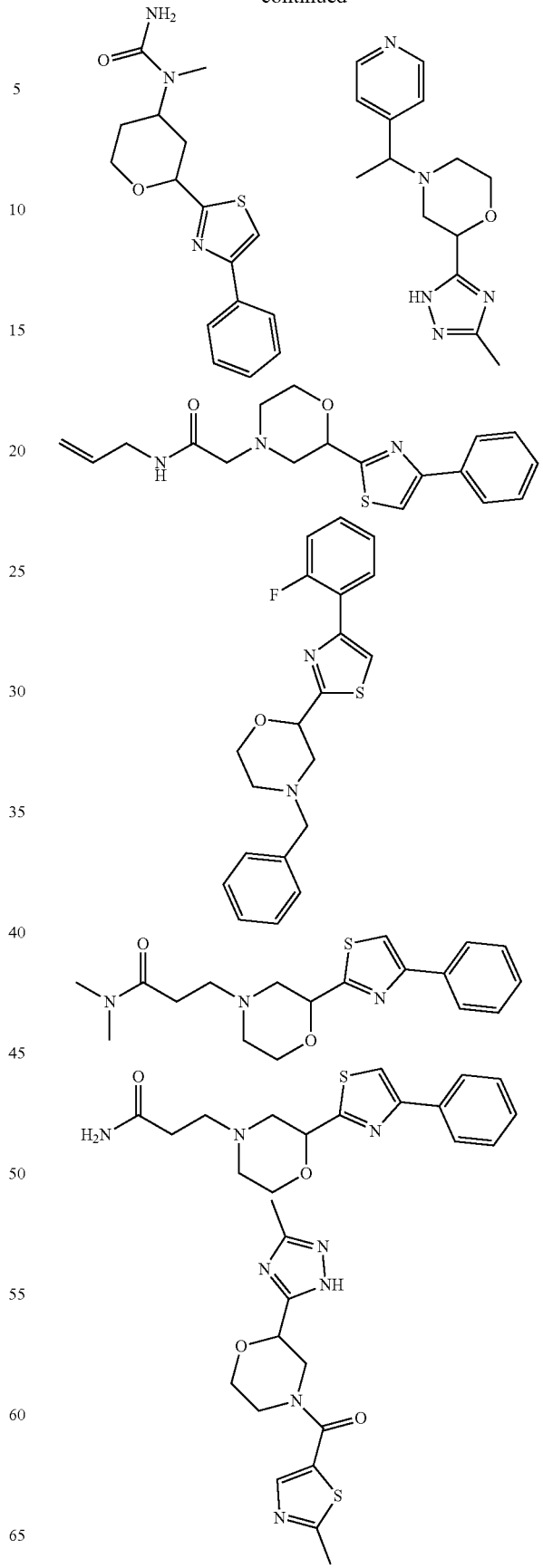

-continued

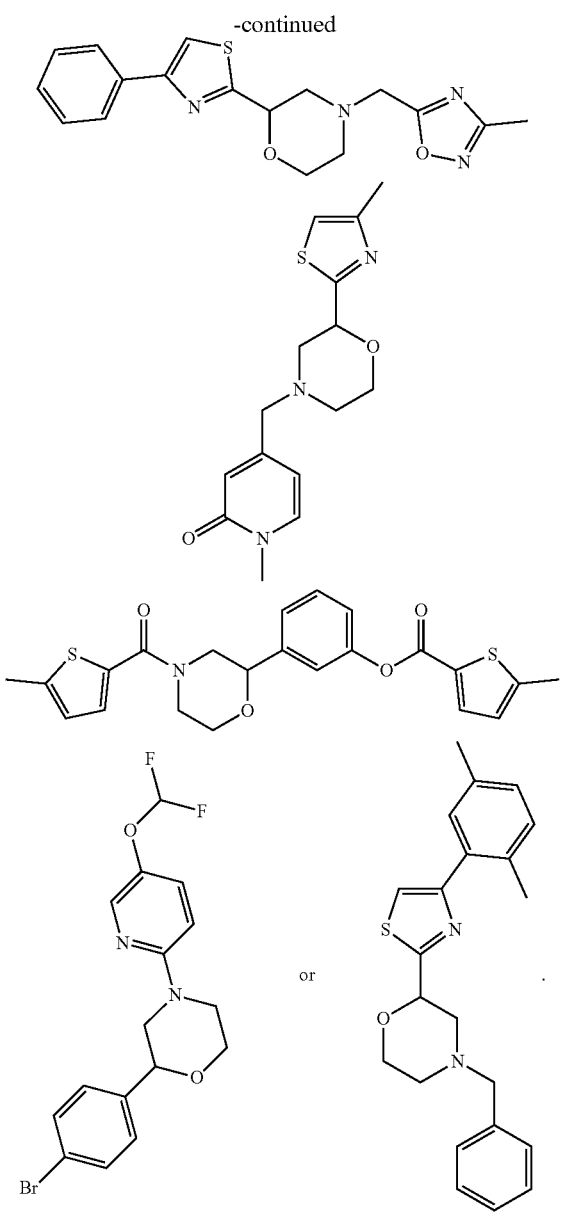

In one embodiment, the compound of Formula XXI is selected with the proviso that if Ar is pyridyl, then $R^5$ is not phenyl.

In one embodiment, the compound of Formula XXIa is selected with the proviso that if Ar is pyridyl, then $R^5$ is not phenyl.

In certain embodiments, the compounds for use in the compositions and methods provided herein are of Formula XXII:

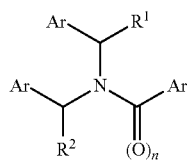

Formula XXII or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

n is 0 or 1;

p is 0-2; and each Ar is independently selected from aryl or heteroaryl.

In another embodiment, the compound of Formula XXII is a compound of Formula XXIIa:

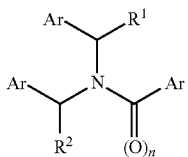

Formula XXIIa or pharmaceutically acceptable derivatives thereof, wherein $R^{1a}$ is H or alkyl;

$R^{2a}$ is H;

n is 0 or 1; and each Ar is independently selected from aryl or heteroaryl.

In another embodiment, Formula XXIIa is:

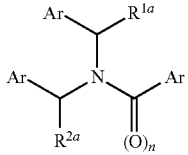

Formula XXIIa or pharmaceutically acceptable derivatives thereof, wherein $R^{1a}$ is H or alkyl;

$R^{2a}$ is H;

n is 0 or 1; and each Ar is independently selected from aryl or heteroaryl.

In one embodiment, $R^{1a}$ is H or $CH_3$;

$R^{2a}$ is H;

n is 0 or 1; and

Ar is independently selected from Ph,

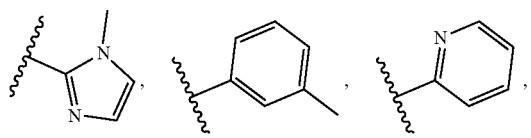

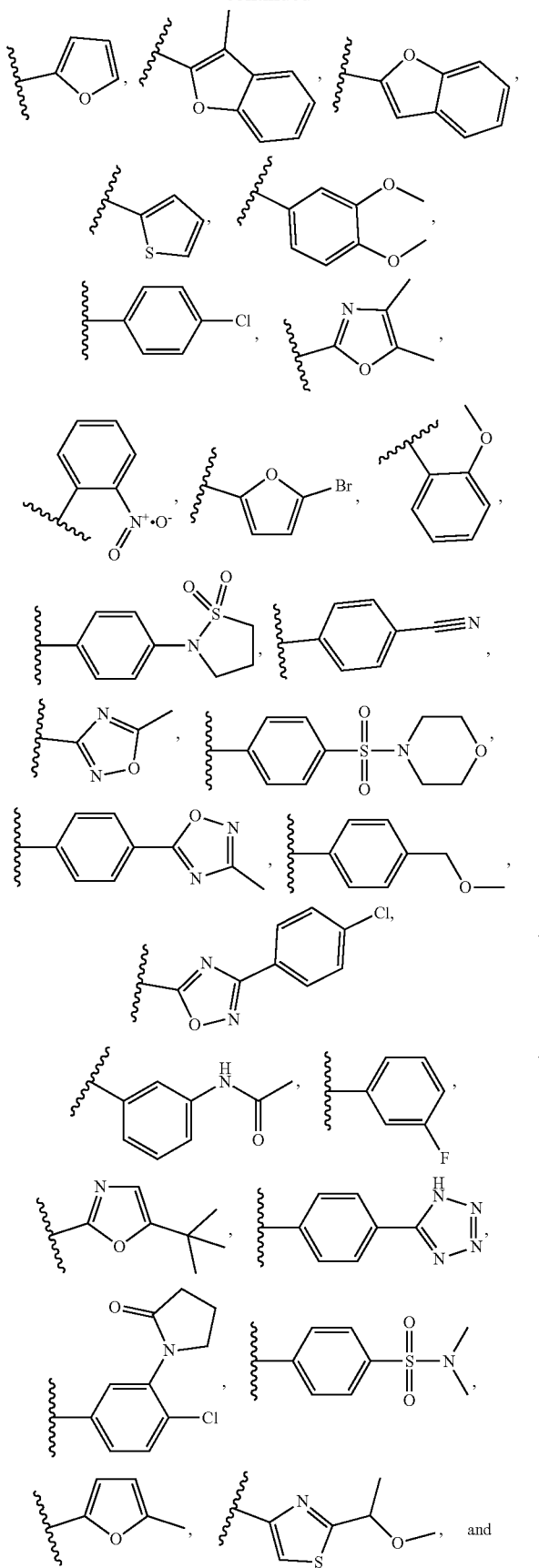
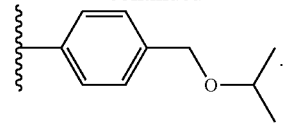
In one embodiment, $R^{1a}$ is H or $CH_3$;
$R^{2a}$ is H;
n is 0 or 1; and
Ar is independently selected from
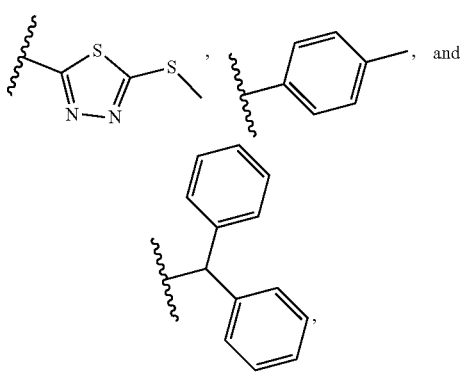
In one embodiment, the compound of Formula XXIIa is:
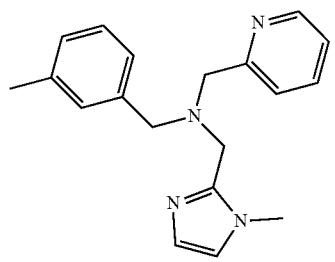
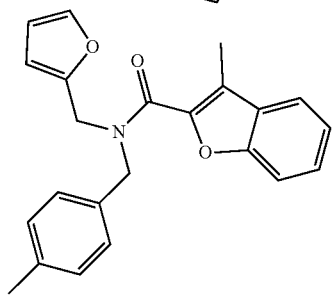
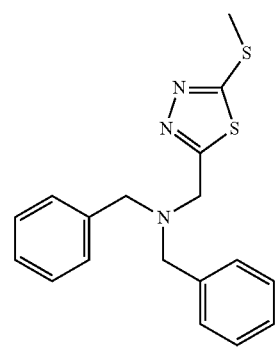

269
-continued
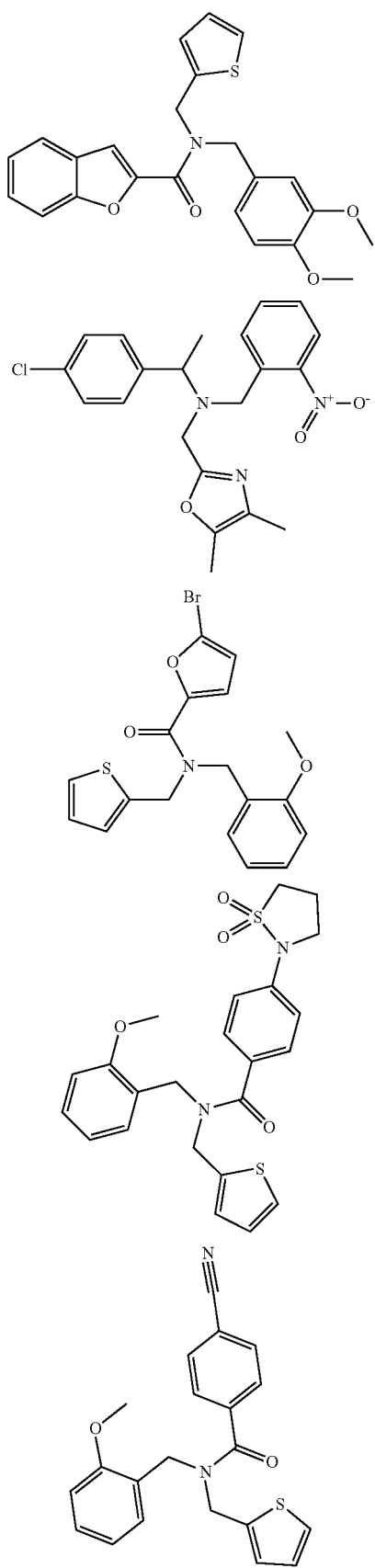
270
-continued
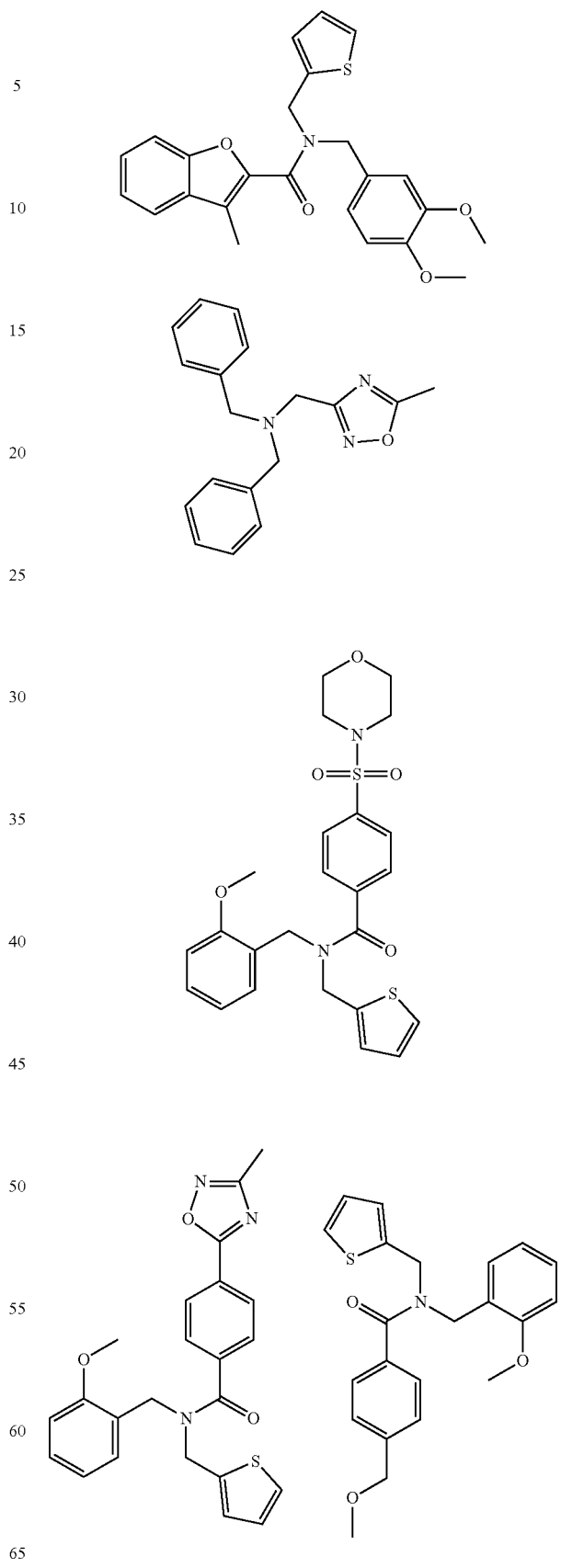

271
-continued
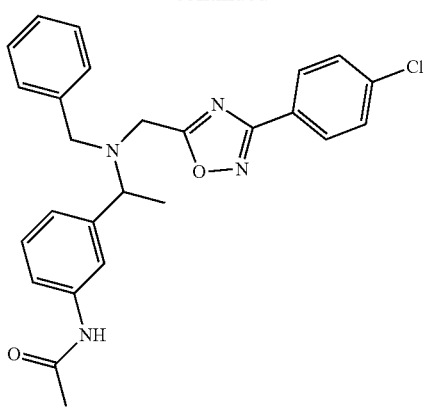
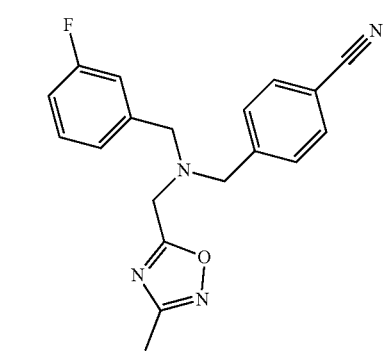
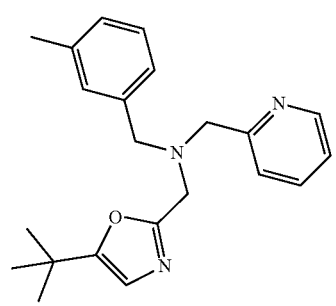
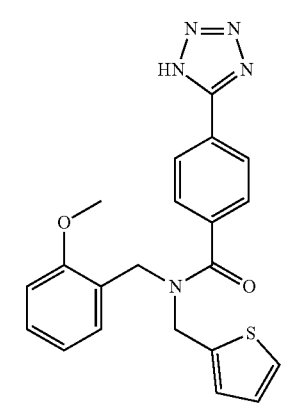
272
-continued
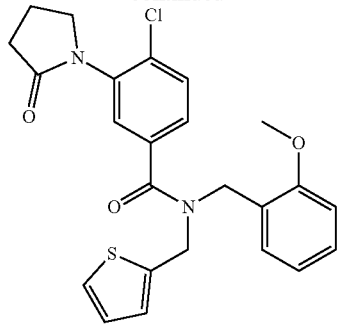
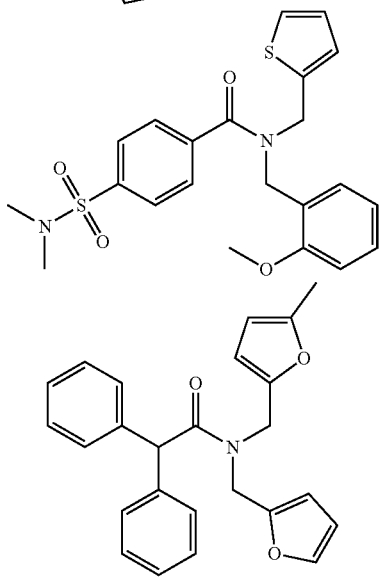
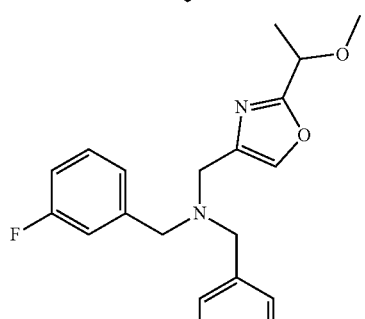
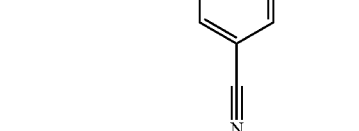
or
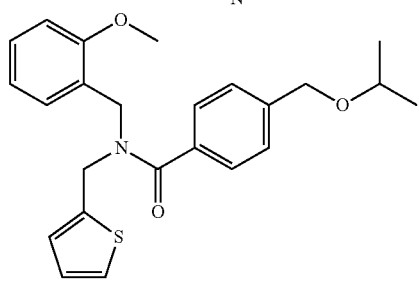
In certain embodiments, the compounds for use in the compositions and methods provided herein are selected from the group consisting of the following:

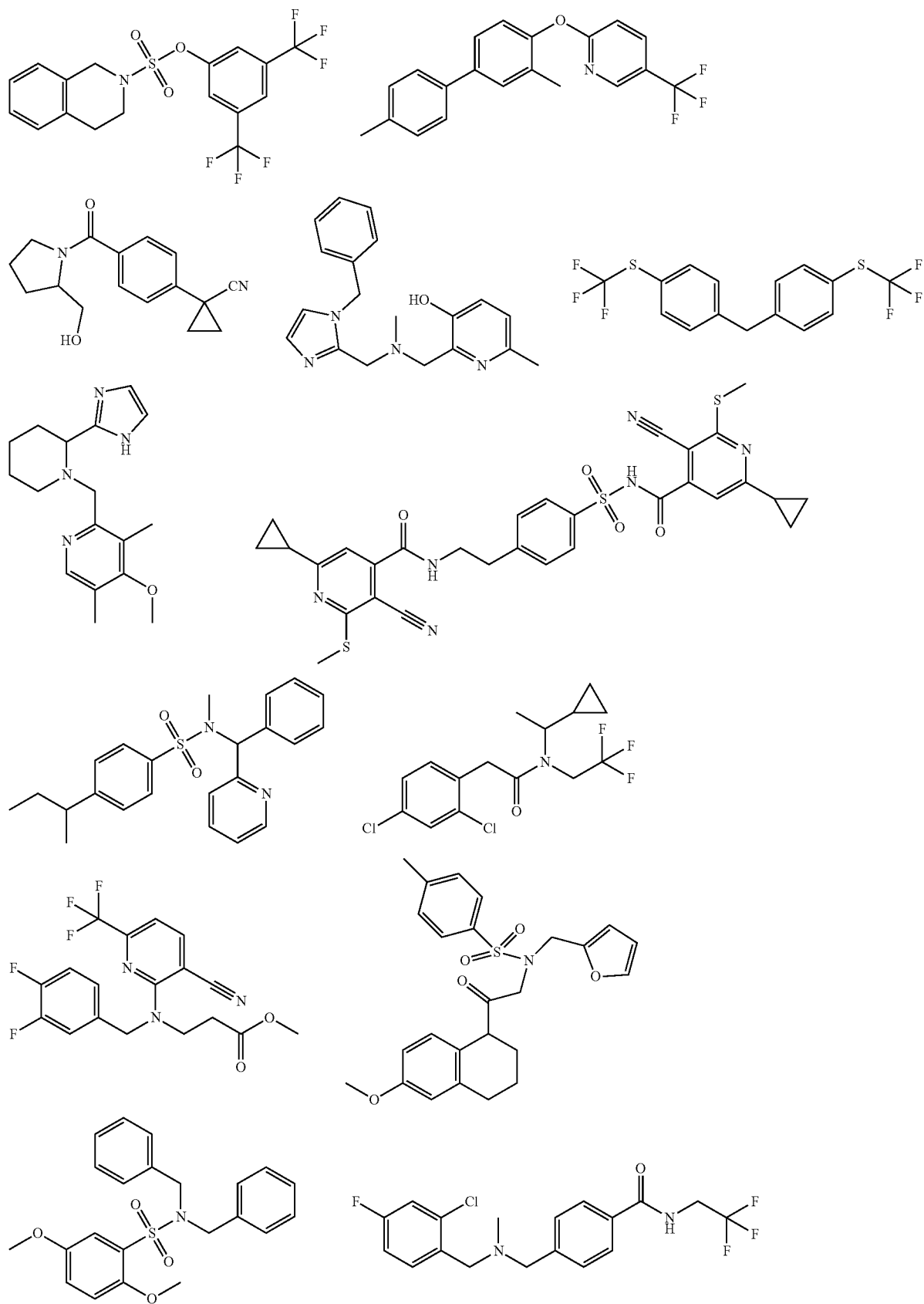

275
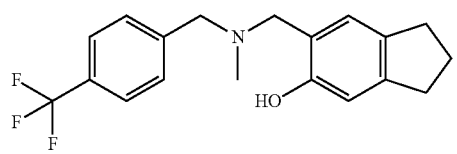
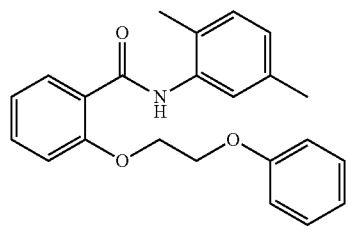
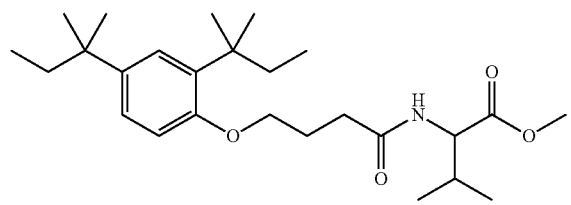
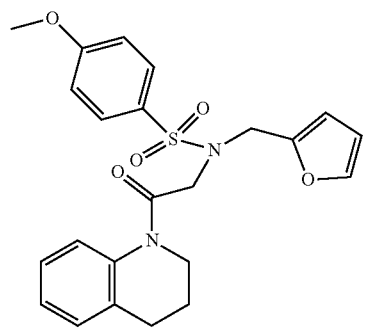
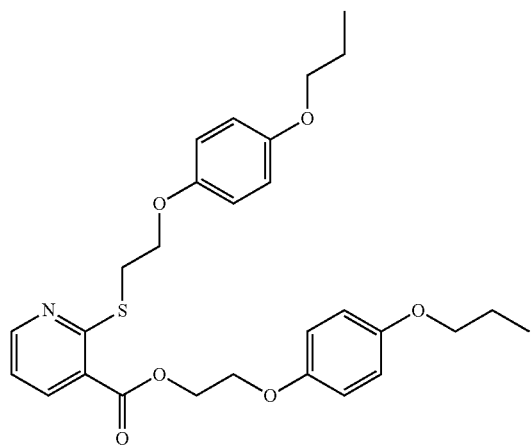
276
-continued
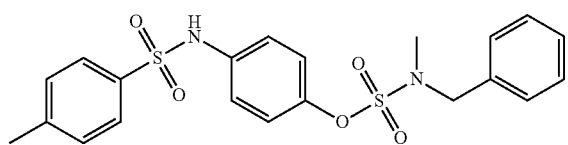
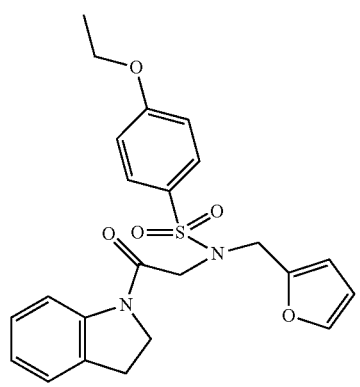
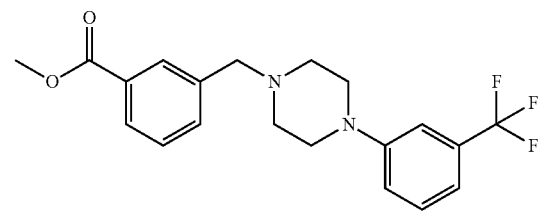
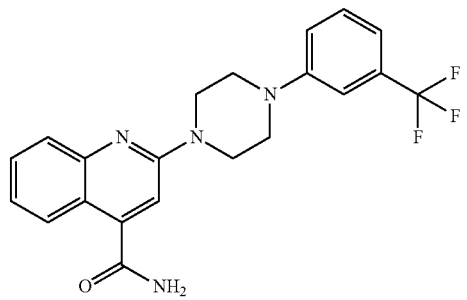
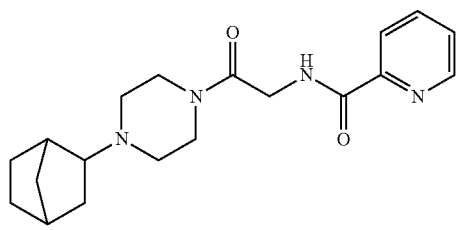

-continued
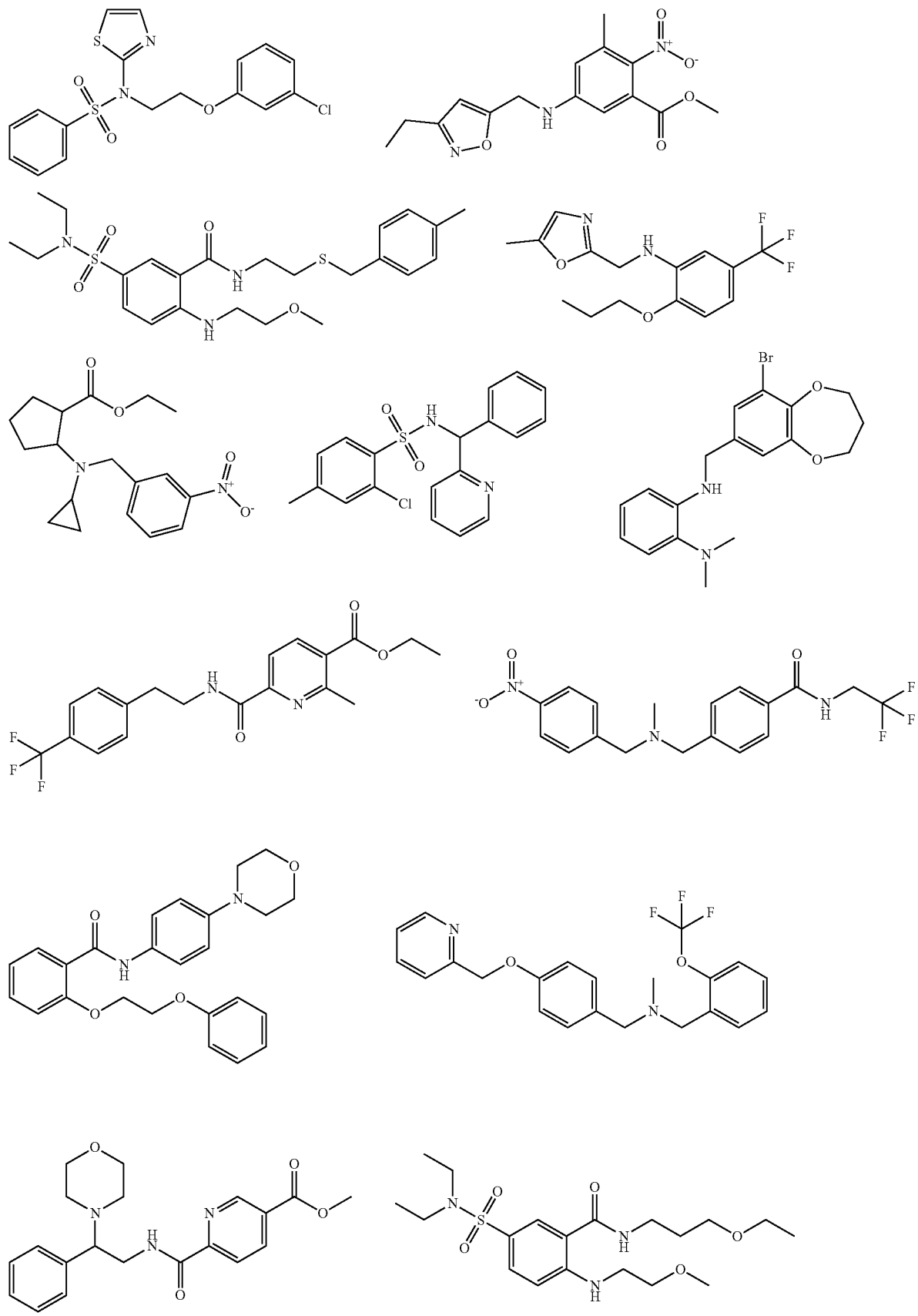

279                                                                      280
-continued
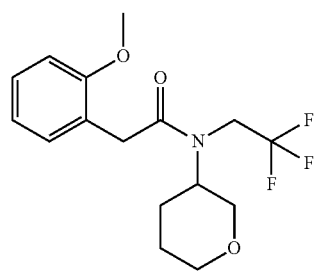 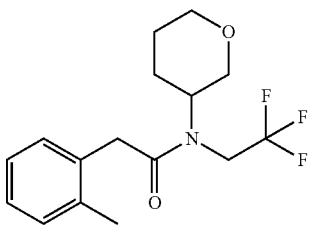 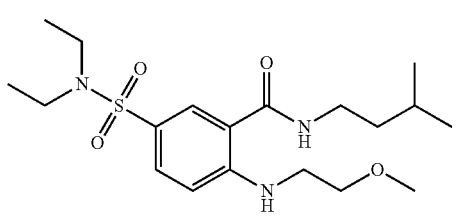
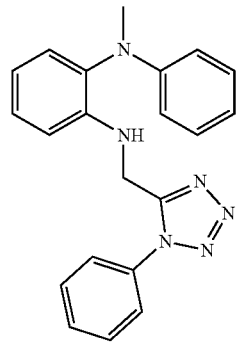 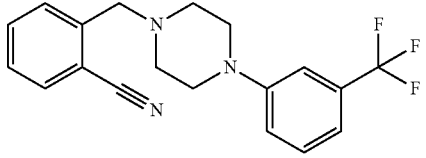
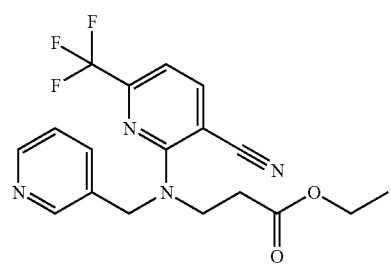 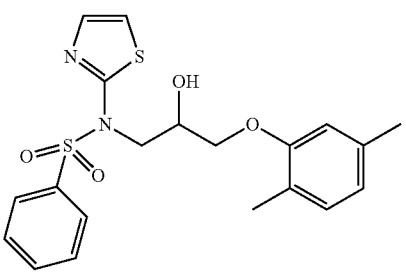
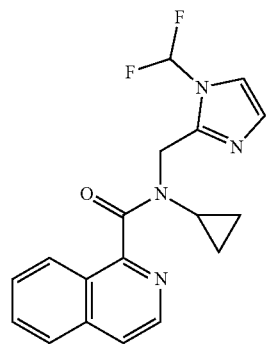 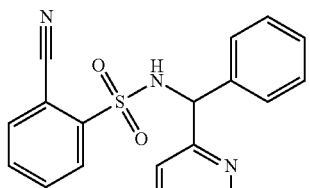 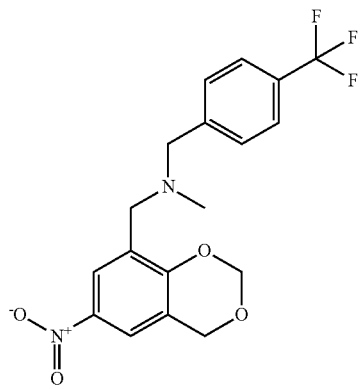
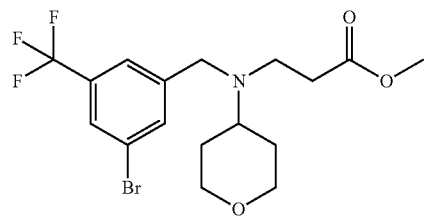 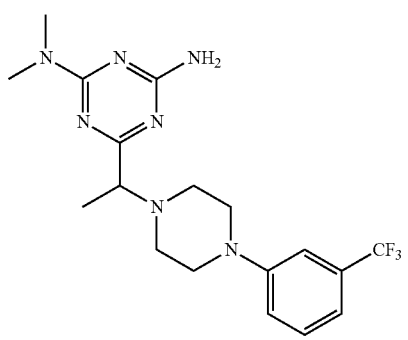

-continued
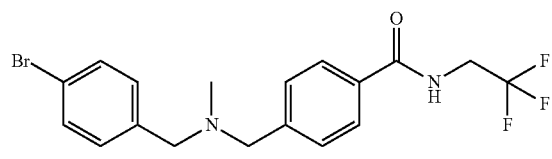
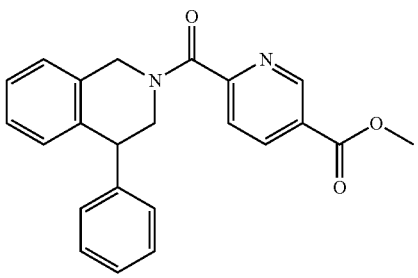
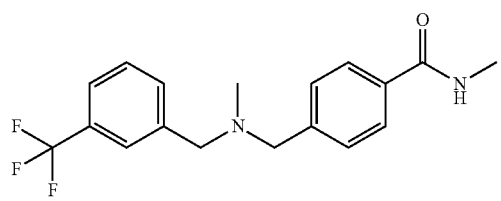
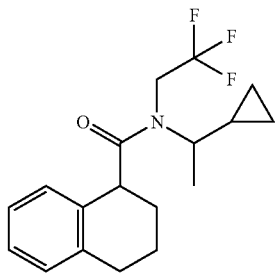
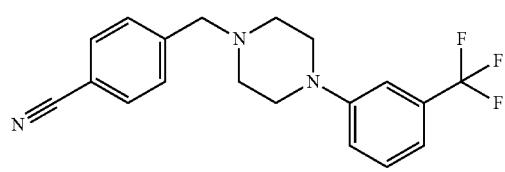
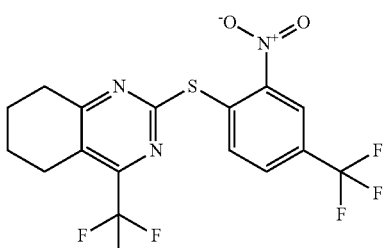
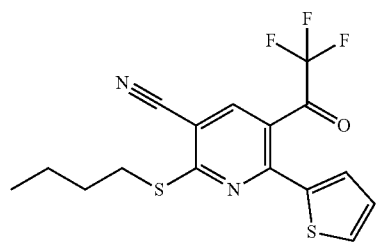
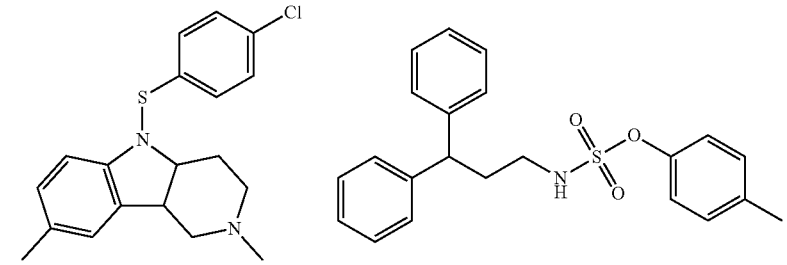
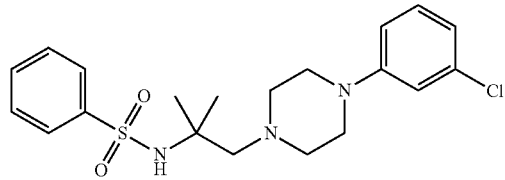
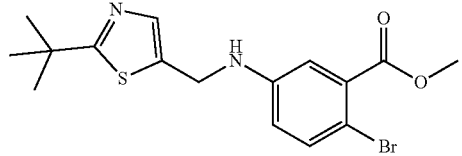
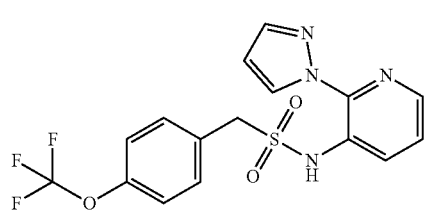
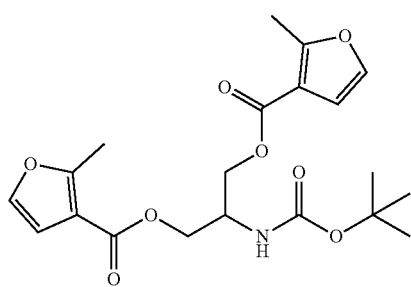

283
-continued
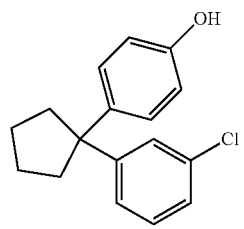 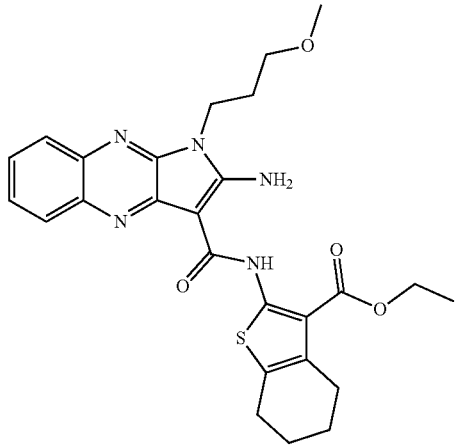 284 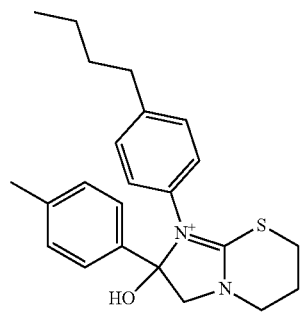
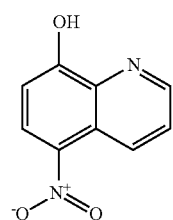 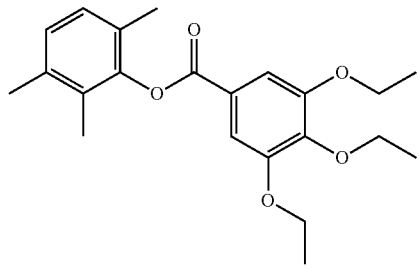
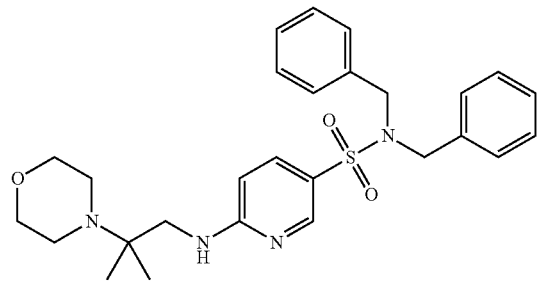 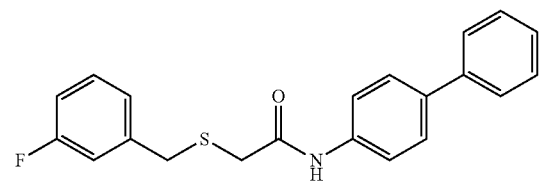
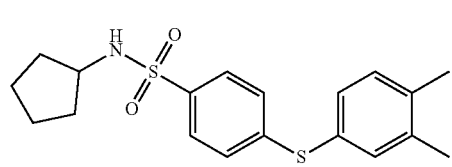 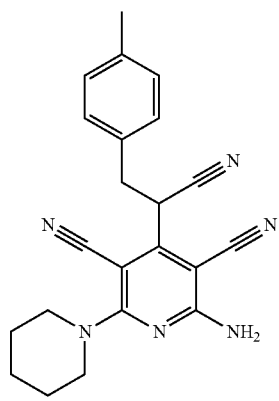

-continued
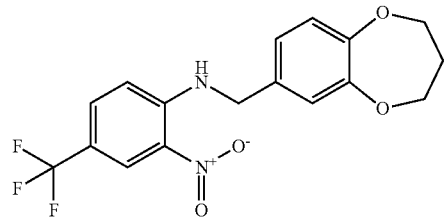
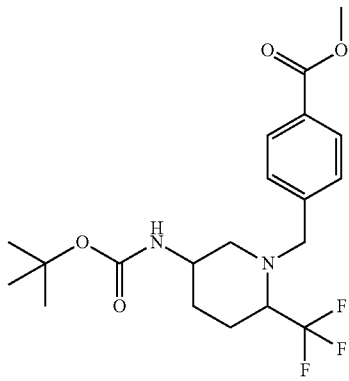
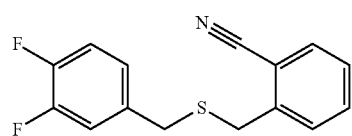
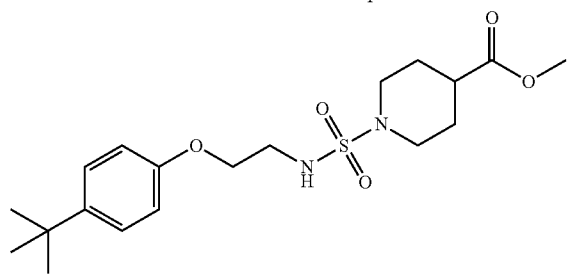
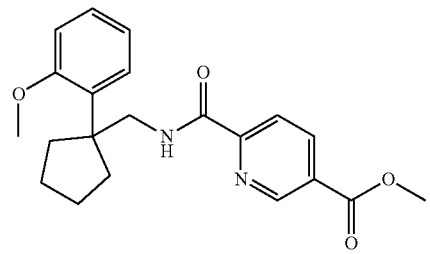
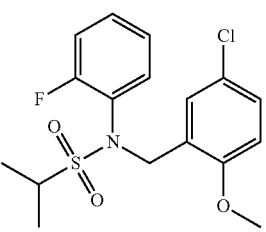
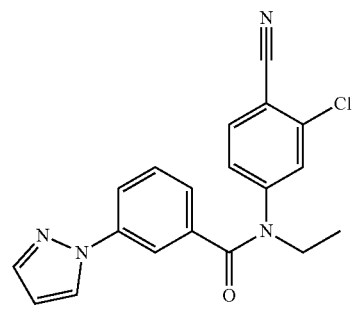
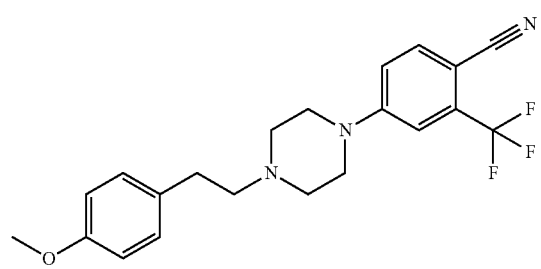
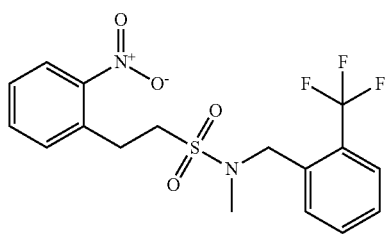
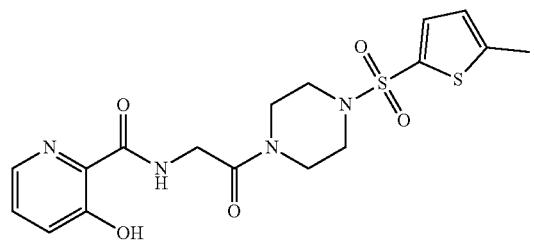
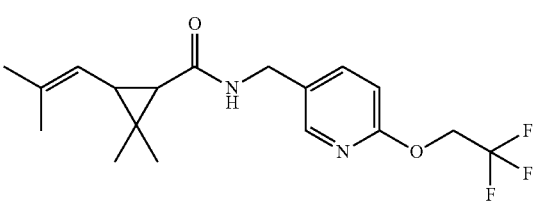
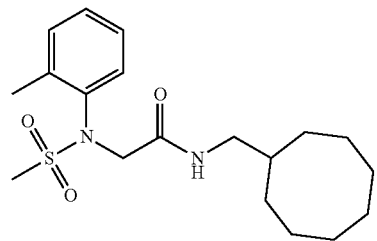
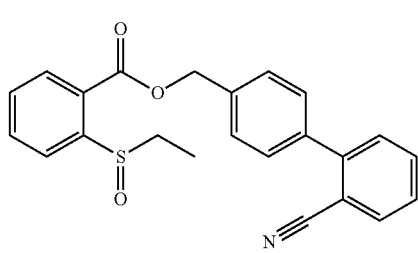

287
288
-continued
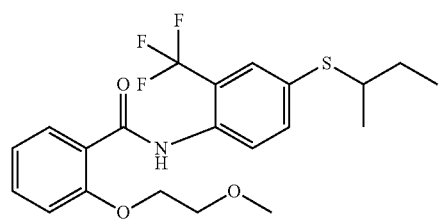
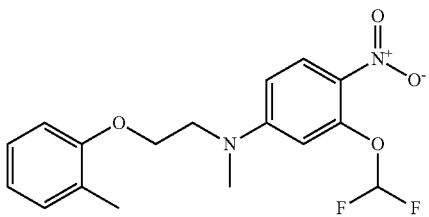
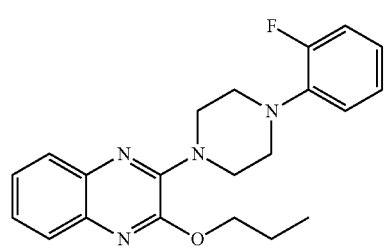
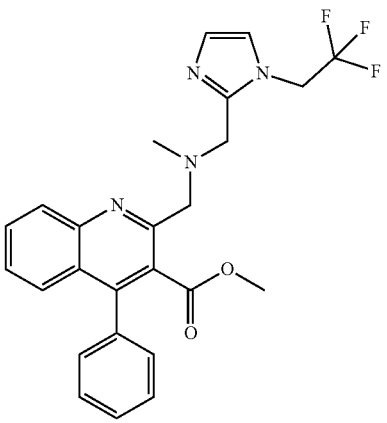
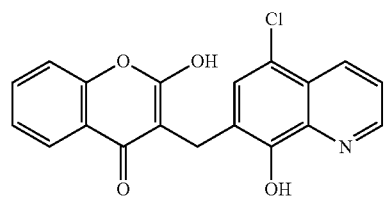
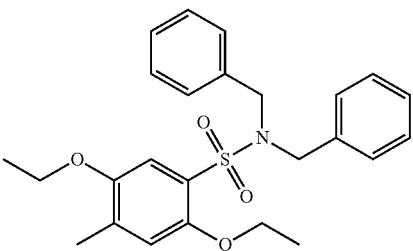
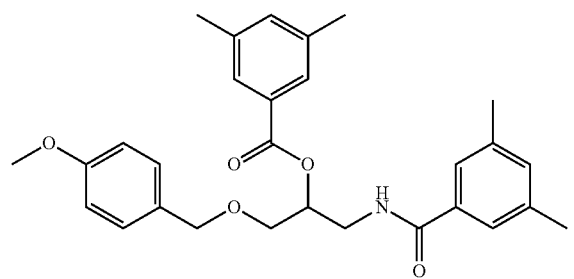
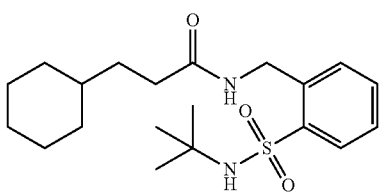
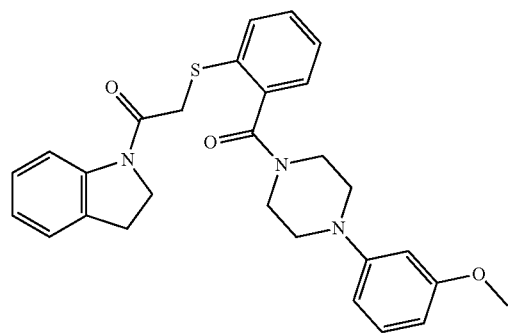
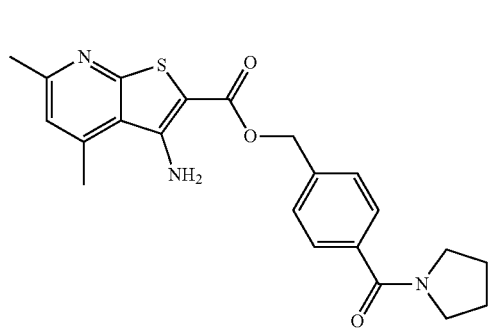

-continued
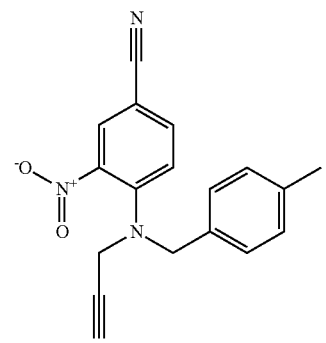
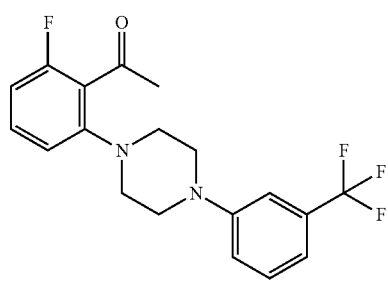
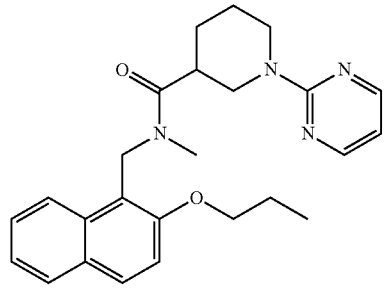
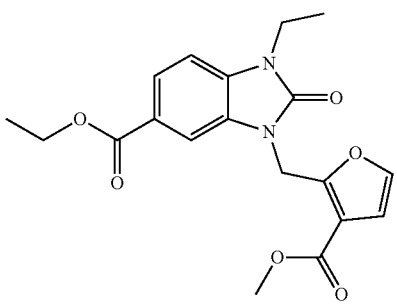
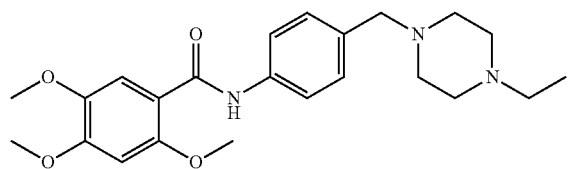
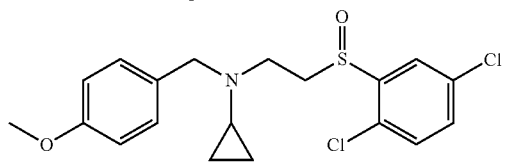
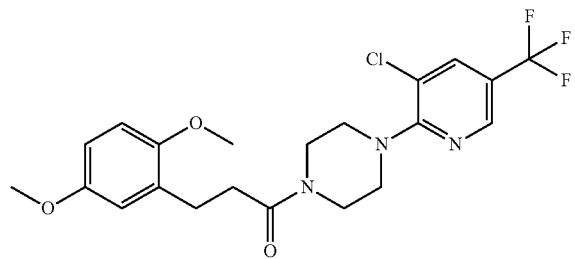
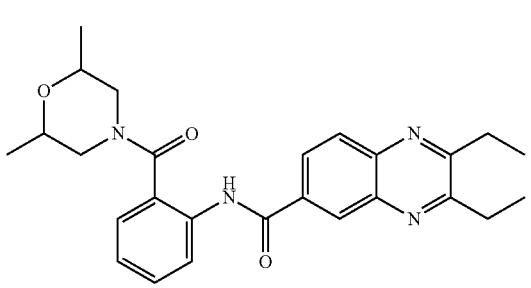
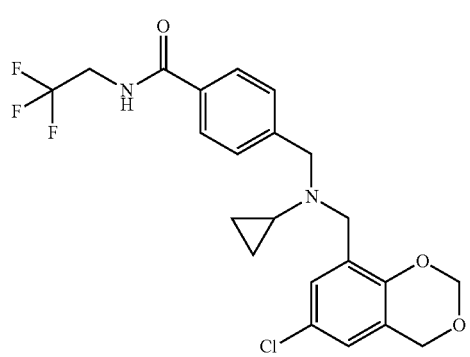
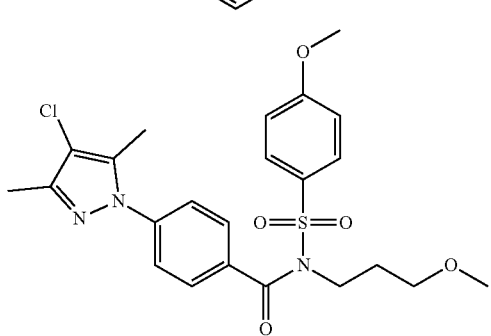
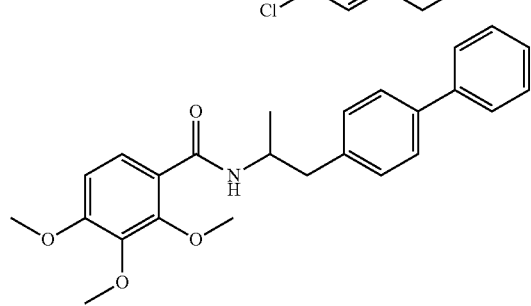

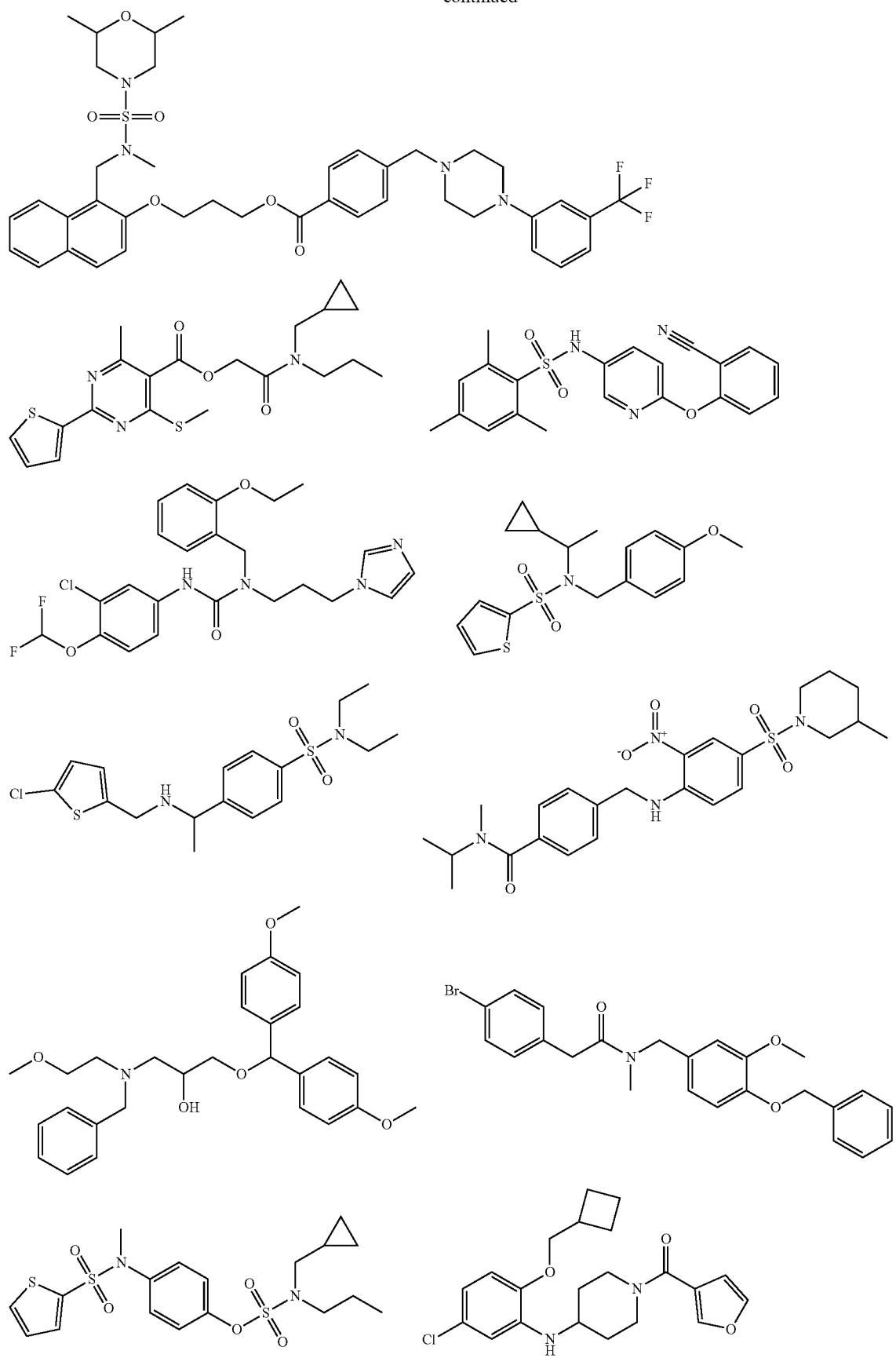

293
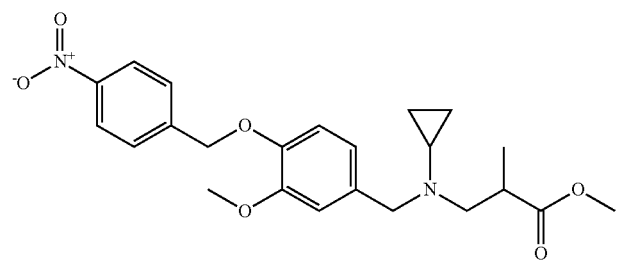
-continued
294
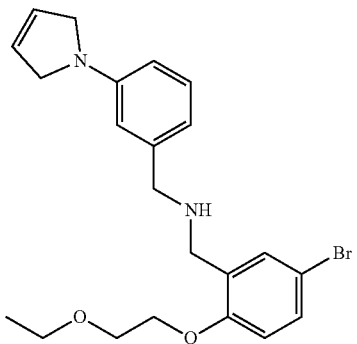
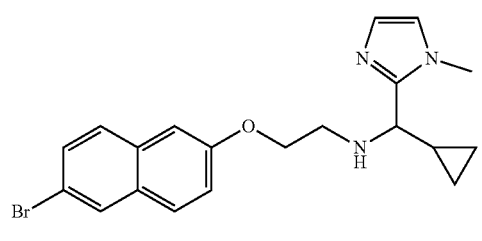
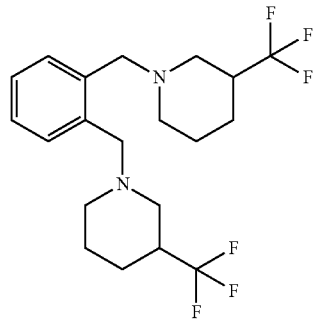
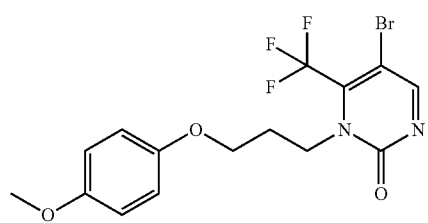
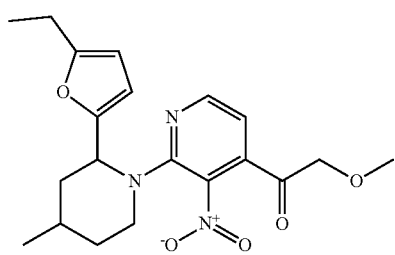
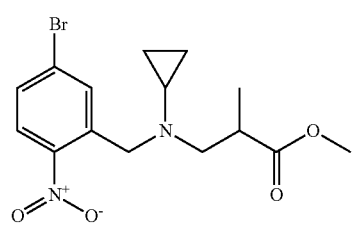
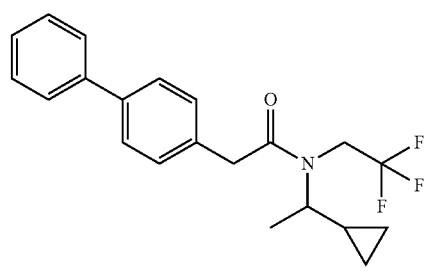
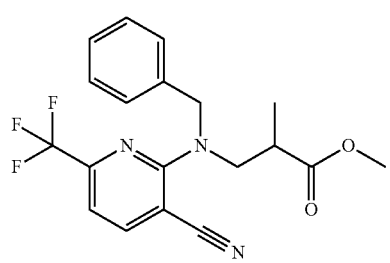
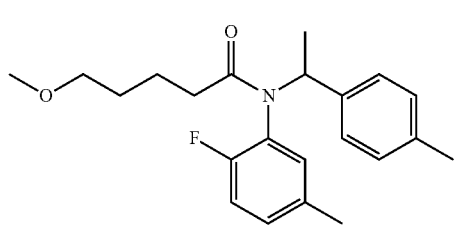

-continued
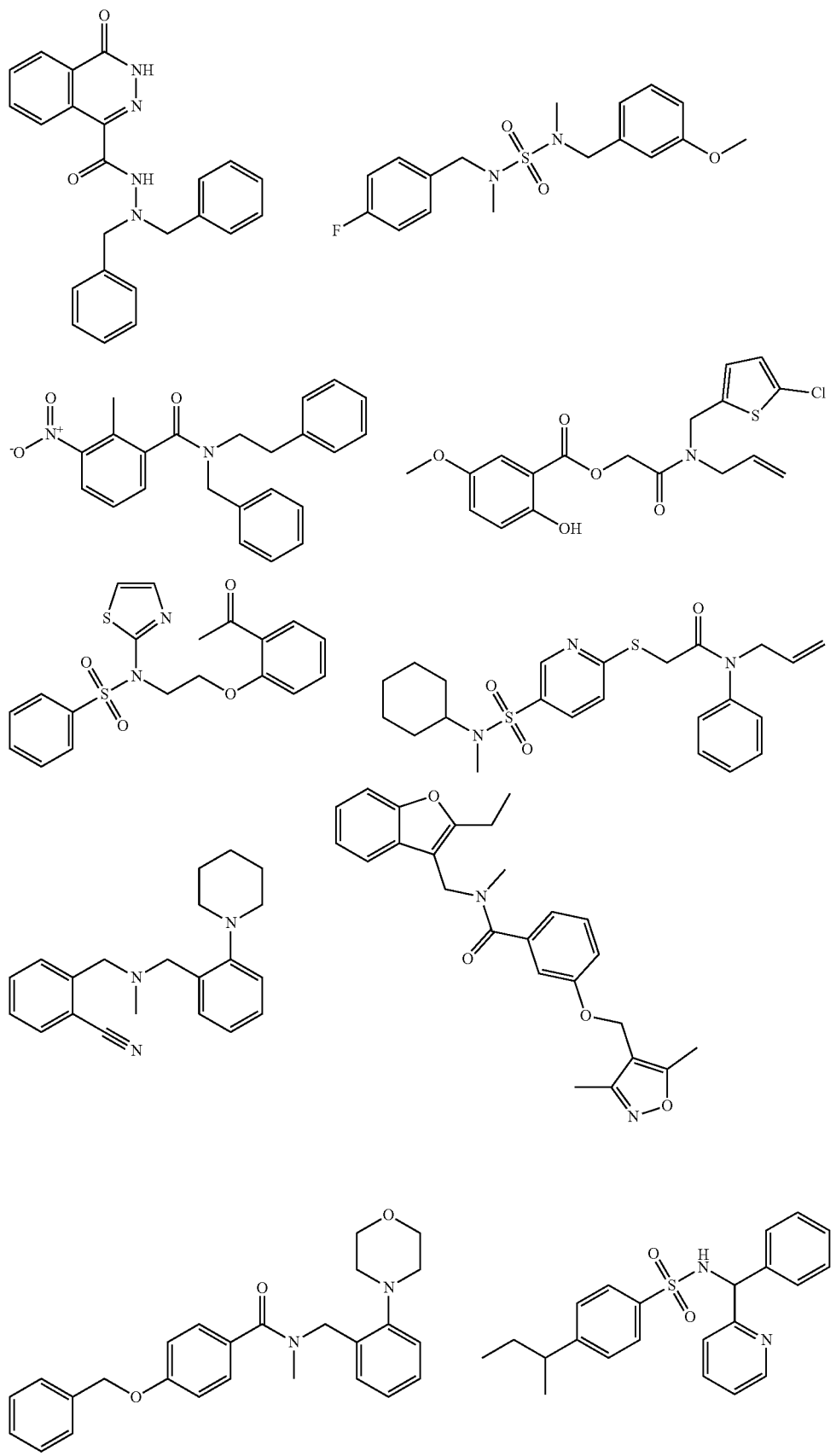

-continued
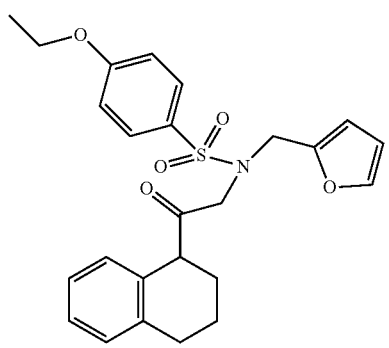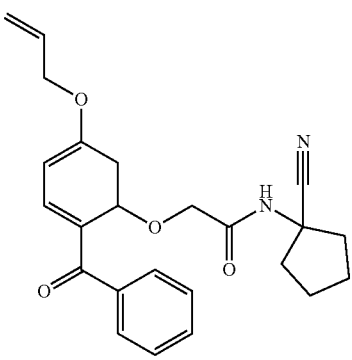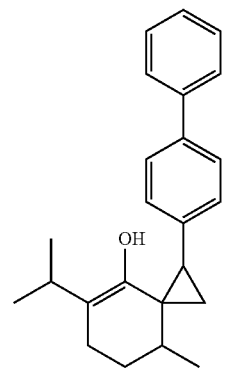
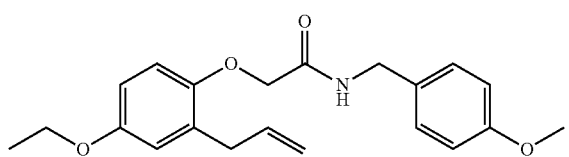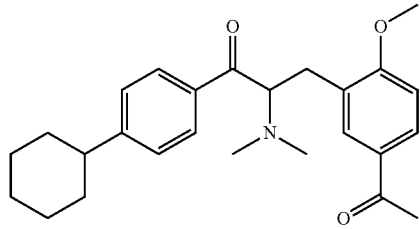
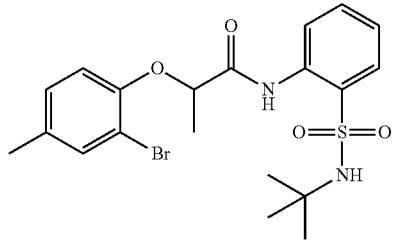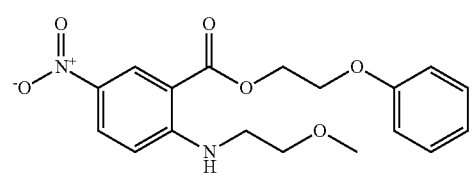
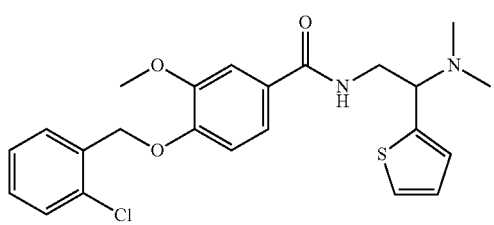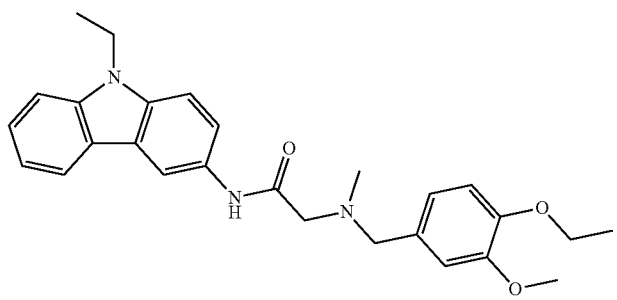
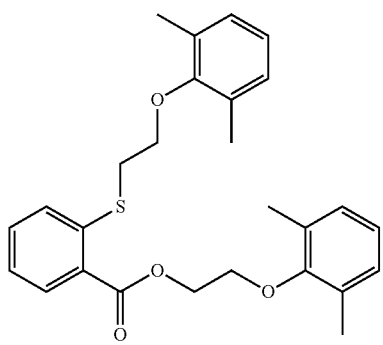 and 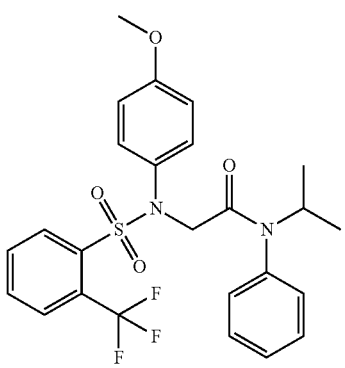.

5. Synthesis of the Compounds

The compounds provided herein may be obtained from commercial sources or readily synthesized by methods well known to those of skill in the art.

5.1 Synthetic Procedures

Amide

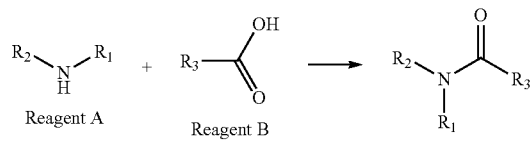

Reagent A + Reagent B → product

A vial was charged with 0.6 mmol of Reagent B, 1.6 mmol of DIPEA, and dry acetonitrile (1 mL). To the stirred reaction mixture 0.5 mmol of Reagent A (in case of amine salt, an additional 1.5 equivalent amount of DIPEA was added to the reaction mixture), and 0.72 mmol of 2-chloro-N-methylpyridinium iodide was added. The reaction vial was placed into a water bath and left at 100° C. for 6 hrs. Reaction mixture was cooled to room temperature and diluted by 6 mL of water. Then the vial was sonicated. If crystalline precipitate was formed it was filtered off. In case an oily product was formed the vial was left overnight, then the water layer was removed and 2-propanol (1 mL) was added to cause the crystallization. The precipitate was filtered, washed twice with a sodium carbonate solution, and then washed with methanol. Purification of the final compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

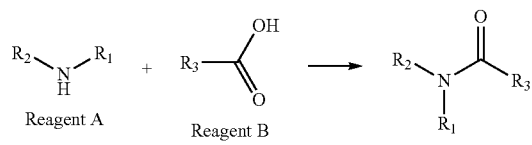

Reagent A + Reagent B → product

A vial was charged with 0.6 mmol of Reagent B, a solvent (1 mL of a solution of 200 g HOBt in 1 L of DMF), 0.57 mmol of Reagent A (in case of using amine salt, an additional 1.5 equivalent amount of DIPEA was added to the reaction mixture to transfer the amine to base form) and 0.66 mmol of EDC. In case the reaction mixture becomes highly viscous 0.5 mL of DMF were added. In case the reaction mixture was a homogeneous the it was kept at room temperature for 72 hrs. Otherwise the reaction mixture was sonicated at room temperature for 5 days. Reaction mixture was diluted with 6 mL of 1% sodium phosphate water solution. Then the vial was sonicated. In case a crystalline precipitate was formed it was filtered off. In case an oily product was formed the product was dissolved in methanol and precipitated by an addition of 4% hydrochloric acid. Alternatively 2-propanol (1 mL) was mixed with the crude product and the mixture was sonicated. Then the solution was diluted with 5% aqueous sodium hydrogen carbonate (the procedure repeated 2-3 times if necessary). Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

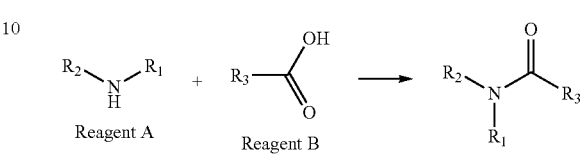

Reagent A + Reagent B → product

A vial was charged with 0.57 mmol of Reagent B and dry DMF (1 mL). To the stirred reaction mixture 0.57 mmol of N,N-carbodiimidazole was added. After 1 hr of stirring the vial was open and the reaction mixture was left for 2 hrs in a drying oven at 60° C. Then 0.52 mmol of Reagent A (in case of amine salt, an additional 1.5 equivalent amount of DIPEA was added to the reaction mixture) was added, the vial was firmly closed, and the reaction mixture was stirred. The reaction vial was placed into a water bath and left at 100° C. for a time specified on the vial label. Reaction mixture was cooled to room temperature and water was added until the vial was full. Then the vial was sonicated. In case a crystalline precipitate was formed the vial was passed to the filtration. In case an oily product was formed the vial was left overnight, then the water layer was removed and 2-propanol (1 mL) was added to cause the crystallization. The precipitate was filtered, washed twice with a sodium carbonate solution, and then washed with a water/2-propanol (1:1) solution. Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

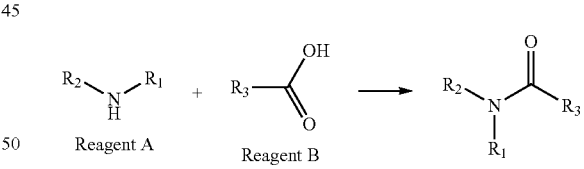

Reagent A + Reagent B → product

In a large vial 1.2 mmol of a Reagent B was loaded, then 1 mmol of a Reagent A (in case of amine salt, an additional 1.5 equivalent amount of DIPEA was added to the reaction mixture) and polymeric EDC (3 mmol, MW 833 g/mol) were added. 10 ml of solvent (30 g of pentaflourophenol in 1 L of dichloromethane) were added, the vial was closed and mixture was stirred. The vial was shaked continuously for 72 hours using shaker. Reaction mixture was filtered, collecting filtrate in a big tared vial. Precipitated polymer was preserved. Filtrate was evaporated, residue was weighed. If amount of the residue was low, then a small portion of methanol (about 5 ml) was added to the precipitated polymer and shaked for 4 hours. Methanol solution was filtered to the vial with dried residue after the first filtration. Filtrate was evaporated again and the residue was passed to the chromatography. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Oxadiazole Synthesis

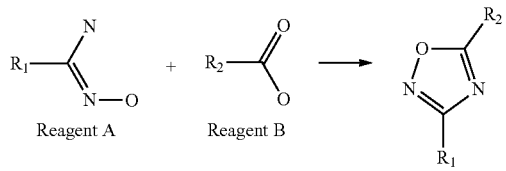

Reagent A    Reagent B 0.6 mmol of Reagent B was loaded into a small vial. 0.6 mL of solvent (a solution of 200 g N-oxybenzotriazole in 1 L of DMF) and 0.6 mmol of Reagent A (in case of amine salt, an additional 1.5 equivalent amount of DIPEA was added to the reaction mixture) were added to it. 0.9 mmol of EDC was added to the reactionary mixture after this. If the reactionary mixture was homogeneous it should be kept at the room temperature for 72 hours. If not, it should be sonicated for 5 days at the room temperature without any serious heating. 0.6 mmol of TEA was added after this and the vial with the reactionary mixture was put into bain-marie and heated at 100 C for a time indicated on the vial label (ca. 3 h). The reactionary mixture was cooled than and 3 mL of CH2CL2 with water in amount enough to fill the vial was added to it. The organic layer was washed out with water two times. All water was removed after this and the product was forwarded for the further drying. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

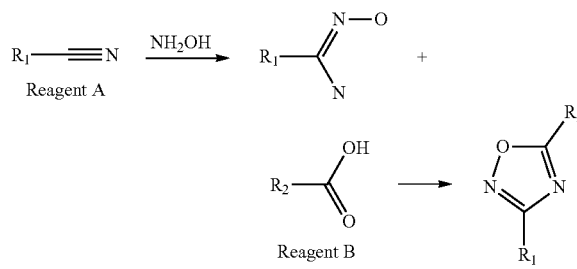

Reagent A

Reagent B 1.6 mmol of Reagent A was loaded in small vial then 2 ml of ethanol, 2.4 mmol of hydroxylamine and 3.2 mmol of TEA were added. If the reaction mixture is not homogenous then another portion of ethanol (1 mL) was added, stirred for 3-4 hours on shaker and left at rt overnight. Then it was heated at 80° C. for 3 hours and the solvent was removed under reduced pressure. The solid residue was dissolved in 1 mL of solvent (1 mL of a solution of 200 g HOBt in 1 L of DMF), 1.6 mmol of Reagent B and 2.4 mmol of CDI and sonicated for 3 days at rt. In case the reaction mixture was viscous additional 1 mL of DMF was added. Then 1.6 mmol of TEA were added and the vial was heated at 100° C. for 3 hours. The reaction mixture was cooled, diluted with 3 ml of water and extracted by 3 mL of $CH_2C_{12}$. The organic layer was washed out with water two times. All water was removed after this and the product was forwarded for the further drying. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Amino/Amide Synthesis

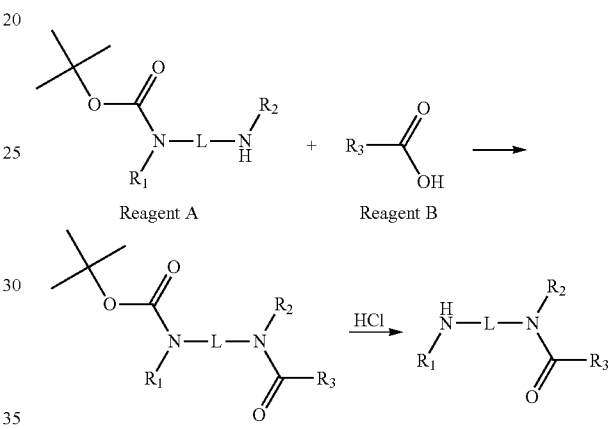

1.6 mmol of Reagent A (in case of amine salt, an additional 1.5 equivalent amount of DIPEA was added to the reaction mixture), 1.7 mmol of Reagent B, were added to 1 mL of a solution of 200 g Benzotriazole-N-oxide in 1 L of DMF. To the stirred mixture 1.9 mmol of EDC was then added. The resulting mixture was stirred at room temperature for 72 hours. The mixture was then diluted with 5 ml of 1% sodium phosphate solution, treated with ultrasound. After that 2 mL of HCl solution in 1,4-dioxane was added and the mixture was treated with ultrasound for 4 hours. The solid or oily crude product formed was isolated and purified via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Oxypyrimidine Synthesis

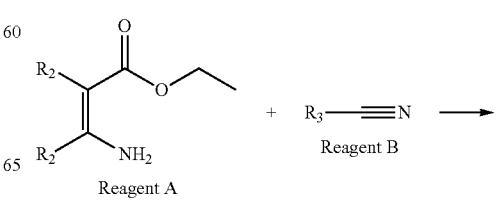

Reagent A

Reagent B

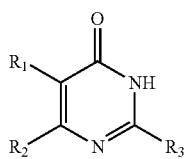

A small vial was charged with 1.6 mmol of Reagent A, 1.6 mmol of Reagent B and 1 ml of 4M dioxane solution of HCl. The vial was heated at 100° C. for 4 h. In case reaction mixture was too viscous additional 0.5 ml of dioxane were added. Then it was diluted with 3 ml of water and extracted by 3 mL of $CHCl_3$. Organic layer was washed with water (2*2 mL), dried and evaporated. The solid residue was purified by preparative chromatography. In case of reasonable amount of residue formed during extraction procedure it was separated from solution and purified by preparative chromatography. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Enamine Synthesis

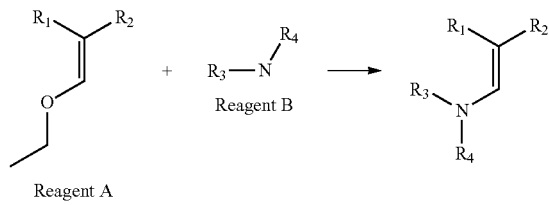

A vial was charged with 1.6 mmol of Reagent A, 1 ml of DMF and 1.6 mmol of Reagent B. The reaction mixture was stirred and heated at 100° C. for 4 h. Then it was cooled to rt. In case of residue formed it was filtered off and purified by preparative chromatography. Otherwise the reaction mixture was diluted with 3 ml of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Halogen Displacement: Carbon-Oxygen/Nitrogen/Sulfur Bond Formation

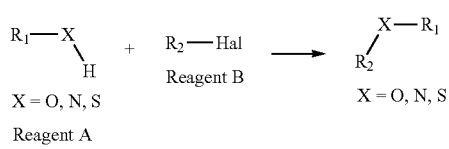

To a stirred solution containing 0.6 mmol of Reagent A (in case of amine salt, an additional 1.5 equivalent amount of DIPEA was added to the reaction mixture), 0.72 mmol of DIPEA, 80 mg of potassium iodide in 1 mL of DMF and 0.6 mmol of Reagent B was added. The reaction mixture was allowed to stir on a boiling water bath for ca. 5 min. Upon a complete dissolution of the reagents the stirred reaction mixture was heated on the water bath for the time specified on the vial label. The reaction mixture was triturated with an excess of deionized water and sonicated until a crystalline precipitate was formed. In case the trituration with water did not cause the product precipitation 1 mL of 2-propanol with the subsequent sonication were applied instead. The precipitate was filtered, washed twice with methanol, and dried. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

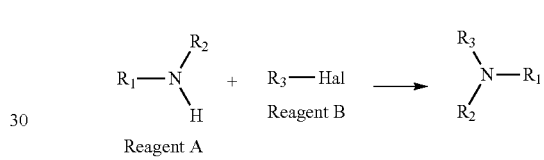

A vial was charged with 0.6 mmol of Reagent A (in case of amine salt, an additional 1.5 equivalent amount of DIPEA was added to the reaction mixture), dry DMF (2 mL), and 1.4 mmol of DIPEA. To the stirred reaction mixture 0.6 mmol of Reagent B was added. The firmly closed reaction vial was placed into a water bath and the reaction mixture was stirred at 100° C. until a complete dissolution of the reaction component occurs. Then the homogeneous reaction mixture was heated in the water bath at 100° C. for 6 hrs. The vial was passed to the polymer scavenger purification. The solvent was removed under reduced pressure. Ethyl acetate (10 mL) and then wet anion resin (5 g) were added to the residue. The stirred mixture was heated in a water bath at 70° C. for 6 hrs. Then the resin was filtered off. The solution was transferred into a pre-weighted vial and the solvent was removed under reduced pressure. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Amine Synthesis: Mannich Reaction

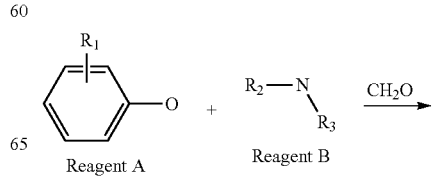

Ether Synthesis

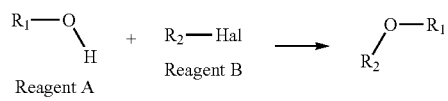

A small vial was charged with 0.6 mmol of Reagent A (in case of amine salt, an additional 1.5 equivalent amount of DIPEA was added to the reaction mixture), followed by 80 mg of potassium iodide in 0.7 mL DMF, and then 0.6 mmol of Reagent B. After stirring 1 mL 4M solution of KOH in methanol was added, the vial was closed tightly and shaked. Next the vial was sonicated for 24 h at the temperature no more than 35° C. After that the vial was filled with chloroform to the brim. After stirring the organic layer was washed twice with water and dried. Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Bicyclic Synthesis

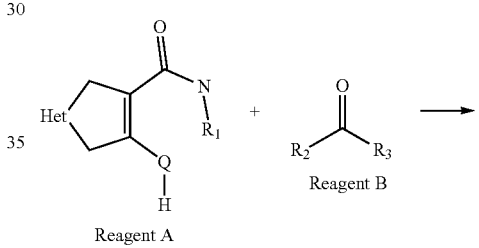

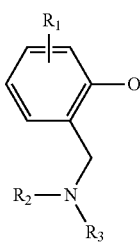

A vial was charged with 1.6 mmol of Reagent A, 2 ml of methanol and 6.4 mmol of formaline. If the solution was not homogenous additional 0.5 mL of methanol were added. The reaction mixture was sonicated for 1 h. Then 1.6 mmol of Reagent B were added and sonicated for another 1 h. In case of substantial amount of residue formed it was filtered off, washed by iPrOH (water then iPrOH if TEA is present in the reaction mixture) and purified by preparative HPLC. Otherwise the reaction mixture was diluted with 3 mL of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Oxamide Synthesis

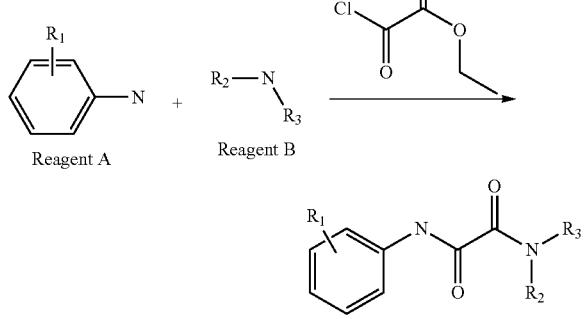

A vial was charged with 1.6 mmol of Reagent A, 1 mL of acetonitrile, 2.9 mmol of DIPEA and 1.6 mmol of ethyl chlorooxalate. The reaction mixture was stirred for 30 min at rt and 1.76 mmol of Reagent B were added. The vial was heated at 100° C. for 6 h. The reaction mixture was cooled to rt, diluted with 3 mL of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

A vial was charged with 1.6 mmol of Reagent A, 1 mL of pyridine and 1.6 mmol of Reagent B, stirred. Then 6.4 mmol of $Me_3SiCl$ were added and the reaction mixture was stirred and heated at 100° C. for 8 h. Then it was cooled to rt and 1.9 mmol of TEA were added and the vial was heated for another 30 min at 100° C. Then the reaction mixture was diluted with 3 ml of water and extracted by 3 mL of $CHCl_3$. The organic layer was washed with water (3*2 mL), dried and evaporated. The solid residue was purified by preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Methyl Amine Synthesis: Reductive Amination

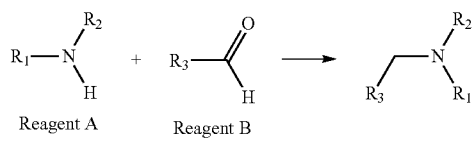

Reagent A    Reagent B 0.6 mmol of Reagent A (in case of amine salt, an additional 1.5 equivalent amount of DIPEA was added to the reaction mixture) was dissolved in 3 mL of methanol and the reaction mixture was stirred in a vial at r. t. Then 0.6 mmol of Reagent B was added to the stirred solution. The vial with the reaction mixture was sonicated at 58-60° C. for 60-90 min until a complete dissolution of the reagents. Up to 5 mL of acetonitrile could be added to complete the dissolution of the reagents. The reaction vial was cooled to 0° C. and sodium borohydride (150 mg) was added to the reaction mixture in small portions. The reaction mixture was stirred in the open vial until sodium borohydride was dissolved. The reaction vial was sonicated for 2 hrs at r. t., closed, and allowed to stand overnight at r. t. Then the open reaction vial was sonicated at 50° C. until methanol was nearly completely evaporated. The reaction mixture was triturated with 5 mL of methanol and stirred until the large part of it was dissolved. The insoluble part largely consisted of inorganic salts. The product was purified by passing the methanolic suspension through ionic polymer scavengers. In the case of an incomplete dissolution of the product in methanol 5 mL of deionized water could be added to the methanolic suspension causing precipitation of the product and dissolution of the inorganic contaminants. In the case of an emulsion formation upon addition of methanol the reaction mixture was filtered through a small chromatographic column filled with 8 g of silica gel. The product was eluted with methanol and the solvent removed under reduced pressure to yield the product. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfonamide Synthesis

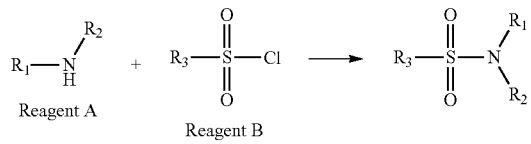

Reagent A    Reagent B

A vial was charged with 0.6 mmol of Reagent A (in case of amine salt, an additional 1.5 equivalent amount of DIPEA was added to the reaction mixture), acetonitrile (1 mL), and 0.72 mmol of triethylamine. To the stirred reaction mixture 0.6 mmol of Reagent B was added. The vial was placed in a water bath and heated at 100° C. for 2 hrs. 2% Hydrochloric acid (2 mL) was added to the reaction mixture and the vial was shaken. In case a solid precipitate was formed the vial was passed to the filtration. In case an oily product was formed the vial was sonicated to cause the crystallization. Additional measures to cause the crystallization of the oily product, e.g., varying the amount of water and an increase of the sonication time, can be taken. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfide Synthesis

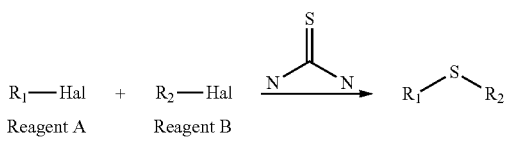

Reagent A    Reagent B

A vial was charged with 1.6 mmol of Reagent A, 0.7 ml of DMF and 1.76 mmol of thiourea. The reaction mixture was stirred and heated at 100° C. for 2 h. Then it was cooled to rt and 1 mL of 4M KOH solution and 1.6 mmol of Reagent B were added. The reaction mixture was sonicated for 24 h. Then it was diluted with 3 mL of water and extracted by 3 mL of CHCl$_3$. In case of residue formed it was filtered off and purified by preparative chromatography. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfone Synthesis

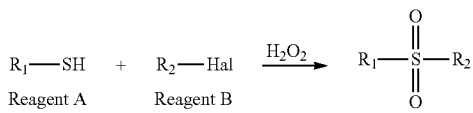

Reagent A    Reagent B

A vial was charged with 1.6 mmol of Reagent A, 1 mL of i-PrOH, 1.6 mmol of Reagent B and 1 mL of 4M KOH solution. The reaction mixture was sonicated at 50-60° C. for 2 h. Then 1 ml of methanol, 0.175 mL of CH$_3$COOH, 0.45 mL of 50% H$_2$O$_2$ and 0.175 mL of 10% solution of ammonium molibdate were added. The reaction mixture was sonicated at 70° C. for 5 h. Then it was diluted with 3 mL of water and extracted by 3 mL of CHCl$_3$. In case of residue formed it was filtered off and purified by preparative chromatography. The organic layer was washed with 10% NaHCO$_3$ solution (5 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Thiazole Synthesis

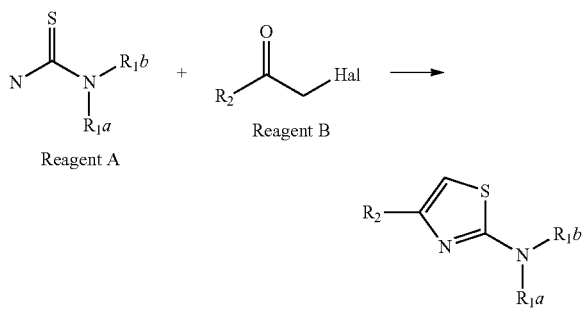

A vial was charged with 1.6 mmol of Reagent A, 1.5 mL of DMF and 1.6 mmol of Reagent B. The reaction mixture was heated at 100° C. for 2 hours. After cooling to rt 0.2 ml of DIPEA, 3 mL of water were added and extracted by 3 mL of CHCl$_3$. Organic layer was washed by water (2*1 mL), dried and evaporated. The solid residue was purified via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Urea Synthesis

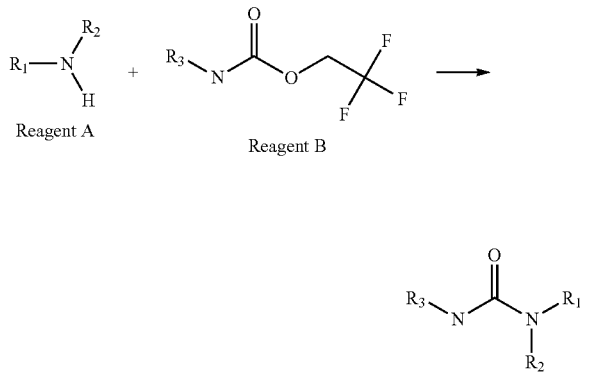

A vial was charged with 0.6 mmol of Reagent A (in case of amine salt, an additional 1.5 equivalent amount of DIPEA was added to the reaction mixture), 2 mL of acetonitrile and 0.6 mmol of DIPEA. The vial was left for 30 minutes, then 0.6 mmol of Reagent B was loaded. A vial was placed in a boiling water bath and heated up for 8 hours, then left for 30 minutes to cool down. 1 mL of water was added to the mixture and the vial was sonicated. If the residue has crystallized, the mixture was stirred until uniform and passed to filtration, otherwise the water was added until vial was full and standard workup was used. Filtered solid was washed with 1 ml of 1:1 isopropyl alcohol-water mixture 2 times. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

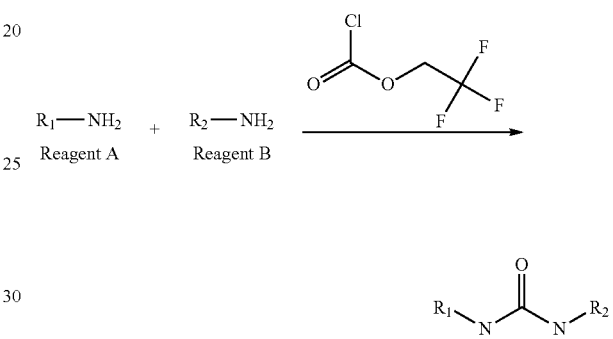

A vial was charged with 0.6 mmol of Reagent A (in case of amine salt, an additional 1.5 equivalent amount of DIPEA was added to the reaction mixture), 2 mL of acetonitrile, 0.9 mmol of DIPEA, and then 0.6 mmol of 2,2,2-trifluoroethylchloroformate dropwise. After left for 0.5 hrs, 0.73 mmol of Reagent B was added to the mixture. The vial was placed in the water boiling bath for 8 hrs. After 0.5 hrs cooling down 1 mL of water was added and the vial was passed to sonication. The outcome precipitate was filtered and washed twice with 1 ml of 50% water solution of 2-propanol). Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Piperidino-Oxypyrimidine Synthesis

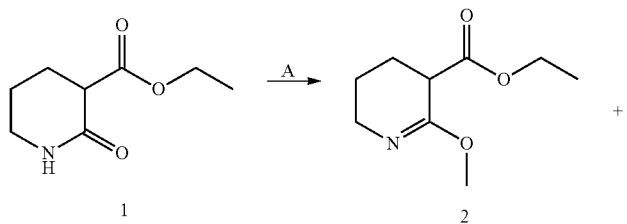

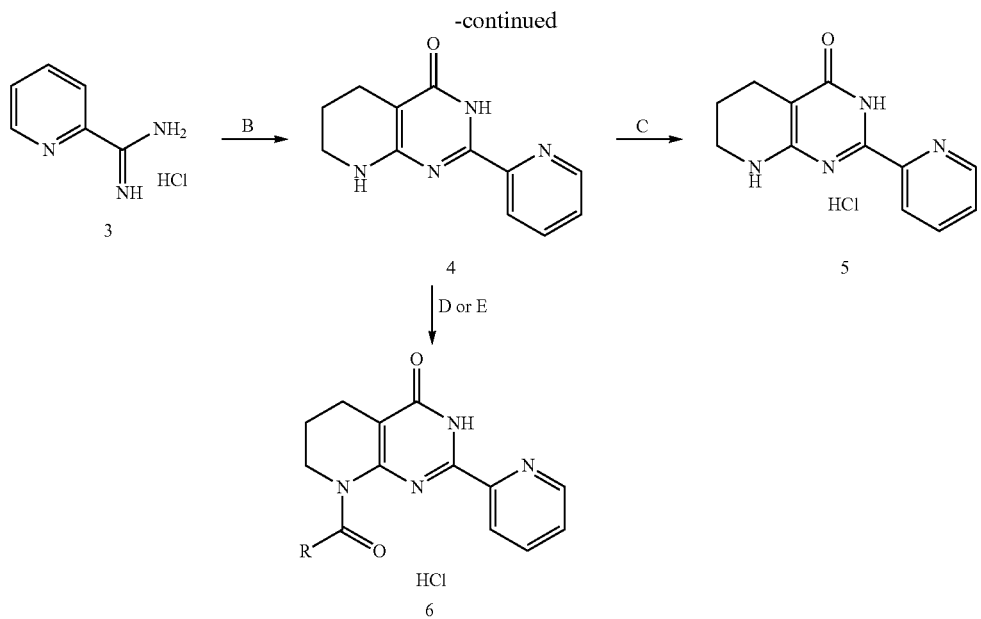

Step A: To a solution of compound 1 (50.0 g, 290 mmol) in chloroform (400 mL) Me$_3$OBF$_4$ (34.5 g, 220 mmol) was added. The resulting mixture was stirred at room temperature for 6 h and then washed with saturated aqueous solution of K$_2$CO$_3$ (2×300 mL). The organic layer was separated, dried over MgSO$_4$, and evaporated in vacuo. The residue was purified by vacuum distillation (b.p. 78° C. at 1 torr) to give 45.6 g (247 mmol, 85%) of compound 2 as a colorless oil.

Step B: Na (12.7 g, 550 mmol) was dissolved in EtOH (200 mL). Compound 3 (37.5 g, 238 mmol) was added to the solution and the resulting mixture was stirred at room temperature for 0.5 h. Then compound 2 (45.6 g, 247 mmol) was added, the reaction was refluxed for 4 h, and then evaporated under reduced pressure. The residue was dissolved in water and neutralized with 10% HCl. The precipitated solid was filtered and re-crystallized from i-PrOH to yield 40.8 g (179 mmol, 75%) of compound 4 as white solid.

Step C: To a suspension of compound 4 (0.020 g, 0.088 mmol) of in dry acetonitrile (2 mL) a solution of 10% HCl in dry dioxane was added dropwise until pH 3. After standing for 0.5 h the solvents were removed in vacuum to obtain 0.023 g (0.088 mmol, 100%) of target compound 5.

Step D: To a solution of compound 4 (0.150 g, 0.66 mmol) and DIPEA (0.256 g, 1.98 mmol) in acetonitrile the corresponding acid chloride was added (1-3 eq.). The resulting mixture was stirred under reflux for 3 hours and then evaporated in vacuo. The residue was purified by HPLC. The obtained product was suspended in dry acetonitrile. 10% HCl in dry dioxane was added dropwise until pH 3. After standing for 0.5 h the solvents were removed under reduced pressure to yield target amides 6.

Step E: To a solution of compound 4 (0.150 g, 0.66 mmol) in acetonitrile [(4-methoxybenzyl)oxy]acetic acid (0.129 g, 0.66 mmol), DIPEA (0.46 mL, 2.64 mmol), and DMAP (0.005 g, 0.04 mmol) were added. Then TBTU (0.847 g, 2.64 mmol) was added, the resulting mixture was refluxed for 8 hours, and evaporated under reduced pressure. The residue was purified by HPLC to yield the target amide 6.

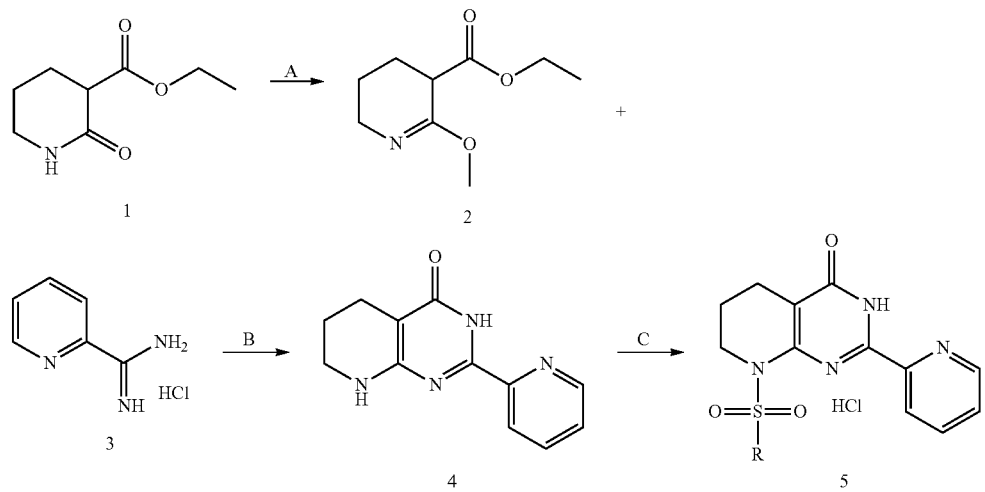

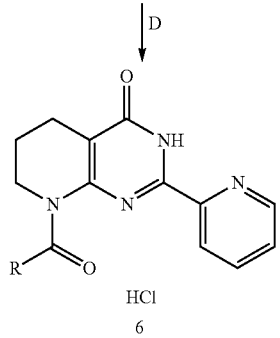

Step A: To a solution of compound 1 (50.0 g, 290 mmol) in chloroform (400 mL) Me₃OBF₄ (34.5 g, 220 mmol) was added. The resulting mixture was stirred at room temperature for 6 h and then washed with saturated aqueous solution of K₂CO₃ (2×300 mL). The organic layer was separated, dried over MgSO₄, and evaporated in vacuo. The residue was purified by vacuum distillation (b.p. 78° C. at 1 torr) to give 45.6 g (247 mmol, 85%) of compound 2 as a colorless oil.

Step B: Na (12.7 g, 550 mmol) was dissolved in EtOH (200 mL). Compound 3 (37.5 g, 238 mmol) was added to the solution and the resulting mixture was stirred at room temperature for 0.5 h. Then compound 2 (45.6 g, 247 mmol) was added, the reaction was refluxed for 4 h, and then evaporated under reduced pressure. The residue was dissolved in water and neutralized with 10% HCl. The precipitated solid was filtered and re-crystallized from i-PrOH to yield 40.8 g (179 mmol, 75%) of compound 4 as white solid.

Step C: To a solution of compound 4 (0.150 g, 0.66 mmol) and DIPEA (0.256 g, 1.98 mmol) in acetonitrile corresponding sulfonyl chloride (0.99 mmol, 1.5 equiv.) was added. The resulting mixture was stirred under reflux for 2 h and then evaporated in vacuo. The residue was purified by HPLC to yield the target compounds 5.

Step D: To a solution of compound 4 (0.150 g, 0.66 mmol) and DIPEA (0.256 g, 1.98 mmol) in acetonitrile the corresponding acid chloride was added (1.3-4 eq.). The resulting mixture was stirred under reflux for 3 h and then evaporated in vacuo. The residue was purified by HPLC to yield the target amides 6.

Thieno-Oxypyrimidine Synthesis

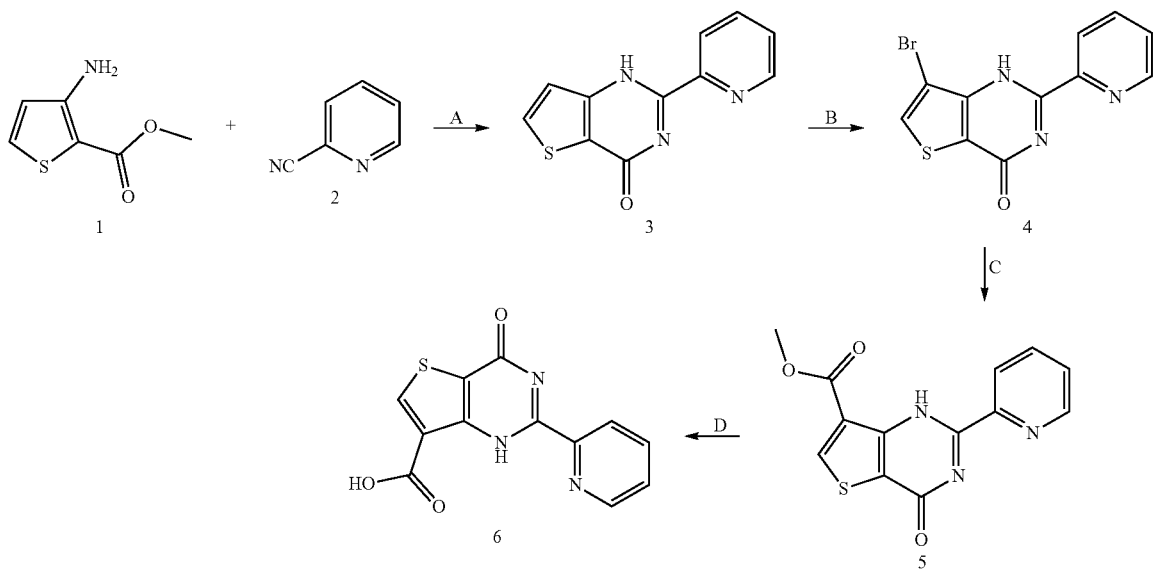

Step A: To a solution compound 1 (30 g, 0.19 mol) in 300 mL dioxane HCl was added compound 2 (23.85 g, 0.23 mol). The reaction mixture was stirred at rt overnight, diluted dioxane (300 mL), refluxed for 3 h, cooled and evaporated. The resulting residue was washed by mixture EtOAc-iPrOH (1:2). The yield was 36 g (0.157 mol, 83%).

Step B: To a solution compound 3 (36 g, 0.157 mol) in 650 mL acetic acid bromine (35 mL) was added at rt. The reaction mixture was refluxed 48 h, cooled, evaporated, diluted with water. The resulting precipitate was filtered, washed with water and dried. The yield was 45 g (0.146 mol, 93%).

Step C: The mixture compound 4 (35 g, 0.114 mol) and 1,1′-Bis(diphenylphosphino)ferrocene]dichloropalladium (II) complex with dichloromethane CAS95464054 (2% mol) in methanol (500 ml) was stirred overnight under CO (10 bar) in autoclave. The reaction mixture was filtered and evaporated. The resulting residue was washed with water and dried. The yield was 26 g (0.091 mol, 80%).

Step D: Compound 5 (16 g, 0.055 mol) was added to a solution NaOH (21 g, 0.525 mol) in 600 mL methanol. The reaction mixture was refluxed overnight, evaporated. The solid residue was washed by water and air-dried. The yield was 12.7 g (0.046 mol, 84%).

The resulting residue was filtered off, washed by water and dried under high vacuum. If there was no residue formed the aqueous solution was extracted by 4 mL of DCM and the organic layer was washed by water (2*4 mL) and the solvent was removed under reduced pressure. In case of low purity of the final compound was subjected to preparative HPLC purification.

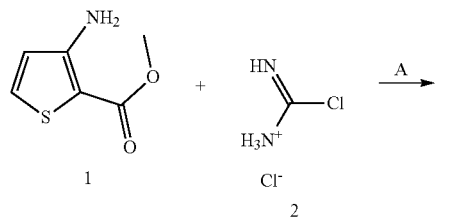
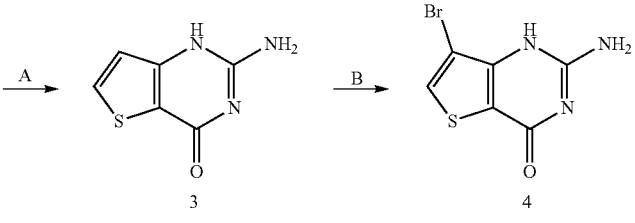

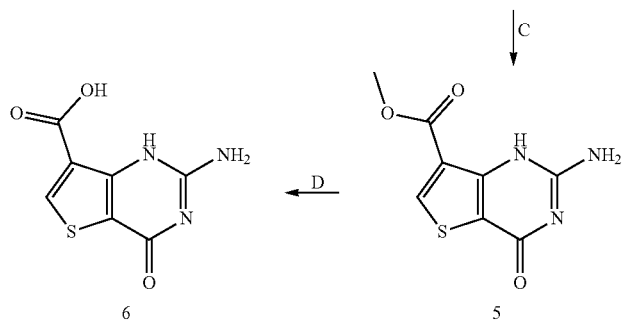
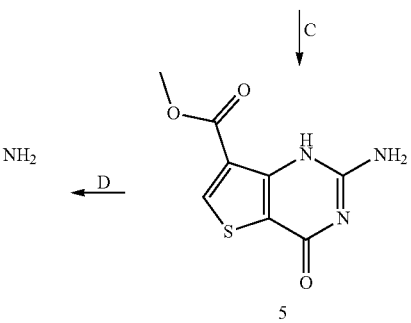

Step A: The mixture of compound 1 (50 g, 0.318 mol), compound 2 (54.86 g, 0.477 mol) and methylsulfonylmethane (150.6 g, 1.59 mol) was refluxed overnight, cooled and evaporated. The resulting residue was washed mixture EtOAc-iPrOH (1:2). The yield was 41.65 g (0.249 mol, 78%).

Step B: To a solution compound 3 (41.65 g, 0.249 mol) in 700 mL acetic acid was added bromine (42 mL) at rt. The reaction mixture was refluxed 48 h, cooled, evaporated, diluted with water. The resulting precipitate was filtered, washed with water and dried. The yield was 51 g (0.207 mol, 83%).

Step C: The mixture of compound 4 (35 g, 0.142 mol) and 1,1'-Bis(diphenylphosphino)ferrocene]dichloropalladium (II) complex with dichloromethane CAS95464054 (2% mol) in methanol (500 ml) was stirred overnight under CO (10 bar) in autoclave. The reaction mixture was filtered and evaporated. The resulting residue was washed with water and dried. The yield was 28 g (0.124 mol, 88%).

Step D: Compound 5 (15 g, 0.067 mol) was added to a solution of NaOH (20 g, 0.5 mol) in 600 mL methanol. The reaction mixture was refluxed overnight, evaporated. The solid residue was washed by water and air-dried. The yield was 11.2 g (0.053 mol, 79%).

Amide synthesis from compound 6: The mixture of 1.1 eq of acid 6 and 1 eq of corresponding amine was dissolved in 1 ml of HOBt solution in DMF (9.5% wt). Then 1.2 eq of EDC was added and reaction mixture was left stirring at rt overnight (16-18 h). After completion of the reaction, monitored by LCMS, the reaction mixture was diluted with 4 mL of distilled water and left at ultrasonic bath for 30-40 min.

Purification and Analytical Procedures:

Purification was performed using HPLC ($H_2O$-MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the $N_2$ flow upon heating to 80° C. On the basis of post-chromatography LCMS analysis fractions were united. Solid fractions were dissolved in 0.5 mL MeOH and transferred into a pre-weighted marked vials. Obtained solutions were again evaporated under the $N_2$ flow upon heating to 80° C. After drying, products were finally characterized by LCMS and $^1$H NMR.

NMR Instrument specifications: Bruker AVANCE DRX 500, Varian UNITYplus 400.

LC/MS Instrument specifications: Agilent 1100 Series LC/MSD system with DAD\ELSD and Agilent LC\MSD VL (G1956A), SL (G1956B) mass-spectrometer. Agilent 1200 Series LC/MSD system with DAD\ELSD and Agilent LC\MSD SL (G6130A), SL (G6140A) mass-spectrometer. All the LC/MS data were obtained using positive/negative mode switching. Column Zorbax SB-C18 1.8 μm 4.6×15 mm Rapid Resolution cartridge (PN 821975-932) Mobile phase A—acetonitrile, 0.1% formic acid, B—water (0.1% formic acid) Flow rate 3 ml/min Gradient 0 min—100% B, 0.01 min—100% B, 1.5 min—0% B, 1.8 min—0% B, 1.81 min—100% B. Injection volume 1 μl. Ionization mode atmospheric pressure chemical ionization (APCI). Scan range m/z 80-1000

TABLE 1
| | Mass Spectral Data | | |
|---|---|---|---|
| Compound | MW | M + H (calculated) | M + H (observed) |
| 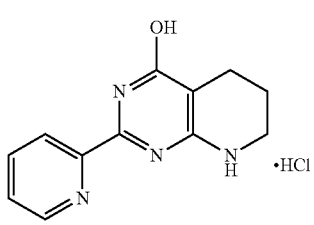 [SMILES: Oc1nc(-c2ccccn2)nc2c1CCCN2 ; Cl] •HCl | 265 | 229.1 | 229.2 |
| 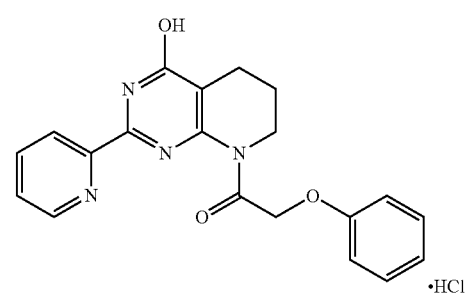 [SMILES: O=C(COc1ccccc1)N1CCCc2c(O)nc(-c3ccccn3)nc21 ; Cl] •HCl | 399 | 363.1 | 363.0 |
| 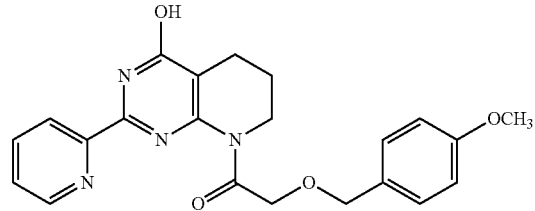 [SMILES: COc1ccc(COCC(=O)N2CCCc3c(O)nc(-c4ccccn4)nc32)cc1] | 406 | 407.2 | 407.2 |
| 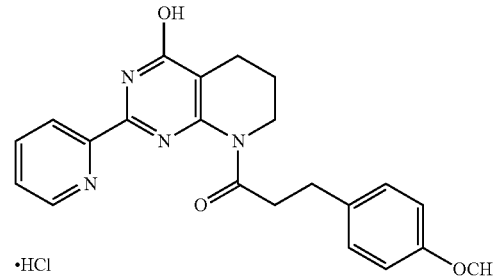 •HCl | 427 | 391.2 | 391.2 |
| 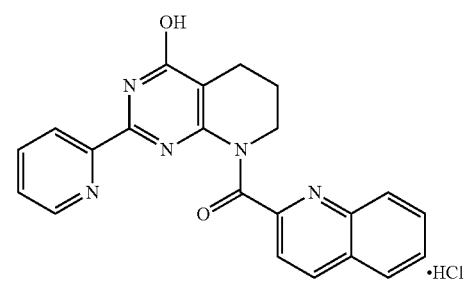 [SMILES: O=C(c1ccc2ccccc2n1)N1CCCc2c(O)nc(-c3ccccn3)nc21 ; Cl] •HCl | 420 | 384.2 | 384.0 |

TABLE 1-continued

| Mass Spectral Data | | | |
|---|---|---|---|
| Compound | MW | M + H (calculated) | M + H (observed) |
| (2-(pyridin-2-yl)-8-(2,3-dihydrobenzofuran-5-carbonyl)-5,6,7,8-tetrahydropyrido[2,3-d]pyrimidin-4-ol · HCl) | 411 | 375.2 | 375.1 |
| (2-(pyridin-2-yl)-8-(1-phenyl-1H-pyrazole-3-carbonyl)-5,6,7,8-tetrahydropyrido[2,3-d]pyrimidin-4-ol · HCl) | 435 | 399.2 | 399.2 |
| (2-(pyridin-2-yl)-8-(4-methoxybutanoyl)-5,6,7,8-tetrahydropyrido[2,3-d]pyrimidin-4-ol) | 328 | 329.2 | 329.2 |
| (2-(pyridin-2-yl)-8-(oxazole-4-carbonyl)-5,6,7,8-tetrahydropyrido[2,3-d]pyrimidin-4-ol) | 323 | 324.1 | 324.2 |
| (2-(pyridin-2-yl)-8-(4-(methylsulfonyl)butanoyl)-5,6,7,8-tetrahydropyrido[2,3-d]pyrimidin-4-ol) | 376 | 377.1 | 377.2 |

TABLE 1-continued
Mass Spectral Data
| Compound | MW | M + H (calculated) | M + H (observed) |
|---|---|---|---|
| 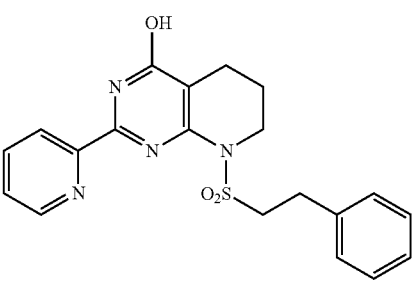 [SMILES: O=S(=O)(CCc1ccccc1)N1CCCc2c(O)nc(-c3ccccn3)nc21] | 396 | 397.1 | 397.2 |
| 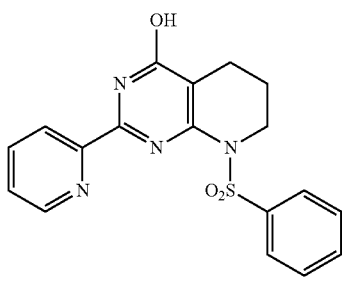 [SMILES: O=S(=O)(c1ccccc1)N1CCCc2c(O)nc(-c3ccccn3)nc21] | 368 | 369.1 | 369.2 |
| 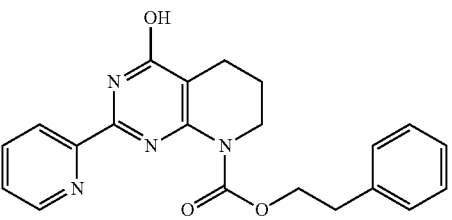 [SMILES: O=C(OCCc1ccccc1)N1CCCc2c(O)nc(-c3ccccn3)nc21] | 376 | 377.2 | 377.2 |
| 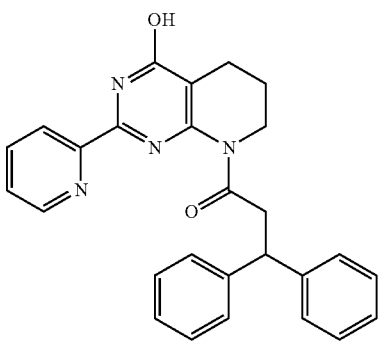 [SMILES: O=C(CC(c1ccccc1)c1ccccc1)N1CCCc2c(O)nc(-c3ccccn3)nc21] | 437 | 437.2 | 437.1 |
| 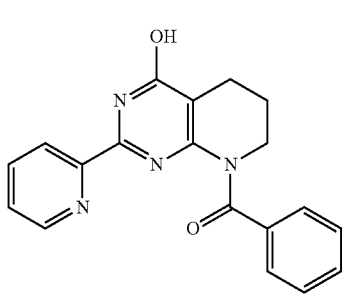 [SMILES: O=C(c1ccccc1)N1CCCc2c(O)nc(-c3ccccn3)nc21] | 332 | 333.1 | 333.2 |

TABLE 1-continued

Mass Spectral Data

| Compound | MW | M + H (calculated) | M + H (observed) |
|---|---|---|---|
| (structure) | 333 | 334.1 | 334.0 |
| (structure) | 375 | 376.2 | 376.2 |
| (structure) | 246 | 245.9 | 246.0 |
| (structure) | 292 | 293.1 | 293.0 |
| (structure) | 322 | 323.1 | 323.0 |
| (structure) | 350 | 351.1 | 351.0 |

TABLE 1-continued

Mass Spectral Data

| Compound | MW | M + H (calculated) | M + H (observed) |
|---|---|---|---|
| 2-amino-7-(4-(3-methoxypropyl)piperidine-1-carbonyl)thieno[3,2-d]pyrimidin-4-ol | 350 | 351.2 | 351.2 |
| 2-amino-7-(4-morpholinopiperidine-1-carbonyl)thieno[3,2-d]pyrimidin-4-ol | 363 | 364.1 | 364.2 |
| 2-amino-7-(4-(2-oxopyrrolidin-1-yl)piperidine-1-carbonyl)thieno[3,2-d]pyrimidin-4-ol | 361 | 362.1 | 362.2 |
| 2-amino-7-(4-phenylpiperazine-1-carbonyl)thieno[3,2-d]pyrimidin-4-ol | 355 | 356.1 | 356.1 |
| 2-amino-7-(4-(pyridin-4-yl)piperazine-1-carbonyl)thieno[3,2-d]pyrimidin-4-ol | 356 | 357.1 | 357 |

TABLE 1-continued
Mass Spectral Data
| Compound | MW | M + H (calculated) | M + H (observed) |
|---|---|---|---|
| 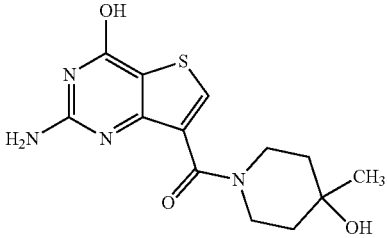 [SMILES: CC1(O)CCN(C(=O)c2csc3c(O)nc(N)nc23)CC1] | 308 | 309.1 | 309.0 |
| 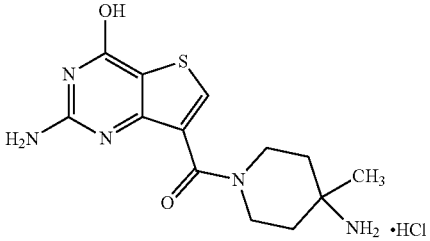 [SMILES: CC1(N)CCN(C(=O)c2csc3c(O)nc(N)nc23)CC1 ; Cl] | 344 | 308.1 | 308.2 |
| 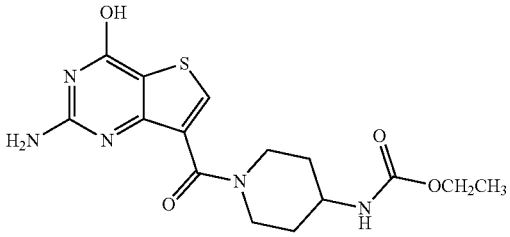 [SMILES: CCOC(=O)NC1CCN(C(=O)c2csc3c(O)nc(N)nc23)CC1] | 365 | 366.1 | 366.0 |
| 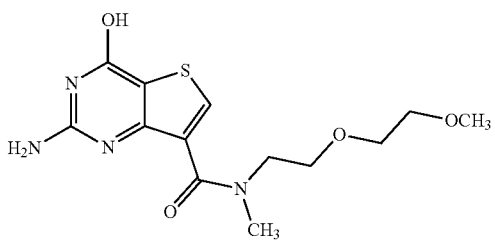 [SMILES: COCCOCCN(C)C(=O)c1csc2c(O)nc(N)nc12] | 326 | 327.1 | 327.0 |
| 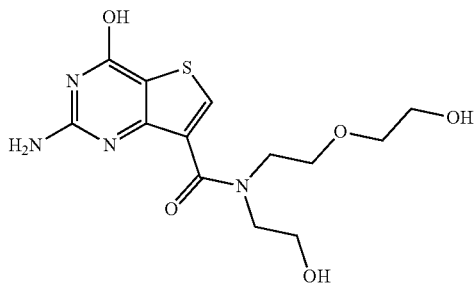 [SMILES: Nc1nc(O)c2scc(C(=O)N(CCO)CCOCCO)c2n1] | 342 | 343.1 | 343.2 |
| 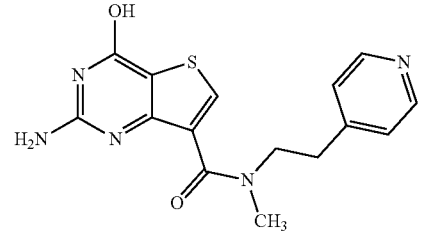 [SMILES: CN(CCc1ccncc1)C(=O)c1csc2c(O)nc(N)nc12] | 329 | 330.1 | 330.2 |

TABLE 1-continued

Mass Spectral Data

| Compound | MW | M + H (calculated) | M + H (observed) |
|---|---|---|---|
| (structure) | 315 | 316.1 | 316.0 |
| (structure) | 340 | 341.1 | 341.2 |
| (structure) | 400 | 401.1 | 401.0 |
| (structure) | 308 | 307.9 | 308.0 |
| (structure) | 354 | 355.1 | 355.2 |
| (structure) | 384 | 385.1 | 385.0 |

TABLE 1-continued

Mass Spectral Data

| Compound | MW | M + H (calculated) | M + H (observed) |
|---|---|---|---|
| | 413 | 413.2 | 413.2 |
| | 413 | 413.2 | 413.2 |
| | 426 | 426.2 | 426.0 |
| | 423 | 424.2 | 424.2 |
| | 417 | 418.1 | 418.2 |

TABLE 1-continued

Mass Spectral Data

| Compound | MW | M + H (calculated) | M + H (observed) |
|---|---|---|---|
| | 418 | 419.1 | 419.0 |
| | 417 | 418.1 | 418.02 |
| | 370 | 371.1 | 371.0 |
| | 442 | 370.1 | 370.2 |
| | 427 | 428.1 | 428.0 |
| | 388 | 389.1 | 389.2 |

TABLE 1-continued

Mass Spectral Data

| Compound | MW | M + H (calculated) | M + H (observed) |
|---|---|---|---|
| | 404 | 405.1 | 405.0 |
| | 391 | 392.1 | 392.2 |
| | 377 | 378.1 | 378.2 |
| | 402 | 403.1 | 403.0 |
| | 463 | 463.2 | 463.2 |

TABLE 1-continued

| Mass Spectral Data | | | |
|---|---|---|---|
| Compound | MW | M + H (calculated) | M + H (observed) |
| 2-amino-7-phenyl-thieno[3,2-d]pyrimidin-4-ol | 243 | 244.3 | 244.0 |
| 2-amino-7-(2-chlorophenyl)-thieno[3,2-d]pyrimidin-4-ol | 278 | 278.0 | 278.0 |
| 7-phenyl-2-(pyridin-2-yl)-thieno[3,2-d]pyrimidin-4-ol | 305 | 306.1 | 306.0 |
| 7-(2-chlorophenyl)-2-(pyridin-2-yl)-thieno[3,2-d]pyrimidin-4-ol | 340 | 340.0 | 339.9 |
| 9-phenyl-2-(pyridin-2-yl)-9H-purin-6-ol | 289 | 290.1 | 290.2 |

TABLE 1-continued
Mass Spectral Data
| Compound | MW | M + H (calculated) | M + H (observed) |
|---|---|---|---|
| 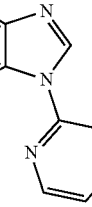 | 290 | 291.1 | 291.0 |
| 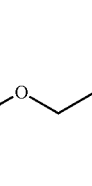 | 351 | 352.1 | 352.2 |
| 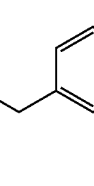 | 315 | 316.1 | 316.0 |
| 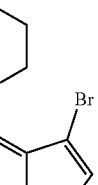 | 377 | 377.0 | 377.0 |
| 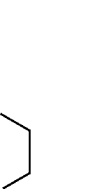 | 298 | 299.1 | 299.1 |
| 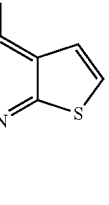 | 308 | 307.9 | 308.0 |

TABLE 1-continued

Mass Spectral Data

| Compound | MW | M + H (calculated) | M + H (observed) |
|---|---|---|---|
| 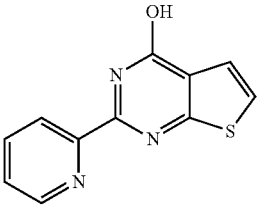 [SMILES: Oc1nc(-c2ccccn2)nc2sccc12] | 229 | 230.0 | 230.0 |
| 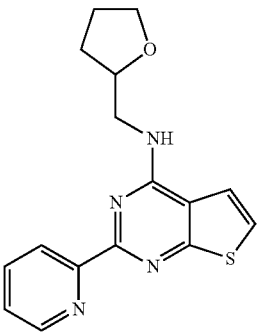 [SMILES: c1ccc(-c2nc(NCC3CCCO3)c3ccsc3n2)nc1] | 312 | 313.1 | 313.0 |
| 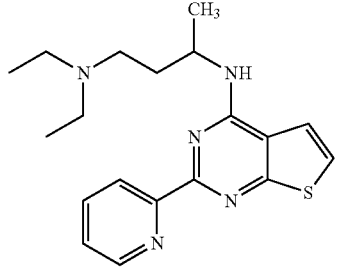 [SMILES: CCN(CC)CCC(C)Nc1nc(-c2ccccn2)nc2sccc12] | 356 | 356.2 | 356.2 |

6. Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans. In some embodiments, the active compound is administered in a method to achieve a therapeutically effective concentration of the drug. In some embodiments, a companion diagnostic (see, e.g., Olsen D and Jorgensen J T, *Front. Oncol.,* 2014 May 16, 4:105, doi: 10.3389/fonc.2014.00105) is used to determine the therapeutic concentration and safety profile of the active compound in specific patients or patient populations.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 μg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil. In some embodiments, the suspension is a suspension of microparticles or nanoparticles. In some embodiments, the emulsion is an emulsion of microparticles or nanoparticles.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. In some embodiments, the suspension is a suspension of microparticles or nanoparticles. In some embodiments, the emulsion is an emulsion of microparticles or nanoparticles. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Targeted Formulations

The compounds provided herein, or pharmaceutically acceptable salts thereof, may also be formulated to be targeted to a particular tissue, receptor, or other area of the body of the subject to be treated, including liposome-, resealed erythrocyte-, and antibody-based delivery systems. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, the antibody-based delivery system is an antibody-drug conjugate ("ADC"), e.g., as described in Hamilton G S, *Biologicals*, 2015 September, 43(5):318-32; Kim E G and Kim K M, *Biomol. Ther. (Seoul)*, 2015 November, 23(6):493-509; and Peters C and Brown S, *Biosci. Rep.*, 2015 Jun. 12, 35(4) pii: e00225, each of which is incorporated herein by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms or progression of a disease or disorder disclosed herein, and a label that indicates that the compound or pharmaceutically acceptable salt thereof is used for treatment, prevention or amelioration of one or more symptoms or progression of a disease or disorder disclosed herein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

7. Methods of Treatment 7.1 Cancer

In one embodiment, provided herein is a method of treating or preventing cancer, which comprises administering to a patient a compound provided herein, or a derivative thereof.

In another embodiment, provided herein is method of managing cancer, which comprises administering to a patient a compound provided herein, or a derivative thereof.

Also provided herein are methods of treating patients who have been previously treated for cancer but are non-responsive to standard therapies, as well as those who have not previously been treated. Also provided are methods of treating patients regardless of patient's age, although some diseases or disorders are more common in certain age groups. Also provided are methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, pancreatic cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound provided herein or a derivative thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant [M3V]). In one embodiment, the acute myeloid leukemia is myelomonocytic leukemia (M4 or M4 variant with eosinophilia [M4E]). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or a derivative thereof effective to treat, prevent or manage acute myeloid leukemia alone or in combination. In some embodiments, the methods comprise the step of administering to the subject a compound provided herein or a derivative thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or a derivative thereof effective to treat, prevent or manage acute lymphocytic leukemia alone or in combination with a second active agent. In some embodiments, the methods comprise the step of administering to the subject a compound provided herein or a derivative thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or a derivative thereof effective to treat, prevent or manage chronic myelogenous leukemia. In some embodiments, the methods comprise the step of administering to the subject a compound provided herein or a derivative thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or a derivative thereof effective to treat, prevent or manage chronic lymphocytic leukemia. In some embodiments, the methods comprise the step of administering to the subject a compound provided herein or a derivative thereof in combination with a second active agent in amounts effective to treat, prevent or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a compound provided herein, or a derivative thereof to a patient having relapsed/refractory multiple myeloma with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m²/day. One of ordinary skill in the art would readily know how to convert doses from mg/kg/day to mg/m²/day to given either the height or weight of a subject or both (see, www.fda.gov/cder/cancer/animalframe.htm). For example, a dose of 1 mg/kg/day for a 65 kg human is approximately equal to 38 mg/m²/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the compound provided herein, or a derivative thereof. In certain embodiments, the patient to be treated with one of the methods provided herein has been treated with anticancer therapy prior to the administration of the compound provided herein, or a derivative thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancer described herein.

In one embodiment, provided herein is a method of treating, preventing, or managing cancer, comprising administering to a patient a compound provided herein, or a derivative thereof; in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the patient.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/ day, from about 50 to about 250 mg/m²/day, or from about 50 to about 200 mg/m²/day. In certain embodiments, GM-CSF may be administered in an amount of from about 60 to about 500 mcg/m² intravenously over 2 hours or from about 5 to about 12 mcg/m²/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, CA); sargramostim, which is sold in the United States under the trade name Leukine® (Immunex, Seattle, WA); and recombinant EPO, which is sold in the United States under the trade name Epogen® (Amgen, Thousand Oaks, CA).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a compound provided herein, or a derivative thereof, of are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with a compound provided herein, or a derivative thereof, include monoclonal and polyclonal antibodies. Examples of antibodies include, but are not limited to, trastuzumab (Herceptin®), rituximab (Rituxan®), bevacizumab (Avastin™) pertuzumab (Omnitarg™), tositumomab (Bexxar®), edrecolomab (Panorex®), and G250. The compounds provided herein or an enantiomer or a mixture of enantiomers thereof, or a pharmaceutically acceptable salt, solvate, hydrate, co-crystal, clathrate, or polymorph thereof can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of a compound provided herein, or a derivative thereof. However, like some large molecules, many are believed to be capable of providing a synergistic effect when administered with (e.g., before, after or simultaneously) a compound provided herein, or a derivative thereof. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitior or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a compound provided herein, or a derivative thereof, may be modified or delayed during or shortly following administration of a compound provided herein, or a derivative thereof, as deemed appropriate by the practitioner of skill in the art. In certain embodiments, subjects being administered a compound provided herein, or a derivative thereof, alone or in combination with other therapies may receive supportive care including antiemetics, myeloid growth factors, and transfusions of platelets, when appropriate. In some embodiments, subjects being administered a compound provided herein, or a derivative thereof, may be administered a growth factor as a second active agent according to the judgment of the practitioner of skill in the art. In some embodiments, provided is administration of a compound provided herein, or a derivative thereof, in combination with erythropoietin or darbepoetin (Aranesp).

In certain embodiments, a compound provided herein, or a derivative thereof, is administered with gemcitabine and cisplatinum to patients with locally advanced or metastatic transitional cell bladder cancer.

In certain embodiments, a compound provided herein, or a derivative thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, or a derivative thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, or a derivative thereof, is administered with temozolomide to patients with neuroendocrine tumors.

In certain embodiments, a compound provided herein, or a derivative thereof, is administered with gemcitabine to patients with recurrent or metastatic head or neck cancer.

In certain embodiments, a compound provided herein, or a derivative thereof, is administered with gemcitabine to patients with pancreatic cancer.

In certain embodiments, a compound provided herein, or a derivative thereof, is administered to patients with colon cancer in combination with ARISA®, avastatin, taxol, and/or taxotere.

In certain embodiments, a compound provided herein, or a derivative thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, or a derivative thereof, is administered in combination with fluorouracil, leucovorin, and irinotecan to patients with Dukes C & D colorectal cancer or to patients who have been previously treated for metastatic colorectal cancer.

In certain embodiments, a compound provided herein, or a derivative thereof, is administered to patients with refractory colorectal cancer in combination with capecitabine, xeloda, and/or CPT-11.

In certain embodiments, a compound provided herein, or a derivative thereof, is administered with capecitabine and irinotecan to patients with refractory colorectal cancer or to patients with unresectable or metastatic colorectal carcinoma.

In certain embodiments, a compound provided herein, or a derivative thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, or a derivative thereof, is administered in combination with pegylated interferon alpha to patients with Kaposi's sarcoma.

In certain embodiments, a compound provided herein, or a derivative thereof, is administered in combination with fludarabine, carboplatin, and/or topotecan to patients with refractory or relapsed or high-risk acute myeloid leukemia.

In certain embodiments, a compound provided herein, or a derivative thereof, is administered in combination with liposomal daunorubicin, topotecan and/or cytarabine to patients with unfavorable karotype acute myeloblastic leukemia.

In certain embodiments, a compound provided herein, or a derivative thereof, is administered in combination with gemcitabine, abraxane, erlotinib, geftinib, and/or irinotecan to patients with non-small cell lung cancer.

In certain embodiments, a compound provided herein, or a derivative thereof, is administered in combination with carboplatin and irinotecan to patients with non-small cell lung cancer.

In certain embodiments, a compound provided herein, or a derivative thereof, is administered with doxetaxol to patients with non-small cell lung cancer who have been previously treated with carbo/VP 16 and radiotherapy.

In certain embodiments, a compound provided herein, or a derivative thereof, is administered in combination with carboplatin and/or taxotere, or in combination with carboplatin, pacilitaxel and/or thoracic radiotherapy to patients with non-small cell lung cancer.

In certain embodiments, a compound provided herein, or a derivative thereof, is administered in combination with taxotere to patients with stage IIIB or IV non-small cell lung cancer.

In certain embodiments, a compound provided herein, or a derivative thereof, is administered in combination with oblimersen (Genasense®) to patients with small cell lung cancer.

In certain embodiments, a compound provided herein, or a derivative thereof, is administered in combination with ABT-737 (Abbott Laboratories) and/or obatoclax (GX15-070) to patients with lymphoma and other blood cancers.

In certain embodiments, a compound provided herein, or a derivative thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, or a derivative thereof, is administered in combination with taxotere, IL-2, IFN, GM-CSF, PLX4032 (Plexxikon) and/or dacarbazine to patients with various types or stages of melanoma.

In certain embodiments, a compound provided herein, or a derivative thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, or a derivative thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, or a derivative thereof, is administered to patients with relapsed or refractory multiple myeloma in combination with doxorubicin (Doxil®), vincristine and/or dexamethasone (Decadron®).

In certain embodiments, a compound provided herein, or a derivative thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, or a derivative thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, or a derivative thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, or a derivative thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, or a derivative thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, or a derivative thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) a compound provided herein, or a derivative thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, or a derivative thereof, alleviates or reduces adverse effects which are of such severity that it would otherwise limit the amount of anti-cancer drug.

In one embodiment, a compound provided herein, or a derivative thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, or a derivative thereof, is administered in combination with specific agents such as heparin, aspirin, coumadin, or G CSF to avoid adverse effects that are associated with anti-cancer drugs such as but not limited to neutropenia or thrombocytopenia.

In one embodiment, a compound provided herein, or a derivative thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound provided herein, or a derivative thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein, or a derivative thereof, and conventional therapy may provide a unique treatment regimen that is unexpectedly effective in certain patients. Without being limited by theory, it is believed that the compound provided herein, or a derivative thereof, may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, or a derivative thereof, and other active ingredient can be administered to a patient prior to, during, or after the occurrence of the adverse effect associated with conventional therapy.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

In certain embodiments, a compound provided herein, or a derivative thereof, and doxetaxol are administered to patients with non-small cell lung cancer who were previously treated with carbo/VP 16 and radiotherapy.

In certain embodiments, a compound provided herein, or a derivative thereof, is administered to patients with various types or stages of cancer, in combination with an immune oncology drug or a combination of immune oncology drugs. In one embodiment, a compound provided herein, or a derivative thereof, is administered to patients with various types or stages of cancer, in combination with Opdivo, Keytruda, Yervoy or a combination thereof.

7.2 Inflammation

As discussed herein, activation of MAPKs is a component of the inflammatory response. Thus, the compounds provided herein, which are MAPK inhibitors, are useful in the treatment of inflammatory diseases.

In one embodiment, the inflammatory disease is inflammation-associated cancer development. As disclosed here, the compounds provided herein are useful in treatment of cancer. It is well recognized that the immune inflammatory state serves as a key mediator of the middle stages of tumor development. It is also well known that chronic inflammation can predispose an individual to cancer. Chronic inflammation is caused by a variety of factors, including bacterial, viral, and parasitic infections. The longer the inflammation persists, the higher the risk of associated carcinogenesis. Anti-inflammatory cancer therapy prevents premalignant cells from turning fully cancerous or impede existing tumors from spreading to distant sites in the body. Thus, in one embodiment, the compounds provided herein are useful in treating inflammatory cancers. Such cancers, and the chronic inflammatory conditions that predispose susceptible cells to neoplastic transformation, include gastric adenocarcinoma (gastritis), mucosa-associated lymphoid tissue (MALT) lymphoma (gastritis), bladder, liver and rectal carcinomas (schistosomiasis), cholangiocarcinoma and colon carcinoma (cholangitis), gall bladder cncer (chronic cholecystitis), ovarian and cervical carcinoma (pelvic inflammatory disease, chronic cervicitis), skin carcinoma (osteomyelitis), colorectal carcinoma (inflammatory bowel disease), esophageal carcinoma (reflux esophagitis, Barrett's esophagus), bladder cancer (bladder inflammation (cystitis)), mesothelioma and lung carcinoma (asbestosis, silicosis), oral squamous cell carcinoma (gingivitis, lichen planus), pancreatic carcinoma (pancreatitis, protease mutation), vulvar squamous cell carcinoma (lichen sclerosis), salivary gland carcinoma (slaladenitis), lung carcinoma (bronchitis) and MALT lymphoma (Sjogren syndrome, Hashimoto's thyroiditis). Shacter, et al., 2002, Oncology, 16(2), 217-26.

In certain embodiments, the compounds provided herein are useful in treating inflammatory diseases in the airways, such as nonspecific bronchial hyper-reactivity, chronic bronchitis, cystic fibrosis, and acute respiratory distress syndrome (ARDS).

In certain embodiments, the compounds provided herein are useful in treating asthma and idiopathic lung fibrosis or idiopathic pulmonary fibrosis (IPF), pulmonary fibrosis, and interstitial lung disease. As known to one of skill in the art, the differentiation of fibroblasts into cell types called myofibroblasts occurs during wound healing, when the cells contribute to the deposition of extracellular matrix (ECM) in the transient process of wound repair. In chronic inflammatory diseases such as asthma, pathological tissue remodeling often occurs, and is mediated by the functions of increased numbers of myofibroblasts in the diseased tissue, see Hinz, B. et al. Am J Pathol. 2007; 170: 1807-1816. In certain embodiments, the compounds provided herein prevent or reduce TGF-β-induced myofibroblast differentiation, as measured by the expression of alpha smooth muscle actin (α-SMA), a hallmark of myofibroblast differentiation (Serini, G. and Gabbiani, G. 1999; Exp. Cell Res. 250: 273-283).

In certain embodiments, the compounds provided herein are useful in treating psoriasis, chronic plaque psoriasis, psoriatic arthritis, acanthosis, atopic dermatitis, various forms of eczema, contact dermatitis (includes allergic dermatitis), systemic sclerosis (scleroderma), wound healing, and drug eruption.

In one embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, eczema, Sjögren's syndrome, burns, dermatitis, neuroinflammation, allergy pain, autoimmune myositis, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, acute gout, pneumonitis, myocarditis, pericarditis, myositis, eczema, alopecia, vitiligo, bullous skin diseases, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs. endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, postsurgical syndromes, sarcoidosis, Herxheimer reactions, encephalitis, myelitis, SIRS associated with viral infections such as influenza, herpes zoster, herpes simplex, coronavirus or dry eye syndrome (or keratoconjunctivitis sicca (KCS)).

In certain embodiments, the compounds provided herein are useful in treating neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

In certain embodiments, the compounds provided herein are useful in treating Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury.

When used for the treatment of inflammatory disease, the compounds provided herein may be administered in dosages, routes of administration and/or to achieve pK profiles as described herein for the treatment of cancer.

8. EXAMPLES

The following examples are offered to illustrate but not to limit the disclosure.

Example 1

Protocol for MAPK Cell-Based Phosphorylation Assay

Cell lines: Tumor-derived pancreatic cancer cell lines PANC-1 were purchased from ATCC and were maintained according to ATCC recommendation.

Method: Cells were plated at 7500 cells/well density in 96-wells plate, starved ON, and the small molecules to be tested were added to the cells in the final concentration of 30 µM with 0.3% DMSO for 6 hours incubation at 37° C. Next, cells were stimulated with 1.5 ng/ml EGF for 15 min. followed by cell fixation with 4% Formaldehyde in PBS at RT for 20 min. Phosphorylation level of MAPK was determined by Cell-direct ELISA.

Cell-direct ELISA: For each well, cells were permeabilized with PBS-Triton 0.1%, quenched with $H_2O_2$ 0.6% in PBS-Triton 0.1%, and probed with anti-phospho-MAPK antibodies (R&D Systems) followed by HRP-conjugated secondary antibody (Jackson Immunoresearch, West Grove, PA). Next, a solution 50 µM of the fluorescent substrate AmpliFlu Red (Sigma) was added and incubated at RT for 20 min. At the end of the incubation time, fluorescence was measured at 595 nm on a microplate reader (AF2200; Eppendorf, Inc., Hamburg, Germany).

Table 2 shows inhibition data for selected compounds tested in the cellular assay described above.

TABLE 2

| % Inhibition of MAPK phosphorylation @ 30 µM in the PANC-1 pancreatic cancer cell line | |
|---|---|
| Compound | PANC-1 |
| 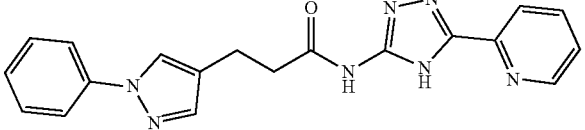 | B |
| 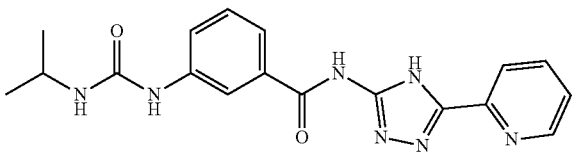 [SMILES: CC(C)NC(=O)Nc1cccc(C(=O)Nc2nnc(-c3ccccn3)[nH]2)c1] | A |
| 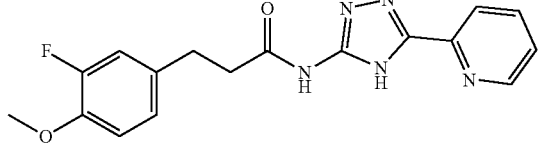 | C |
| 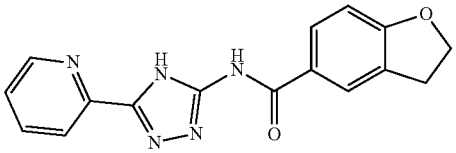 [SMILES: O=C(Nc1nnc(-c2ccccn2)[nH]1)c1ccc2c(c1)CCO2] | A |

TABLE 2-continued

% Inhibition of MAPK phosphorylation @ 30 μM in the PANC-1 pancreatic cancer cell line

| Compound | PANC-1 |
|---|---|
| (indol-3-yl-acetamide linked to 5-(pyridin-2-yl)-4H-1,2,4-triazol-3-amine) | C |
| (5,6,7,8-tetrahydro-3-phenylimidazo[1,5-a]pyridine-6-carboxamide linked to 5-(pyridin-2-yl)-4H-1,2,4-triazol-3-amine) | A |
| (1-phenyl-1H-pyrazole-3-carboxamide linked to 5-(pyridin-2-yl)-4H-1,2,4-triazol-3-amine) | A |
| (1-(3-fluorophenyl)-1H-pyrazole-3-carboxamide linked to 5-(pyridin-2-yl)-4H-1,2,4-triazol-3-amine) | A |
| (2-(5-methoxy-1H-indol-1-yl)acetamide linked to 5-(pyridin-2-yl)-4H-1,2,4-triazol-3-amine) | A |
| (3-(1H-indol-3-yl)propanamide linked to 5-(pyridin-2-yl)-4H-1,2,4-triazol-3-amine) | B |

TABLE 2-continued

% Inhibition of MAPK phosphorylation @ 30 μM in the PANC-1 pancreatic cancer cell line

| Compound | PANC-1 |
|---|---|
| | A |
| | A |
| | A |
| | A |
| | A |
| | B |
| | A |
| | B |
| | A |

TABLE 2-continued

% Inhibition of MAPK phosphorylation @ 30 μM in the PANC-1 pancreatic cancer cell line

| Compound | PANC-1 |
|---|---|
| | A |
| | A |
| | C |
| | B |
| | A |
| | A |
| | C |
| | A |
| | A |

TABLE 2-continued

% Inhibition of MAPK phosphorylation @ 30 μM in the PANC-1 pancreatic cancer cell line

| Compound | PANC-1 |
|---|---|
| | A |
| | A |
| | A |
| | A |
| | B |
| | A |
| | A |

TABLE 2-continued
% Inhibition of MAPK phosphorylation @ 30 µM in the PANC-1 pancreatic cancer cell line
| Compound | PANC-1 |
|---|---|
| 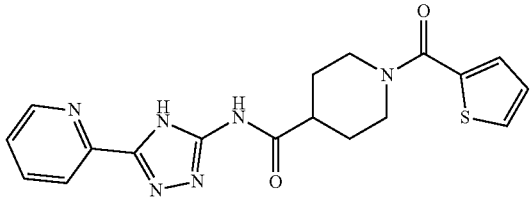 [SMILES: O=C(Nc1nnc(-c2ccccn2)[nH]1)C1CCN(C(=O)c2cccs2)CC1] | A |
| 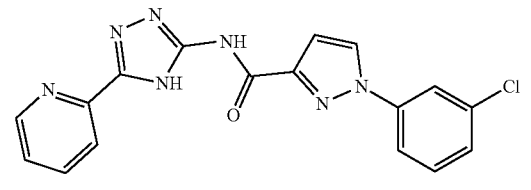 [SMILES: O=C(Nc1nnc(-c2ccccn2)[nH]1)c1ccn(-c2cccc(Cl)c2)n1] | B |
| 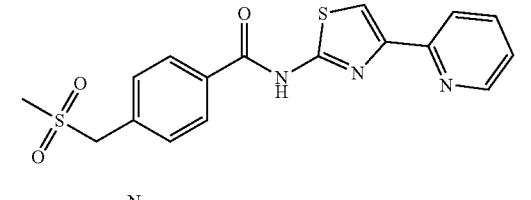 | A |
| 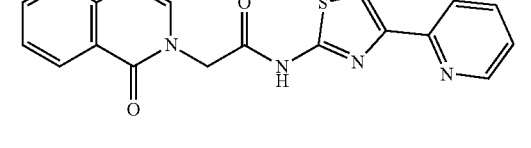 | A |
| 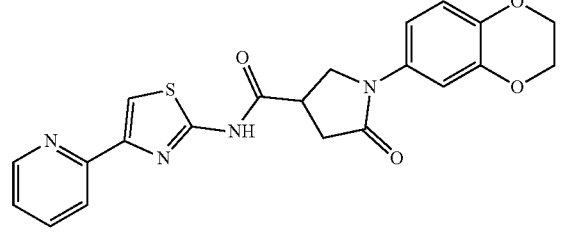 | B |
| 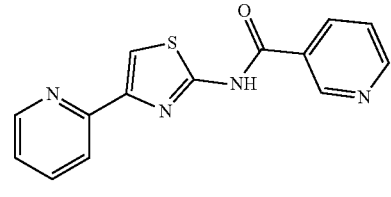 [SMILES: O=C(Nc1nc(-c2ccccn2)cs1)c1cccnc1] | A |
| 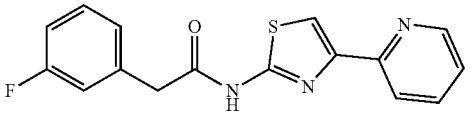 [SMILES: O=C(Cc1cccc(F)c1)Nc1nc(-c2ccccn2)cs1] | A |
| 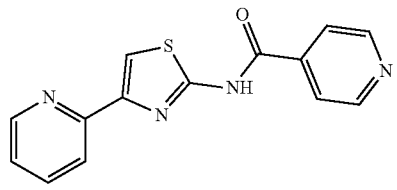 [SMILES: O=C(Nc1nc(-c2ccccn2)cs1)c1ccncc1] | B |

TABLE 2-continued

% Inhibition of MAPK phosphorylation @ 30 μM in the PANC-1 pancreatic cancer cell line

| Compound | PANC-1 |
|---|---|
| (4-fluoro-N-(4-(pyridin-2-yl)thiazol-2-yl)benzamide structure) | A |
| (2-(pyridin-2-yl)-5-(2-chlorophenyl)thieno[2,3-d]pyrimidin-4(3H)-one structure) | B |
| (2-(pyridin-2-yl)-6-phenylthieno[2,3-d]pyrimidin-4(3H)-one structure) | B |
| (2-(pyridin-2-yl)-benzothieno[3,2-d]pyrimidin-4(3H)-one structure) | D |
| (4-hydroxy-6-methyl-2-(pyridin-2-yl)pyrimidine propanamide with 4-isopropylphenyl structure) | A |
| (2-(pyridin-2-yl)-6-methyl-5-phenyl-4-((1-methoxypropan-2-yl)amino)thieno[2,3-d]pyrimidine structure) | D |

TABLE 2-continued

% Inhibition of MAPK phosphorylation @ 30 μM in the PANC-1 pancreatic cancer cell line

| Compound | PANC-1 |
|---|---|
| (4-cyanobenzoyl hydrazide linked to 6-ethyl-2-(pyridin-2-yl)pyrimidin-4-yl) | D |
| 2-(pyridin-2-yl)-5-phenyl-N-(2-hydroxypropyl)thieno[2,3-d]pyrimidin-4-amine | B |
| 2-(pyridin-2-yl)-6-methyl-5-phenyl-N-(3-hydroxypropyl)thieno[2,3-d]pyrimidin-4-amine | A |
| methyl 2-chloro-5-(((3-isobutyl-1,2,4-oxadiazol-5-yl)methyl)amino)benzoate | A |
| N-((1-methyl-1H-imidazol-2-yl)methyl)-N-(3-methylbenzyl)-1-(pyridin-2-yl)methanamine | B |

TABLE 2-continued
% Inhibition of MAPK phosphorylation @ 30 μM in the PANC-1 pancreatic cancer cell line
| Compound | PANC-1 |
|---|---|
| 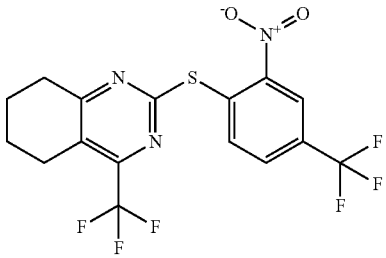 | A |
| 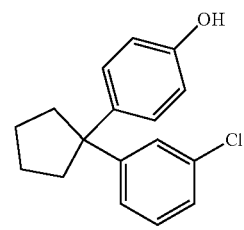 [SMILES: Oc1ccc(C2(c3cccc(Cl)c3)CCCC2)cc1] | D |
| 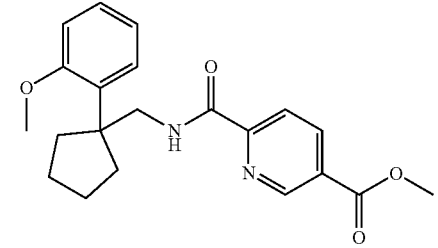 [SMILES: COC(=O)c1ccc(C(=O)NCC2(c3ccccc3OC)CCCC2)nc1] | A |
| 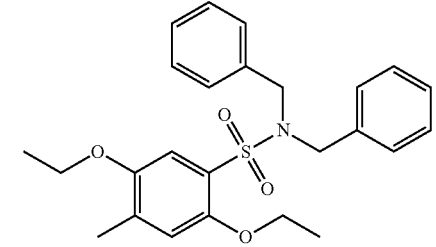 [SMILES: CCOc1cc(S(=O)(=O)N(Cc2ccccc2)Cc2ccccc2)c(OCC)cc1C] | A |
| 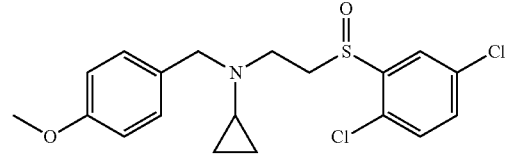 [SMILES: COc1ccc(CN(CCS(=O)c2cc(Cl)ccc2Cl)C2CC2)cc1] | B |
| 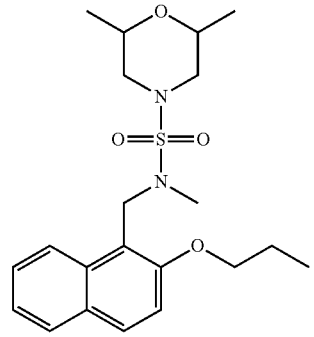 [SMILES: CCCOc1ccc2ccccc2c1CN(C)S(=O)(=O)N1CC(C)OC(C)C1] | A |

TABLE 2-continued

% Inhibition of MAPK phosphorylation @ 30 μM in the PANC-1 pancreatic cancer cell line

| Compound | PANC-1 |
|---|---|
| | A |
| | B |
| | A |
| | D |
| | A |

TABLE 2-continued
% Inhibition of MAPK phosphorylation @ 30 μM in the PANC-1 pancreatic cancer cell line
| Compound | PANC-1 |
|---|---|
| 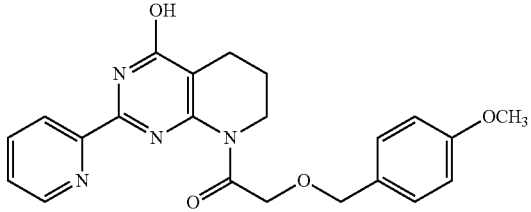 [SMILES: COc1ccc(COCC(=O)N2CCCc3c(O)nc(-c4ccccn4)nc32)cc1] | A |
| 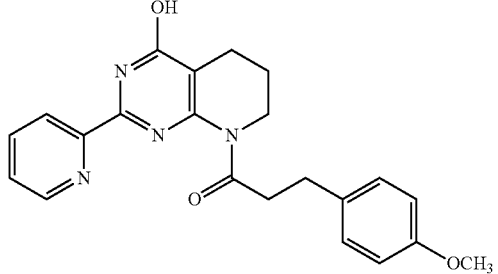 [SMILES: COc1ccc(CCC(=O)N2CCCc3c(O)nc(-c4ccccn4)nc32)cc1] | B |
| 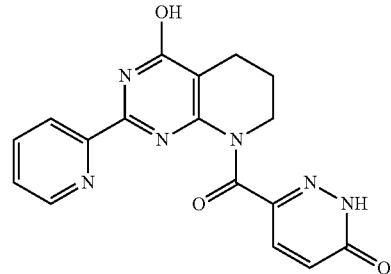 [SMILES: O=C(c1ccc(=O)[nH]n1)N1CCCc2c(O)nc(-c3ccccn3)nc21] | A |
| 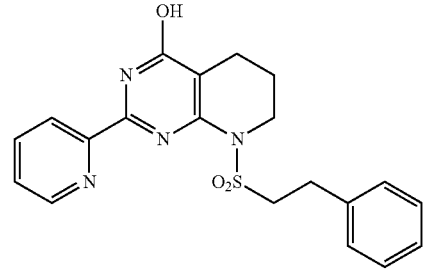 [SMILES: O=S(=O)(CCc1ccccc1)N1CCCc2c(O)nc(-c3ccccn3)nc21] | B |
| 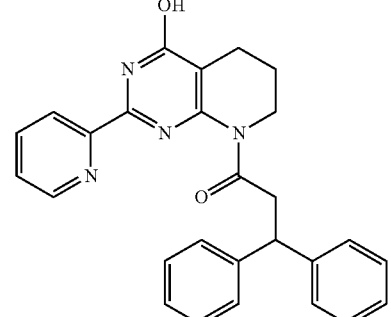 | A |

TABLE 2-continued

% Inhibition of MAPK phosphorylation @ 30 μM in the PANC-1 pancreatic cancer cell line

| Compound | PANC-1 |
|---|---|
| (structure) | A |
| (structure) | A |
| (structure) | D |
| (structure) | A |
| (structure) | A |
| (structure) | A |

TABLE 2-continued
% Inhibition of MAPK phosphorylation @ 30 μM in the PANC-1 pancreatic cancer cell line
| Compound | PANC-1 |
|---|---|
| 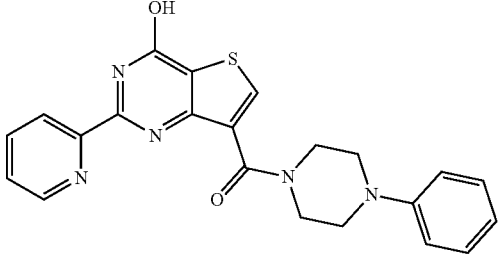 [SMILES: O=C(c1csc2c(O)nc(-c3ccccn3)nc12)N1CCN(c2ccccc2)CC1] | D |
| 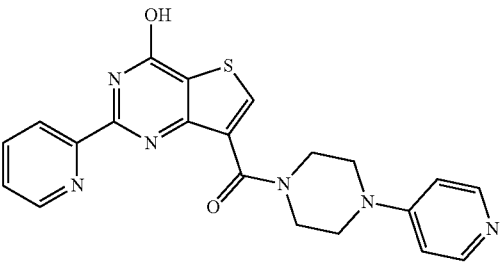 [SMILES: O=C(c1csc2c(O)nc(-c3ccccn3)nc12)N1CCN(c2ccncc2)CC1] | B |
| 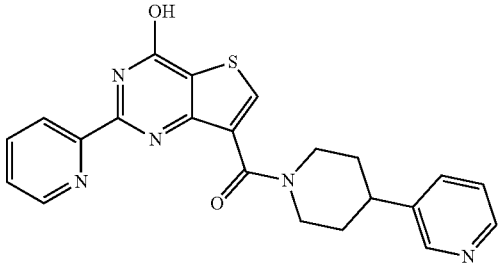 [SMILES: O=C(c1csc2c(O)nc(-c3ccccn3)nc12)N1CCC(c2cccnc2)CC1] | A |
| 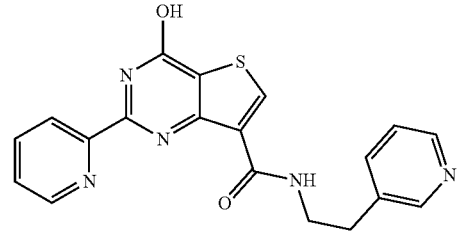 [SMILES: O=C(NCCc1cccnc1)c1csc2c(O)nc(-c3ccccn3)nc12] | A |
| 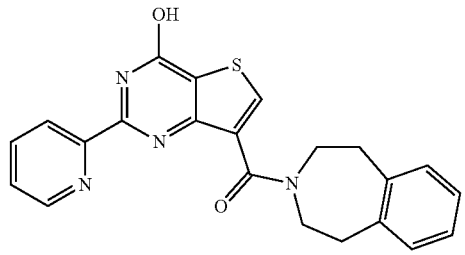 [SMILES: O=C(c1csc2c(O)nc(-c3ccccn3)nc12)N1CCc2ccccc2CC1] | B |

TABLE 2-continued
% Inhibition of MAPK phosphorylation @ 30 μM in the PANC-1 pancreatic cancer cell line
| Compound | PANC-1 |
|---|---|
| 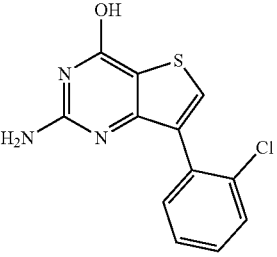 [SMILES: Nc1nc(O)c2scc(-c3ccccc3Cl)c2n1] | A |
| 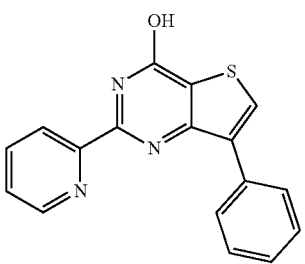 [SMILES: Oc1nc(-c2ccccn2)nc2c(-c3ccccc3)csc12] | D |
| 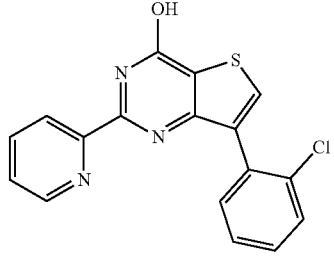 [SMILES: Oc1nc(-c2ccccn2)nc2c(-c3ccccc3Cl)csc12] | D |
| 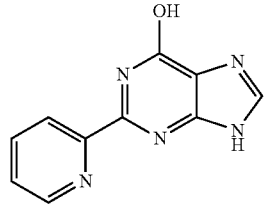 [SMILES: Oc1nc(-c2ccccn2)nc2[nH]cnc12] | A |
| 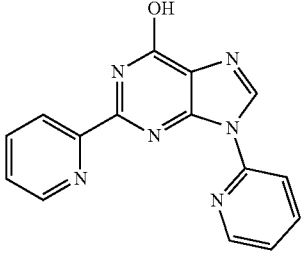 [SMILES: Oc1nc(-c2ccccn2)nc2c1ncn2-c1ccccn1] | A |
| 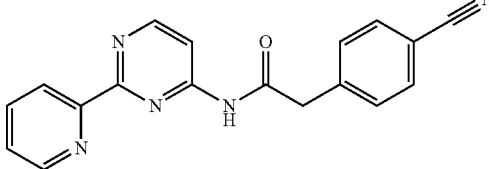 | A |

TABLE 2-continued
% Inhibition of MAPK phosphorylation @ 30 μM in the PANC-1 pancreatic cancer cell line
| Compound | PANC-1 |
|---|---|
| 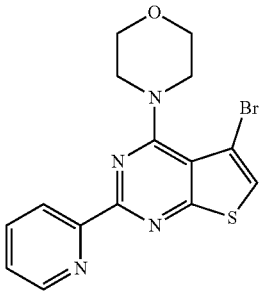 [SMILES: Brc1csc2nc(-c3ccccn3)nc(N3CCOCC3)c12] | A |
| 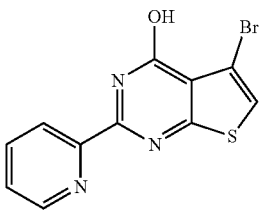 [SMILES: Oc1nc(-c2ccccn2)nc2scc(Br)c12] | D |
| 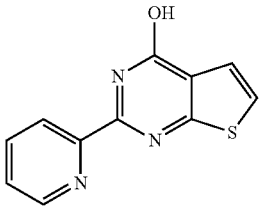 [SMILES: Oc1nc(-c2ccccn2)nc2sccc12] | A |
| 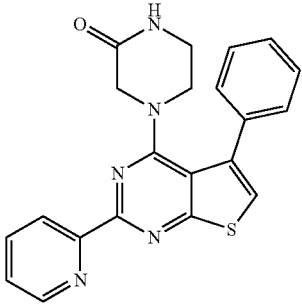 [SMILES: O=C1CN(c2nc(-c3ccccn3)nc3scc(-c4ccccc4)c23)CCN1] | A |
| 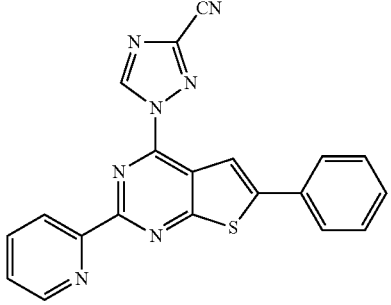 [SMILES: N#Cc1ncn(-c2nc(-c3ccccn3)nc3sc(-c4ccccc4)cc23)n1] | D |

TABLE 2-continued
% Inhibition of MAPK phosphorylation @ 30 μM in the PANC-1 pancreatic cancer cell line
| Compound | PANC-1 |
|---|---|
| 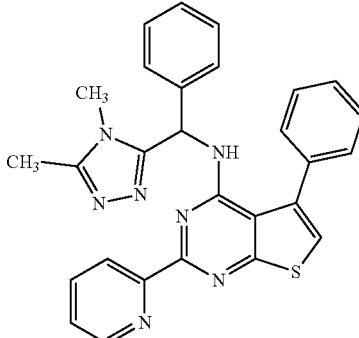 | C |
| 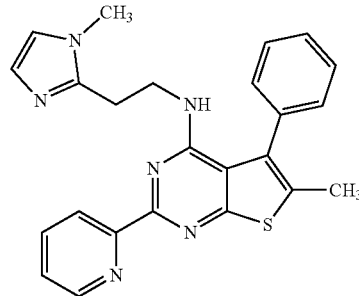 [SMILES: Cc1sc2nc(-c3ccccn3)nc(NCCc3nccn3C)c2c1-c1ccccc1] | A |
| 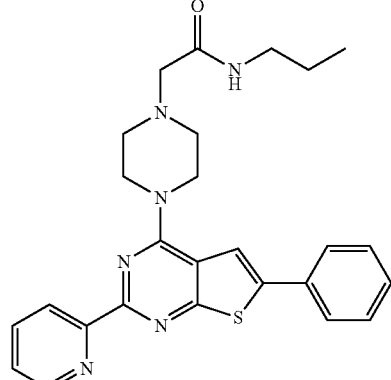 | D |
| 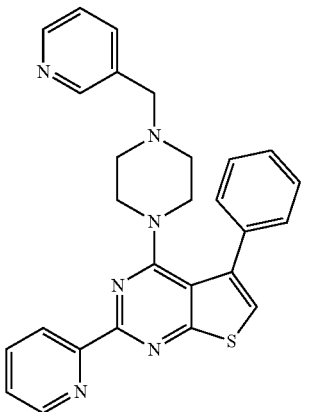 [SMILES: c1ccc(-c2csc3nc(-c4ccccn4)nc(N4CCN(Cc5cccnc5)CC4)c23)cc1] | A |

TABLE 2-continued
% Inhibition of MAPK phosphorylation @ 30 μM in the PANC-1 pancreatic cancer cell line
| Compound | PANC-1 |
|---|---|
| 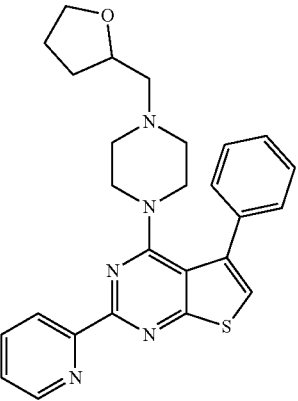 [SMILES: c1ccc(-c2csc3nc(-c4ccccn4)nc(N4CCN(CC5CCCO5)CC4)c23)cc1] | A |
| 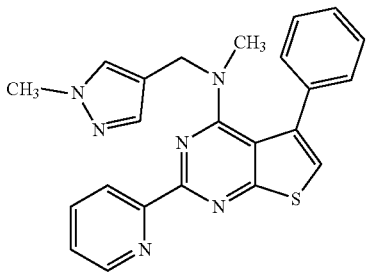 [SMILES: CN(Cc1cnn(C)c1)c1nc(-c2ccccn2)nc2scc(-c3ccccc3)c12] | B |
| 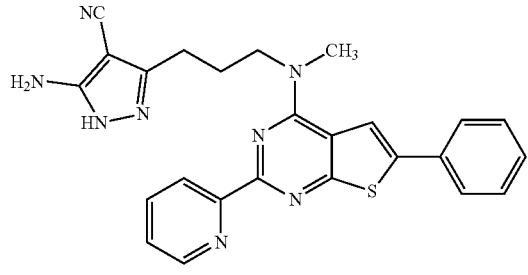 [SMILES: CN(CCCc1n[nH]c(N)c1C#N)c1nc(-c2ccccn2)nc2sc(-c3ccccc3)cc12] | B |
| 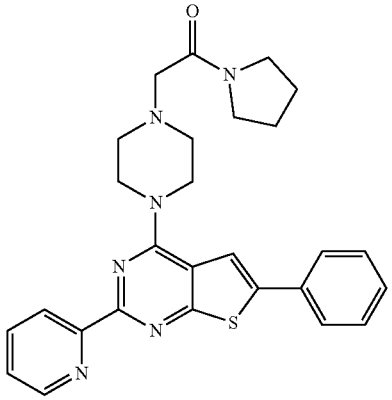 [SMILES: O=C(CN1CCN(c2nc(-c3ccccn3)nc3sc(-c4ccccc4)cc23)CC1)N1CCCC1] | D |

TABLE 2-continued
% Inhibition of MAPK phosphorylation @ 30 μM in the PANC-1 pancreatic cancer cell line
| Compound | PANC-1 |
|---|---|
| 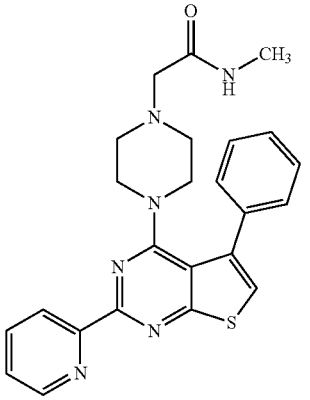 [SMILES: CNC(=O)CN1CCN(c2nc(-c3ccccn3)nc3scc(-c4ccccc4)c23)CC1] | A |
| 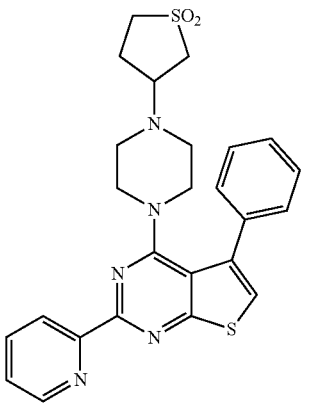 [SMILES: O=S1(=O)CCC(N2CCN(c3nc(-c4ccccn4)nc4scc(-c5ccccc5)c34)CC2)C1] | A |
| 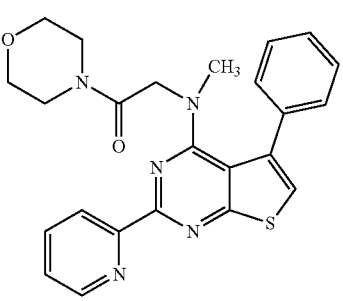 [SMILES: CN(CC(=O)N1CCOCC1)c1nc(-c2ccccn2)nc2scc(-c3ccccc3)c12] | A |
| 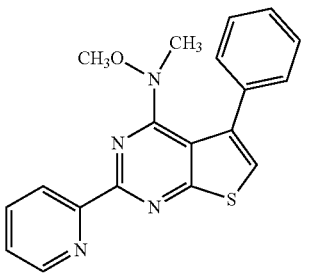 | B |

TABLE 2-continued
% Inhibition of MAPK phosphorylation @ 30 μM in the PANC-1 pancreatic cancer cell line
| Compound | PANC-1 |
|---|---|
| 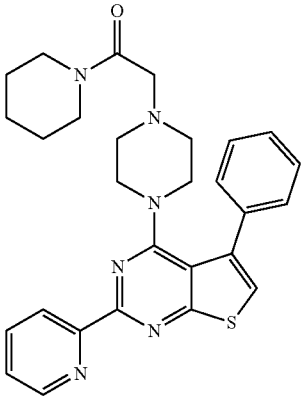 [SMILES: O=C(CN1CCN(c2nc(-c3ccccn3)nc3scc(-c4ccccc4)c23)CC1)N1CCCCC1] | B |
| 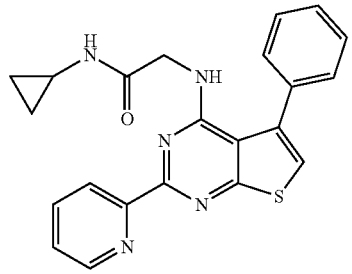 [SMILES: O=C(CNc1nc(-c2ccccn2)nc2scc(-c3ccccc3)c12)NC1CC1] | B |
| 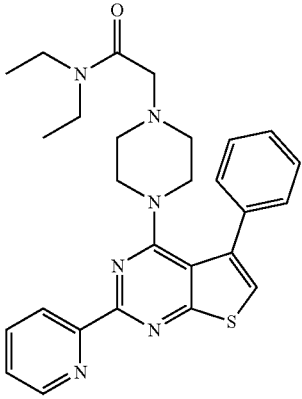 [SMILES: CCN(CC)C(=O)CN1CCN(c2nc(-c3ccccn3)nc3scc(-c4ccccc4)c23)CC1] | B |
| 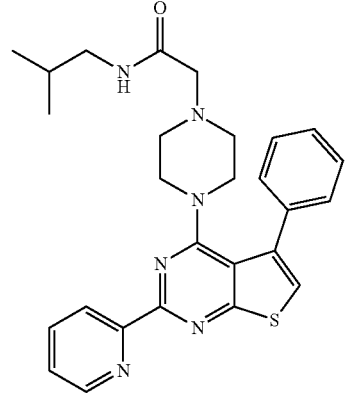 [SMILES: CC(C)CNC(=O)CN1CCN(c2nc(-c3ccccn3)nc3scc(-c4ccccc4)c23)CC1] | A |

TABLE 2-continued
% Inhibition of MAPK phosphorylation @ 30 μM in the PANC-1 pancreatic cancer cell line
| Compound | PANC-1 |
|---|---|
| 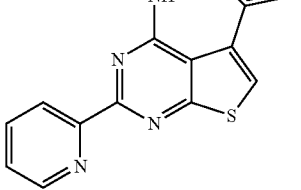 | A |
| 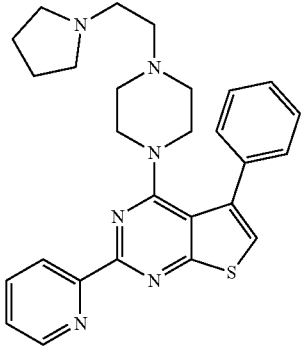 [SMILES: c1ccc(-c2csc3nc(-c4ccccn4)nc(N4CCN(CCN5CCCC5)CC4)c23)cc1] | D |
| 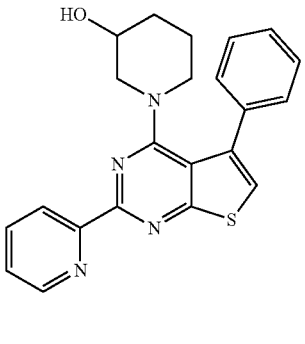 [SMILES: OC1CCCN(c2nc(-c3ccccn3)nc3scc(-c4ccccc4)c23)C1] | C |
| 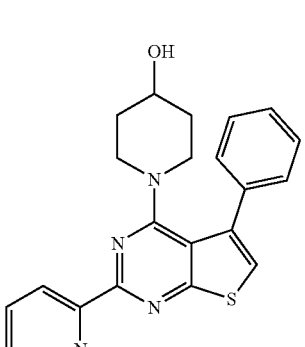 | A |

TABLE 2-continued
% Inhibition of MAPK phosphorylation @ 30 μM in the PANC-1 pancreatic cancer cell line
| Compound | PANC-1 |
|---|---|
| 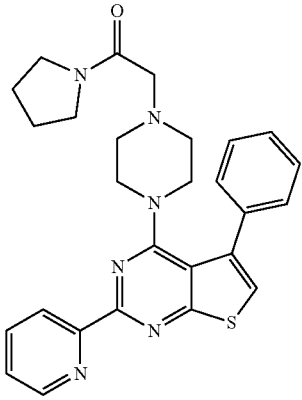 [SMILES: O=C(CN1CCN(c2nc(-c3ccccn3)nc3scc(-c4ccccc4)c23)CC1)N1CCCC1] | A |
| 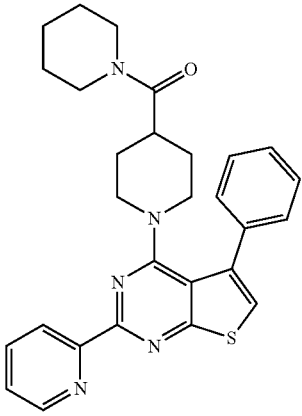 [SMILES: O=C(C1CCN(c2nc(-c3ccccn3)nc3scc(-c4ccccc4)c23)CC1)N1CCCCC1] | A |
| 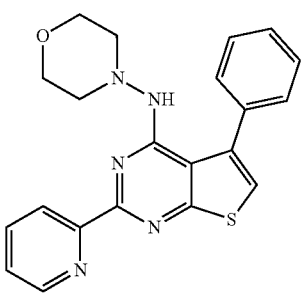 [SMILES: c1ccc(-c2csc3nc(-c4ccccn4)nc(NN4CCOCC4)c23)cc1] | A |
| 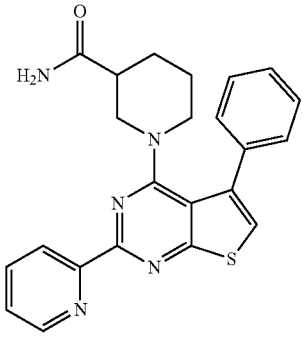 [SMILES: NC(=O)C1CCCN(c2nc(-c3ccccn3)nc3scc(-c4ccccc4)c23)C1] | A |

TABLE 2-continued

% Inhibition of MAPK phosphorylation @ 30 μM in the PANC-1 pancreatic cancer cell line

| Compound | PANC-1 |
|---|---|
| (2-methoxyethylamino-phenyl-pyridin-2-yl-thieno[2,3-d]pyrimidine structure) | D |
| (acetyl-piperazinyl-phenyl-pyridin-2-yl-thieno[2,3-d]pyrimidine structure) | B |
| (4-oxopiperidinyl-phenyl-pyridin-2-yl-thieno[2,3-d]pyrimidine structure) | B |
| (4-carboxamide-piperidinyl-phenyl-pyridin-2-yl-thieno[2,3-d]pyrimidine structure) | A |

TABLE 2-continued

% Inhibition of MAPK phosphorylation @ 30 μM in the PANC-1 pancreatic cancer cell line

| Compound | PANC-1 |
|---|---|
| 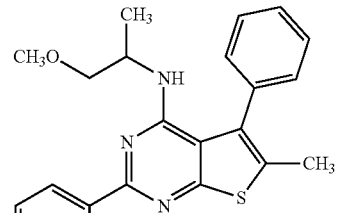 | D |
| | A |

A = 1-25% inhibition, B = 25-50% inhibition, C = 51-75% inhibition, D = 76-100% inhibition

Example 2

Protocol for Cell Proliferation Assay

Cell lines: Tumor-derived pancreatic cancer cell lines MIA-PACA2 were purchased from ATCC and grown in complete DMEM-High Glucose medium supplemented with penicillin (100 U/mL), streptomycin (100 μg/mL), and 10% heat-inactivated FBS at 37° C. in a humidified incubator with 5% CO2.

Method: Cells are plated at 1000 cells/well density in 96-wells plate, starved ON, and the next day tested small molecules are added to the cells in the final concentration of 30 μM with 0.3% DMSO 3 hours prior to 10% FBS addition. After serum addition cells are incubated for 6 days at 37° C. in a humidified incubator with 5% $CO_2$.

Assay: At the end of the incubation period, cell cultures are tested using the CellTiter 96® AQueous One Solution Cell Proliferation Assay kit (Promega Corporation, Madison, WI) according to the manufacturer specifications. Briefly, assay is performed by adding 20 μl of the CellTiter 96 Aqueous One Solution Reagent directly to culture wells, followed by for 1-4 hours incubation at 37° C. in a humidified incubator with 5% $C_{O2}$. At the end of incubation time, absorbance at 492 nm is recorded with the 96-well plate reader Eppendorf AF2200, and degree of small molecule-dependent proliferation inhibition is calculated from raw data assuming No Serum cells value as 100%.

Table 3 shows inhibition data for selected compounds tested in the cellular assay described above.

TABLE 3

% Inhibition of cell proliferation @ 30 μM in MIA-PACA2 pancreatic cancer cell lines

| Compound | MIA-PACA2 |
|---|---|
| | D |
| | B |
| | A |

TABLE 3-continued
% Inhibition of cell proliferation @ 30 μM in MIA-PACA2 pancreatic cancer cell lines
| Compound | MIA-PACA2 |
|---|---|
| 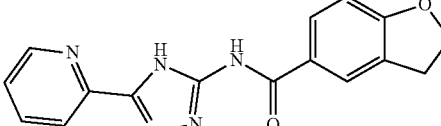 | D |
| 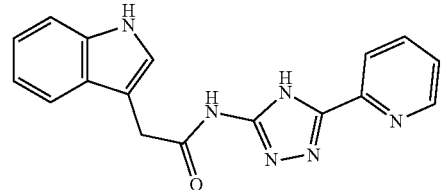 [SMILES: O=C(Cc1c[nH]c2ccccc12)Nc1nnc(-c2ccccn2)[nH]1] | A |
| 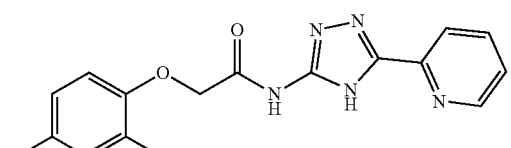 | C |
| 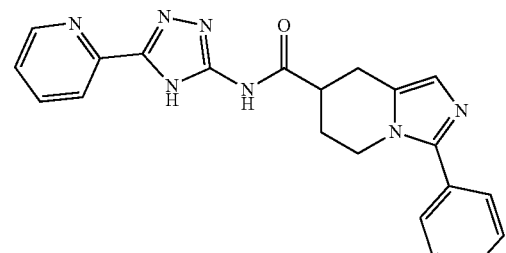 | A |
| 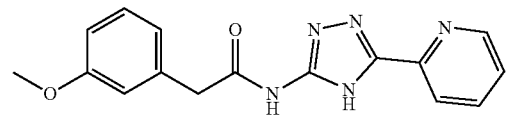 [SMILES: COc1cccc(CC(=O)Nc2nnc(-c3ccccn3)[nH]2)c1] | B |
| 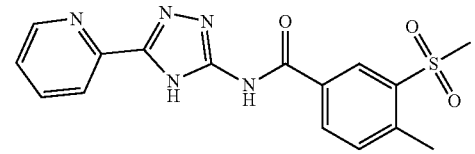 [SMILES: Cc1ccc(C(=O)Nc2nnc(-c3ccccn3)[nH]2)cc1S(C)(=O)=O] | C |
| 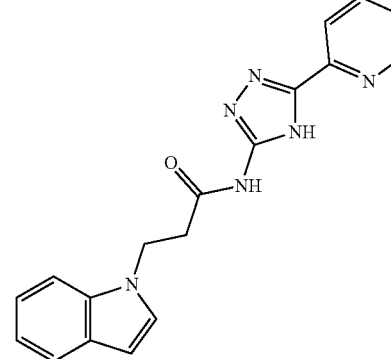 | C |

TABLE 3-continued

% Inhibition of cell proliferation @ 30 μM in MIA-PACA2 pancreatic cancer cell lines

| Compound | MIA-PACA2 |
|---|---|
| 5-methyl-2-phenyl-oxazole-4-carboxamide linked to 5-(pyridin-2-yl)-4H-1,2,4-triazol-3-amine | D |
| 1-phenyl-pyrazole-3-carboxamide linked to 5-(pyridin-2-yl)-4H-1,2,4-triazol-3-amine | D |
| 3-methyl-benzofuran-2-carboxamide linked to 5-(pyridin-2-yl)-4H-1,2,4-triazol-3-amine | D |
| 2-(2-chlorophenoxy)propanamide linked to 5-(pyridin-2-yl)-4H-1,2,4-triazol-3-amine | D |
| 1-(3-fluorophenyl)-pyrazole-3-carboxamide linked to 5-(pyridin-2-yl)-4H-1,2,4-triazol-3-amine | D |
| 3-(4-methoxyphenyl)propanamide linked to 5-(pyridin-2-yl)-4H-1,2,4-triazol-3-amine | C |
| 2-(5-methoxyindol-1-yl)acetamide linked to 5-(pyridin-2-yl)-4H-1,2,4-triazol-3-amine | D |

TABLE 3-continued

% Inhibition of cell proliferation @ 30 μM in MIA-PACA2 pancreatic cancer cell lines

| Compound | MIA-PACA2 |
|---|---|
| (indole-propanamide-triazole-pyridine structure) | C |
| (quinoline-carboxamide-triazole-pyridine structure) | B |
| (4-methylphenyl-acetamide-triazole-pyridine structure) | B |
| (pyridine-triazole-carboxamide-thiazole-methylpyrazole structure) | D |
| (oxo-tetrahydrobenzofuran-carboxamide-triazole-pyridine structure) | D |
| (dioxopyrrolidinyl-methyl-benzamide-triazole-pyridine structure) | A |
| (trifluoromethylbenzyl-methylamino-methyl-oxadiazole-chlorophenyl structure) | B |

TABLE 3-continued

% Inhibition of cell proliferation @ 30 μM in MIA-PACA2 pancreatic cancer cell lines

| Compound | MIA-PACA2 |
|---|---|
| | C |
| | D |
| | A |
| | C |
| | B |
| | B |
| | A |
| | C |
| | A |
| | D |

TABLE 3-continued

% Inhibition of cell proliferation @ 30 μM in MIA-PACA2 pancreatic cancer cell lines

| Compound | MIA-PACA2 |
|---|---|
| [structure] | D |
| [structure] | D |
| [structure] | C |
| [structure] | C |
| [structure] | D |
| [structure] | A |
| [structure] | D |
| [structure] | D |

TABLE 3-continued

% Inhibition of cell proliferation @ 30 μM in MIA-PACA2 pancreatic cancer cell lines

| Compound | MIA-PACA2 |
|---|---|
| (structure) | D |
| (structure) | D |
| (structure) | C |
| (structure) | C |
| (structure) | B |
| (structure) | D |
| (structure) | D |
| (structure) | C |
| (structure) | D |

TABLE 3-continued
% Inhibition of cell proliferation @ 30 μM in MIA-PACA2 pancreatic cancer cell lines
| Compound | MIA-PACA2 |
|---|---|
| 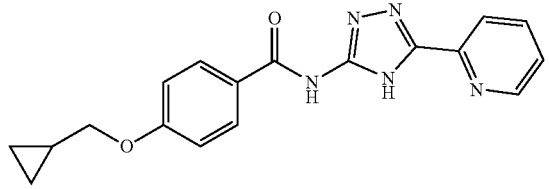 [SMILES: O=C(Nc1nnc(-c2ccccn2)[nH]1)c1ccc(OCC2CC2)cc1] | D |
| 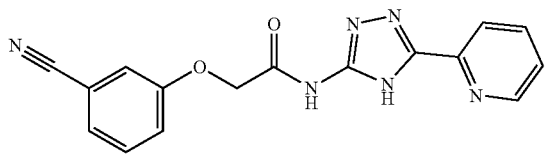 [SMILES: N#Cc1cccc(OCC(=O)Nc2nnc(-c3ccccn3)[nH]2)c1] | B |
| 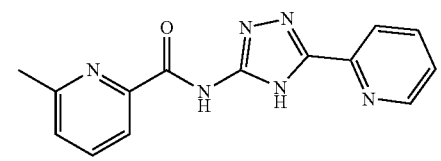 [SMILES: Cc1cccc(C(=O)Nc2nnc(-c3ccccn3)[nH]2)n1] | C |
| 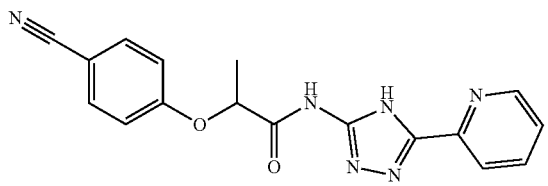 [SMILES: CC(Oc1ccc(C#N)cc1)C(=O)Nc1nnc(-c2ccccn2)[nH]1] | D |
| 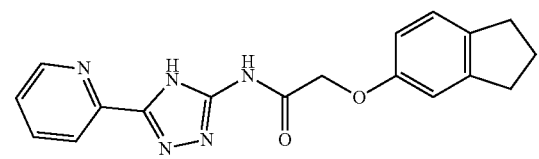 [SMILES: O=C(COc1ccc2c(c1)CCC2)Nc1nnc(-c2ccccn2)[nH]1] | A |
| 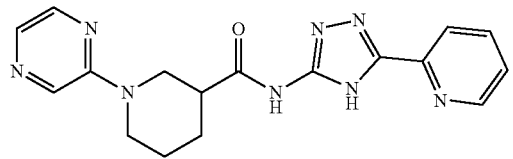 [SMILES: O=C(Nc1nnc(-c2ccccn2)[nH]1)C1CCCN(c2cnccn2)C1] | D |
| 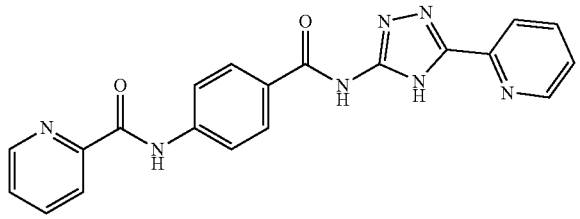 [SMILES: O=C(Nc1nnc(-c2ccccn2)[nH]1)c1ccc(NC(=O)c2ccccn2)cc1] | B |
| 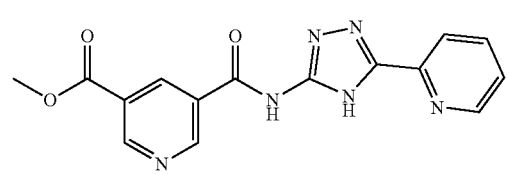 [SMILES: COC(=O)c1cncc(C(=O)Nc2nnc(-c3ccccn3)[nH]2)c1] | B |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | C |
| | C |
| | B |
| | B |
| | C |

TABLE 3-continued
% Inhibition of cell proliferation @ 30 μM in MIA-PACA2 pancreatic cancer cell lines
| Compound | MIA-PACA2 |
|---|---|
| 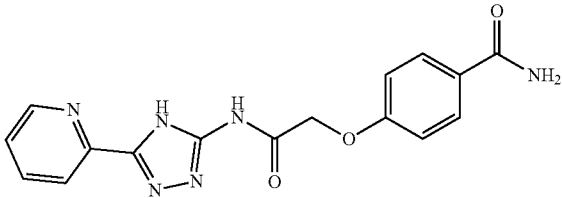 [SMILES: NC(=O)c1ccc(OCC(=O)Nc2nnc(-c3ccccn3)[nH]2)cc1] | A |
| 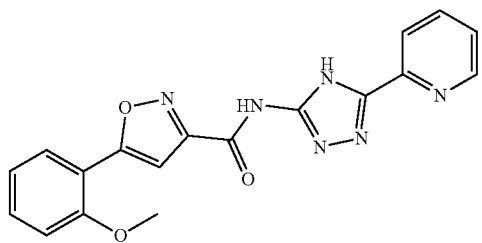 [SMILES: COc1ccccc1-c1cc(C(=O)Nc2nnc(-c3ccccn3)[nH]2)no1] | D |
| 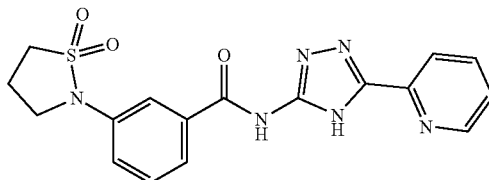 | A |
| 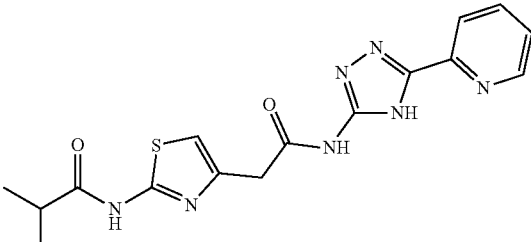 | D |
| 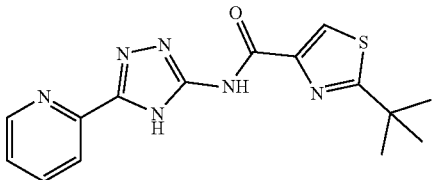 | D |
| 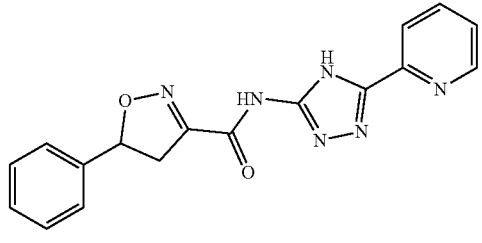 [SMILES: O=C(Nc1nnc(-c2ccccn2)[nH]1)C1=NOC(c2ccccc2)C1] | B |
| 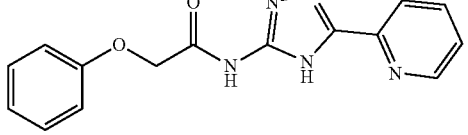 | B |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | D |
| | C |
| | A |
| | D |
| | C |

TABLE 3-continued
% Inhibition of cell proliferation @ 30 μM in MIA-PACA2 pancreatic cancer cell lines
| Compound | MIA-PACA2 |
|---|---|
| 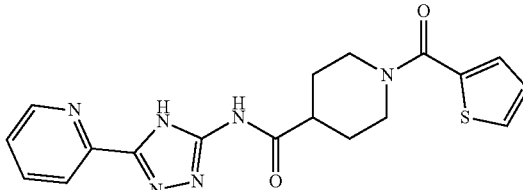 | D |
| 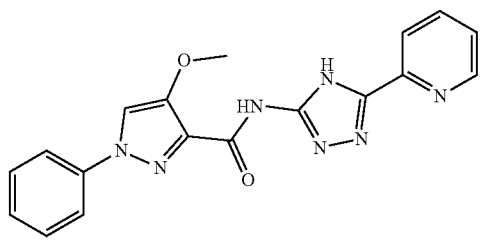 [SMILES: COc1cn(-c2ccccc2)nc1C(=O)Nc1nnc(-c2ccccn2)[nH]1] | C |
| 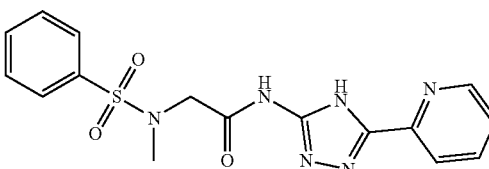 | A |
| 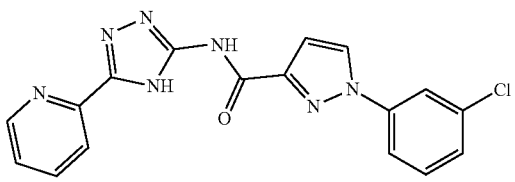 [SMILES: O=C(Nc1nnc(-c2ccccn2)[nH]1)c1ccn(-c2cccc(Cl)c2)n1] | D |
| 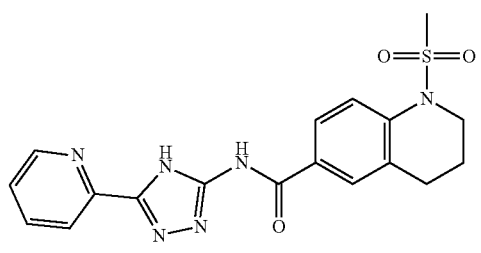 [SMILES: CS(=O)(=O)N1CCCc2cc(C(=O)Nc3nnc(-c4ccccn4)[nH]3)ccc21] | D |
| 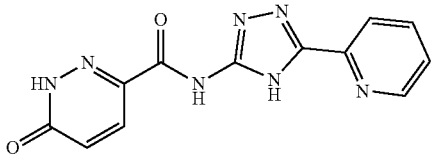 [SMILES: O=C(Nc1nnc(-c2ccccn2)[nH]1)c1ccc(=O)[nH]n1] | B |
| 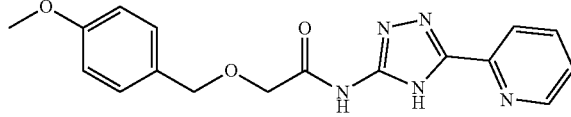 | A |

TABLE 3-continued

% Inhibition of cell proliferation @ 30 μM in MIA-PACA2 pancreatic cancer cell lines

| Compound | MIA-PACA2 |
|---|---|
| (structure) | D |
| (structure) | D |
| (structure) | D |
| (structure) | D |
| (structure) | D |
| (structure) | D |
| (structure) | D |

TABLE 3-continued

% Inhibition of cell proliferation @ 30 µM in MIA-PACA2 pancreatic cancer cell lines

| Compound | MIA-PACA2 |
|---|---|
| (structure) | D |
| (structure) | D |
| (structure) | D |
| (structure) | D |
| (structure) | D |
| (structure) | D |
| (structure) | D |
| (structure) | D |

TABLE 3-continued

% Inhibition of cell proliferation @ 30 μM in MIA-PACA2 pancreatic cancer cell lines

| Compound | MIA-PACA2 |
|---|---|
| 3-methoxy-N-(4-(pyridin-2-yl)thiazol-2-yl)benzamide | D |
| 6-methoxy-N-(5-(pyridin-2-yl)thiazol-2-yl)nicotinamide | D |
| 5-(4-methoxyphenyl)-2-(pyridin-2-yl)-3H-thieno[2,3-d]pyrimidin-4-one | D |
| 2-(pyridin-2-yl)-5-(thiophen-2-yl)-3H-thieno[2,3-d]pyrimidin-4-one | D |
| N,5-dimethyl-4-oxo-2-(pyridin-2-yl)-3,4-dihydrothieno[2,3-d]pyrimidine-6-carboxamide | C |
| 5-(2-chlorophenyl)-2-(pyridin-2-yl)-3H-thieno[2,3-d]pyrimidin-4-one | D |

TABLE 3-continued

% Inhibition of cell proliferation @ 30 μM in MIA-PACA2 pancreatic cancer cell lines

| Compound | MIA-PACA2 |
|---|---|
| | D |
| | A |
| | D |
| | D |
| | C |
| | A |

TABLE 3-continued
% Inhibition of cell proliferation @ 30 μM in MIA-PACA2 pancreatic cancer cell lines
| Compound | MIA-PACA2 |
|---|---|
| 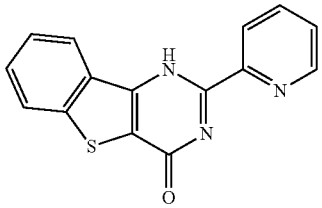 [SMILES: O=c1nc(-c2ccccn2)[nH]c2c1sc1ccccc12] | D |
| 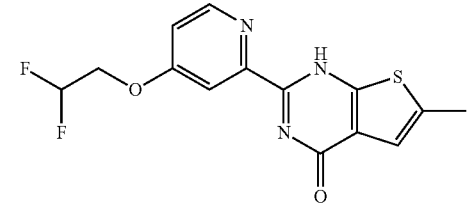 [SMILES: Cc1cc2c(=O)nc(-c3cc(OCC(F)F)ccn3)[nH]c2s1] | D |
| 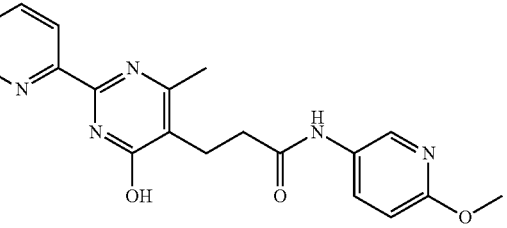 | D |
| 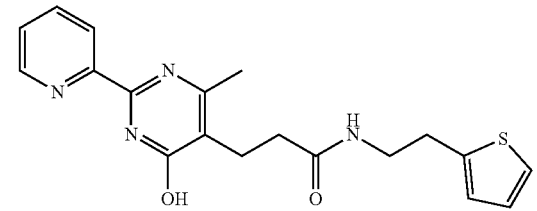 [SMILES: Cc1nc(-c2ccccn2)nc(O)c1CCC(=O)NCCc1cccs1] | D |
| 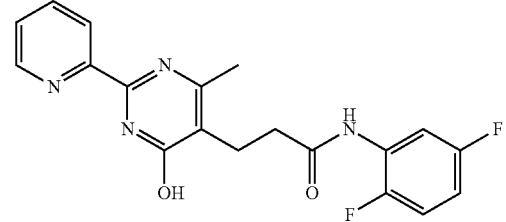 [SMILES: Cc1nc(-c2ccccn2)nc(O)c1CCC(=O)Nc1cc(F)ccc1F] | D |
| 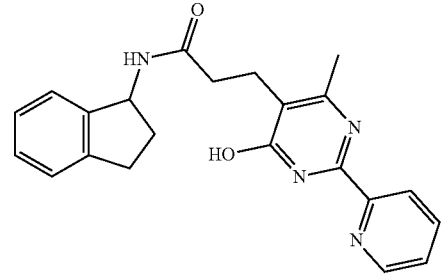 [SMILES: Cc1nc(-c2ccccn2)nc(O)c1CCC(=O)NC1CCc2ccccc21] | D |

TABLE 3-continued

% Inhibition of cell proliferation @ 30 μM in MIA-PACA2 pancreatic cancer cell lines

| Compound | MIA-PACA2 |
|---|---|
| | D |
| | D |
| | A |
| | D |
| | D |

TABLE 3-continued
% Inhibition of cell proliferation @ 30 μM in MIA-PACA2 pancreatic cancer cell lines
| Compound | MIA-PACA2 |
|---|---|
| 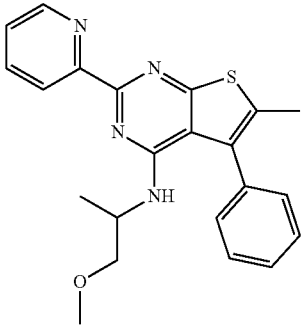 [SMILES: COCC(C)Nc1nc(-c2ccccn2)nc2sc(C)c(-c3ccccc3)c12] | D |
| 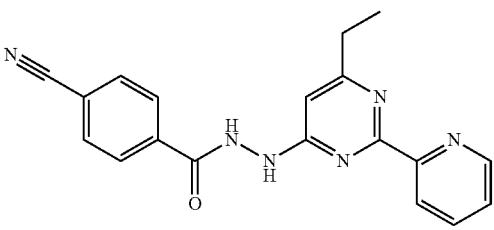 [SMILES: CCc1cc(NNC(=O)c2ccc(C#N)cc2)nc(-c2ccccn2)n1] | D |
| 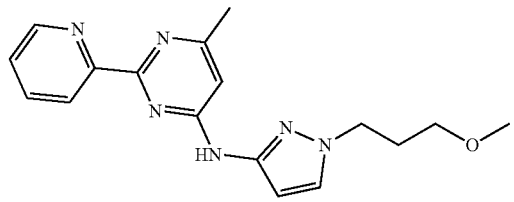 [SMILES: COCCCn1ccc(Nc2cc(C)nc(-c3ccccn3)n2)n1] | B |
| 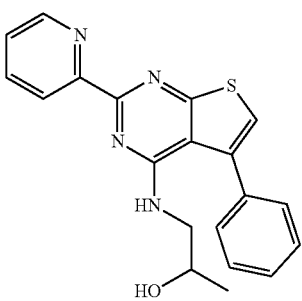 [SMILES: CC(O)CNc1nc(-c2ccccn2)nc2scc(-c3ccccc3)c12] | D |
| 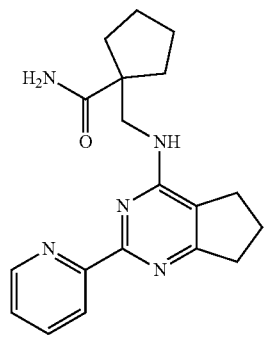 [SMILES: NC(=O)C1(CNc2nc(-c3ccccn3)nc3c2CCC3)CCCC1] | D |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | D |
| | D |

TABLE 3-continued

% Inhibition of cell proliferation @ 30 μM in MIA-PACA2 pancreatic cancer cell lines

| Compound | MIA-PACA2 |
|---|---|
| | A |
| | D |
| | D |
| | D |
| | D |
| | D |

TABLE 3-continued
% Inhibition of cell proliferation @ 30 μM in MIA-PACA2 pancreatic cancer cell lines
| Compound | MIA-PACA2 |
|---|---|
| 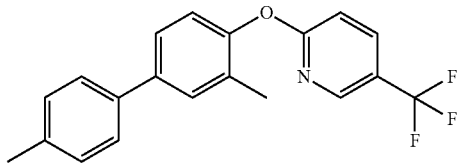 [SMILES: Cc1ccc(-c2ccc(Oc3ccc(C(F)(F)F)cn3)c(C)c2)cc1] | D |
| 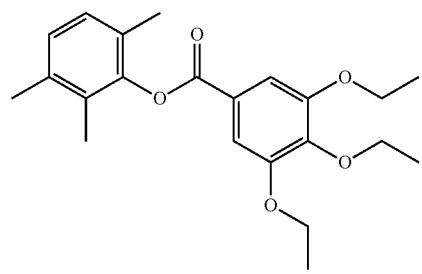 [SMILES: CCOc1cc(C(=O)Oc2c(C)ccc(C)c2C)cc(OCC)c1OCC] | D |
| 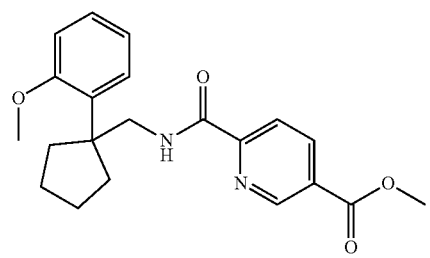 [SMILES: COC(=O)c1ccc(C(=O)NCC2(c3ccccc3OC)CCCC2)nc1] | D |
| 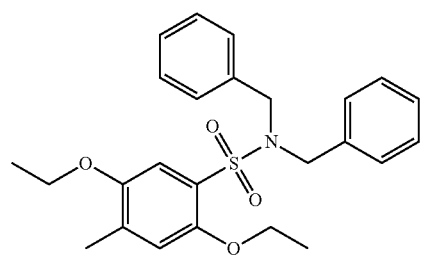 [SMILES: CCOc1cc(S(=O)(=O)N(Cc2ccccc2)Cc2ccccc2)c(OCC)cc1C] | D |
| 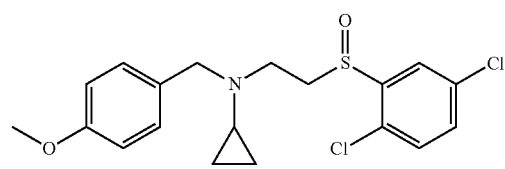 [SMILES: COc1ccc(CN(CCS(=O)c2cc(Cl)ccc2Cl)C2CC2)cc1] | C |
| 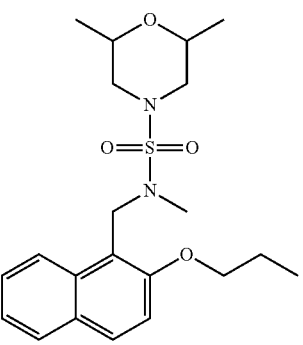 [SMILES: CCCOc1ccc2ccccc2c1CN(C)S(=O)(=O)N1CC(C)OC(C)C1] | D |

TABLE 3-continued
% Inhibition of cell proliferation @ 30 μM in MIA-PACA2 pancreatic cancer cell lines
| Compound | MIA-PACA2 |
|---|---|
| 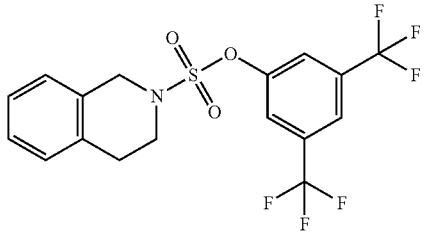 [SMILES: O=S(=O)(Oc1cc(C(F)(F)F)cc(C(F)(F)F)c1)N1CCc2ccccc2C1] | B |
| 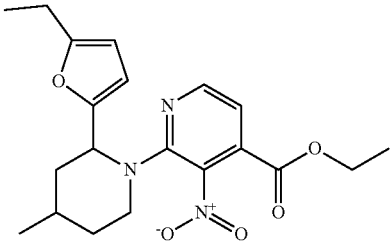 | D |
| 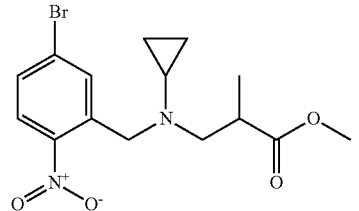 [SMILES: COC(=O)C(C)CN(Cc1cc(Br)ccc1[N+](=O)[O-])C1CC1] | A |
| 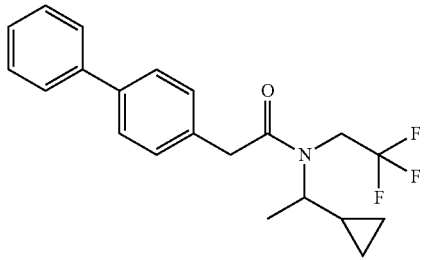 [SMILES: CC(C1CC1)N(CC(F)(F)F)C(=O)Cc1ccc(-c2ccccc2)cc1] | D |
| 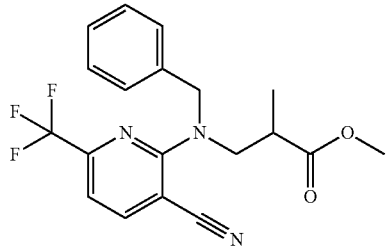 [SMILES: COC(=O)C(C)CN(Cc1ccccc1)c1nc(C(F)(F)F)ccc1C#N] | C |
| 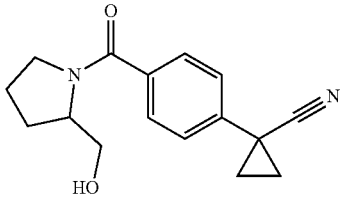 [SMILES: N#CC1(c2ccc(C(=O)N3CCCC3CO)cc2)CC1] | C |

TABLE 3-continued
% Inhibition of cell proliferation @ 30 µM in MIA-PACA2 pancreatic cancer cell lines
| Compound | MIA-PACA2 |
|---|---|
| 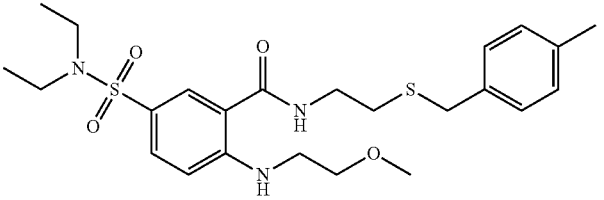 [SMILES: CCN(CC)S(=O)(=O)c1ccc(NCCOC)c(C(=O)NCCSCc2ccc(C)cc2)c1] | D |
| 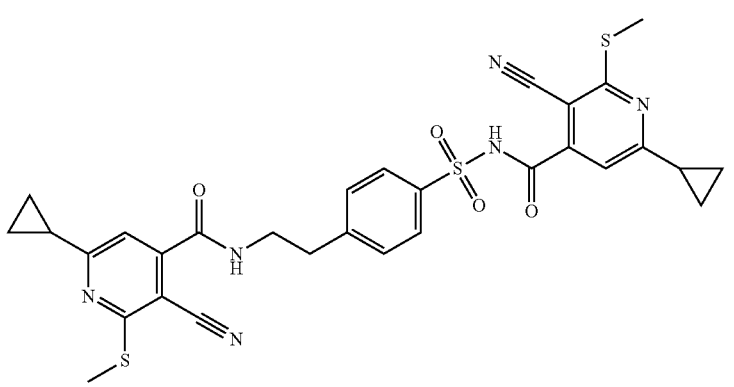 [SMILES: CSc1nc(C2CC2)cc(C(=O)NCCc2ccc(S(=O)(=O)NC(=O)c3cc(C4CC4)nc(SC)c3C#N)cc2)c1C#N] | A |
| 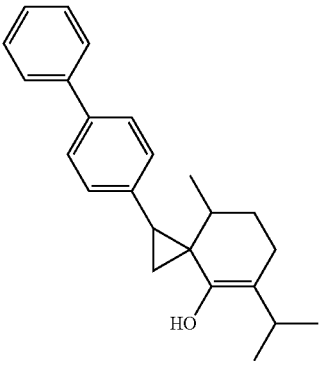 [SMILES: CC(C)C1=C(O)C2(CC2c2ccc(-c3ccccc3)cc2)C(C)CC1] | D |
| 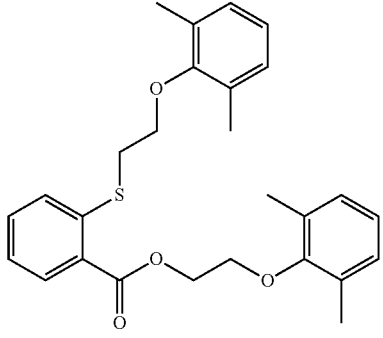 [SMILES: Cc1cccc(C)c1OCCOC(=O)c1ccccc1SCCOc1c(C)cccc1C] | C |
| 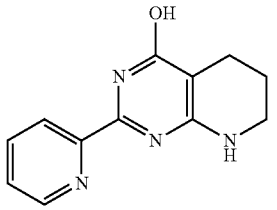 [SMILES: Oc1nc(-c2ccccn2)nc2c1CCCN2] | A |

TABLE 3-continued

% Inhibition of cell proliferation @ 30 μM in MIA-PACA2 pancreatic cancer cell lines

| Compound | MIA-PACA2 |
|---|---|
| [structure] | D |
| [structure] | D |
| [structure] | D |
| [structure] | D |
| [structure] | D |

TABLE 3-continued

% Inhibition of cell proliferation @ 30 μM in MIA-PACA2 pancreatic cancer cell lines

| Compound | MIA-PACA2 |
|---|---|
| | D |
| | A |
| | D |
| | A |
| | A |

TABLE 3-continued

% Inhibition of cell proliferation @ 30 µM in MIA-PACA2 pancreatic cancer cell lines

| Compound | MIA-PACA2 |
|---|---|
| 2-(pyridin-2-yl)-8-(phenylsulfonyl)-5,6,7,8-tetrahydropyrido[2,3-d]pyrimidin-4-ol | B |
| 2-phenylethyl 4-hydroxy-2-(pyridin-2-yl)-5,6-dihydropyrido[2,3-d]pyrimidine-8(7H)-carboxylate | D |
| 8-(3,3-diphenylpropanoyl)-2-(pyridin-2-yl)-5,6,7,8-tetrahydropyrido[2,3-d]pyrimidin-4-ol | D |
| 2-(pyridin-2-yl)-8-(4-(pyridin-3-yl)butanoyl)-5,6,7,8-tetrahydropyrido[2,3-d]pyrimidin-4-ol | D |
| 2-amino-7-bromothieno[3,2-d]pyrimidin-4-ol | A |
| 2-amino-7-(4-methylpiperidine-1-carbonyl)thieno[3,2-d]pyrimidin-4-ol | A |

TABLE 3-continued
% Inhibition of cell proliferation @ 30 μM in MIA-PACA2 pancreatic cancer cell lines
| Compound | MIA-PACA2 |
|---|---|
| 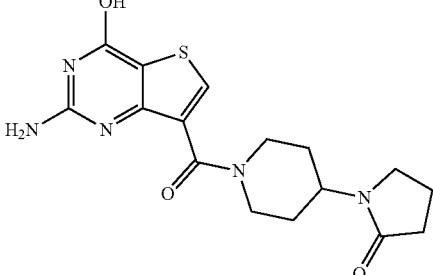 [SMILES: Nc1nc(O)c2scc(C(=O)N3CCC(N4CCCC4=O)CC3)c2n1] | B |
| 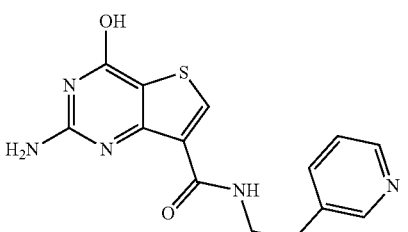 | A |
| 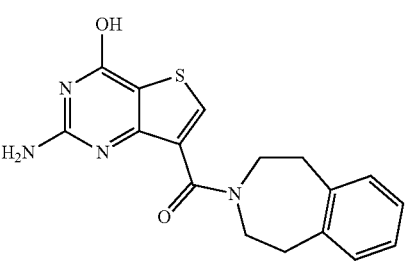 [SMILES: Nc1nc(O)c2scc(C(=O)N3CCc4ccccc4CC3)c2n1] | A |
| 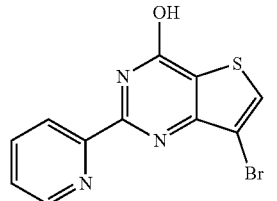 | D |
| 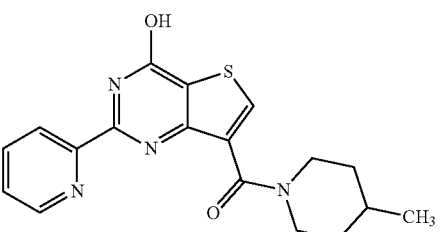 | D |
| 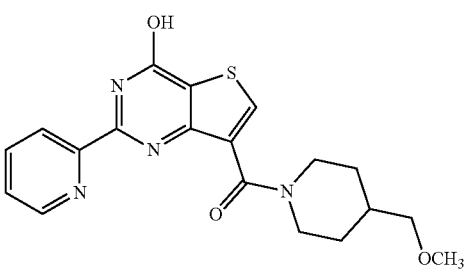 [SMILES: COCC1CCN(C(=O)c2csc3c(O)nc(-c4ccccn4)nc23)CC1] | D |

TABLE 3-continued

% Inhibition of cell proliferation @ 30 μM in MIA-PACA2 pancreatic cancer cell lines

| Compound | MIA-PACA2 |
|---|---|
| (structure) | D |
| (structure) | D |
| (structure) | A |
| (structure) | A |
| (structure) | D |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | A |
| | C |
| | B |

TABLE 3-continued

% Inhibition of cell proliferation @ 30 μM in MIA-PACA2 pancreatic cancer cell lines

| Compound | MIA-PACA2 |
|---|---|
| (structure) | A |
| (structure) | B |
| (structure) | D |
| (structure) | D |
| (structure) | B |
| (structure) | D |

TABLE 3-continued
% Inhibition of cell proliferation @ 30 μM in MIA-PACA2 pancreatic cancer cell lines
| Compound | MIA-PACA2 |
|---|---|
| 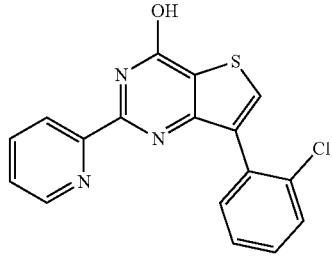 [SMILES: Oc1nc(-c2ccccn2)nc2c(-c3ccccc3Cl)csc12] | D |
| 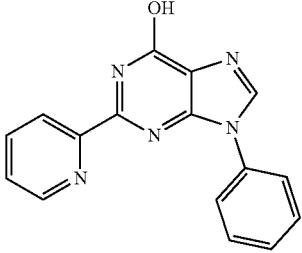 [SMILES: Oc1nc(-c2ccccn2)nc2c1ncn2-c1ccccc1] | B |
| 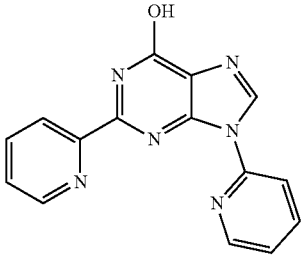 [SMILES: Oc1nc(-c2ccccn2)nc2c1ncn2-c1ccccn1] | D |
| 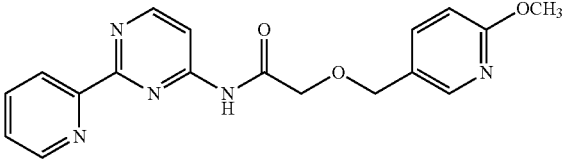 [SMILES: COc1ccc(COCC(=O)Nc2ccnc(-c3ccccn3)n2)cn1] | A |
| 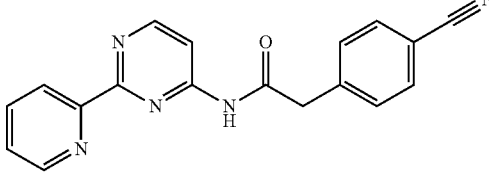 | D |
| 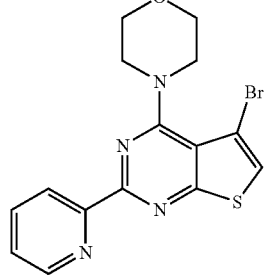 | B |

TABLE 3-continued
% Inhibition of cell proliferation @ 30 μM in MIA-PACA2 pancreatic cancer cell lines
| Compound | MIA-PACA2 |
|---|---|
| 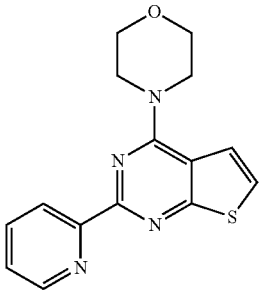 [SMILES: c1ccc(-c2nc(N3CCOCC3)c3ccsc3n2)nc1] | C |
| 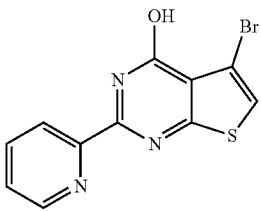 [SMILES: Oc1nc(-c2ccccn2)nc2scc(Br)c12] | D |
| 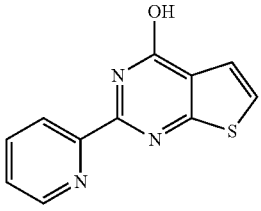 [SMILES: Oc1nc(-c2ccccn2)nc2sccc12] | D |
| 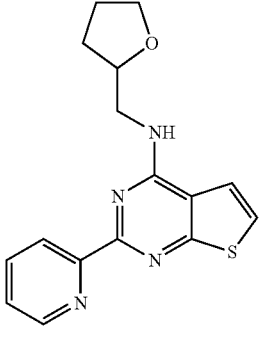 [SMILES: c1ccc(-c2nc(NCC3CCCO3)c3ccsc3n2)nc1] | D |
| 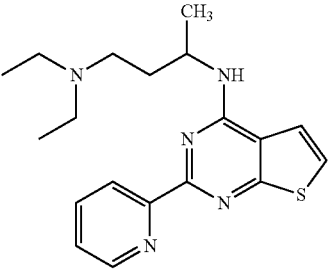 [SMILES: CCN(CC)CCC(C)Nc1nc(-c2ccccn2)nc2sccc12] | D |

TABLE 3-continued

% Inhibition of cell proliferation @ 30 μM in MIA-PACA2 pancreatic cancer cell lines

| Compound | MIA-PACA2 |
|---|---|
| 4-(2-(pyridin-2-yl)-5-phenylthieno[2,3-d]pyrimidin-4-yl)piperazin-2-one | A |
| 1-(2-hydroxyethyl)-4-(2-(pyridin-2-yl)-5-phenylthieno[2,3-d]pyrimidin-4-yl)piperazin-2-one | C |
| 1-(2-(pyridin-2-yl)-6-phenylthieno[2,3-d]pyrimidin-4-yl)-1H-1,2,4-triazole-3-carbonitrile | D |
| N-((4,5-dimethyl-4H-1,2,4-triazol-3-yl)(phenyl)methyl)-2-(pyridin-2-yl)-5-phenylthieno[2,3-d]pyrimidin-4-amine | D |

TABLE 3-continued

% Inhibition of cell proliferation @ 30 μM in MIA-PACA2 pancreatic cancer cell lines

| Compound | MIA-PACA2 |
|---|---|
|  | D |
|  | D |
|  | D |
|  | D |
|  | D |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | D |

TABLE 3-continued
% Inhibition of cell proliferation @ 30 μM in MIA-PACA2 pancreatic cancer cell lines
| Compound | MIA-PACA2 |
|---|---|
| 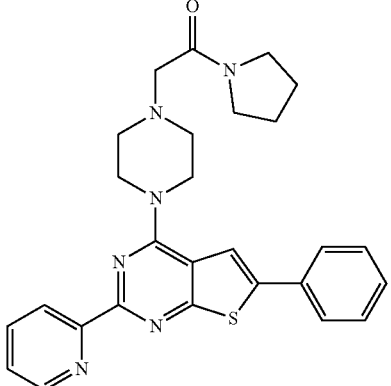 | D |
| 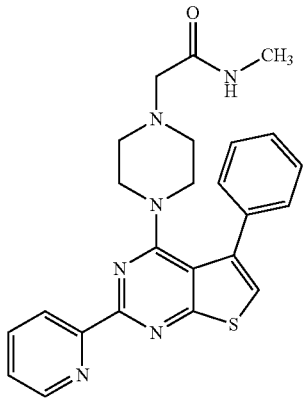 [SMILES: CNC(=O)CN1CCN(c2nc(-c3ccccn3)nc3scc(-c4ccccc4)c23)CC1] | A |
| 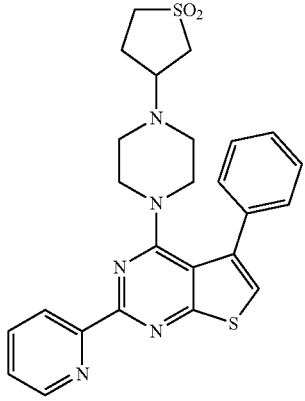 [SMILES: O=S1(=O)CCC(N2CCN(c3nc(-c4ccccn4)nc4scc(-c5ccccc5)c34)CC2)C1] | D |
| 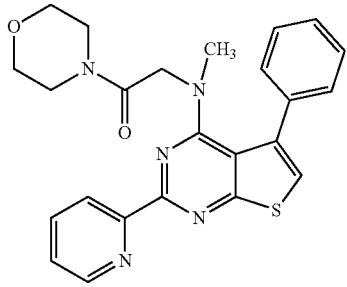 [SMILES: CN(CC(=O)N1CCOCC1)c1nc(-c2ccccn2)nc2scc(-c3ccccc3)c12] | C |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | D |

TABLE 3-continued
% Inhibition of cell proliferation @ 30 µM in MIA-PACA2 pancreatic cancer cell lines
| Compound | MIA-PACA2 |
|---|---|
| 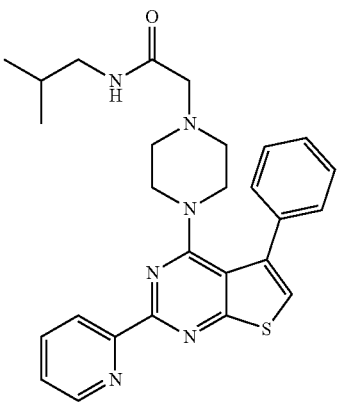 [SMILES: CC(C)CNC(=O)CN1CCN(c2nc(-c3ccccn3)nc3scc(-c4ccccc4)c23)CC1] | D |
| 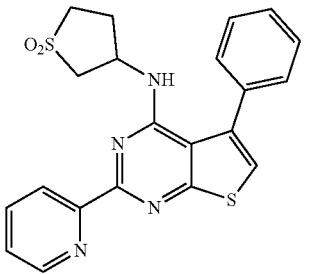 [SMILES: O=S1(=O)CCC(Nc2nc(-c3ccccn3)nc3scc(-c4ccccc4)c23)C1] | D |
| 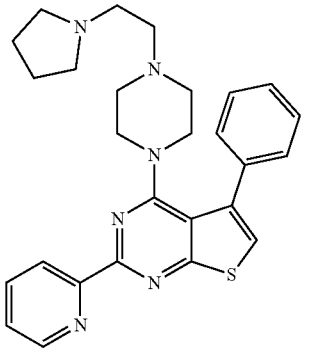 [SMILES: c1ccc(-c2csc3nc(-c4ccccn4)nc(N4CCN(CCN5CCCC5)CC4)c23)cc1] | D |
| 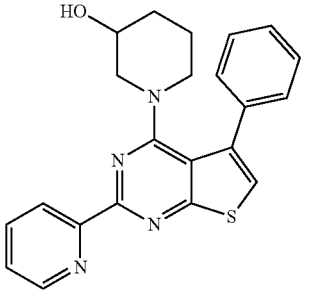 [SMILES: OC1CCCN(c2nc(-c3ccccn3)nc3scc(-c4ccccc4)c23)C1] | D |

TABLE 3-continued
% Inhibition of cell proliferation @ 30 µM in MIA-PACA2 pancreatic cancer cell lines
| Compound | MIA-PACA2 |
|---|---|
| 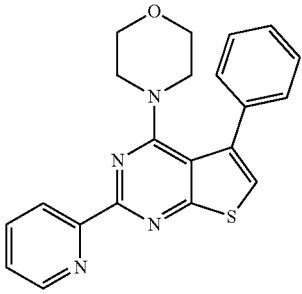 [SMILES: c1ccc(-c2csc3nc(-c4ccccn4)nc(N4CCOCC4)c23)cc1] | D |
| 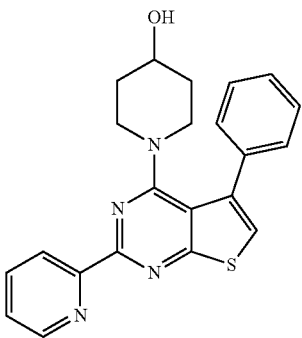 [SMILES: OC1CCN(c2nc(-c3ccccn3)nc3scc(-c4ccccc4)c23)CC1] | D |
| 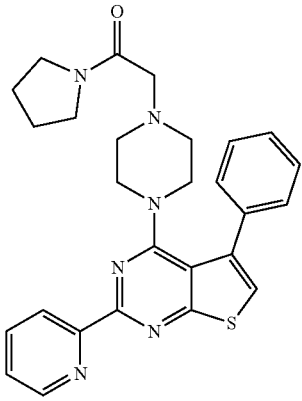 [SMILES: O=C(CN1CCN(c2nc(-c3ccccn3)nc3scc(-c4ccccc4)c23)CC1)N1CCCC1] | D |
| 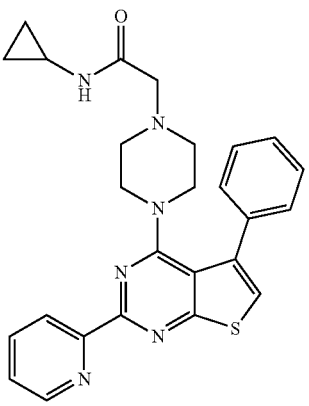 [SMILES: O=C(CN1CCN(c2nc(-c3ccccn3)nc3scc(-c4ccccc4)c23)CC1)NC1CC1] | D |

TABLE 3-continued

% Inhibition of cell proliferation @ 30 μM in MIA-PACA2 pancreatic cancer cell lines

| Compound | MIA-PACA2 |
|---|---|
| | D |
| | D |
| | D |
| | D |

TABLE 3-continued

% Inhibition of cell proliferation @ 30 μM in MIA-PACA2 pancreatic cancer cell lines

| Compound | MIA-PACA2 |
|---|---|
| *[structure: 4-(4-acetylpiperazin-1-yl)-5-phenyl-2-(pyridin-2-yl)thieno[2,3-d]pyrimidine]* | D |
| *[structure: 1-(5-phenyl-2-(pyridin-2-yl)thieno[2,3-d]pyrimidin-4-yl)piperidin-4-one]* | D |
| *[structure: 1-(5-phenyl-2-(pyridin-2-yl)thieno[2,3-d]pyrimidin-4-yl)piperidine-4-carboxamide]* | D |
| *[structure: N-(1-methoxypropan-2-yl)-6-methyl-5-phenyl-2-(pyridin-2-yl)thieno[2,3-d]pyrimidin-4-amine]* | D |
| *[structure: 2-amino-6-hydroxypurine (guanine)]* | A |

TABLE 3-continued

% Inhibition of cell proliferation @ 30 μM in MIA-PACA2 pancreatic cancer cell lines

| Compound | MIA-PACA2 |
|---|---|
| 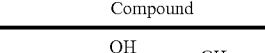 | A |

A = 1-25% inhibition, B = 25-50% inhibition, C = 51-75% inhibition, D = 76-100% inhibition

Example 3

Protocol for Mouse TNF Alpha and IL6 Quantification Assay

Cell lines: Abelson murine leukemia virus transformed macrophage cell line RAW 264.7 was purchased from ATCC and grown in complete DMEM-High Glucose medium supplemented with penicillin (100 U/mL), streptomycin (100 μg/mL), and 10% heat-inactivated FBS at 37° C. in a humidified incubator with 5% $CO_2$.

Method: Cells were plated at 40000 cells/well density in a 96-wells plate. After a 3-hour incubation, macrophages were starved with DMEM plus 0.5% FBS o/n. The next day the small molecules to be tested were added to the cells in the final concentration of 30 μM (with 0.3% DMSO) 3 hours prior to LPS stimulation (100 ng/ml). After LPS stimulation cells were incubated at 37° C. for 16 h. At the end of the incubation period, culture media were collected and production of LPS-induced TNFα and IL6 cytokine was measured using ELISA detection kits.

Sandwich ELISA: The ELISA Immunoassays Quantikine Mouse TNF-alpha (catalog number MTA00B) and IL6 (catalog number M6000B) were purchased from R&D Systems Inc., Minneapolis, MN These 4.5 hours solid phase ELISAs were used to measure mouse TNFα or IL6 levels in macrophages culture supernatants. Assays were executed according to the manufacturer specifications.

Table 4 shows inhibition data for selected compounds tested in the cellular assay described above.

TABLE 4

IL-6 and TNFα % Inhibition @ 30 μM in RAW 264.7 murine leukemia virus transformed macrophage cell lines

| Compound | IL-6 | TNF-α |
|---|---|---|
| | B | A |
| | 0 | A |
| | 0 | A |
| | 0 | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 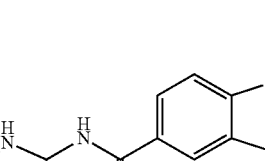 | A | B |
| 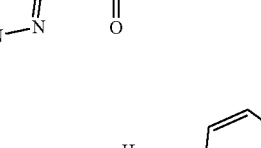 | A | 0 |
| 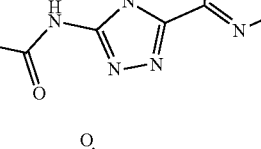 | B | A |
| 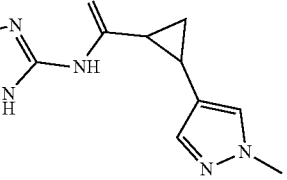 | 0 | A |
| 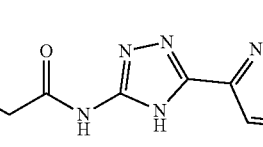 | B | A |
| 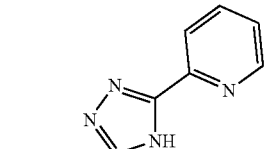 | A | A |
| 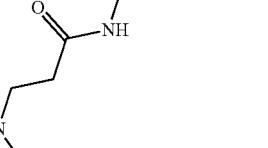 | A | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 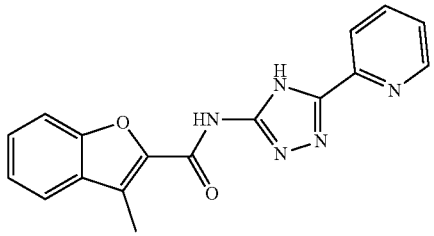 [SMILES: Cc1c(C(=O)Nc2nnc(-c3ccccn3)[nH]2)oc2ccccc12] | 0 | A |
| 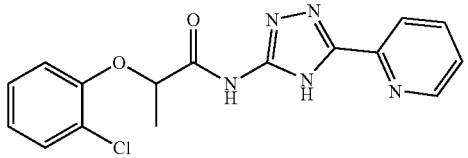 [SMILES: CC(Oc1ccccc1Cl)C(=O)Nc1nnc(-c2ccccn2)[nH]1] | B | A |
| 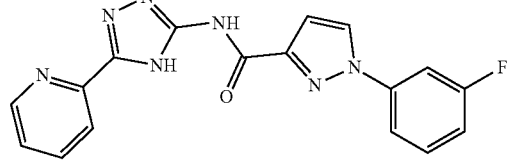 | B | 0 |
| 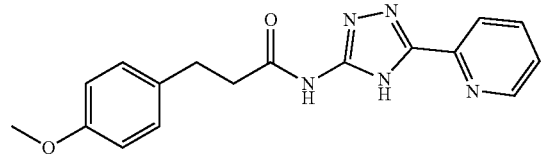 [SMILES: COc1ccc(CCC(=O)Nc2nnc(-c3ccccn3)[nH]2)cc1] | A | 0 |
| 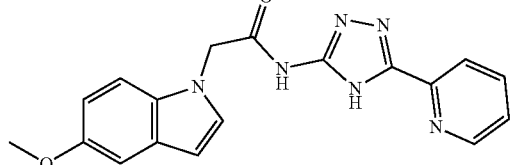 | B | A |
| 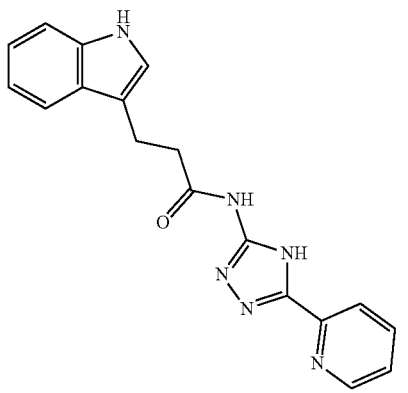 [SMILES: O=C(CCc1c[nH]c2ccccc12)Nc1nnc(-c2ccccn2)[nH]1] | C | 0 |
| 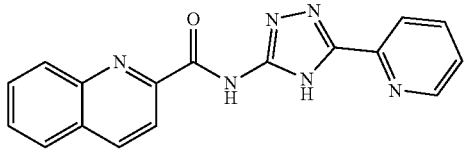 [SMILES: O=C(Nc1nnc(-c2ccccn2)[nH]1)c1ccc2ccccc2n1] | A | 0 |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 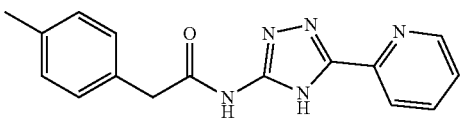 [SMILES: Cc1ccc(CC(=O)Nc2nnc(-c3ccccn3)[nH]2)cc1] | A | 0 |
| 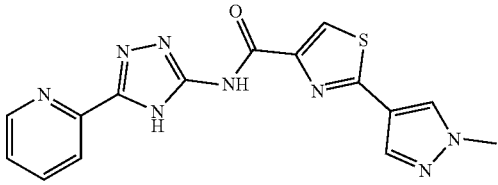 [SMILES: Cn1cc(-c2nc(C(=O)Nc3nnc(-c4ccccn4)[nH]3)cs2)cn1] | C | A |
| 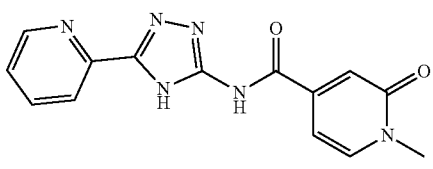 [SMILES: Cn1ccc(C(=O)Nc2nnc(-c3ccccn3)[nH]2)cc1=O] | 0 | A |
| 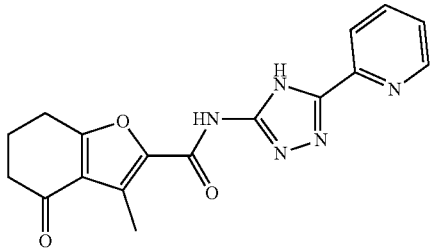 [SMILES: Cc1c(C(=O)Nc2nnc(-c3ccccn3)[nH]2)oc2c1C(=O)CCC2] | A | 0 |
| 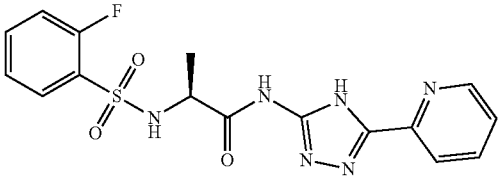 [SMILES: C[C@H](NS(=O)(=O)c1ccccc1F)C(=O)Nc1nnc(-c2ccccn2)[nH]1] | C | A |
| 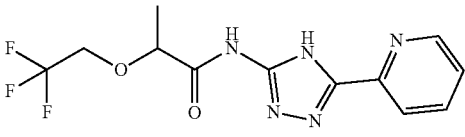 [SMILES: CC(OCC(F)(F)F)C(=O)Nc1nnc(-c2ccccn2)[nH]1] | 0 | A |
| 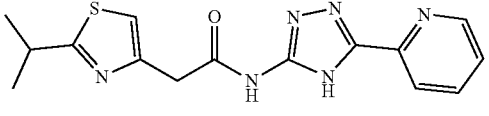 [SMILES: CC(C)c1nc(CC(=O)Nc2nnc(-c3ccccn3)[nH]2)cs1] | A | 0 |
| 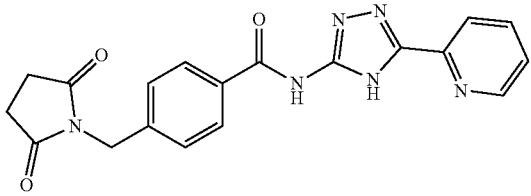 [SMILES: O=C(Nc1nnc(-c2ccccn2)[nH]1)c1ccc(CN2C(=O)CCC2=O)cc1] | 0 | A |
| 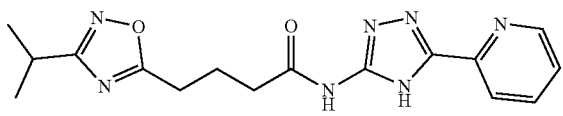 [SMILES: CC(C)c1noc(CCCC(=O)Nc2nnc(-c3ccccn3)[nH]2)n1] | 0 | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | A | 0 |
| | A | A |
| | A | 0 |
| | B | A |
| | B | A |
| | A | 0 |
| | A | 0 |
| | 0 | A |
| | A | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | A | 0 |
| | A | A |
| | B | A |
| | A | 0 |
| | A | 0 |
| | 0 | A |
| | A | 0 |
| | A | 0 |

TABLE 4-continued

IL-6 and TNFα % Inhibition @ 30 µM in RAW 264.7 murine leukemia virus transformed macrophage cell lines

| Compound | IL-6 | TNF-α |
|---|---|---|
| | 0 | A |
| | A | A |
| | A | 0 |
| | A | 0 |
| | B | A |
| | A | A |
| | A | 0 |
| | A | 0 |
| | A | A |
| | A | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | A | A |
| (structure) | 0 | A |
| (structure) | A | A |
| (structure) | B | 0 |
| (structure) | A | 0 |
| (structure) | 0 | A |
| (structure) | B | A |
| (structure) | B | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | A | A |
| | B | A |
| | A | A |
| | 0 | A |
| | A | 0 |
| | B | A |
| | A | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | C | 0 |
| | C | A |
| | B | A |
| | 0 | A |
| | 0 | A |
| | B | 0 |
| | B | 0 |
| | A | 0 |

TABLE 4-continued

IL-6 and TNFα % Inhibition @ 30 µM in RAW 264.7 murine leukemia virus transformed macrophage cell lines

| Compound | IL-6 | TNF-α |
|---|---|---|
| | B | A |
| | B | A |
| | B | A |
| | 0 | A |
| | A | 0 |
| | 0 | A |
| | A | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | D | 0 |
| (structure) | C | 0 |
| (structure) | C | 0 |
| (structure) | B | A |
| (structure) | 0 | A |
| (structure) | C | A |
| (structure) | C | A |
| (structure) | B | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 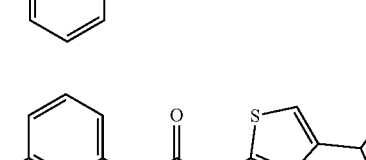 | A | A |
| 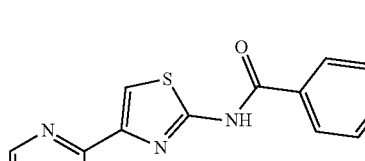 | A | A |
| 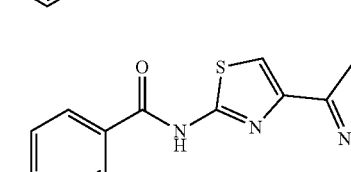 | B | A |
| 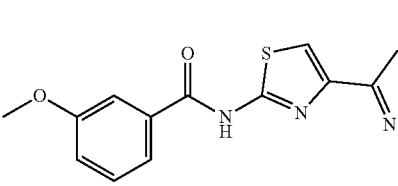 | B | B |
| 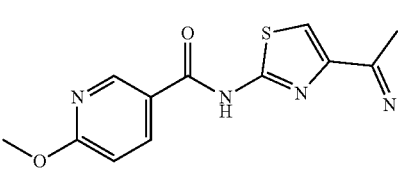 | A | 0 |
| 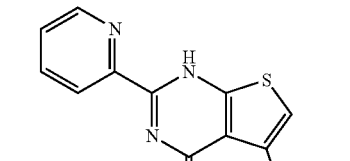 | D | C |
|  | B | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| 2-(pyridin-2-yl)-5-(thiophen-2-yl)-1H-thieno[2,3-d]pyrimidin-4(1H)-one | 0 | A |
| 5-(2-chlorophenyl)-2-(pyridin-2-yl)-1H-thieno[2,3-d]pyrimidin-4(1H)-one | 0 | A |
| 6-methyl-5-phenyl-2-(pyridin-2-yl)-1H-thieno[2,3-d]pyrimidin-4(1H)-one | 0 | A |
| 2-(pyridin-2-yl)-1H-thieno[3,2-d]pyrimidin-4(1H)-one | A | 0 |
| 6-phenyl-2-(pyridin-2-yl)-1H-thieno[2,3-d]pyrimidin-4(1H)-one | C | D |
| N,N-diethyl-5-methyl-4-oxo-2-(pyridin-2-yl)-1,4-dihydrothieno[2,3-d]pyrimidine-6-carboxamide | A | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | D | D |
| | A | A |
| | A | A |
| | B | B |
| | 0 | A |
| | 0 | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
|  | 0 | A |
|  | 0 | A |
|  | A | 0 |
|  | D | D |
|  | D | D |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
|  | B | 0 |
|  | B | A |
|  | B | A |
|  | A | A |
|  | A | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 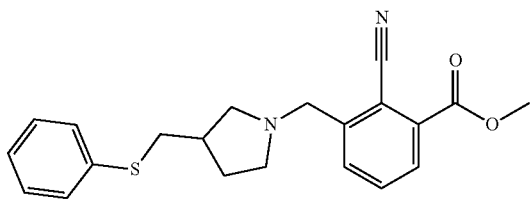 [SMILES: COC(=O)c1cccc(CN2CCC(CSc3ccccc3)C2)c1C#N] | B | 0 |
| 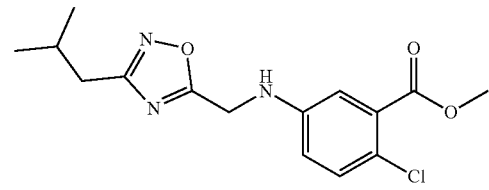 [SMILES: COC(=O)c1cc(NCc2nc(CC(C)C)no2)ccc1Cl] | B | A |
| 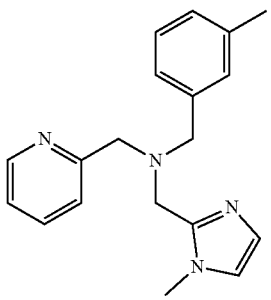 [SMILES: Cc1cccc(CN(Cc2ccccn2)Cc2nccn2C)c1] | B | A |
| 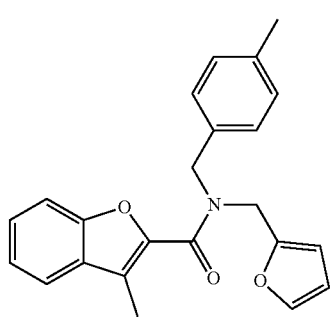 [SMILES: Cc1ccc(CN(Cc2ccco2)C(=O)c2oc3ccccc3c2C)cc1] | A | 0 |
| 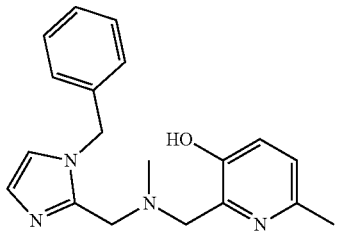 [SMILES: Cc1ccc(O)c(CN(C)Cc2nccn2Cc2ccccc2)n1] | A | 0 |
| 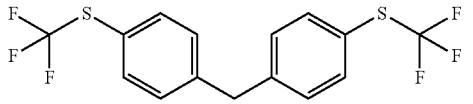 [SMILES: FC(F)(F)Sc1ccc(Cc2ccc(SC(F)(F)F)cc2)cc1] | A | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | 0 | A |
| (structure) | C | 0 |
| (structure) | B | B |
| (structure) | D | D |
| (structure) | 0 | A |
| (structure) | C | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| | 0 | A |
| | A | A |
| | 0 | A |
| | A | C |
| | C | 0 |
| | B | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | A | A |
| (structure) | B | 0 |
| (structure) | B | B |
| (structure) | A | B |
| (structure) | 0 | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | A | 0 |
| (structure) | B | A |
| (structure) | D | A |
| (structure) | C | A |
| (structure) | D | B |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | A | 0 |
| (structure) | D | A |
| (structure) | D | B |
| (structure) | D | A |
| (structure) | D | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | C | 0 |
| (structure) | D | A |
| (structure) | A | A |
| (structure) | B | 0 |
| (structure) | B | 0 |
| (structure) | 0 | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | D | B |
| (structure) | B | 0 |
| (structure) | A | A |
| (structure) | D | A |
| (structure) | A | A |
| (structure) | A | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| 2-amino-4-hydroxy-thieno[3,2-d]pyrimidine-7-carbonyl-[4-(2-ethoxyethyl)piperidine] | 0 | A |
| 2-amino-4-hydroxy-thieno[3,2-d]pyrimidine-7-carbonyl-[4-(3-methoxypropyl)piperidine] | 0 | A |
| 2-amino-4-hydroxy-thieno[3,2-d]pyrimidine-7-carbonyl-[4-morpholinopiperidine] | 0 | A |
| 2-amino-4-hydroxy-thieno[3,2-d]pyrimidine-7-carbonyl-[4-(2-oxopyrrolidin-1-yl)piperidine] | A | 0 |
| 2-amino-4-hydroxy-thieno[3,2-d]pyrimidine-7-carbonyl-[4-(ethoxycarbonylamino)piperidine] | 0 | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 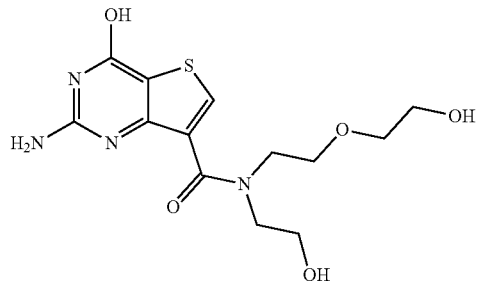 [SMILES: Nc1nc(O)c2scc(C(=O)N(CCO)CCOCCO)c2n1] | A | 0 |
| 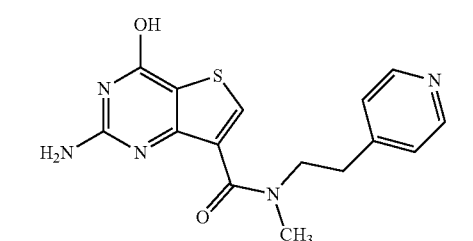 | A | 0 |
| 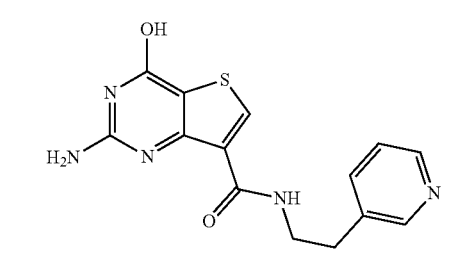 [SMILES: Nc1nc(O)c2scc(C(=O)NCCc3cccnc3)c2n1] | A | A |
| 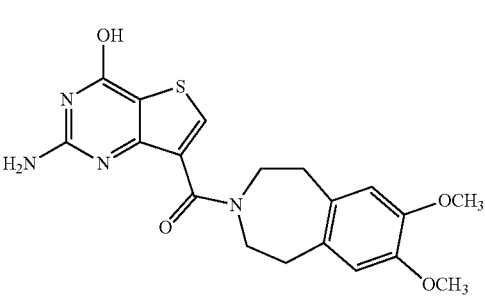 [SMILES: COc1cc2c(cc1OC)CCN(C(=O)c1csc3c(O)nc(N)nc13)CC2] | A | A |
| 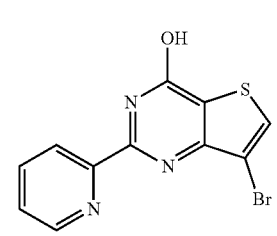 [SMILES: Oc1nc(-c2ccccn2)nc2c(Br)csc12] | D | D |
| 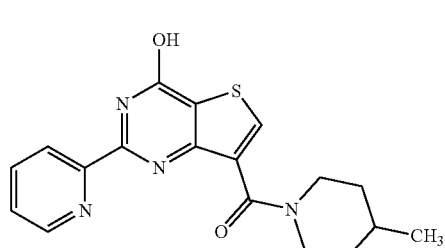 | B | 0 |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 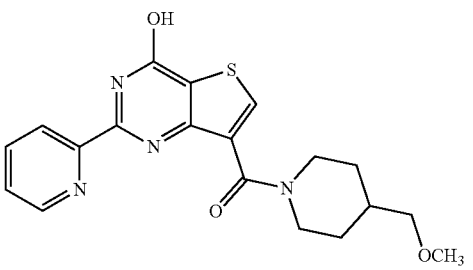 [SMILES: COCC1CCN(C(=O)c2csc3c(O)nc(-c4ccccn4)nc23)CC1] | D | A |
| 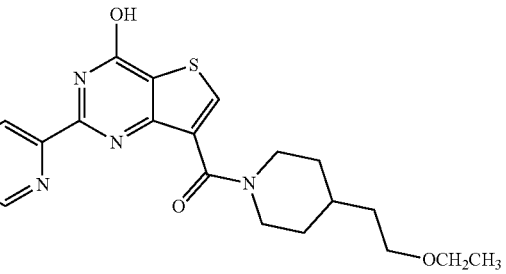 | D | A |
| 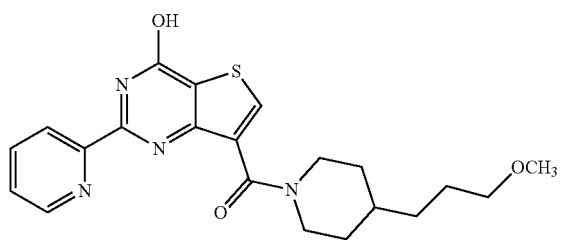 [SMILES: COCCCC1CCN(C(=O)c2csc3c(O)nc(-c4ccccn4)nc23)CC1] | C | A |
| 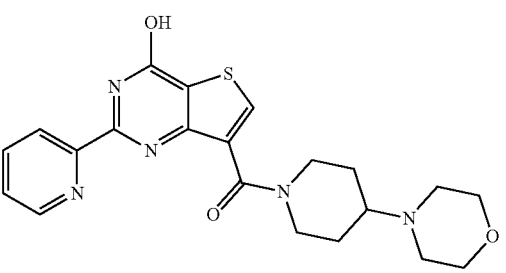 [SMILES: O=C(c1csc2c(O)nc(-c3ccccn3)nc12)N1CCC(N2CCOCC2)CC1] | A | 0 |
| 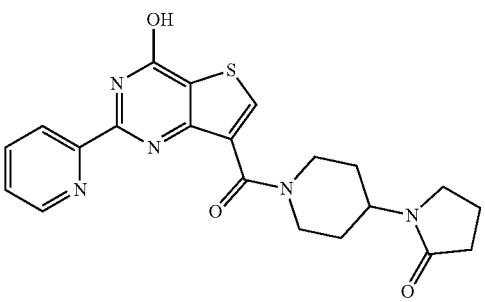 [SMILES: O=C(c1csc2c(O)nc(-c3ccccn3)nc12)N1CCC(N2CCCC2=O)CC1] | A | B |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 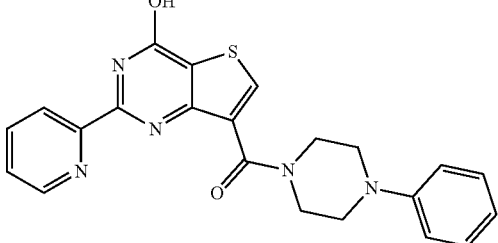 | D | C |
| 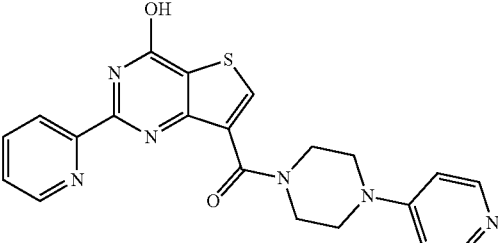 | A | 0 |
| 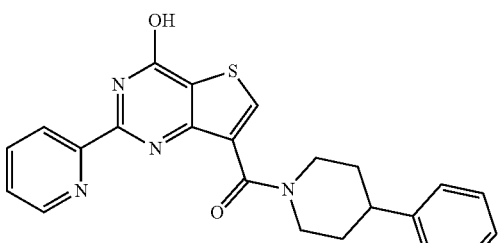 | D | A |
| 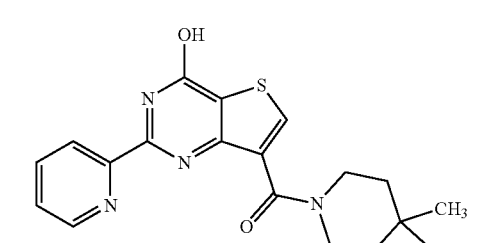 | C | 0 |
| 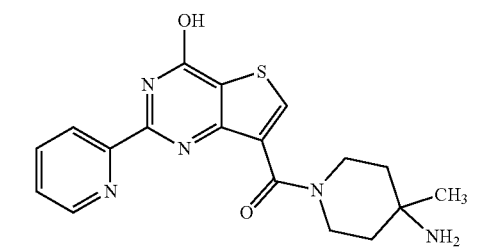 [SMILES: CC1(N)CCN(C(=O)c2csc3c(O)nc(-c4ccccn4)nc23)CC1] | A | 0 |
| 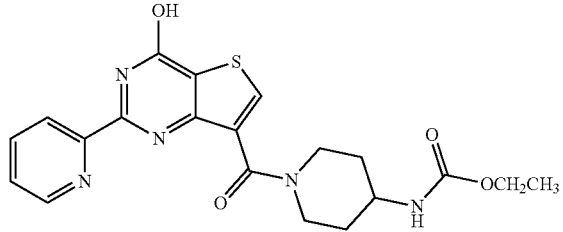 [SMILES: CCOC(=O)NC1CCN(C(=O)c2csc3c(O)nc(-c4ccccn4)nc23)CC1] | C | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | B | 0 |
| (structure) | C | 0 |
| (structure) | B | 0 |
| (structure) | C | 0 |
| (structure) | B | A |
| (structure) | A | 0 |

TABLE 4-continued
IL-6 and TNFα % Inhibition @ 30 µM in RAW 264.7 murine leukemia virus transformed macrophage cell lines
| Compound | IL-6 | TNF-α |
|---|---|---|
| 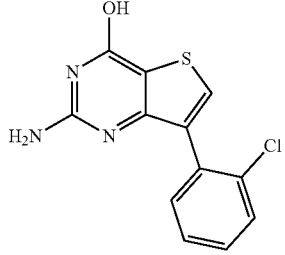 [SMILES: Nc1nc(O)c2scc(-c3ccccc3Cl)c2n1] | B | 0 |
| 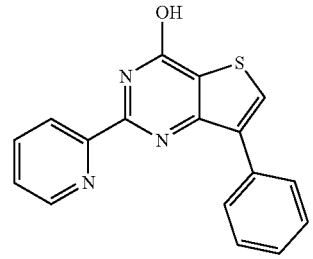 [SMILES: Oc1nc(-c2ccccn2)nc2c(-c3ccccc3)csc12] | D | D |
| 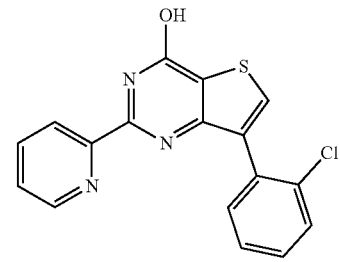 [SMILES: Oc1nc(-c2ccccn2)nc2c(-c3ccccc3Cl)csc12] | D | C |
| 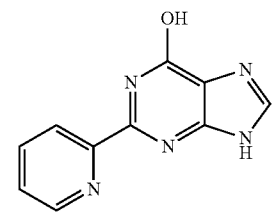 [SMILES: Oc1nc(-c2ccccn2)nc2[nH]cnc12] | D | D |
| 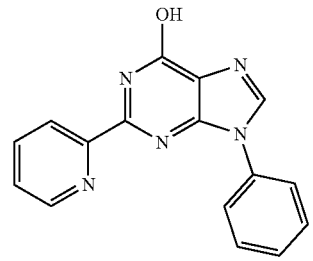 | A | 0 |
| 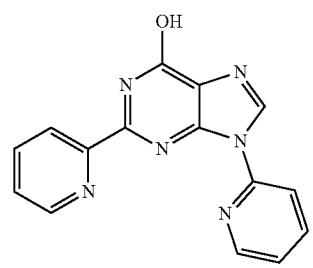 [SMILES: Oc1nc(-c2ccccn2)nc2c1ncn2-c1ccccn1] | B | 0 |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (pyridin-2-yl-pyrimidin-4-yl)-NH-C(O)-CH2-(4-cyanophenyl) | A | A |
| 5-bromo-4-morpholino-2-(pyridin-2-yl)thieno[2,3-d]pyrimidine | C | 0 |
| 4-morpholino-2-(pyridin-2-yl)thieno[2,3-d]pyrimidine | A | A |
| 5-bromo-4-hydroxy-2-(pyridin-2-yl)thieno[2,3-d]pyrimidine | D | D |
| N-((tetrahydrofuran-2-yl)methyl)-2-(pyridin-2-yl)thieno[2,3-d]pyrimidin-4-amine | C | A |

TABLE 4-continued

IL-6 and TNFα % Inhibition @ 30 µM in RAW 264.7 murine leukemia virus transformed macrophage cell lines

| Compound | IL-6 | TNF-α |
|---|---|---|
| (structure) | A | 0 |
| (structure) | A | A |
| (structure) | D | D |
| (structure) | D | D |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | A | 0 |
| (structure) | D | D |
| (structure) | D | D |
| (structure) | B | B |
| (structure) | A | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 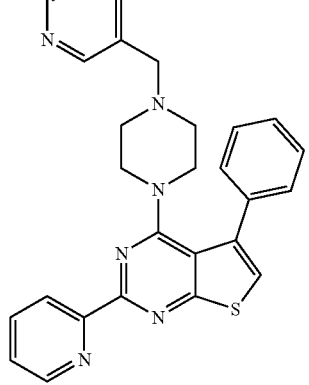 | D | C |
| 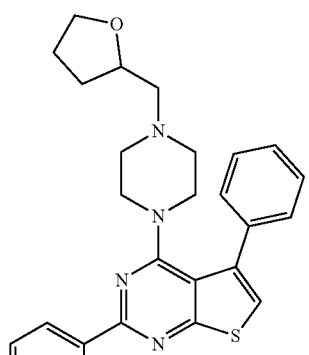 | C | B |
| 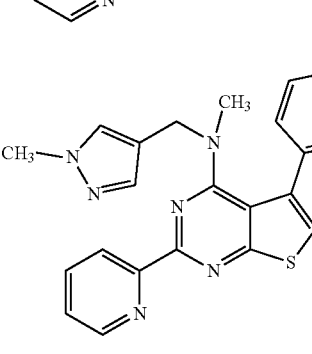 | D | B |
| 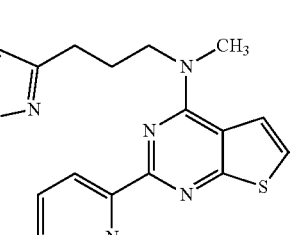 | D | C |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 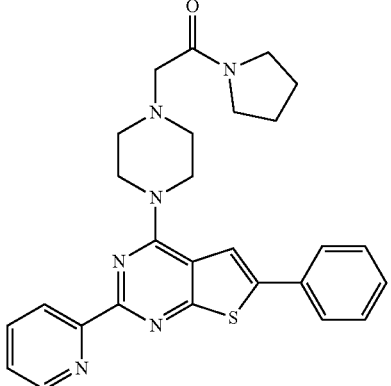 | D | D |
| 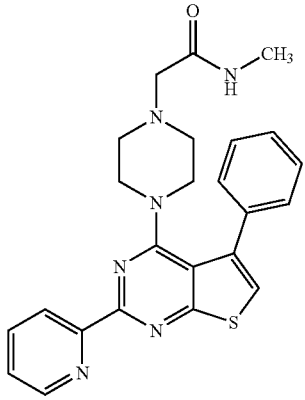 [SMILES: CNC(=O)CN1CCN(c2nc(-c3ccccn3)nc3scc(-c4ccccc4)c23)CC1] | A | A |
| 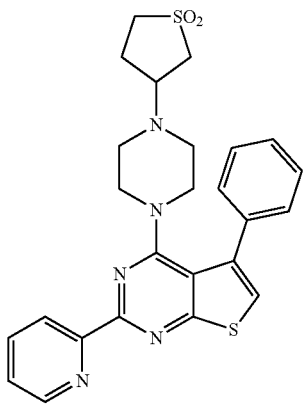 [SMILES: O=S1(=O)CCC(N2CCN(c3nc(-c4ccccn4)nc4scc(-c5ccccc5)c34)CC2)C1] | A | A |
| 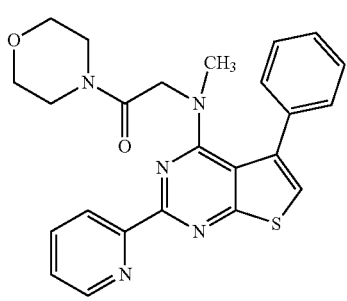 [SMILES: CN(CC(=O)N1CCOCC1)c1nc(-c2ccccn2)nc2scc(-c3ccccc3)c12] | A | A |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | B | A |
| (structure) | B | A |
| (structure) | B | B |
| (structure) | D | C |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure) | D | B |
| (structure) | A | 0 |
| (structure) | B | 0 |
| (structure) | B | A |

TABLE 4-continued
IL-6 and TNFα % Inhibition @ 30 μM in RAW 264.7 murine leukemia virus transformed macrophage cell lines
| Compound | IL-6 | TNF-α |
|---|---|---|
| 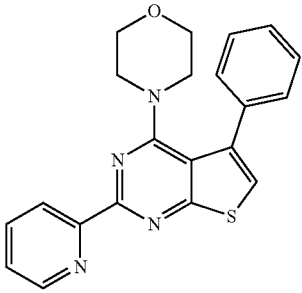 [SMILES: c1ccc(-c2csc3nc(-c4ccccn4)nc(N4CCOCC4)c23)cc1] | A | A |
| 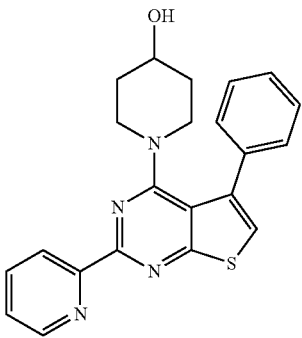 [SMILES: OC1CCN(c2nc(-c3ccccn3)nc3scc(-c4ccccc4)c23)CC1] | B | A |
| 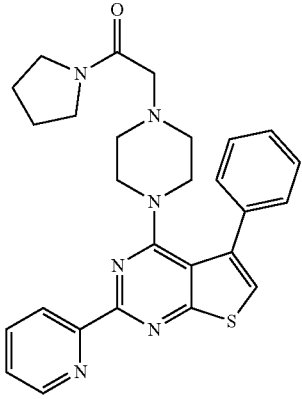 [SMILES: O=C(CN1CCN(c2nc(-c3ccccn3)nc3scc(-c4ccccc4)c23)CC1)N1CCCC1] | A | A |
| 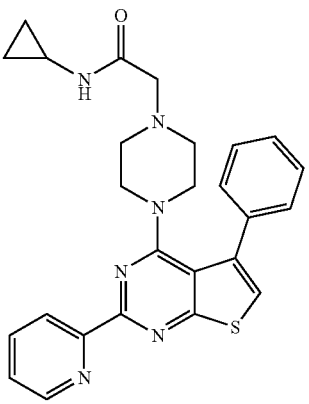 [SMILES: O=C(CN1CCN(c2nc(-c3ccccn3)nc3scc(-c4ccccc4)c23)CC1)NC1CC1] | D | B |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (morpholin-4-ylamino-5-phenyl-2-(pyridin-2-yl)thieno[2,3-d]pyrimidin-4-amine) | C | B |
| (1-(5-phenyl-2-(pyridin-2-yl)thieno[2,3-d]pyrimidin-4-yl)piperidine-3-carboxamide) | A | A |
| (N-(2-methoxyethyl)-5-phenyl-2-(pyridin-2-yl)thieno[2,3-d]pyrimidin-4-amine) | D | D |
| (1-(4-(5-phenyl-2-(pyridin-2-yl)thieno[2,3-d]pyrimidin-4-yl)piperazin-1-yl)ethan-1-one) | B | B |

TABLE 4-continued

IL-6 and TNFα % Inhibition @ 30 μM in RAW 264.7 murine leukemia virus transformed macrophage cell lines

| Compound | IL-6 | TNF-α |
|---|---|---|
| (structure: 4-(4-oxopiperidin-1-yl)-5-phenyl-2-(pyridin-2-yl)thieno[2,3-d]pyrimidine) | A | A |
| (structure: 1-(5-phenyl-2-(pyridin-2-yl)thieno[2,3-d]pyrimidin-4-yl)piperidine-4-carboxamide) | A | A |
| (structure: N-(1-methoxypropan-2-yl)-6-methyl-5-phenyl-2-(pyridin-2-yl)thieno[2,3-d]pyrimidin-4-amine) | D | D |
| (structure: 2-amino-5,6-dimethyl-4-hydroxythieno[2,3-d]pyrimidine) | A | A |

0 = 0% inhibition,
A = 1-25% inhibition,
B = 26-50% inhibition,
C = 51-75% inhibition,
D = 76-100% inhibition This disclosure is not to be limited in scope by the embodiments disclosed in the examples which are intended as single illustrations of individual aspects, and any methods which are functionally equivalent are within the scope of this disclosure. Indeed, various modifications in addition to those shown and described herein will become apparent to those skilled in the art from the foregoing description. Such modifications are intended to fall within the scope of the appended claims.

Various references such as patents, patent applications, and publications are cited herein, the disclosures of which are hereby incorporated by reference herein in their entireties.

What is claimed is:

1. A compound of Formula VIb1:

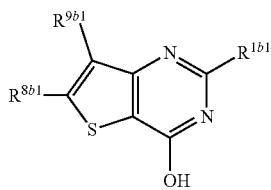

Formula VIb1 or a pharmaceutically acceptable salt thereof,
wherein
$R^{1b1}$ is 2-pyridyl or $NH_2$;
$R^{8b1}$ is H;
$R^{9b1}$ is aryl, halo, or $C(O)R^4$;
$R^4$ is $NR^6R^7$; and
$R^6$ and $R^7$ are independently selected from hydrogen, alkyl, alkenyl, alkynyl, aryl, heteroaryl, heterocyclyl, cycloalkyl, or $R^6$ and $R^7$ are combined to form a cyclic structure including the nitrogen atom to which they are both attached,
wherein each of the alkyl, alkenyl, alkynyl, aryl, heteroaryl, heterocyclyl, cycloalkyl, and cyclic structure are optionally substituted with one or more substituents Q independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents $Q^a$, and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$,
wherein each R$^a$, R$^b$, R$^c$, and R$^d$ is independently (i) hydrogen or deuterium or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents $Q^a$; or (iii) R$^b$ and R$^c$ together with the N atom to which they are attached form heterocyclyl, optionally substituted with one or more substituents $Q^a$;
wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl;
and (c) —C(O)Re, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$^2$NR$^f$R$^g$, —SR$^e$, —S(O)R$^e$, —S(O)$_2$R$^e$, —S(O)NR$^f$R$^g$, and —S(O)$_2$NR$^f$R$^g$;

wherein each R$^e$, R$^f$, R$^g$, and R$^h$ is independently (i) hydrogen or deuterium or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl;

wherein heteroaryl is a monocyclic or multicyclic aromatic ring system of about 5 to about 15 atoms, wherein one or more of the atoms in the ring system is nitrogen, oxygen, or sulfur; and wherein heterocyclyl is a monocyclic or multicyclic non-aromatic ring system of about 5 to about 15 atoms, wherein one or more of the atoms in the ring system is nitrogen, oxygen, or sulfur.

2. A method of treating cancer, comprising administering to a subject the compound or pharmaceutically acceptable salt thereof of claim 1, wherein the cancer is leukemia, hepatocellular carcinoma, prostate cancer, pancreatic cancer, ovarian cancer, or glioblastoma.

3. The method of claim 2, wherein the cancer is hepatocellular carcinoma, prostate cancer, pancreatic cancer, ovarian cancer, or glioblastoma.

4. The method of claim 3, wherein the cancer is pancreatic cancer.

5. A method of treating an inflammatory disease, comprising administering to a subject the compound or pharmaceutically acceptable salt thereof of claim 1, wherein the inflammatory disease is gastritis, schistosomiasis, cholangitis, chronic cholecystitis, pelvic inflammatory disease, chronic cervicitis, osteomyelitis, inflammatory bowel disease, reflux esophagitis, Barrett's esophagus, bladder inflammation (cystitis), asbestosis, silicosis, gingivitis, lichen planus, pancreatitis, protease mutation, lichen sclerosis, slaladenitis, bronchitis, Sjogren syndrome or Hashimoto's thyroiditis.

6. A pharmaceutical composition, comprising an effective amount of the compound or pharmaceutically acceptable salt thereof of claim 1 and a pharmaceutically acceptable carrier.

7. The compound or pharmaceutically acceptable salt thereof of claim 1, wherein the compound is selected from the group consisting of:

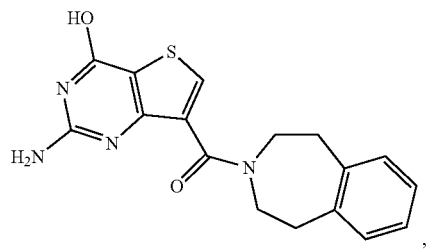

,

585
-continued
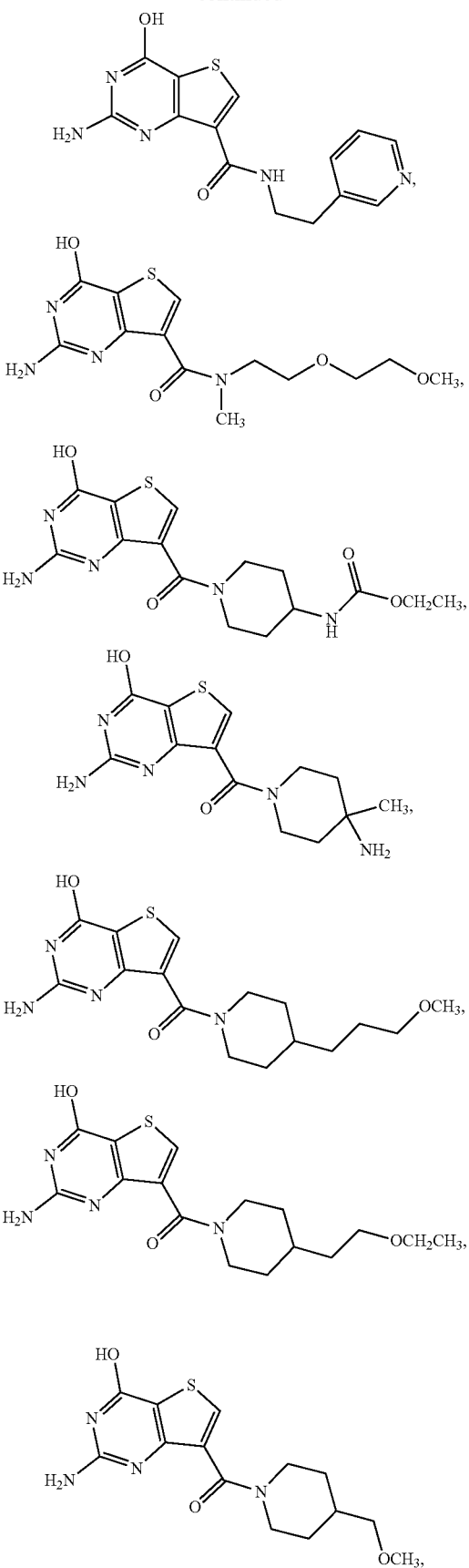
586
-continued
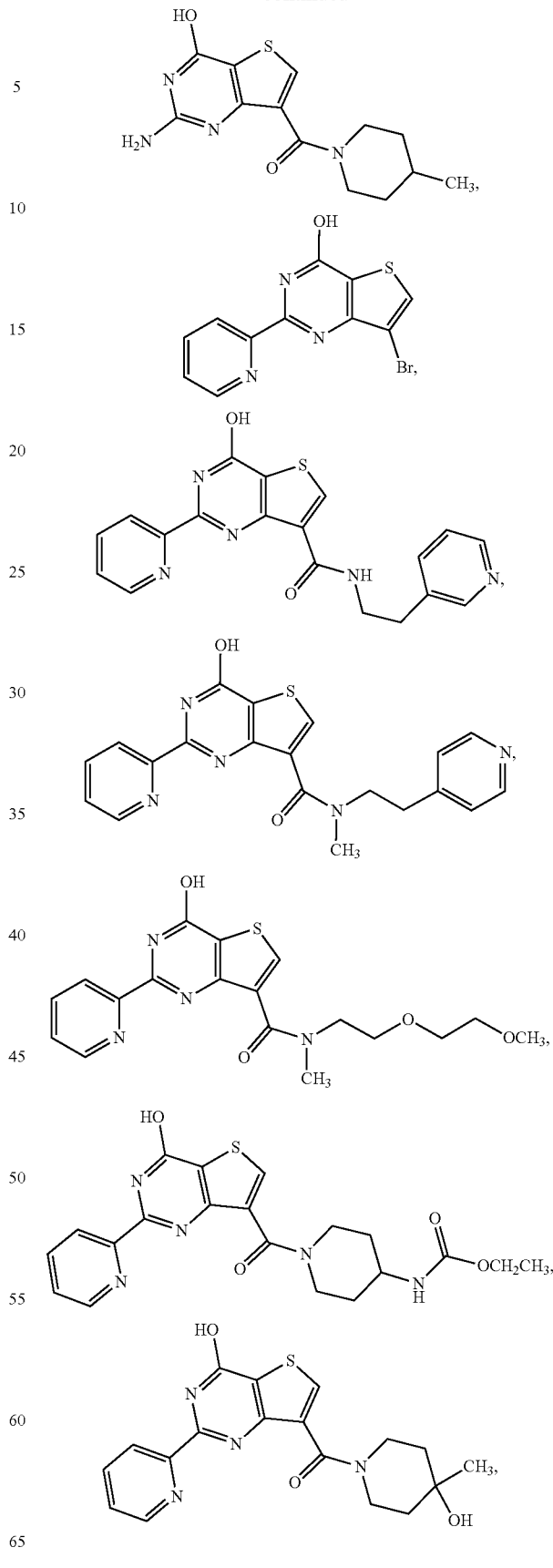

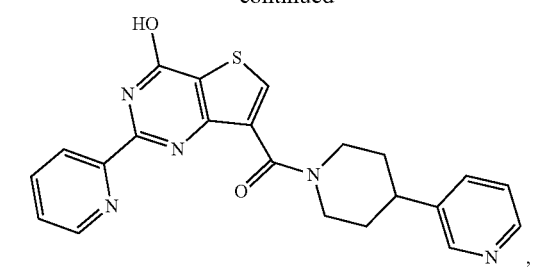
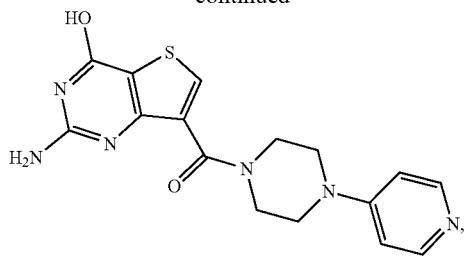
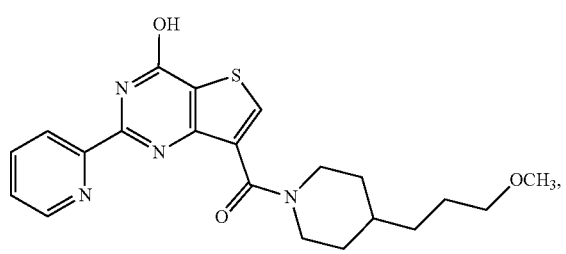
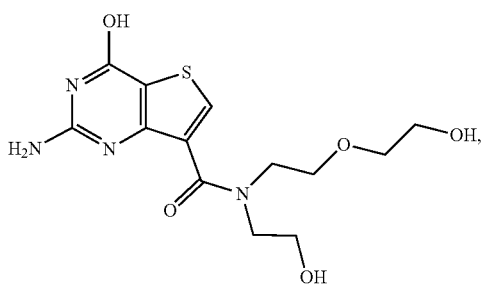
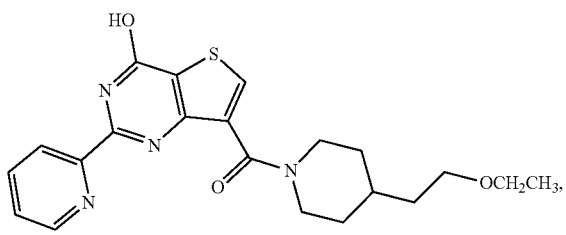
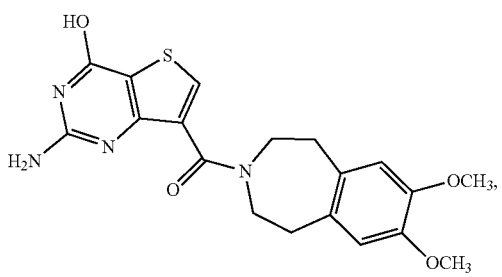
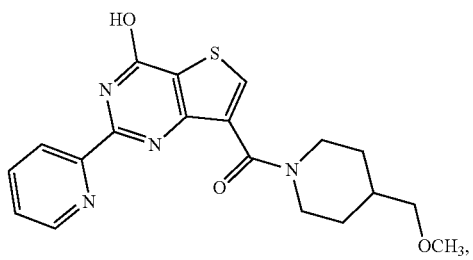
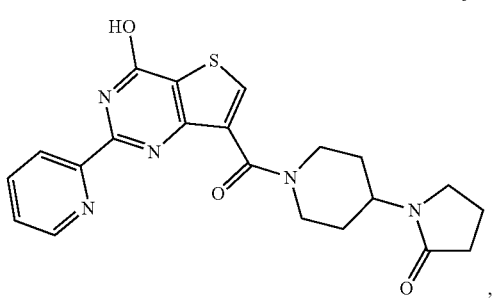
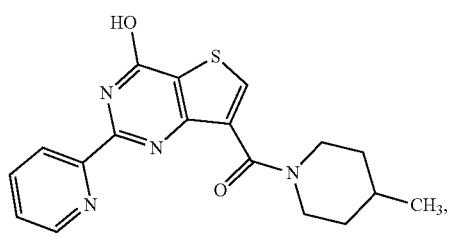
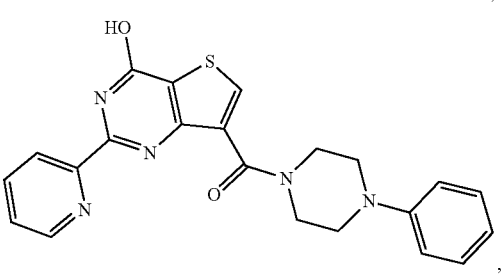
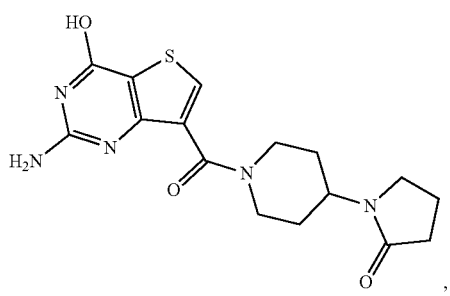
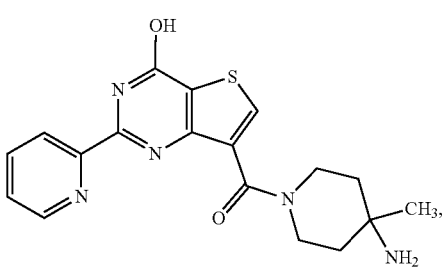

589
-continued
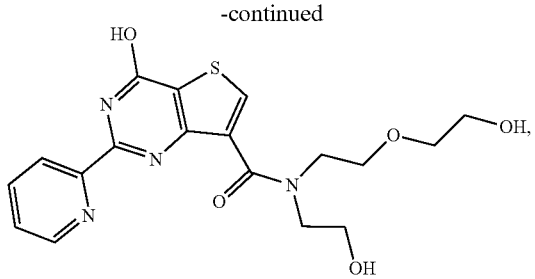
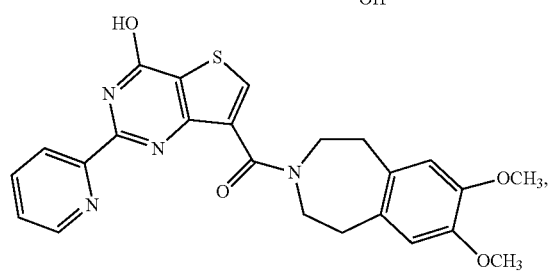
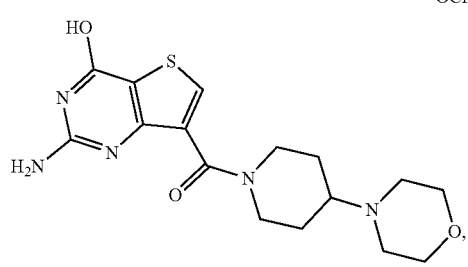
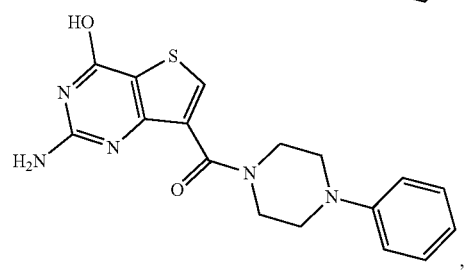
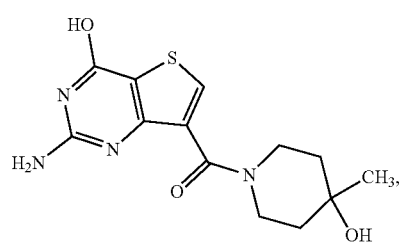
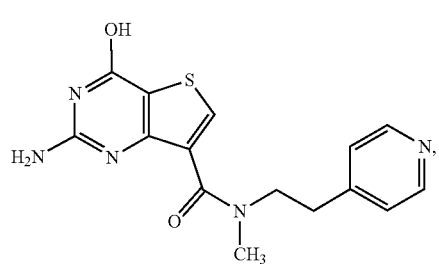
590
-continued
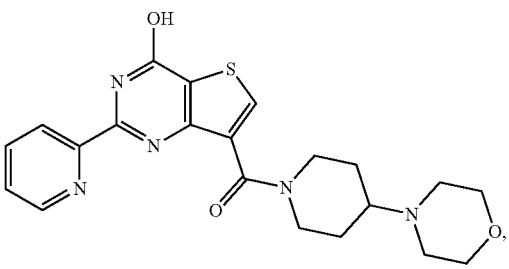
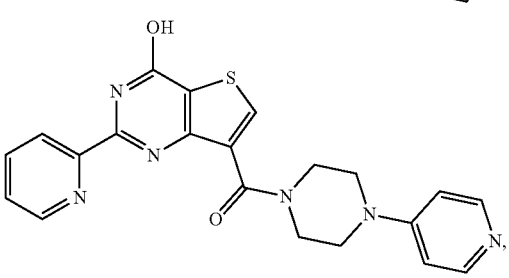
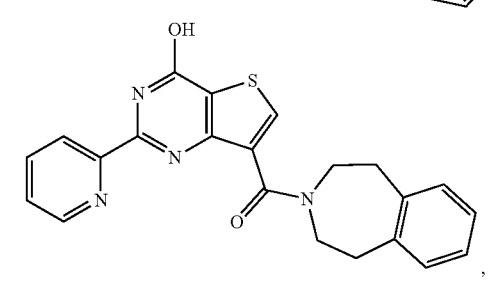
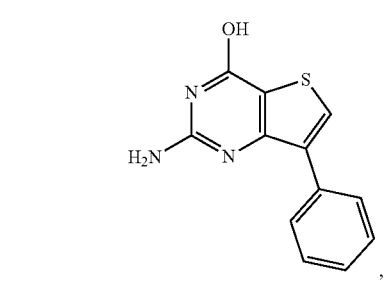
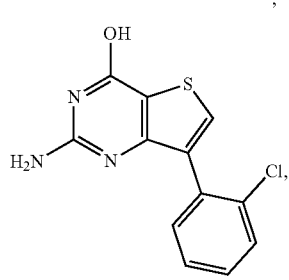
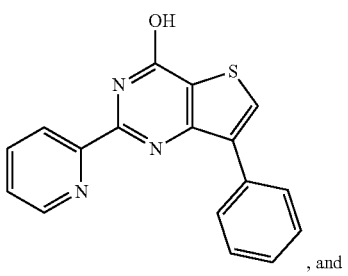
, and -continued

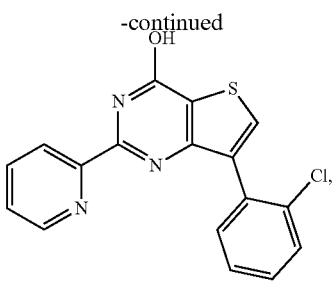

or a pharmaceutically acceptable salt thereof.

8. A method of treating cancer, comprising administering to a subject the compound or pharmaceutically acceptable salt of thereof claim 7, wherein the cancer is leukemia, hepatocellular carcinoma, prostate cancer, pancreatic cancer, ovarian cancer, or glioblastoma.

9. The method of claim 8, wherein the cancer is hepatocellular carcinoma, prostate cancer, pancreatic cancer, ovarian cancer, or glioblastoma.

10. The method of claim 9, wherein the cancer is pancreatic cancer.

11. A method of treating an inflammatory disease, comprising administering to a subject the compound or pharmaceutically acceptable salt thereof of claim 7, wherein the inflammatory disease is gastritis, schistosomiasis, cholangitis, chronic cholecystitis, pelvic inflammatory disease, chronic cervicitis, osteomyelitis, inflammatory bowel disease, reflux esophagitis, Barrett's esophagus, bladder inflammation (cystitis), asbestosis, silicosis, gingivitis, lichen planus, pancreatitis, protease mutation, lichen sclerosis, slaladenitis, bronchitis, Sjogren syndrome, or Hashimoto's thyroiditis.

12. A pharmaceutical composition comprising the compound or pharmaceutically acceptable salt thereof of claim 7 and a pharmaceutically acceptable carrier.

13. The method of claim 2, wherein the cancer is leukemia.

14. The method of claim 13, wherein the leukemia is chronic lymphocytic leukemia (CLL), chronic myelocytic leukemia (CML), acute lymphoblastic leukemia (ALL), acute myeloid leukemia (AML), or acute myeloblasts leukemia (AML).

15. The method of claim 8, wherein the cancer is leukemia.

16. The method of claim 15, wherein the leukemia is chronic lymphocytic leukemia (CLL), chronic myelocytic leukemia (CML), acute lymphoblastic leukemia (ALL), acute myeloid leukemia (AML), or acute myeloblasts leukemia (AML).

* * * * *